(12) United States Patent
Fujii et al.

(10) Patent No.: US 8,399,449 B2
(45) Date of Patent: *Mar. 19, 2013

(54) FUSED HETEROCYCLIC DERIVATIVE AND USE THEREOF

(75) Inventors: Nobuhiro Fujii, Osaka (JP); Yuya Oguro, Tsukuba (JP); Satoshi Sasaki, Tsukuba (JP); Shigeru Kondo, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 161 days.

This patent is subject to a terminal disclaimer.

(21) Appl. No.: 12/919,413

(22) PCT Filed: Feb. 25, 2009

(86) PCT No.: PCT/JP2009/054007
§ 371 (c)(1),
(2), (4) Date: Aug. 25, 2010

(87) PCT Pub. No.: WO2009/107850
PCT Pub. Date: Sep. 3, 2009

(65) Prior Publication Data
US 2011/0003788 A1    Jan. 6, 2011

(30) Foreign Application Priority Data

Feb. 26, 2008  (JP) ................. 2008-045134
Oct. 1, 2008   (JP) ................. 2008-256755

(51) Int. Cl.
| | |
|---|---|
| A61K 31/4375 | (2006.01) |
| A61K 31/4355 | (2006.01) |
| A61K 31/4365 | (2006.01) |
| A61K 31/437 | (2006.01) |
| A61K 31/438 | (2006.01) |
| A61K 31/496 | (2006.01) |
| A61K 31/497 | (2006.01) |
| A61K 31/506 | (2006.01) |
| A61K 31/5377 | (2006.01) |
| A61K 31/541 | (2006.01) |
| A61K 31/55 | (2006.01) |
| A61K 31/551 | (2006.01) |
| A61P 35/00 | (2006.01) |
| C07D 471/04 | (2006.01) |
| C07D 471/14 | (2006.01) |
| C07D 491/10 | (2006.01) |
| C07D 495/04 | (2006.01) |

(52) U.S. Cl. ............ 514/210.18; 514/212.08; 514/218; 514/228.2; 514/232.8; 514/253.03; 514/255.05; 514/256; 514/278; 514/291; 514/292; 514/293; 514/300; 514/301; 540/524; 540/575; 544/58.4; 544/121; 544/126; 544/328; 544/361; 544/405; 546/19; 546/90; 546/82; 546/84; 546/89; 546/113; 546/114

(58) Field of Classification Search .................. None
See application file for complete search history.

(56) References Cited

U.S. PATENT DOCUMENTS

| | | |
|---|---|---|
| 5,360,799 A | 11/1994 | Bachy et al. |
| 2007/0060595 A1 | 3/2007 | Yoshizawa et al. |
| 2008/0249154 A1 | 10/2008 | Ohmoto et al. |
| 2009/0227561 A1 | 9/2009 | Fujii et al. |

FOREIGN PATENT DOCUMENTS

| | | |
|---|---|---|
| EP | 0 587 473 | 3/1994 |
| JP | 3-223289 | 2/1991 |
| JP | 3-223289 | 10/1991 |
| WO | 93/13664 | 7/1993 |
| WO | 99/62908 | 12/1999 |
| WO | 00/75145 | 12/2000 |
| WO | 02/051831 | 7/2002 |
| WO | 03/059884 | 7/2003 |
| WO | 2004/020599 | 3/2004 |
| WO | 2004/058772 | 7/2004 |
| WO | 2005/013986 | 2/2005 |
| WO | 2005/035516 | 4/2005 |
| WO | 2005/063241 | 7/2005 |
| WO | 2005/097107 | 10/2005 |
| WO | 2006/030032 | 3/2006 |
| WO | 2007/022268 | 2/2007 |

OTHER PUBLICATIONS

Rautio et al., Prodrugs: Design and Clinical Applications, 7 Nat. Rev. Drug Dis., 255-70 (2008).*
International Search Report issued in International Application No. PCT/JP2009/054007 and mailed Dec. 3, 2009.
Written Opinion of the International Searching Authority issued in International Application No. PCT/JP2009/054007 and mailed Dec. 3, 2009.
STN Database including CAS registry No. 401466-82-8, ACS Chemical Library, Copyright 2009, entered STN: Mar. 16, 2002—5 pages.
Nybakken, et al., "Hedgehog signal transduction: recent findings", Current Opinion in Genetics & Development, vol. 12, 2002, pp. 503-511.
Kalderon, Daniel, "Transducing the Hedgehog Signal", Cell, vol. 103, Oct. 27, 2000, pp. 371-374.

(Continued)

*Primary Examiner* — Nizal S. Chandrakumar
*Assistant Examiner* — Timothy R Rozof
(74) *Attorney, Agent, or Firm* — Hamre, Schumann, Mueller & Larson, P.C.

(57) ABSTRACT

The present invention provides a compound having a superior Smo inhibitory activity and lower toxicity, which is sufficiently satisfactory as a pharmaceutical product. The present invention provides a compound represented by the formula (I) wherein ring A is 5- to 7-membered ring optionally having substituent(s), where substituents are optionally bonded to each other to form a ring; X is O, S or $NR^1$ ($R^1$ is a hydrogen atom or a hydrocarbon group optionally having substituent(s)); $R^2$ is carbamoyl optionally having substituent(s); and $R^3$ is hydroxy optionally having substituent(s), or a salt thereof.

16 Claims, No Drawings

OTHER PUBLICATIONS

Pepinsky, et al., "Identification of a Palmitic Acid-modified Form of Human Sonic hedgehog", The Journal of Biological Chemistry, vol. 273, No. 22, May 29, 1998, pp. 14037-14045.

Taylor, et al., "Enhanced Potency of Human Sonic Hedgehog by Hydrophobic Modification", Biochemistry, vol. 40, 2001, pp. 4359-4371.

Ruiz I Altaba, et al., "GLI and Hedgehog in Cancer: Tumours, Embryos and Stem Cells", Nature Reviews Cancer, vol. 2, May 2002, pp. 361-372.

Wang, et al., "Shifting paradigms in Hedgehog signaling", Current Opinion in Cell Biology, vol. 19, 2007, pp. 159-165.

Roessler, et al., Mutations in the human *Sonic Hedgehog* gene cause holoprosencephaly, Nature Genetics, vol. 14, Nov. 1996, pp. 357-360.

Binns, et al., "A congenital Cyclopian-Type Malformation in Lambs Induced by Maternal Ingestion of a Range Plant, *Veratrum californicum*", Am. J. Vet. Res., vol. 24, No. 103, Nov. 1963, pp. 1164-1175.

Incardona, et al., "The teratogenic *Veratrum* alkaloid cyclopamine inhibits Sonic hedgehog signal transduction", Development, vol. 125, 1998, pp. 3553-3562.

Chiang, et al., "Cyclopia and defective axial patterning in mice lacking *Sonic hedgehog* gene function", Nature, vol. 383, Oct. 1996, pp. 407-413.

Ma, et al., "Hedgehog-Mediated Patterning of the Mammalian Embryo Requires Transporter-like Function of Dispatched", Cell, vol. 111, Oct. 2002, pp. 63-75.

Rubin, et al., "Targeting the Hedgehog pathway in cancer", Nature Reviews Drug Discovery, vol. 5, Dec. 2006, pp. 1026-1033.

Evangelista, et al., "The Hedgehog Signaling Pathway in Cancer", Clin Cancer Res, vol. 12, No. 20, Oct. 2006, pp. 5924-5928.

Pasca di Magliano, "Hedgehog Signalling in Cancer Formation and Maintenance", Nature Reviews Cancer, vol. 3 Dec. 2003, pp. 903-911.

Cohen, Jr., "The Hedgehog Signaling Network", American Journal of Medical Genetics, vol. 123A, 2003, pp. 5-28.

Berman, et al., "Widespread requirement for Hedgehog ligand stimulation in growth of digestive tract tumours", Nature, vol. 425, 2003, pp. 846-851.

Thayer, et al., "Hedgehog is an early and late mediator of pancreatic cancer tumorigenesis", Nature, vol. 425, 2003, pp. 851-856.

Ruiz I Altaba, et al., "The Gli code: an information nexus regulating cell fate, stemness and cancer", Trends in Cell Biology, vol. 17, No. 9, 2007, pp. 438-447.

Dahmane, et al., "The Sonic Hedgehog-Gli pathway regulates dorsal brain growth and tumorigenesis", Development, vol. 128, 2001, pp. 5201-5212.

Williams, et al., "Identification of a small molecule inhibitor of the hedgehog signaling pathway: Effects on basal cell carcinoma-like lesions", Proc. Natl. Acad. Sci., vol. 100, No. 8, Apr. 2003, pp. 4616-4621.

Chen, et al., "Small molecule modulation of Smoothened activity", Proc. Natl. Acad. Sci., vol. 99, No. 22, Oct. 2002, pp. 14071-14076.

Hussain, et al., "Radical Causes of Cancer", Nature Reviews, Cancer, vol. 3, No. 4, pp. 276-285, Apr. 2003.

\* cited by examiner

SEQUENCE LISTING

<160> NUMBER OF SEQ ID NOS: 10

<210> SEQ ID NO 1
<211> LENGTH: 28
<212> TYPE: DNA
<213> ORGANISM: Artificial
<220> FEATURE:
<223> OTHER INFORMATION: PCR primer

<400> SEQUENCE: 1
gaagatctgc cagcccaggc tccggggc                28

<210> SEQ ID NO 2
<211> LENGTH: 29
<212> TYPE: DNA
<213> ORGANISM: Artificial
<220> FEATURE:
<223> OTHER INFORMATION: PCR primer

<400> SEQUENCE: 2
cccaagcttc tgcccgcaca gccctgctc               29

<210> SEQ ID NO 3
<211> LENGTH: 88
<212> TYPE: DNA
<213> ORGANISM: Artificial
<220> FEATURE:
<223> OTHER INFORMATION: synthetic DNA for 8 x Gli-binding site

<400> SEQUENCE: 3
ggggtaccga ccacccagac cacccagacc acccacacca cccagaccac ccagaccacc      60
cagaccaccc agaccaccca agatcttc                                         88

<210> SEQ ID NO 4
<211> LENGTH: 88
<212> TYPE: DNA
<213> ORGANISM: Artificial
<220> FEATURE:

<223> OTHER INFORMATION: synthetic DNA for 8 x Gli-binding site

<400> SEQUENCE: 4
gaagatcttg ggtggtctgg gtggtctggg tggtctgggt ggtctgggtg gtgtgggtgg    60
tctgggtggt ctgggtggtc ggtacccc    88

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
ctgggtgggg atcggagaca    20

<210> SEQ ID NO 6
<211> LENGTH: 24
<212> TYPE: DNA
<213> ORGANISM: Artificial
<220> FEATURE:
<223> OTHER INFORMATION: PCR primer

<400> SEQUENCE: 6
gcgctttccc atcagttcct tatt    24

<210> SEQ ID NO 7
<211> LENGTH: 27
<212> TYPE: DNA
<213> ORGANISM: Artificial
<220> FEATURE:
<223> OTHER INFORMATION: PCR primer

<400> SEQUENCE: 7
ggggtaccat gctgctgctg ctggcca    27

<210> SEQ ID NO 8
<211> LENGTH: 28
<212> TYPE: DNA
<213> ORGANISM: Artificial
<220> FEATURE:
<223> OTHER INFORMATION: PCR primer

<400> SEQUENCE: 8
gctctagatc agctggactt gaccgcca    28

<210> SEQ ID NO 9
<211> LENGTH: 20
<212> TYPE: DNA
<213> ORGANISM: Artificial
<220> FEATURE:
<223> OTHER INFORMATION: PCR primer

<400> SEQUENCE: 9
atgctgctgc tgctggccag    20

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
tcagccgccg gatttggccg    20

FUSED HETEROCYCLIC DERIVATIVE AND USE THEREOF

TECHNICAL FIELD

The present invention relates to a fused heterocyclic derivative and use thereof. More particularly, the present invention relates to a compound having a strong Smo inhibitory activity and useful for the prophylaxis or treatment of cancer and the like, and use thereof.

BACKGROUND OF THE INVENTION

The study of morphogenesis during the developmental stage has been conducted based on the screening of variant using *Drosophila*. Hedgehog gene (hh) was found as one of the genes that cause morphological abnormality of *Drosophila* embryo due to mutation thereof. Hedgehog gene product (Hh) is a secretory protein, which is produced as an about 45 kDa precursor and then divided, due to autolysis, into a 20 kDa N-terminal side domain, which is a main active principle, and a 25 kDa C-terminal side domain. The 20 kDa N-terminal side domain, which is a main active principle, is modified by fatty acid on the N-terminal and cholesterol on the C-terminal thereof. The Hedgehog signal transduction system is formed by the protein group described below. Hh receptor is Patched (Ptch), which is a twelve-transmembrane-type protein. Ptch acts on Smoothened (Smo), which is a seven-transmembrane-type protein, and suppresses the function of Smo in the absence of Hh. When Hh is bound to the receptor Ptch, suppression of Smo is released and Smo is activated. The signal produced by the activation of Smo activates transcription factor Ci, which regulates the expression of the gene group involved in the morphogenesis (non-patent document 1).

A pathway corresponding to the *Drosophila* Hedgehog signal transduction system has been confirmed also in mammals. In human, for example, three types of gene products, sonic hedgehog (Shh), indian hedgehog (Ihh) and deseart hedgehog (Dhh), are known to correspond to *Drosophila* Hh, and undergo post-translational modification as in *Drosophila* Hh (non-patent document 2). In human Shh, a 19 kDa active principle is cleaved out from a 45 kDa precursor protein by autolysis, and fatty acid and cholesterol are added to the N-terminal and C-terminal thereof, respectively (non-patent document 3). Such modification is considered to be essential for the maintenance of Shh activity and, for example, 40 times enhanced activity was achieved by the addition of palmitic acid to *Escherichia coli* recombinant human Shh free of N-terminal modification with fatty acid, and 160 times enhanced activity was achieved by the addition of myristic acid thereto (non-patent document 4). On the other hand, as a human gene corresponding to *Drosophila* Smo, human Smo is known, and as a human gene corresponding to *Drosophila* Ptch, 2 types of Ptch1 and Ptch2 are known. In addition, a transcription factor corresponding to *Drosophila* Ci is considered to be Gli in human, and 3 types of Gli1, Gli2 and Gli3 are known (non-patent document 5). Shh/Ihh/Dhh are each bound to Ptch1 and activate Smo by inhibiting the bond between Ptch1 and Smo. Shh/Ihh/Dhh are also bound to Ptch2, Hip1, Gas1 and Cdo/Boc, besides Ptch1, and regulate the activation of Smo. A signal transduction from Smo induces nuclear localization of Gli1 and Gli2, and activate transcription of Gli1 (non-patent document 6).

The Hedgehog signal is involved in the morphogenesis in the developmental stages also in mammals. In human, for example, patients with Holoprosencephaly, which is a congenital developmental abnormality, showed mutation in Shh (non-patent document 7). Moreover, a natural compound Cyclopamine derived from white hellebore known as a compound inducing Cyclopus in sheep (non-patent document 8) was confirmed to inhibit Smo as action mechanism thereof (non-patent document 9). Furthermore, an Shh knockout mouse was prepared, and its phenotype was found to include Cyclopus, malformation of extremities (non-patent document 10), and neural plate malformation (non-patent document 11).

Hedgehog signal is inherently a developmental signal, which is promoted in tumor tissues and functions as a cancer cell growth and survival signal. Hedgehog signal is considered to function for the growth and survival of cancer cells in an autocrine mode, or function between cancer cells and cancer interstitial cells in a paracrine mode, in tumor tissues (non-patent document 12). In an autocrine mode, it works for the growth and maintenance of cancer cells, via transcription activation by Gli-1, by abnormal cell cycle control due to increased expression of Cyclin D and decreased expression of p21, promotion of proliferation signal by activation of EGFR pathway and the like. On the other hand, in a paracrine mode, since Shh expressed in cancer cells acts on Smo in cancer interstitial cells, growth factors such as insulin-like growth factor-1, fibroblast growth factor, platelet-derived growth factor and the like are transmitted from cancer interstitial cells to cancer cells, and function for the growth and survival of cancer cells. It is also considered that promotion of VEGF, PDGF pathway and the like by Gli-1 promotes tumor angiogenesis (non-patent document 13). As to the mechanism of promotion of Hedgehog signal, a cancer in which Hedgehog signal is promoted due to mutation of Ptch1 and a cancer which is promoted by overexpression of Shh, which is one of the ligands, have been reported (non-patent document 14). As a cancer in which Hedgehog signal is promoted due to mutation, basal cell cancer and medulloblastoma are known, and mutation of Ptch1 observed in these cancers activates Hedgehog signal in a ligand independent manner (non-patent document 15). As a cancer in which Hedgehog signal is promoted by overexpression of Shh, pancreatic cancer (non-patent document 16) and the like have been reported. In a transgenic mouse in which Shh is forcedly expressed in the pancreas, Hedgehog signal is suggested to be involved not only in the growth and maintenance of cancer, but also carcinogenic process, since a PanIN-like lesion in the initial stages of cancer progress was found in the pancreas (non-patent document 17). Furthermore, Hedgehog signal is considered to function for the growth and survival of cancer stem cells, and play a key role in the metastasis or postoperative recurrence of tumor and the like (non-patent document 18).

As the Hedgehog signal inhibitor, the following are known. Cyclopamine, which is a naturally occurring Smo inhibitory compound, has been reported to show a tumor growth suppressive effect on glioma (non-patent document 19) and the like. As a synthetic low-molecular-weight compound inhibiting Smo, CUR-61414 (non-patent document 20) and SANT-1, 2, 3, 4 (non-patent document 21) have been reported. It has been reported with regard to the Hedgehog signal inhibitory antibody that administration of an anti-Shh antibody to a cancer-bearing nude mouse transplanted with colorectal cancer cell line HT-29 resulted in cancer regression (patent document 1).

As a compound similar to the compound described in the present specification, patent document 2 discloses the following compounds having an antibacterial activity.

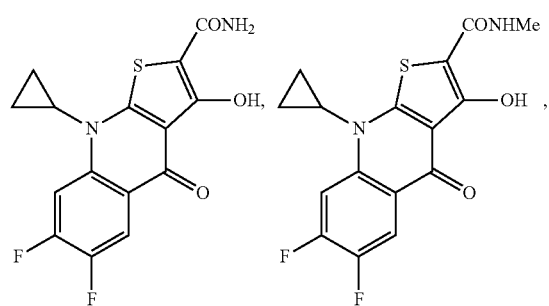
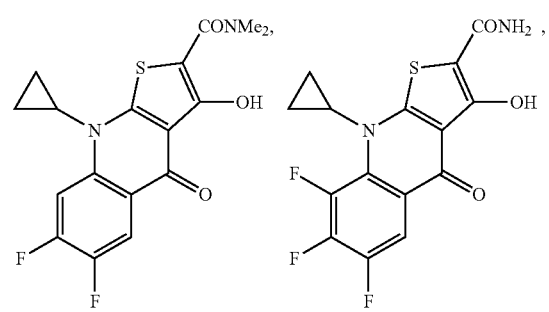
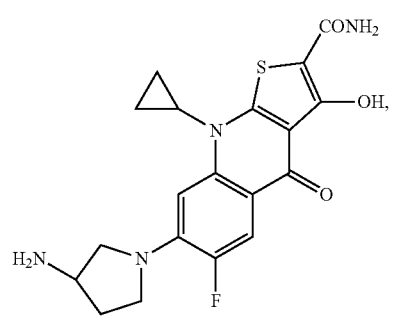
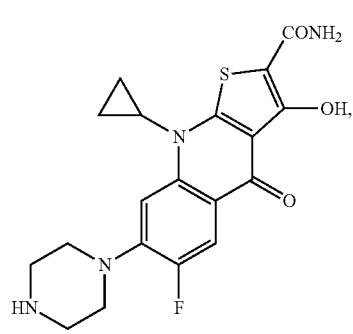
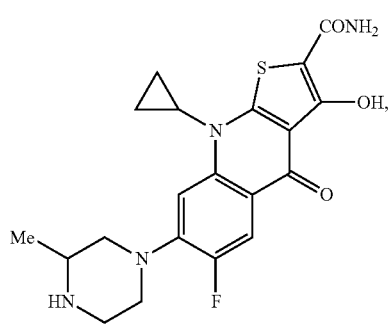
-continued
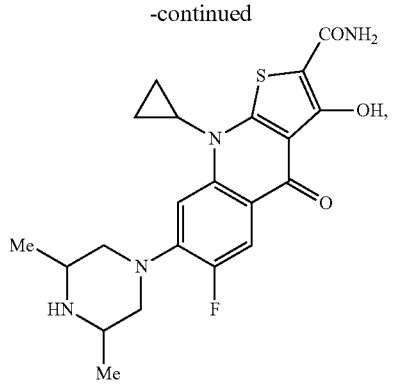
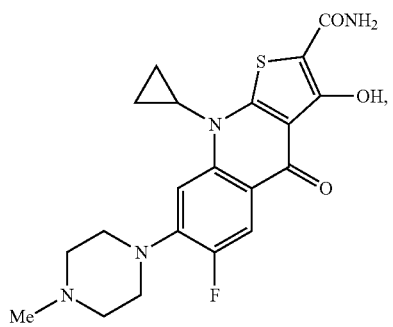
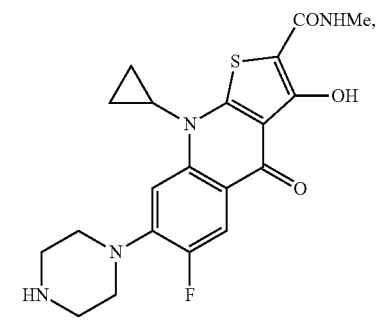
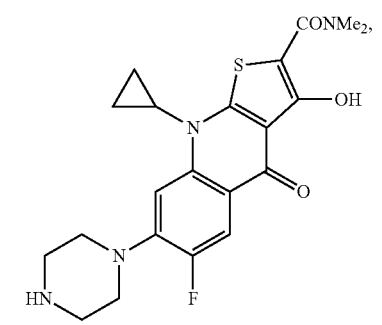
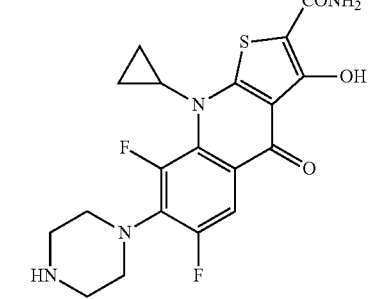

As a compound having an antibacterial activity, patent document 3 discloses the following compounds.

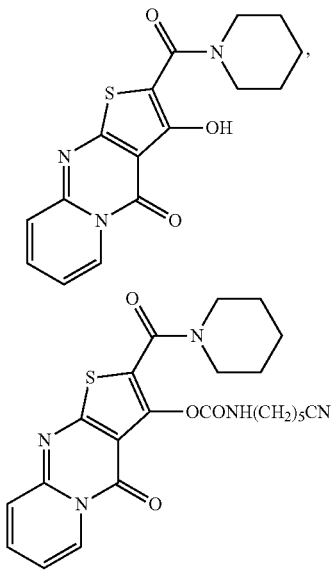

patent document 1: WO2004/020599
patent document 2: JP-A-3-223289
patent document 3: WO93/13664
non-patent document 1: Curr. Opin. Genet. Dev., vol. 12, pages 503-511 (2002)
non-patent document 2: Cell, vol. 103, pages 371-374 (2000)
non-patent document 3: J. Biol. Chem., vol. 273, pages 14037-14045 (1998)
non-patent document 4: Biochemistry, vol. 40, pages 4359-4371 (2001)
non-patent document 5: Nature Rev. Cancer, vol. 2, pages 361-372 (2002)
non-patent document 6: Curr. Opin. Cell Biol., vol. 19, pages 159-165 (2007)
non-patent document 7: Nat. Genet., vol. 14, pages 357-360 (1996)
non-patent document 8: Am. J. Vet. Res., vol. 24, pages 1164-1175 (1963)
non-patent document 9: Development, vol. 125, pages 3553-3562 (1998)
non-patent document 10: Nature, vol. 383, pages 407-413 (1996)
non-patent document 11: Cell, vol. 111, pages 63-75 (2002)
non-patent document 12: Nat. Rev. Drug Discov., vol. 5, pages 1026-1033 (2006)
non-patent document 13: Clin Cancer Res., vol. 12, pages 5924-5928 (2006)
non-patent document 14: Nature Rev. Cancer, vol. 3, pages 903-911 (2003)
non-patent document 15: Am. J. Med. Gen., vol. 123A, pages 5-28 (2003)
non-patent document 16: Nature, vol. 425, pages 846-851 (2003)
non-patent document 17: Nature, vol. 425, pages 851-856 (2003)
non-patent document 18: Trends Cell Biol., vol. 17, pages 438-227 (2007)
non-patent document 19: Development, vol. 128, pages 5201-5212 (2001)
non-patent document 20: Proc. Natl. Acad. Sci. U.S.A., vol. 100, pages 4616-4621 (2003)
non-patent document 21: Proc. Natl. Acad. Sci. U.S.A., vol. 99, pages 14071-14076 (2002)

DISCLOSURE OF THE INVENTION

Problems to be Solved by the Invention

An object of the present invention is to provide a compound having a superior Smo inhibitory activity, low toxicity and sufficiently satisfactory as a pharmaceutical product.
The present inventors have conducted intensive studies in an attempt to solve the above-mentioned problems and found that a compound represented by the following formula and a salt thereof have a superior Smo inhibitory activity, which resulted in the completion of the present invention.
Accordingly, the present invention provides the following.
[1] A compound represented by the formula

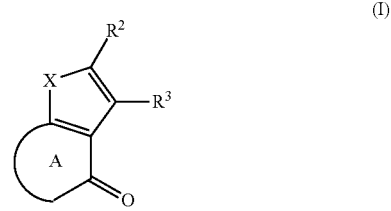

wherein
ring A is a 5- to 7-membered ring optionally having substituent(s), where substituents are optionally bonded to each other to form a ring;
X is O, S or NR$^1$ (R$^1$ is a hydrogen atom or a hydrocarbon group optionally having substituent(s));
R$^2$ is carbamoyl optionally having substituent(s); and
R$^3$ is hydroxy optionally having substituent(s), except the following compounds;

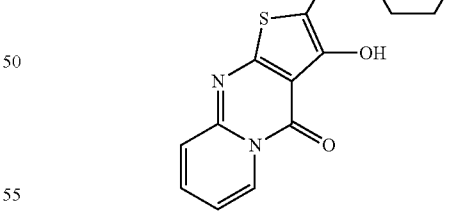

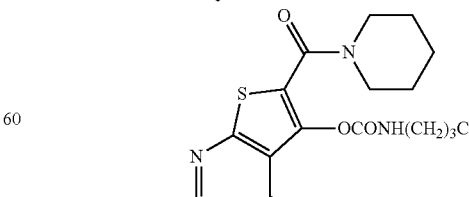

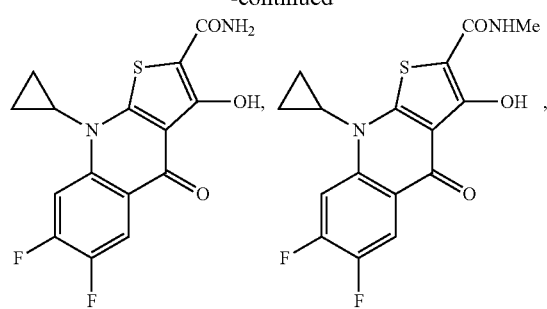
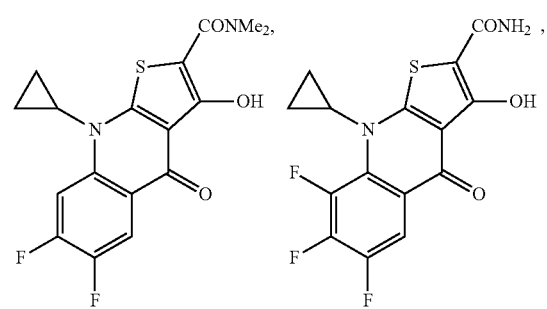
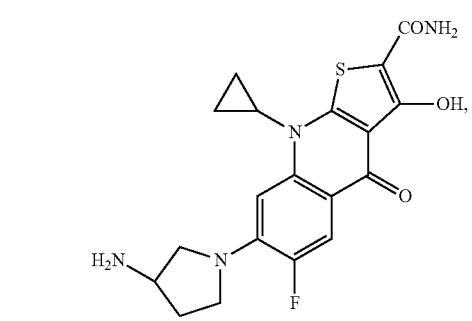
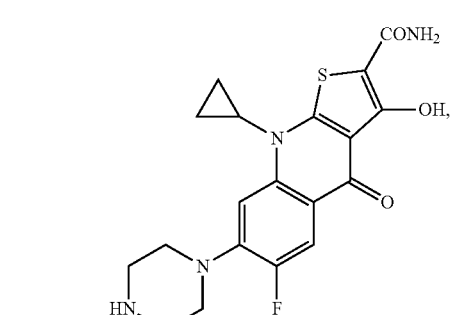
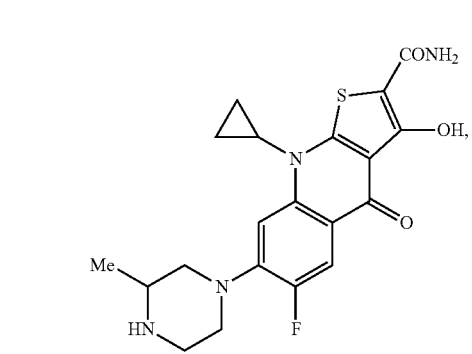
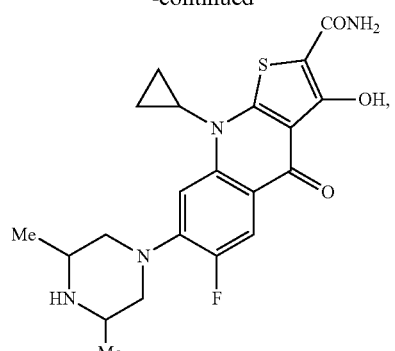
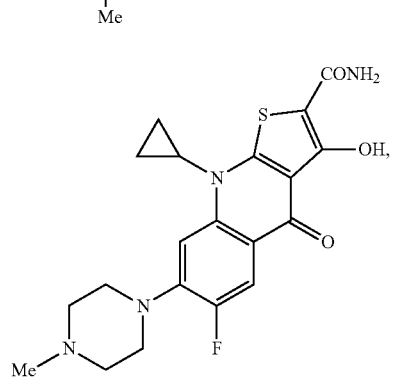
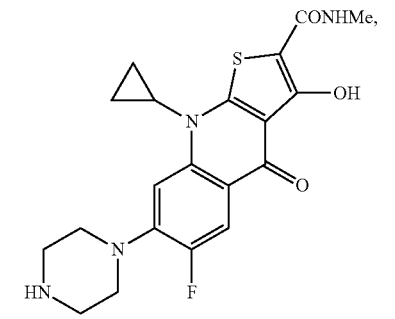
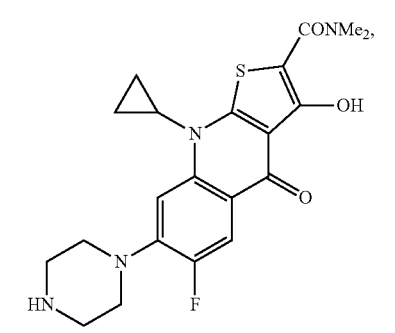
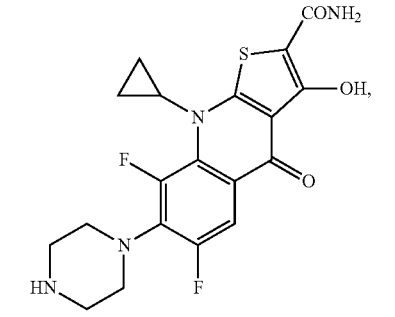

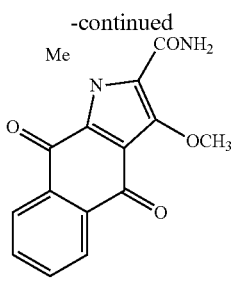

(hereinafter sometimes to be abbreviated as compound (1)) or a salt thereof.

[2] The compound of the above-mentioned [1], which is represented by the formula

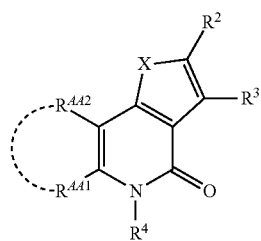

(I''')

wherein
X, $R^2$ and $R^3$ are as defined in the above-mentioned [1],
$R^{AA1}$ and $R^{AA2}$ are the same or different and each is a hydrogen atom or a substituent, or $R^{AA1}$ and $R^{AA2}$ are optionally bonded to each other to form a 5- to 7-membered ring optionally having substituent(s), and
$R^4$ is a hydrogen atom or a hydrocarbon group optionally having substituent(s)
(hereinafter sometimes to be abbreviated as compound (I''')).

[3] The compound of the above-mentioned [2], which is represented by the formula

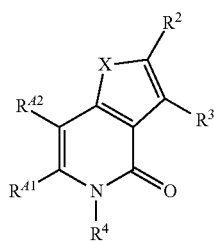

(I'')

wherein
X, $R^2$ and $R^3$ are as defined in the above-mentioned [1],
$R^{A1}$ and $R^{A2}$ are the same or different and each is a hydrogen atom or a substituent, and
$R^4$ is a hydrogen atom or a hydrocarbon group optionally having substituent(s)
(hereinafter sometimes to be abbreviated as compound (I'')).

[4] The compound of the above-mentioned [3], wherein X is O, S or N($C_{1-6}$ alkyl),
$R^2$ is carbamoyl optionally having substituent(s),
$R^3$ is hydroxy optionally having $C_{1-6}$ alkyl optionally having substituent(s),
$R^{A1}$ is a hydrogen atom or a $C_{1-6}$ alkyl group,
$R^{A2}$ is a hydrogen atom or a $C_{1-6}$ alkyl group, and $R^4$ is a hydrogen atom or $C_{1-6}$ alkyl optionally having substituent(s).

[5] The compound of the above-mentioned [1], which is represented by the formula

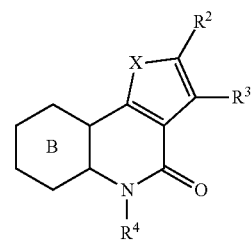

(I')

wherein
X, $R^2$ and $R^3$ are as defined in the above-mentioned [1],
ring B is a 6-membered ring optionally having substituent(s); and
$R^4$ is a hydrogen atom or a hydrocarbon group optionally having substituent(s)
(hereinafter sometimes to be abbreviated as compound (I')).

[6] The compound of the above-mentioned [5], wherein ring B is a 6-membered ring optionally having substituent(s),
X is O, S or N($C_{1-6}$ alkyl),
$R^2$ is carbamoyl optionally having substituent(s),
$R^3$ is hydroxy optionally having $C_{1-6}$ alkyl optionally having substituent(s), and
$R^4$ is a hydrogen atom or $C_{1-6}$ alkyl optionally having substituent(s).

[7] N-[1-(2-Hydroxyethyl)piperidin-4-yl]-3-methoxy-1-methyl-4-oxo-5-(2-oxo-2-phenylethyl)-4,5-dihydro-1H-pyrrolo[3,2-c]quinoline-2-carboxamide or a salt thereof.

[8] N-[1-(Hydroxyacetyl)piperidin-4-yl]-3-methoxy-1-methyl-4-oxo-5-(2-oxo-2-phenylethyl)-4,5-dihydro-1H-pyrrolo[3,2-c]quinoline-2-carboxamide or a salt thereof.

[9] 3-Ethoxy-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof.

[10] N-[1-(Hydroxyacetyl)piperidin-4-yl]-1,6-dimethyl-4-oxo-5-(2-oxo-2-phenylethyl)-3-(2,2,2-trifluoroethoxy)-4,5-dihydro-1H-pyrrolo[3,2-c]pyridine-2-carboxamide or a salt thereof.

[11] 6-Ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide or a salt thereof.

[12] A prodrug of the compound of the above-mentioned [1].

[13] A pharmaceutical agent comprising the compound of the above-mentioned [1] or a prodrug thereof.

[14] The pharmaceutical agent of the above-mentioned [13], which is an Smo inhibitor.

[15] The pharmaceutical agent of the above-mentioned [13], which is an agent for the prophylaxis or treatment of cancer.

[16] A method of inhibiting Smo in a mammal, which comprises administering an effective amount of the compound of the above-mentioned [1] or a prodrug thereof to the mammal.

[17] A method for the prophylaxis or treatment of cancer in a mammal, which comprises administering an effective amount of the compound of the above-mentioned [1] or a prodrug thereof to the mammal.

[18] Use of the compound of the above-mentioned [1] or a prodrug thereof for the production of an Smo inhibitor.

[19] Use of the compound of the above-mentioned [1] or a prodrug thereof for the production of an agent for the prophylaxis or treatment of cancer.

In the present specification, compound (I) encompasses compound (I'), compound (I'') and compound (I''').

Effect of the Invention

Since the compound of the present invention has a strong Smo inhibitory action, it can provide a clinically useful agent for the prophylaxis or treatment of cancer, a cancer growth inhibitor and a cancer metastasis suppressive agent.

DETAILED DESCRIPTION OF THE INVENTION

The present invention is explained in detail in the following.

In compound (I), X is O, S or $NR^1$ ($R^1$ is a hydrogen atom or a hydrocarbon group optionally having substituent(s)).

Examples of the "hydrocarbon group optionally having substituent(s)" for $R^1$ include alkyl optionally having substituent(s), alkenyl optionally having substituent(s), alkynyl optionally having substituent(s), cycloalkyl optionally having substituent(s), aryl optionally having substituent(s) and the like.

Examples of the "alkyl" of the above-mentioned "alkyl optionally having substituent(s)" include $C_{1-6}$ alkyl (e.g., methyl, ethyl, propyl, isopropyl, butyl, isobutyl, sec-butyl, tert-butyl, pentyl, hexyl) and the like.

Examples of the substituent that the above-mentioned "alkyl optionally having substituent(s)" may have include the following "substituent group A" and the like, and 1 to 5 (preferably 1 to 3) substituents may be present at substitutable position(s):
(substituent group A)
(1) halogen atom (e.g., fluorine atom, chlorine atom, bromine atom, iodine atom),
(2) cyano,
(3) $C_{1-6}$ alkyl (e.g., methyl, ethyl, propyl, isopropyl, butyl, isobutyl, sec-butyl, tert-butyl, pentyl, hexyl) optionally having 1 to 3 substituents selected from
    (1') $C_{6-10}$ aryl (e.g., phenyl, naphthyl),
    (2') amino,
    (3') $C_{1-6}$ alkoxy-carbonylamino (e.g., methoxycarbonylamino, ethoxycarbonylamino, propoxycarbonylamino),
    (4') hydroxy,
    (5') $C_{1-6}$ alkoxy (e.g., methoxy, ethoxy, propoxy), and
    (6') heterocyclic group (e.g., pyrrolidinyl, benzodioxolyl),
(4) $C_{2-6}$ alkenyl (e.g., vinyl, allyl),
(5) $C_{2-6}$ alkynyl (e.g., ethynyl, propargyl),
(6) $C_{3-6}$ cycloalkyl (e.g., cyclopropyl, cyclobutyl, cyclopentyl, cyclohexyl) optionally having one hydroxy,
(7) $C_{6-10}$ aryl (e.g., phenyl, naphthyl) optionally having 1 to 3 substituents selected from
    (a) halogen atom (e.g., fluorine atom, chlorine atom),
    (b) hydroxy,
    (c) cyano,
    (d) $C_{1-6}$ alkyl-sulfonyl (e.g., methylsulfonyl), and
    (e) $C_{1-6}$ alkoxy (e.g., methoxy, ethoxy, propoxy) optionally having 1 to 3 halogen atoms (e.g., fluorine atom),
(8) $C_{1-6}$ alkyl-carbonyl (e.g., acetyl, ethylcarbonyl, propylcarbonyl, butylcarbonyl) optionally having 1 to 3 substituents selected from
    (1') hydroxy,
    (2') $C_{1-6}$ alkoxy (e.g., methoxy, ethoxy),
    (3') amino,
    (4') $C_{1-6}$ alkylamino (e.g., methylamino, ethylamino, propylamino, isopropylamino),
    (5') $C_{1-6}$ alkyl-sulfonyl (e.g., methylsulfonyl), and
    (6') $C_{1-6}$ alkyl-carbonyloxy (e.g., methylcarbonyloxy),
(9) $C_{6-10}$ aryl-carbonyl (e.g., benzoyl, naphthoyl) optionally having 1 to 3 substituents selected from
    (a) halogen atom (e.g., chlorine atom), and
    (b) $C_{1-6}$ alkoxy (e.g., methoxy),
(10) carbamoyl,
(11) $C_{1-6}$ alkyl-carbamoyl (e.g., methylcarbamoyl, ethylcarbamoyl) optionally having one hydroxy,
(12) di-$C_{1-6}$ alkyl-carbamoyl (e.g., dimethylcarbamoyl, diethylcarbamoyl),
(13) $C_{6-10}$ aryl-carbamoyl (e.g., phenylcarbamoyl, naphthylcarbamoyl),
(14) 5- to 7-membered cyclic carbamoyl (e.g., 1-pyrrolidinylcarbonyl, 1-piperidylcarbonyl, 1-piperazinylcarbonyl, 4-morpholinylcarbonyl, 4-thiomorpholinylcarbonyl, 1-homopiperazinylcarbonyl),
(15) carboxyl,
(16) $C_{1-6}$ alkoxy-carbonyl (e.g., methoxycarbonyl, ethoxycarbonyl, butoxycarbonyl),
(17) $C_{6-10}$ aryloxy-carbonyl (e.g., phenoxycarbonyl),
(18) amino optionally having 1 or 2 substituents selected from
    (a) $C_{1-6}$ alkoxy-carbonyl (e.g., tert-butoxycarbonyl), and
    (b) $C_{1-6}$ alkyl-carbonyl (e.g., methylcarbonyl) optionally having one hydroxy or $C_{1-6}$ alkyl-carbonyloxy (e.g., methylcarbonyloxy),
(19) $C_{1-6}$ alkylamino (e.g., methylamino, ethylamino, propylamino, isopropylamino, butylamino),
(20) di-$C_{1-6}$ alkylamino (e.g., dimethylamino, diethylamino, dipropylamino) optionally having one hydroxy,
(21) $C_{1-6}$ alkyl-carbonylamino (e.g., acetylamino, ethylcarbonylamino) optionally having 1 to 3 substituents selected from
    (a) $C_{1-6}$ alkyl-carbonyl-oxy (e.g., methylcarbonyloxy),
    (b) $C_{1-6}$ alkoxy (e.g., methoxy), and
    (c) hydroxy,
(22) di-($C_{1-6}$ alkyl-carbonyl)amino (e.g., di-(acetyl)amino, di-(ethylcarbonyl)amino, di-(propylcarbonyl)amino),
(23) $C_{1-6}$ alkoxy-carbonylamino (e.g., methoxycarbonylamino, ethoxycarbonylamino, propoxycarbonylamino, tert-butoxycarbonylamino),
(24) N—$C_{1-6}$ alkyl-N—($C_{1-6}$ alkyl-carbonyl)amino (e.g., N-acetyl-N-methylamino, N-acetyl-N-ethylamino),
(25) ureido,
(26) $C_{1-6}$ alkyl-ureido (e.g., methylureido, ethylureido),
(27) hydroxy,
(28) $C_{1-6}$ alkoxy (e.g., methoxy, ethoxy, propoxy, isopropoxy, butoxy, isobutoxy, sec-butoxy, tert-butoxy) optionally having 1 to 3 $C_{6-10}$ aryl (e.g., phenyl),
(29) $C_{6-10}$ aryloxy (e.g., phenoxy, naphthoxy),
(30) heterocyclic group (e.g., 5- or 6-membered aromatic heterocyclic group such as 1-pyrrolyl, 2-pyridyl, 3-pyridyl, 4-pyridyl, 1-pyrazolyl, 1-imidazolyl, 2-imidazolyl, 2-pyrazinyl, 2-furyl, 2-thiazolyl, 4-pyrimidinyl and the like; 3- to 8-membered nonaromatic heterocyclic group such as 3-azetidinyl, 1-pyrrolidinyl, 2-pyrrolidinyl, 3-pyrrolidinyl, 1-piperidyl, 2-piperidyl, 3-piperidyl, 4-piperidyl, 1-piperazinyl, 1-morpholinyl, morpholino, 2-tetrahydrofuryl, tetrahydrothiopyran-4-yl, tetrahydropyran-4-yl, 3-azepanyl, 4-azepanyl and the like; a group obtained by fusing a nonaromatic heterocyclic group such as 1,3-benzodioxol-5-yl and the like and a benzene ring) optionally having 1 to 3 (preferably 1 or 2) substituents selected from
    (1') $C_{1-6}$ alkyl (e.g., methyl, ethyl, propyl) optionally having 1 to 3 substituents selected from (a) halogen atom (e.g., fluorine atom), and
(b) hydroxy,
(2') hydroxy,
(3') oxo,
(4') cyano,
(5') carbamoyl,
(6') $C_{1-6}$ alkoxy (e.g., methoxy),
(7') $C_{1-6}$ alkyl-carbamoyl (e.g., methylcarbamoyl),
(8') $C_{1-6}$ alkoxy-carbonyl (e.g., tert-butoxycarbonyl), and
(9') $C_{1-6}$ alkyl-carbonyl (e.g., acetyl, propionyl) optionally having 1 to 3 substituents selected from
(a) hydroxy,
(b) $C_{1-6}$ alkoxy (e.g., methoxy, ethoxy, propoxy),
(c) amino,
(d) $C_{1-6}$ alkylamino (e.g., methylamino, ethylamino, propylamino, isopropylamino),
(e) di-$C_{1-6}$ alkylamino (e.g., dimethylamino), and
(f) $C_{1-6}$ alkyl-carbonyloxy (e.g., methylcarbonyloxy),
(31) oxo,
(32) thioxo,
(33) $C_{1-6}$ alkyl-sulfonyl (e.g., methylsulfonyl),
(34) heterocyclyl-carbonyl (e.g., pyrrolidinylcarbonyl, tetrahydrofurylcarbonyl).

Examples of the "alkenyl" of the above-mentioned "alkenyl optionally having substituent(s)" include $C_{2-6}$ alkenyl (e.g., vinyl, allyl) and the like.

Examples of the substituent of the above-mentioned "alkenyl optionally having substituent(s)" include the above-mentioned substituent group A and the like, and 1 to 5 (preferably 1 to 3) substituents may be present at substitutable position(s).

Examples of the "alkynyl" of the above-mentioned "alkynyl optionally having substituent(s)" include $C_{2-6}$ alkynyl (e.g., ethynyl, propargyl) and the like.

Examples of the substituent that the above-mentioned "alkynyl optionally having substituent(s)" may have include the above-mentioned substituent group A and the like, and 1 to 5 (preferably 1 to 3) substituents may be present at substitutable position(s).

Examples of the "cycloalkyl" of the above-mentioned "cycloalkyl optionally having substituent(s)" include $C_{3-6}$ cycloalkyl (e.g., cyclopropyl, cyclobutyl, cyclopentyl, cyclohexyl) and the like.

Examples of the substituent that the above-mentioned "cycloalkyl optionally having substituent(s)" may have include
(1) the above-mentioned substituent group A,
(2) $C_{1-6}$ alkyl optionally having 1 to 3 substituents selected from the above-mentioned substituent group A and the like, and 1 to 5 (preferably 1 to 3) substituents may be present at substitutable position(s).

Moreover, the "cycloalkyl optionally having substituent(s)" may be a group obtained by fusing $C_{3-6}$ cycloalkyl and a benzene ring (e.g., 1,2,3,4-tetrahydronaphthalen-1-yl).

Examples of the "aryl" of the above-mentioned "aryl optionally having substituent(s)" include $C_{6-10}$ aryl (e.g., phenyl, naphthyl) and the like.

Examples of the substituent that the above-mentioned "aryl optionally having substituent(s)" may have include
(1) the above-mentioned substituent group A (except oxo and thioxo),
(2) $C_{1-6}$ alkyl optionally having 1 to 3 substituents selected from the above-mentioned substituent group A and the like, and 1 to 5 (preferably 1 to 3) substituents may be present at substitutable position(s).

X is preferably O, S or $NR^{1'}$ ($R^{1'}$ is alkyl optionally having substituent(s)), and particularly preferably O, S or $N(C_{1-6}$ alkyl) (particularly, N(methyl)).

$R^2$ is carbamoyl optionally having substituent(s). Examples of the "carbamoyl optionally having substituent(s)" for $R^2$ include
(1) carbamoyl optionally having 1 or 2 substituent(s) selected from "hydrocarbon group optionally having substituent(s)" and "heterocyclic group optionally having substituent(s)",
(2) cyclic carbamoyl optionally having substituent(s) and the like.

Examples of the above-mentioned "hydrocarbon group optionally having substituent(s)" include those similar to the aforementioned "hydrocarbon group optionally having substituent(s)" for $R^1$.

Examples of the "heterocyclic group" of the above-mentioned "heterocyclic group optionally having substituent(s)", and the "heterocyclic group" recited as an example of the substituent that the above-mentioned "alkyl optionally having substituent(s)" may have and the like include aromatic heterocyclic group and saturated or unsaturated nonaromatic heterocyclic group (aliphatic heterocyclic group), each containing, as a ring system-constituting atom (ring atom), 1 to 3 kinds (preferably 1 or 2 kinds) of at least one (preferably 1 to 4, more preferably 1 or 2) hetero atom selected from oxygen atom, sulfur atom (the sulfur atom may be oxidized) and nitrogen atom, and a group having a bond at carbon atom and the like are used.

Examples of the "aromatic heterocyclic group" include
(1) 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, and
(2) 8- to 12-membered condensed polycyclic aromatic heterocyclic group such as benzofuranyl, isobenzofuranyl, benzo[b]thienyl, indolyl, isoindolyl, 1H-indazolyl, benzimidazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like, and the like.

Examples of the "nonaromatic heterocyclic group" include
(1) 3- to 8-membered (preferably 5- or 6-membered) saturated or unsaturated (preferably saturated) nonaromatic heterocyclic group (aliphatic heterocyclic group) such as oxiranyl, azepanyl, azetidinyl, oxetanyl, thietanyl, pyrrolidinyl, tetrahydrofuryl, thioranyl, piperidyl, tetrahydropyranyl, tetrahydrothiopyranyl, morpholinyl, thiomorpholinyl, piperazinyl and the like,
(2) nonaromatic heterocyclic group wherein the double bond in the above-mentioned monocyclic aromatic heterocyclic group or condensed polycyclic aromatic heterocyclic group is partly or entirely saturated, such as 1,2,3,4-tetrahydroquinolyl, 1,2,3,4-tetrahydroisoquinolyl and the like, and
(3) a group wherein nonaromatic heterocyclic group such as benzodioxolyl and the like and benzene ring are fused and the like.

Examples of the "substituent" of the above-mentioned "heterocyclic group optionally having substituent(s)" include
(1) the above-mentioned substituent group A,
(2) those similar to the above-mentioned "hydrocarbon group optionally having substituent(s)" (preferably $C_{1-6}$ alkyl optionally having 1 to 3 substituents selected from the above-mentioned substituent group A)
and the like, and substituents in a substitutable number may be present at substitutable position(s).

As cyclic carbamoyl of the "cyclic carbamoyl optionally having substituent(s)", 5- to 7-membered cyclic carbamoyl is used, and examples thereof include pyrrolidin-1-ylcarbonyl, piperidin-1-ylcarbonyl, piperazin-1-ylcarbonyl, morpholin-4-ylcarbonyl, thiomorpholin-4-ylcarbonyl, homopiperazin-1-ylcarbonyl and the like.

Examples of the "substituent" of the "cyclic carbamoyl optionally having substituent(s)" include the above-mentioned substituent group A and the like, and 1 to 3 substituents may be present at substitutable position(s).

In addition, the substituents of the cyclic carbamoyl optionally having substituent(s) may be bonded to each other to form a 5- to 7-membered ring. In other words, the 5- to 7-membered ring and cyclic carbamoyl may form a fused ring system. The fused ring system includes a spiro fused ring system.

Examples of the 5- to 7-membered ring include
(1) 5- to 7-membered homocyclic ring (e.g., cyclohexane, cyclohexene, cyclohexanediene, cycloheptane, benzene), and
(2) 5- to 7-membered heterocycle (e.g., piperidine, piperazine, morpholine, thiomorpholine, pyridine, pyrazine, pyrimidine, pyridazine, triazine, pyran, dihydropyran, tetrahydropyran, 1,3-dioxole). Among these, cyclohexane ring, benzene ring and 1,3-dioxole ring are preferable.

As $R^2$,
(A) carbamoyl optionally having 1 or 2 substituents selected from
(1) $C_{1-6}$ alkyl optionally having 1 or 2 (preferably 1) substituents selected from
    (1') halogen atom,
    (2') cyano,
    (3') amino,
    (4') $C_{1-6}$ alkylamino,
    (5') di-$C_{1-6}$ alkylamino optionally having one hydroxy,
    (6') $C_{1-6}$ alkoxy-carbonylamino,
    (7') hydroxy,
    (8') di-$C_{1-6}$ alkyl-carbamoyl,
    (9') 5- to 7-membered cyclic carbamoyl,
    (10') heterocyclic group optionally having 1 to 3 (preferably 1) substituents selected from
        (a) hydroxy,
        (b) $C_{1-6}$ alkyl optionally having one hydroxy,
        (c) oxo,
        (d) $C_{1-6}$ alkoxy-carbonyl, and
        (e) $C_{1-6}$ alkyl-carbonyl optionally having 1 to 3 (preferably 1) substituents selected from $C_{1-6}$ alkyl-carbonyloxy and hydroxy,
    (11') $C_{1-6}$ alkoxy-carbonyl,
    (12') $C_{3-6}$ cycloalkyl optionally having one hydroxy,
    (13') $C_{1-6}$ alkoxy,
    (14') $C_{2-6}$ alkynyl,
    (15') $C_{6-10}$ aryl optionally having 1 to 3 (preferably 1 or 2) $C_{1-6}$ alkoxy,
    (16') carbamoyl, and
    (17') $C_{1-6}$ alkyl-carbonyl-amino optionally having 1 to 3 (preferably 1) substituents selected from
        (a) $C_{1-6}$ alkyl-carbonyloxy,
        (b) $C_{1-6}$ alkoxy, and
        (c) hydroxy,
(2) $C_{3-6}$ cycloalkyl or 1,2,3,4-tetrahydronaphthalenyl optionally having 1 or 2 substituents selected from
    (1') amino optionally having one substituent selected from
        (a) $C_{1-6}$ alkoxy-carbonyl, and
        (b) $C_{1-6}$ alkyl-carbonyl optionally having 1 to 3 (preferably 1) substituents selected from hydroxy and $C_{1-6}$ alkyl-carbonyloxy,
    (2') hydroxy,
    (3') carboxy,
    (4') $C_{1-6}$ alkoxy-carbonyl,
    (5') $C_{1-6}$ alkyl-carbamoyl optionally having one hydroxy,
    (6') $C_{1-6}$ alkyl optionally having one hydroxy, and
    (7') $C_{1-6}$ alkoxy-carbonylamino (e.g., tert-butoxycarbonylamino),
(3) $C_{6-10}$ aryl, and
(4) heterocyclic group optionally having 1 to 4 (preferably 1) substituents selected from
    (1') $C_{1-6}$ alkyl optionally having 1 to 5 substituents selected from
        (a) $C_{6-10}$ aryl,
        (b) hydroxy, and
        (c) halogen atom,
    (2') $C_{1-6}$ alkyl-carbonyl optionally having 1 to 3 (preferably 1) substituents selected from
        (a) $C_{1-6}$ alkyl-carbonyloxy,
        (b) hydroxy,
        (c) $C_{1-6}$ alkoxy,
        (d) $C_{1-6}$ alkyl-sulfonyl, and
        (e) amino,
    (3') $C_{1-6}$ alkoxy-carbonyl, and
    (4') 5- or 6-membered aromatic heterocyclic group optionally having 1 to 3 (preferably 1) substituents selected from
        (a) $C_{1-6}$ alkyl optionally having 1 to 3 halogen atoms,
        (b) cyano,
        (c) carbamoyl,
        (d) $C_{1-6}$ alkoxy, and
        (e) $C_{1-6}$ alkyl-carbamoyl,
    (5') oxo,
    (6') $C_{1-6}$ alkyl-carbamoyl,
    (7') $C_{1-6}$ alkyl-sulfonyl,
    (8') $C_{6-10}$ aryl optionally having 1 to 3 (preferably 1) substituents selected from
        (a) hydroxy,
        (b) cyano, and
        (c) $C_{1-6}$ alkyl-sulfonyl,
    (9') heterocyclyl-carbonyl, and
    (10') $C_{6-10}$ aryloxy-carbonyl (e.g., phenoxycarbonyl),
(B) 5- to 7-membered cyclic carbamoyl optionally having 1 to 3 (preferably 1) substituents selected from
(1) $C_{1-6}$ alkyl optionally having 1 to 3 (preferably 1) substituents selected from
    (a) heterocyclic group,
    (b) amino,
    (c) $C_{1-6}$ alkoxy, and
    (d) $C_{6-10}$ aryl,
(2) amino optionally having one $C_{1-6}$ alkyl-carbonyl,
(3) N—$C_{1-6}$ alkyl-N—($C_{1-6}$ alkyl-carbonyl)amino,
(4) heterocyclic group,
(5) $C_{1-6}$ alkyl-carbonyl optionally having one substituent selected from
    (a) hydroxy,
    (b) $C_{1-6}$ alkoxy,
    (c) amino,
    (d) $C_{1-6}$ alkylamino,
    (e) di-$C_{1-6}$ alkylamino, and
    (f) $C_{1-6}$ alkyl-carbonyloxy, (6) C$_{6-10}$ aryl, and
(7) oxo, or
(C) 5- to 7-membered cyclic carbamoyl fused with 5- to 7-membered ring is preferable.

R$^3$ is hydroxy optionally having substituent(s). As the "substituent" of the "hydroxy optionally having substituent(s)" for R$^3$, the aforementioned "hydrocarbon group optionally having substituent(s)" for R$^1$, the aforementioned "heterocyclic group optionally having substituent(s)" and the like can be mentioned.

As R$^3$, hydroxy optionally having alkyl optionally having substituent(s) is preferable, hydroxy optionally having
(1) C$_{1-6}$ alkyl optionally having one C$_{1-6}$ alkoxy,
(2) C$_{1-6}$ alkyl optionally having 1 to 5 (preferably 1 to 3) halogen atoms,
(3) C$_{1-6}$ alkyl optionally having one C$_{6-10}$ aryl, or
(4) C$_{1-6}$ alkyl optionally having one heterocyclic group is more preferable, and
hydroxy substituted by
(1) C$_{1-6}$ alkyl optionally having one C$_{1-6}$ alkoxy,
(2) C$_{1-6}$ alkyl optionally having 1 to 5 (preferably 1 to 3) halogen atoms,
(3) C$_{1-6}$ alkyl optionally having one C$_{6-10}$ aryl, or
(4) C$_{1-6}$ alkyl optionally having one heterocyclic group is still more preferable.

Ring A is a 5- to 7-membered ring optionally having substituent(s). As the "5- to 7-membered ring" of the "5- to 7-membered ring optionally having substituent(s)" for ring A,
(1) 5- to 7-membered homocyclic ring (e.g., cyclohexane, cyclohexene, cyclohexanediene, cycloheptane, benzene), and
(2) 5- to 7-membered heterocycle (e.g., piperidine, piperazine, morpholine, thiomorpholine, pyridine, pyrazine, pyrimidine, pyridazine, triazine, pyran, dihydropyran, tetrahydropyran, 1,3-dioxole)
can be mentioned.

Examples of the "substituent" that the "5- to 7-membered ring" of the "5- to 7-membered ring optionally having substituent(s)" for ring A may have include
(1) the above-mentioned substituent group A,
(2) those similar to the above-mentioned "hydrocarbon group optionally having substituent(s)" (preferably, C$_{1-6}$ alkyl optionally having 1 to 3 substituents selected from the above-mentioned substituent group A)
and the like, and substituents in a substitutable number may be present at substitutable position(s).

In addition, as to the "substituent" that the "5- to 7-membered ring" of the "5- to 7-membered ring optionally having substituent(s)" for ring A may have, two substituents are optionally bonded to each other to form a ring. As the ring formed by such "substituents" bonded to each other,
(1) 5- to 7-membered homocyclic ring (e.g., cyclohexane, cyclohexene, cyclohexanediene, cycloheptane, benzene), and
(2) 5- to 7-membered heterocycle (e.g., piperidine, piperazine, morpholine, thiomorpholine, pyridine, pyrazine, pyrimidine, pyridazine, triazine, pyran, dihydropyran, tetrahydropyran, 1,3-dioxole)
can be mentioned.

The ring formed by the substituents of ring A, which are bonded to each other, may have substituent(s) and examples of the substituent include
(1) the above-mentioned substituent group A,
(2) those similar to the above-mentioned "hydrocarbon group optionally having substituent(s)" (preferably C$_{1-6}$ alkyl optionally having 1 to 3 substituents selected from the above-mentioned substituent group A)
and the like, and substituents in a substitutable number may be present at substitutable position(s).

Compound (I) specifically has a structure represented by the following formula.

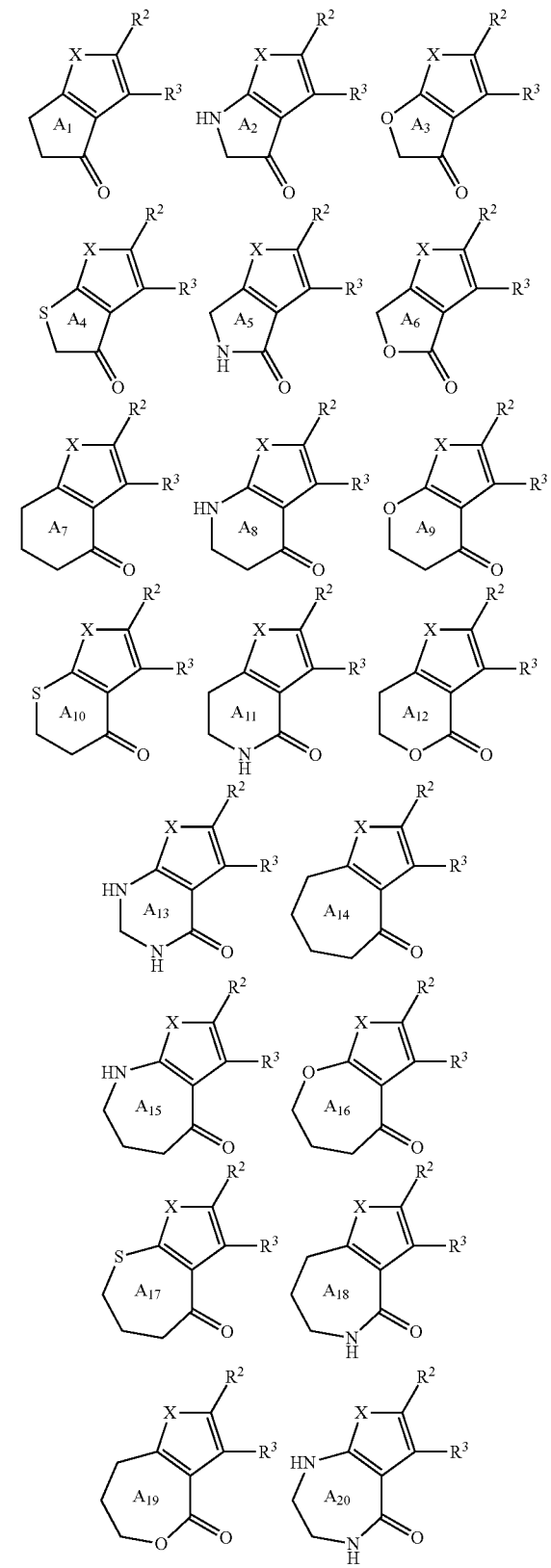

wherein ring $A_1$-ring $A_{20}$ optionally further have substituent(s), the substituents are optionally bonded to each other to form a ring, —CH$_2$—CH$_2$— part constituting the ring in ring $A_1$, ring $A_7$, ring $A_8$, ring $A_9$, ring $A_{10}$, ring $A_{11}$, ring $A_{12}$, ring $A_{14}$, ring $A_{15}$, ring $A_{16}$, ring $A_{17}$, ring $A_{18}$, ring $A_{19}$ and ring $A_{20}$ is optionally converted to —CH=CH—, —NH—CH$_2$— part constituting the ring in ring $A_2$, ring $A_5$, ring $A_8$, ring $A_{11}$, ring $A_{13}$, ring $A_{15}$, ring $A_{18}$ and ring $A_{20}$ is optionally converted to —N=CH—, and other symbols are as defined above.

As the substituent that ring $A_1$-ring $A_{20}$ may have, those similar to the "substituent" that the "5- to 7-membered ring" of the "5- to 7-membered ring optionally having substituent(s)" for ring A may have can be mentioned.

As compound (I), a compound represented by the formula

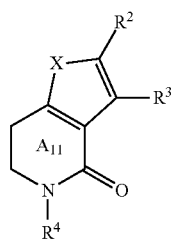

wherein each symbol is as defined above, is preferable.

Of the above-mentioned compounds, compound (I''') represented by the formula

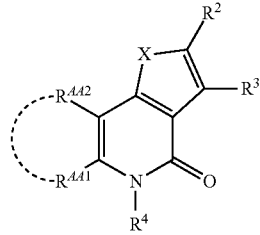

(I''')

wherein X, $R^2$ and $R^3$ are as defined above, $R^{AA1}$ and $R^{AA2}$ are the same or different and each is a hydrogen atom or a substituent, or $R^{AA1}$ and $R^{AA2}$ are optionally bonded to each other to form a 5- to 7-membered ring optionally having substituent(s), and $R^4$ is a hydrogen atom or a hydrocarbon group optionally having substituent(s), is preferable.

Compound (I''') is explained in detail in the following.

X, $R^2$ and $R^3$ are as defined above.

$R^4$ is a hydrogen atom or a hydrocarbon group optionally having substituent(s). As the "hydrocarbon group optionally having substituent(s)" for $R^4$, those similar to the aforementioned "hydrocarbon group optionally having substituent(s)" for $R^1$ can be mentioned.

As $R^4$, a hydrogen atom or alkyl optionally having substituent(s) is preferable. Particularly,
(1) hydrogen atom,
(2) $C_{1-6}$ alkyl optionally having one substituent selected from
(1') $C_{3-6}$ cycloalkyl,
(2') $C_{6-10}$ aryl optionally having (i) 1 or 2 $C_{1-6}$ alkoxy optionally having 1 to 3 halogen atoms or (ii) 1 to 3 halogen atoms,
(3') $C_{1-6}$ alkyl-carbonyl,
(4') $C_{6-10}$ aryl-carbonyl optionally having one halogen atom or $C_{1-6}$ alkoxy,
(5') $C_{1-6}$ alkoxy-carbonyl,
(6') $C_{6-10}$ aryl-carbamoyl,
(7') heterocyclic group optionally having 1 or 2 $C_{1-6}$ alkyl optionally having 1 to 3 halogen atoms,
(8') $C_{6-10}$ aryloxy,
(9') carboxy,
(10') cyano, and
(11') $C_{1-6}$ alkoxy optionally having one $C_{6-10}$ aryl,
(3) $C_{1-6}$ alkyl optionally having 1 to 3 halogen atoms
and the like are preferable.

(1) $R^{AA1}$ and $R^{AA2}$ are the same or different and each is a hydrogen atom or a substituent. As the substituent, those similar to the aforementioned substituent for ring A can be mentioned.

As $R^{AA1}$, a hydrogen atom or $C_{1-6}$ alkyl group is preferable.
As $R^{AA2}$, a hydrogen atom or $C_{1-6}$ alkyl group is preferable.
Alternatively,
(2) $R^{AA1}$ and $R^{AA2}$ are bonded to each other to form a 5- to 7-membered ring optionally having substituent(s). As the "5- to 7-membered ring optionally having substituent(s)", those similar to the above-mentioned "5- to 7-membered ring optionally having substituent(s)" for ring A can be mentioned. The 5- to 7-membered ring optionally has a substitutable number of substituents at substitutable positions.

In one embodiment, compound (I') represented by the formula

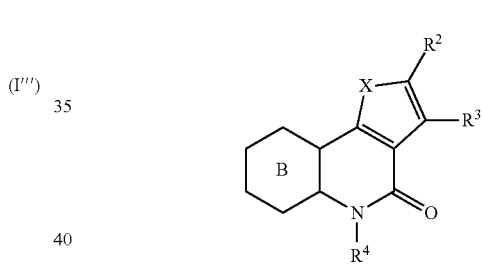

(I')

wherein X, $R^2$ and $R^3$ are as defined above, ring B is a 6-membered ring optionally having substituent(s), and $R^4$ is a hydrogen atom or a hydrocarbon group optionally having substituent(s), in which $R^{AA1}$ and $R^{AA2}$ are bonded to each other to form a 6-membered ring optionally having substituent(s), is preferable from among the above-mentioned compounds (I''').

Compound (I') is explained in detail in the following.

X, $R^2$, $R^3$ and $R^4$ are as defined above.

In the formula (I'), preferable examples of $R^2$ include
(A) carbamoyl optionally having 1 or 2 substituents selected from
(1) $C_{1-6}$ alkyl (e.g., methyl, ethyl, propyl, isopropyl, n-butyl, 2-methylpropyl, 2,2-dimethylpropyl, 1-methylbutyl, 1-ethylpropyl) optionally having 1 or 2 substituents selected from
(1') halogen atom (e.g., fluorine atom),
(2') cyano,
(3') amino,
(4') $C_{1-6}$ alkylamino (e.g., isopropylamino),
(5') di-$C_{1-6}$ alkylamino (e.g., dimethylamino, diethylamino, di-1-propylamino) optionally having one hydroxy,
(6') $C_{1-6}$ alkoxy-carbonylamino (e.g., tert-butoxycarbonylamino),
(7') hydroxy,
(8') di-$C_{1-6}$ alkyl-carbamoyl (e.g., diethylcarbamoyl), (9') 5- to 7-membered cyclic carbamoyl (e.g., 1-pyrrolidinylcarbonyl), (10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, morpholino, 2-pyridyl, 3-pyridyl, 4-pyridyl, 2-pyrazinyl, 2-furyl, 2-tetrahydrofuryl, 1,3-benzodioxol-5-yl) optionally having one
  (a) hydroxy,
  (b) $C_{1-6}$ alkyl (e.g., methyl, ethyl) optionally having one hydroxy,
  (c) oxo,
  (d) $C_{1-6}$ alkoxy-carbonyl (e.g., tert-butoxycarbonyl), or
  (e) $C_{1-6}$ alkyl-carbonyl (e.g., methylcarbonyl) optionally having one substituent selected from $C_{1-6}$ alkyl-carbonyloxy (e.g., methylcarbonyloxy) and hydroxy, (11') $C_{1-6}$ alkoxy-carbonyl (e.g., ethoxycarbonyl), (12') $C_{3-6}$ cycloalkyl (e.g., cyclopropyl, cyclohexyl) optionally having one hydroxy, (13') $C_{1-6}$ alkoxy (e.g., methoxy, i-propoxy), (14') $C_{2-6}$ alkynyl (e.g., ethynyl), (15') $C_{6-10}$ aryl (e.g., phenyl) optionally having 1 or 2 $C_{1-6}$ alkoxy (e.g., methoxy), (16') carbamoyl, and (17') $C_{1-6}$ alkyl-carbonyl-amino (e.g., methylcarbonylamino) optionally having one substituent selected from
  (a) $C_{1-6}$ alkyl-carbonyl-oxy (e.g., methylcarbonyloxy),
  (b) $C_{1-6}$ alkoxy (e.g., methoxy), and
  (c) hydroxy, (2) $C_{3-6}$ cycloalkyl (e.g., cyclopropyl, cyclohexyl) or 1,2,3,4-tetrahydronaphthalenyl (e.g., 1,2,3,4-tetrahydronaphthalen-1-yl) optionally having 1 or 2 substituents selected from
  (1') amino optionally having one substituent selected from
    (a) $C_{1-6}$ alkoxy-carbonyl (e.g., tert-butoxycarbonyl), and
    (b) $C_{1-6}$ alkyl-carbonyl (e.g., methylcarbonyl) optionally having one hydroxy or $C_{1-6}$ alkyl-carbonyloxy (e.g., methylcarbonyloxy),
  (2') hydroxy,
  (3') carboxy,
  (4') $C_{1-6}$ alkoxy-carbonyl (e.g., methoxycarbonyl),
  (5') $C_{1-6}$ alkyl-carbamoyl (e.g., ethylcarbamoyl) optionally having one hydroxy,
  (6') $C_{1-6}$ alkyl (e.g., methyl) optionally having one hydroxy, and
  (7') $C_{1-6}$ alkoxy-carbonylamino (e.g., tert-butoxycarbonylamino), (3) $C_{6-10}$ aryl (e.g., phenyl), and (4) heterocyclic group (e.g., 3-azetidinyl, 3-pyrrolidinyl, 4-piperidyl, 2-tetrahydrofuryl, 3-azepanyl, 4-azepanyl, tetrahydrothiopyran-4-yl, tetrahydropyran-4-yl) optionally having 1 to 4 substituents selected from
  (1') $C_{1-6}$ alkyl (e.g., methyl, ethyl, n-propyl) optionally having 1 to 5 substituents selected from
    (a) $C_{6-10}$ aryl (e.g., phenyl),
    (b) hydroxy, and
    (c) halogen atom,
  (2') $C_{1-6}$ alkyl-carbonyl (e.g., methylcarbonyl, ethylcarbonyl, i-propylcarbonyl, i-butylcarbonyl) optionally having one substituent selected from
    (a) $C_{1-6}$ alkyl-carbonyloxy (e.g., methylcarbonyloxy),
    (b) hydroxy,
    (c) $C_{1-6}$ alkoxy (e.g., methoxy),
    (d) $C_{1-6}$ alkyl-sulfonyl (e.g., methylsulfonyl), and
    (e) amino,
  (3') $C_{1-6}$ alkoxy-carbonyl (e.g., tert-butoxycarbonyl), (4') 5- or 6-membered aromatic heterocyclic group (e.g., 2-pyridyl, 3-pyridyl, 4-pyridyl, 2-thiazolyl, 4-pyrimidinyl) optionally having one substituent selected from
  (a) $C_{1-6}$ alkyl (e.g., methyl) optionally having 1 to 3 halogen atoms (e.g., fluorine atom),
  (b) cyano,
  (c) carbamoyl,
  (d) $C_{1-6}$ alkoxy (e.g., methoxy), and
  (e) $C_{1-6}$ alkyl-carbamoyl (e.g., methylcarbamoyl), (5') oxo, (6') $C_{1-6}$ alkyl-carbamoyl (e.g., ethylcarbamoyl), (7') $C_{1-6}$ alkyl-sulfonyl (e.g., methylsulfonyl), (8') $C_{6-10}$ aryl (e.g., phenyl) optionally having one substituent selected from
  (a) hydroxy,
  (b) cyano, and
  (c) $C_{1-6}$ alkyl-sulfonyl (e.g., methylsulfonyl), (9') heterocyclyl-carbonyl (e.g., 2-pyrrolidinylcarbonyl, 2-tetrahydrofurylcarbonyl), and (10') $C_{6-10}$ aryloxy-carbonyl (e.g., phenoxycarbonyl), (B) 5- to 7-membered cyclic carbamoyl (e.g., 1-pyrrolidinylcarbonyl, 1-piperidylcarbonyl, 1-piperazinylcarbonyl, 1-homopiperazinylcarbonyl, morpholinocarbonyl, thiomorpholinocarbonyl) optionally having one substituent selected from
(1) $C_{1-6}$ alkyl (e.g., methyl, ethyl) optionally having one substituent selected from
  (a) heterocyclic group (e.g., 1-pyrrolidinyl, benzodioxol-5-yl),
  (b) amino,
  (c) $C_{1-6}$ alkoxy (e.g., methoxy), and
  (d) $C_{6-10}$ aryl (e.g., phenyl), (2) amino optionally having one $C_{1-6}$ alkyl-carbonyl (e.g., acetyl), (3) N—$C_{1-6}$ alkyl-N—($C_{1-6}$ alkyl-carbonyl)amino (e.g., N-acetyl-N-ethylamino), (4) heterocyclic group (e.g., 1-pyrrolidinyl, 2-pyridyl), (5) $C_{1-6}$ alkyl-carbonyl (e.g., acetyl, propionyl) optionally having one substituent selected from
  (a) hydroxy,
  (b) $C_{1-6}$ alkoxy (e.g., methoxy, ethoxy),
  (c) amino,
  (d) $C_{1-6}$ alkylamino (e.g., isopropylamino),
  (e) di-$C_{1-6}$ alkylamino (e.g., dimethylamino), and
  (f) $C_{1-6}$ alkyl-carbonyloxy (e.g., methylcarbonyloxy), (6) $C_{6-10}$ aryl (e.g., phenyl), and (7) oxo, and (C) 5- to 7-membered cyclic carbamoyl fused with 5- to 7-membered ring (e.g., cyclohexane ring, benzene ring, 1,3-dioxolering) (e.g., 1-piperidylcarbonyl).

In the formula (I'), preferable examples of $R^3$ include hydroxy optionally having
(1) $C_{1-6}$ alkyl (e.g., methyl, ethyl, n-butyl) optionally having one
  (a) $C_{1-6}$ alkoxy (e.g., ethoxy),
  (b) $C_{6-10}$ aryl (e.g., phenyl), or
  (c) heterocyclic group (e.g., 4-pyridyl, morpholino, 2-tetrahydrofuryl), or (2) $C_{1-6}$ alkyl (e.g., methyl, ethyl) optionally having 1 to 3 halogen atoms (e.g., fluorine atom)

[preferably, hydroxy substituted by
(1) $C_{1-6}$ alkyl (e.g., methyl, ethyl, n-butyl) optionally having one
  (a) $C_{1-6}$ alkoxy (e.g., ethoxy),
  (b) $C_{6-10}$ aryl (e.g., phenyl), or
  (c) heterocyclic group (e.g., 4-pyridyl, morpholino, 2-tetrahydrofuryl), or (2) $C_{1-6}$ alkyl (e.g., methyl, ethyl) optionally having 1 to 3 halogen atoms (e.g., fluorine atom)].

In the formula (I'), preferable examples of $R^4$ include
(1) hydrogen atom,
(2) $C_{1-6}$ alkyl (e.g., methyl, ethyl, n-propyl, n-butyl, n-pentyl, i-pentyl, 2-ethylbutyl) optionally having one substituent selected from
    (1') $C_{3-6}$ cycloalkyl (e.g., cyclopropyl, cyclohexyl),
    (2') $C_{6-10}$ aryl (e.g., phenyl) optionally having (i) one $C_{1-6}$ alkoxy (e.g., methoxy) optionally having 1 to 3 halogen atoms (e.g., fluorine atom) or (ii) 1 to 3 halogen atoms (e.g., fluorine atom, chlorine atom),
    (3') $C_{1-6}$ alkyl-carbonyl (e.g., methylcarbonyl, tert-butyl-carbonyl),
    (4') $C_{6-10}$ aryl-carbonyl (e.g., benzoyl),
    (5') $C_{1-6}$ alkoxy-carbonyl (e.g., methoxycarbonyl, ethoxycarbonyl, tert-butoxycarbonyl),
    (6') $C_{6-10}$ aryl-carbamoyl (e.g., phenylcarbamoyl),
    (7') heterocyclic group (e.g., 2-pyridyl, 3-pyridyl, 4-pyridyl, 1-pyrrolyl, 2-imidazolyl, 2-furyl, 2-tetrahydrofuryl) optionally having 1 or 2 $C_{1-6}$ alkyl (e.g., methyl) optionally having 1 to 3 halogen atoms (e.g., fluorine atom),
    (8') $C_{6-10}$ aryloxy (e.g., phenoxy),
    (9') carboxy,
    (10') cyano, and
    (11') $C_{1-6}$ alkoxy (e.g., methoxy) optionally having one $C_{6-10}$ aryl (e.g., phenyl), and
(3) $C_{1-6}$ alkyl (e.g., ethyl) optionally having 1 to 3 halogen atoms (e.g., fluorine atom).

Ring B is a 6-membered ring optionally having substituent(s). As the "6-membered ring" of the "6-membered ring optionally having substituent(s)",
(1) homocyclic ring (e.g., cyclohexane, cyclohexene, cyclohexanediene, benzene), and
(2) heterocycle (e.g., piperidine, piperazine, morpholine, thiomorpholine, pyridine, pyrazine, pyrimidine, pyridazine, triazine, pyran, dihydropyran, tetrahydropyran) can be mentioned.

Examples of the substituent that the ring B may have include
(1) the above-mentioned substituent group A,
(2) $C_{1-6}$ alkyl optionally having 1 to 3 substituents selected from the above-mentioned substituent group A and the like, and substituents in a substitutable number may be present at substitutable position(s).

As ring B, cyclohexene ring optionally having substituent(s), benzene ring optionally having substituent(s), or pyridine ring optionally having substituent(s) is preferable, and cyclohexene ring, benzene ring optionally having one halogen atom (e.g., fluorine atom), or pyridine ring is more preferable. Particularly, benzene ring and pyridine ring are preferable.

Of compounds (I'), a compound wherein
ring B is a 6-membered ring optionally having substituent(s),
    X is O, S or N($C_{1-6}$ alkyl),
    $R^2$ is carbamoyl optionally having substituent(s),
    $R^3$ is hydroxy optionally having $C_{1-6}$ alkyl optionally having substituent(s), and
    $R^4$ is a hydrogen atom or $C_{1-6}$ alkyl optionally having substituent(s)
is preferable.

Specific examples of preferable compound (1') include the following.
[Compound (I'-1)]
Compound (I') wherein
X is O, S or N($C_{1-6}$ alkyl) (particularly N(methyl));

$R^2$ is
(A) carbamoyl optionally having 1 or 2 substituents selected from
    (1) $C_{1-6}$ alkyl (e.g., methyl, ethyl, propyl, isopropyl, 2,2-dimethylpropyl, 1-methylbutyl) optionally having one substituent selected from
        (1') halogen atom (e.g., fluorine atom),
        (2') cyano,
        (3') amino,
        (4') $C_{1-6}$ alkylamino (e.g., isopropylamino),
        (5') di-$C_{1-6}$ alkylamino (e.g., dimethylamino, diethylamino) optionally having one hydroxy,
        (6') $C_{1-6}$ alkoxy-carbonylamino (e.g., tert-butoxycarbonylamino),
        (7') hydroxy,
        (8') di-$C_{1-6}$ alkyl-carbamoyl (e.g., diethylcarbamoyl),
        (9') 5- to 7-membered cyclic carbamoyl (e.g., 1-pyrrolidinylcarbonyl),
        (10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, 2-pyridyl, 3-pyridyl) optionally having one
            (a) hydroxy, or
            (b) $C_{1-6}$ alkyl (e.g., methyl, ethyl) optionally having one hydroxy, and
        (11') $C_{1-6}$ alkoxy-carbonyl (e.g., ethoxycarbonyl),
    (2) $C_{3-6}$ cycloalkyl (e.g., cyclohexyl) optionally having 1 or 2 substituents selected from
        (1') amino, and
        (2') hydroxy,
    (3) $C_{6-10}$ aryl (e.g., phenyl), and
    (4) heterocyclic group (e.g., 3-pyrrolidinyl, 4-piperidyl) optionally having one $C_{1-6}$ alkyl (e.g., methyl) optionally having 1 or 2 substituents selected from
        (a) $C_{6-10}$ aryl (e.g., phenyl), and
        (b) hydroxy, or
(B) 5- to 7-membered cyclic carbamoyl (e.g., 1-pyrrolidinylcarbonyl, 1-piperidylcarbonyl, 1-homopiperazinylcarbonyl) optionally having one substituent selected from
    (1) $C_{1-6}$ alkyl (e.g., methyl, ethyl) optionally having one substituent selected from
        (a) heterocyclic group (e.g., 1-pyrrolidinyl, benzodioxol-5-yl), and
        (b) amino,
    (2) amino,
    (3) N—$C_{1-6}$ alkyl-N—($C_{1-6}$ alkyl-carbonyl)amino (e.g., N-acetyl-N-ethylamino),
    (4) heterocyclic group (e.g., 1-pyrrolidinyl), and
    (5) $C_{1-6}$ alkyl-carbonyl (e.g., acetyl, propionyl) optionally having one substituent selected from
        (a) hydroxy,
        (b) $C_{1-6}$ alkoxy (e.g., methoxy),
        (c) amino, and
        (d) $C_{1-6}$ alkylamino (e.g., isopropylamino);
$R^3$ is hydroxy optionally having $C_{1-6}$ alkyl (e.g., methyl, ethyl) optionally having one $C_{1-6}$ alkoxy (e.g., ethoxy);
$R^4$ is
(1) hydrogen atom, or
(2) $C_{1-6}$ alkyl (e.g., methyl, ethyl) optionally having one substituent selected from
    (1') $C_{3-6}$ cycloalkyl (e.g., cyclopropyl),
    (2') $C_{6-10}$ aryl (e.g., phenyl) optionally having one $C_{1-6}$ alkoxy (e.g., methoxy),
    (3') $C_{1-6}$ alkyl-carbonyl (e.g., tert-butylcarbonyl),
    (4') $C_{6-10}$ aryl-carbonyl (e.g., benzoyl),
    (5') $C_{1-6}$ alkoxy-carbonyl (e.g., ethoxycarbonyl),
    (6') $C_{6-10}$ aryl-carbamoyl (e.g., phenylcarbamoyl), (7') heterocyclic group (e.g., 2-pyridyl),
(8') $C_{6-10}$ aryloxy (e.g., phenoxy), and
(9') carboxy; and
ring B is benzene ring.
[Compound (I'-2)]
Compound (I') wherein
X is O, S or N($C_{1-6}$ alkyl) (particularly N(methyl));
$R^2$ is
(A) carbamoyl optionally having 1 or 2 substituents selected from
(1) $C_{1-6}$ alkyl (e.g., methyl, ethyl, propyl, isopropyl, 2-methylpropyl, 2,2-dimethylpropyl, 1-methylbutyl) optionally having 1 or 2 substituents selected from
    (1') halogen atom (e.g., fluorine atom),
    (2') cyano,
    (3') amino,
    (4') $C_{1-6}$ alkylamino (e.g., isopropylamino),
    (5') di-$C_{1-6}$ alkylamino (e.g., dimethylamino, diethylamino) optionally having one hydroxy,
    (6') $C_{1-6}$ alkoxy-carbonylamino (e.g., tert-butoxycarbonylamino),
    (7') hydroxy,
    (8') di-$C_{1-6}$ alkyl-carbamoyl (e.g., diethylcarbamoyl),
    (9') 5- to 7-membered cyclic carbamoyl (e.g., 1-pyrrolidinylcarbonyl),
    (10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, 2-pyridyl, 3-pyridyl) optionally having one (a) hydroxy, or (b) $C_{1-6}$ alkyl (e.g., methyl, ethyl) optionally having one hydroxy,
    (11') $C_{1-6}$ alkoxy-carbonyl (e.g., ethoxycarbonyl), and
    (12') $C_{3-6}$ cycloalkyl (e.g., cyclohexyl),
(2) $C_{3-6}$ cycloalkyl (e.g., cyclohexyl) optionally having 1 or 2 substituents selected from
    (1') amino, and
    (2') hydroxy,
(3) $C_{6-10}$ aryl (e.g., phenyl), and
(4) heterocyclic group (e.g., 3-pyrrolidinyl, 4-piperidyl) optionally having one substituent selected from
    (1') $C_{1-6}$ alkyl (e.g., methyl) optionally having 1 or 2 substituents selected from
        (a) $C_{6-10}$ aryl (e.g., phenyl), and
        (b) hydroxy,
    (2') $C_{1-6}$ alkyl-carbonyl (e.g., methylcarbonyl) optionally having one substituent selected from
        (a) $C_{1-6}$ alkyl-carbonyloxy (e.g., methylcarbonyloxy), and
        (b) hydroxy,
    (3') $C_{1-6}$ alkoxy-carbonyl (e.g., tert-butoxycarbonyl), and
    (4') 5- or 6-membered aromatic heterocyclic group (e.g., 4-pyridyl), or
(B) 5- to 7-membered cyclic carbamoyl (e.g., 1-pyrrolidinylcarbonyl, 1-piperidylcarbonyl, 1-homopiperazinylcarbonyl) optionally having one substituent selected from
(1) $C_{1-6}$ alkyl (e.g., methyl, ethyl) optionally having one substituent selected from
    (a) heterocyclic group (e.g., 1-pyrrolidinyl, benzodioxol-5-yl), and
    (b) amino,
(2) amino,
(3) N—$C_{1-6}$ alkyl-N—($C_{1-6}$ alkyl-carbonyl)amino (e.g., N-acetyl-N-ethylamino),
(4) heterocyclic group (e.g., 1-pyrrolidinyl), and
(5) $C_{1-6}$ alkyl-carbonyl (e.g., acetyl, propionyl) optionally having one substituent selected from
    (a) hydroxy,
    (b) $C_{1-6}$ alkoxy (e.g., methoxy),
    (c) amino, and
    (d) $C_{1-6}$ alkylamino (e.g., isopropylamino);
$R^3$ is hydroxy optionally having
(1) $C_{1-6}$ alkyl (e.g., methyl, ethyl) optionally having one $C_{1-6}$ alkoxy (e.g., ethoxy), or
(2) $C_{1-6}$ alkyl (e.g., methyl, ethyl) optionally having 1 to 3 halogen atoms (e.g., fluorine atom)
[preferably, hydroxyl substituted by
(1) $C_{1-6}$ alkyl (e.g., methyl, ethyl) optionally having one $C_{1-6}$ alkoxy (e.g., ethoxy), or
(2) $C_{1-6}$ alkyl (e.g., methyl, ethyl) optionally having 1 to 3 halogen atoms (e.g., fluorine atom)];
$R^4$ is
(1) hydrogen atom, or
(2) $C_{1-6}$ alkyl (e.g., methyl, ethyl) optionally having one substituent selected from
    (1') $C_{3-6}$ cycloalkyl (e.g., cyclopropyl),
    (2') $C_{6-10}$ aryl (e.g., phenyl) optionally having one $C_{1-6}$ alkoxy (e.g., methoxy),
    (3') $C_{1-6}$ alkyl-carbonyl (e.g., tert-butylcarbonyl),
    (4') $C_{6-10}$ aryl-carbonyl (e.g., benzoyl),
    (5') $C_{1-6}$ alkoxy-carbonyl (e.g., ethoxycarbonyl),
    (6') $C_{6-10}$ aryl-carbamoyl (e.g., phenylcarbamoyl),
    (7') heterocyclic group (e.g., 2-pyridyl),
    (8') $C_{6-10}$ aryloxy (e.g., phenoxy), and
    (9') carboxy; and
ring B is cyclohexene ring or benzene ring (particularly, benzene ring).
[Compound (I'-3)]
Compound (I') wherein
X is O, S or N($C_{1-6}$ alkyl) (particularly N(methyl));
$R^2$ is
(A) carbamoyl optionally having 1 or 2 substituents selected from
(1) $C_{1-6}$ alkyl (e.g., methyl, ethyl, propyl, isopropyl, n-butyl, 2-methylpropyl, 2,2-dimethylpropyl, 1-methylbutyl, 1-ethylpropyl) optionally having 1 or 2 substituents selected from
    (1') halogen atom (e.g., fluorine atom),
    (2') cyano,
    (3') amino,
    (4') $C_{1-6}$ alkylamino (e.g., isopropylamino),
    (5') di-$C_{1-6}$ alkylamino (e.g., dimethylamino, diethylamino, di-i-propylamino) optionally having one hydroxy,
    (6') $C_{1-6}$ alkoxy-carbonylamino (e.g., tert-butoxycarbonylamino),
    (7') hydroxy,
    (8') di-$C_{1-6}$ alkyl-carbamoyl (e.g., diethylcarbamoyl),
    (9') 5- to 7-membered cyclic carbamoyl (e.g., 1-pyrrolidinylcarbonyl),
    (10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, morpholino, 2-pyridyl, 3-pyridyl, 4-pyridyl, 2-pyrazinyl, 2-furyl, 2-tetrahydrofuryl, 1,3-benzodioxol-5-yl) optionally having one
        (a) hydroxy,
        (b) $C_{1-6}$ alkyl (e.g., methyl, ethyl) optionally having one hydroxy,
        (c) oxo,
        (d) $C_{1-6}$ alkoxy-carbonyl (e.g., tert-butoxycarbonyl), or
        (e) $C_{1-6}$ alkyl-carbonyl (e.g., methylcarbonyl) optionally having one substituent selected from $C_{1-6}$ alkyl-carbonyloxy (e.g., methylcarbonyloxy) and hydroxy,
    (11') $C_{1-6}$ alkoxy-carbonyl (e.g., ethoxycarbonyl),
    (12') $C_{3-6}$ cycloalkyl (e.g., cyclopropyl, cyclohexyl) optionally having one hydroxy,
    (13') $C_{1-6}$ alkoxy (e.g., methoxy, i-propoxy), (14') C$_{2-6}$ alkynyl (e.g., ethynyl), (15') C$_{6-10}$ aryl (e.g., phenyl) optionally having 1 or 2 C$_{1-6}$ alkoxy (e.g., methoxy), (16') carbamoyl, and (17') C$_{1-6}$ alkyl-carbonyl-amino (e.g., methylcarbonylamino) optionally having one substituent selected from
(a) C$_{1-6}$ alkyl-carbonyl-oxy (e.g., methylcarbonyloxy),
(b) C$_{1-6}$ alkoxy (e.g., methoxy), and
(c) hydroxy, (2) C$_{3-6}$ cycloalkyl (e.g., cyclopropyl, cyclohexyl) or 1,2,3,4-tetrahydronaphthalenyl (e.g., 1,2,3,4-tetrahydronaphthalen-1-yl) optionally having 1 or 2 substituents selected from (1') amino optionally having one substituent selected from
(a) C$_{1-6}$ alkoxy-carbonyl (e.g., tert-butoxycarbonyl), and
(b) C$_{1-6}$ alkyl-carbonyl (e.g., methylcarbonyl) optionally having one hydroxy or C$_{1-6}$ alkyl-carbonyloxy (e.g., methylcarbonyloxy), (2') hydroxy, (3') carboxy, (4') C$_{1-6}$ alkoxy-carbonyl (e.g., methoxycarbonyl), (5') C$_{1-6}$ alkyl-carbamoyl (e.g., ethylcarbamoyl) optionally having one hydroxy, (6') C$_{1-6}$ alkyl (e.g., methyl) optionally having one hydroxy, and (7') C$_{1-6}$ alkoxy-carbonylamino (e.g., tert-butoxycarbonylamino), (3) C$_{6-10}$ aryl (e.g., phenyl), and (4) heterocyclic group (e.g., 3-azetidinyl, 3-pyrrolidinyl, 4-piperidyl, 2-tetrahydrofuryl, 3-azepanyl, 4-azepanyl, tetrahydrothiopyran-4-yl, tetrahydropyran-4-yl) optionally having 1 to 4 substituents selected from (1') C$_{1-6}$ alkyl (e.g., methyl, ethyl, n-propyl) optionally having 1 to 5 substituents selected from
(a) C$_{6-10}$ aryl (e.g., phenyl),
(b) hydroxy, and
(c) halogen atom, (2') C$_{1-6}$ alkyl-carbonyl (e.g., methylcarbonyl, ethylcarbonyl, i-propylcarbonyl, i-butylcarbonyl) optionally having one substituent selected from
(a) C$_{1-6}$ alkyl-carbonyloxy (e.g., methylcarbonyloxy),
(b) hydroxy,
(c) C$_{1-6}$ alkoxy (e.g., methoxy),
(d) C$_{1-6}$ alkyl-sulfonyl (e.g., methylsulfonyl), and
(e) amino, (3') C$_{1-6}$ alkoxy-carbonyl (e.g., tert-butoxycarbonyl), (4') 5- or 6-membered aromatic heterocyclic group (e.g., 2-pyridyl, 3-pyridyl, 4-pyridyl, 2-thiazolyl, 4-pyrimidinyl) optionally having one substituent selected from
(a) C$_{1-6}$ alkyl (e.g., methyl) optionally having 1 to 3 halogen atoms (e.g., fluorine atom),
(b) cyano,
(c) carbamoyl,
(d) C$_{1-6}$ alkoxy (e.g., methoxy), and
(e) C$_{1-6}$ alkyl-carbamoyl (e.g., methylcarbamoyl), (5') oxo, (6') C$_{1-6}$ alkyl-carbamoyl (e.g., ethylcarbamoyl), (7') C$_{1-6}$ alkyl-sulfonyl (e.g., methylsulfonyl), (8') C$_{6-10}$ aryl (e.g., phenyl) optionally having one substituent selected from
(a) hydroxy,
(b) cyano, and
(c) C$_{1-6}$ alkyl-sulfonyl (e.g., methylsulfonyl), (9') heterocyclyl-carbonyl (e.g., 2-pyrrolidinylcarbonyl, 2-tetrahydrofurylcarbonyl), and (10') C$_{6-10}$ aryloxy-carbonyl (e.g., phenoxycarbonyl), (B) 5- to 7-membered cyclic carbamoyl (e.g., 1-pyrrolidinylcarbonyl, 1-piperidylcarbonyl, 1-piperazinylcarbonyl, 1-homopiperazinylcarbonyl, morpholinocarbonyl, thiomorpholinocarbonyl) optionally having one group selected from (1) C$_{1-6}$ alkyl (e.g., methyl, ethyl) optionally having one substituent selected from
(a) heterocyclic group (e.g., 1-pyrrolidinyl, benzodioxol-5-yl),
(b) amino,
(c) C$_{1-6}$ alkoxy (e.g., methoxy), and
(d) C$_{6-10}$ aryl (e.g., phenyl), (2) amino optionally having one C$_{1-6}$ alkyl-carbonyl (e.g., acetyl), (3) N—C$_{1-6}$ alkyl-N—(C$_{1-6}$ alkyl-carbonyl)amino (e.g., N-acetyl-N-ethylamino), (4) heterocyclic group (e.g., 1-pyrrolidinyl, 2-pyridyl), (5) C$_{1-6}$ alkyl-carbonyl (e.g., acetyl, propionyl) optionally having one substituent selected from
(a) hydroxy,
(b) C$_{1-6}$ alkoxy (e.g., methoxy, ethoxy),
(c) amino,
(d) C$_{1-6}$ alkylamino (e.g., isopropylamino),
(e) di-C$_{1-6}$ alkylamino (e.g., dimethylamino), and
(f) C$_{1-6}$ alkyl-carbonyloxy (e.g., methylcarbonyloxy), (6) C$_{6-10}$ aryl (e.g., phenyl), and (7) oxo, or (C) 5- to 7-membered cyclic carbamoyl (e.g., 1-piperidylcarbonyl) fused with 5- to 7-membered ring (e.g., cyclohexane ring, benzene ring, 1,3-dioxole ring);

R$^3$ is hydroxy optionally having (1) C$_{1-6}$ alkyl (e.g., methyl, ethyl, n-butyl) optionally having one
(a) C$_{1-6}$ alkoxy (e.g., ethoxy),
(b) C$_{6-10}$ aryl (e.g., phenyl), or
(c) heterocyclic group (e.g., 4-pyridyl, morpholino, 2-tetrahydrofuryl), or (2) C$_{1-6}$ alkyl (e.g., methyl, ethyl) optionally having 1 to 3 halogen atoms (e.g., fluorine atom)

[preferably, hydroxy substituted by
(1) C$_{1-6}$ alkyl (e.g., methyl, ethyl, n-butyl) optionally having one
(a) C$_{1-6}$ alkoxy (e.g., ethoxy),
(b) C$_{6-10}$ aryl (e.g., phenyl), or
(c) heterocyclic group (e.g., 4-pyridyl, morpholino, 2-tetrahydrofuryl), or (2) C$_{1-6}$ alkyl (e.g., methyl, ethyl) optionally having 1 to 3 halogen atoms (e.g., fluorine atom)];

R$^4$ is (1) hydrogen atom, (2) C$_{1-6}$ alkyl (e.g., methyl, ethyl, n-propyl, n-butyl, n-pentyl, i-pentyl, 2-ethylbutyl) optionally having one substituent selected from
(1') C$_{3-6}$ cycloalkyl (e.g., cyclopropyl, cyclohexyl),
(2') C$_{6-10}$ aryl (e.g., phenyl) optionally having (i) one C$_{1-6}$ alkoxy (e.g., methoxy) optionally having 1 to 3 halogen atoms (e.g., fluorine atom) or (ii) 1 to 3 halogen atoms (e.g., fluorine atom, chlorine atom),
(3') C$_{1-6}$ alkyl-carbonyl (e.g., methylcarbonyl, tert-butyl-carbonyl),
(4') C$_{6-10}$ aryl-carbonyl (e.g., benzoyl),
(5') C$_{1-6}$ alkoxy-carbonyl (e.g., methoxycarbonyl, ethoxycarbonyl, tert-butoxycarbonyl),
(6') C$_{6-10}$ aryl-carbamoyl (e.g., phenylcarbamoyl),
(7') heterocyclic group (e.g., 2-pyridyl, 3-pyridyl, 4-pyridyl, 1-pyrrolyl, 2-imidazolyl, 2-furyl, 2-tetrahydrofuryl) optionally having 1 or 2 C$_{1-6}$ alkyl (e.g., methyl) optionally having 1 to 3 halogen atoms (e.g., fluorine atom),
(8') C$_{6-10}$ aryloxy (e.g., phenoxy),
(9') carboxy, (10') cyano, and (11') $C_{1-6}$ alkoxy (e.g., methoxy) optionally having one $C_{6-10}$ aryl (e.g., phenyl), or (3) $C_{1-6}$ alkyl (e.g., ethyl) optionally having 1 to 3 halogen atoms (e.g., fluorine atom); and ring B is cyclohexene ring, benzene ring optionally having one halogen atom (e.g., fluorine atom), or pyridine ring (particularly, benzene ring and pyridine ring).

[Compound (I'-4)]

N-[1-(2-hydroxyethyl)piperidin-4-yl]-3-methoxy-1-methyl-4-oxo-5-(2-oxo-2-phenylethyl)-4,5-dihydro-1H-pyrrolo[3,2-c]quinoline-2-carboxamide;

N-[1-(hydroxyacetyl)piperidin-4-yl]-3-methoxy-1-methyl-4-oxo-5-(2-oxo-2-phenylethyl)-4,5-dihydro-1H-pyrrolo[3,2-c]quinoline-2-carboxamide;

or a salt thereof.

In another embodiment, of the above-mentioned compounds (I'''), a compound (I'') represented by the formula

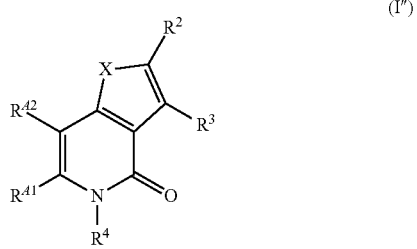

(I'')

wherein X, $R^2$, $R^3$ and $R^4$ are as defined above, and $R^{41}$ and $R^{42}$ are the same or different and each is a hydrogen atom or a substituent, is preferable.

In the following, compound (I'') is described in detail.

X, $R^2$, $R^3$ and $R^4$ are as defined above.

In the formula (I''), preferable examples of $R^2$ is (A) carbamoyl optionally having 1 or 2 substituents selected from (1) $C_{1-6}$ alkyl (e.g., methyl, ethyl, propyl, isopropyl, 2-methylpropyl, 2,2-dimethylpropyl, 1-methylbutyl) optionally having 1 or 2 substituents selected from (1') halogen atom (e.g., fluorine atom), (2') cyano, (3') amino, (4') $C_{1-6}$ alkylamino (e.g., isopropylamino), (5') di-$C_{1-6}$ alkylamino (e.g., dimethylamino, diethylamino) optionally having one hydroxy, (6') $C_{1-6}$ alkoxy-carbonylamino (e.g., tert-butoxycarbonylamino), (7') hydroxy, (8') di-$C_{1-6}$ alkyl-carbamoyl (e.g., diethylcarbamoyl), (9') 5- to 7-membered cyclic carbamoyl (e.g., 1-pyrrolidinylcarbonyl), (10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, 2-pyridyl, 3-pyridyl, 2-tetrahydrofuryl) optionally having one (a) hydroxy, or (b) $C_{1-6}$ alkyl (e.g., methyl, ethyl) optionally having one hydroxy, (11') $C_{1-6}$ alkoxy-carbonyl (e.g., ethoxycarbonyl), and (12') $C_{3-6}$ cycloalkyl (e.g., cyclohexyl), (2) $C_{3-6}$ cycloalkyl (e.g., cyclohexyl) optionally having 1 or 2 substituents selected from (1') amino, and (2') hydroxy, (3) $C_{6-10}$ aryl (e.g., phenyl), and (4) heterocyclic group (e.g., 3-pyrrolidinyl, 4-piperidyl, S-oxido-tetrahydrothiopyran-4-yl) optionally having one substituent selected from (1') $C_{1-6}$ alkyl (e.g., methyl) optionally having 1 or 2 substituents selected from (a) $C_{6-10}$ aryl (e.g., phenyl), and (b) hydroxy, (2') $C_{1-6}$ alkyl-carbonyl (e.g., methylcarbonyl) optionally having one substituent selected from (a) $C_{1-6}$ alkyl-carbonyloxy (e.g., methylcarbonyloxy), and (b) hydroxy, (3') $C_{1-6}$ alkoxy-carbonyl (e.g., tert-butoxycarbonyl), and (4') 5- or 6-membered aromatic heterocyclic group (e.g., 4-pyridyl), or (B) 5- to 7-membered cyclic carbamoyl (e.g., 1-pyrrolidinylcarbonyl, 1-piperidylcarbonyl, 1-homopiperazinylcarbonyl) optionally having one substituent selected from (1) $C_{1-6}$ alkyl (e.g., methyl, ethyl) optionally having one substituent selected from (a) heterocyclic group (e.g., 1-pyrrolidinyl, benzodioxol-5-yl), and (b) amino, (2) amino, (3) N—$C_{1-6}$ alkyl-N—($C_{1-6}$ alkyl-carbonyl)amino (e.g., N-acetyl-N-ethylamino), (4) heterocyclic group (e.g., 1-pyrrolidinyl), and (5) $C_{1-6}$ alkyl-carbonyl (e.g., acetyl, propionyl) optionally having one substituent selected from (a) hydroxy, (b) $C_{1-6}$ alkoxy (e.g., methoxy), (c) amino, and (d) $C_{1-6}$ alkylamino (e.g., isopropylamino).

In the formula (I''), preferable examples of $R^3$ is hydroxy optionally having (1) $C_{1-6}$ alkyl (e.g., methyl, ethyl, n-propyl, i-propyl) optionally having one $C_{1-6}$ alkoxy (e.g., ethoxy), or (2) $C_{1-6}$ alkyl (e.g., methyl, ethyl, n-propyl, i-propyl) optionally having 1 to 3 halogen atoms (e.g., fluorine atom)

[preferably, hydroxyl substituted by (1) $C_{1-6}$ alkyl (e.g., methyl, ethyl) optionally having one $C_{1-6}$ alkoxy (e.g., ethoxy), or (2) $C_{1-6}$ alkyl (e.g., methyl, ethyl) optionally having 1 to 3 halogen atoms (e.g., fluorine atom)].

In the formula (I''), preferable examples of $R^4$ is (1) hydrogen atom, or (2) $C_{1-6}$ alkyl (e.g., methyl, ethyl) optionally having one substituent selected from (1') $C_{3-6}$ cycloalkyl (e.g., cyclopropyl), (2') $C_{6-10}$ aryl (e.g., phenyl) optionally having (i) 1 or 2 $C_{1-6}$ alkoxy (e.g., methoxy), or (ii) 1 to 3 halogen atoms (e.g., chlorine atom), (3') $C_{1-6}$ alkyl-carbonyl (e.g., tert-butylcarbonyl), (4') $C_{6-10}$ aryl-carbonyl (e.g., benzoyl) optionally having one halogen atom (e.g., chlorine atom) or $C_{1-6}$ alkoxy (e.g., methoxy), (5') $C_{1-6}$ alkoxy-carbonyl (e.g., ethoxycarbonyl), (6') $C_{6-10}$ aryl-carbamoyl (e.g., phenylcarbamoyl), (7') heterocyclic group (e.g., 2-pyridyl), (8') $C_{6-10}$ aryloxy (e.g., phenoxy), and (9') carboxy; and $R^{41}$ is a hydrogen atom or a $C_{1-6}$ alkyl group (e.g., methyl, ethyl, n-propyl).

$R^{A1}$ and $R^{A2}$ are the same or different and each is a hydrogen atom or a substituent. As the substituent, those similar to the substituent of the aforementioned ring A can be mentioned.

As $R^{A1}$, a hydrogen atom or $C_{1-6}$ alkyl group is preferable.
As $R^{A2}$, a hydrogen atom or $C_{1-6}$ alkyl group is preferable.
Of compounds (I"), a compound wherein
X is O, S or N($C_{1-6}$ alkyl),
$R^2$ is carbamoyl optionally having substituent(s),
$R^3$ is hydroxy optionally having $C_{1-6}$ alkyl optionally having substituent(s),
$R^{A1}$ is a hydrogen atom or a $C_{1-6}$ alkyl group (e.g., methyl, ethyl, n-propyl),
$R^{A2}$ is a hydrogen atom or a $C_{1-6}$ alkyl group (e.g., methyl), and
$R^4$ is a hydrogen atom or $C_{1-6}$ alkyl optionally having substituent(s)
is preferable.

Specific examples of preferable compound (1") include the following.
[Compound (I"-1)]
Compound (I") wherein
X is O, S or N($C_{1-6}$ alkyl) (particularly N(methyl));
$R^2$ is
(A) carbamoyl optionally having 1 or 2 substituents selected from
(1) $C_{1-6}$ alkyl (e.g., methyl, ethyl, propyl, isopropyl, 2-methylpropyl, 2,2-dimethylpropyl, 1-methylbutyl) optionally having 1 or 2 substituents selected from
(1') halogen atom (e.g., fluorine atom),
(2') cyano,
(3') amino,
(4') $C_{1-6}$ alkylamino (e.g., isopropylamino),
(5') di-$C_{1-6}$ alkylamino (e.g., dimethylamino, diethylamino) optionally having one hydroxy,
(6') $C_{1-6}$ alkoxy-carbonylamino (e.g., tert-butoxycarbonylamino),
(7') hydroxy,
(8') di-$C_{1-6}$ alkyl-carbamoyl (e.g., diethylcarbamoyl),
(9') 5- to 7-membered cyclic carbamoyl (e.g., 1-pyrrolidinylcarbonyl),
(10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, 2-pyridyl, 3-pyridyl) optionally having one
(a) hydroxy, or
(b) $C_{1-6}$ alkyl (e.g., methyl, ethyl) optionally having one hydroxy,
(11') $C_{1-6}$ alkoxy-carbonyl (e.g., ethoxycarbonyl), and
(12') $C_{3-6}$ cycloalkyl (e.g., cyclohexyl),
(2) $C_{3-6}$ cycloalkyl (e.g., cyclohexyl) optionally having 1 or 2 substituents selected from
(1') amino, and
(2') hydroxy,
(3) $C_{6-10}$ aryl (e.g., phenyl), and
(4) heterocyclic group (e.g., 3-pyrrolidinyl, 4-piperidyl) optionally having one substituent selected from
(1') $C_{1-6}$ alkyl (e.g., methyl) optionally having 1 or 2 substituents selected from
(a) $C_{6-10}$ aryl (e.g., phenyl), and
(b) hydroxy,
(2') $C_{1-6}$ alkyl-carbonyl (e.g., methylcarbonyl) optionally having one substituent selected from
(a) $C_{1-6}$ alkyl-carbonyloxy (e.g., methylcarbonyloxy), and
(b) hydroxy,
(3') $C_{1-6}$ alkoxy-carbonyl (e.g., tert-butoxycarbonyl), and (4') 5- or 6-membered aromatic heterocyclic group (e.g., 4-pyridyl), or
(B) 5- to 7-membered cyclic carbamoyl (e.g., 1-pyrrolidinylcarbonyl, 1-piperidylcarbonyl, 1-homopiperazinylcarbonyl) optionally having one group selected from
(1) $C_{1-6}$ alkyl (e.g., methyl, ethyl) optionally having one substituent selected from
(a) heterocyclic group (e.g., 1-pyrrolidinyl, benzodioxol-5-yl), and
(b) amino,
(2) amino,
(3) N—$C_{1-6}$ alkyl-N—($C_{1-6}$ alkyl-carbonyl)amino (e.g., N-acetyl-N-ethylamino),
(4) heterocyclic group (e.g., 1-pyrrolidinyl), and
(5) $C_{1-6}$ alkyl-carbonyl (e.g., acetyl, propionyl) optionally having one substituent selected from
(a) hydroxy,
(b) $C_{1-6}$ alkoxy (e.g., methoxy),
(c) amino, and
(d) $C_{1-6}$ alkylamino (e.g., isopropylamino);
$R^3$ is hydroxy optionally having
(1) $C_{1-6}$ alkyl (e.g., methyl, ethyl) optionally having one $C_{1-6}$ alkoxy (e.g., ethoxy), or
(2) $C_{1-6}$ alkyl (e.g., methyl, ethyl) optionally having 1 to 3 halogen atoms (e.g., fluorine atom)
[preferably, hydroxy substituted by
(1) $C_{1-6}$ alkyl (e.g., methyl, ethyl) optionally having one $C_{1-6}$ alkoxy (e.g., ethoxy), or
(2) $C_{1-6}$ alkyl (e.g., methyl, ethyl) optionally having 1 to 3 halogen atoms (e.g., fluorine atom)];
$R^4$ is
(1) hydrogen atom, or
(2) $C_{1-6}$ alkyl (e.g., methyl, ethyl) optionally having one substituent selected from
(1') $C_{3-6}$ cycloalkyl (e.g., cyclopropyl),
(2') $C_{6-10}$ aryl (e.g., phenyl) optionally having one $C_{1-6}$ alkoxy (e.g., methoxy),
(3') $C_{1-6}$ alkyl-carbonyl (e.g., tert-butylcarbonyl),
(4') $C_{6-10}$ aryl-carbonyl (e.g., benzoyl),
(5') $C_{1-6}$ alkoxy-carbonyl (e.g., ethoxycarbonyl),
(6') $C_{6-10}$ aryl-carbamoyl (e.g., phenylcarbamoyl),
(7') heterocyclic group (e.g., 2-pyridyl),
(8') $C_{6-10}$ aryloxy (e.g., phenoxy), and
(9') carboxy;
$R^{A1}$ is a hydrogen atom or a $C_{1-6}$ alkyl group (e.g., methyl, ethyl, n-propyl); and
$R^{A2}$ is a hydrogen atom or a $C_{1-6}$ alkyl group (e.g., methyl).
[Compound (I"-2)]
Compound (I") wherein
X is O, S or N($C_{1-6}$ alkyl) (particularly N(methyl));
$R^2$ is
(A) carbamoyl optionally having 1 or 2 substituents selected from
(1) $C_{1-6}$ alkyl (e.g., methyl, ethyl, propyl, isopropyl, 2-methylpropyl, 2,2-dimethylpropyl, 1-methylbutyl) optionally having 1 or 2 substituents selected from
(1') halogen atom (e.g., fluorine atom),
(2') cyano,
(3') amino,
(4') $C_{1-6}$ alkylamino (e.g., isopropylamino),
(5') di-$C_{1-6}$ alkylamino (e.g., dimethylamino, diethylamino) optionally having one hydroxy,
(6') $C_{1-6}$ alkoxy-carbonylamino (e.g., tert-butoxycarbonylamino),
(7') hydroxy,
(8') di-$C_{1-6}$ alkyl-carbamoyl (e.g., diethylcarbamoyl), (9') 5- to 7-membered cyclic carbamoyl (e.g., 1-pyrrolidinylcarbonyl),
(10') heterocyclic group (e.g., 1-pyrrolidinyl, 2-pyrrolidinyl, 3-pyrrolidinyl, 1-pyrazolyl, 1-imidazolyl, 1-piperidyl, 2-piperidyl, 3-piperidyl, 4-piperidyl, 1-piperazinyl, 1-morpholinyl, 2-pyridyl, 3-pyridyl, 2-tetrahydrofuryl) optionally having one
   (a) hydroxy, or
   (b) $C_{1-6}$ alkyl (e.g., methyl, ethyl) optionally having one hydroxy,
(11') $C_{1-6}$ alkoxy-carbonyl (e.g., ethoxycarbonyl), and
(12') $C_{3-6}$ cycloalkyl (e.g., cyclohexyl),
(2) $C_{3-6}$ cycloalkyl (e.g., cyclohexyl) optionally having 1 or 2 substituents selected from
   (1') amino, and
   (2') hydroxy,
(3) $C_{6-10}$ aryl (e.g., phenyl), and
(4) heterocyclic group (e.g., 3-pyrrolidinyl, 4-piperidyl, S-oxido-tetrahydrothiopyran-4-yl) optionally having one substituent selected from
   (1') $C_{1-6}$ alkyl (e.g., methyl) optionally having 1 or 2 substituents selected from
      (a) $C_{6-10}$ aryl (e.g., phenyl), and
      (b) hydroxy,
   (2') $C_{1-6}$ alkyl-carbonyl (e.g., methylcarbonyl) optionally having one substituent selected from
      (a) $C_{1-6}$ alkyl-carbonyloxy (e.g., methylcarbonyloxy), and
      (b) hydroxy,
   (3') $C_{1-6}$ alkoxy-carbonyl (e.g., tert-butoxycarbonyl), and
   (4') 5- or 6-membered aromatic heterocyclic group (e.g., 4-pyridyl), or
(B) 5- to 7-membered cyclic carbamoyl (e.g., 1-pyrrolidinylcarbonyl, 1-piperidylcarbonyl, 1-homopiperazinylcarbonyl) optionally having one substituent selected from
(1) $C_{1-6}$ alkyl (e.g., methyl, ethyl) optionally having one substituent selected from
   (a) heterocyclic group (e.g., 1-pyrrolidinyl, benzodioxol-5-yl), and
   (b) amino,
(2) amino,
(3) N—$C_{1-6}$ alkyl-N—($C_{1-6}$ alkyl-carbonyl)amino (e.g., N-acetyl-N-ethylamino),
(4) heterocyclic group (e.g., 1-pyrrolidinyl), and
(5) $C_{1-6}$ alkyl-carbonyl (e.g., acetyl, propionyl) optionally having one substituent selected from
   (a) hydroxy,
   (b) $C_{1-6}$ alkoxy (e.g., methoxy),
   (c) amino, and
   (d) $C_{1-6}$ alkylamino (e.g., isopropylamino);
$R^3$ is hydroxy optionally having
(1) $C_{1-6}$ alkyl (e.g., methyl, ethyl, n-propyl, i-propyl) optionally having one $C_{1-6}$ alkoxy (e.g., ethoxy), or
(2) $C_{1-6}$ alkyl (e.g., methyl, ethyl, n-propyl, i-propyl) optionally having 1 to 3 halogen atoms (e.g., fluorine atom)
[preferably, hydroxyl substituted by
(1) $C_{1-6}$ alkyl (e.g., methyl, ethyl) optionally having one $C_{1-6}$ alkoxy (e.g., ethoxy), or
(2) $C_{1-6}$ alkyl (e.g., methyl, ethyl) optionally having 1 to 3 halogen atoms (e.g., fluorine atom)];
$R^4$ is
(1) hydrogen atom, or
(2) $C_{1-6}$ alkyl (e.g., methyl, ethyl) optionally having one substituent selected from
   (1') $C_{3-6}$ cycloalkyl (e.g., cyclopropyl),
   (2') $C_{6-10}$ aryl (e.g., phenyl) optionally having (i) 1 or 2 $C_{1-6}$ alkoxy (e.g., methoxy) or (ii) 1 to 3 halogen atoms (e.g., chlorine atom),
   (3') $C_{1-6}$ alkyl-carbonyl (e.g., tert-butylcarbonyl),
   (4') $C_{6-10}$ aryl-carbonyl (e.g., benzoyl) optionally having one halogen atom (e.g., chlorine atom) or $C_{1-6}$ alkoxy (e.g., methoxy),
   (5') $C_{1-6}$ alkoxy-carbonyl (e.g., ethoxycarbonyl),
   (6') $C_{6-10}$ aryl-carbamoyl (e.g., phenylcarbamoyl),
   (7') heterocyclic group (e.g., 2-pyridyl),
   (8') $C_{6-10}$ aryloxy (e.g., phenoxy), and
   (9') carboxy;
$R^{41}$ is a hydrogen atom or a $C_{1-6}$ alkyl group (e.g., methyl, ethyl, n-propyl); and
$R^{42}$ is a hydrogen atom or a $C_{1-6}$ alkyl group (e.g., methyl).
[Compound (I''-3)]
3-ethoxy-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide;
N-[1-(hydroxyacetyl)piperidin-4-yl]-1,6-dimethyl-4-oxo-5-(2-oxo-2-phenylethyl)-3-(2,2,2-trifluoroethoxy)-4,5-dihydro-1H-pyrrolo[3,2-c]pyridine-2-carboxamide;
6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide;
or a salt thereof.

When compound (I) is a salt, examples of such salt include metal salt, ammonium salt, a salt with organic base, a salt with inorganic acid, a salt with organic acid, a salt with basic or acidic amino acid and the like. Preferable examples of the metal salt include alkali metal salt such as sodium salt, potassium salt and the like; alkaline earth metal salt such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like, and preferable examples of the salt with acidic amino acid include a salt with aspartic acid, glutamic acid and the like.

Of these, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

The production method of the compound of the present invention is described in the following.

In each of the following production methods, when alkylation reaction, amidation reaction (condensation reaction), esterification reaction, reduction reaction, reductive amination reaction, amination reaction, halogenation reaction, oxidation reaction and the like are performed, these reactions are performed according to known methods. Examples of such methods include the methods described in Organic Functional Group Preparations, 2nd edition, Academic Press, Inc. (1989), Comprehensive Organic Transformations, VCH Publishers Inc. (1989) and the like, and the like. Protection and deprotection reactions are performed according to known methods, for example, the methods described in Protective Groups in Organic Synthesis, 3rd edition, John Wiley and Sons, Inc. (1999) or a method analogous thereto.

The solvents indicated in generic terms, which are used in the following reactions are explained in the following.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane and the like.

Examples of the "esters" include ethyl acetate, methyl acetate, tert-butyl acetate and the like.

Examples of the "hydrocarbons" include benzene, toluene, xylene, cyclohexane, hexane, pentane and the like.

Examples of the "amides" include N,N-dimethylformamide, N,N-dimethylacetamide, hexamethylphosphoric triamide and the like.

Examples of the "halogenated hydrocarbons" include dichloromethane, chloroform, carbon tetrachloride, 1,2-dichloroethane, tetrachloroethylene, chlorobenzene and the like.

Examples of the "nitriles" include acetonitrile, propionitrile and the like.

Examples of the "ketones" include acetone, 2-butanone and the like.

Examples of the "organic acids" include formic acid, acetic acid, propionic acid, trifluoroacetic acid, methanesulfonic acid and the like.

Examples of the "aromatic amines" include pyridine, 2,6-lutidine, quinoline and the like.

Examples of the "sulfoxides" include dimethyl sulfoxide and the like.

In the present production methods, a starting material compound and a production intermediate may be salts. As such salt, those similar to the salts of the aforementioned compound (I) can be mentioned.

Compound (I) can be produced, for example, by [Method A] shown below or a method analogous thereto.

[Method A]

Compound (III) is hydrolyzed and the obtained compound (II) is condensed with amine, whereby compound (I) can be produced.

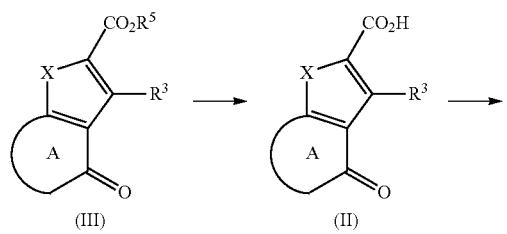

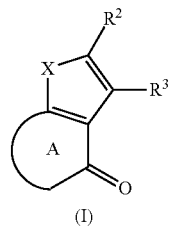

wherein $R^5$ is $C_{1-6}$ alkyl or benzyl, and other symbols are as defined above.

Examples of $C_{1-6}$ alkyl for $R^5$ include methyl, ethyl and the like, preferably ethyl.

Compound (III) can be produced according to the production methods of compound (IIIa) and compound (IIIb) shown below.

Compound (III) can be converted to compound (II) by hydrolysis under acidic or basic conditions in a solvent that does not adversely influence the reaction. Particularly, when $R^5$ is benzyl, a catalytic hydrogenation reaction in a solvent that does not adversely influence the reaction can be used.

As the acid used for hydrolysis, hydrochloric acid, sulfuric acid and the like can be mentioned, and as the base, sodium hydroxide, potassium hydroxide, lithium hydroxide and the like can be mentioned. The amount thereof is generally 1 to 20 molar equivalent, preferably 1 to 10 molar equivalents, per 1 mol of compound (III).

Examples of the catalyst used for the catalytic hydrogenation reaction include Raney-nickel, platinum oxide, or palladium, ruthenium, rhodium, iridium and the like on activated carbon, barium sulfate, calcium carbonate and the like. The amount thereof is generally 0.01 to 1 molar equivalent, preferably 0.05 to 0.5 molar equivalent, per 1 mol of compound (III).

As the hydrogen source, hydrogen, cyclohexene, hydrazine, ammonium formate and the like are used.

Examples of the solvent that does not adversely influence the reaction include ethers, alcohols, hydrocarbons, ketones, nitriles, amides, esters, water and the like, with preference given to alcohols, ethers and water. Two or more kinds of the above-mentioned solvents may be used in a mixture at an appropriate ratio.

The reaction temperature is generally 0 to 100° C., preferably 20 to 60° C.

The reaction time is generally 0.5 to 100 hr, preferably 1 to 48 hr.

The condensation reaction of compound (II) and amine can be performed in a solvent that does not adversely influence the reaction and using, for example, a condensation agent.

The amine to be used in this reaction can be condensed with carboxy group of compound (II) to form a "carbamoyl optionally having substituent(s)" for $R^2$. Such amine may be a commercially available one, or can be produced from the corresponding starting material compound by a method known per se.

Examples of the condensation agent include carbodiimide (e.g., dicyclohexylcarbodiimide (DCCD), water-soluble carbodiimide (WSCD) and the like), phosphate ester (e.g., diethyl cyanophosphonate, diethyl chlorophosphonate, diphenyl phosphoroazide and the like), BOP reagent (1H-benzotriazol-1-yloxytripyrrolidinophosphonium hexafluorophosphate (PyBOP)), 2-ethoxy-1-ethoxycarbonyl-1,2-dihydroquinoline (EEDQ), carbonyldiimidazole and the like, with preference given to WSCD.

The amount of each of the amine and condensation agent to be used is generally 1 to 10 molar equivalents, preferably 1 to 2 molar equivalents, per 1 mol of compound (II).

Examples of the solvent that does not adversely influence the reaction include ethers, hydrocarbons, ketones, nitriles, amides, esters and the like, with preference given to ethers and amides. Two or more kinds of the above-mentioned solvents may be used in a mixture at an appropriate ratio.

The reaction temperature is generally 0 to 100° C., preferably 20 to 60° C.

The reaction time is generally 0.5 to 100 hr, preferably 1 to 48 hr.

In compounds (III), compound (IIIa) wherein $R^3$ is hydroxy can be produced, for example, [Method B] shown below or a method analogous thereto.

[Method B]

Compound (V) is reacted with compound (1) and the obtained compound (IV) is treated with a base to give compound (IIIa).

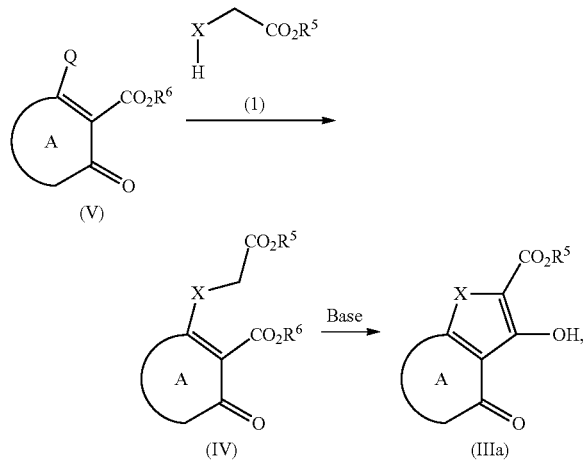

wherein Q is a leaving group, $R^6$ is $C_{1-6}$ alkyl, and other symbols are as defined above.

Examples of the leaving group for Q include halogen atom (e.g., chlorine, bromine, iodine), optionally halogenated $C_{1-6}$ alkylsulfonyloxy (e.g., methylsulfonyloxy, ethylsulfonyloxy, trifluoromethylsulfonyloxy), $C_{6-10}$ arylsulfonyloxy optionally having $C_{1-6}$ alkyl (e.g., benzenesulfonyloxy, 4-toluenesulfonyloxy), methylmercapto, methanesulfonyl and the like, with preference given to halogen atom.

Examples of the $C_{1-6}$ alkyl for $R^6$ include methyl, ethyl and the like.

Compound (V) can be produced according to the production methods of compound (Va) and compound (Va-2) shown below.

The reaction of compound (V) and compound (1) can be performed in the presence of a base as necessary and in a solvent that does not adversely influence the reaction.

Compound (1) may be a commercially available one, or can be produced from the corresponding starting material compound by a method known per se.

The amount of compound (1) to be used is generally 1 to 20 molar equivalents, preferably 1 to 10 molar equivalents, per 1 mol of compound (V). Examples of the base to be used as necessary include sodium hydride, sodium methoxide, sodium ethoxide, sodium carbonate, sodium hydrogen carbonate, sodium hydroxide, triethylamine, diisopropylethylamine, pyridine, 4-dimethylaminopyridine and the like. The amount thereof to be used is generally 1 to 20 molar equivalents, preferably 2 to 10 molar equivalents, per 1 mol of compound (V).

Examples of the solvent that does not adversely influence the reaction include ethers, hydrocarbons, alcohols, amides, esters and the like, with preference given to ethers and amides. Two or more kinds of the above-mentioned solvents may be used in a mixture at an appropriate ratio.

The reaction temperature is generally 0 to 100° C., preferably 20 to 90° C.

The reaction time is generally 0.5 to 100 hr, preferably 1 to 48 hr.

Compound (IV) can be converted to compound (IIIa) using a base in a solvent that does not adversely influence the reaction.

Examples of the base include sodium methoxide, sodium ethoxide, sodium hydroxide, triethylamine and the like and the amount thereof to be used is generally 1 to 20 molar equivalents, preferably 2 to 10 molar equivalents, per 1 mol of compound (IV).

Examples of the solvent that does not adversely influence the reaction include ethers, hydrocarbons, alcohols, amides, esters and the like, with preference given to ethers and amides. Two or more kinds of the above-mentioned solvents may be used in a mixture at an appropriate ratio.

The reaction temperature is generally 0 to 100° C., preferably 20 to 90° C.

The reaction time is generally 0.5 to 100 hr, preferably 1 to 48 hr.

Compound (V) can be directly converted to compound (IIIa) without isolating compound (IV).

In compound (III), compound (IIIb) wherein $R^3$ is alkoxy optionally having substituent(s) can be produced, for example, by [Method C] shown below or a method analogous thereto.

[Method C]

Compound (IIIa) is reacted with halogenated alkyl, sulfate ester, methanesulfonate ester optionally substituted by halogen atom(s) and the like to give compound (IIIb).

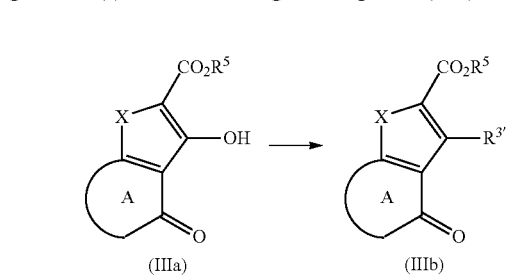

wherein $R^{3'}$ is alkoxy optionally having substituent(s), and other symbols are as defined above.

The "alkoxy optionally having substituent(s)" for $R^{3'}$ means "hydroxy substituted by alkyl optionally having substituent(s)" encompassed in the "hydroxy optionally having substituent(s)" for $R^3$.

The reaction between compound (IIIa) and halogenated alkyl, sulfate ester, methanesulfonate ester optionally substituted by halogen atom(s) and the like can be performed in the presence of a base in a solvent that does not adversely influence the reaction.

The halogenated alkyl, sulfate ester and methanesulfonate ester optionally substituted by halogen atom(s) used in this reaction can alkylate the hydroxyl group of compound (IIIa) to form "alkoxy optionally having substituent(s)" for $R^{3'}$. Such halogenated alkyl, sulfate ester, sulfate ester and methanesulfonate ester optionally substituted by halogen atom(s) may be commercially available ones, or can be produced from the corresponding starting material compound by a method known per se.

The amount of halogenated alkyl and the like to be used is generally 1 to 3 molar equivalents, preferably 1 to 2 molar equivalents, per 1 mol of compound (IIIa). Examples of the base to be used include sodium methoxide, sodium ethoxide, cesium carbonate, sodium carbonate, sodium hydrogen carbonate, sodium hydroxide, triethylamine, diisopropylethylamine, pyridine, 4-dimethylaminopyridine, 1,8-diazabicyclo[5.4.0]undec-7-ene (DBU) and the like, and the amount thereof to be used is generally 1 to 5 molar equivalents, preferably 1 to 3 molar equivalents, per 1 mol of compound (IIIa).

Examples of the solvent that does not adversely influence the reaction include ethers, hydrocarbons, alcohols, ketones, nitriles, amides, esters and the like, with preference given to ethers and amides. Two or more kinds of the above-mentioned solvents may be used in a mixture at an appropriate ratio.

The reaction temperature is generally 0 to 100° C., preferably 20 to 90° C.

The reaction time is generally 0.5 to 100 hr, preferably 1 to 48 hr.

Of compounds (V), 2-oxonicotinate ester (Va) wherein ring A is pyridine ring or fused pyridine ring can be produced, for example, by [Method D] shown below or a method analogous thereto.

[Method D]

Compound (VII) is reacted with malonate ester (3) and hydroxy of the obtained compound (VI) is converted to a leaving group Q to give compound (Va).

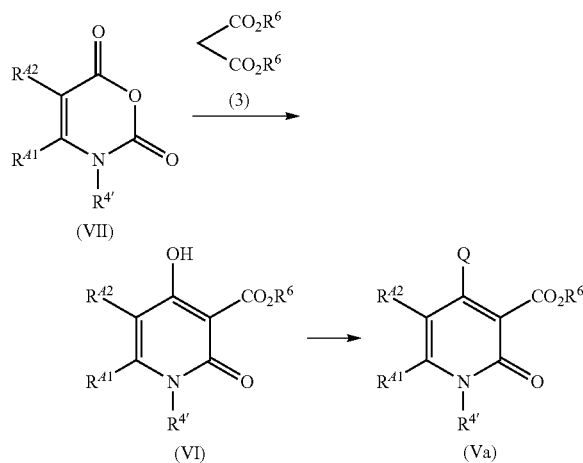

wherein $R^{4'}$ is hydrocarbon group optionally having substituent(s), and other symbols are as defined above.

As the "hydrocarbon group optionally having substituent(s)" for $R^{4'}$, those similar to the "hydrocarbon group optionally having substituent(s)" for $R^4$ can be mentioned.

The reaction of compound (VII) and malonate ester (3) can be performed in the presence of a base in a solvent that does not adversely influence the reaction.

Malonate ester (3) may be a commercially available one, or can be produced from the corresponding starting material compound by a method known per se.

The amount of malonate ester (3) to be used is generally 1 to 2 molar equivalents, preferably 1 to 1.5 molar equivalents, per 1 mol of compound (VII). Examples of the base to be used include sodium hydride, sodium methoxide, sodium ethoxide, sodium carbonate, sodium hydrogen carbonate, sodium hydroxide, triethylamine, diisopropylethylamine, pyridine, 4-dimethylaminopyridine, DBU and the like and the amount thereof to be used is generally 1 to 10 molar equivalents, preferably 1 to 5 molar equivalents, per 1 mol of compound (VII).

Examples of the solvent that does not adversely influence the reaction include ethers, hydrocarbons, ketones, nitriles, amides and the like, with preference given to ethers and amides. Two or more kinds of the above-mentioned solvents may be used in a mixture at an appropriate ratio.

The reaction temperature is generally 0 to 100° C., preferably 0 to 80° C.

The reaction time is generally 0.5 to 100 hr, preferably 1 to 48 hr.

Conversion of hydroxy of compound (VI) to leaving group Q can be performed by, for example, using a halogenating reagent and a sulfonylation reagent in a solvent that does not adversely influence the reaction or without solvent and in the presence of a base as necessary.

Examples of the halogenating reagent include thionyl chloride, phosphoryl chloride, phosphorus pentachloride, phosphorus tribromide and the like.

The amount of the halogenating reagent to be used is generally 1 to 20 molar equivalents, preferably 2 to 10 molar equivalents, per 1 mol of compound (VI).

The reaction temperature is generally 0 to 130° C., preferably 20 to 130° C.

The reaction time is generally 0.5 to 100 hr, preferably 1 to 48 hr.

Examples of the sulfonylation reagent include trifluoromethanesulfonic acid anhydride, methanesulfonyl halide, benzenesulfonyl halide and the like and the amount thereof to be used is generally 1 to 2 molar equivalents, preferably 1 to 1.5 molar equivalents, per 1 mol of compound (VI). Examples of the base to be used as necessary include triethylamine, diisopropylethylamine, pyridine, 4-dimethylaminopyridine and the like and the amount thereof to be used is generally 2 to 5 molar equivalents, preferably 2 to 3 molar equivalents, per 1 mol of compound (VI).

Examples of the solvent that does not adversely influence the reaction include ethers, hydrocarbons, alcohols, amides, esters and the like, with preference given to ethers and amides. Two or more kinds of the above-mentioned solvents may be used in a mixture at an appropriate ratio.

The reaction temperature is generally −10 to 100° C., preferably 0 to 60° C.

The reaction time is generally 0.5 to 100 hr, preferably 1 to 48 hr.

Compound (VII) to be the starting material in [Method D] can be synthesized by a known method, for example, the method described in Journal of Heterocyclic Chemistry, vol. 12, pages 565-572 (1975).

Also, compound (Va) can be produced, for example, by [Method E] shown below or a method analogous thereto.

[Method E]

The hydroxy of compound (VIII-2) is converted to leaving group Q, and the obtained compound (VIII) is hydrolyzed to give compound (Va-2). This compound (Va-2) is reacted with halogenated hydrocarbon and the like to give compound (Va).

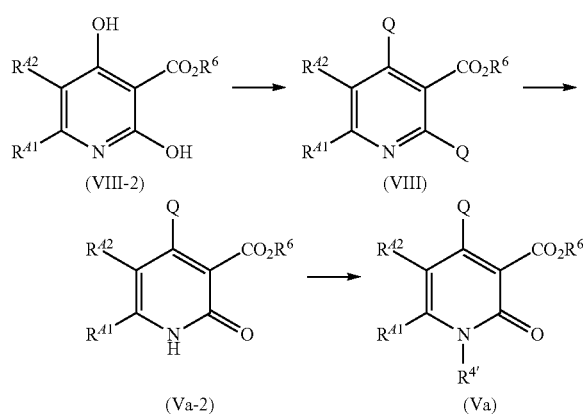

wherein each symbol is as defined above.

Compound (VIII) can be produced according to the synthesis method of compound (Va) in the aforementioned [Method D]. The amount of the halogenating reagent and the sulfonylation reagent to be used can be increased as necessary.

Hydrolysis of compound (VIII) can be performed, for example, after once substituting leaving group Q with acetoxy or alkoxy or directly under alkaline conditions or acidic conditions, in a solvent that does not adversely influence the reaction.

When the leaving group Q is once substituted with acetoxy or alkoxy, for example, sodium acetate, sodium methoxide, sodium ethoxide and the like can be used and the amount thereof to be used is generally 1 to 20 molar equivalents, preferably 1 to 5 molar equivalents, per 1 mol of compound (VIII).

For direct hydrolysis under acidic conditions, for example, acetic acid, hydrochloric acid, sulfuric acid, methanesulfonic acid and the like can be used as an acid.

For direct hydrolysis under alkaline conditions, for example, aqueous sodium hydroxide solution, aqueous potassium hydroxide solution, aqueous lithium hydroxide solution and the like can be used as a base.

Examples of the solvent that does not adversely influence the reaction include ethers, hydrocarbons, alcohols, ketones, nitriles, amides, water and the like, with preference given to ethers, amides and water. Two or more kinds of the above-mentioned solvents may be used in a mixture at an appropriate ratio.

The reaction temperature is generally 0 to 130° C., preferably 20 to 130° C.

The reaction time is generally 0.5 to 100 hr, preferably 1 to 48 hr.

Compound (Va-2) can be converted to compound (Va) by reacting compound (Va-2) with a compound represented by the formula $R^{4'}$-Q' wherein $R^{4'}$ is as defined above and Q' is a leaving group, in a solvent that does not adversely influence the reaction or without solvent in the presence of a base as necessary.

Examples of the leaving group for Q' include halogen atom (e.g., chlorine, bromine, iodine), optionally halogenated $C_{1-6}$ alkylsulfonyloxy (e.g., methylsulfonyloxy, ethylsulfonyloxy, trifluoromethylsulfonyloxy), $C_{6-10}$ arylsulfonyloxy optionally having $C_{1-6}$ alkyl (e.g., benzenesulfonyloxy, 4-toluenesulfonyloxy), methylmercapto, methanesulfonyl and the like, with preference given to halogen atom.

The amount of the compound represented by the formula $R^{4'}$-Q' to be used is generally 1 to 20 molar equivalents, preferably 2 to 10 molar equivalents, per 1 mol of compound (Va-2).

Examples of the base to be used as necessary include triethylamine, diisopropylethylamine, pyridine, 4-dimethylaminopyridine, sodium hydride, potassium carbonate, cesium carbonate, potassium tert-butoxide, sodium tert-butoxide and the like, with preference given to sodium tert-butoxide, and the amount thereof to be used is generally 2 to 5 molar equivalents, preferably 2 to 3 molar equivalents, per 1 mol of compound (Va-2).

Preferably, tetrabutylammonium bromide or the like is added to the reaction.

Examples of the solvent that does not adversely influence the reaction include ethers, hydrocarbons, alcohols, amides, esters and the like, preferably ethers and amides. Two or more kinds of the above-mentioned solvents may be used in a mixture at an appropriate ratio.

The reaction temperature is generally −10 to 100° C., preferably 0 to 60° C.

The reaction time is generally 0.5 to 100 hr, preferably 1 to 48 hr.

Compound (VIII-2) to be the starting material in [Method E] can be synthesized by a known method, for example, the method described in Journal of Organic Chemistry, vol. 46, pages 3040-3048 (1981).

In compounds (I), compound (Ia) and compound (Ib) can be produced, for example, [Method F] shown below or a method analogous thereto.

[Method F]

Compound (Ib) and compound (Ia) can be produced from compound (Ic) by reactions according to [Method E].

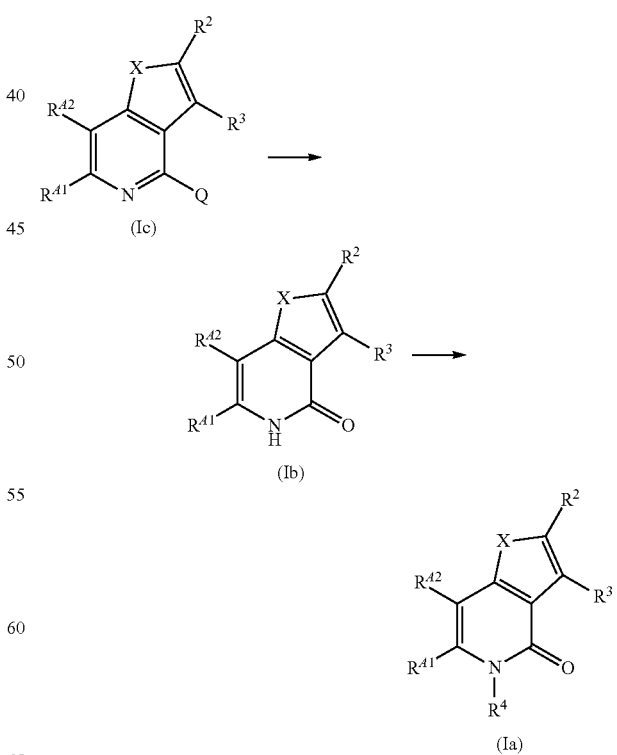

wherein each symbol is as defined above.

The reaction from compound (Ic) to compound (Ib) can be performed according to the reaction from compound (VIII) to compound (Va-2) in [Method E].

The reaction from compound (Ib) to compound (Ia) can be performed according to the reaction from compound (Va-2) to compound (Va) in [Method E].

Compound (Ic) can be produced according to the production method of compound (Ica) and compound (Icb) shown below.

In compounds (Ic), compound (Ica) wherein $R^3$ is hydroxy and compound (Icb) wherein $R^3$ is alkoxy optionally having substituent(s) (shown by $R^{3'}$ in the following formula (Icb)) can be produced, for example, by [Method G] shown below or a method analogous thereto.

[Method G]

Compound (Ica) and compound (Icb) can be produced from compound (VIII) by reactions according to [Method A], [Method B] and [Method C].

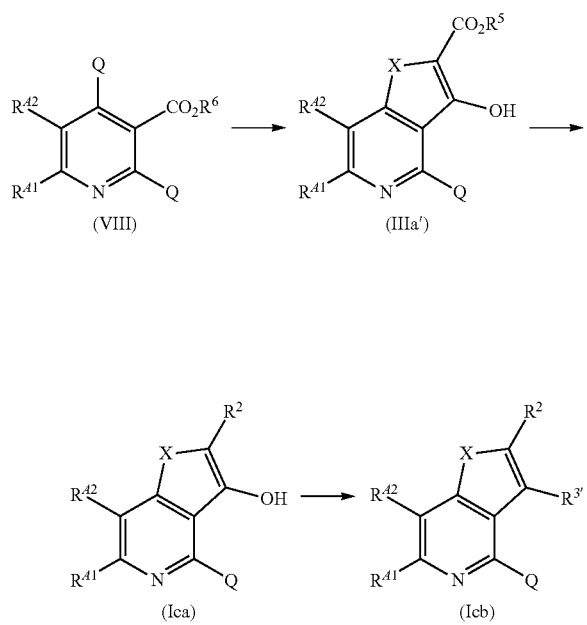

wherein each symbol is as defined above.

The reaction from compound (VIII) to compound (IIIa') can be performed according to [Method B].

The reaction from compound (IIIa') to compound (Ica) can be performed according to [Method A].

The reaction from compound (Ica) to compound (Icb) can be performed according to [Method C].

Also, compound (Ib) can be produced, for example, [Method H] shown below or a method analogous thereto.

[Method H]

Of compounds (Ib), compound (Ib') wherein $R^3$ is alkoxy optionally having substituent(s) (shown by $R^{3'}$ in the following formula (Ib')) can be produced by removing $R^{4''}$ from compound (Id) wherein $R^3$ is alkoxy optionally having substituent(s) (shown by $R^{3'}$ in the following formula (Id)) and $R^4$ is phenacyl optionally having substituent(s), methoxymethyl, 4-methoxybenzyl or 2,4-dimethoxybenzyl (shown by $R^{4''}$ in the following formula (Id)) from among compounds (Ia).

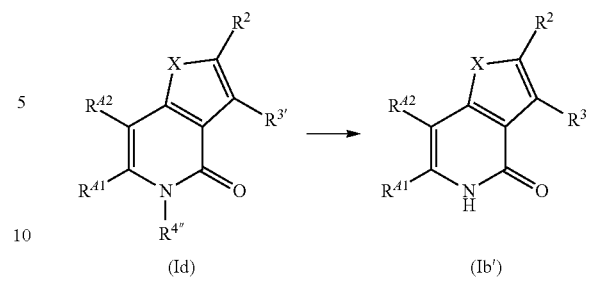

wherein $R^{4''}$ is phenacyl optionally having substituent(s), methoxymethyl, 4-methoxybenzyl or 2,4-dimethoxybenzyl, and other symbols are as defined above.

When $R^{4''}$ is phenacyl optionally having substituent(s), conversion of compound (Id) to compound (Ib') can be performed, for example, in the presence of metal such as zinc and the like under acidic conditions in a solvent that does not adversely influence the reaction. The amount of zinc to be used is generally 1 to 20 molar equivalents, preferably 1 to 10 molar equivalents, per 1 mol of compound (Id). As acid, hydrochloric acid, sulfuric acid and the like are used.

Examples of the solvent that does not adversely influence the reaction include ethers, hydrocarbons, alcohols, ketones, nitriles, amides, water and the like, with preference given to ethers, amides and water. Two or more kinds of the above-mentioned solvents may be used in a mixture at an appropriate ratio.

The reaction temperature is generally 20 to 120° C., preferably 20 to 100° C.

The reaction time is generally 0.5 to 100 hr, preferably 1 to 24 hr.

When $R^{4''}$ is methoxymethyl, conversion of compound (Id) to compound (Ib') can be performed under acidic conditions in a solvent that does not adversely influence the reaction. As acid, hydrochloric acid, sulfuric acid and the like can be used.

Examples of the solvent that does not adversely influence the reaction include ethers, hydrocarbons, alcohols, ketones, nitriles, amides, water and the like, with preference given to ethers, amides and water. Two or more kinds of the above-mentioned solvents may be used in a mixture at an appropriate ratio.

The reaction temperature is generally 0 to 120° C., preferably 20 to 60° C.

The reaction time is generally 0.5 to 100 hr, preferably 1 to 24 hr.

When $R^{4''}$ is 4-methoxybenzyl, conversion of compound (Id) to compound (Ib') can be performed under strong acidic conditions in a solvent that does not adversely influence the reaction. As acid, trifluoroacetic acid, trifluoromethanesulfonic acid and the like can be used. In this case, anisole can be used as a cation scavenger in an amount of generally 1 to 20 molar equivalents, preferably 1 to 5 molar equivalents, per 1 mol of compound (Id).

Examples of the solvent that does not adversely influence the reaction include ethers, hydrocarbons, alcohols, ketones, nitriles, amides, and the like, preferably ethers and amides. Two or more kinds of the above-mentioned solvents may be used in a mixture at an appropriate ratio.

The reaction temperature is generally 0 to 120° C., preferably 20 to 60° C.

The reaction time is generally 0.5 to 100 hr, preferably 1 to 24 hr.

When $R^{4''}$ is 2,4-dimethoxybenzyl, conversion of compound (Id) to compound (Ib') can be performed in the presence of an oxidant such as cerium (IV) diammonium nitrate (CAN), 2,3-dichloro-5,6-dicyano-1,4-benzoquinone (DDQ) and the like in a solvent that does not adversely influence the reaction.

The amount of the oxidant to be used is generally 1 to 20 molar equivalents, preferably 1 to 5 molar equivalents, per 1 mol of compound (Id).

Examples of the solvent that does not adversely influence the reaction include ethers, hydrocarbons, alcohols, ketones, nitriles, amides, water and the like, with preference given to ethers, nitriles, amides and water. Two or more kinds of the above-mentioned solvents may be used in a mixture at an appropriate ratio.

The reaction temperature is generally 0 to 120° C., preferably 20 to 60° C.

The reaction time is generally 0.5 to 100 hr, preferably 1 to 24 hr.

Also, compound (IIIa) can be produced, for example, by [Method I] shown below or a method analogous thereto.
[Method I]
Compound (Vb) is reacted with compound (4) to give compound (IIIa).

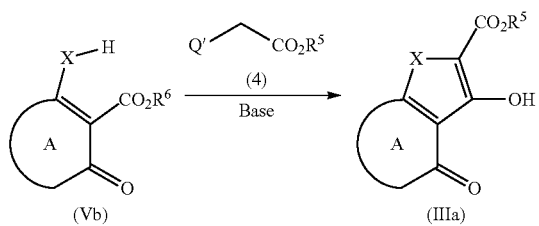

wherein Q' is a leaving group, and other symbols are as defined above.

Examples of the leaving group for Q' include those similar to the leaving group for the aforementioned Q, with preference given to halogen atom.

Compound (4) may be a commercially available reagent, or can be synthesized by a method known per se.

Compound (Vb), for example, 6-amino-2,4-dioxo-1,2,3,4-tetrahydropyrimidine-5-carboxylate derivative and the like, to be the starting material in [Method I] can be synthesized by a known method, for example, the method described in Journal of Chemical Society of Japan, vol. 46, pages 3849-3853 (1973). For example, 2-mercapto-4-oxo-1,4-dihydroquinoline-3-carboxylate derivative and the like can be synthesized by a known method, for example, the method described in Journal of Heterocyclic Chemistry, vol. 27, pages 839-843 (1990).

The reaction between compound (Vb) and compound (4) can be performed in the presence of a base in a solvent that does not adversely influence the reaction.

The amount of compound (4) to be used is generally 1 to 3 molar equivalents, preferably 1 to 2 molar equivalents, per 1 mol of compound (Vb). Examples of the base include sodium methoxide, sodium ethoxide, sodium carbonate, sodium hydrogen carbonate, sodium hydroxide, triethylamine, diisopropylethylamine, pyridine, 4-dimethylaminopyridine and the like and the amount thereof to be used is generally 2 to 5 molar equivalents, preferably 2 to 3 molar equivalents, per 1 mol of compound (Vb).

Examples of the solvent that does not adversely influence the reaction include ethers, hydrocarbons, alcohols, ketones, nitriles, amides, water and the like, with preference given to ethers, amides and water. Two or more kinds of the above-mentioned solvents may be used in a mixture at an appropriate ratio.

The reaction temperature is generally 20 to 120° C., preferably 20 to 100° C.

The reaction time is generally 0.5 to 100 hr, preferably 1 to 24 hr.

A compound within the scope of the present invention can also be produced by applying a means known per se to compound (I) for introduction of substituents and conversion of functional groups. For conversion of substituents, a known conventional method can be used. For example, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, amination of nitro by reduction, alkylation of hydroxy, substitution and amination of hydroxy and the like can be mentioned. When a reactive substituent that causes non-objective reaction is present during the introduction of substituents and conversion of functional groups, a protecting group is introduced in advance as necessary into the reactive substituent by a means known per se, and the protecting group is removed by a means known per se after the objective reaction, whereby the compound within the scope of the present invention can also be produced.

In the above-mentioned production method, when the starting compound or the compound of the present invention has an amino group, a carboxyl group, a hydroxy group or a mercapto group as a substituent, a protecting group generally used in peptide chemistry and the like may be introduced into these groups. The protecting group can be removed according to a conventional method in any step in each scheme.

Compound (I) can be isolated and purified by a means known per se, such as phase transfer, concentration, solvent extraction, fractionation, liquid conversion, crystallization, recrystallization, chromatography and the like. When compound (I) is obtained as a free compound, it can be converted to a desired salt by a method known per se or a method analogous thereto. Conversely, when the compound is obtained as a salt, it can be converted to a free form or other desired salt by a method known per se or a method analogous thereto.

Compound (I) may be used as a prodrug. A prodrug of compound (I) means a compound converted to compound (I) by a reaction due to an enzyme, a gastric acid, etc. under the physiological condition in the living body, that is, a compound converted to compound (I) by oxidation, reduction, hydrolysis, etc. due to an enzyme, a compound converted to compound (I) by hydrolysis etc. due to gastric acid, and the like.

A prodrug of compound (I) may be a compound obtained by subjecting an amino in compound (I) to an acylation, alkylation or phosphorylation (e.g., a compound obtained by subjecting an amino in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in compound (I) to acylation, alkylation, phosphorylation or boration (e.g., a compound obtained by subjecting hydroxy in the compound (I) of the present invention to acetylation, palmitoylation, propanoylation, pivaloylation, succinylation, fumarylation, alanylation or dimethylaminomethylcarbonylation); a compound obtained by subjecting carboxy in compound (I) to esterification or amidation (e.g., a compound obtained by subjecting carboxy in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from compound (I) by a method known per se.

A prodrug of compound (I) may also be a compound converted into compound (I) under physiological conditions, such as those described in IYAKUHIN no KAIHATSU (Development of Pharmaceuticals), Vol. 7, Design of Molecules, p. 163-198, Published by HIROKAWA SHOTEN (1990).

When compound (I) has an isomer such as optical isomer, stereoisomer, positional isomer, rotational isomer and the like, any isomer and a mixture thereof are encompassed in compound (I). For example, when compound (I) has an optical isomer, an optical isomer resolved from a racemate is also encompassed in compound (I). Such isomers can be obtained as independent products by a synthesis means or a separation means (concentration, solvent extraction, column chromatography, recrystallization and the like) known per se.

Compound (I) may be a crystal, and both a single crystal and crystal mixtures are encompassed in compound (I). Crystals can be produced by crystallization according to crystallization methods known per se.

Compound (I) may also be a cocrystal.

Compound (I) may be a hydrate, a non-hydrate, a solvate or a non-solvate, both of which are encompassed in compound (I) and the like.

A compound labeled with an isotope (e.g., $^2$H, $^3$H, $^{14}$C, $^{35}$S, $^{125}$I etc.) is also encompassed in compound (I).

Compound (I) of the present invention, or a salt thereof, or a prodrug thereof (sometimes to be abbreviated as "the compound of the present invention" in the present specification) interacts, for example, with human Smo protein and changes the steric structure thereof, whereby formation of a complex with a protein involved in the signal transduction in the cytoplasm is inhibited and the Hedgehog signal transduction system is inhibited. Alternatively, the compound of the present invention interacts with human Smo protein and directly inhibits formation of a complex of human Smo protein with a protein involved in the Hedgehog signal transduction system in the cytoplasm, whereby the Hedgehog signal transduction system is inhibited. Alternatively, the compound of the present invention interacts with a site of an Smo protein, for example, phosphorylation site and the like, which is modified by a protein involved in the Hedgehog signal transduction system, whereby modification such as phosphorylation of Smo and the like is inhibited and the Hedgehog signal transduction system is inhibited.

Inhibition of the Hedgehog signal transduction system can be measured, for example, by quantifying a decrease in the expression level of a reporter gene connected to the downstream of the Gli binding site based on the fluorescence intensity according to Experimental Example 1. Alternatively, it can be measured by quantifying the expression of Gli-1 mRNA in a cell extract by quantitative PCR method and the like. A compound that inhibits Hedgehog signal targets Smo, which can be confirmed, for example, by binding fluorescence-labeled Cyclopamine and a test compound to cells expressing Smo, measuring the fluorescence level of the cell, and comparing the value with that without addition of a test compound to find a decrease.

Accordingly, the compound of the present invention is useful as an Smo inhibitor for mammals (e.g., mouse, rat, hamster, rabbit, cat, dog, bovine, sheep, monkey, human, etc.). The compound of the present invention is used as a pharmaceutical agent such as an agent for the prophylaxis or treatment of diseases possibly influenced by Smo, for example, cancer [e.g., colorectal cancer (e.g., colon cancer, rectal cancer, anal cancer, familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic duct cancer, pancreatic endocrine tumor, etc.), pharyngeal cancer, laryngeal cancer, esophageal cancer, gastric cancer (e.g., papillary adenocarcinoma, mucinous adenocarcinoma, adenosquamous cancer, etc.), duodenal cancer, small intestinal cancer, breast cancer (e.g., invasive ductal breast carcinoma, ductal cancer in situ, inflammatory breast cancer, etc.), ovarian cancer (e.g., ovarian epithelial cancer, extragonadal germ cell tumor, ovarian germ cell tumor, ovarian low malignant potential tumor, etc.), testicular tumor, prostate cancer (e.g., hormone-dependent prostate cancer, non-hormone dependent prostate cancer, etc.), liver cancer (e.g., hepatocellular carcinoma, primary liver cancer, extrahepatic bile duct cancer, etc.), thyroid cancer (e.g., medullary thyroid cancer, etc.), kidney cancer (e.g., renal cell carcinoma, renal pelvis and ureter transitional cell cancer, etc.), uterus cancer (e.g., cervical cancer, cancer of uterine body, uterine sarcoma, etc.), brain tumor (e.g., medulloblastoma, glioma, pineal astrocytoma, pilocytic astrocytoma, diffuse astrocytoma, anaplastic astrocytoma, pituitary adenoma, etc.), retinoblastoma, skin cancer (e.g., basal cell carcinoma, malignant melanoma, etc.), sarcoma (e.g., rhabdomyosarcoma, leiomyosarcoma, soft tissue sarcoma, etc.), malignant bone tumor, urinary bladder cancer, blood cancer (e.g., multiple myeloma, leukemia, malignant lymphoma, Hodgkin's disease, chronic myeloproliferative disorder, etc.), cancer unknown primary etc.], a cancer growth inhibitor, a cancer metastasis inhibitor, an apoptosis promoter and the like. Among these, the compound of the present invention is effective, for example, for brain tumor, skin cancer, lung cancer, pancreatic cancer, cancer of the bile duct, prostate cancer, esophagus cancer, gastric cancer, colorectal cancer, sarcoma and breast cancer. Especially, the compound of the present invention is effective for glioma, medulloblastoma, basal cell tumor, small cell lung cancer, pancreatic cancer, cancer of the bile duct, prostate cancer, esophagus cancer, gastric cancer, colorectal cancer, rhabdomyosarcoma and breast cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pharmaceutical field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be blended. A prepared injection is generally filled in an ampoule.

While the content of the compound of the present invention in the pharmaceutical agent of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the pharmaceutical agent of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, pharmaceutical agents inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, episteride, and the like), aderenal cortex hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), thyroid hormone, and DDS (Drug Delivery System) preparations thereof, and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS (Drug Delivery System) preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine, and the like), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factors" in the "pharmaceutical agents inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα, and the like], (2) insulin or substances possessing substantially the same activity as insulin [e.g., insulin, IGF (insulin-like growth factor)-1, IGF-2, and the like], (3) FGF (fibroblast growth factor) or substances possessing substantially the same activity as FGF [e.g., acidic FGF, basic FGF, KGF (keratinocyte growth factor), FGF-10, and the like], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin, and the like].

Examples of the "cell growth factor receptors" include any receptors capable of binding to the aforementioned cell growth factors, including EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

As the "pharmaceutical agents inhibiting the action of cell growth factors or cell growth factor receptors", EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK(MEK1/2) inhibitor, MET inhibitor, CDK inhibitor, Akt inhibitor, ERK inhibitor and the like are used. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R), 3-dihydroxypropoxy]-3,4-difluoro-2-(2-fluoro-4-iodophenylamino)benzamide (PD-0325901), Everolimus (RAD001) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), other angiogenesis inhibitors (e.g., humagillin, shark extract, COX-2 inhibitor, and the like), α-blockers (e.g., tamsulosin hydrochloride, and the like), bisphosphonic acids (e.g., pamidronate, zoledronate, and the like), thalidomide, 5-azacytidine, decitabine, proteasome inhibitor (e.g., bortezomib, and the like), antitumor antibody such as anti-CD20 antibody and the like, toxin labeled antibody and the like can also be used.

By combining the compound of the present invention and a concomitant drug, a superior effect such as (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods: (1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (e.g., the compound of the present invention and the concomitant drug are administered in this order, or in the reverse order). The dose of the concomitant drug is appropriately determined in accordance with its clinical dose, and the ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered by intravenous, intramuscular, subcutaneous or intra-organ administration, or directly to the lesion.

As a pharmacologically acceptable carrier which may be used for preparing the combination agent of the present invention, those similar to the aforementioned pharmacologically acceptable carriers, that can be used for the production of the pharmaceutical agent of the present invention, can be mentioned. Where necessary, the aforementioned additives that can be used for the production of the pharmaceutical agent of the present invention, such as preservatives, antioxidants, colorants, sweetening agents, adsorbents, wetting agents and the like can also be appropriately used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the entire preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the entire preparation.

The content of additives in the combination agent of the present invention varies depending on the dosage form, and is usually from about 1 to 99.99% by weight, preferably from about 10 to 90% by weight, based on the entire preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH adjuster (e.g., hydrochloric acid, sodium hydroxide and the like), a preservative (e.g., ethyl paraoxybenzoate, benzoic acid, methylparaben, propylparaben, benzyl alcohol and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch and the like), a disintegrating agent (e.g., starch, calcium carbonate and the like), a binder (e.g., starch, gum arabic, carboxymethylcellulose, polyvinylpyrrolidone, hydroxypropylcellulose and the like), a lubricant (e.g., talc, magnesium stearate, polyethylene glycol 6000 and the like) and the like may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid-acrylic acid copolymer, manufactured by Rohm, Del.), pigment (e.g., iron oxide red, titanium dioxide, etc.) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acid [e.g., cacao butter, Witepsols (manufactured by Dynamit Nobel, Germany), etc.], glycerides of medium chain fatty acid [e.g., Miglyols (manufactured by Dynamit Nobel, Germany), etc.], or vegetable oils (e.g., sesame oil, soybean oil, cotton seed oil and the like), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se, for example, a method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof.

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as tromethamol and the like, etc. are listed.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

The injection of the present invention appropriately contains additives usually used in an injection, for example, a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH regulator (e.g., hydrochloric acid, sodium hydroxide and the like), a preservative (e.g., ethyl parahydroxybenzoate, benzoic acid and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like. These additives are generally blended in a proportion usually used in an injection.

It is advantageous that pH of an injection be controlled from pH 2 to 12, preferably from pH 2.5 to 8.0, by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (manufactured by Rohm Pharma) such as Eudoragit RS-100, RL-100, RS-30D, RL-30D, RL-PO, RS-PO (ethyl acrylate/methyl methacrylate/trimethylchloride methacrylate/ethyl ammonium copolymer), Eudoragit NE-30D (methyl methacrylate/ethyl acrylate copolymer), and the like, hydrogenated oils such as hydrogenated castor oil (e.g., Lubri wax (manufactured by Freund Corporation) and the like), waxes such as carnauba wax, fatty acid glycerin ester, paraffin and the like, polyglycerin fatty acid esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (all of which are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 µm, further preferably, from about 500 to about 1400 µm.

Preparation of the Nucleus can be Effected by a Usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned productions method, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 µm to about 1500 µm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral administration agents and parenteral administration agents such as an injection and the like are used, and oral administration agents are preferable.

The immediate-release preparation, usually, may contain, in addition to an active component drug, also carriers, additives and excipients conventionally used in the pharmaceutical field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95 w/w %, preferably from about 1 to about 60 w/w % based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (e.g., Actisol, manufactured by Asahi Kasei Corporation), crospovidone (e.g., Kollidon CL, manufactured by BASF), low substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by absorbing water in contact with water, causing swelling, or making a channel between an effective ingredient and an excipient constituting the nucleus, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the immediate-release preparation.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (manufactured by Nippon Aerosil))), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one preparation for oral administration (e.g., granule, fine particle, tablet, capsule and the like) or made into one preparation for oral administration appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof.

Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include gelatins, dextrins, animal proteins or vegetable proteins such as soybean, wheat and psyllium seed protein and the like; rubber substances such as gum Arabic, guar gum, agar, xanthan and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the administration subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg body weight of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin and the like, macrolide type such as clarithromycin and the like etc.) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is explained in detail in the following by referring to Reference Examples, Examples, Formulation Examples and Experimental Examples, which are not to be construed as limitative.

In the Reference Examples and Examples, the purity of the compounds was measured under the following HPLC conditions.
measurement device: SHIMADZU Corporation LC-10 Avp system
column: CAPSEL PAK C18UG120 S-3 µm, 2.0×50 mm
solvent: Solution A; 0.1% trifluoroacetic acid-containing water,
Solution B; 0.1% trifluoroacetic acid-containing acetonitrile
gradient cycle: 0.00 min (Solution A/Solution B=90/10), 4.00 min (Solution A/Solution B=5/95), 5.50 min (Solution A/Solution B=5/95), 5.51 min (Solution A/Solution B=90/10), 8.00 min (Solution A/Solution B=90/10)
injection volume: 2 µl
flow rate: 0.5 ml/min
detection method: UV 220 nm In the Reference Examples and Examples, the purification of the compounds by preparative HPLC was performed under the following conditions.
1) measurement device: Gilson Company Inc., High Throughput Purification System
column: YMC CombiPrep ODS-A, S-5 µm, 50×20 mm
detection method: UV 220 nm
solvent: Solution A; 0.1% trifluoroacetic acid-containing water,
Solution B; 0.1% trifluoroacetic acid-containing acetonitrile
gradient cycle: representative example 0.00 min (Solution A/Solution B=98/2), 1.00 min (Solution A/Solution B=98/2), 5.20 min (Solution A/Solution B=0/100), 6.40 min (Solution A/Solution B=0/100), 6.50 min (Solution A/Solution B=98/2), 6.60 min (Solution A/Solution B=98/2), flow rate: 25 mL/min, or 0.00 min (Solution A/Solution B=90/10), 1.00 min (Solution A/Solution B=90/10), 4.00 min (Solution A/Solution B=10/95), 8.50 min (Solution A/Solution B=10/95), 8.60 min (Solution A/Solution B=90/10), 8.70 min (Solution A/Solution B=90/10)
flow rate: 20 ml/min
2) measurement device: Gilson Company Inc., High Throughput Purification System
column: YMC CombiPrep, ProC18 RS, S-5 µm, 20×50 mm (YMC)
solvent: SOLUTION A; 10 mM ammonium carbonate-containing water,
SOLUTION B; acetonitrile
gradient cycle: 0.00 min (SOLUTION A/SOLUTION B=95/5), 2.00 min (SOLUTION A/SOLUTION B=95/5), 4.02 min (SOLUTION A/SOLUTION B=5/95), 6.40 min (SOLUTION A/SOLUTION B=5/95), 6.50 min (SOLUTION A/SOLUTION B=95/5), 8.00 min (SOLUTION A/SOLUTION B=95/5)
3) measurement device: Gilson Company Inc., High Throughput Purification System
column: YMC CombiPrep, ProC18 RS, S-5 µm, 20×50 mm (YMC)
solvent: SOLUTION A; 0.1% trifluoroacetic acid-containing water,
SOLUTION B; 0.1% trifluoroacetic acid-containing acetonitrile
gradient cycle: 0.00 min (SOLUTION A/SOLUTION B=98/2), 1.00 min (SOLUTION A/SOLUTION B=98/2), 5.20 min (SOLUTION A/SOLUTION B=60/40), 5.40 min (SOLUTION A/SOLUTION B=5/95), 6.40 min (SOLUTION A/SOLUTION B=5/95), 6.50 min (SOLUTION A/SOLUTION B=98/2), 6.60 min (SOLUTION A/SOLUTION B=98/2)
injection volume: 500 µl, flow rate: 20 ml/min, detection method: UV 220 nm, 254 nm In the Reference Examples and Examples, mass spectrum (MS) was measured under the following conditions.
measurement device: Micromass platform II or Waters ZMD
ionization method: Atmospheric Pressure Chemical Ionization: APCI or electron impact ionization method (Electron Spray Ionization: ESI)

In the Reference Examples and Examples, HPLC-mass spectrum (LC-MS) was measured under the following conditions.
1) measurement device: Micromass ZMD, Agilent Technologies HP1100 and 1200 LC/MSD
column: CAPCELL PAK C18UG120, S-3 µm, 1.5×35 mm
solvent: SOLUTION A; 0.05% trifluoroacetic acid-containing water,
SOLUTION B; 0.04% trifluoroacetic acid-containing acetonitrile
gradient cycle: 0.00 min (Solution A/Solution B=90/10), 2.00 min (Solution A/Solution B=5/95), 2.75 min (Solution A/Solution B=5/95), 2.76 min (Solution A/Solution B=90/10), 3.45 min (Solution A/Solution B=90/10)
injection volume: 2 µl
flow rate: 0.5 ml/min
detection method: UV 220 nm
ionization method: electron impact ionization method (Electron Spray Ionization: ESI)
2) measurement device: Waters, 4-ch LC/MS system with MUX
column: CAPCELL PAK C18 UG-120, S-3 µm, 1.5×35 mm (Shiseido Co., Ltd.)
solvent: SOLUTION A; 5 mM ammonium acetate-containing water,
SOLUTION B; 5 mM ammonium acetate-containing acetonitrile gradient cycle: gradient: 0.00 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.30 min (SOLUTION A/SOLUTION B=100/0)
injection volume: 2 μL, flow rate: 0.5 mL/min, detection method: UV 220 nm
ionization method: electrospray ionization method (ESI)
measurement mode: full scan (positive+negative ions)
measured mass value range: m/z=150-750

$^1$H-NMR spectrum was measured using tetramethylsilane as the internal standard, using BRUKER AVANCE DPX-300 (300 MHz), AV300 (300 MHz), AV400 (400 MHz) and VARIAN Mercury-300 (300 MHz), and all δ values are expressed in ppm.

As the Microwave reaction apparatus, Emrys Optimizer, Biotage Japan Ltd. was used.

Unless otherwise specified, the numerical value of mixed solvent shows a volume mixing ratio of each solvent. Unless otherwise specified, % means weight %. While the room temperature (ambient temperature) in the present specification means a temperature of from about 10° C. to about 35° C., it is not particularly strictly limited.

Other abbreviations used in the specification mean the following:
s: singlet
d: doublet
t: triplet
q: quartet
m: multiplet
sext: sextet
br: broad
J: coupling constant
Hz: Hertz
CDCl$_3$: deuterated chloroform
DMSO-d$_6$: dimethyl sulfoxide-d$_6$
CD$_3$OD: deuterated methanol
$^1$H-NMR: proton nuclear magnetic resonance
LC/MS: liquid chromatography-mass spectrometry spectrum
DMF: N,N-dimethylformamide
DMSO: dimethyl sulfoxide
THF: tetrahydrofuran
WSCD: water-soluble carbodiimide (1-ethyl-3-(3-dimethylaminopropyl)carbodiimide) hydrochloride
HOBt: 1-hydroxybenzotriazole
Boc: tert-butoxycarbonyl
K$_2$CO$_3$: potassium carbonate
M: mol concentration Reference Example 1

Production of ethyl 4-hydroxy-2-oxo-1,2-dihydroquinoline-3-carboxylate

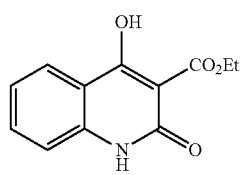 [SMILES: CCOC(=O)c1c(Cl)c2ccccc2[nH]c1=O]

To a solution of methyl anthranilate (121 g, 0.8 mol) and diethyl malonate (128 g, 0.8 mol) in ethanol (900 mL) was added a 20% solution (274 g) of sodium ethoxide in ethanol, and the mixture was stirred at room temperature for 30 min. Ethanol was evaporated, and the mixture was stirred at 140° C. for 12 hr. After cooling, the obtained solid was washed with diethyl ether, and dissolved in water. Insoluble materials were filtered off, the filtrate was acidified with 5N hydrochloric acid, and the precipitated solid was collected by filtration. The obtained solid was washed with water, and dried under reduced pressure to give the title compound (161 g, 86%) as a pale-yellow powder.

$^1$H-NMR (300 MHz, DMSO-d$_6$) δ:1.31 (3H, t, J=7.1 Hz), 4.34 (2H, q, J=7.1 Hz), 7.19-7.29 (2H, m), 7.63 (1H, td, J=7.8, 1.2 Hz), 7.94 (1H, d, J=8.1 Hz), 11.51 (1H, br s), 13.40 (1H, br s).

Reference Example 2

Production of ethyl 2,4-dichloroquinoline-3-carboxylate

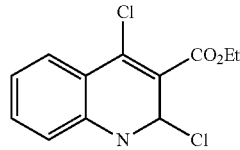

A mixture of the compound of Reference Example 1 (75 g, 0.32 mol) and phosphorus oxychloride (200 mL) was stirred at 110° C. for 6 hr. After cooling, the reaction mixture was concentrated under reduced pressure, the residue was dissolved in a small amount of ethyl acetate and the mixture was poured into ice water. The obtained mixture was extracted with ethyl acetate, and the extract was washed successively with 1N aqueous sodium hydroxide solution, water and brine, dried over magnesium sulfate, and concentrated under reduced pressure. The residue was purified by aminosilica gel chromatography (eluate; ethyl acetate/hexane=1/5) to give the title compound (68 g, 79%) as a white solid.

$^1$H-NMR (300 MHz, CDCl$_3$) δ:1.47 (3H, t, J=7.2 Hz), 4.54 (2H, q, J=7.2 Hz), 7.71 (1H, t, J=7.5 Hz), 7.85 (1H, t, J=7.5 Hz), 8.06 (1H, d, J=8.2 Hz), 8.24 (1H, d, J=8.2 Hz).

Reference Example 3

Production of ethyl 4-chloro-2-oxo-1,2-dihydroquinoline-3-carboxylate

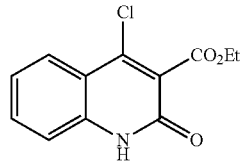

A mixture of the compound of Reference Example 2 (68.0 g, 0.25 mol) and sodium acetate (21.7 g, 0.26 mol) in acetic acid (200 mL) was stirred at 120° C. for 20 hr. After cooling, the reaction mixture was added to water, and the precipitated solid was collected by filtration. The obtained solid was washed with water, and dried under reduced pressure to give the title compound (58.8 g, 94%) as a white solid.

$^1$H-NMR (300 MHz, CDCl$_3$) δ:1.46 (3H, t, J=7.2 Hz), 4.53 (2H, q, J=7.2 Hz), 7.34 (1H, t, J=7.8 Hz), 7.43 (1H, d, J=8.1 Hz), 7.63 (1H, t, J=7.8 Hz), 8.00 (1H, d, J=8.1 Hz), 12.41 (1H, br s).

Reference Example 4

Production of ethyl 4-chloro-2-oxo-1-(2-oxo-2-phenylethyl)-1,2-dihydroquinoline-3-carboxylate

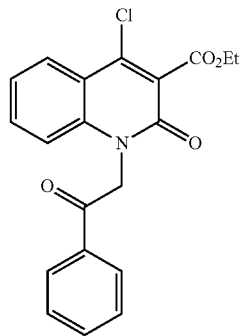 [SMILES: CCOC(=O)c1c(Cl)c2ccccc2n(CC(=O)c2ccccc2)c1=O]

To a solution of the compound of Reference Example 3 (10.0 g, 39.7 mmol) in DMF (160 mL) was added sodium hydride (60% in oil, 1.7 g, 41.7 mmol) under ice-cooling, and the mixture was stirred for 15 min. Phenacyl bromide (8.7 g, 43.7 mmol) was added to the obtained mixture under ice-cooling, and the mixture was stirred for 1 hr. The reaction mixture was added to water (1.5 L), and the mixture was extracted with ethyl acetate. The extract was washed with brine, dried over magnesium sulfate, and concentrated under reduced pressure. The residue was purified by silica gel chromatography (eluate; ethyl acetate/hexane=1/2-1/1) to give the title compound (10.5 g, 71%) as a pale-yellow solid.

$^1$H-NMR (300 MHz, CDCl$_3$) δ:1.42 (3H, t, J=7.2 Hz), 4.47 (2H, q, J=7.2 Hz), 5.80 (2H, s), 7.02 (1H, d, J=8.1 Hz), 7.34 (1H, t, J=7.8 Hz), 7.53-7.60 (3H, m), 7.65-7.70 (1H, m), 8.06-8.13 (3H, m).

Reference Example 5

Production of ethyl 3-hydroxy-4-oxo-5-(2-oxo-2-phenylethyl)-4,5-dihydrothieno[3,2-c]quinoline-2-carboxylate

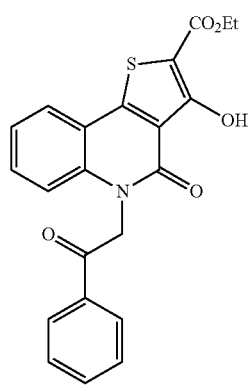 [SMILES: CCOC(=O)c1sc2c(c1O)c(=O)n(CC(=O)c1ccccc1)c1ccccc21]

A 20% solution (17.2 g, 50.5 mmol) of sodium ethoxide in ethanol was diluted with ethanol (50 mL), ethyl thioglycolate (6.1 g, 50.5 mmol) was added to the obtained solution, and the mixture was stirred at room temperature for 5 min. The compound of Reference Example 4 (9.3 g, 25.3 mmol) was added to the mixture, and the mixture was stirred at room temperature for 18 hr. The reaction mixture was diluted with ice water (50 mL), 2N hydrochloric acid (30 mL) was added and the mixture was stirred for 30 min. The precipitated solid was collected by filtration, washed with water and diethyl ether, and dried under reduced pressure to give the title compound (10.0 g, 96%) as a white powder.

$^1$H-NMR (300 MHz, DMSO-d$_6$) δ:1.32 (3H, t, J=7.0 Hz), 4.25-4.35 (2H, m), 6.01 (2H, s), 7.40 (1H, t, J=7.2 Hz), 7.55-7.67 (4H, m), 7.77 (1H, t, J=7.5 Hz), 8.00-8.07 (1H, m), 8.07-8.19 (2H, m), 10.40-10.65 (1H, br).

Reference Example 6

Production of ethyl 3-methoxy-4-oxo-5-(2-oxo-2-phenylethyl)-4,5-dihydrothieno[3,2-c]quinoline-2-carboxylate

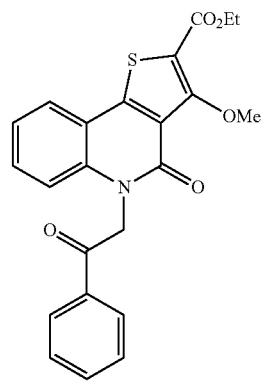

A mixture of the compound of Reference Example 5 (7.0 g, 17.1 mmol) and DBU (4.3 g, 18.3 mmol) in DMF (150 mL) was stirred at room temperature for 10 min, and iodomethane (4.0 g, 28.0 mmol) was added. The mixture was stirred at room temperature for 4 hr, and concentrated under reduced pressure. The residue was diluted with water, and extracted twice with ethyl acetate-THF mixed solution. The extract was combined, washed with brine, dried over magnesium sulfate, and concentrated under reduced pressure. The residue was washed with ethyl acetate-diethyl ether mixed solution, and dried under reduced pressure to give the title compound (5.7 g, 79%) as a pale-green powder.

$^1$H-NMR (300 MHz, DMSO-d$_6$) δ:1.34 (3H, t, J=7.1 Hz), 3.95 (3H, s), 4.34 (2H, q, J=7.1 Hz), 5.98 (2H, s), 7.37 (1H, t,

J=7.5 Hz), 7.49 (1H, d, J=8.7 Hz), 7.57-7.67 (3H, m), 7.76 (1H, t, J=7.5 Hz), 8.06 (1H, d, J=7.8 Hz), 8.16-8.19 (2H, m).

Reference Example 7

Production of 3-methoxy-4-oxo-5-(2-oxo-2-phenylethyl)-4,5-dihydrothieno[3,2-c]quinoline-2-carboxylic acid

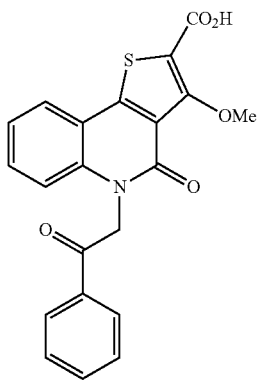 [SMILES: COc1c(C(=O)O)sc2c1c(=O)n(CC(=O)c1ccccc1)c1ccccc21]

A mixed solution of the compound of Reference Example 6 (5.7 g, 13.5 mmol) and 2N aqueous sodium hydroxide solution (60 mL) in THF (200 mL)-ethanol (100 mL) was stirred at room temperature for 18 hr. The reaction mixture was neutralized with 2N hydrochloric acid (60 mL), and the precipitated solid was collected by filtration. The obtained solid was washed successively with water and diethyl ether, and dried under reduced pressure to give the title compound (4.2 g, 79%) as a pale-pink powder.

$^1$H-NMR (300 MHz, DMSO-$d_6$) δ:3.93 (3H, s), 5.98 (2H, s), 7.35 (1H, t, J=7.8 Hz), 7.48 (1H, d, J=8.7 Hz), 7.56-7.67 (3H, m), 7.77 (1H, t, J=7.2 Hz), 8.04 (1H, dd, J=8.1, 1.2 Hz), 8.16-8.19 (2H, m).

Reference Example 8

Production of ethyl 3-ethoxy-4-oxo-5-(2-oxo-2-phenylethyl)-4,5-dihydrothieno[3,2-c]quinoline-2-carboxylate

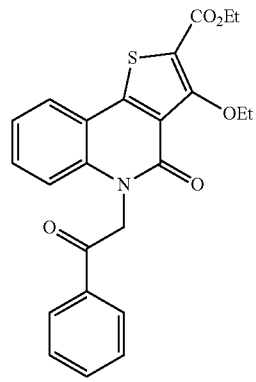

In the same manner as in Reference Example 6, the title compound (461 mg, 87%) was obtained as a white powder from the compound (500 mg, 1.22 mmol) of Reference Example 5, DBU (280 mg, 1.84 mmol) and iodoethane (302 mg, 1.84 mmol).

$^1$H-NMR (300 MHz, DMSO-$d_6$) δ:1.34 (6H, t, J=7.0 Hz), 4.21 (2H, q, J=7.0 Hz), 4.34 (2H, q, J=7.0 Hz), 5.98 (2H, s), 7.35 (1H, t, J=7.5 Hz), 7.49 (1H, d, J=8.4 Hz), 7.57-7.67 (3H, m), 7.76 (1H, t, J=7.2 Hz), 8.06 (1H, dd, J=7.8, 1.2 Hz), 8.16-8.19 (2H, m).

Reference Example 9

Production of 3-ethoxy-4-oxo-5-(2-oxo-2-phenylethyl)-4,5-dihydrothieno[3,2-c]quinoline-2-carboxylic acid

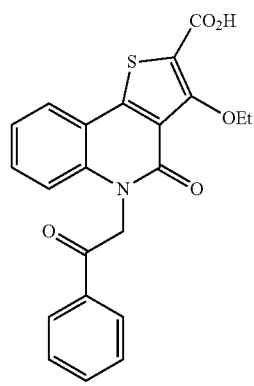 [SMILES: CCOc1c(C(=O)O)sc2c1c(=O)n(CC(=O)c1ccccc1)c1ccccc21]

In the same manner as in Reference Example 7, the title compound (392 mg, 95%) was obtained as a pale-pink powder from the compound (440 mg, 1.01 mmol) of Reference Example 8.

$^1$H-NMR (300 MHz, DMSO-$d_6$) δ:1.33 (3H, t, J=7.0 Hz), 4.20 (2H, q, J=7.0 Hz), 6.00 (2H, s), 7.35 (1H, t, J=7.5 Hz), 7.47 (1H, d, J=8.4 Hz), 7.56-7.67 (3H, m), 7.77 (1H, t, J=7.5 Hz), 8.04 (1H, dd, J=7.8, 1.2 Hz), 8.16-8.19 (2H, m).

Reference Example 10

Production of ethyl 4-chloro-1-(4-methoxybenzyl)-2-oxo-1,2-dihydroquinoline-3-carboxylate

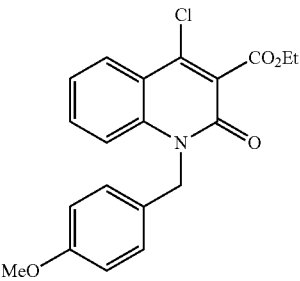 [SMILES: CCOC(=O)c1c(Cl)c2ccccc2n(Cc2ccc(OC)cc2)c1=O]

In the same manner as in Reference Example 4, the title compound (10.8 g, 79%) was obtained as a white powder from the compound (10.0 g, 39.8 mmol) of Reference Example 3 and 4-methoxybenzyl chloride (7.48 mL, 47.8 mmol).

$^1$H-NMR (300 MHz, DMSO-$d_6$) δ:1.34 (3H, t, J=7.1 Hz), 3.70 (3H, s), 4.40 (2H, q, J=7.1 Hz), 5.48 (2H, s), 6.89 (2H, d,

J=8.7 Hz), 7.19 (2H, d, J=8.7 Hz), 7.42 (1H, t, J=7.8 Hz), 7.61 (1H, d, J=8.7 Hz), 7.69-7.75 (1H, m), 8.04 (1H, dd, J=7.8, 1.2 Hz).

Reference Example 11

Production of ethyl 3-hydroxy-5-(4-methoxybenzyl)-4-oxo-4,5-dihydrothieno[3,2-c]quinoline-2-carboxylate

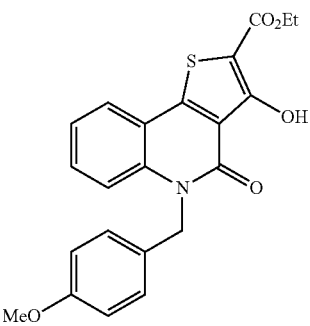 [SMILES: CCOC(=O)c1sc2c(c1O)c(=O)n(Cc1ccc(OC)cc1)c1ccccc21]

In the same manner as in Reference Example 5, the title compound (10.4 g, 88%) was obtained as a white powder from the compound (10.6 g, 31.0 mmol) of Reference Example 10.

$^1$H-NMR (300 MHz, DMSO-$d_6$) δ:1.32 (3H, t, J=7.0 Hz), 3.70 (3H, s), 4.32 (2H, q, J=7.0 Hz), 5.53 (2H, s), 6.87 (2H, d, J=8.9 Hz), 7.23 (2H, d, J=8.9 Hz), 7.34-7.39 (1H, m), 7.58-7.66 (2H, m), 8.00-8.03 (1H, m), 10.77 (1H, s).

Reference Example 12

Production of ethyl 3-methoxy-5-(4-methoxybenzyl)-4-oxo-4,5-dihydrothieno[3,2-c]quinoline-2-carboxylate

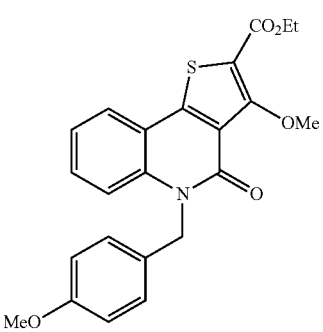 [SMILES: CCOC(=O)c1sc2c(c1OC)c(=O)n(Cc1ccc(OC)cc1)c1ccccc21]

In the same manner as in Reference Example 6, the title compound (5.2 g, 64%) was obtained as a white powder from the compound (7.5 g, 19.8 mmol) of Reference Example 11.

$^1$H-NMR (300 MHz, DMSO-$d_6$) δ:1.34 (3H, t, J=7.1 Hz), 3.70 (3H, s), 4.01 (3H, s), 4.34 (2H, q, J=7.1 Hz), 5.50 (2H, s), 6.87 (2H, d, J=8.7 Hz), 7.20 (2H, d, J=8.7 Hz), 7.27-7.32 (1H, m), 7.48-7.60 (2H, m), 8.01 (1H, dd, J=7.7, 1.4 Hz).

Reference Example 13

Production of 3-methoxy-5-(4-methoxybenzyl)-4-oxo-4,5-dihydrothieno[3,2-c]quinoline-2-carboxylic acid

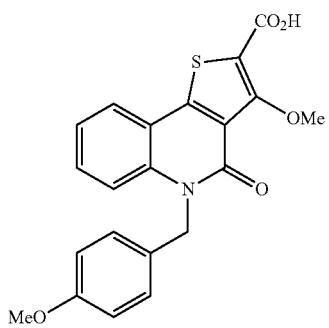 [SMILES: COc1ccc(Cn2c(=O)c3c(OC)c(C(=O)O)sc3c3ccccc32)cc1]

In the same manner as in Reference Example 7, the title compound (4.75 g, 98%) was obtained as a white powder from the compound (5.0 g, 12.3 mmol) of Reference Example 12.

$^1$H-NMR (300 MHz, DMSO-$d_6$) δ:3.70 (3H, s), 3.93 (3H, s), 5.51 (2H, s), 6.87 (2H, d, J=8.7 Hz), 7.20 (2H, d, J=8.7 Hz), 7.27-7.32 (1H, m), 7.48-7.59 (2H, m), 7.99 (1H, dd, J=7.8, 1.2 Hz), 13.40 (1H, s).

Reference Example 14

Production of 1-(pyridin-2-ylmethyl)-2H-3,1-benzooxazine-2,4(1H)-dione

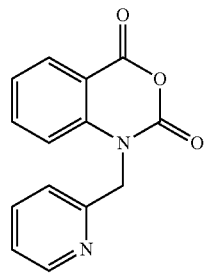 [SMILES: O=c1oc(=O)n(Cc2ccccn2)c2ccccc12]

To a solution of isatoic anhydride (25.4 g, 0.156 mol) in DMF (300 mL) were added 2-(chloromethyl)pyridine hydrochloride (28.1 g, 0.171 mol) and sodium hydride (66% in oil, 12.5 g, 0.34 mol) under ice-cooling. The obtained mixture was stirred at room temperature for 42 hr. Water (750 mL) was added to the reaction mixture and the mixture was ice-cooled. The precipitated solid was collected by filtration, and recrystallized from acetone-diisopropyl ether to give the title compound (13.4 g, 34%).

$^1$H-NMR (300 MHz, DMSO-$d_6$) δ:5.36 (2H, s), 7.24-7.34 (3H, m), 7.49 (1H, d, J=8.1 Hz), 7.73 (1H, ddd, J=8.6, 7.2, 1.5

Hz), 7.77 (1H, td, J=7.7, 1.6 Hz), 8.03 (1H, dd, J=7.8, 1.8 Hz), 8.50 (1H, ddd, J=4.9, 1.7, 1.0 Hz).

Reference Example 15

Production of ethyl 4-hydroxy-2-oxo-1-(pyridin-2-ylmethyl)-1,2-dihydroquinoline-3-carboxylate

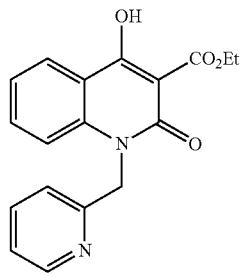 [SMILES: CCOC(=O)c1c(O)c2ccccc2n(Cc2ccccn2)c1=O]

To a solution of diethyl malonate (15.6 g, 97.4 mmol) in DMF (90 mL) was added sodium hydride (66% in oil, 2.60 g, 72 mmol) under ice-cooling, and the mixture was stirred at the same temperature for 10 min. The compound of Reference Example 14 (16.5 g, 64.9 mmol) was added to the obtained mixture by small portions, and the mixture was stirred at 120° C. for 6 hr. The reaction mixture was concentrated under reduced pressure, ice water was added to the residue and the mixture was washed with diethyl ether. The aqueous layer was weakly basified with 5N hydrochloric acid (8 mL) under ice-cooling. The precipitated crystals were collected by filtration, washed with water, and recrystallized from ethyl acetate-diisopropyl ether to give the title compound (12.8 g, 60%).

$^1$H-NMR (300 MHz, CDCl$_3$) δ:1.50 (3H, t, J=7.1 Hz), 4.53 (2H, q, J=7.1 Hz), 5.61 (2H, br s), 7.12-7.18 (2H, m), 7.18-7.25 (1H, m), 7.36 (1H, d, J=8.7 Hz), 7.51-7.59 (2H, m), 8.18 (1H, dd, J=8.3, 1.7 Hz), 8.56 (1H, dd, J=5.3, 2.0 Hz), 14.53 (1H, s).

Reference Example 16

Production of ethyl 4-chloro-2-oxo-1-(pyridin-2-ylmethyl)-1,2-dihydroquinoline-3-carboxylate

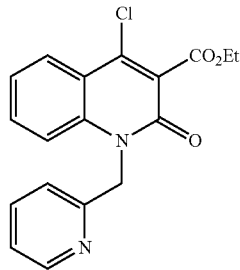 [SMILES: CCOC(=O)c1c(Cl)c2ccccc2n(Cc2ccccn2)c1=O]

To a mixture of the compound of Reference Example 15 (16.1 g, 49.6 mmol) and toluene (50 mL) was added phosphorus oxychloride (12 mL, 0.13 mol), and the mixture was stirred at 110° C. for 1 hr. The reaction mixture was allowed to cool, and the solvent was removed by decantation. Water was added to the residue and the mixture was washed with diethyl ether. The aqueous layer was neutralized with sodium carbonate and extracted twice with chloroform. The combined organic layer was washed with water and brine, dried over sodium sulfate, filtered, and concentrated under reduced pressure. The residue was purified by silica gel column chromatography (eluate; ethyl acetate/hexane=1/1-3/1) and crystallized from ethyl acetate-hexane to give the title compound (2.54 g, 15%).

$^1$H-NMR (300 MHz, CDCl$_3$) δ:1.44 (3H, t, J=7.2 Hz), 4.50 (2H, q, J=7.2 Hz), 5.64 (2H, br s), 7.15-7.26 (2H, m), 7.31 (1H, ddd, J=8.2, 5.9, 2.3 Hz), 7.52-7.63 (3H, m), 8.06 (1H, dt, J=7.8, 0.8 Hz), 8.56 (1H, ddd, J=4.7, 1.9, 0.8 Hz).

Reference Example 17

Production of ethyl 3-hydroxy-4-oxo-5-(pyridin-2-ylmethyl)-4,5-dihydrothieno[3,2-c]quinoline-2-carboxylate

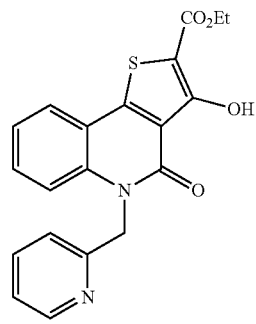 [SMILES: CCOC(=O)c1sc2c(c1O)c(=O)n(Cc1ccccn1)c1ccccc21]

A 20% solution (4.51 g, 13 mmol) of sodium ethoxide in ethanol was diluted with ethanol (15 mL), and ethyl thioglycolate (1.74 mL, 15.9 mmol) was added to the obtained solution. The mixture was stirred at room temperature for 10 min. The compound of Reference Example 16 (2.27 g, 6.62 mmol) was added to the mixture, and the mixture was stirred at room temperature for 5.5 hr. The reaction mixture was neutralized with ice water and 2N hydrochloric acid (3.2 mL) under ice-cooling, and extracted twice with chloroform. The combined organic layer was washed with water and brine, dried over sodium sulfate, filtered, and concentrated under reduced pressure. The obtained solid was washed with ethanol to give the title compound (2.50 g, 99%).

$^1$H-NMR (300 MHz, CDCl$_3$) δ:1.43 (3H, t, J=7.1 Hz), 4.43 (2H, q, J=7.1 Hz), 5.69 (2H, br s), 7.16-7.24 (2H, m), 7.25-7.32 (1H, m), 7.49 (1H, ddd, J=8.6, 7.1, 1.5 Hz), 7.57 (1H, d, J=8.1 Hz), 7.60 (1H, td, J=7.7, 1.8 Hz), 7.82 (1H, dd, J=8.1, 1.5 Hz), 8.57 (1H, ddd, J=4.9, 1.6, 0.8 Hz), 10.68 (1H, s).

Reference Example 18

Production of ethyl 3-methoxy-4-oxo-5-(pyridin-2-ylmethyl)-4,5-dihydrothieno[3,2-c]quinoline-2-carboxylate

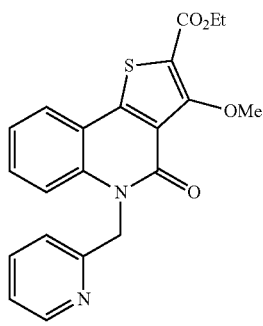 [SMILES: CCOC(=O)c1sc2c(c1OC)c(=O)n(Cc1ccccn1)c1ccccc21]

To a suspension of the compound of Reference Example 17 (2.26 g, 5.94 mmol) in DMF (20 mL) was added DBU (1.06 mL, 7.09 mmol), and iodomethane (0.74 mL, 12 mmol) was added to the obtained solution. The obtained mixture was stirred at room temperature for 14 hr, water was added, and the mixture was extracted twice with ethyl acetate. The combined organic layer was washed with water, 0.5N sodium hydroxide solution and water, dried by passing through basic silica gel (eluted with ethyl acetate), and concentrated under reduced pressure. The residue was crystallized from ethyl acetate-diisopropyl ether to give the title compound (1.16 g, 50%).

$^1$H-NMR (300 MHz, CDCl$_3$) δ:1.43 (3H, t, J=7.1 Hz), 4.17 (3H, s), 4.41 (2H, q, J=7.1 Hz), 5.70 (2H, br s), 7.14-7.26 (3H, m), 7.45 (1H, ddd, J=8.6, 7.0, 1.6 Hz), 7.51 (1H, dd, J=8.6, 0.8 Hz), 7.57 (1H, td, J=7.7, 1.8 Hz), 7.83 (1H, ddd, J=7.7, 1.5, 0.3 Hz), 8.57 (1H, ddd, J=5.0, 2.0, 0.9 Hz).

Reference Example 19

Production of 3-methoxy-4-oxo-5-(pyridin-2-ylmethyl)-4,5-dihydrothieno[3,2-c]quinoline-2-carboxylic acid

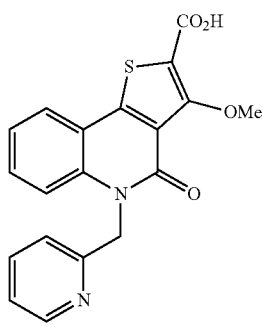 [SMILES: COc1c(C(=O)O)sc2c1c(=O)n(Cc1ccccn1)c1ccccc21]

To a suspension of the compound of Reference Example 18 (1.21 g, 3.07 mmol) in THF (10 mL) and ethanol (10 mL) was added 5N aqueous sodium hydroxide solution (1.2 mL, 6.0 mmol). The obtained mixture was stirred at room temperature for 45 min, ethanol (5 mL) was added and the mixture was further stirred for 135 min. The reaction mixture was ice-cooled, neutralized with 1N hydrochloric acid (6.0 mL), and chloroform and water were added. The organic layer was separated, and the aqueous layer was extracted twice with chloroform. The combined organic layer was washed with water and brine, dried over sodium sulfate, filtered, and concentrated under reduced pressure. The residue was recrystallized from chloroform-diisopropyl ether to give the title compound (1.11 g, 99%).

$^1$H-NMR (300 MHz, DMSO-d$_6$) δ:3.96 (3H, s), 5.65 (2H, s), 7.23-7.33 (3H, m), 7.43 (1H, d, J=8.7 Hz), 7.54 (1H, ddd, J=8.6, 7.3, 1.4 Hz), 7.73 (1H, td, J=7.7, 1.9 Hz), 7.97-8.02 (1H, m), 8.45-8.48 (1H, m), 13.38 (1H, br s).

Reference Example 20

Production of ethyl 3-(2-ethoxyethoxy)-4-oxo-5-(2-oxo-2-phenylethyl)-4,5-dihydrothieno[3,2-c]quinoline-2-carboxylate

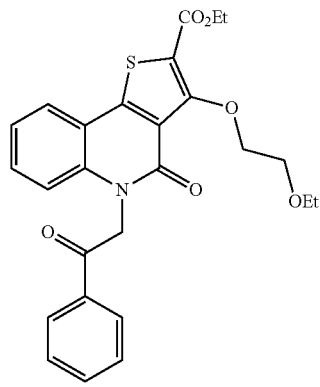 [SMILES: CCOCCOc1c(C(=O)O)sc2c1c(=O)n(CC(=O)c1ccccc1)c1ccccc21]

To a suspension of the compound of Reference Example 5 (1.35 g, 3.31 mmol) in DMF (20 mL) were added DBU (1.48 mL, 9.90 mmol) and 2-bromoethylethylether (1.12 mL, 9.93 mmol), and the mixture was stirred at 60° C. for 30 hr. Chloroform and water were added to the reaction mixture, the organic layer was separated and the aqueous layer was extracted with chloroform. The combined organic layer was washed with 0.5N sodium hydroxide solution and water, and concentrated under reduced pressure. The residue was purified by silica gel column chromatography (eluate; ethyl acetate/hexane=1/3-2/3) and recrystallized from dichloromethane-diisopropyl ether to give the title compound (1.36 g, 86%).

$^1$H-NMR (300 MHz, CDCl$_3$) δ:1.17 (3H, t, J=7.1 Hz), 1.43 (3H, t, J=7.1 Hz), 3.56 (2H, q, J=7.1 Hz), 3.89 (2H, dd, J=5.5, 4.6 Hz), 4.40 (2H, q, J=7.1 Hz), 4.45 (2H, dd, J=5.5, 4.6 Hz), 5.85 (2H, s), 6.97 (1H, d, J=8.1 Hz), 7.21-7.28 (1H, m), 7.45

(1H, ddd, J=8.7, 7.2, 1.4 Hz), 7.51-7.58 (2H, m), 7.63-7.69 (1H, m), 7.86 (1H, dd, J=7.8, 1.5 Hz), 8.07-8.12 (2H, m).

Reference Example 21

Production of 3-(2-ethoxyethoxy)-4-oxo-5-(2-oxo-2-phenylethyl)-4,5-dihydrothieno[3,2-c]quinoline-2-carboxylic acid

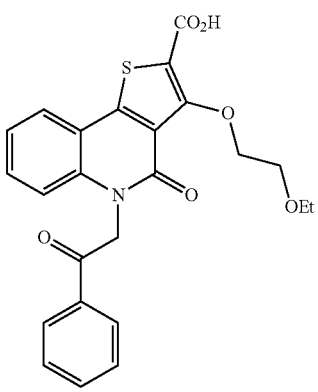

To a suspension of the compound of Reference Example 20 (1.20 g, 2.50 mmol) in THF (16 mL) and ethanol (16 mL) was added 5N aqueous sodium hydroxide solution (1.0 mL, 5.0 mmol). The obtained mixture was stirred at room temperature for 3 hr. The reaction mixture was acidified with 1N hydrochloric acid, and water was added. The precipitated crystals were collected by filtration and washed with water to give the title compound (1.09 g, 97%).

$^1$H-NMR (300 MHz, DMSO-$d_6$) δ:1.01 (3H, t, J=6.9 Hz), 3.40 (2H, q, J=6.9 Hz), 3.71 (2H, t, J=5.0 Hz), 4.30 (2H, t, J=5.0 Hz), 5.97 (2H, s), 7.33 (1H, t, J=7.7 Hz), 7.46 (1H, d, J=8.7 Hz), 7.54-7.66 (3H, m), 7.76 (1H, t, J=7.2 Hz), 8.02 (1H, d, J=7.8 Hz), 8.16 (2H, d, J=7.5 Hz), 13.27 (1H, br s).

Reference Example 22

Production of ethyl 3-hydroxy-4-oxo-5-(2-oxo-2-phenylethyl)-4,5-dihydrofuro[3,2-c]quinoline-2-carboxylate

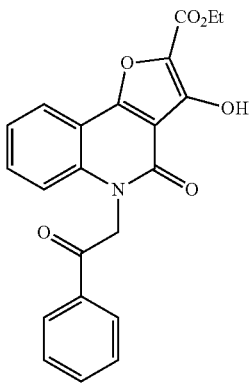 [SMILES: CCOC(=O)c1oc2c(c1O)c(=O)n(CC(=O)c1ccccc1)c1ccccc21]

In the same manner as in Reference Example 5, the title compound (1.10 g, 69%) was obtained as a white powder from the compound of Reference Example 4 (1.50 g, 4.06 mmol), a 20% solution (2.76 g, 8.11 mmol) of sodium ethoxide in ethanol and ethyl glycolate (1.01 g, 9.73 mmol).

$^1$H-NMR (300 MHz, DMSO-$d_6$) δ:1.34 (3H, t, J=7.1 Hz), 4.35 (2H, q, J=7.1 Hz), 5.96 (2H, s), 7.39 (1H, t, J=7.7 Hz), 7.51 (1H, d, J=8.4 Hz), 7.60-7.67 (3H, m), 7.74-7.79 (1H, m), 8.05 (1H, dd, J=7.7, 1.4 Hz), 8.15-8.18 (2H, m), 9.80-11.10 (1H, br).

Reference Example 23

Production of ethyl 3-methoxy-4-oxo-5-(2-oxo-2-phenylethyl)-4,5-dihydrofuro[3,2-c]quinoline-2-carboxylate

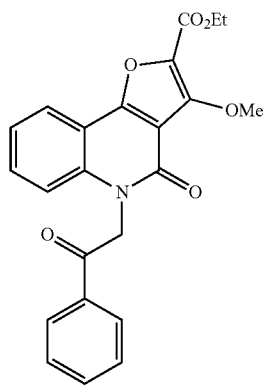 [SMILES: CCOC(=O)c1oc2c(c1OC)c(=O)n(CC(=O)c1ccccc1)c1ccccc21]

In the same manner as in Reference Example 6, the title compound (250 mg, 23%) was obtained as a white powder from the compound of Reference Example 22 (1.05 g, 2.68 mmol), DBU (612 mg, 4.02 mmol) and iodomethane (250 μL, 4.02 mmol).

$^1$H-NMR (300 MHz, DMSO-$d_6$) δ:1.35 (3H, t, J=7.1 Hz), 4.14 (3H, s), 4.37 (2H, q, J=7.1 Hz), 5.99 (2H, s), 7.39-7.45 (1H, m), 7.55 (1H, d, J=8.7 Hz), 7.62-7.68 (3H, m), 7.74-7.80 (1H, m), 8.09 (1H, dd, J=7.8, 1.5 Hz), 8.16-8.18 (2H, m).

Reference Example 24

Production of 3-methoxy-4-oxo-5-(2-oxo-2-phenylethyl)-4,5-dihydrofuro[3,2-c]quinoline-2-carboxylic acid

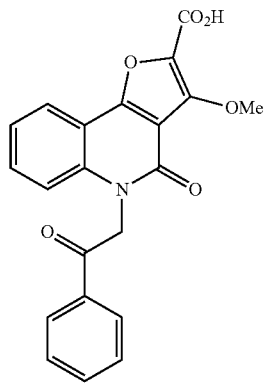 [SMILES: COc1c(C(=O)O)oc2c1c(=O)n(CC(=O)c1ccccc1)c1ccccc21]

In the same manner as in Reference Example 7, the title compound (160 mg, 72%) was obtained as a white powder from the compound of Reference Example 23 (240 mg, 0.592 mmol), 8N aqueous sodium hydroxide solution (1.0 mL) and ethanol (14 mL).

$^1$H-NMR (300 MHz, DMSO-d$_6$) δ:4.12 (3H, s), 5.99 (2H, s), 7.42 (1H, t, J=7.6 Hz), 7.54 (1H, d, J=7.8 Hz), 7.62-7.67 (3H, m), 7.77 (1H, t, J=7.8 Hz), 8.07 (1H, dd, J=7.6, 1.5 Hz), 8.16-8.18 (2H, m), 12.60-14.10 (1H, br).

Reference Example 25

Production of ethyl 4-[(2-ethoxy-2-oxoethyl)(methyl)amino]-2-oxo-1-(2-oxo-2-phenylethyl)-1,2-dihydroquinoline-3-carboxylate

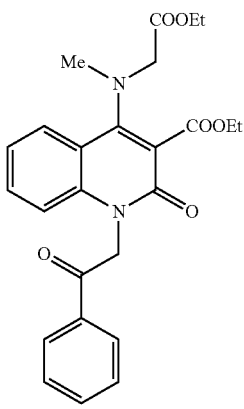 [SMILES: CCOC(=O)CN(C)c1c(C(=O)OCC)c(=O)n(CC(=O)c2ccccc2)c2ccccc12]

A mixture of the compound of Reference Example 4 (24.1 g, 65.2 mmol), sarcosine ethyl ester hydrochloride (12.0 g, 78.2 mmol), triethylamine (18.1 mL, 130 mmol) and ethanol (200 mL) was stirred at 85° C. for 15 hr, sarcosine ethyl ester hydrochloride (3.00 g, 19.6 mmol) and triethylamine (18.1 mL, 130 mmol) were further added, and the mixture was stirred at 85° C. for 7 hr. After cooling, water was added to the reaction mixture, and the precipitated solid was collected by filtration. The obtained solid was washed with water, and dried under reduced pressure to give the title compound (24.6 g, 84%) as a white powder.

$^1$H-NMR (300 MHz, DMSO-d$_6$) δ:1.21-1.31 (6H, m), 2.93 (3H, s), 3.95 (2H, s), 4.15-4.31 (4H, m), 5.87 (2H, s), 7.31 (1H, t, J=7.8 Hz), 7.40 (1H, d, J=8.4 Hz), 7.55-7.65 (3H, m), 7.72-7.78 (1H, m), 8.05 (1H, dd, J=7.8, 1.5 Hz), 8.12-8.15 (2H, m).

Reference Example 26

Production of ethyl 3-hydroxy-1-methyl-4-oxo-5-(2-oxo-2-phenylethyl)-4,5-dihydro-1H-pyrrolo[3,2-c]quinoline-2-carboxylate

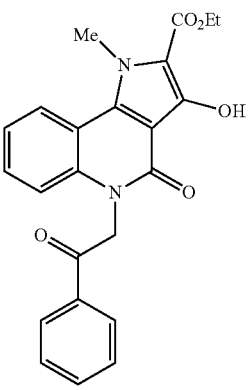 [SMILES: CCOC(=O)c1c(O)c2c(=O)n(CC(=O)c3ccccc3)c3ccccc3c2n1C]

A mixture of the compound of Reference Example 25 (1.25 g, 2.77 mmol), a 20% solution (1.23 g, 3.33 mmol) of sodium ethoxide in ethanol and ethanol (25 mL) was stirred at 55° C. for 15 hr. The reaction mixture was diluted with water, 1N hydrochloric acid (5 mL) was added and the mixture was stirred for 30 min. The precipitated solid was collected by filtration, washed with water, ethanol and ethyl acetate, and recrystallized from dimethylformamide-ethanol to give the title compound (760 mg, 68%) as a white powder.

$^1$H-NMR (300 MHz, DMSO-d$_6$) δ:1.33 (3H, t, J=7.2 Hz), 4.30-4.38 (5H, m), 5.93 (2H, s), 7.30-7.40 (2H, m), 7.48-7.53 (1H, m), 7.61-7.66 (2H, m), 7.73-7.79 (1H, m), 8.15-8.18 (2H, m), 8.34-8.37 (1H, m), 9.00 (1H, s).

Reference Example 27

Production of ethyl 3-methoxy-1-methyl-4-oxo-5-(2-oxo-2-phenylethyl)-4,5-dihydro-1H-pyrrolo[3,2-c]quinoline-2-carboxylate

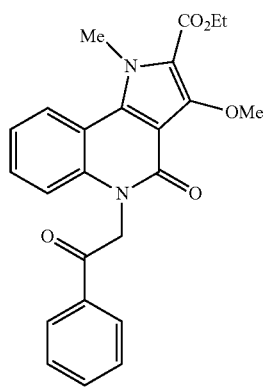 [SMILES: CCOC(=O)c1c(OC)c2c(=O)n(CC(=O)c3ccccc3)c3ccccc3c2n1C]

In the same manner as in Reference Example 6, the title compound (420 mg, 55%) was obtained as a white powder from the compound of Reference Example 26 (740 mg, 1.83 mmol), DBU (410 μL, 2.74 mmol) and iodomethane (171 μL, 2.74 mmol).

$^1$H-NMR (300 MHz, DMSO-d$_6$) δ:1.35 (3H, t, J=7.1 Hz), 3.89 (3H, s), 4.29-4.37 (5H, m), 5.96 (2H, s), 7.30-7.40 (2H, m), 7.48-7.53 (1H, m), 7.61-7.66 (2H, m), 7.73-7.78 (1H, m), 8.15-8.18 (2H, m), 8.38 (1H, dd, J=8.3, 1.4 Hz).

Reference Example 28

Production of 3-methoxy-1-methyl-4-oxo-5-(2-oxo-2-phenylethyl)-4,5-dihydro-1H-pyrrolo[3,2-c]quinoline-2-carboxylic acid

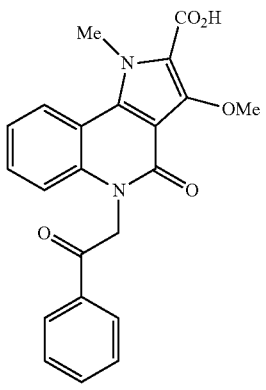 [SMILES: COc1c(C(=O)O)n(C)c2c1c(=O)n(CC(=O)c1ccccc1)c1ccccc21]

In the same manner as in Reference Example 7, the title compound (345 mg, 91%) was obtained as a white powder from the compound of Reference Example 27 (405 mg, 0.968 mmol), 8N aqueous sodium hydroxide solution (1.5 mL) and ethanol (15 mL).
$^1$H-NMR (300 MHz, DMSO-d$_6$) δ:3.88 (3H, s), 4.31 (3H, s), 5.95 (2H, s), 7.29-7.39 (2H, m), 7.46-7.52 (1H, m), 7.61-7.66 (2H, m), 7.73-7.78 (1H, m), 8.16-8.18 (2H, m), 8.38 (1H, dd, J=8.3, 1.1 Hz), 12.92 (1H, s).

Reference Example 29

Production of ethyl 3-ethoxy-1-methyl-4-oxo-5-(2-oxo-2-phenylethyl)-4,5-dihydro-1H-pyrrolo[3,2-c]quinoline-2-carboxylate

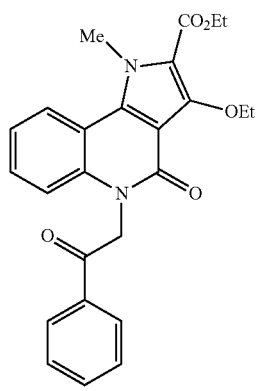 [SMILES: CCOC(=O)c1c(OCC)c2c(=O)n(CC(=O)c3ccccc3)c3ccccc3c2n1C]

In the same manner as in Reference Example 6, the title compound (2.10 g, quant.) was obtained as a white powder from the compound (1.90 g, 4.70 mmol) of Reference Example 26, DBU (1.05 mL, 7.05 mmol) and iodoethane (564 μL, 7.05 mmol).
$^1$H-NMR (300 MHz, DMSO-d$_6$) δ:1.27-1.37 (6H, m), 4.16 (2H, q, J=6.9 Hz), 4.29-4.36 (5H, m), 5.95 (2H, s), 7.27-7.39 (2H, m), 7.50 (1H, t, J=8.0 Hz), 7.63 (2H, t, J=7.3 Hz), 7.76 (1H, t, J=7.4 Hz), 8.17 (2H, d, J=7.3 Hz), 8.38 (1H, d, J=8.1 Hz).

Reference Example 30

Production of 3-ethoxy-1-methyl-4-oxo-5-(2-oxo-2-phenylethyl)-4,5-dihydro-1H-pyrrolo[3,2-c]quinoline-2-carboxylic acid

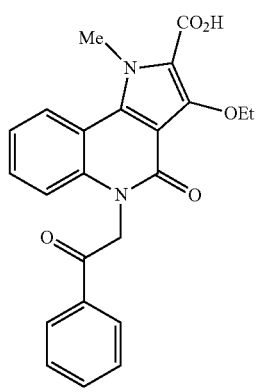 [SMILES: CCOc1c(C(=O)O)n(C)c2c1c(=O)n(CC(=O)c1ccccc1)c1ccccc21]

In the same manner as in Reference Example 7, the title compound (1.62 g, 89%) was obtained as a white powder from the compound of Reference Example 29 (1.95 g, 4.51 mmol), 8N aqueous sodium hydroxide solution (2.0 mL) and ethanol (14 mL).
$^1$H-NMR (300 MHz, DMSO-d$_6$) δ:1.27 (3H, t, J=7.0 Hz), 4.16 (2H, q, J=7.0 Hz), 4.31 (3H, s), 5.95 (2H, s), 7.27-7.39 (2H, m), 7.49 (1H, t, J=7.4 Hz), 7.63 (2H, t, J=7.4 Hz), 7.76 (1H, t, J=7.4 Hz), 8.15-8.18 (2H, m), 8.38 (1H, d, J=7.2 Hz), 12.83 (1H, s).

Reference Example 31

Production of ethyl 4-chloro-6-methyl-2-oxo-1,2-dihydropyridine-3-carboxylate

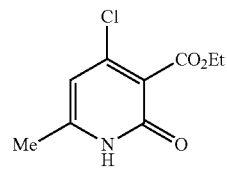 [SMILES: CCOC(=O)c1c(Cl)cc(C)[nH]c1=O]

A mixture of ethyl 4-hydroxy-6-methyl-2-oxo-1,2-dihydropyridine-3-carboxylate (3.00 g, 15.2 mmol), phosphorus oxychloride (7.75 mL), n-butyltriethylammonium chloride (13.8 g, 60.8 mmol) and acetonitrile (60 mL) was stirred at 40° C. for 30 min and under refluxing conditions for 30 min. After cooling, the reaction mixture was concentrated under reduced pressure, water was added to the residue and the mixture was extracted with ethyl acetate. The extract was washed with brine, dried over magnesium sulfate, and concentrated under reduced pressure. The residue was washed with ethyl acetate-hexane mixed solution, and dried under reduced pressure to give the title compound (1.45 g, 44%) as a white powder.

$^1$H-NMR (300 MHz, DMSO-d$_6$) δ:1.26 (3H, t, J=7.0 Hz), 2.20 (3H, s), 4.25 (2H, q, J=7.0 Hz), 6.26 (1H, s), 12.29 (1H, s).

Reference Example 32

Production of ethyl 4-chloro-6-methyl-2-oxo-1-(2-oxo-2-phenylethyl)-1,2-dihydropyridine-3-carboxylate

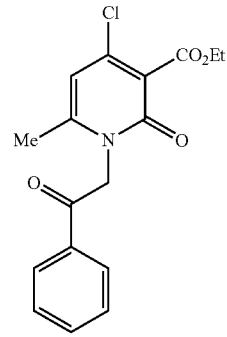 [SMILES: CCOC(=O)c1c(Cl)cc(C)n(CC(=O)c2ccccc2)c1=O]

A mixture of the compound of Reference Example 31 (9.00 g, 41.7 mmol), potassium carbonate (17.3 g, 125 mmol), phenacyl bromide (16.6 g, 83.5 mmol) and DMF (100 mL) was stirred at room temperature for 15 hr. The reaction mixture was poured into water (100 mL), and the mixture was extracted with ethyl acetate. The extract was washed with brine, dried over magnesium sulfate, and concentrated under reduced pressure. The residue was purified by aminosilica gel chromatography (eluate; ethyl acetate/hexane=1/9-7/3) to give the title compound (3.18 g, 23%) as a white powder.

$^1$H-NMR (300 MHz, DMSO-d$_6$) δ:1.25 (3H, t, J=7.0 Hz), 2.30 (3H, s), 4.25 (2H, q, J=7.0 Hz), 5.63 (2H, s), 6.54 (1H, d, J=0.6 Hz), 7.61 (2H, t, J=7.5 Hz), 7.72-7.78 (1H, m), 8.07-8.10 (2H, m).

Reference Example 33

Production of ethyl 3-hydroxy-1,6-dimethyl-4-oxo-5-(2-oxo-2-phenylethyl)-4,5-dihydro-1H-pyrrolo[3,2-c]pyridine-2-carboxylate

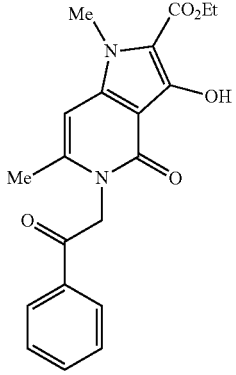 [SMILES: CCOC(=O)c1c(O)c2c(=O)n(CC(=O)c3ccccc3)c(C)cc2n1C]

A mixture of the compound of Reference Example 32 (2.00 g, 5.99 mmol), sarcosine ethyl ester hydrochloride (1.84 g, 12.0 mmol), triethylamine (4.98 mL, 36.0 mmol) and ethanol (20 mL) was stirred at 80° C. for 15 hr, a 20% solution (3.5 mL) of sodium ethoxide in ethanol was added, and the mixture was stirred at 100° C. for 24 hr. After cooling, the reaction mixture was diluted with water (50 mL), 6N hydrochloric acid was added to adjust to pH 3-4, and the mixture was stirred for 30 min. The precipitated solid was collected by filtration, and washed with water and ethyl acetate/THF to give the title compound (1.50 g, 68%) as a white powder.

$^1$H-NMR (300 MHz, DMSO-d$_6$) δ:1.31 (3H, t, J=7.1 Hz), 2.26 (3H, s), 3.77 (3H, s), 4.30 (2H, q, J=7.0 Hz), 5.57 (2H, s), 6.52 (1H, s), 7.54-7.67 (2H, m), 7.69-7.79 (1H, m), 8.03-8.18 (2H, m), 8.90 (1H, s).

Reference Example 34

Production of ethyl 3-methoxy-1,6-dimethyl-4-oxo-5-(2-oxo-2-phenylethyl)-4,5-dihydro-1H-pyrrolo[3,2-c]pyridine-2-carboxylate

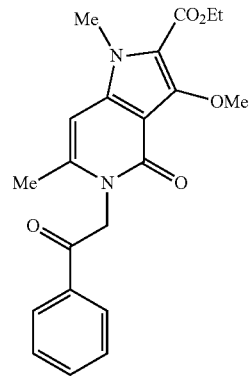 [SMILES: CCOC(=O)c1c(OC)c2c(=O)n(CC(=O)c3ccccc3)c(C)cc2n1C]

In the same manner as in Reference Example 6, the title compound (390 mg, 26%) was obtained as a white powder from the compound of Reference Example 33 (1.45 g, 3.94 mmol), DBU (882 μL, 5.90 mmol) and iodomethane (367 μL, 5.90 mmol).

$^1$H-NMR (300 MHz, DMSO-d$_6$) δ:1.30 (3H, t, J=7.1 Hz), 2.28 (3H, s), 3.81 (3H, s), 3.86 (3H, s), 4.27 (2H, q, J=7.0 Hz), 5.60 (2H, s), 6.59 (1H, s), 7.54-7.66 (2H, m), 7.69-7.79 (1H, m), 8.05-8.16 (2H, m).

Reference Example 35

Production of 3-methoxy-1,6-dimethyl-4-oxo-5-(2-oxo-2-phenylethyl)-4,5-dihydro-1H-pyrrolo[3,2-c]pyridine-2-carboxylic acid

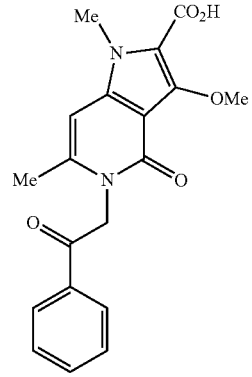 [SMILES: COc1c(C(=O)O)n(C)c2cc(C)n(CC(=O)c3ccccc3)c(=O)c12]

In the same manner as in Reference Example 7, the title compound (305 mg, 89%) was obtained as a white powder from the compound of Reference Example 34 (370 mg, 0.968 mmol), 8N aqueous sodium hydroxide solution (1 mL) and ethanol (7 mL).

$^1$H-NMR (300 MHz, DMSO-$d_6$) δ:2.28 (3H, s), 3.81 (3H, s), 3.86 (3H, s), 5.60 (2H, s), 6.58 (1H, s), 7.61 (2H, t, J=7.4 Hz), 7.74 (1H, t, J=7.3 Hz), 8.11 (2H, d, J=7.7 Hz), 12.50 (1H, br s).

Reference Example 36

Production of methyl(2Z)-3-aminopenta-2-enoate

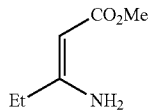

A mixture of methyl 3-oxovalerate (75.0 g, 576 mmol), ammonium acetate (222 g, 2.88 mmol) and methanol (750 mL) was stirred at room temperature for 3 days. The mixture was concentrated under reduced pressure, water (500 mL) was added to the residue and the mixture was extracted with ethyl acetate (200 mL). The extract was washed with brine, dried over magnesium sulfate, concentrated under reduced pressure, and dried to give the title compound (68.5 g, 92%) as a pale-yellow oil.

$^1$H-NMR (300 MHz, DMSO-$d_6$) δ:1.06 (3H, t, J=7.6 Hz), 2.09 (2H, q, J=7.6 Hz), 3.49 (3H, s), 4.34 (1H, s), 6.94 (1H, s), 7.72 (1H, br s).

Reference Example 37

Production of ethyl 6-ethyl-4-hydroxy-2-oxo-1,2-dihydropyridine-3-carboxylate

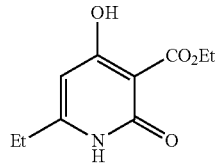

To a solution of the compound of Reference Example 36 (50.0 g, 387 mmol) and diethyl malonate (58.8 mL, 387 mmol) in ethanol (400 mL) was added a 20% solution (133 g) of sodium ethoxide in ethanol, and the mixture was stirred at 150° C. for 15 hr while evaporating ethanol. After cooling, the obtained solid was collected by filtration, washed with ethyl acetate, and dissolved in water. Insoluble material was filtered off, the filtrate was acidified with 5N hydrochloric acid, and the precipitated solid was collected by filtration. The obtained solid was washed with water and ethyl acetate-hexane to give the title compound (36.4 g, 45%) as a white powder.

$^1$H-NMR (300 MHz, DMSO-$d_6$) δ: 1.12 (3H, t, J=7.6 Hz), 1.26 (3H, t, J=7.1 Hz), 2.42 (2H, q, J=7.6 Hz), 4.25 (2H, q, J=7.0 Hz), 5.79 (1H, s), 11.37 (1H, brs), 12.57 (1H, s).

Reference Example 38

Production of ethyl 4-chloro-6-ethyl-2-oxo-1,2-dihydropyridine-3-carboxylate

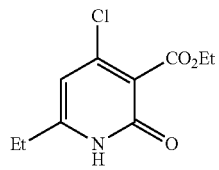

A mixture of the compound of Reference Example 37 (15.0 g, 71.0 mmol) and phosphorus oxychloride (19.9 mL, 213 mmol) was stirred at 80° C. for 30 min. The mixture was concentrated under reduced pressure, ice water was added to the residue, and the precipitated solid was collected by filtration, and washed with water and ethyl acetate to give the title compound (9.80 g, 60%) as a white solid.

$^1$H-NMR (300 MHz, DMSO-$d_6$) δ: 1.15 (3H, t, J=7.5 Hz), 1.26 (3H, t, J=7.0 Hz), 2.44-2.55 (2H, m), 4.25 (2H, q, J=7.1 Hz), 6.26 (1H, s), 12.28 (1H, s).

Reference Example 39

Production of ethyl 4-chloro-6-ethyl-2-oxo-1-(2-oxo-2-phenylethyl)-1,2-dihydropyridine-3-carboxylate

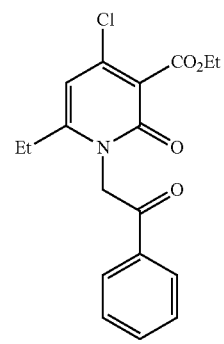 [SMILES: CCOC(=O)c1c(Cl)cc(CC)n(CC(=O)c2ccccc2)c1=O]

In the same manner as in Reference Example 32, the title compound (1.00 g, 7%) was obtained as a white powder from the compound of Reference Example 38 (9.50 g, 41.4 mmol), potassium carbonate (13.7 g, 99.2 mmol), phenacyl bromide (9.88 g, 49.6 mmol) and DMF (100 mL).

$^1$H-NMR (300 MHz, DMSO-$d_6$) δ:1.14 (3H, t, J=7.4 Hz), 1.24 (3H, t, J=7.1 Hz), 2.62 (2H, q, J=7.4 Hz), 4.25 (2H, q, J=7.1 Hz), 5.61 (2H, s), 6.44 (1H, s), 7.54-7.66 (2H, m), 7.70-7.79 (1H, m), 8.05-8.13 (2H, m).

Reference Example 40

Production of ethyl 6-ethyl-3-hydroxy-1-methyl-4-oxo-5-(2-oxo-2-phenylethyl)-4,5-dihydro-1H-pyrrolo[3,2-c]pyridine-2-carboxylate

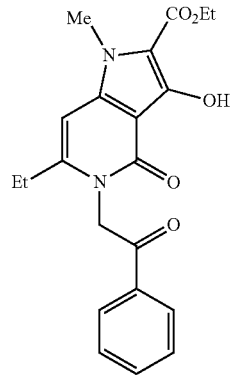

A mixture of the compound of Reference Example 39 (950 mg, 2.73 mmol), sarcosine ethyl ester hydrochloride (839 mg, 5.46 mmol), triethylamine (2.27 mL, 16.4 mmol) and ethanol (10 mL) was stirred at 80° C. for 10 hr, triethylamine (2.27 mL, 16.4 mmol) was further added, and the mixture was stirred at 100° C. for 15 hr. After cooling, water was added to the reaction mixture, and the mixture was acidified with 1N hydrochloric acid and extracted with ethyl acetate. The extract was washed successively with water and brine, dried over magnesium sulfate, and concentrated under reduced pressure. The residue was purified by silica gel chromatography (eluate; ethyl acetate/methanol=10/1) to give the title compound (698 mg, 67%) as a brown solid.

$^1$H-NMR (300 MHz, DMSO-$d_6$) δ:1.18 (3H, t, J=7.4 Hz), 1.31 (3H, t, J=7.1 Hz), 2.56 (2H, q, J=7.6 Hz), 3.80 (3H, s), 4.30 (2H, q, J=7.2 Hz), 5.55 (2H, s), 6.43 (1H, s), 7.60 (2H, t, J=7.6 Hz), 7.68-7.79 (1H, m), 8.00-8.21 (2H, m), 8.90 (1H, s).

Reference Example 41

Production of ethyl 6-ethyl-3-methoxy-1-methyl-4-oxo-5-(2-oxo-2-phenylethyl)-4,5-dihydro-1H-pyrrolo[3,2-c]pyridine-2-carboxylate

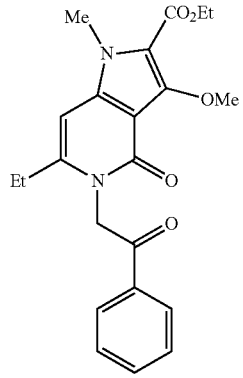

In the same manner as in Reference Example 6, the title compound (156 mg, 23%) was obtained as a white powder from the compound of Reference Example 40 (650 mg, 1.70 mmol).

$^1$H-NMR (300 MHz, DMSO-$d_6$) δ:1.19 (3H, t, J=7.3 Hz), 1.30 (3H, t, J=7.1 Hz), 2.58 (2H, q, J=7.4 Hz), 3.84 (3H, s), 3.85 (3 H, s), 4.27 (2H, q, J=7.0 Hz), 5.58 (2H, s), 6.50 (1H, s), 7.61 (2H, t, J=7.6 Hz), 7.67-7.82 (1H, m), 8.03-8.19 (2H, m).

Reference Example 42

Production of 6-ethyl-3-methoxy-1-methyl-4-oxo-5-(2-oxo-2-phenylethyl)-4,5-dihydro-1H-pyrrolo[3,2-c]pyridine-2-carboxylic acid

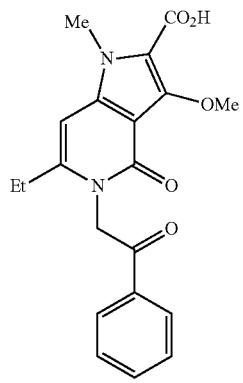 [SMILES: CCc1cc2c(c(OC)c(C(=O)O)n2C)c(=O)n1CC(=O)c1ccccc1]

In the same manner as in Reference Example 7, the title compound (110 mg, 79%) was obtained as a white powder from the compound of Reference Example 41 (150 mg, 0.378 mmol).

$^1$H-NMR (300 MHz, DMSO-$d_6$) δ:1.19 (3H, t, J=7.3 Hz), 2.57 (2H, q, J=7.3 Hz), 3.84 (3H, s), 3.85 (3H, s), 5.58 (2H, s), 6.48 (1H, s), 7.61 (2H, t, J=7.6 Hz), 7.67-7.86 (1H, m), 7.97-8.31 (2H, m), 12.51 (1H, br s).

Reference Example 43

Production of ethyl 3-ethoxy-1,6-dimethyl-4-oxo-5-(2-oxo-2-phenylethyl)-4,5-dihydro-1H-pyrrolo[3,2-c]pyridine-2-carboxylate

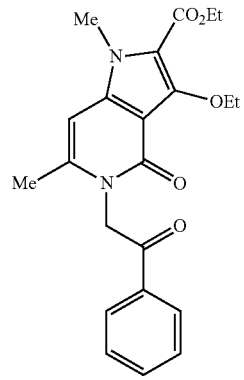 [SMILES: CCOC(=O)c1c(OCC)c2c(=O)n(CC(=O)c3ccccc3)c(C)cc2n1C]

In the same manner as in Reference Example 6, the title compound (560 mg, 52%) was obtained as a white powder from the compound of Reference Example 33 (1.00 g, 2.71 mmol) and iodoethane (326 μL, 4.07 mmol).

$^1$H-NMR (300 MHz, DMSO-$d_6$) δ:1.24 (3H, t, J=7.0 Hz), 1.30 (3H, t, J=7.1 Hz), 2.28 (3H, s), 3.81 (3H, s), 4.15 (2H, q, J=7.0 Hz), 4.26 (2H, q, J=7.1 Hz), 5.60 (2H, s), 6.58 (1H, s), 7.61 (2H, t, J=7.6 Hz), 7.69-7.78 (1H, m), 8.06-8.14 (2H, m).

Reference Example 44

Production of 3-ethoxy-1,6-dimethyl-4-oxo-5-(2-oxo-2-phenylethyl)-4,5-dihydro-1H-pyrrolo[3,2-c]pyridine-2-carboxylic acid

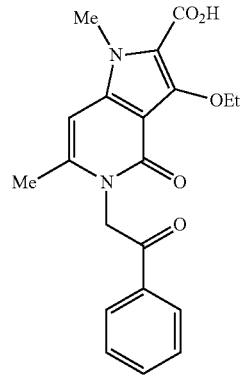 [SMILES: CCOc1c(C(=O)O)n(C)c2cc(C)n(CC(=O)c3ccccc3)c(=O)c12]

In the same manner as in Reference Example 7, the title compound (380 mg, 74%) was obtained as a white powder from the compound of Reference Example 43 (550 mg, 1.39 mmol).

$^1$H-NMR (300 MHz, DMSO-$d_6$) δ:1.22 (3H, t, J=7.0 Hz), 2.28 (3H, s), 3.81 (3H, s), 4.16 (2H, q, J=7.0 Hz), 5.60 (2H, s), 6.57 (1H, s), 7.61 (2H, t, J=7.6 Hz), 7.69-7.79 (1H, m), 8.03-8.16 (2H, m), 12.38 (1H, br s).

Reference Example 45

Production of ethyl 1,6-dimethyl-4-oxo-5-(2-oxo-2-phenylethyl)-3-propoxy-4,5-dihydro-1H-pyrrolo[3,2-c]pyridine-2-carboxylate

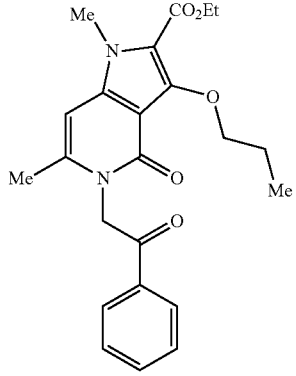 [SMILES: CCCOc1c(C(=O)OCC)n(C)c2cc(C)n(CC(=O)c3ccccc3)c(=O)c12]

In the same manner as in Reference Example 6, the title compound (152 mg, 18%) was obtained as a white powder from the compound (750 mg, 2.04 mmol) of Reference Example 33 and 1-bromopropane (277 µL, 3.05 mmol).

$^1$H-NMR (300 MHz, DMSO-$d_6$) δ:0.94 (3H, t, J=7.5 Hz), 1.30 (3H, t, J=7.1 Hz), 1.57-1.73 (2H, m), 2.28 (3H, s), 3.80 (3H, s), 4.08 (2H, t, J=6.5 Hz), 4.26 (2H, q, J=7.1 Hz), 5.60 (2H, s), 6.58 (1H, s), 7.56-7.66 (2H, m), 7.69-7.78 (1H, m), 8.06-8.15 (2H, m).

Reference Example 46

Production of 1,6-dimethyl-4-oxo-5-(2-oxo-2-phenylethyl)-3-propoxy-4,5-dihydro-1H-pyrrolo[3,2-c]pyridine-2-carboxylic acid

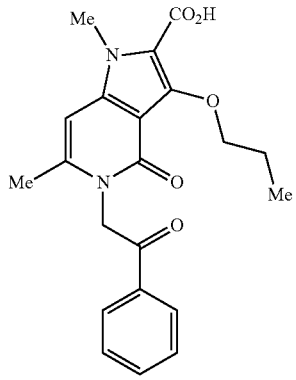 [SMILES: CCCOc1c(C(=O)O)n(C)c2cc(C)n(CC(=O)c3ccccc3)c(=O)c12]

In the same manner as in Reference Example 7, the title compound (105 mg, 81%) was obtained as a white powder from the compound of Reference Example 45 (140 mg, 0.341 mmol).

$^1$H-NMR (300 MHz, DMSO-$d_6$) δ:0.88-0.94 (3H, m), 1.58-1.67 (2H, m), 2.27 (3H, s), 3.81 (3H, s), 4.08 (2H, t, J=6.6 Hz), 5.60 (2H, s), 6.57 (1H, s), 7.55-7.65 (2H, m), 7.69-7.77 (1H, m), 8.06-8.14 (2H, m).

Reference Example 47

Production of ethyl 6-ethyl-3-ethoxy-1-methyl-4-oxo-5-(2-oxo-2-phenylethyl)-4,5-dihydro-1H-pyrrolo[3,2-c]pyridine-2-carboxylate

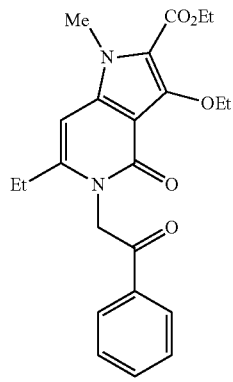 [SMILES: CCOC(=O)c1c(OCC)c2c(=O)n(CC(=O)c3ccccc3)c(CC)cc2n1C]

A mixture of the compound of Reference Example 40 (330 mg, 0.863 mmol), potassium carbonate (715 mg, 5.18 mmol), iodoethane (138 µL, 1.73 mmol) and DMF (5 mL) was stirred at room temperature for 15 hr. The reaction mixture was diluted with water, and extracted twice with ethyl acetate. The extract was combined, washed with saturated brine, dried over magnesium sulfate, and concentrated under reduced pressure. The residue was collected by filtration, and dried to give the title compound (189 mg, 46%) as a white powder.

$^1$H-NMR (300 MHz, DMSO-$d_6$) δ:1.13-1.35 (9H, m), 2.57 (2H, q, J=7.2 Hz), 3.84 (3H, s), 4.10-4.19 (2H, m), 4.26 (2H, q, J=7.2 Hz), 5.58 (2H, s), 6.49 (1H, s), 7.61 (2H, t, J=7.6 Hz), 7.70-7.77 (1H, m), 8.07-8.14 (2H, m).

Reference Example 48

Production of 3-ethoxy-6-ethyl-1-methyl-4-oxo-5-(2-oxo-2-phenylethyl)-4,5-dihydro-1H-pyrrolo[3,2-c]pyridine-2-carboxylic acid

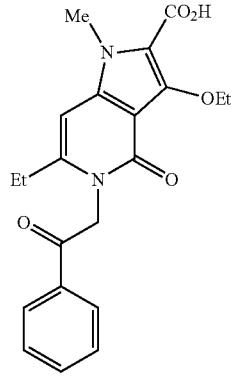 [SMILES: CCOc1c(C(=O)O)n(C)c2cc(CC)n(CC(=O)c3ccccc3)c(=O)c12]

A solution of the compound of Reference Example 47 (160 mg, 0.390 mmol) and 8N aqueous sodium hydroxide solution (1 mL) in ethanol (7 mL) was stirred at 60° C. for 1 hr. The reaction mixture was diluted with water, acidified with 6N hydrochloric acid, and the precipitated solid was collected by filtration. The obtained solid was washed with water, and dried under reduced pressure to give the title compound (74.0 mg, 50%) as a white powder.

$^1$H-NMR (300 MHz, DMSO-d$_6$) δ:1.13-1.25 (6H, m), 2.57 (2H, q, J=7.3 Hz), 3.84 (3H, s), 4.15 (2H, q, J=7.0 Hz), 5.57 (2H, s), 6.47 (1H, s), 7.61 (2H, t, J=7.5 Hz), 7.69-7.78 (1H, m), 8.08-8.15 (2H, m), 12.35 (1H, br s).

Reference Example 49

Production of ethyl 1,6-dimethyl-4-oxo-5-(2-oxo-2-phenylethyl)-3-(2,2,2-trifluoroethoxy)-4,5-dihydro-1H-pyrrolo[3,2-c]pyridine-2-carboxylate

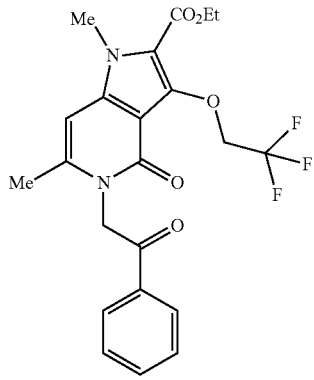 [SMILES: CCOC(=O)c1c(OCC(F)(F)F)c2c(=O)n(CC(=O)c3ccccc3)c(C)cc2n1C]

A mixture of the compound of Reference Example 33 (750 mg, 2.04 mmol), 1,1,1-trifluoro-2-iodoethane (603 μL, 6.12 mmol), potassium fluoride (119 mg, 2.04 mmol) and dimethyl sulfoxide (10 mL) was stirred at 100° C. for 15 hr. The reaction mixture was diluted with water, and the mixture was extracted with ethyl acetate. The extract was washed with saturated brine, dried over magnesium sulfate, and concentrated under reduced pressure. The residue was purified by aminosilica gel chromatography (eluate; ethyl acetate) to give the title compound (125 mg, 14%) as a white solid.

$^1$H-NMR (300 MHz, DMSO-d$_6$) δ:1.28 (3H, t, J=7.2 Hz), 2.30 (3H, s), 3.83 (3H, s), 4.19-4.31 (2H, m), 4.84 (2H, q, J=9.3 Hz), 5.64 (2H, s), 6.66 (1H, s), 7.57-7.66 (2H, m), 7.69-7.79 (1H, m), 8.07-8.15 (2H, m).

Reference Example 50

Production of 1,6-dimethyl-4-oxo-5-(2-oxo-2-phenylethyl)-3-(2,2,2-trifluoroethoxy)-4,5-dihydro-1H-pyrrolo[3,2-c]pyridine-2-carboxylic acid

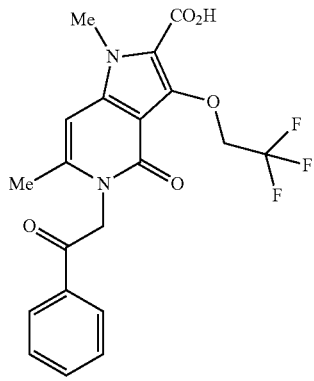 [SMILES: Cc1cc2c(c(OCC(F)(F)F)c(C(=O)O)n2C)c(=O)n1CC(=O)c1ccccc1]

A solution of the compound of Reference Example 49 (110 mg, 0.244 mmol) and 8N aqueous sodium hydroxide solution (1 mL) in ethanol (7 mL) was stirred at 60° C. for 1 hr. The reaction mixture was diluted with water and acidified with 6N hydrochloric acid, and the precipitated solid was collected by filtration. The obtained solid was washed with water, and dried under reduced pressure to give the title compound (78.0 mg, 76%) as a white powder.

$^1$H-NMR (300 MHz, DMSO-d$_6$) δ:2.29 (3H, s), 3.83 (3H, s), 4.82 (2H, q, J=9.3 Hz), 5.63 (2H, s), 6.64 (1H, s), 7.61 (2H, t, J=7.6 Hz), 7.70-7.78 (1H, m), 8.07-8.15 (2H, m), 12.57 (1H, br s).

Reference Example 51

Production of ethyl(2Z)-3-aminohex-2-enoate

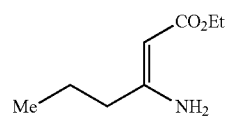

In the same manner as in Reference Example 36, the title compound (109 g, quant.) was obtained as a pale-yellow oil from ethyl 3-oxohexanoate (100 g, 632 mmol), ammonium acetate (244 g, 3.16 mmol) and methanol (750 mL).

$^1$H-NMR (300 MHz, DMSO-d$_6$) δ:0.87 (3H, t, J=7.4 Hz), 1.11-1.17 (3H, m), 1.42-1.58 (2H, m), 2.00-2.07 (2H, m), 3.96 (2H, q, J=7.2 Hz), 4.30 (1H, s), 6.90 (1H, br s), 7.73 (1H, br s).

Reference Example 52

Production of ethyl 4-hydroxy-2-oxo-6-n-propyl-1,2-dihydropyridine-3-carboxylate

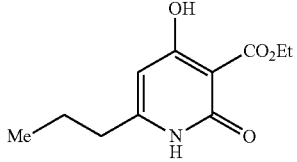 [SMILES: CCCc1cc(O)c(C(=O)OCC)c(=O)[nH]1]

In the same manner as in Reference Example 37, the title compound (27.5 g, 34%) was obtained as a white powder from the compound of Reference Example 51 (50.0 g, 0.387 mmol), diethyl malonate (58.8 mL, 387 mmol) and ethanol (400 mL).

$^1$H-NMR (300 MHz, DMSO-d$_6$) δ:0.87 (3H, t, J=7.4 Hz), 1.26 (3H, t, J=7.2 Hz), 1.49-1.65 (2H, m), 2.38 (2H, t), 4.25 (2H, q, J=7.0 Hz), 5.79 (1H, s), 11.37 (1H, s), 12.56 (1H, s).

Reference Example 53

Production of ethyl 4-chloro-2-oxo-6-propyl-1,2-dihydropyridine-3-carboxylate

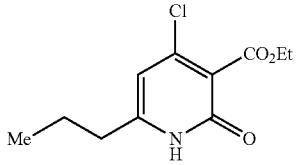 [SMILES: CCCc1cc(Cl)c(C(=O)OCC)c(=O)[nH]1]

A mixture of the compound of Reference Example 52 (37.0 g, 164 mmol) and phosphorus oxychloride (45.9 mL, 493 mmol) was stirred at 80° C. for 30 min. The mixture was concentrated under reduced pressure, and ice water was added to the residue. The precipitated solid was collected by filtration, and washed with water and ethyl acetate to give the title compound (17.6 g, 44%) as a white solid.

$^1$H-NMR (300 MHz, DMSO-$d_6$) δ:0.87 (3H, t, J=7.4 Hz), 1.26 (3H, t, J=7.1 Hz), 1.52-1.65 (2H, m), 2.40-2.48 (2H, m), 4.25 (2H, q, J=7.1 Hz), 6.27 (1H, s), 12.17 (1H, br s).

Reference Example 54

Production of ethyl 4-chloro-2-oxo-1-(2-oxo-2-phenylethyl)-6-propyl-1,2-dihydropyridine-3-carboxylate

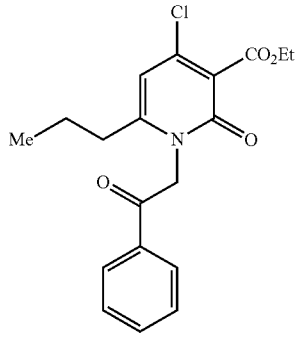 [SMILES: CCCc1cc(Cl)c(C(=O)OCC)c(=O)n1CC(=O)c1ccccc1]

In the same manner as in Reference Example 4, the title compound (7.15 g, 28%) was obtained as a white powder from the compound of Reference Example 53 (17.0 g, 69.8 mmol), sodium hydride (60% in oil, 3.07 g, 76.7 mmol), phenacyl bromide (16.7 g, 83.8 mmol) and DMF (150 mL).

$^1$H-NMR (300 MHz, DMSO-$d_6$) δ:0.91 (3H, t, J=7.3 Hz), 1.24 (3H, t, J=7.1 Hz), 1.47-1.64 (2H, m), 2.55-2.66 (2H, m), 4.24 (2H, q, J=7.1 Hz), 5.59 (2H, s), 6.47 (1H, s), 7.61 (2H, t, J=7.6 Hz), 7.70-7.80 (1H, m), 8.06-8.17 (2H, m).

Reference Example 55

Production of ethyl 3-hydroxy-1-methyl-4-oxo-5-(2-oxo-2-phenylethyl)-6-propyl-4,5-dihydro-1H-pyrrolo[3,2-c]pyridine-2-carboxylate

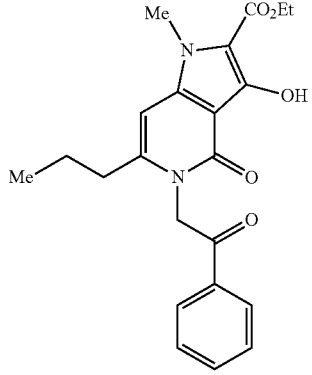 [SMILES: CCCc1cc2c(c(O)c(C(=O)OCC)n2C)c(=O)n1CC(=O)c1ccccc1]

A mixture of the compound of Reference Example 54 (7.00 g, 19.3 mmol), sarcosine ethyl ester hydrochloride (5.94 g, 38.7 mmol), triethylamine (29.7 mL, 193 mmol) and ethanol (100 mL) was stirred for 2 days under refluxing conditions. The mixture was concentrated under reduced pressure, water (200 mL) was added to the residue, and the mixture was acidified with 5N hydrochloric acid (3 mL). The precipitated solid was collected by filtration, and washed with water and hexane-ethyl acetate to give the title compound (5.70 g, 74%) as a white solid.

$^1$H-NMR (300 MHz, DMSO-$d_6$) δ:0.92 (3H, t, J=7.3 Hz), 1.31 (3H, t, J=7.1 Hz), 1.50-1.65 (2H, m), 2.49-2.57 (2H, m), 3.78 (3H, s), 4.30 (2H, q, J=7.1 Hz), 5.52 (2H, s), 6.45 (1H, s), 7.60 (2H, t, J=7.5 Hz), 7.68-7.78 (1H, m), 8.07-8.15 (2H, m), 8.90 (1H, br s).

Reference Example 56

Production of ethyl 3-ethoxy-1-methyl-4-oxo-5-(2-oxo-2-phenylethyl)-6-propyl-4,5-dihydro-1H-pyrrolo[3,2-c]pyridine-2-carboxylate

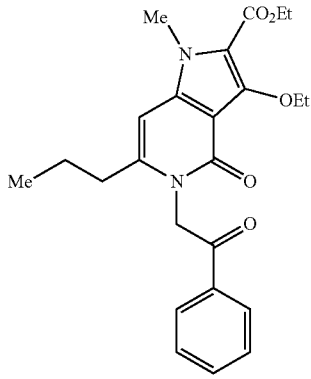 [SMILES: CCCc1cc2c(c(OCC)c(C(=O)OCC)n2C)c(=O)n1CC(=O)c1ccccc1]

A mixture of the compound of Reference Example 55 (1.00 g, 8.08 mmol), diethyl sulfate (397 μL, 3.03 mmol), potassium carbonate (1.05 g, 7.57 mmol) and acetone (20 mL) was stirred for 15 hr under refluxing conditions. Water (30 mL) was added to the mixture, and the precipitated solid was collected by filtration, and washed with water and ethyl acetate-hexane to give the title compound (876 mg, 82%) as a white solid.

$^1$H-NMR (300 MHz, DMSO-$d_6$) δ:0.93 (3H, t, J=7.4 Hz), 1.23 (3H, t, J=7.0 Hz), 1.30 (3H, t, J=7.1 Hz), 1.52-1.66 (2H, m), 2.51-2.58 (2H, m), 3.83 (3H, s), 4.14 (2H, q, J=7.1 Hz), 4.26 (2H, q, J=7.1 Hz), 5.54 (2H, s), 6.51 (1H, s), 7.61 (2H, t, J=7.6 Hz), 7.69-7.77 (1H, m), 8.08-8.15 (2H, m).

Reference Example 57

Production of 3-ethoxy-1-methyl-4-oxo-5-(2-oxo-2-phenylethyl)-6-propyl-4,5-dihydro-1H-pyrrolo[3,2-c]pyridine-2-carboxylic acid

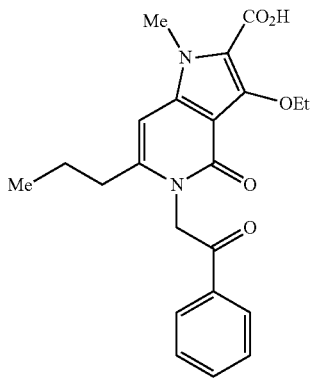 [SMILES: CCCc1cc2c(c(OCC)c(C(=O)O)n2C)c(=O)n1CC(=O)c1ccccc1]

A solution of the compound of Reference Example 56 (850 mg, 2.00 mmol) and 8N aqueous sodium hydroxide solution (2 mL) in ethanol (14 mL) was stirred at 60° C. for 30 min. The reaction mixture was diluted with water, acidified with 5N hydrochloric acid, and the precipitated solid was collected by filtration. The obtained solid was washed with water, and dried under reduced pressure to give the title compound (705 mg, 89%) as a white powder.

$^1$H-NMR (300 MHz, DMSO-d$_6$) δ:0.93 (3H, t, J=7.4 Hz), 1.21 (3H, t, J=7.0 Hz), 1.50-1.66 (2H, m), 2.50-2.58 (2H, m), 3.83 (3H, s), 4.15 (2H, q, J=7.1 Hz), 5.54 (2H, s), 6.50 (1H, s), 7.61 (2H, t, J=7.6 Hz), 7.69-7.78 (1H, m), 8.08-8.16 (2H, m), 12.42 (1H, br s).

Reference Example 58

Production of ethyl 6-ethyl-3-(2-fluoroethoxy)-1-methyl-4-oxo-5-(2-oxo-2-phenylethyl)-4,5-dihydro-1H-pyrrolo[3,2-c]pyridine-2-carboxylate

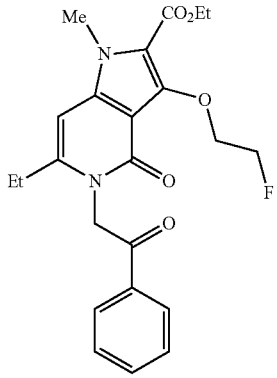 [SMILES: CCOC(=O)c1c(OCCF)c2c(=O)n(CC(=O)c3ccccc3)c(CC)cc2n1C]

In the same manner as in Reference Example 6, the title compound (649 mg, 77%) was obtained as a white powder from the compound of Reference Example 40 (750 mg, 1.96 mmol), DBU (440 μL, 2.94 mmol) and 1-fluoro-2-iodoethane (512 mg, 2.94 mmol).

$^1$H-NMR (300 MHz, DMSO-d$_6$) δ:1.19 (3H, t, J=7.3 Hz), 1.30 (3H, t, J=7.1 Hz), 2.58 (2H, q, J=7.3 Hz), 3.85 (3H, s), 4.26 (2H, q, J=7.1 Hz), 4.32-4.36 (1H, m), 4.42-4.47 (1H, m), 4.53-4.59 (1H, m), 4.69-4.75 (1H, m), 5.58 (2H, s), 6.51 (1H, s), 7.61 (2H, t, J=7.6 Hz), 7.70-7.77 (1H, m), 8.08-8.14 (2H, m).

Reference Example 59

Production of 6-ethyl-3-(2-fluoroethoxy)-1-methyl-4-oxo-5-(2-oxo-2-phenylethyl)-4,5-dihydro-1H-pyrrolo[3,2-c]pyridine-2-carboxylic acid

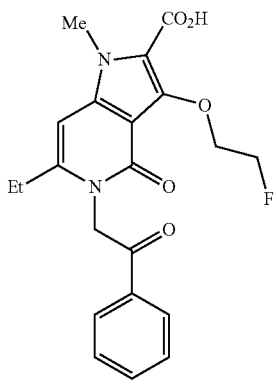 [SMILES: CCc1cc2c(c(OCCF)c(C(=O)O)n2C)c(=O)n1CC(=O)c1ccccc1]

A solution of the compound of Reference Example 58 (620 mg, 1.45 mmol) and 8N aqueous sodium hydroxide solution (1 mL) in ethanol (7 mL) was stirred at 60° C. for 30 min. The reaction mixture was diluted with water, acidified with 5N hydrochloric acid, and the precipitated solid was collected by filtration. The obtained solid was washed with water, and dried under reduced pressure to give the title compound (470 mg, 56%) as a white powder.

$^1$H-NMR (300 MHz, DMSO-d$_6$) δ:1.19 (3H, t, J=7.4 Hz), 2.58 (2H, q, J=7.4 Hz), 3.85 (3H, s), 4.32-4.36 (1H, m), 4.42-4.47 (1H, m), 4.54-4.59 (1H, m), 4.70-4.74 (1H, m), 5.58 (2H, s), 6.50 (1H, s), 7.61 (2H, t, J=7.6 Hz), 7.70-7.77 (1H, m), 8.09-8.15 (2H, m), 12.48 (1H, br s).

Reference Example 60

Production of ethyl 6-ethyl-1-methyl-4-oxo-5-(2-oxo-2-phenylethyl)-3-(2,2,2-trifluoroethoxy)-4,5-dihydro-1H-pyrrolo[3,2-c]pyridine-2-carboxylate

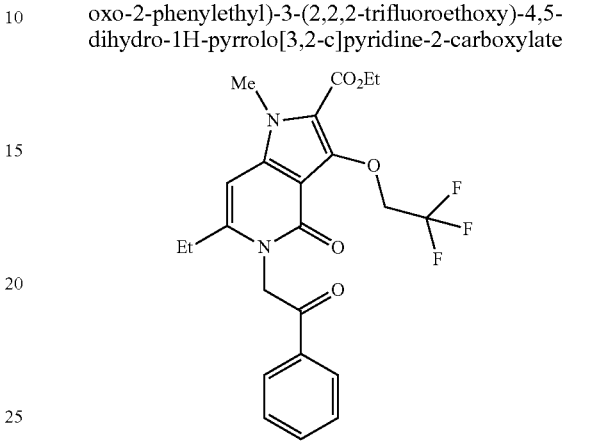

A mixture of the compound of Reference Example 40 (1.00 g, 2.61 mmol), 1,1,1-trifluoro-2-iodoethane (1.29 mL, 13.1 mmol), cesium carbonate (4.27 g, 13.1 mmol) and dimethyl sulfoxide (10 mL) was stirred at 100° C. for 5 hr. The reaction mixture was filtered, the filtrate was diluted with 1N hydrochloric acid (30 mL), and the mixture was extracted with ethyl acetate. The extract was washed with water and brine, dried over magnesium sulfate, and concentrated under reduced pressure. The residue was purified by aminosilica gel chromatography (eluate; hexane/ethyl acetate=9/1-0/10) to give the title compound (278 mg, 23%) as a white solid.

$^1$H-NMR (300 MHz, DMSO-d$_6$) δ:1.19 (3H, t, J=7.4 Hz), 1.28 (3H, t, J=7.1 Hz), 2.59 (2H, q, J=7.4 Hz), 3.86 (3H, s), 4.26 (2H, q, J=7.1 Hz), 4.83 (2H, q, J=9.3 Hz), 5.62 (2H, s), 6.56 (1H, s), 7.61 (2H, t, J=7.5 Hz), 7.70-7.78 (1H, m), 8.08-8.14 (2H, m).

Reference Example 61

Production of 6-ethyl-1-methyl-4-oxo-5-(2-oxo-2-phenylethyl)-3-(2,2,2-trifluoroethoxy)-4,5-dihydro-1H-pyrrolo[3,2-c]pyridine-2-carboxylic acid

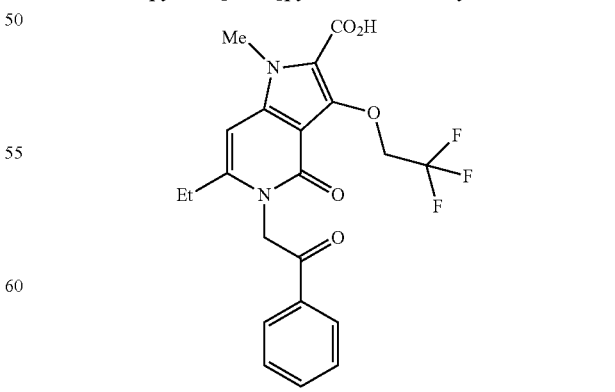

A solution of the compound of Reference Example 60 (270 mg, 0.581 mmol) and 8N aqueous sodium hydroxide solution (1 mL) in ethanol (7 mL) was stirred at 60° C. for 1 hr. The reaction mixture was diluted with water, acidified with 5N hydrochloric acid, and the precipitated solid was collected by filtration. The obtained solid was washed with water, and dried under reduced pressure to give the title compound (235 mg, 93%) as a white powder.

$^1$H-NMR (300 MHz, DMSO-$d_6$) δ:1.19 (3H, t, J=7.4 Hz), 2.58 (2H, q, J=7.4 Hz), 3.86 (3H, s), 4.82 (2H, q, J=9.2 Hz), 5.61 (2H, s), 6.54 (1H, s), 7.61 (2H, t, J=7.6 Hz), 7.70-7.77 (1H, m), 8.07-8.16 (2H, m), 12.74 (1H, br s).

Reference Example 62

Production of ethyl 4-chloro-2-oxo-1,2,5,6,7,8-hexahydroquinoline-3-carboxylate

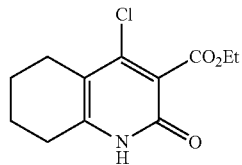 [SMILES: CCOC(=O)c1c(Cl)c2c([nH]c1=O)CCCC2]

A mixture of ethyl 4-hydroxy-2-oxo-1,2,5,6,7,8-hexahydroquinoline-3-carboxylate (26.0 g, 110 mmol) and phosphorus oxychloride (51.3 mL) was stirred at 130° C. for 1.5 hr. After cooling, the reaction mixture was concentrated under reduced pressure, and ice was added to the residue. The mixture was neutralized with saturated sodium hydrogen carbonate solution, and extracted with ethyl acetate. The extract was washed successively with saturated sodium hydrogen carbonate solution, water and brine, dried over magnesium sulfate, and concentrated under reduced pressure. The residue was collected by filtration, and washed with ethyl acetate-hexane to give the title compound (4.65 g, 17%) as a white solid.

$^1$H-NMR (300 MHz, DMSO-$d_6$) δ:1.25 (3H, t, J=7.1 Hz), 1.61-1.74 (4H, m), 2.37-2.45 (2H, m), 2.51-2.57 (2H, m), 4.24 (2H, q, J=7.2 Hz), 12.09 (1H, s).

Reference Example 63

Production of ethyl 4-chloro-2-oxo-1-(2-oxo-2-phenylethyl)-1,2,5,6,7,8-hexahydroquinoline-3-carboxylate

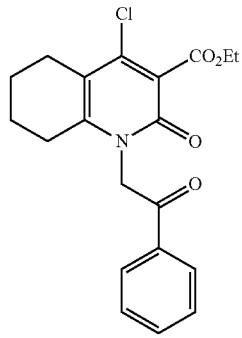 [SMILES: CCOC(=O)c1c(Cl)c2c(n(CC(=O)c3ccccc3)c1=O)CCCC2]

In the same manner as in Reference Example 4, the title compound (710 mg, 16%) was obtained as a white powder from the compound of Reference Example 62 (3.00 g, 11.7 mmol), sodium hydride (60% in oil, 516 mg, 12.9 mmol) and phenacyl bromide (2.57 g, 12.9 mmol).

$^1$H-NMR (300 MHz, DMSO-$d_6$) δ:1.25 (3H, t, J=7.1 Hz), 1.60-1.80 (4H, m), 2.50-2.65 (4H, m), 4.26 (2H, q, J=7.1 Hz), 5.66 (2H, s), 7.61 (2H, t, J=7.4 Hz), 7.74 (1H, t, J=7.4 Hz), 8.09 (2H, d, J=7.4 Hz).

Reference Example 64

Production of ethyl 3-hydroxy-4-oxo-5-(2-oxo-2-phenylethyl)-4,5,6,7,8,9-hexahydrothieno[3,2-c]quinoline-2-carboxylate

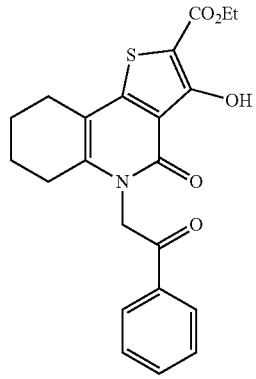 [SMILES: CCOC(=O)c1sc2c3c(n(CC(=O)c4ccccc4)c(=O)c2c1O)CCCC3]

In the same manner as in Reference Example 5, the title compound (751 mg, 100%) was obtained as a white powder from the compound of Reference Example 63 (690 mg, 1.85 mmol), 20% solution (1.26 g, 3.69 mmol) of sodium ethoxide in ethanol, ethyl thioglycolate (486 μL, 4.43 mmol) and ethanol (15 mL).

$^1$H-NMR (300 MHz, DMSO-$d_6$) δ:1.29 (3H, t, J=7.0 Hz), 1.65-1.85 (4H, m), 2.50-2.65 (4H, m), 4.28 (2H, q, J=7.0 Hz), 5.72 (2H, s), 7.62 (2H, t, J=7.7 Hz), 7.73-7.78 (1H, m), 8.10-8.13 (2H, m), 10.39 (1H, s).

Reference Example 65

Production of ethyl 3-methoxy-4-oxo-5-(2-oxo-2-phenylethyl)-4,5,6,7,8,9-hexahydrothieno[3,2-c]quinoline-2-carboxylate

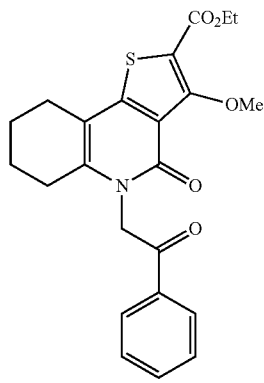 [SMILES: CCOC(=O)c1sc2c3c(n(CC(=O)c4ccccc4)c(=O)c2c1OC)CCCC3]

In the same manner as in Reference Example 6, the title compound (238 mg, 31%) was obtained as a white powder from the compound of Reference Example 64 (740 mg, 1.80 mmol), iodomethane (168 μL, 2.70 mmol), DBU (404 μL, 2.70 mmol) and DMF (15 mL).

$^1$H-NMR (300 MHz, DMSO-$d_6$) δ:1.31 (3H, t, J=7.0 Hz), 1.65-1.85 (4H, m), 2.45-2.65 (4H, m), 3.89 (3H, s), 4.29 (2H, q, J=7.0 Hz), 5.67 (2H, s), 7.62 (2H, t, J=7.4 Hz), 7.75 (1H, t, J=7.4 Hz), 8.11 (2H, d, J=7.4 Hz).

Reference Example 66

Production of 3-methoxy-4-oxo-5-(2-oxo-2-phenylethyl)-4,5,6,7,8,9-hexahydrothieno[3,2-c]quinoline-2-carboxylic acid

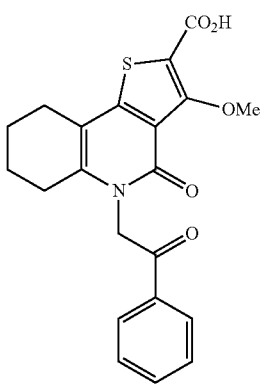 [SMILES: COc1c(C(=O)O)sc2c3c(n(CC(=O)c4ccccc4)c(=O)c12)CCCC3]

A solution of the compound of Reference Example 65 (220 mg, 0.517 mmol) and 8N aqueous sodium hydroxide solution (1 mL) in ethanol (7 mL) was stirred at 60° C. for 1 hr. The reaction mixture was acidified with 6N hydrochloric acid (1.5 mL), and the precipitated solid was collected by filtration. The obtained solid was washed with water, and dried under reduced pressure to give the title compound (162 mg, 79%) as a white powder.

$^1$H-NMR (300 MHz, DMSO-d$_6$) δ:1.66-1.88 (4H, m), 2.52-2.61 (4H, m), 3.86 (3H, s), 5.66 (2H, s), 7.62 (2H, t, J=7.6 Hz), 7.70-7.79 (1H, m), 8.03-8.11 (2H, m), 13.12 (1H, s).

Reference Example 67

Production of ethyl 4-chloro-3-hydroxy-6-methylthieno[3,2-c]pyridine-2-carboxylate

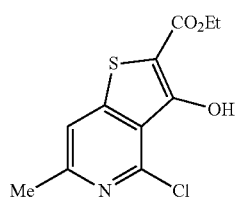 [SMILES: CCOC(=O)c1sc2cc(C)nc(Cl)c2c1O]

To a suspension of ethyl 2,4-dichloro-6-methylpyridine-3-carboxylate (10.0 g, 42.7 mmol) in acetonitrile (45 mL) were added potassium carbonate (8.85 g, 64.1 mmol) and ethyl thioglycolate (4.68 mL, 42.7 mmol), and the mixture was stirred for 15 hr under refluxing conditions. The reaction mixture was diluted with water (150 mL), 6N hydrochloric acid (15 mL) was added and the mixture was stirred for 30 min. The precipitated solid was collected by filtration, washed with water and ethanol-diisopropyl ether (1/1), and dried under reduced pressure to give the title compound (10.9 g, 94%) as a white powder.

$^1$H-NMR (300 MHz, DMSO-d$_6$) δ:1.32 (3H, t, J=7.1 Hz), 2.54 (3H, s), 4.36 (2H, q, J=7.1 Hz), 7.87 (1H, s), 10.75 (1H, s).

Reference Example 68

Production of ethyl 4-chloro-3-ethoxy-6-methylthieno[3,2-c]pyridine-2-carboxylate

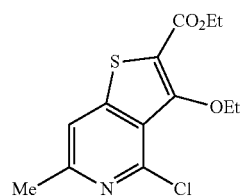 [SMILES: CCOC(=O)c1sc2cc(C)nc(Cl)c2c1OCC]

In the same manner as in Reference Example 6, the title compound (4.30 g, 78%) was obtained as a white powder from the compound of Reference Example 67 (4.97 g, 18.3 mmol), DBU (4.10 mL, 27.4 mmol) and iodoethane (2.19 mL, 27.4 mmol).

$^1$H-NMR (300 MHz, DMSO-d$_6$) δ:1.33 (3H, t, J=7.2 Hz), 1.43 (3H, t, J=7.1 Hz), 2.54 (3H, s), 4.25 (2H, q, J=7.0 Hz), 4.34 (2H, q, J=7.1 Hz), 7.92 (1H, s).

Reference Example 69

Production of 4-chloro-3-ethoxy-6-methylthieno[3,2-c]pyridine-2-carboxylic acid

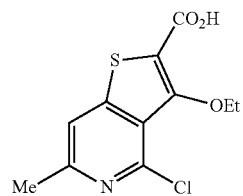

A mixed solution of the compound of Reference Example 68 (4.30 g, 14.3 mmol) and 8N aqueous sodium hydroxide solution (15 mL) in THF (22 mL)-ethanol (22 mL) was stirred for 5 hr under refluxing conditions. The reaction mixture was acidified with 6N hydrochloric acid (22 mL) and the precipitated solid was collected by filtration. The obtained solid was washed with water, and dried under reduced pressure to give the title compound (3.80 g, 97%) as a white powder.

$^1$H-NMR (300 MHz, DMSO-$d_6$) δ:1.40 (3H, t, J=6.9 Hz), 2.54 (3H, s), 4.26 (2H, q, J=6.9 Hz), 7.90 (1H, s), 13.65 (1H, s).

Reference Example 70

Production of 4-chloro-N-[2-(diethylamino)ethyl]-3-ethoxy-N,6-dimethylthieno[3,2-c]pyridine-2-carboxamide

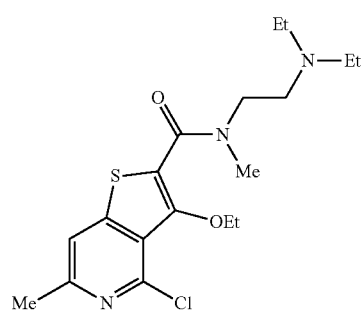 [SMILES: CCOc1c(C(=O)N(C)CCN(CC)CC)sc2cc(C)nc(Cl)c12]

In the same manner as in Example 25, the title compound (800 mg, 59%) was obtained as a colorless oil from the compound of Reference Example 69 (1.00 g, 3.68 mmol) and N,N-diethyl-N'-methylethane-1,2-diamine (773 μL, 4.78 mmol).

$^1$H-NMR (300 MHz, DMSO-$d_6$) δ:0.65-1.10 (6H, m), 1.33 (3H, t, J=6.9 Hz), 2.20-2.70 (6H, m), 2.53 (3H, s), 3.04 (3H, s), 3.35-3.65 (2H, m), 4.05-4.20 (2H, m), 7.89 (1H, s).

Reference Example 71

Production of ethyl 4-chloro-3-hydroxy-6,7-dimethylthieno[3,2-c]pyridine-2-carboxylate

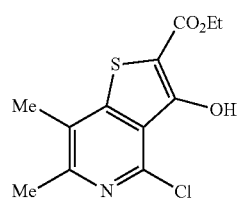 [SMILES: CCOC(=O)c1sc2c(C)c(C)nc(Cl)c2c1O]

A 20% solution (1.73 g, 5.08 mmol) of sodium ethoxide in ethanol was diluted with ethanol (5 mL), and ethyl thioglycolate (610 mg, 5.08 mmol) was added. Ethyl 2,4-dichloro-5,6-dimethylpyridine-3-carboxylate (630 mg, 2.54 mmol) was added to the mixture, and the mixture was stirred at room temperature for 18 hr. 2N Hydrochloric acid (3 mL) was added to the reaction mixture and the mixture was partitioned between brine and ethyl acetate. The organic layer was dried over magnesium sulfate and concentrated. The obtained solid was washed with diisopropyl ether-hexane, and dried under reduced pressure to give the title compound (374 mg, 52%) as a white powder.

$^1$H-NMR (300 MHz, CDCl$_3$) δ:1.43 (3H, t, J=7.2 Hz), 2.40 (3H, s), 2.61 (3H, s), 4.44 (2H, q, J=7.2 Hz), 10.63 (1H, s).

Reference Example 72

Production of ethyl 4-chloro-3-ethoxy-6,7-dimethylthieno[3,2-c]pyridine-2-carboxylate

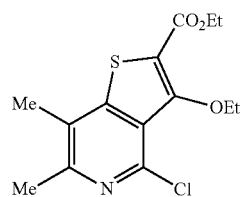 [SMILES: CCOC(=O)c1sc2c(C)c(C)nc(Cl)c2c1OCC]

In the same manner as in Reference Example 6, the title compound (350 mg, 91%) was obtained as a white solid from the compound of Reference Example 71 (350 mg, 1.22 mmol), DBU (380 mg, 2.02 mmol) and iodoethane (315 mg, 2.02 mmol).

$^1$H-NMR (300 MHz, CDCl$_3$) δ:1.43 (3H, t, J=7.2 Hz), 1.54 (3H, t, J=7.2 Hz), 2.42 (3H, s), 2.60 (3H, s), 4.31 (2H, q, J=7.2 Hz), 4.41 (2H, q, J=7.2 Hz).

Reference Example 73

Production of 4-chloro-3-ethoxy-6,7-dimethylthieno[3,2-c]pyridine-2-carboxylic acid

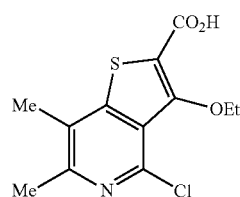 [SMILES: CCOc1c(C(=O)O)sc2c(C)c(C)nc(Cl)c12]

A mixed solution of the compound of Reference Example 72 (250 mg, 0.80 mmol) and 4N aqueous sodium hydroxide solution (2 mL) in THF (2 ml)-ethanol (1 mL) was stirred at room temperature for 18 hr. The reaction mixture was partitioned between 1N hydrochloric acid and ethyl acetate, and the organic layer was dried over magnesium sulfate and concentrated under reduced pressure to give the title compound (210 mg, 92%) as a white solid.

$^1$H-NMR (300 MHz, DMSO-d$_6$) δ:1.40 (3H, t, J=7.1 Hz), 2.40 (3H, s), 2.53 (3H, s), 4.25 (2H, q, J=7.0 Hz).

Reference Example 74

Production of 4-chloro-N-[2-(diethylamino)ethyl]-3-ethoxy-N,6,7-trimethylthieno[3,2-c]pyridine-2-carboxamide

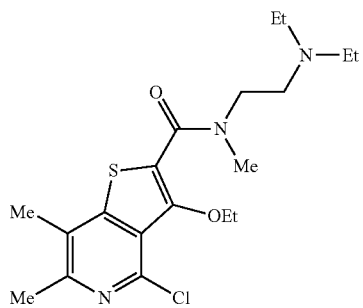 [SMILES: CCOc1c(C(=O)N(C)CCN(CC)CC)sc2c(C)c(C)nc(Cl)c12]

In the same manner as in Example 25, the title compound (230 mg, 79%) was obtained as a colorless oil from the compound of Reference Example 73 (210 mg, 0.73 mmol) and N,N-diethyl-N'-methylethane-1,2-diamine (144 mg, 1.10 mmol).

$^1$H-NMR (300 MHz, CDCl$_3$) δ:0.80-1.10 (6H, m), 1.42 (3H, t, J=6.9 Hz), 2.30-2.50 (5H, m), 2.60-2.80 (7H, m), 3.19 (3H, s), 3.45-3.70 (2H, m), 4.18 (2H, q, J=7.0 Hz).

Reference Example 75

Production of ethyl 3-hydroxy-6-methyl-4-oxo-5-(2-oxo-2-phenylethyl)-4,5-dihydrothieno[3,2-c]pyridine-2-carboxylate

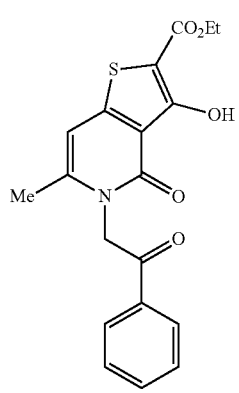 [SMILES: CCOC(=O)c1sc2cc(C)n(CC(=O)c3ccccc3)c(=O)c2c1O]

In the same manner as in Reference Example 5, the title compound (8.31 g, 88%) was obtained as a white powder from the compound of Reference Example 32 (8.50 g, 25.5 mmol), ethyl thioglycolate (6.70 mL, 61.1 mmol), a 20% solution (17.4 g, 51.0 mmol) of sodium ethoxide in ethanol and ethanol (100 mL).

$^1$H-NMR (300 MHz, DMSO-d$_6$) δ:1.28 (3H, t, J=7.2 Hz), 2.33 (3H, s), 4.27 (2H, q, J=7.1 Hz), 5.71 (2H, s), 6.93 (1H, d, J=0.9 Hz), 7.62 (2H, t, J=7.5 Hz), 7.69-7.83 (1H, m), 8.01-8.21 (2H, m), 10.34 (1H, s).

Reference Example 76

Production of ethyl 3-methoxy-6-methyl-4-oxo-5-(2-oxo-2-phenylethyl)-4,5-dihydrothieno[3,2-c]pyridine-2-carboxylate

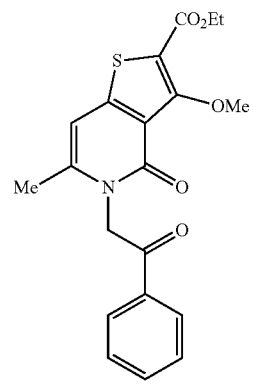 [SMILES: CCOC(=O)c1sc2cc(C)n(CC(=O)c3ccccc3)c(=O)c2c1OC]

A mixture of the compound of Reference Example 75 (3.00 g, 8.08 mmol), dimethyl sulfate (4.58 mL, 48.4 mmol), potassium carbonate (3.35 g, 24.2 mmol) and acetone (60 mL) was stirred for 3 days under refluxing conditions. Water (120 mL) was added to the mixture, and the precipitated solid was collected by filtration, and washed with water, ethanol and ethyl acetate to give the title compound (2.45 g, 79%) as a white solid.

$^1$H-NMR (300 MHz, DMSO-d$_6$) δ:1.30 (3H, t, J=7.1 Hz), 2.31 (3H, s), 3.88 (3H, s), 4.28 (2H, q, J=7.2 Hz), 5.66 (2H, s), 6.85 (1H, d, J=0.8 Hz), 7.58-7.67 (2H, m), 7.70-7.80 (1H, m), 8.06-8.15 (2H, m).

Reference Example 77

Production of ethyl 3-ethoxy-6-methyl-4-oxo-5-(2-oxo-2-phenylethyl)-4,5-dihydrothieno[3,2-c]pyridine-2-carboxylate

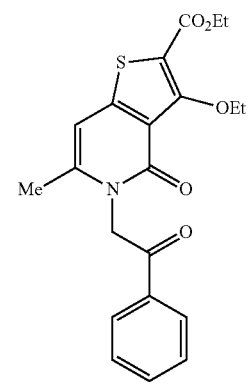 [SMILES: CCOC(=O)c1sc2cc(C)n(CC(=O)c3ccccc3)c(=O)c2c1OCC]

In the same manner as in Reference Example 6, the title compound (585 mg, 54%) was obtained as a white powder from the compound of Reference Example 75 (1.00 g, 2.69 mmol), DBU (604 μL, 4.04 mmol) and iodoethane (323 μL, 4.04 mmol).

¹H-NMR (300 MHz, DMSO-d₆) δ:1.23-1.35 (6H, m), 2.31 (3H, s), 4.14 (2H, q, J=7.0 Hz), 4.27 (2H, q, J=7.1 Hz), 5.67 (2H, s), 6.84 (1H, d, J=0.8 Hz), 7.57-7.67 (2H, m), 7.71-7.79 (1H, m), 8.07-8.15 (2H, m).

Reference Example 78

Production of 3-methoxy-6-methyl-4-oxo-5-(2-oxo-2-phenylethyl)-4,5-dihydrothieno[3,2-c]pyridine-2-carboxylic acid

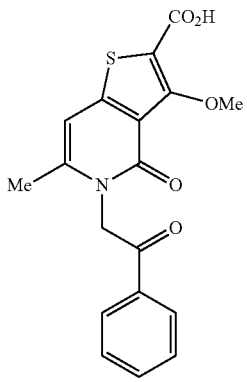 [SMILES: COc1c(C(=O)O)sc2cc(C)n(CC(=O)c3ccccc3)c(=O)c12]

In the same manner as in Reference Example 7, the title compound (1.25 g, 67%) was obtained as a white powder from the compound of Reference Example 76 (2.00 g, 5.19 mmol), 8N aqueous sodium hydroxide solution (3 mL) and ethanol (21 mL).

¹H-NMR (300 MHz, DMSO-d₆) δ:2.31 (3H, m), 3.86 (3H, s), 5.66 (2H, s), 6.83 (1H, d, J=0.8 Hz), 7.58-7.68 (2H, m), 7.71-7.80 (1H, m), 8.08-8.17 (2H, m), 13.07 (1H, br s).

Reference Example 79

Production of 3-ethoxy-6-methyl-4-oxo-5-(2-oxo-2-phenylethyl)-4,5-dihydrothieno[3,2-c]pyridine-2-carboxylic acid

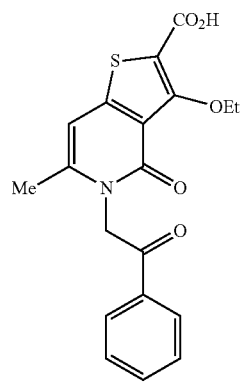

In the same manner as in Reference Example 7, the title compound (311 mg, 67%) was obtained as a white powder from the compound of Reference Example 77 (500 mg, 1.25 mmol), 8N aqueous sodium hydroxide solution (1 mL) and ethanol (7 mL).

¹H-NMR (300 MHz, DMSO-d₆) δ:1.27 (3H, t, J=7.0 Hz), 2.30 (3H, s), 4.14 (2H, q, J=7.0 Hz), 5.66 (2H, s), 6.82 (1H, s), 7.58-7.66 (2H, m), 7.71-7.79 (1H, m), 8.08-8.17 (2H, m), 13.05 (1H, br s).

Reference Example 80

Production of ethyl 4-hydroxy-1-methyl-2-oxo-1,2-dihydroquinoline-3-carboxylate

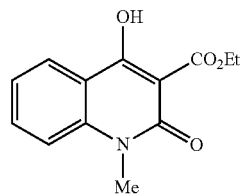 [SMILES: CCOC(=O)c1c(O)c2ccccc2n(C)c1=O]

To a solution of diethyl malonate (68.0 g, 0.425 mol) in DMF (400 mL) was added sodium hydride (66% in oil, 10.8 g, 0.30 mol) under ice-cooling, and the mixture was stirred at the same temperature for 5 min and at room temperature for 15 min. N-Methylisatoic anhydride (50.8 g, 0.287 mol) was added to the obtained mixture by small portions, and the mixture was stirred at 120° C. for 3 hr. Diisopropyl ether (500 mL) was added to the reaction mixture, and the precipitated solid was collected by filtration and washed with diisopropyl ether. The obtained solid was suspended in a mixture of methanol (250 mL) and water (500 mL), 5N hydrochloric acid (60 mL) was added dropwise, and the mixture was extracted twice with ethyl acetate. The combined organic layer was washed with water, and concentrated under reduced pressure. The residue was washed with diisopropyl ether to give the title compound (41.4 g, 58%).

¹H-NMR (300 MHz, CDCl₃) δ:1.49 (3H, t, J=7.1 Hz), 3.66 (3H, s), 4.51 (2H, q, J=7.1 Hz), 7.23-7.30 (1H, m), 7.32 (1H, d, J=8.7 Hz), 7.69 (1H, ddd, J=8.7, 7.1, 1.6 Hz), 8.19 (1H, dd, J=8.0, 1.6 Hz), 14.21 (1H, s).

Reference Example 81

Production of ethyl 4-chloro-1-methyl-2-oxo-1,2-dihydroquinoline-3-carboxylate

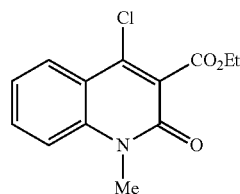 [SMILES: CCOC(=O)c1c(Cl)c2ccccc2n(C)c1=O]

A mixture of the compound of Reference Example 80 (58.0 g, 0.235 mol) and phosphorus oxychloride (33 mL, 0.35 mol) was stirred at 110° C. for 30 min. The reaction mixture was concentrated under reduced pressure, and ice water and ethyl acetate were added. The organic layer was separated, and the aqueous layer was extracted with ethyl acetate. The combined organic layer was washed with water, 1N sodium hydroxide solution (3 times) and water, and concentrated under reduced pressure. The residue was crystallized from ethyl acetate-diisopropyl ether to give the title compound (47.7 g, 76%).

¹H-NMR (300 MHz, CDCl₃) δ:1.42 (3H, t, J=7.1 Hz), 3.73 (3H, s), 4.48 (2H, q, J=7.1 Hz), 7.35 (1H, ddd, J=8.7, 7.1, 1.0

Hz), 7.40 (1H, d, J=8.7 Hz), 7.68 (1H, ddd, J=8.7, 7.1, 1.4 Hz), 8.07 (1H, dd, J=8.0, 1.4 Hz).

Reference Example 82

Production of ethyl 3-hydroxy-5-methyl-4-oxo-4,5-dihydrothieno[3,2-c]quinoline-2-carboxylate

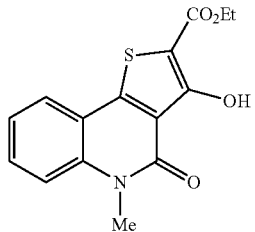 [SMILES: CCOC(=O)c1sc2c(c1O)c(=O)n(C)c1ccccc21]

A 20% solution (23.2 g, 68 mmol) of sodium ethoxide in ethanol was diluted with ethanol (70 mL), ethyl thioglycolate (9.0 mL, 82 mmol) was added to the obtained solution, and the mixture was stirred at room temperature for 10 min. The compound of Reference Example 81 (9.04 g, 34.0 mmol) was added to this mixture, and the mixture was stirred at room temperature for 4 hr. The reaction mixture was neutralized with ice water and 2N hydrochloric acid (40 mL) under ice-cooling, and the mixture was extracted twice with chloroform. The combined organic layer was washed with water and brine, dried over sodium sulfate, filtered, and concentrated under reduced pressure. The residue was recrystallized from THF-diisopropyl ether to give the title compound (9.12 g, 88%).

$^1$H-NMR (300 MHz, CDCl$_3$) δ:1.42 (3H, t, J=7.2 Hz), 3.76 (3H, s), 4.41 (2H, q, J=7.2 Hz), 7.34 (1H, ddd, J=7.9, 7.2, 0.8 Hz), 7.44-7.49 (1H, m), 7.63 (1H, ddd, J=8.6, 7.2, 1.4 Hz), 7.83 (1H, dd, J=7.9, 1.4 Hz), 10.76 (1H, s).

Reference Example 83

Production of ethyl 3-methoxy-5-methyl-4-oxo-4,5-dihydrothieno[3,2-c]quinoline-2-carboxylate

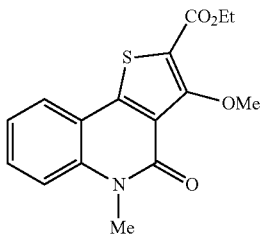

To a suspension of the compound of Reference Example 82 (3.04 g, 10.0 mmol) in DMF (30 mL) was added DBU (1.65 mL, 11 mmol), and iodomethane (0.81 mL, 13 mmol) was added to the obtained solution under ice-cooling. The obtained mixture was stirred at room temperature for 21 hr, water was added and the precipitated solid was collected by filtration. This was dissolved in ethanol by heating, treated with activated carbon, filtered, and concentrated under reduced pressure. The residue was dissolved in ethyl acetate, and the mixture was washed with water and 0.5N sodium hydroxide solution, filtered through Celite (trade name), further washed twice with water, and concentrated under reduced pressure. The residue was recrystallized from ethanol-diisopropyl ether to give the title compound (1.51 g, 48%).

$^1$H-NMR (300 MHz, CDCl$_3$) δ:1.42 (3H, t, J=7.2 Hz), 3.76 (3H, s), 4.14 (3H, s), 4.40 (2H, q, J=7.2 Hz), 7.24-7.31 (1H, m), 7.41 (1H, d, J=8.7 Hz), 7.59 (1H, ddd, J=8.7, 7.3, 1.5 Hz), 7.84 (1H, dd, J=8.1, 1.5 Hz).

Reference Example 84

Production of 3-methoxy-5-methyl-4-oxo-4,5-dihydrothieno[3,2-c]quinoline-2-carboxylic acid

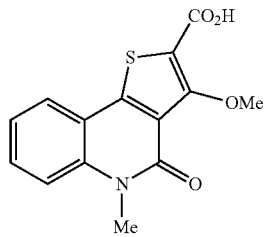 [SMILES: COc1c(C(=O)O)sc2c1c(=O)n(C)c1ccccc21]

To a suspension of the compound of Reference Example 83 (1.90 g, 5.99 mmol) in THF (20 mL) and ethanol (20 mL) was added 5N sodium hydroxide solution (2.4 mL, 12 mmol). The obtained mixture was stirred at room temperature for 1.5 hr. 1N Hydrochloric acid (13 mL) was added to the reaction mixture, and the precipitated solid was collected by filtration, and recrystallized from methanol to give the title compound (1.14 g, 66%).

$^1$H-NMR (300 MHz, DMSO-d$_6$) δ:3.66 (3H, d, J=1.1 Hz), 3.95 (3H, s), 7.30-7.37 (1H, m), 7.58-7.71 (2H, m), 7.94-8.00 (1H, m).

Reference Example 85

Production of ethyl 3-(benzyloxy)-5-methyl-4-oxo-4,5-dihydrothieno[3,2-c]quinoline-2-carboxylate

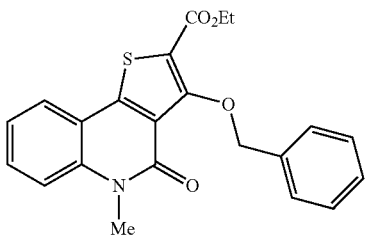 [SMILES: CCOC(=O)c1sc2c(c1OCc1ccccc1)c(=O)n(C)c1ccccc21]

To a suspension of the compound of Reference Example 82 (1.00 g, 3.30 mmol) in DMF (10 mL) was added DBU (0.592 mL, 3.96 mmol), and benzylbromide (0.510 mL, 4.29 mmol) was added to the obtained solution. The obtained mixture was stirred at room temperature for 15 hr. Ethyl acetate and water were added to the reaction mixture and the organic layer was separated. The aqueous layer was extracted twice with ethyl acetate. The combined organic layer was washed with water and 0.5N sodium hydroxide solution, filtered through Celite (trade name), further washed with water, and concentrated under reduced pressure. The residue was purified by silica gel column chromatography (eluate; ethyl acetate/hexane=1/4-1/2-2/1) to give the title compound (980 mg, 75%).

¹H-NMR (300 MHz, CDCl₃) δ:1.36 (3H, t, J=7.2 Hz), 3.78 (3H, s), 4.36 (2H, q, J=7.2 Hz), 5.34 (2H, s), 7.24-7.44 (5H, m), 7.59 (1H, ddd, J=8.6, 7.1, 1.4 Hz), 7.63-7.69 (2H, m), 7.85 (1H, dd, J=7.8, 1.4 Hz).

Reference Example 86

Production of ethyl 3-butoxy-5-methyl-4-oxo-4,5-dihydrothieno[3,2-c]quinoline-2-carboxylate

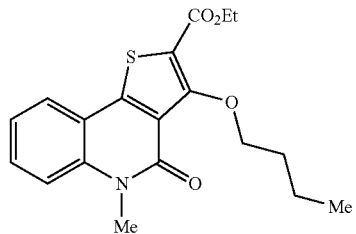

To a suspension of the compound of Reference Example 82 (1.00 g, 3.30 mmol) in DMF (10 mL) was added DBU (0.592 mL, 3.96 mmol), and 1-iodobutane (0.488 mL, 4.29 mmol) was added to the obtained solution. The obtained mixture was stirred at room temperature for 15 hr. Ethyl acetate and water were added to the reaction mixture, the organic layer was separated, and the aqueous layer was extracted twice with ethyl acetate. The combined organic layer was washed with water and 0.5N aqueous sodium hydroxide solution, filtered through Celite (trade name), further washed with water, and concentrated under reduced pressure. The residue was purified by silica gel column chromatography (eluate; ethyl acetate/hexane=1/4-1/2-2/1) to give the title compound (1.05 g, 89%).

¹H-NMR (300 MHz, CDCl₃) δ:1.01 (3H, t, J=7.5 Hz), 1.42 (3H, t, J=7.2 Hz), 1.50-1.66 (2H, m), 1.87-1.99 (2H, m), 3.74 (3H, s), 4.28 (2H, t, J=6.6 Hz), 4.39 (2H, q, J=7.2 Hz), 7.27 (1H, ddd, J=8.0, 7.1, 0.9 Hz), 7.40 (1H, d, J=8.1 Hz), 7.58 (1H, ddd, J=8.6, 7.1, 1.4 Hz), 7.81-7.86 (1H, m).

Reference Example 87

Production of ethyl 5-methyl-4-oxo-3-(pyridin-4-ylmethoxy)-4,5-dihydrothieno[3,2-c]quinoline-2-carboxylate

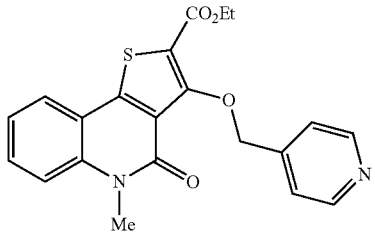

To a suspension of the compound of Reference Example 82 (1.00 g, 3.30 mmol) in DMF (20 mL) was added DBU (1.18 mL, 7.89 mmol), and 4-(chloromethyl)pyridine hydrochloride (704 mg, 4.29 mmol) was added to the obtained solution. The obtained mixture was stirred at room temperature for 18 hr, at 45° C. for 2 hr, and at 60° C. for 18 hr. DBU (1.18 mL, 7.89 mmol) and 4-(chloromethyl)pyridine hydrochloride (704 mg, 4.29 mmol) were added, and the mixture was stirred at 60° C. for 10 hr. Chloroform and water were added to the reaction mixture, the organic layer was separated, and the aqueous layer was extracted with chloroform. The combined organic layer was washed with water, and concentrated under reduced pressure. The residue was crystallized from ethyl acetate-diisopropyl ether to give the title compound (678 mg, 53%).

¹H-NMR (300 MHz, CDCl₃) δ:1.35 (3H, t, J=7.2 Hz), 3.77 (3H, s), 4.37 (2H, q, J=7.2 Hz), 5.36 (2H, s), 7.27-7.34 (1H, m), 7.43 (1H, d, J=8.4 Hz), 7.58-7.65 (3H, m), 7.86 (1H, dd, J=7.8, 1.2 Hz), 8.61-8.65 (2H, m).

Reference Example 88

Production of ethyl 5-methyl-3-(2-morpholin-4-ylethoxy)-4-oxo-4,5-dihydrothieno[3,2-c]quinoline-2-carboxylate

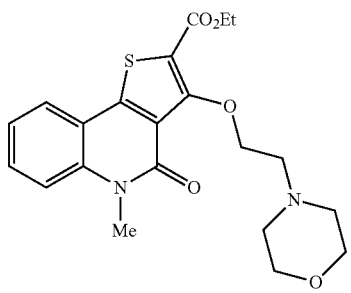 [SMILES: CCOC(=O)c1sc2c(c1OCCN1CCOCC1)c(=O)n(C)c1ccccc21]

To a suspension of the compound of Reference Example 82 (1.00 g, 3.30 mmol) in DMF (20 mL) was added DBU (1.18 mL, 7.89 mmol), and 4-(2-chloroethyl)morpholine hydrochloride (798 mg, 4.29 mmol) was added to the obtained solution. The obtained mixture was stirred at room temperature for 17 hr. Chloroform and water were added to the reaction mixture and the organic layer was separated. The aqueous layer was extracted with chloroform. The combined organic layer was washed with water, and concentrated under reduced pressure. The residue was recrystallized from ethyl acetate-diisopropyl ether to give the title compound (2.16 g, 85%).

¹H-NMR (300 MHz, CDCl₃) δ:1.41 (3H, t, J=7.1 Hz), 2.63 (4H, br t, J=4.7 Hz), 2.96 (2H, t, J=5.7 Hz), 3.72 (4H, br t, J=4.7 Hz), 3.74 (3H, s), 4.38 (2H, q, J=7.1 Hz), 4.43 (2H, t, J=5.7 Hz), 7.24-7.31 (1H, m), 7.40 (1H, d, J=8.5 Hz), 7.58 (1H, ddd, J=8.5, 7.2, 1.5 Hz), 7.81-7.86 (1H, m).

Reference Example 89

Production of ethyl 5-methyl-4-oxo-3-(tetrahydrofuran-2-ylmethoxy)-4,5-dihydrothieno[3,2-c]quinoline-2-carboxylate

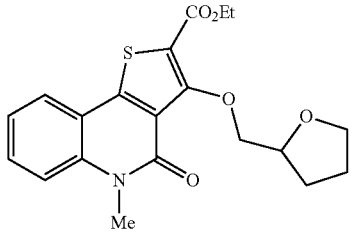 [SMILES: CCOC(=O)c1sc2c(c1OCC1CCCO1)c(=O)n(C)c1ccccc21]

To a suspension of the compound of Reference Example 82 (1.00 g, 3.30 mmol) in DMF (20 mL) was added DBU (0.740 mL, 4.95 mmol), and 2-(bromomethyl)tetrahydrofuran (90% containing) (0.617 mL, 4.9 mmol) was added to the obtained solution. The obtained mixture was stirred at 40° C. for 19 hr and at 80° C. for 23 hr, DBU (0.740 mL, 4.95 mmol) and 2-(bromomethyl)tetrahydrofuran (90% containing) (0.617 mL, 4.9 mmol) were added, and the mixture was stirred at 80° C. for 66 hr. Ethyl acetate and water were added to the reaction mixture and the organic layer was separated. The aqueous layer was extracted with ethyl acetate. The combined organic layer was washed with 0.5N aqueous sodium hydroxide solution, filtered through Celite (trade name), washed with water, and concentrated under reduced pressure. The residue was purified by silica gel column chromatography (eluate; ethyl acetate/hexane=3/17-2/1) and crystallized from ethyl acetate-diisopropyl ether to give the title compound (821 mg, 64%).

$^1$H-NMR (300 MHz, CDCl$_3$) δ:1.42 (3H, t, J=7.2 Hz), 1.84-2.19 (4H, m), 3.74 (3H, s), 3.76-3.85 (1H, m), 3.89-3.98 (1H, m), 4.22-4.49 (5H, m), 7.27 (1H, ddd, J=8.0, 7.1, 1.0 Hz), 7.39 (1H, d, J=8.1 Hz), 7.58 (1H, ddd, J=8.6, 7.1, 1.4 Hz), 7.81-7.86 (1H, m).

Reference Example 90

Production of ethyl 3-(2-ethoxyethoxy)-5-methyl-4-oxo-4,5-dihydrothieno[3,2-c]quinoline-2-carboxylate

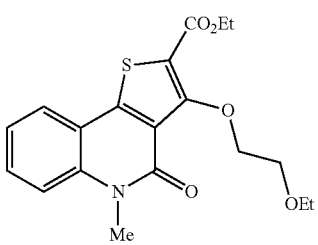

To a suspension of the compound of Reference Example 82 (1.00 g, 3.30 mmol) in DMF (20 mL) was added DBU (1.48 mL, 9.90 mmol), and 1-bromo-2-ethoxyethane (1.12 mL, 9.93 mmol) was added to the obtained solution. The obtained mixture was stirred at 60° C. for 24 hr. Ethyl acetate and water were added to the reaction mixture, the organic layer was separated, and aqueous layer was extracted with ethyl acetate. The combined organic layer was washed with 0.5N aqueous sodium hydroxide solution, filtered through Celite (trade name), further washed with water, and concentrated under reduced pressure. The residue was purified by silica gel column chromatography (eluate; ethyl acetate/hexane=1/4-1/1) and crystallized from ethyl acetate-hexane to give the title compound (986 mg, 80%).

$^1$H-NMR (300 MHz, CDCl$_3$) δ:1.19 (3H, t, J=7.0 Hz), 1.43 (3H, t, J=7.1 Hz), 3.59 (2H, q, J=7.0 Hz), 3.74 (3H, s), 3.93 (2H, t, J=5.0 Hz), 4.40 (2H, q, J=7.1 Hz), 4.46 (2H, t, J=5.0 Hz), 7.26-7.31 (1H, m), 7.40 (1H, d, J=8.5 Hz), 7.58 (1H, ddd, J=8.5, 7.2, 1.4 Hz), 7.84 (1H, dd, J=8.0, 1.4 Hz).

Reference Example 91

Production of 3-(benzyloxy)-5-methyl-4-oxo-4,5-dihydrothieno[3,2-c]quinoline-2-carboxylic acid

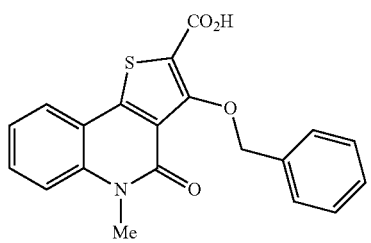 [SMILES: Cn1c(=O)c2c(OCc3ccccc3)c(C(=O)O)sc2c2ccccc21]

To a solution of the compound of Reference Example 85 (867 mg, 2.20 mmol) in THF (7 mL) and ethanol (7 mL) was added 5N aqueous sodium hydroxide solution (0.88 mL, 4.4 mmol). The obtained mixture was stirred at room temperature for 3 hr. 1N Hydrochloric acid (5.0 mL) was added to the reaction mixture, and the precipitated solid was collected by filtration, washed with water, and air dried to give the title compound (665 mg, 83%).

$^1$H-NMR (300 MHz, DMSO-d$_6$) δ:3.69 (3H, s), 5.22 (2H, s), 7.30-7.41 (4H, m), 7.57-7.72 (4H, m), 7.98 (1H, d, J=8.1 Hz), 13.31 (1H, br s).

Reference Example 92

Production of 3-butoxy-5-methyl-4-oxo-4,5-dihydrothieno[3,2-c]quinoline-2-carboxylic acid

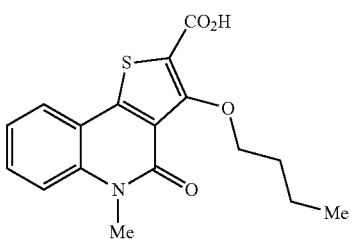

To a solution of the compound of Reference Example 86 (923 mg, 2.57 mmol) in THF (7 mL) and ethanol (7 mL) was added 5N aqueous sodium hydroxide solution (1.0 mL, 5.0 mmol). The obtained mixture was stirred at room temperature for 3 hr. 1N Hydrochloric acid (6.0 mL) was added to the reaction mixture, and the precipitated solid was collected by filtration, washed with water, and air dried to give the title compound (872 mg, quantitative).

$^1$H-NMR (300 MHz, DMSO-d$_6$) δ:0.94 (3H, t, J=7.5 Hz), 1.41-1.55 (2H, m), 1.71-1.82 (2H, m), 3.65 (3H, s), 4.16 (2H, t, J=6.6 Hz), 7.32 (1H, t, J=7.2 Hz), 7.54-7.70 (2H, m), 7.91-7.98 (1H, m), 13.21 (1H, br s).

Reference Example 93

Production of 5-methyl-4-oxo-3-(pyridin-4-yl-methoxy)-4,5-dihydrothieno[3,2-c]quinoline-2-carboxylic acid

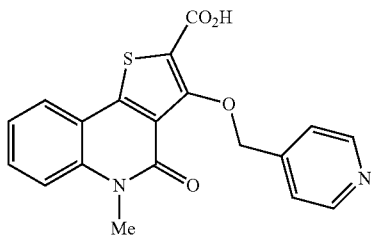 [SMILES: Cn1c(=O)c2c(OCc3ccncc3)c(C(=O)O)sc2c2ccccc21]

To a suspension of the compound of Reference Example 87 (723 mg, 1.83 mmol) in THF (6 mL) and ethanol (6 mL) was added 5N aqueous sodium hydroxide solution (0.74 mL, 3.7 mmol). The obtained mixture was stirred at room temperature for 4 hr. 1N Hydrochloric acid (3.7 mL) was added to the reaction mixture and the mixture was diluted with water. The precipitated solid was collected by filtration, washed with water, and air dried to give the title compound (424 mg, 63%).

$^1$H-NMR (300 MHz, DMSO-$d_6$) δ:3.67 (3H, s), 5.28 (2H, s), 7.32-7.38 (1H, m), 7.59-7.72 (4H, m), 7.98 (1H, dd, J=7.8, 1.2 Hz), 8.59 (2H, dd, J=4.5, 1.5 Hz).

Reference Example 94

Production of 5-methyl-3-(2-morpholin-4-ylethoxy)-4-oxo-4,5-dihydrothieno[3,2-c]quinoline-2-carboxylic acid

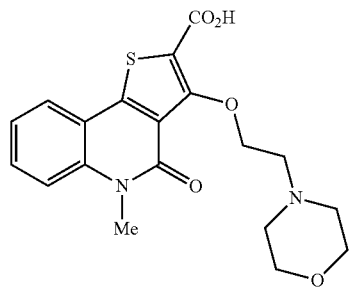 [SMILES: Cn1c(=O)c2c(OCCN3CCOCC3)c(C(=O)O)sc2c2ccccc21]

To a suspension of the compound of Reference Example 88 (832 mg, 2.00 mmol) in THF (7 mL) and ethanol (7 mL) was added 5N aqueous sodium hydroxide solution (0.80 mL, 4.0 mmol). The obtained mixture was stirred at room temperature for 4 hr. 1N Hydrochloric acid (4.0 mL) was added to the reaction mixture and the mixture was diluted with water, and concentrated under reduced pressure. Methanol was added to the residue and the mixture was concentrated under reduced pressure, and crystallized from water-methanol to give the title compound (477 mg, 61%).

$^1$H-NMR (300 MHz, DMSO-$d_6$) δ:3.00-3.20 (6H, m), 3.67 (3H, s), 3.84 (4H, br t, J=4.4 Hz), 4.53 (2H, br t, J=5.0 Hz), 7.31 (1H, ddd, J=8.0, 6.3, 1.8 Hz), 7.55-7.67 (2H, m), 7.88-7.91 (1H, m).

Reference Example 95

Production of 5-methyl-4-oxo-3-(tetrahydrofuran-2-ylmethoxy)-4,5-dihydrothieno[3,2-c]quinoline-2-carboxylic acid

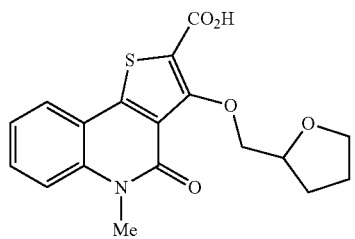 [SMILES: Cn1c(=O)c2c(OCC3CCCO3)c(C(=O)O)sc2c2ccccc21]

To a suspension of the compound of Reference Example 89 (728 mg, 1.88 mmol) in THF (6 mL) and ethanol (6 mL) was added 5N aqueous sodium hydroxide solution (0.76 mL, 3.8 mmol). The obtained mixture was stirred at room temperature for 4 hr. 1N Hydrochloric acid (3.8 mL) was added to the reaction mixture and the mixture was diluted with water and the mixture was extracted 3 times with chloroform. The combined organic layer was washed with aqueous sodium chloride solution, dried over sodium sulfate, filtered, and concentrated under reduced pressure. The obtained solid was washed with diisopropyl ether to give the title compound (659 mg, 97%).

$^1$H-NMR (300 MHz, DMSO-$d_6$) δ:1.73-2.04 (4H, m), 3.56-3.78 (2H, m), 3.65 (3H, s), 4.02-4.10 (1H, m), 4.19-4.30 (2H, m), 7.29-7.37 (1H, m), 7.57-7.71 (2H, m), 7.92-7.99 (1H, m), 13.20 (1H, br s).

Reference Example 96

Production of 3-(2-ethoxyethoxy)-5-methyl-4-oxo-4,5-dihydrothieno[3,2-c]quinoline-2-carboxylic acid

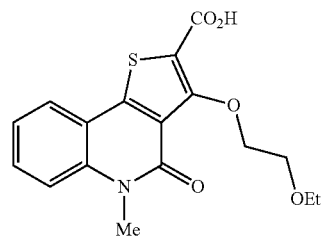 [SMILES: CCOCCOc1c(C(=O)O)sc2c1c(=O)n(C)c1ccccc21]

To a suspension of the compound of Reference Example 90 (826 mg, 2.20 mmol) in THF (7 mL) and ethanol (7 mL) was added 5N aqueous sodium hydroxide solution (0.88 mL, 4.4 mmol). The obtained mixture was stirred at room temperature for 2.5 hr, 5N aqueous sodium hydroxide solution (4.4 mL, 22 mmol) was added, and the mixture was stirred at 50° C. for 3.5 hr. The reaction mixture was acidified with 1N hydrochloric acid and diluted with water, and the precipitated solid was collected by filtration, washed with water, and air dried to give the title compound (719 mg, 94%).

$^1$H-NMR (300 MHz, DMSO-$d_6$) δ:1.03 (3H, t, J=6.9 Hz), 3.44 (2H, q, J=6.9 Hz), 3.66 (3H, s), 3.75 (2H, t, J=5.0 Hz), 4.33 (2H, t, J=5.0 Hz), 7.33 (1H, t, J=7.4 Hz), 7.58-7.71 (2H, m), 7.96 (1H, d, J=8.1 Hz), 13.21 (1H, br s).

Reference Example 97

Production of 1-butyl-2H-3,1-benzoxazine-2,4(1H)-dione

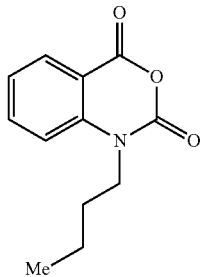 [SMILES: CCCCn1c(=O)oc(=O)c2ccccc21]

To a solution of isatoic anhydride (8.16 g, 50.0 mmol) in DMF (100 mL) was added sodium hydride (66% in oil, 2.00 g, 55 mmol) under ice-cooling, and the mixture was stirred at the same temperature for 10 min. 1-Iodobutane (8.5 mL, 75 mmol) was added to the obtained mixture and the mixture was stirred at room temperature for 64 hr. Ice water was added to the reaction mixture and the mixture was extracted twice with ethyl acetate. The combined organic layer was washed twice with water and concentrated under reduced pressure to give the title compound (10.5 g), which was used for the next reaction without purification.

$^1$H-NMR (300 MHz, CDCl$_3$) δ:1.01 (3H, t, J=7.4 Hz), 1.48 (2H, sext, J=7.4 Hz), 1.69-1.81 (2H, m), 4.02-4.10 (2H, m), 7.17 (1H, d, J=8.6 Hz), 7.25-7.32 (1H, m), 7.75 (1H, ddd, J=8.6, 7.4, 1.7 Hz), 8.16 (1H, dd, J=7.8, 1.7 Hz).

Reference Example 98

Production of ethyl 1-butyl-4-hydroxy-2-oxo-1,2-dihydroquinoline-3-carboxylate

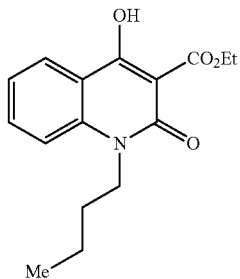 [SMILES: CCCCn1c(=O)c(C(=O)OCC)c(O)c2ccccc21]

To a solution of diethyl malonate (12.0 g, 74.9 mmol) in DMF (70 mL) was added sodium hydride (66% in oil, 2.00 g, 55 mmol) under ice-cooling, and the mixture was stirred at the same temperature for 10 min. A solution of the compound of Reference Example 97 (10.5 g) in DMF (20 mL) was added dropwise to the obtained mixture, and the mixture was stirred at 120° C. for 6 hr. The reaction mixture was concentrated under reduced pressure, ice water was added to the residue and the obtained aqueous layer was washed with diethyl ether. The aqueous layer was weakly acidified with 5N hydrochloric acid (12 mL) under ice-cooling, and extracted twice with ethyl acetate. The combined organic layer was washed with water, and concentrated under reduced pressure. The residue was purified by silica gel column chromatography (eluate; ethyl acetate/hexane=1/9-1/2) to give the title compound (9.96 g, 69%, 2 steps) as a solid.

$^1$H-NMR (300 MHz, CDCl$_3$) δ:0.99 (3H, t, J=7.4 Hz), 1.482 (2H, sext, J=7.4 Hz), 1.485 (3H, t, J=7.1 Hz), 1.64-1.76 (2H, m), 4.17-4.26 (2H, m), 4.50 (2H, q, J=7.1 Hz), 7.20-7.26 (1H, m), 7.29 (1H, d, J=8.4 Hz), 7.66 (1H, ddd, J=8.6, 7.4, 1.6 Hz), 8.18 (1H, dd, J=8.3, 1.6 Hz), 14.20 (1H, s).

Reference Example 99

Production of ethyl 1-butyl-4-chloro-2-oxo-1,2-dihydroquinoline-3-carboxylate

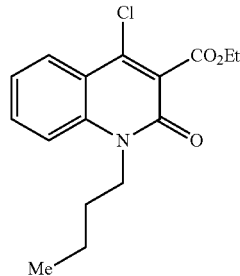 [SMILES: CCCCn1c(=O)c(C(=O)OCC)c(Cl)c2ccccc21]

A mixture of the compound of Reference Example 98 (9.73 g, 33.6 mmol) and phosphorus oxychloride (4.7 mL, 50 mmol) was stirred at 110° C. for 30 min. The reaction mixture was concentrated under reduced pressure, and ice water and ethyl acetate were added. The organic layer was separated, and the aqueous layer was extracted with ethyl acetate. The combined organic layer was washed with water, saturated sodium hydrogen carbonate solution and water (twice), and concentrated under reduced pressure. The residue was subjected to silica gel column chromatography (eluate; ethyl acetate/hexane=1/9-1/3), and the fractions containing the desired product were combined, and washed with 1N sodium hydroxide solution and water (twice). The insoluble material was filtered off and the filtrate was concentrated under reduced pressure. The residue was crystallized from ethyl acetate-diisopropyl ether to give the title compound (6.07 g, 59%).

$^1$H-NMR (300 MHz, CDCl$_3$) δ:1.00 (3H, t, J=7.4 Hz), 1.42 (3H, t, J=7.2 Hz), 1.42-1.56 (2H, m), 1.67-1.79 (2H, m), 4.23-4.31 (2H, m), 4.47 (2H, q, J=7.2 Hz), 7.33 (1H, ddd, J=8.1, 7.2, 0.9 Hz), 7.37-7.41 (1H, m), 7.66 (1H, ddd, J=8.7, 7.2, 1.4 Hz), 8.07 (1H, dd, J=8.1, 1.4 Hz).

Reference Example 100

Production of ethyl 5-butyl-3-hydroxy-4-oxo-4,5-dihydrothieno[3,2-c]quinoline-2-carboxylate

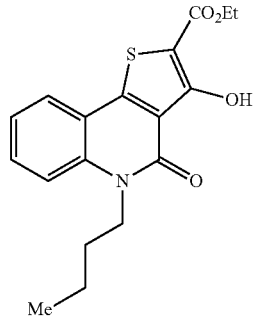 [SMILES: CCCCn1c(=O)c2c(O)c(C(=O)OCC)sc2c2ccccc21]

A 20% solution (16.0 g, 47 mmol) of sodium ethoxide in ethanol was diluted with ethanol (45 mL), ethyl thioglycolate (6.2 mL, 55 mmol) was added to the obtained solution, and the mixture was stirred at room temperature for 10 min. The compound of Reference Example 99 (7.21 g, 23.4 mmol) was added to this mixture, and the mixture was stirred at room temperature for 5 hr. The reaction mixture was neutralized with ice water and 2N hydrochloric acid (25 mL) under ice-cooling, and the mixture was extracted twice with ethyl acetate. The combined organic layer was washed twice with water, and concentrated under reduced pressure. The residue was crystallized from ethyl acetate-diisopropyl ether to give the title compound (6.44 g, 80%).

$^1$H-NMR (300 MHz, CDCl$_3$) δ:1.02 (3H, t, J=7.4 Hz), 1.42 (3H, t, J=7.2 Hz), 1.44-1.58 (2H, m), 1.71-1.83 (2H, m), 4.29-4.36 (2H, m), 4.41 (2H, q, J=7.2 Hz), 7.32 (1H, ddd, J=8.0, 7.2, 0.9 Hz), 7.43-7.48 (1H, m), 7.61 (1H, ddd, J=8.6, 7.3, 1.6 Hz), 7.81-7.86 (1H, m), 10.81 (1H, s).

Reference Example 101

Production of ethyl 5-butyl-3-methoxy-4-oxo-4,5-dihydrothieno[3,2-c]quinoline-2-carboxylate

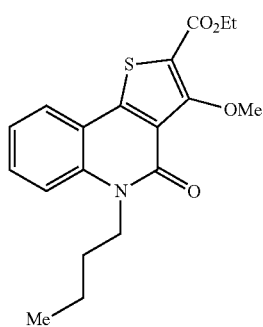 [SMILES: CCCCn1c(=O)c2c(OC)c(C(=O)OCC)sc2c2ccccc21]

To a suspension of the compound of Reference Example 100 (3.11 g, 9.00 mmol) in DMF (30 mL) was added DBU (1.62 mL, 10.8 mmol), and iodomethane (1.12 mL, 18.0 mmol) was added to the obtained solution. The obtained mixture was stirred at room temperature for 14 hr, water was added and the mixture was extracted twice with ethyl acetate. The combined organic layer was washed with water and 0.5N aqueous sodium hydroxide solution, filtered through Celite (trade name), further washed twice with water, and concentrated under reduced pressure. The residue was purified by silica gel column chromatography (eluate; ethyl acetate/hexane=1/4-1/1) and recrystallized from ethyl acetate-hexane to give the title compound (1.03 g, 32%).

$^1$H-NMR (300 MHz, CDCl$_3$) δ:1.01 (3H, t, J=7.4 Hz), 1.40-1.60 (2H, m), 1.42 (3H, t, J=7.2 Hz), 1.69-1.81 (2H, m), 4.14 (3H, s), 4.28-4.36 (2H, m), 4.40 (2H, q, J=7.2 Hz), 7.22-7.29 (1H, m), 7.39 (1H, d, J=8.5 Hz), 7.57 (1H, ddd, J=8.5, 7.1, 1.4 Hz), 7.84 (1H, dd, J=8.0, 1.4 Hz).

Reference Example 102

Production of ethyl 5-butyl-3-(2-ethoxyethoxy)-4-oxo-4,5-dihydrothieno[3,2-c]quinoline-2-carboxylate

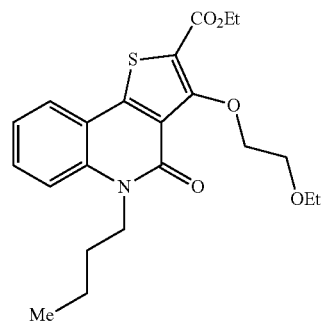

To a suspension of the compound of Reference Example 100 (1.14 g, 3.30 mmol) in DMF (20 mL) was added DBU (1.48 mL, 9.90 mmol), and 1-bromo-2-ethoxyethane (1.12 mL, 9.93 mmol) was added to the obtained solution. The obtained mixture was stirred at 60° C. for 30 hr and ethyl acetate and water were added to the reaction mixture. The organic layer was separated, and the aqueous layer was extracted with ethyl acetate. The combined organic layer was washed with 0.5N aqueous sodium hydroxide solution and water, and concentrated under reduced pressure. The residue was purified by silica gel column chromatography (eluate; ethyl acetate/hexane=1/4-1/2) to give the title compound (1.28 g, 93%) as a solid.

$^1$H-NMR (300 MHz, CDCl$_3$) δ:1.01 (3H, t, J=7.4 Hz), 1.18 (3H, t, J=7.0 Hz), 1.42 (3H, t, J=7.2 Hz), 1.43-1.57 (2H, m), 1.65-1.79 (2H, m), 3.58 (2H, q, J=7.0 Hz), 3.92 (2H, dd, J=5.6, 4.7 Hz), 4.30 (2H, br t, J=7.8 Hz), 4.39 (2H, q, J=7.2 Hz), 4.47 (2H, t, J=5.1 Hz), 7.21-7.28 (1H, m), 7.37 (1H, d, J=8.5 Hz), 7.56 (1H, ddd, J=8.5, 7.1, 1.4 Hz), 7.83 (1H, dd, J=8.1, 1.4 Hz).

Reference Example 103

Production of 5-butyl-3-methoxy-4-oxo-4,5-dihydrothieno[3,2-c]quinoline-2-carboxylic acid

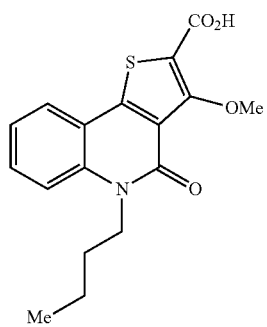 [SMILES: CCCCn1c(=O)c2c(OC)c(C(=O)O)sc2c2ccccc21]

To a suspension of the compound of Reference Example 101 (1.81 g, 5.04 mmol) in THF (15 mL) and ethanol (15 mL)

was added 5N aqueous sodium hydroxide solution (2.0 mL, 10 mmol). The obtained mixture was stirred at room temperature for 1.5 hr. The reaction mixture was ice-cooled, 1N hydrochloric acid (15 mL) and ethyl acetate were added, and the precipitated solid was collected by filtration, and washed with water and ethyl acetate to give a solid. The filtrate was separated, and the aqueous layer was extracted with ethyl acetate. The combined organic layer was washed with water, and concentrated under reduced pressure. The residue and the solid obtained earlier were combined, and the mixture was recrystallized from methanol-diisopropyl ether to give the title compound (1.43 g, 86%).

$^1$H-NMR (300 MHz, DMSO-d$_6$) δ:0.95 (3H, t, J=7.3 Hz), 1.43 (2H, sext, J=7.3 Hz), 1.56-1.68 (2H, m), 3.95 (3H, s), 4.29 (2H, t, J=7.5 Hz), 7.29-7.36 (1H, m), 7.60-7.71 (2H, m), 7.95-8.00 (1H, m).

Reference Example 104

Production of 5-butyl-3-(2-ethoxyethoxy)-4-oxo-4,5-dihydrothieno[3,2-c]quinoline-2-carboxylic acid

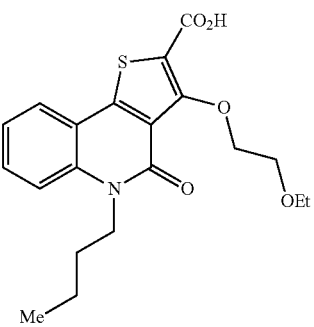 [SMILES: CCCCn1c(=O)c2c(OCCOCC)c(C(=O)O)sc2c2ccccc21]

To a solution of the compound of Reference Example 102 (1.16 g, 2.78 mmol) in THF (9 mL) and ethanol (9 mL) was added 5N aqueous sodium hydroxide solution (1.12 mL, 5.6 mmol). The obtained mixture was stirred at room temperature for 2.5 hr, 5N aqueous sodium hydroxide solution (4.48 mL, 22 mmol) was added, and the mixture was stirred at 50° C. for 3 hr. The reaction mixture was acidified with 1N hydrochloric acid, and extracted twice with chloroform. The combined organic layer was washed with water, and concentrated under reduced pressure. The residue was crystallized from ethyl acetate-diisopropyl ether to give the title compound (965 mg, 89%).

$^1$H-NMR (300 MHz, DMSO-d$_6$) δ:0.95 (3H, t, J=7.3 Hz), 1.02 (3H, t, J=7.0 Hz), 1.43 (2H, sext, J=7.3 Hz), 1.56-1.68 (2H, m), 3.43 (2H, q, J=7.0 Hz), 3.74 (2H, t, J=5.0 Hz), 4.24-4.40 (2H, m), 4.30 (2H, t, J=5.0 Hz), 7.32 (1H, t, J=7.4 Hz), 7.59-7.71 (2H, m), 7.97 (1H, d, J=7.5 Hz), 13.20 (1H, br s).

Reference Example 105

Production of ethyl 3-hydroxy-5-(4-methoxybenzyl)-1-methyl-4-oxo-4,5-dihydro-1H-pyrrolo[3,2-c]quinoline-2-carboxylate

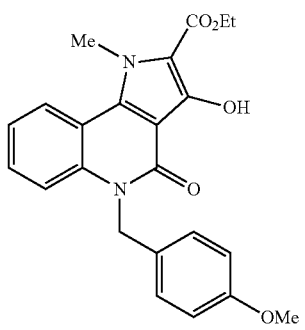 [SMILES: CCOC(=O)c1c(O)c2c(=O)n(Cc3ccc(OC)cc3)c3ccccc3c2n1C]

In the same manner as in Reference Example 25, ethyl 4-[(2-ethoxy-2-oxoethyl)(methyl)amino]-1-(4-methoxybenzyl)-2-oxo-1,2-dihydroquinoline-3-carboxylate (14.7 g, 63%) was obtained as a white powder from the compound of Reference Example 10 (19.2 g, 51.6 mmol).

In the same manner as in Reference Example 26, the title compound (10.35 g, 49%) was obtained as a white solid from the ethyl 4-[(2-ethoxy-2-oxoethyl)(methyl)amino]-1-(4-methoxybenzyl)-2-oxo-1,2-dihydroquinoline-3-carboxylate (14.73 g).

$^1$H-NMR (300 MHz, CDCl$_3$) δ:1.33 (3H, t, J=7.1 Hz), 3.69 (3H, s), 4.27 (3H, s), 4.34 (2H, q, J=7.1 Hz), 5.47 (2H, s), 6.86 (2H, d, J=8.7 Hz), 7.16 (2H, d, J=8.7 Hz), 7.27-7.30 (1H, m), 7.48 (2H, d, J=3.3 Hz), 8.32 (1H, d, J=8.1 Hz), 9.10 (1H, s).

Reference Example 106

Production of ethyl 3-methoxy-5-(4-methoxybenzyl)-1-methyl-4-oxo-4,5-dihydro-1H-pyrrolo[3,2-c]quinoline-2-carboxylate

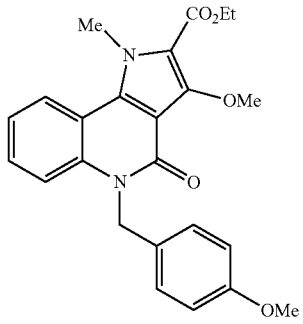 [SMILES: CCOC(=O)c1c(OC)c2c(=O)n(Cc3ccc(OC)cc3)c3ccccc3c2n1C]

In the same manner as in Reference Example 6, the title compound (6.51 g, 61%) was obtained as a pale-yellow solid from the compound of Reference Example 105 (10.4 g, 25.5 mmol).

$^1$H-NMR (300 MHz, DMSO-d$_6$) δ:1.35 (3H, t, J=7.1 Hz), 3.69 (3H, s), 3.94 (3H, s), 4.26 (3H, s), 4.34 (2H, q, J=7.1 Hz), 5.51 (2H, br s), 6.86 (2H, d, J=8.7 Hz), 7.15 (1H, d, J=8.4 Hz), 7.25-7.31 (1H, m), 7.47 (2H, d, J=3.6 Hz), 8.34 (1H, d, J=8.1 Hz).

Reference Example 107

Production of 3-methoxy-5-(4-methoxybenzyl)-1-methyl-4-oxo-4,5-dihydro-1H-pyrrolo[3,2-c]quinoline-2-carboxylic acid

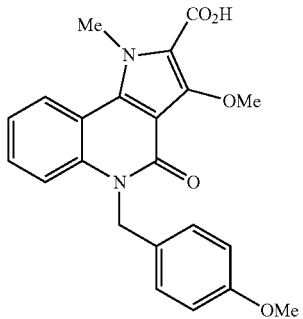 [SMILES: COc1ccc(Cn2c(=O)c3c(OC)c(C(=O)O)n(C)c3c3ccccc32)cc1]

In the same manner as in Reference Example 28, the title compound (5.67 g, 96%) was obtained as a pale-yellow solid from the compound of Reference Example 106 (6.50 g, 15.5 mmol).
$^1$H-NMR (300 MHz, DMSO-d$_6$) δ:3.70 (3H, s), 3.94 (3H, s), 4.28 (3H, s), 5.51 (2H, br s), 6.86 (2H, d, J=8.7 Hz), 7.15 (1H, d, J=8.4 Hz), 7.25-7.30 (1H, m), 7.46 (2H, d, J=3.9 Hz), 8.34 (1H, d, J=8.4 Hz), 12.90 (1H, br s).

Reference Example 110

Production of ethyl 6-fluoro-4-hydroxy-2-oxo-1,2-dihydroquinoline-3-carboxylate

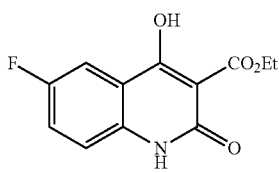 [SMILES: CCOC(=O)c1c(O)c2cc(F)ccc2[nH]c1=O]

In the same manner as in Reference Example 1, the title compound (8.60 g, 56%) was obtained as a pale-yellow solid from ethyl 2-amino-5-fluorobenzoate (10.3 g, 61.0 mmol), diethyl malonate (9.2 mL, 61.0 mmol), a 20% solution (21.0 g, 61.0 mmol) of sodium ethoxide in ethanol and ethanol (70 mL).
$^1$H-NMR (300 MHz, CDCl$_3$) δ:1.52 (3H, t, J=7.2 Hz), 4.54 (2H, q, J=7.1 Hz), 7.20-7.29 (1H, m), 7.31-7.42 (1H, m), 7.75 (1H, dd, J=8.6, 2.7 Hz), 11.02 (1H, br s), 14.31 (1H, s).

Reference Example 111

Production of ethyl 2,4-dichloro-6-fluoroquinoline-3-carboxylate

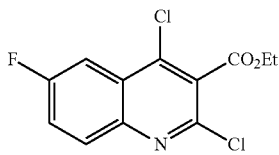 [SMILES: CCOC(=O)c1c(Cl)nc2ccc(F)cc2c1Cl]

In the same manner as in Reference Example 2, the title compound (2.2 g, 96%) was obtained as a white solid from the compound of Reference Example 110 (2.0 g, 7.8 mmol) and phosphorus oxychloride (9.0 mL).
$^1$H-NMR (300 MHz, CDCl$_3$) δ:1.46 (3H, t, J=7.1 Hz), 4.54 (2H, q, J=7.2 Hz), 7.54-7.68 (1H, m), 7.86 (1H, dd, J=9.1, 2.8 Hz), 8.07 (1H, dd, J=9.2, 5.2 Hz).

Reference Example 112

Production of ethyl 4-chloro-6-fluoro-2-oxo-1,2-dihydroquinoline-3-carboxylate

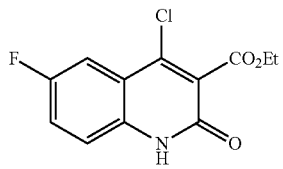 [SMILES: CCOC(=O)c1c(Cl)c2cc(F)ccc2[nH]c1=O]

In the same manner as in Reference Example 3, the title compound (1.6 g, 79%) was obtained as a white solid from the compound of Reference Example 111 (2.2 g, 7.5 mmol), sodium acetate (615 mg, 7.5 mmol) and acetic acid (20 mL).
$^1$H-NMR (300 MHz, CDCl$_3$) δ:1.40-1.51 (3H, m), 4.46-4.57 (2H, m), 7.36-7.46 (2H, m), 7.69 (1H, dd, J=9.1, 1.9 Hz), 12.36 (1H, br s).

Reference Example 113

Production of ethyl 4-chloro-6-fluoro-2-oxo-1-(2-oxo-2-phenylethyl)-1,2-dihydroquinoline-3-carboxylate

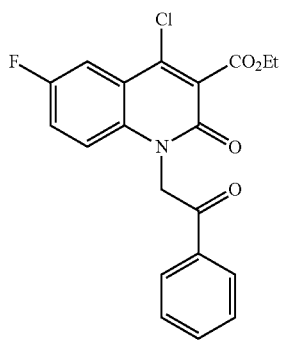 [SMILES: CCOC(=O)c1c(Cl)c2cc(F)ccc2n(CC(=O)c2ccccc2)c1=O]

In the same manner as in Reference Example 4, the title compound (1.3 g, 57%) was obtained as a pale-yellow solid from the compound of Reference Example 112 (1.6 g, 5.9 mmol), sodium hydride (60% in oil, 248 mg, 6.2 mmol), phenacyl bromide (1.3 g, 6.5 mmol) and DMF (20 mL).
$^1$H-NMR (300 MHz, CDCl$_3$) δ:1.42 (3H, t, J=7.1 Hz), 4.47 (2H, q, J=7.1 Hz), 5.79 (2H, s), 7.00 (1H, dd, J=9.3, 4.2 Hz), 7.27-7.38 (1H, m), 7.49-7.61 (2H, m), 7.63-7.73 (1H, m), 7.80 (1H, dd, J=9.1, 2.8 Hz), 8.02-8.12 (2H, m).

Reference Example 114

Production of ethyl 8-fluoro-3-hydroxy-4-oxo-5-(2-oxo-2-phenylethyl)-4,5-dihydrothieno[3,2-c]quinoline-2-carboxylate

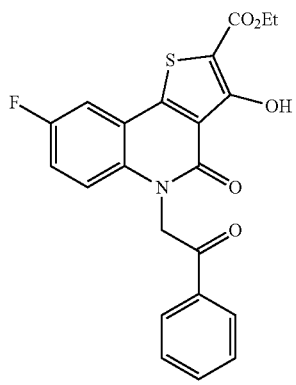 [SMILES: CCOC(=O)c1sc2c(c1O)c(=O)n(CC(=O)c1ccccc1)c1ccc(F)cc21]

In the same manner as in Reference Example 5, the title compound (1.3 g, 94%) was obtained as a yellow solid from the compound of Reference Example 113 (1.3 g, 3.3 mmol), a 20% solution (2.3 g, 6.7 mmol) of sodium ethoxide in ethanol, ethyl thioglycolate (0.97 g, 8.0 mmol) and ethanol (14 mL).

$^1$H-NMR (300 MHz, DMSO-$d_6$) δ:1.32 (3H, t, J=7.1 Hz), 4.32 (2H, q, J=7.2 Hz), 6.02 (2H, s), 7.47-7.58 (1H, m), 7.59-7.70 (3H, m), 7.72-7.82 (1H, m), 8.00 (1H, dd, J=8.7, 2.8 Hz), 8.11-8.21 (2H, m), 10.52 (1H, br s).

Reference Example 115

Production of ethyl 8-fluoro-3-methoxy-4-oxo-5-(2-oxo-2-phenylethyl)-4,5-dihydrothieno[3,2-c]quinoline-2-carboxylate

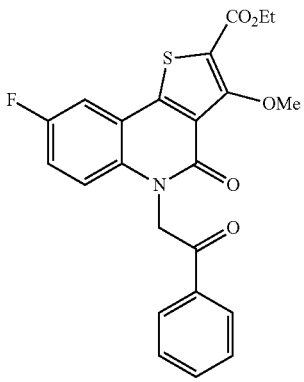 [SMILES: CCOC(=O)c1sc2c(c1OC)c(=O)n(CC(=O)c1ccccc1)c1ccc(F)cc21]

In the same manner as in Reference Example 6, the title compound (880 mg, 65%) was obtained as a yellow solid from the compound of Reference Example 114 (1.3 g, 3.1 mmol), iodomethane (0.31 mL, 5.0 mmol), DBU (0.75 mL, 5.0 mmol) and DMF (40 mL).

$^1$H-NMR (300 MHz, CDCl$_3$) δ:1.43 (3H, t, J=7.5 Hz), 4.12 (3H, s), 4.42 (2H, q, J=7.2 Hz), 5.84 (2H, s), 6.98 (1H, dd, J=9.3, 4.2 Hz), 7.16-7.25 (1H, m), 7.49-7.60 (3H, m), 7.64-7.72 (1H, m), 8.03-8.15 (2H, m).

Reference Example 116

Production of 8-fluoro-3-methoxy-4-oxo-5-(2-oxo-2-phenylethyl)-4,5-dihydrothieno[3,2-c]quinoline-2-carboxylic acid

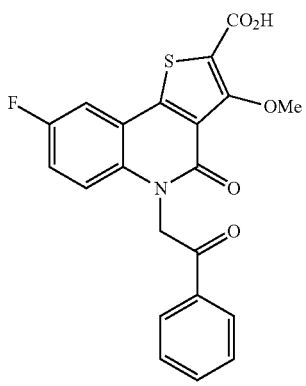 [SMILES: COc1c(C(=O)O)sc2c1c(=O)n(CC(=O)c1ccccc1)c1ccc(F)cc21]

In the same manner as in Reference Example 7, the title compound (602 mg, 73%) was obtained as a pale-brown solid from the compound of Reference Example 115 (880 mg, 2.0 mmol), 8N aqueous sodium hydroxide solution (5.7 mL), ethanol (32 mL) and THF (9.1 mL).

$^1$H-NMR (300 MHz, DMSO-$d_6$) δ:3.92 (3H, s), 5.98 (2H, s), 7.39-7.60 (2H, m), 7.60-7.69 (2H, m), 7.72-7.81 (2H, m), 7.91-8.01 (1H, m), 8.12-8.23 (2H, m).

Reference Example 117

Production of ethyl 8-fluoro-3-hydroxy-1-methyl-4-oxo-5-(2-oxo-2-phenylethyl)-4,5-dihydro-1H-pyrrolo[3,2-c]quinoline-2-carboxylate

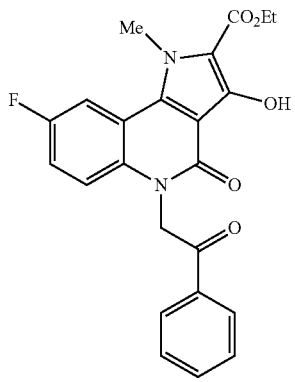 [SMILES: CCOC(=O)c1c(O)c2c(=O)n(CC(=O)c3ccccc3)c3ccc(F)cc3c2n1C]

In the same manner as in Reference Example 25, the title compound (4.1 g, 83%) was obtained as a pale-brown solid from the compound of Reference Example 113 (4.6 g, 12 mmol), sarcosine ethyl ester hydrochloride (4.5 g, 30 mmol), triethylamine (6.0 mL, 43 mmol), ethanol (35 mL), a 20% solution (3.4 g, 9.9 mmol) of sodium ethoxide in ethanol and ethanol (35 mL).

¹H-NMR (300 MHz, DMSO-d₆) δ:1.33 (3H, t, J=8.9 Hz), 4.26-4.42 (5H, m), 5.94 (2H, s), 7.33-7.50 (2H, m), 7.58-7.69 (2H, m), 7.71-7.80 (1H, m), 8.03-8.23 (3H, m), 9.01 (1H, br s).

Reference Example 118

Production of ethyl 8-fluoro-3-methoxy-1-methyl-4-oxo-5-(2-oxo-2-phenylethyl)-4,5-dihydro-1H-pyrrolo[3,2-c]quinoline-2-carboxylate

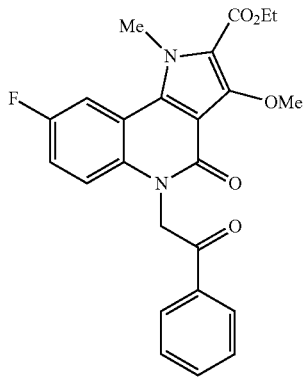 [SMILES: CCOC(=O)c1c(OC)c2c(=O)n(CC(=O)c3ccccc3)c3ccc(F)cc3c2n1C]

A solution of the compound of Reference Example 117 (3.4 g, 8.0 mmol), dimethylsulfuric acid (1.1 mL, 12 mmol) and DBU (2.4 mL, 16 mmol) in DMF (100 mL) was stirred at room temperature for 2.5 hr. Dimethylsulfuric acid (1.1 mL, 12 mmol) and DBU (2.4 mL, 16 mmol) were added to the reaction mixture, and the mixture was stirred at room temperature for 1 day. Dimethylsulfuric acid (0.75 mL, 8.0 mmol) and DBU (1.8 mL, 11 mmol) were further added, and the mixture was stirred at room temperature for 21 hr, diluted with water, and the precipitated solid was collected by filtration. The obtained solid was washed with water, and dried under reduced pressure to give the title compound (2.8 g, 80%) as a white solid.
¹H-NMR (300 MHz, DMSO-d₆) δ:1.35 (3H, t, J=7.1 Hz), 3.88 (3H, s), 4.21-4.42 (5H, m), 5.96 (2H, s), 7.28-7.51 (2H, m), 7.55-7.69 (2H, m), 7.71-7.81 (1H, m), 7.98-8.39 (3H, m).

Reference Example 119

Production of 8-fluoro-3-methoxy-1-methyl-4-oxo-5-(2-oxo-2-phenylethyl)-4,5-dihydro-1H-pyrrolo[3,2-c]quinoline-2-carboxylic acid

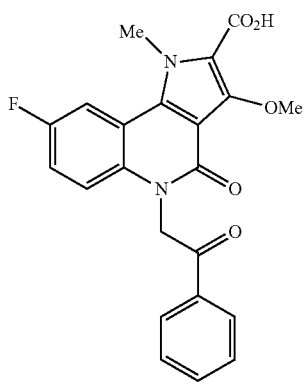 [SMILES: COc1c(C(=O)O)n(C)c2c1c(=O)n(CC(=O)c1ccccc1)c1ccc(F)cc21]

In the same manner as in Reference Example 7, the title compound (2.4 g, 90%) was obtained as a pale-yellow solid from the compound of Reference Example 118 (2.8 g, 6.4 mmol).

¹H-NMR (300 MHz, DMSO-d₆) δ:3.85 (3H, s), 4.30 (3H, s), 5.95 (2H, s), 7.19-7.49 (2H, m), 7.53-7.69 (2H, m), 7.70-7.82 (1H, m), 7.97-8.26 (3H, m).

Reference Example 120

Production of 1-ethyl-3-methoxy-4-oxo-5-(2-oxo-2-phenylethyl)-4,5-dihydro-1H-pyrrolo[3,2-c]quinoline-2-carboxylic acid

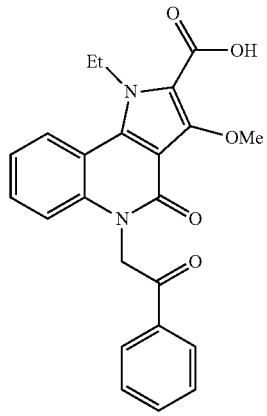 [SMILES: CCn1c(C(=O)O)c(OC)c2c(=O)n(CC(=O)c3ccccc3)c3ccccc3c21]

A solution of the compound of Reference Example 4 (1.0 g, 2.7 mmol), N-ethylglycine ethyl ester hydrochloride (499 mg, 3.0 mmol) and triethylamine (3.8 mL, 27 mmol) in 1-butanol (10 mL) was heated under reflux for 6 hr. N-Ethylglycine ethyl ester hydrochloride (499 mg, 3.0 mmol) was added and the mixture was heated under reflux for 17 hr. N-Ethylglycine ethyl ester hydrochloride (499 mg, 3.0 mmol) and triethylamine (0.41 mL, 3.0 mmol) were added, and the mixture was heated under reflux for 6 hr, and N-ethylglycine ethyl ester hydrochloride (499 mg, 3.0 mmol) and triethylamine (0.41 mL, 3.0 mmol) were added, and the mixture was heated under reflux for 6 hr. Water was added to the reaction mixture, and the precipitated solid was collected by filtration. The obtained solid was washed with water, and dried under reduced pressure. A mixture of the obtained solid and a 20% solution (777 mg, 2.3 mmol) of sodium ethoxide in ethanol and ethanol (150 mL) was stirred at room temperature for 5 hr. A 20% solution (777 mg, 2.3 mmol) of sodium ethoxide in ethanol was added, and the reaction mixture was stirred at room temperature for 1 hr. The reaction mixture was diluted with water, neutralized with 5N hydrochloric acid, and the mixture was stirred for 30 min. The precipitated solid was collected by filtration, washed with water, dried under reduced pressure, and recrystallized from DMF-diethyl ether. To a solution of the obtained solid and DBU (0.19 mL, 1.3 mmol) in DMF (8.0 mL) was added dimethylsulfuric acid (0.092 mL, 0.97 mmol) under ice-cooling, and the mixture was stirred at room temperature for 14 hr. DBU (0.19 mL, 1.3 mmol) and dimethylsulfuric acid (0.092 mL, 0.97 mmol) were further added under ice-cooling, and the mixture was stirred at room temperature for 4 hr, and diluted with water. The precipitated solid was collected by filtration, the obtained solid was washed with water, and dried under reduced pressure. A mixed solution of the obtained solid and 8N sodium hydroxide solution (1.4 mL) in THF (2.3 mL)-ethanol (8.0 mL) was stirred at room temperature for 15 hr. 8N Sodium hydroxide solution (0.70 mL) was added, and the mixture was stirred at room temperature for 3.5 hr. 8N Sodium hydroxide solution (0.14 mL) was further added, and the mixture was stirred at room temperature for 3 hr. The reaction mixture was neutralized with 1N hydrochloric acid and concentrated under reduced pressure, and the precipitated solid was collected by filtration. The obtained solid was washed with water, and dried under reduced pressure to give the title compound (180 mg, 16%) as a white solid.

$^1$H-NMR (300 MHz, DMSO-d$_6$) δ:1.51 (3H, t, J=6.5 Hz), 3.86 (3H, s), 4.85 (2H, q, J=7.0 Hz), 5.97 (2H, s), 7.27-7.43 (2H, m), 7.44-7.54 (1H, m), 7.58-7.69 (2H, m), 7.71-7.83 (1H, m), 8.01-8.45 (3H, m), 12.89 (1H, br s).

Reference Example 121

Production of tert-butyl (1-benzylazepan-4-yl)carbamate

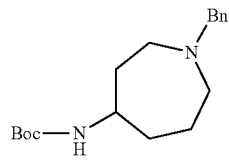 [SMILES: CC(C)(C)OC(=O)NC1CCCN(Cc2ccccc2)CC1]

To a solution of 1-benzylazepan-4-amine (400 mg, 2.0 mmol) and triethylamine (0.82 mL, 5.9 mmol) in THF (5.0 mL) was added di-tert-butyl dicarbonate (591 mg, 2.7 mmol) under ice-cooling, and the mixture was stirred at room temperature for 4 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by amino-silica gel chromatography (eluate; ethyl acetate/hexane=10/90-100/0) to give the title compound (447 mg, quant.) as a colorless oil.

$^1$H-NMR (300 MHz, CDCl$_3$) δ:1.45 (9H, s), 1.53-1.77 (5H, m), 1.78-1.93 (1H, m), 2.37-2.58 (2H, m), 2.61-2.83 (2H, m), 3.61 (2H, s), 3.73-4.00 (1H, m), 4.92-5.27 (1H, m), 7.07-7.44 (5H, m).

Reference Example 122

Production of tert-butyl azepan-4-ylcarbamate

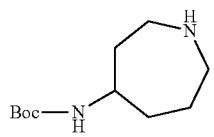 [SMILES: CC(C)(C)OC(=O)NC1CCCNCC1]

A solution of the compound of Reference Example 121 (447 mg, 1.5 mmol) and palladium-carbon (65 mg) in ethanol (10 mL) was stirred at room temperature for 4.5 hr under a hydrogen atmosphere. Palladium-carbon was filtered off, and the filtrate was concentrated under reduced pressure. The residue was dissolved in methanol (10 mL), palladium-carbon (120 mg) was added, and the mixture was stirred at room temperature for 4.5 hr under a hydrogen atmosphere. Palladium-carbon was filtered off, and the filtrate was concentrated under reduced pressure to give the title compound (315 mg, quant.) as a colorless oil.

$^1$H-NMR (300 MHz, CDCl$_3$) δ:1.34-1.76 (13H, m), 1.78-2.07 (2H, m), 2.39-2.70 (1H, m), 2.71-3.04 (4H, m), 3.66-3.94 (1H, m), 4.60-5.01 (1H, m).

Reference Example 123

Production of 2-{4-[(tert-butoxycarbonyl)amino]azepan-1-yl}-2-oxoethyl acetate

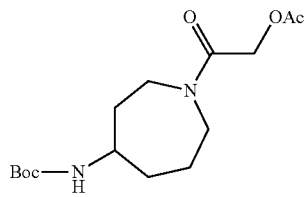 [SMILES: CC(=O)OCC(=O)N1CCCC(NC(=O)OC(C)(C)C)CC1]

In the same manner as in Example 544, the title compound (220 mg, 96%) was obtained as a white solid from the compound of Reference Example 122 (157 mg, 0.73 mmol).

$^1$H-NMR (300 MHz, CDCl$_3$) δ:1.37-1.55 (11H, m), 1.61-2.00 (4H, m), 2.07-2.23 (4H, m), 3.21-3.77 (4H, m), 4.35-4.59 (1H, m), 4.59-4.81 (2H, m).

Reference Example 124

Production of Methyl 2-aminopyridine-3-carboxylate

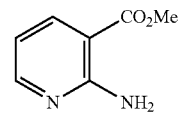

To a solution of 2-aminopyridine-3-carboxylic acid (4.3 g, 31 mmol) in methanol (62 mL) was added dropwise sulfuric acid (31 mL) under ice-cooling, and the reaction mixture was stirred at room temperature for 30 min. The reaction mixture was stirred at 70° C. for 15 hr. and neutralized with sodium bicarbonate under ice-cooling. The reaction mixture was extracted twice with ethyl acetate, and the extracts were combined, and washed with brine. The extract was dried over magnesium sulfate, and concentrated under reduced pressure to give the title compound (4.3 g, 90%) as a white solid.

$^1$H-NMR (300 MHz, CDCl$_3$) δ:3.89 (3H, s), 6.38 (2H, br s), 6.63 (1H, dd, J=7.8, 4.8 Hz), 8.13 (1H, dd, J=7.7, 1.9 Hz), 8.22 (1H, dd, J=4.7, 1.9 Hz).

Reference Example 125

Production of ethyl 4-hydroxy-2-oxo-1,2-dihydro-1,8-naphthyridine-3-carboxylate

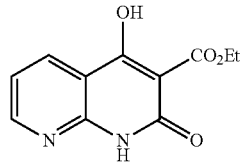 [SMILES: CCOC(=O)c1c(O)c2cccnc2[nH]c1=O]

In the same manner as in Reference Example 1, the title compound (2.6 g, 53%) was obtained as a pale-red solid from the compound of Reference Example 124 (3.1 g, 21 mmol).

¹H-NMR (300 MHz, DMSO-d₆) δ:1.30 (3H, t, J=7.1 Hz), 4.32 (2H, q, J=7.1 Hz), 7.27 (1H, dd, J=7.9, 4.7 Hz), 8.22-8.38 (1H, m), 8.60 (1H, dd, J=4.6, 1.8 Hz), 11.86 (1H, s), 13.29 (1H, br s).

Reference Example 126

Production of ethyl 2,4-dichloro-1,8-naphthyridine-3-carboxylate

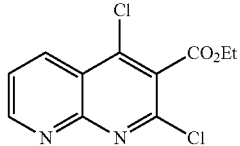 [SMILES: CCOC(=O)c1c(Cl)nc2ncccc2c1Cl]

In the same manner as in Reference Example 2, the title compound (2.3 g, 77%) was obtained as a pale-yellow solid from the compound of Reference Example 125 (2.6 g, 11 mmol).
¹H-NMR (300 MHz, CDCl₃) δ:1.47 (3H, t, J=7.2 Hz), 4.56 (2H, q, J=7.2 Hz), 7.67 (1H, dd, J=8.4, 4.2 Hz), 8.62 (1H, dd, J=8.3, 1.9 Hz), 9.21 (1H, dd, J=4.2, 1.9 Hz).

Reference Example 127

Production of ethyl 4-chloro-2-oxo-1,2-dihydro-1,8-naphthyridine-3-carboxylate

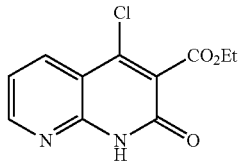 [SMILES: CCOC(=O)c1c(Cl)c2cccnc2[nH]c1=O]

In the same manner as in Reference Example 3, the title compound (1.5 g, 71%) was obtained as a white solid from the compound of Reference Example 126 (2.2 g, 8.3 mmol).
¹H-NMR (300 MHz, DMSO-d₆) δ:1.31 (3H, t, J=7.1 Hz), 4.37 (2H, q, J=7.1 Hz), 7.43 (1H, dd, J=8.1, 4.7 Hz), 8.33 (1H, dd, J=8.1, 1.7 Hz), 8.69 (1H, dd, J=4.7, 1.7 Hz), 12.88 (1H, br s).

Reference Example 128

Production of ethyl 4-chloro-2-oxo-1-(2-oxo-2-phenylethyl)-1,2-dihydro-1,8-naphthyridine-3-carboxylate

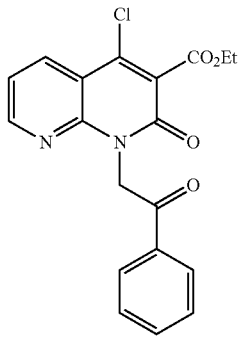 [SMILES: CCOC(=O)c1c(Cl)c2cccnc2n(CC(=O)c2ccccc2)c1=O]

In the same manner as in Reference Example 4, the title compound (1.1 g, 51%) was obtained as a pale-yellow oil from the compound of Reference Example 127 (1.5 g, 5.7 mmol).

¹H-NMR (300 MHz, CDCl₃) δ:1.42 (3H, t, J=7.1 Hz), 4.48 (2H, q, J=7.1 Hz), 5.98 (2H, s), 7.27-7.33 (1H, m), 7.48-7.58 (2H, m), 7.59-7.69 (1H, m), 8.02-8.12 (2H, m), 8.36 (1H, dd, J=8.0, 1.8 Hz), 8.54 (1H, dd, J=4.7, 1.7 Hz).

Reference Example 129

Production of ethyl 3-hydroxy-1-methyl-4-oxo-5-(2-oxo-2-phenylethyl)-4,5-dihydro-1H-pyrrolo[3,2-c][1,8]naphthyridine-2-carboxylate

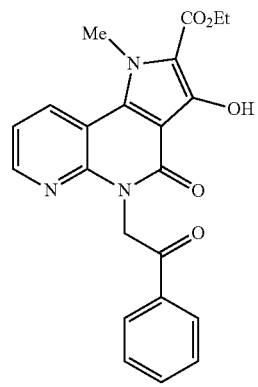 [SMILES: CCOC(=O)c1c(O)c2c(=O)n(CC(=O)c3ccccc3)c3ncccc3c2n1C]

In the same manner as in Reference Example 33, the title compound (653 mg, 55%) was obtained as a pale-yellow solid from the compound of Reference Example 128 (1.1 g, 2.9 mmol).
¹H-NMR (300 MHz, CDCl₃) δ:1.45 (3H, t, J=7.1 Hz), 4.36 (3H, s), 4.46 (2H, q, J=7.2 Hz), 6.00 (2H, s), 7.20 (1H, dd, J=7.9, 4.7 Hz), 7.45-7.58 (2H, m), 7.58-7.69 (1H, m), 8.02-8.15 (2H, m), 8.33-8.51 (2H, m), 8.70 (1H, s).

Reference Example 130

Production of ethyl 3-methoxy-1-methyl-4-oxo-5-(2-oxo-2-phenylethyl)-4,5-dihydro-1H-pyrrolo[3,2-c][1,8]naphthyridine-2-carboxylate

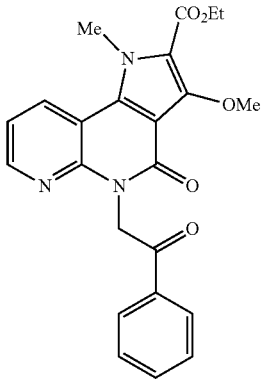 [SMILES: CCOC(=O)c1c(OC)c2c(=O)n(CC(=O)c3ccccc3)c3ncccc3c2n1C]

In the same manner as in Reference Example 115, the title compound (420 mg, 79%) was obtained as a white solid from the compound of Reference Example 129 (512 mg, 1.3 mmol).
¹H-NMR (300 MHz, DMSO-d₆) δ:1.35 (3H, t, J=7.1 Hz), 3.91 (3H, s), 4.24-4.44 (5H, m), 5.97 (2H, s), 7.36 (1H, dd, J=8.1, 4.5 Hz), 7.55-7.69 (2H, m), 7.68-7.82 (1H, m), 8.06-8.24 (2H, m), 8.46 (1H, dd, J=4.6, 1.4 Hz), 8.75 (1H, dd, J=8.1, 1.5 Hz).

Reference Example 131

Production of 3-methoxy-1-methyl-4-oxo-5-(2-oxo-2-phenylethyl)-4,5-dihydro-1H-pyrrolo[3,2-c][1,8]naphthyridine-2-carboxylic acid

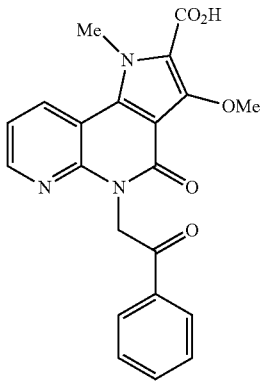 [SMILES: COc1c(C(=O)O)n(C)c2c1c(=O)n(CC(=O)c1ccccc1)c1ncccc21]

In the same manner as in Reference Example 7, the title compound (264 mg, 75%) was obtained as a white solid from the compound of Reference Example 130 (380 mg, 0.91 mmol).
$^1$H-NMR (300 MHz, DMSO-d$_6$) δ:3.90 (3H, s), 4.32 (3H, s), 5.97 (2H, s), 7.35 (1H, dd, J=8.1, 4.7 Hz), 7.54-7.68 (2H, m), 7.69-7.81 (1H, m), 8.03-8.27 (2H, m), 8.33-8.56 (1H, m), 8.75 (1H, d, J=7.2 Hz), 13.04 (1H, br s).

Reference Example 132

Production of Methyl 4-aminopyridine-3-carboxylate

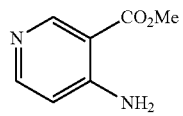

In the same manner as in Reference Example 124, the title compound (4.9 g, 89%) was obtained as a pale-yellow solid from 4-aminopyridine-3-carboxylic acid (5.0 g, 36 mmol), sulfuric acid (36 mL) and methanol (72 mL).
$^1$H-NMR (300 MHz, CDCl$_3$) δ:3.91 (3H, s), 6.20 (2H, br s), 6.51 (1H, d, J=5.9 Hz), 8.20 (1H, d, J=6.0 Hz), 8.90 (1H, s).

Reference Example 133

Production of ethyl 4-hydroxy-2-oxo-1,2-dihydro-1,6-naphthyridine-3-carboxylate

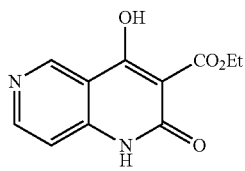 [SMILES: CCOC(=O)c1c(O)c2cnccc2[nH]c1=O]

In the same manner as in Reference Example 1, the title compound (3.5 g, 49%) was obtained as a pale-yellow powder from the compound of Reference Example 132 (4.7 g, 31 mmol).

$^1$H-NMR (300 MHz, DMSO-d$_6$) δ:1.28 (3H, t, J=7.1 Hz), 4.26 (2H, q, J=7.0 Hz), 7.20 (1H, d, J=6.0 Hz), 8.50 (1H, d, J=6.0 Hz), 8.92-9.09 (1H, m), 11.66 (1H, br s).

Reference Example 134

Production of ethyl 2,4-dichloro-1,6-naphthyridine-3-carboxylate

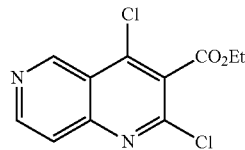 [SMILES: CCOC(=O)c1c(Cl)nc2ccncc2c1Cl]

In the same manner as in Reference Example 2, the title compound (2.7 g, 66%) was obtained as a pale-yellow solid from the compound of Reference Example 133 (3.5 g, 15 mmol).
$^1$H-NMR (300 MHz, CDCl$_3$) δ:1.47 (3H, t, J=7.2 Hz), 4.56 (2H, q, J=7.1 Hz), 7.87 (1H, dd, J=5.9, 0.8 Hz), 8.92 (1H, d, J=5.9 Hz), 9.66 (1H, d, J=0.9 Hz).

Reference Example 135

Production of ethyl 4-chloro-2-oxo-1,2-dihydro-1,6-naphthyridine-3-carboxylate

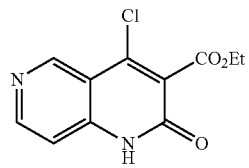 [SMILES: CCOC(=O)c1c(Cl)c2cnccc2[nH]c1=O]

In the same manner as in Reference Example 3, the title compound (733 mg, 30%) was obtained as a pale-brown solid from the compound of Reference Example 134 (2.6 g, 9.7 mmol).
$^1$H-NMR (300 MHz, DMSO-d$_6$) δ:1.31 (3H, t, J=7.1 Hz), 4.36 (2H, q, J=7.1 Hz), 7.29 (1H, d, J=5.7 Hz), 8.63 (1H, d, J=5.7 Hz), 9.06 (1H, s), 12.72 (1H, br s).

Reference Example 136

Production of ethyl 4-chloro-2-oxo-1-(2-oxo-2-phenylethyl)-1,2-dihydro-1,6-naphthyridine-3-carboxylate

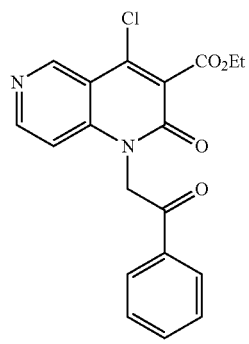 [SMILES: CCOC(=O)c1c(Cl)c2cnccc2n(CC(=O)c2ccccc2)c1=O]

In the same manner as in Reference Example 4, the title compound (344 mg, 33%) was obtained as a pale-yellow solid from the compound of Reference Example 135 (710 mg, 2.8 mmol).

¹H-NMR (300 MHz, CDCl₃) δ:1.42 (3H, t, J=7.2 Hz), 4.48 (2H, q, J=7.2 Hz), 5.73 (2H, s), 6.86 (1H, d, J=5.9 Hz), 7.49-7.63 (2H, m), 7.64-7.79 (1H, m), 7.95-8.19 (2H, m), 8.64 (1H, br s), 9.30 (1H, br s).

Reference Example 137

Production of ethyl 3-hydroxy-1-methyl-4-oxo-5-(2-oxo-2-phenylethyl)-4,5-dihydro-1H-pyrrolo[3,2-c][1,6]naphthyridine-2-carboxylate

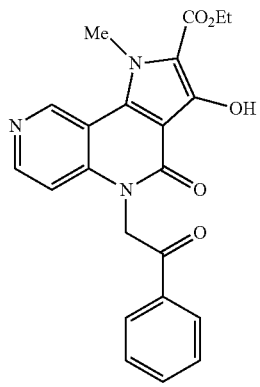 [SMILES: CCOC(=O)c1c(O)c2c(=O)n(CC(=O)c3ccccc3)c3ccncc3c2n1C]

A mixture of the compound of Reference Example 136 (574 mg, 1.6 mmol), sarcosine ethyl ester hydrochloride (286 mg, 1.9 mmol), triethylamine (0.65 mL, 4.7 mmol), and ethanol (29 mL) was heated under reflux for 2.5 hr. Sarcosine ethyl ester hydrochloride (286 mg, 1.9 mmol) and triethylamine (0.43 mL, 3.1 mmol) were further added and the mixture was heated under reflux for 5.5 hr. Sarcosine ethyl ester hydrochloride (286 mg, 1.9 mmol) and triethylamine (0.65 mL, 4.7 mmol) were added and the mixture was heated under reflux for 46 hr. Triethylamine (0.65 mL, 4.7 mmol) was added, and the mixture was heated under reflux for 3 hr. Triethylamine (0.65 mL, 4.7 mmol) was added and the mixture was heated under reflux for 64 hr. Triethylamine (0.65 mL, 4.7 mmol) was further added and the mixture was heated under reflux for 3 hr. Triethylamine (0.65 mL, 4.7 mmol) was further added and the mixture was heated under reflux for 3 hr. The reaction mixture was concentrated under reduced pressure, water was added to the residue, and the mixture was acidified with 20% aqueous citric acid solution and stirred for 30 min under ice-cooling. The precipitated solid was collected by filtration, the obtained solid was washed with water, and dried under reduced pressure. The solid was washed with ethyl acetate-hexane mixed solvent and hexane to give the title compound (485 mg, 77%) as a pale-brown powder.

¹H-NMR (300 MHz, DMSO-d₆) δ:1.34 (3H, t, J=7.1 Hz), 4.27-4.43 (5H, m), 5.91 (2H, s), 7.42 (1H, d, J=6.0 Hz), 7.58-7.69 (2H, m), 7.71-7.82 (1H, m), 8.08-8.23 (2H, m), 8.50 (1H, d, J=5.9 Hz), 9.07 (1H, br s), 9.49 (1H, s).

Reference Example 138

Production of ethyl 3-methoxy-1-methyl-4-oxo-5-(2-oxo-2-phenylethyl)-4,5-dihydro-1H-pyrrolo[3,2-c][1,6]naphthyridine-2-carboxylate

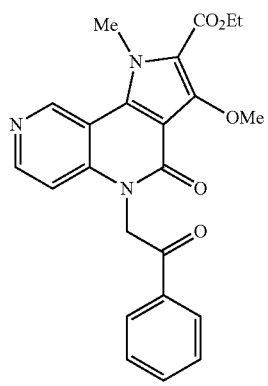 [SMILES: CCOC(=O)c1c(OC)c2c(=O)n(CC(=O)c3ccccc3)c3ccncc3c2n1C]

In the same manner as in Reference Example 115, the title compound (313 mg, 64%) was obtained as a white solid from the compound of Reference Example 137 (471 mg, 1.2 mmol).

¹H-NMR (300 MHz, DMSO-d₆) δ:1.35 (3H, t, J=6.0 Hz), 3.88 (3H, s), 4.28-4.40 (5H, m), 5.94 (2H, s), 7.43 (1H, d, J=6.0 Hz), 7.59-7.69 (2H, m), 7.72-7.82 (1H, m), 8.11-8.22 (2H, m), 8.51 (1H, d, J=6.0 Hz), 9.52 (1H, s).

Reference Example 139

Production of 3-methoxy-1-methyl-4-oxo-5-(2-oxo-2-phenylethyl)-4,5-dihydro-1H-pyrrolo[3,2-c][1,6]naphthyridine-2-carboxylic acid

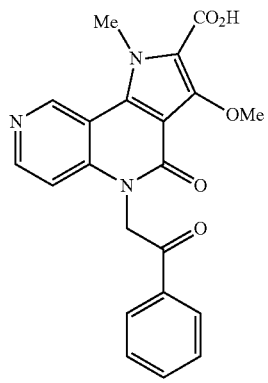 [SMILES: COc1c(C(=O)O)n(C)c2c1c(=O)n(CC(=O)c1ccccc1)c1ccncc21]

In the same manner as in Reference Example 7, the title compound (259 mg, 92%) was obtained as a white solid from the compound of Reference Example 138 (301 mg, 0.72 mmol).

¹H-NMR (300 MHz, DMSO-d₆) δ:3.87 (3H, s), 4.36 (3H, s), 5.94 (2H, s), 7.42 (1H, d, J=6.0 Hz), 7.57-7.70 (2H, m), 7.71-7.83 (1H, m), 8.07-8.26 (2H, m), 8.49 (1H, d, J=5.9 Hz), 9.51 (1H, s), 13.01 (1H, br s).

Reference Example 140

Production of ethyl 6-ethyl-3-hydroxy-1-methyl-4-oxo-4,5-dihydro-1H-pyrrolo[3,2-c]pyridine-2-carboxylate

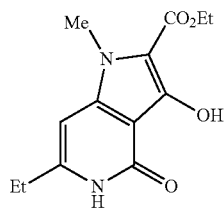 [SMILES: CCOC(=O)c1c(O)c2c(=O)[nH]c(CC)cc2n1C]

In the same manner as in Reference Example 40, the title compound (4.87 g, 85%) was obtained as a brown powder from the compound of Reference Example 38 (5.00 g, 21.8 mmol).

¹H-NMR (300 MHz, DMSO-d₆) δ:1.18 (3H, t, J=7.6 Hz), 1.30 (3H, t, J=7.1 Hz), 2.39-2.49 (2H, m), 3.73 (3H, s), 4.29 (2H, q, J=7.1 Hz), 6.25 (1H, s), 8.87 (1H, br s), 10.81 (1H, br s).

Reference Example 141

Production of ethyl 6-ethyl-1-methyl-4-oxo-3-(2,2,2-trifluoroethoxy)-4,5-dihydro-1H-pyrrolo[3,2-c]pyridine-2-carboxylate

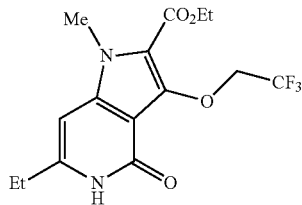 [SMILES: CCOC(=O)c1c(OCC(F)(F)F)c2c(=O)[nH]c(CC)cc2n1C]

A mixture of the compound of Reference Example 140 (200 mg, 0.757 mmol), cesium carbonate (271 mg, 0.832 mmol), 2,2,2-trifluoroethyl trifluoromethanesulfonate (0.109 mL, 0.757 mmol), dimethyl sulfoxide (2.0 mL) and DMF (2.0 mL) was stirred at 60° C. for 2 hr. The reaction mixture was diluted with water, and the precipitated solid was collected by filtration. The obtained solid was washed with water and diisopropyl ether, and dried under reduced pressure to give the title compound (161 mg, 61%) as a white solid.

¹H-NMR (300 MHz, DMSO-d₆) δ:1.19 (3H, t, J=7.5 Hz), 1.27 (3H, t, J=7.0 Hz), 2.51-2.56 (2H, m), 3.79 (3H, s), 4.24 (2H, q, J=7.0 Hz), 4.97 (2H, q, J=9.3 Hz), 6.38 (1H, s), 11.06 (1H, br s).

Reference Example 142

Production of ethyl 6-ethyl-5-(3-methoxybenzyl)-1-methyl-4-oxo-3-(2,2,2-trifluoroethoxy)-4,5-dihydro-1H-pyrrolo[3,2-c]pyridine-2-carboxylate

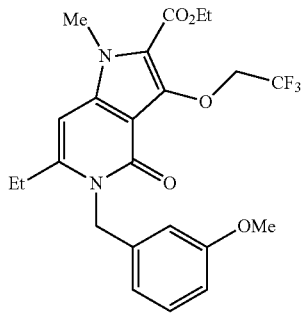

A mixture of the compound of Reference Example 141 (500 mg, 1.44 mmol), sodium tert-butoxide (180 mg, 1.87 mmol), lithium bromide (250 mg, 2.88 mmol), 1-(chloromethyl)-3-methoxybenzene (0.313 mL, 2.16 mmol), DME (8.0 mL) and DMF (2.0 mL) was stirred at 60° C. for 13 hr. Water (50 mL) was added to the reaction mixture, and the mixture was extracted with ethyl acetate. The extract was washed with brine, dried over sodium sulfate, and concentrated under reduced pressure. The residue was purified by silica gel chromatography (eluate; ethyl acetate/hexane=3/97-70/30) to give the title compound (508 mg, 76%) as a yellow oil.

¹H-NMR (300 MHz, DMSO-d₆) δ:1.14-1.36 (6H, m), 2.60 (2H, q, J=7.2 Hz), 3.70 (3H, s), 3.85 (3H, s), 4.26 (2H, q, J=7.2 Hz), 4.89 (2H, q, J=9.3 Hz), 5.28 (2H, br s), 6.44-6.67 (3H, m), 6.74-6.95 (1H, m), 7.22 (1H, t, J=7.9 Hz).

Reference Example 143

Production of 6-ethyl-5-(3-methoxybenzyl)-1-methyl-4-oxo-3-(2,2,2-trifluoroethoxy)-4,5-dihydro-1H-pyrrolo[3,2-c]pyridine-2-carboxylic acid

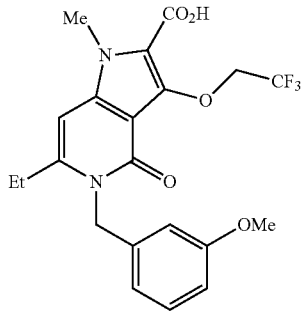 [SMILES: CCc1cc2c(c(OCC(F)(F)F)c(C(=O)O)n2C)c(=O)n1Cc1cccc(OC)c1]

In the same manner as in Reference Example 49, the title compound (333 mg, 66%) was obtained as a white powder from the compound of Reference Example 142 (508 mg, 1.09 mmol).

¹H-NMR (300 MHz, DMSO-d₆) δ:1.17 (3H, t, J=7.3 Hz), 2.60 (2H, q, J=7.3 Hz), 3.70 (3H, s), 3.85 (3H, s), 4.87 (2H, q, J=9.4 Hz), 5.30 (2H, br s), 6.43-6.67 (3H, m), 6.81 (1H, dd, J=7.9, 2.3 Hz), 7.22 (1H, t, J=7.9 Hz), 12.70 (1H, br s).

Reference Example 144

Production of ethyl 5-benzyl-6-ethyl-1-methyl-4-oxo-3-(2,2,2-trifluoroethoxy)-4,5-dihydro-1H-pyrrolo[3,2-c]pyridine-2-carboxylate

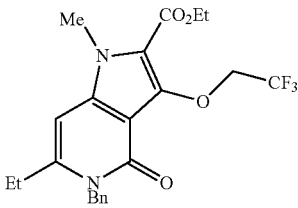 [SMILES: CCOC(=O)c1c(OCC(F)(F)F)c2c(=O)n(Cc3ccccc3)c(CC)cc2n1C]

In the same manner as in Reference Example 142, the title compound (312 mg, 62%) was obtained as a yellow oil from the compound of Reference Example 141 (400 mg, 1.16 mmol) and benzyl bromide (0.207 mL, 1.74 mmol).

$^1$H-NMR (300 MHz, DMSO-$d_6$) δ:1.16 (3H, t, J=7.3 Hz), 1.29 (3H, t, J=7.1 Hz), 2.61 (2H, q, J=7.3 Hz), 3.85 (3H, s), 4.26 (2H, q, J=7.1 Hz), 4.89 (2H, q, J=9.3 Hz), 5.34 (2H, br s), 6.54 (1H, s), 7.03-7.09 (2H, m), 7.20-7.27 (1H, m), 7.28-7.36 (2H, m).

Reference Example 145

Production of 5-benzyl-6-ethyl-1-methyl-4-oxo-3-(2,2,2-trifluoroethoxy)-4,5-dihydro-1H-pyrrolo[3,2-c]pyridine-2-carboxylic acid

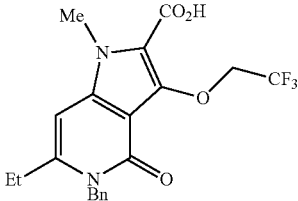 [SMILES: CCc1cc2c(c(OCC(F)(F)F)c(C(=O)O)n2C)c(=O)n1Cc1ccccc1]

In the same manner as in Reference Example 49, the title compound (213 mg, 73%) was obtained as a white powder from the compound of Reference Example 144 (312 mg, 0.715 mmol).

$^1$H-NMR (300 MHz, DMSO-$d_6$) δ:1.16 (3H, t, J=7.3 Hz), 2.60 (2H, q, J=7.3 Hz), 3.85 (3H, s), 4.87 (2H, q, J=9.3 Hz), 5.34 (2H, br s), 6.52 (1H, s), 7.01-7.10 (2H, m), 7.17-7.39 (3H, m), 12.73 (1H, br s).

Reference Example 146

Production of ethyl 5-(2,5-dimethoxybenzyl)-6-ethyl-1-methyl-4-oxo-3-(2,2,2-trifluoroethoxy)-4,5-dihydro-1H-pyrrolo[3,2-c]pyridine-2-carboxylate

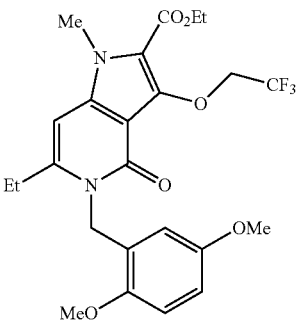

In the same manner as in Reference Example 142, the title compound (121 mg, 21%) was obtained as a white powder from the compound of Reference Example 141 (400 mg, 1.16 mmol) and 2-(chloromethyl)-1,4-dimethoxybenzene (325 mg, 1.74 mmol).

$^1$H-NMR (300 MHz, DMSO-$d_6$) δ:1.17 (3H, t, J=7.3 Hz), 1.29 (3H, t, J=7.2 Hz), 2.53-2.61 (2H, m), 3.56 (3H, s), 3.83 (3H, s), 3.86 (3H, s), 4.26 (2H, q, J=7.2 Hz), 4.87 (2H, q, J=9.3 Hz), 5.19 (2H, br s), 5.93 (1H, d, J=3.0 Hz), 6.58 (1H, s), 6.79 (1H, dd, J=8.9, 3.0 Hz), 6.97 (1H, d, J=8.9 Hz).

Reference Example 147

Production of 5-(2,5-dimethoxybenzyl)-6-ethyl-1-methyl-4-oxo-3-(2,2,2-trifluoroethoxy)-4,5-dihydro-1H-pyrrolo[3,2-c]pyridine-2-carboxylic acid

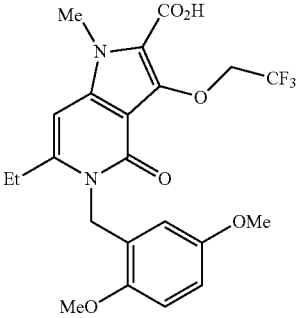 [SMILES: CCc1cc2c(c(OCC(F)(F)F)c(C(=O)O)n2C)c(=O)n1Cc1cc(OC)ccc1OC]

In the same manner as in Reference Example 49, the title compound (82.7 mg, 72%) was obtained as a white powder from the compound of Reference Example 146 (121 mg, 0.244 mmol).

$^1$H-NMR (300 MHz, DMSO-$d_6$) δ:1.17 (3H, t, J=7.3 Hz), 2.52-2.60 (2H, m), 3.56 (3H, s), 3.83 (3H, s), 3.86 (3H, s), 4.85 (2H, q, J=9.3 Hz), 5.19 (2H, br s), 5.92 (1H, d, J=3.0 Hz), 6.56 (1H, s), 6.79 (1H, dd, J=9.0, 3.0 Hz), 6.97 (1H, d, J=9.0 Hz), 12.74 (1H, br s).

Reference Example 148

Production of ethyl 4-chloro-6-ethyl-1-[2-(3-methoxyphenyl)-2-oxoethyl]-2-oxo-1,2-dihydropyridine-3-carboxylate

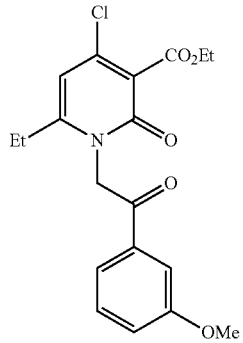 [SMILES: CCOC(=O)c1c(Cl)cc(CC)n(CC(=O)c2cccc(OC)c2)c1=O]

In the same manner as in Reference Example 142, the title compound (879 mg, 53%) was obtained as a yellow oil from the compound of Reference Example 38 (1.00 g, 4.35 mmol) and 2-bromo-1-(3-methoxyphenyl)ethanone (1.99 g, 8.71 mmol).

$^1$H-NMR (300 MHz, DMSO-d$_6$) δ:1.13 (3H, t, J=7.4 Hz), 1.24 (3H, t, J=7.1 Hz), 2.61 (2H, q, J=7.4 Hz), 3.85 (3H, s), 4.25 (2H, q, J=7.1 Hz), 5.60 (2H, s), 6.44 (1H, s), 7.28-7.35 (1H, m), 7.48-7.59 (2H, m), 7.66-7.74 (1H, m).

Reference Example 149

Production of ethyl 6-ethyl-3-hydroxy-5-[2-(3-methoxyphenyl)-2-oxoethyl]-1-methyl-4-oxo-4,5-dihydro-1H-pyrrolo[3,2-c]pyridine-2-carboxylate

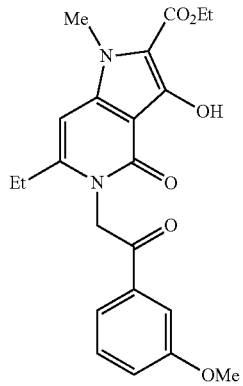 [SMILES: CCOC(=O)c1c(O)c2c(=O)n(CC(=O)c3cccc(OC)c3)c(CC)cc2n1C]

In the same manner as in Reference Example 40, the title compound (526 mg, 55%) was obtained as a green powder from the compound of Reference Example 148 (879 mg, 2.33 mmol).

$^1$H-NMR (300 MHz, DMSO-d$_6$) δ:1.18 (3H, t, J=7.4 Hz), 1.31 (3H, t, J=7.1 Hz), 2.52-2.61 (2H, m), 3.80 (3H, s), 3.85 (3H, s), 4.30 (2H, q, J=7.1 Hz), 5.54 (2H, s), 6.43 (1H, s), 7.26-7.36 (1H, m), 7.48-7.60 (2H, m), 7.68-7.76 (1H, m), 8.89 (1H, br s).

Reference Example 150

Production of ethyl 6-ethyl-5-[2-(3-methoxyphenyl)-2-oxoethyl]-1-methyl-4-oxo-3-(2,2,2-trifluoroethoxy)-4,5-dihydro-1H-pyrrolo[3,2-c]pyridine-2-carboxylate

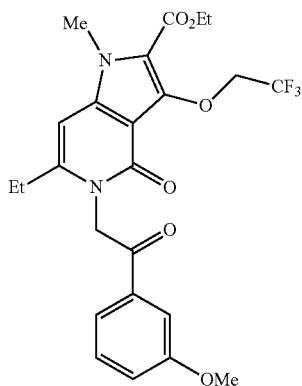

A mixture of the compound of Reference Example 149 (470 mg, 1.14 mmol), cesium carbonate (446 mg, 1.37 mmol), 2,2,2-trifluoroethyl trifluoromethanesulfonate (0.197 mL, 1.37 mmol) and DMF (4.7 mL) was stirred at room temperature for 1 hr. The reaction mixture was diluted with water, and the precipitated solid was collected by filtration. The obtained solid was washed with water, diisopropyl ether and ethanol, and dried under reduced pressure to give the title compound (423 mg, 75%) as a green powder.

$^1$H-NMR (300 MHz, DMSO-d$_6$) δ:1.19 (3H, t, J=7.3 Hz), 1.28 (3H, t, J=7.2 Hz), 2.59 (2H, q, J=7.3 Hz), 3.83-3.90 (6H, m), 4.26 (2H, q, J=7.2 Hz), 4.83 (2H, q, J=9.3 Hz), 5.61 (2H, s), 6.55 (1H, s), 7.27-7.34 (1H, m), 7.48-7.61 (2H, m), 7.68-7.76 (1H, m).

Reference Example 151

Production of 6-ethyl-5-[2-(3-methoxyphenyl)-2-oxoethyl]-1-methyl-4-oxo-3-(2,2,2-trifluoroethoxy)-4,5-dihydro-1H-pyrrolo[3,2-c]pyridine-2-carboxylic acid

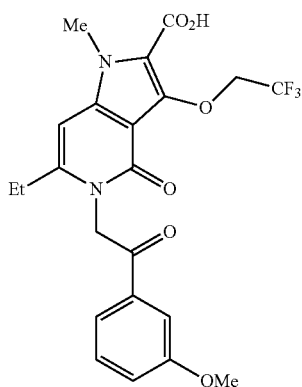 [SMILES: CCc1cc2c(c(OCC(F)(F)F)c(C(=O)O)n2C)c(=O)n1CC(=O)c1cccc(OC)c1]

In the same manner as in Reference Example 49, the title compound (300 mg, 86%) was obtained as a brown powder from the compound of Reference Example 150 (370 mg, 0.748 mmol).

$^1$H-NMR (300 MHz, DMSO-d$_6$) δ:1.19 (3H, t, J=7.3 Hz), 2.58 (2H, q, J=7.3 Hz), 3.83-3.91 (6H, m), 4.82 (2H, q, J=9.3 Hz), 5.60 (2H, s), 6.54 (1H, s), 7.26-7.37 (1H, m), 7.47-7.62 (2H, m), 7.67-7.83 (1H, m), 12.70 (1H, br s).

Reference Example 152

Production of ethyl 4-chloro-1-[2-(3-chlorophenyl)-2-oxoethyl]-6-ethyl-2-oxo-1,2-dihydropyridine-3-carboxylate

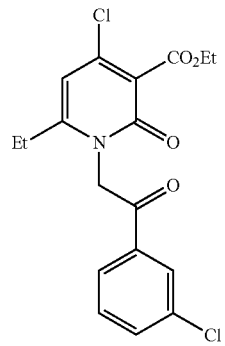 [SMILES: CCOC(=O)c1c(Cl)cc(CC)n(CC(=O)c2cccc(Cl)c2)c1=O]

In the same manner as in Reference Example 142, the title compound (486 mg, 29%) was obtained as a white powder from the compound of Reference Example 38 (1.50 g, 6.53 mmol) and 2-bromo-1-(3-chlorophenyl)ethanone (2.02 g, 8.65 mmol).

$^1$H-NMR (300 MHz, DMSO-d$_6$) δ:1.14 (3H, t, J=7.4 Hz), 1.24 (3H, t, J=7.1 Hz), 2.63 (2H, q, J=7.4 Hz), 4.25 (2H, q, J=7.1 Hz), 5.61 (2H, s), 6.45 (1H, s), 7.59-7.70 (1H, m), 7.77-7.86 (1H, m), 8.00-8.07 (1H, m), 8.08-8.17 (1H, m).

Reference Example 153

Production of ethyl 5-[2-(3-chlorophenyl)-2-oxoethyl]-6-ethyl-3-hydroxy-1-methyl-4-oxo-4,5-dihydro-1H-pyrrolo[3,2-c]pyridine-2-carboxylate

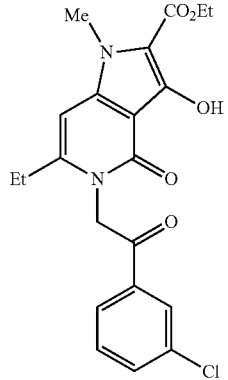 [SMILES: CCOC(=O)c1c(O)c2c(=O)n(CC(=O)c3cccc(Cl)c3)c(CC)cc2n1C]

In the same manner as in Reference Example 40, the title compound (460 mg, 87%) was obtained as a green powder from the compound of Reference Example 152 (486 mg, 1.27 mmol).

$^1$H-NMR (300 MHz, DMSO-d$_6$) δ:1.18 (3H, t, J=7.4 Hz), 1.31 (3H, t, J=7.0 Hz), 2.57 (2H, q, J=7.4 Hz), 3.80 (3H, s), 4.30 (2H, q, J=7.0 Hz), 5.53 (2H, s), 6.44 (1H, s), 7.61-7.68 (1H, m), 7.80 (1H, ddd, J=7.8, 2.0, 0.9 Hz), 8.05 (1H, dt, J=7.8, 0.9 Hz), 8.13 (1H, t, J=2.0 Hz), 8.90 (1H, s).

Reference Example 154

Production of ethyl 5-[2-(3-chlorophenyl)-2-oxoethyl]-6-ethyl-1-methyl-4-oxo-3-(2,2,2-trifluoroethoxy)-4,5-dihydro-1H-pyrrolo[3,2-c]pyridine-2-carboxylate

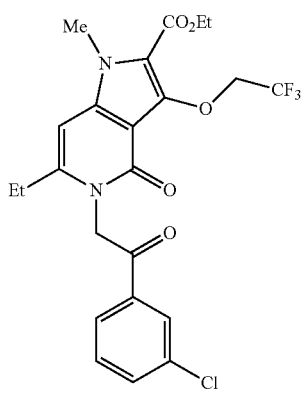

In the same manner as in Reference Example 150, the title compound (348 mg, 63%) was obtained as a green powder from the compound of Reference Example 153 (460 mg, 1.10 mmol).

$^1$H-NMR (300 MHz, DMSO-d$_6$) δ:1.19 (3H, t, J=7.3 Hz), 1.28 (3H, t, J=7.1 Hz), 2.60 (2H, q, J=7.3 Hz), 3.86 (3H, s), 4.26 (2H, q, J=7.1 Hz), 4.83 (2H, q, J=9.3 Hz), 5.61 (2H, s), 6.56 (1H, s), 7.61-7.69 (1H, m), 7.78-7.84 (1H, m), 8.03-8.09 (1H, m), 8.14 (1H, t, J=1.7 Hz).

Reference Example 155

Production of 5-[2-(3-chlorophenyl)-2-oxoethyl]-6-ethyl-1-methyl-4-oxo-3-(2,2,2-trifluoroethoxy)-4,5-dihydro-1H-pyrrolo[3,2-c]pyridine-2-carboxylic acid

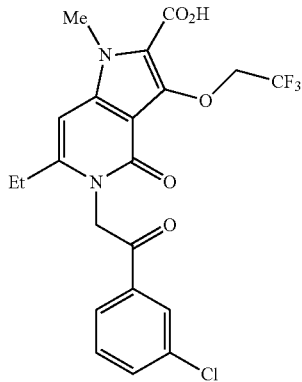

In the same manner as in Reference Example 49, the title compound (192 mg, 59%) was obtained as a brown powder from the compound of Reference Example 154 (348 mg, 0.698 mmol).

$^1$H-NMR (300 MHz, DMSO-d$_6$) δ:1.19 (3H, t, J=7.3 Hz), 2.60 (2H, q, J=7.3 Hz), 3.86 (3H, s), 4.81 (2H, q, J=9.2 Hz), 5.60 (2H, s), 6.55 (1H, s), 7.58-7.71 (1H, m), 7.76-7.86 (1H, m), 8.00-8.10 (1H, m), 8.14 (1H, t, J=1.7 Hz), 12.72 (1H, br s).

Reference Example 156

Production of ethyl 6-ethyl-5-(2-methoxybenzyl)-1-methyl-4-oxo-3-(2,2,2-trifluoroethoxy)-4,5-dihydro-1H-pyrrolo[3,2-c]pyridine-2-carboxylate

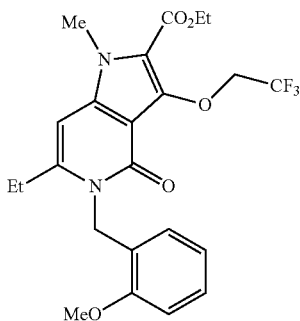 [SMILES: CCOC(=O)c1c(OCC(F)(F)F)c2c(=O)n(Cc3ccccc3OC)c(CC)cc2n1C]

In the same manner as in Reference Example 142, the title compound (138 mg, 26%) was obtained as a white powder from the compound of Reference Example 141 (400 mg, 1.16 mmol) and 1-(chloromethyl)-2-methoxybenzene (272 mg, 1.74 mmol).

$^1$H-NMR (300 MHz, DMSO-$d_6$) δ:1.17 (3H, t, J=7.4 Hz), 1.29 (3H, t, J=7.1 Hz), 2.53-2.61 (2H, m), 3.86 (3H, s), 3.88 (3H, s), 4.26 (2H, q, J=7.1 Hz), 4.86 (2H, q, J=9.3 Hz), 5.22 (2H, br s), 6.41 (1H, dd, J=7.5, 1.2 Hz), 6.57 (1H, s), 6.82 (1H, td, J=7.5, 0.9 Hz), 7.01-7.09 (1H, m), 7.18-7.28 (1H, m).

Reference Example 157

Production of 6-ethyl-5-(2-methoxybenzyl)-1-methyl-4-oxo-3-(2,2,2-trifluoroethoxy)-4,5-dihydro-1H-pyrrolo[3,2-c]pyridine-2-carboxylic acid

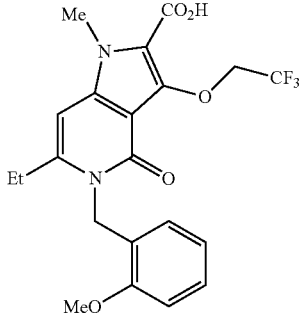 [SMILES: CCc1cc2c(c(OCC(F)(F)F)c(C(=O)O)n2C)c(=O)n1Cc1ccccc1OC]

In the same manner as in Reference Example 49, the title compound (104 mg, 80%) was obtained as a white powder from the compound of Reference Example 156 (138 mg, 0.296 mmol).

$^1$H-NMR (300 MHz, DMSO-$d_6$) δ:1.17 (3H, t, J=7.3 Hz), 2.53-2.60 (2H, m), 3.86 (3H, s), 3.88 (3H, s), 4.84 (2H, q, J=9.3 Hz), 5.22 (2H, br s), 6.40 (1H, dd, J=7.5, 1.3 Hz), 6.55 (1H, s), 6.82 (1H, td, J=7.5, 0.9 Hz), 7.00-7.11 (1H, m), 7.16-7.31 (1H, m), 12.72 (1H, br s).

Reference Example 158

Production of ethyl 6-ethyl-5-(4-methoxybenzyl)-1-methyl-4-oxo-3-(2,2,2-trifluoroethoxy)-4,5-dihydro-1H-pyrrolo[3,2-c]pyridine-2-carboxylate

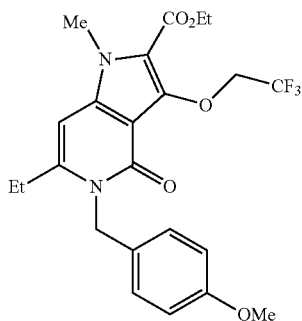

In the same manner as in Reference Example 142, the title compound (175 mg, 43%) was obtained as a white powder from the compound of Reference Example 141 (300 mg, 0.866 mmol) and 1-(chloromethyl)-4-methoxybenzene (0.175 mL, 1.30 mmol).

$^1$H-NMR (300 MHz, DMSO-$d_6$) δ:1.16 (3H, t, J=7.2 Hz), 1.29 (3H, t, J=7.2 Hz), 2.62 (2H, q, J=7.2 Hz), 3.71 (3H, s), 3.84 (3H, s), 4.26 (2H, q, J=7.2 Hz), 4.90 (2H, q, J=9.3 Hz), 5.26 (2H, br s), 6.51 (1H, s), 6.82-6.92 (2H, m), 6.97-7.08 (2H, m).

Reference Example 159

Production of 6-ethyl-5-(4-methoxybenzyl)-1-methyl-4-oxo-3-(2,2,2-trifluoroethoxy)-4,5-dihydro-1H-pyrrolo[3,2-c]pyridine-2-carboxylic acid

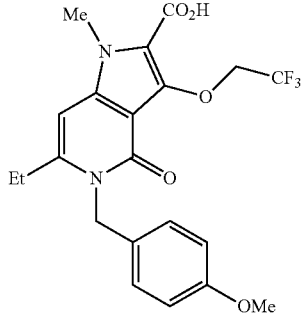 [SMILES: CCc1cc2c(c(OCC(F)(F)F)c(C(=O)O)n2C)c(=O)n1Cc1ccc(OC)cc1]

In the same manner as in Reference Example 49, the title compound (157 mg, 96%) was obtained as a white powder from the compound of Reference Example 158 (175 mg, 0.375 mmol).

$^1$H-NMR (300 MHz, DMSO-$d_6$) δ:1.16 (3H, t, J=7.3 Hz), 2.62 (2H, q, J=7.3 Hz), 3.71 (3H, s), 3.84 (3H, s), 4.88 (2H, q,

J=9.3 Hz), 5.26 (2H, br s), 6.49 (1H, s), 6.81-6.92 (2H, m), 6.96-7.09 (2H, m), 12.70 (1H, br s).

Reference Example 160

Production of ethyl 5-(2-chlorobenzyl)-6-ethyl-1-methyl-4-oxo-3-(2,2,2-trifluoroethoxy)-4,5-dihydro-1H-pyrrolo[3,2-c]pyridine-2-carboxylate

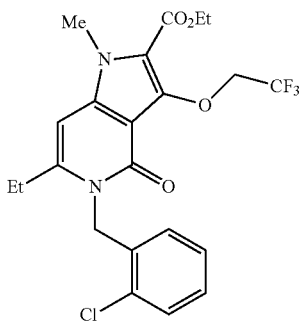 [SMILES: CCOC(=O)c1c(OCC(F)(F)F)c2c(=O)n(Cc3ccccc3Cl)c(CC)cc2n1C]

In the same manner as in Reference Example 142, the title compound (163 mg, 30%) was obtained as a white powder from the compound of Reference Example 141 (400 mg, 1.16 mmol) and 1-chloro-2-(chloromethyl)benzene (0.226 mL, 1.74 mmol).

$^1$H-NMR (300 MHz, DMSO-$d_6$) δ:1.18 (3H, t, J=7.4 Hz), 1.29 (3H, t, J=7.1 Hz), 2.53-2.62 (2H, m), 3.87 (3H, s), 4.27 (2H, q, J=7.1 Hz), 4.86 (2H, q, J=9.3 Hz), 5.32 (2H, s), 6.55 (1H, dd, J=7.6, 1.5 Hz), 6.62 (1H, s), 7.21-7.33 (2H, m), 7.52 (1-H, dd, J=7.7, 1.3 Hz).

Reference Example 161

Production of 5-(2-chlorobenzyl)-6-ethyl-1-methyl-4-oxo-3-(2,2,2-trifluoroethoxy)-4,5-dihydro-1H-pyrrolo[3,2-c]pyridine-2-carboxylic acid

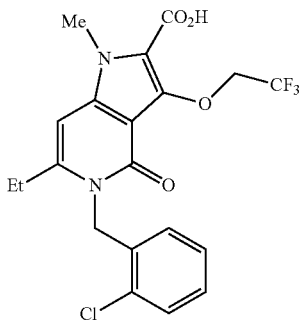 [SMILES: CCc1cc2c(c(OCC(F)(F)F)c(C(=O)O)n2C)c(=O)n1Cc1ccccc1Cl]

In the same manner as in Reference Example 49, the title compound (138 mg, 90%) was obtained as a white powder from the compound of Reference Example 160 (163 mg, 0.346 mmol).

$^1$H-NMR (300 MHz, DMSO-$d_6$) δ:1.18 (3H, t, J=7.4 Hz), 2.52-2.62 (2H, m), 3.87 (3H, s), 4.83 (2H, q, J=9.3 Hz), 5.32 (2H, s), 6.50 (1H, dd, J=7.7, 1.6 Hz), 6.60 (1H, s), 7.22-7.33 (2H, m), 7.52 (1H, dd, J=7.7, 1.3 Hz), 12.76 (1H, br s).

Reference Example 162

Production of ethyl 4-chloro-6-ethyl-2-oxo-1-(2-phenylethyl)-1,2-dihydropyridine-3-carboxylate

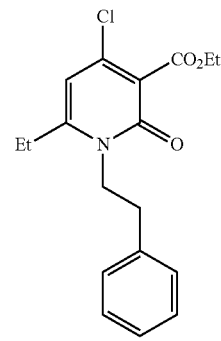 [SMILES: CCOC(=O)c1c(Cl)cc(CC)n(CCc2ccccc2)c1=O]

In the same manner as in Reference Example 142, the title compound (480 mg, 16%) was obtained as a white powder from the compound of Reference Example 38 (2.00 g, 8.71 mmol) and (2-bromoethyl)benzene (1.77 mL, 11.3 mmol).

$^1$H-NMR (300 MHz, DMSO-$d_6$) δ:1.14 (3H, t, J=7.4 Hz), 1.28 (3H, t, J=7.1 Hz), 2.63 (2H, q, J=7.4 Hz), 2.85-2.93 (2H, m), 4.07-4.15 (2H, m), 4.29 (2H, q, J=7.1 Hz), 6.30 (1H, s), 7.19-7.28 (3H, m), 7.28-7.38 (2H, m).

Reference Example 163

Production of ethyl 6-ethyl-3-hydroxy-1-methyl-4-oxo-5-(2-phenylethyl)-4,5-dihydro-1H-pyrrolo[3,2-c]pyridine-2-carboxylate

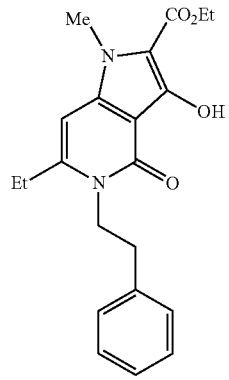

In the same manner as in Reference Example 40, the title compound (481 mg, 80%) was obtained as a white powder from the compound of Reference Example 162 (480 mg, 1.44 mmol).

$^1$H-NMR (300 MHz, DMSO-$d_6$) δ:1.20 (3H, t, J=7.3 Hz), 1.31 (3H, t, J=7.1 Hz), 2.63 (2H, q, J=7.3 Hz), 2.80-2.94 (2H, m), 3.75 (3H, s), 4.01-4.16 (2H, m), 4.30 (2H, q, J=7.1 Hz), 6.34 (1H, s), 7.11-7.41 (5H, m), 8.94 (1H, br s).

Reference Example 164

Production of ethyl 6-ethyl-1-methyl-4-oxo-5-(2-phenylethyl)-3-(2,2,2-trifluoroethoxy)-4,5-dihydro-1H-pyrrolo[3,2-c]pyridine-2-carboxylate

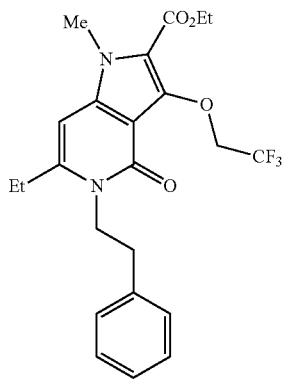 [SMILES: CCc1cc2c(c(OCC(F)(F)F)c(C(=O)O)n2C)c(=O)n1CCc1ccccc1]

In the same manner as in Reference Example 150, the title compound (185 mg, 31%) was obtained as a white powder from the compound of Reference Example 163 (482 mg, 1.31 mmol).

$^1$H-NMR (300 MHz, DMSO-$d_6$) δ:1.22 (3H, t, J=7.3 Hz), 1.29 (3H, t, J=7.2 Hz), 2.67 (2H, q, J=7.3 Hz), 2.82-2.94 (2H, m), 3.82 (3H, s), 4.10-4.20 (2H, m), 4.26 (2H, q, J=7.2 Hz), 4.90 (2H, q, J=9.3 Hz), 6.46 (1H, s), 7.15-7.38 (5H, m).

Reference Example 165

Production of 6-ethyl-1-methyl-4-oxo-5-(2-phenylethyl)-3-(2,2,2-trifluoroethoxy)-4,5-dihydro-1H-pyrrolo[3,2-c]pyridine-2-carboxylic acid

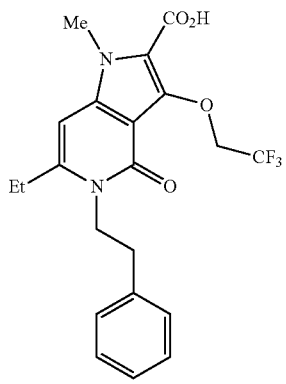

In the same manner as in Reference Example 49, the title compound (143 mg, 83%) was obtained as a brown powder from the compound of Reference Example 164 (185 mg, 0.411 mmol).

$^1$H-NMR (300 MHz, DMSO-$d_6$) δ:1.21 (3H, t, J=7.2 Hz), 2.66 (2H, q, J=7.2 Hz), 2.81-2.94 (2H, m), 3.81 (3H, s), 4.05-4.30 (2H, m), 4.89 (2H, q, J=9.3 Hz), 6.44 (1H, s), 7.09-7.48 (5H, m), 12.67 (1H, br s).

Reference Example 166

Production of ethyl 5-(3-chlorobenzyl)-6-ethyl-1-methyl-4-oxo-3-(2,2,2-trifluoroethoxy)-4,5-dihydro-1H-pyrrolo[3,2-c]pyridine-2-carboxylate

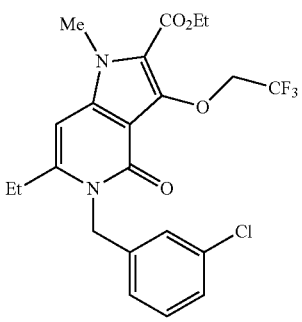

In the same manner as in Reference Example 142, the title compound (325 mg, 60%) was obtained as a white powder from the compound of Reference Example 141 (400 mg, 1.16 mmol) and 1-chloro-3-(chloromethyl)benzene (357 mg, 1.74 mmol).

$^1$H-NMR (300 MHz, DMSO-$d_6$) δ:1.17 (3H, t, J=7.4 Hz), 1.29 (3H, t, J=7.1 Hz), 2.60 (2H, q, J=7.1 Hz), 3.85 (3H, s), 4.26 (2H, q, J=7.4 Hz), 4.88 (2H, q, J=9.3 Hz), 5.33 (2H, br s), 6.56 (1H, s), 6.96-7.05 (1H, m), 7.10-7.18 (1H, m), 7.27-7.43 (2H, m).

Reference Example 167

Production of 5-(3-chlorobenzyl)-6-ethyl-1-methyl-4-oxo-3-(2,2,2-trifluoroethoxy)-4,5-dihydro-1H-pyrrolo[3,2-c]pyridine-2-carboxylic acid

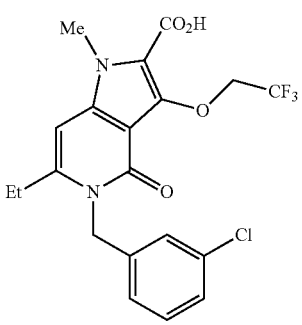 [SMILES: CCc1cc2c(c(OCC(F)(F)F)c(C(=O)O)n2C)c(=O)n1Cc1cccc(Cl)c1]

In the same manner as in Reference Example 49, the title compound (281 mg, 92%) was obtained as a white powder from the compound of Reference Example 166 (325 mg, 0.690 mmol).

$^1$H-NMR (300 MHz, DMSO-$d_6$) δ:1.17 (3H, t, J=7.2 Hz), 2.60 (2H, q, J=7.2 Hz), 3.85 (3H, s), 4.86 (2H, q, J=9.3 Hz), 5.34 (2H, br s), 6.54 (1H, s), 6.95-7.05 (1H, m), 7.10-7.18 (1H, m), 7.26-7.43 (2H, m), 12.74 (1H, s).

Reference Example 168

Production of ethyl 5-(4-chlorobenzyl)-6-ethyl-1-methyl-4-oxo-3-(2,2,2-trifluoroethoxy)-4,5-dihydro-1H-pyrrolo[3,2-c]pyridine-2-carboxylate

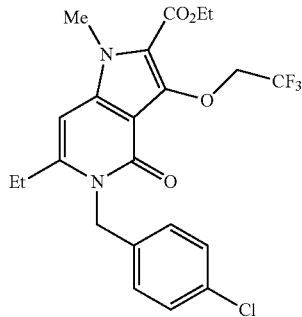 [SMILES: CCOC(=O)c1c(OCC(F)(F)F)c2c(=O)n(Cc3ccc(Cl)cc3)c(CC)cc2n1C]

In the same manner as in Reference Example 142, the title compound (213 mg, 39%) was obtained as a white powder from the compound of Reference Example 141 (400 mg, 1.16 mmol) and 1-chloro-4-(chloromethyl)benzene (357 mg, 1.74 mmol).

$^1$H-NMR (300 MHz, DMSO-d$_6$) δ:1.16 (3H, t, J=7.3 Hz), 1.29 (3H, t, J=7.1 Hz), 2.60 (2H, q, J=7.1 Hz), 3.85 (3H, s), 4.26 (2H, q, J=7.3 Hz), 4.88 (2H, q, J=9.3 Hz), 5.32 (2H, br s), 6.55 (1H, s), 7.03-7.16 (2H, m), 7.66-7.43 (2H, m).

Reference Example 169

Production of 5-(4-chlorobenzyl)-6-ethyl-1-methyl-4-oxo-3-(2,2,2-trifluoroethoxy)-4,5-dihydro-1H-pyrrolo[3,2-c]pyridine-2-carboxylic acid

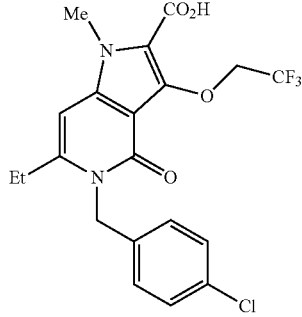 [SMILES: CCc1cc2c(c(OCC(F)(F)F)c(C(=O)O)n2C)c(=O)n1Cc1ccc(Cl)cc1]

In the same manner as in Reference Example 49, the title compound (188 mg, 94%) was obtained as a white powder from the compound of Reference Example 168 (213 mg, 0.452 mmol).

$^1$H-NMR (300 MHz, DMSO-d$_6$) δ:1.16 (3H, t, J=7.3 Hz), 2.59 (2H, q, J=7.3 Hz), 3.84 (3H, s), 4.86 (2H, q, J=9.3 Hz), 5.32 (2H, br s), 6.53 (1H, s), 7.01-7.20 (2H, m), 7.28-7.49 (2H, m), 12.75 (1-H, br s).

Reference Example 170

Production of ethyl 3-ethoxy-6-ethyl-4-oxo-5-(2-oxo-2-phenylethyl)-4,5-dihydrothieno[3,2-c]pyridine-2-carboxylate

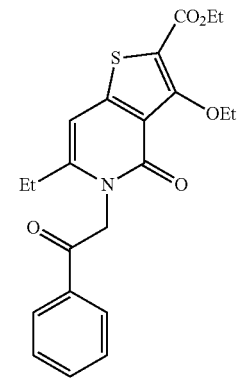 [SMILES: CCOC(=O)c1sc2cc(CC)n(CC(=O)c3ccccc3)c(=O)c2c1OCC]

In the same manner as in Reference Example 5, ethyl 6-ethyl-3-hydroxy-4-oxo-5-(2-oxo-2-phenylethyl)-4,5-dihydrothieno[3,2-c]pyridine-2-carboxylate was obtained from the compound of Reference Example 39 (3.6 g, 10.3 mmol), ethyl thioglycolate (14.4 mL, 103 mmol) and triethylamine (2.3 mL, 20.6 mmol). The title compound (900 mg, 47%) was obtained as a white solid from the thus-obtained ethyl 6-ethyl-3-hydroxy-4-oxo-5-(2-oxo-2-phenylethyl)-4,5-dihydrothieno[3,2-c]pyridine-2-carboxylate (1.8 g, 4.7 mmol) by a method similar to that in Reference Example 43.

$^1$H-NMR (300 MHz, DMSO-d$_6$) δ:1.17 (3H, t, J=7.4 Hz), 1.23-1.36 (6H, m), 2.61 (2H, q, J=7.4 Hz), 4.14 (2H, q, J=7.1 Hz), 4.28 (2H, q, J=7.0 Hz), 5.65 (2H, s), 6.83 (1H, s), 7.62 (2H, t, J=7.6 Hz), 7.70-7.79 (1H, m), 8.12 (2H, d, J=7.2 Hz).

Reference Example 171

Production of 3-(2,2-difluoroethoxy)-6-ethyl-1-methyl-4-oxo-5-(2-oxo-2-phenylethyl)-4,5-dihydro-1H-pyrrolo[3,2-c]pyridine-2-carboxylic acid

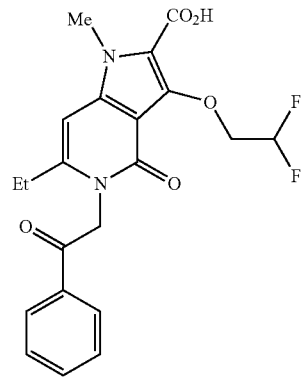 [SMILES: CCc1cc2c(c(OCC(F)F)c(C(=O)O)n2C)c(=O)n1CC(=O)c1ccccc1]

In the same manner as in Reference Example 56, ethyl 3-(2,2-difluoroethoxy)-6-ethyl-1-methyl-4-oxo-5-(2-oxo-2-phenylethyl)-4,5-dihydro-1H-pyrrolo[3,2-c]pyridine-2-carboxylate was obtained from the compound of Reference Example 40 (500 mg, 1.31 mmol), 2,2-difluoroethyl trifluoromethanesulfonate (336 mg, 1.57 mmol) and cesium carbonate (554 mg, 1.70 mmol). The title compound (314 mg, 83%) was obtained as a white powder from the thus-obtained ethyl 3-(2,2-difluoroethoxy)-6-ethyl-1-methyl-4-oxo-5-(2-oxo-2-phenylethyl)-4,5-dihydro-1H-pyrrolo[3,2-c]pyridine-2-carboxylate (400 mg, 0.90 mmol) by a method similar to that in Reference Example 59.

$^1$H-NMR (300 MHz, DMSO-d$_6$) δ:1.19 (3H, t, J=7.2 Hz), 2.58 (2H, q, J=7.3 Hz), 3.85 (3H, s), 4.40 (2H, td, J=14.6, 1.2 Hz), 5.60 (2H, s), 6.26 (1H, tt, J=55.0, 3.9 Hz), 6.77 (1H, s), 7.58-7.76 (3H, m), 8.12 (2H, d, J=7.5 Hz), 12.50-12.70 (1H, br).

Reference Example 172

Production of ethyl 6-ethyl-1-methyl-4-oxo-5-(2-oxo-2-phenylethyl)-3-propoxy-4,5-dihydro-1H-pyrrolo[3,2-c]pyridine-2-carboxylate

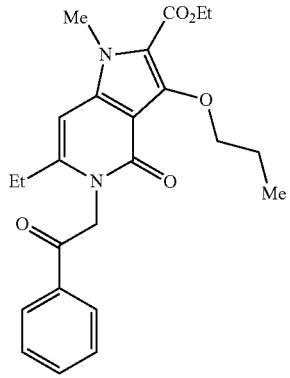 [SMILES: CCCOc1c(C(=O)OCC)n(C)c2cc(CC)n(CC(=O)c3ccccc3)c(=O)c12]

In the same manner as in Reference Example 56, The title compound (177 mg, 83%) was obtained as a brown powder from the compound of Reference Example 40 (191 mg, 0.50 mmol), dipropyl sulfate (364 mg, 2.0 mmol), potassium carbonate (414 mg, 3.0 mmol) and acetone (20 mL).

$^1$H-NMR (300 MHz, CDCl$_3$) δ:1.01 (3H, t, J=7.5 Hz), 1.28 (3H, t, J=7.3 Hz), 1.40 (3H, t, J=7.5 Hz), 1.75-1.89 (2H, m), 2.51 (2H, q, J=7.2 Hz), 3.88 (3H, s), 4.21 (2H, t, J=6.7 Hz), 4.36 (2H, q, J=7.2 Hz), 5.59 (2H, s), 6.19 (1H, s), 7.47-7.56 (2H, m), 7.59-7.67 (1H, m), 8.02-8.09 (2H, m)

Reference Example 173

Production of 6-ethyl-1-methyl-4-oxo-5-(2-oxo-2-phenylethyl)-3-propoxy-4,5-dihydro-1H-pyrrolo[3,2-c]pyridine-2-carboxylic acid

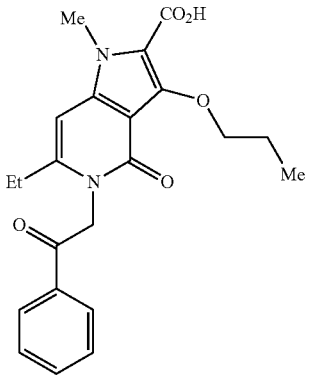 [SMILES: CCCOc1c(C(=O)O)n(C)c2cc(CC)n(CC(=O)c3ccccc3)c(=O)c12]

In the same manner as in Reference Example 59, the title compound (237 mg, 93%) was obtained as a pale-yellow powder from the compound of Reference Example 172 (274 mg, 0.65 mmol).

$^1$H-NMR (300 MHz, DMSO-d$_6$) δ:0.91 (3H, t, J=7.5 Hz), 1.18 (3H, t, J=7.3 Hz), 1.55-1.70 (2H, m), 2.57 (2H, q, J=7.4 Hz), 3.84 (3H, s), 4.07 (2H, t, J=6.5 Hz), 5.58 (2H, s), 6.47 (1H, s), 7.56-7.66 (2H, m), 7.69-7.78 (1H, m), 8.07-8.16 (2H, m), 12.42 (1H, s).

Reference Example 174

Production of 6-ethyl-1-methyl-3-(1-methylethoxy)-4-oxo-5-(2-oxo-2-phenylethyl)-4,5-dihydro-1H-pyrrolo[3,2-c]pyridine-2-carboxylic acid

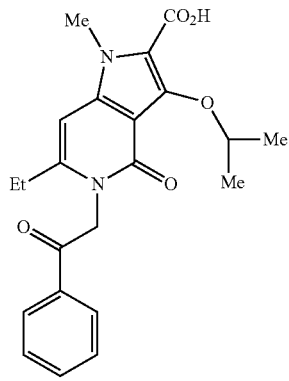 [SMILES: CCc1cc2c(c(OC(C)C)c(C(=O)O)n2C)c(=O)n1CC(=O)c1ccccc1]

In the same manner as in Reference Example 56, ethyl 6-ethyl-1-methyl-3-(1-methylethoxy)-4-oxo-5-(2-oxo-2-phenylethyl)-4,5-dihydro-1H-pyrrolo[3,2-c]pyridine-2-carboxylate (291 mg, 46%) was obtained as a pale-purple powder from the compound of Reference Example 40 (574 mg, 1.50 mmol), potassium carbonate (1.04 g, 7.5 mmol) and diisopropyl sulfate (1.37 g, 7.5 mmol). The title compound (242 mg, 97%) was obtained as a colorless powder from the thus-obtained ethyl 6-ethyl-1-methyl-3-(1-methylethoxy)-4-oxo-5-(2-oxo-2-phenylethyl)-4,5-dihydro-1H-pyrrolo[3,2-c]pyridine-2-carboxylate (267 mg, 0.63 mmol) by a method similar to that in Reference Example 59.

$^1$H-NMR (300 MHz, DMSO-d$_6$) δ:1.13-1.23 (9H, m), 2.57 (2H, q, J=7.5 Hz), 3.84 (3H, s), 4.65-4.80 (1H, m), 5.58 (2H, s), 6.47 (1H, s), 7.56-7.66 (2H, m), 7.69-7.78 (1H, m), 8.07-8.16 (2H, m), 12.29 (1H, s).

Reference Example 175

Production of 6-ethyl-1-methyl-4-oxo-5-(2-oxo-2-phenylethyl)-3-(2,2,3,3-tetrafluoropropoxy)-4,5-dihydro-1H-pyrrolo[3,2-c]pyridine-2-carboxylic acid

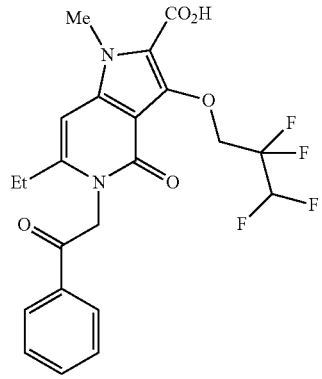 [SMILES: CCc1cc2c(c(OCC(F)(F)C(F)F)c(C(=O)O)n2C)c(=O)n1CC(=O)c1ccccc1]

In the same manner as in Reference Example 150, ethyl 6-ethyl-1-methyl-4-oxo-5-(2-oxo-2-phenylethyl)-3-(2,2,3, 3-tetrafluoropropoxy)-4,5-dihydro-1H-pyrrolo[3,2-c]pyridine-2-carboxylate (460 mg, 93%) was obtained as a gray powder from the compound of Reference Example 40 (382 mg, 1.00 mmol), 2,2,3,3-tetrafluoropropyl trifluoromethanesulfonate (913 mg, 3.46 mmol), cesium carbonate (391 mg, 1.20 mmol) and DMF (10 mL). The title compound (310 mg, 95%) was obtained as a gray powder from the thus-obtained ethyl 6-ethyl-1-methyl-4-oxo-5-(2-oxo-2-phenylethyl)-3-(2,2,3,3-tetrafluoropropoxy)-4,5-dihydro-1H-pyrrolo[3,2-c]pyridine-2-carboxylate (348 mg, 0.70 mmol) by a method similar to that in Reference Example 59.

$^1$H-NMR (300 MHz, DMSO-$d_6$) δ:1.19 (3H, t, J=7.3 Hz), 2.58 (2H, q, J=7.3 Hz), 3.86 (3H, s), 4.70 (2H, t, J=13.1 Hz), 5.62 (2H, s), 6.54 (1H, s), 6.73 (1H, tt, J=52.6, 6.1 Hz), 7.56-7.66 (2H, m), 7.69-7.79 (1H, m), 8.07-8.17 (2H, m), 12.93 (1H, br s).

Reference Example 176

Production of ethyl 3-(cyclopropylmethoxy)-6-ethyl-1-methyl-4-oxo-5-(2-oxo-2-phenylethyl)-4,5-dihydro-1H-pyrrolo[3,2-c]pyridine-2-carboxylate

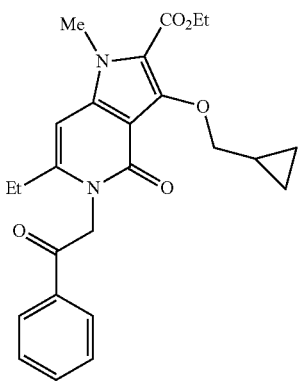 [SMILES: CCOC(=O)c1c(OCC2CC2)c2c(=O)n(CC(=O)c3ccccc3)c(CC)cc2n1C]

In the same manner as in Reference Example 150, the title compound (65 mg, 15%) was obtained as a yellow powder from the compound of Reference Example 40 (382 mg, 1.00 mmol), cesium carbonate (358 mg, 1.10 mmol), cyclopropylmethyl methanesulfonate (750 mg, 5.00 mmol) and DMF (10 mL).

$^1$H-NMR (300 MHz, CDCl$_3$) δ:0.29-0.36 (2H, m), 0.49-0.57 (2H, m), 1.24-1.37 (1H, m), 1.28 (3H, t, J=7.3 Hz), 1.41 (3H, t, J=7.1 Hz), 2.51 (2H, q, J=7.4 Hz), 3.88 (3H, s), 4.10 (2H, d, J=7.2 Hz), 4.37 (2H, q, J=7.1 Hz), 5.59 (2H, s), 6.19 (1H, s), 7.47-7.55 (2H, m), 7.59-7.67 (1H, m), 8.02-8.10 (2H, m).

Reference Example 177

Production of 3-(cyclopropylmethoxy)-6-ethyl-1-methyl-4-oxo-5-(2-oxo-2-phenylethyl)-4,5-dihydro-1H-pyrrolo[3,2-c]pyridine-2-carboxylic acid

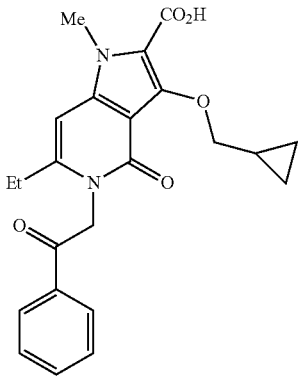

In the same manner as in Reference Example 59, the title compound (112 mg, 83%) was obtained as a colorless powder from the compound of Reference Example 176 (144 mg, 0.33 mmol).

$^1$H-NMR (300 MHz, DMSO-$d_6$) δ:0.17-0.27 (2H, m), 0.39-0.48 (2H, m), 1.03-1.22 (1H, m), 1.18 (3H, t, J=7.3 Hz), 2.56 (2H, q, J=7.3 Hz), 3.84 (3H, s), 3.94 (2H, d, J=7.0 Hz), 5.58 (2H, s), 6.46 (1H, s), 7.56-7.65 (2H, m), 7.69-7.77 (1H, m), 8.07-8.15 (2H, m), 12.43 (1H, br s).

Example 1

Production of 3-methoxy-5-(2-oxo-2-phenylethyl)-2-(piperidin-1-ylcarbonyl)thieno[3,2-c]quinolin-4(5H)-one

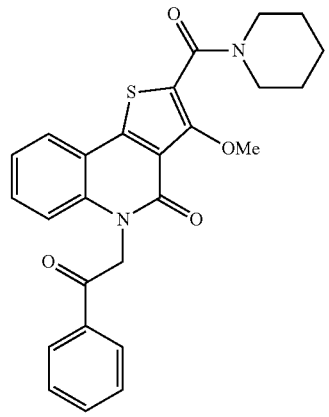 [SMILES: COc1c(C(=O)N2CCCCC2)sc2c1c(=O)n(CC(=O)c1ccccc1)c1ccccc21]

A solution (0.10 M, 0.600 mL, 60 µmol) of the compound of Reference Example 7 in DMF was diluted with DMF (0.200 mL), and a solution (1.0 M, 0.063 mL, 63 µmol) of piperidine in DMF and a solution (0.50 M, 0.126 mL, 63 µmol) of HOBt and WSCD in 1:1 mixture in DMF were added. The obtained mixture was agitated at room temperature for 13 hr. Dichloromethane (2 mL) and saturated aqueous sodium hydrogen carbonate solution (1 mL) were added to the reaction mixture, and the organic layer was filtered through a Teflon (registered trade mark) filter to separate from the aqueous layer, and concentrated under reduced pressure. The residue was purified by preparative HPLC to give the title compound (8.5 mg, 31%).

LC/MS 461 (M+H).

Example 2

Production of N-ethyl-N-(1-{[3-methoxy-4-oxo-5-(2-oxo-2-phenylethyl)-4,5-dihydrothieno[3,2-c]quinolin-2-yl]carbonyl}pyrrolidin-3-yl)acetamide

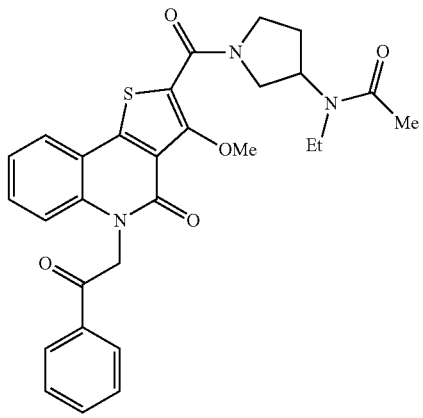 [SMILES: CCN(C(C)=O)C1CCN(C(=O)c2sc3c(c2OC)c(=O)n(CC(=O)c2ccccc2)c2ccccc32)C1]

In the same manner as in Example 1, the title compound was obtained from the compound of Reference Example 7 and N-ethyl-N-pyrrolidin-3-ylacetamide.
LC/MS 532 (M+H).

Example 3

Production of N-[2-(diethylamino)ethyl]-3-methoxy-N-methyl-4-oxo-5-(pyridin-2-ylmethyl)-4,5-dihydrothieno[3,2-c]quinoline-2-carboxamide ditrifluoroacetate

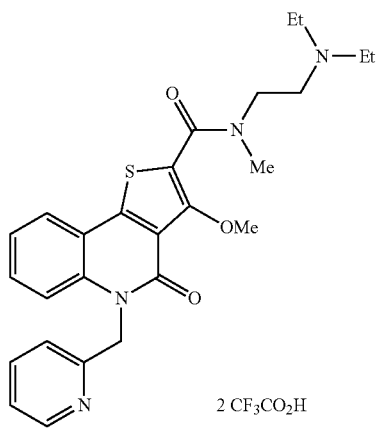 [SMILES: CCN(CC)CCN(C)C(=O)c1sc2c(c1OC)c(=O)n(Cc1ccccn1)c1ccccc21]

To a solution (0.12 M, 0.40 mL, 48 μmol) of the compound of Reference Example 19 in DMF were added a solution (0.66 M, 0.10 mL, 63 μmol) of N,N-diethyl-N'-methylethane-1,2-diamine in DMF and a solution (0.39 M, 0.20 mL, 78 μmol) of HOBt and WSCD in 1:1 mixture in DMF. The obtained mixture was agitated at room temperature for 14 hr. Dichloromethane (2 mL) and saturated aqueous sodium hydrogen carbonate solution (1 mL) were added to the reaction mixture, and the organic layer was filtered through a Teflon (registered trade mark) filter to separate from the aqueous layer, and the filtrate was concentrated under reduced pressure. The residue was purified by preparative HPLC to give the title compound (33.2 mg, 98%).
LC/MS 479 (M+H).

Example 4

Production of 2-{[4-(1,3-benzodioxol-5-ylmethyl)piperazin-1-yl]carbonyl}-3-methoxy-5-(pyridin-2-ylmethyl)thieno[3,2-c]quinolin-4(5H)-one ditrifluoroacetate

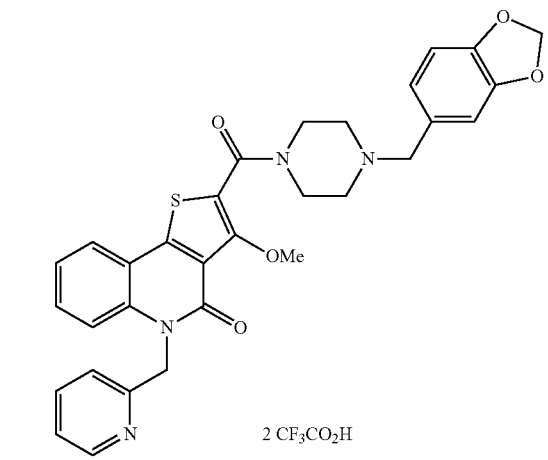 [SMILES: COc1c(C(=O)N2CCN(Cc3ccc4c(c3)OCO4)CC2)sc2c1c(=O)n(Cc1ccccn1)c1ccccc21]

In the same manner as in Example 3, the title compound was obtained from the compound of Reference Example 19 and 1-(1,3-benzodioxol-5-ylmethyl)piperazine.
LC/MS 569 (M+H).

Example 5

Production of N-[2-(dimethylamino)ethyl]-3-methoxy-4-oxo-5-(2-oxo-2-phenylethyl)-4,5-dihydrothieno[3,2-c]quinoline-2-carboxamide trifluoroacetate

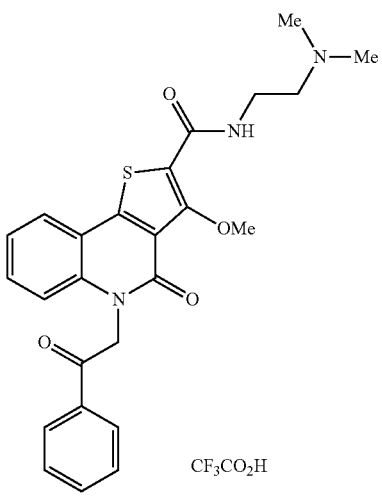 [SMILES: COc1c(C(=O)NCCN(C)C)sc2c1c(=O)n(CC(=O)c1ccccc1)c1ccccc21 ; "CF3CO2H"]

To a solution (0.15 M, 0.40 mL, 60 μmol) of the compound of Reference Example 7 in DMF were added a solution (0.66 M, 0.10 mL, 63 μmol) of N,N-dimethylethane-1,2-diamine in DMF and a solution (0.39 M, 0.20 mL, 78 μmol) of HOBt and WSCD in 1:1 mixture in DMF. The obtained mixture was agitated at room temperature for 14 hr. Dichloromethane (2 mL) and saturated aqueous sodium hydrogen carbonate solution (1 mL) were added to the reaction mixture, and the organic layer was filtered through a Teflon (registered trade mark) filter to separate from the aqueous layer, and the filtrate

Example 6

Production of 3-methoxy-4-oxo-5-(2-oxo-2-phenyl-ethyl)-N-(2-pyrrolidin-1-ylethyl)-4,5-dihydrothieno[3,2-c]quinoline-2-carboxamide trifluoroacetate

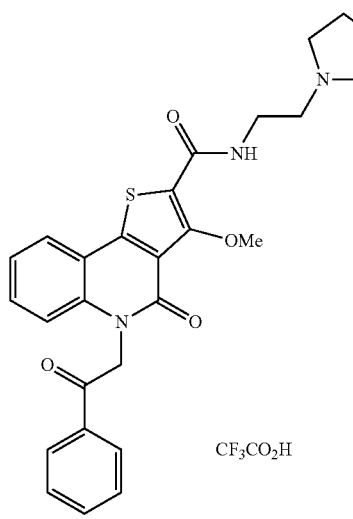

In the same manner as in Example 5, the title compound was obtained from the compound of Reference Example 7 and 2-pyrrolidin-1-ylethanamine.
LC/MS 490 (M+H).

Example 7

Production of N-[3-(1H-imidazol-1-yl)propyl]-3-methoxy-4-oxo-5-(2-oxo-2-phenylethyl)-4,5-dihydrothieno[3,2-c]quinoline-2-carboxamide trifluoroacetate

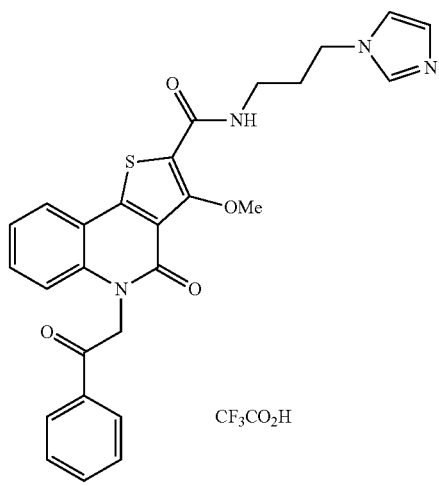 [SMILES: COc1c(C(=O)NCCCn2ccnc2)sc2c1c(=O)n(CC(=O)c1ccccc1)c1ccccc21 ; "CF3CO2H"]

In the same manner as in Example 5, the title compound was obtained from the compound of Reference Example 7 and 3-(1H-imidazol-1-yl)propan-1-amine.
LC/MS 501 (M+H).

Example 8

Production of 3-methoxy-N-[2-(1-methylpyrrolidin-2-yl)ethyl]-4-oxo-5-(2-oxo-2-phenylethyl)-4,5-dihydrothieno[3,2-c]quinoline-2-carboxamide trifluoroacetate

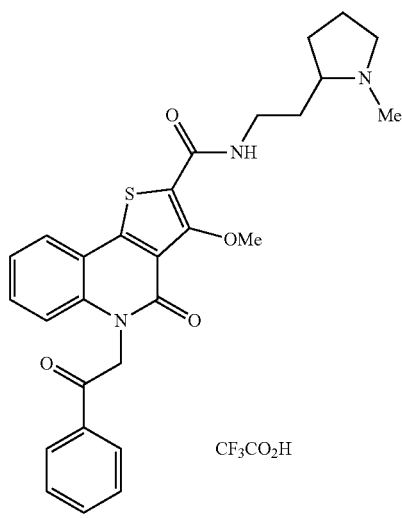 [SMILES: COc1c(C(=O)NCCC2CCCN2C)sc2c1c(=O)n(CC(=O)c1ccccc1)c1ccccc21 ; "CF3CO2H"]

In the same manner as in Example 5, the title compound was obtained from the compound of Reference Example 7 and 2-(1-methylpyrrolidin-2-yl)ethanamine.
LC/MS 504 (M+H).

Example 9

Production of 3-methoxy-4-oxo-5-(2-oxo-2-phenylethyl)-N-(2-piperidin-1-ylethyl)-4,5-dihydrothieno[3,2-c]quinoline-2-carboxamide trifluoroacetate

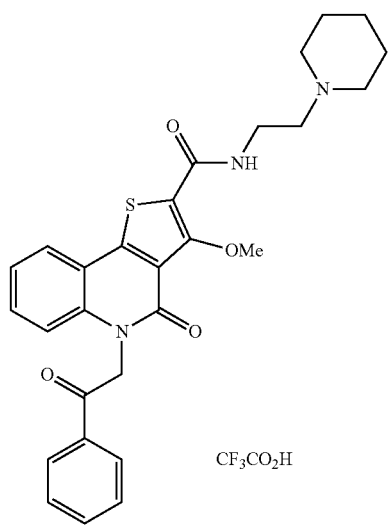 [SMILES: COc1c(C(=O)NCCN2CCCCC2)sc2c1c(=O)n(CC(=O)c1ccccc1)c1ccccc21 ; "CF3CO2H"]

In the same manner as in Example 5, the title compound was obtained from the compound of Reference Example 7 and 2-piperidin-1-ylethanamine.
LC/MS 504 (M+H).

Example 10

Production of N-[3-(diethylamino)propyl]-3-methoxy-4-oxo-5-(2-oxo-2-phenylethyl)-4,5-dihydrothieno[3,2-c]quinoline-2-carboxamide trifluoroacetate

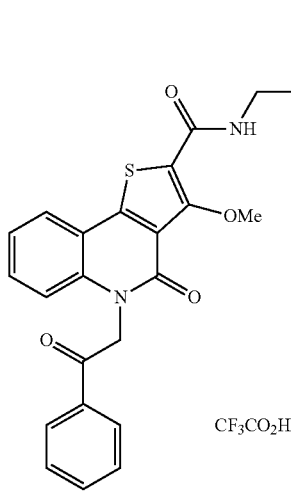

In the same manner as in Example 5, the title compound was obtained from the compound of Reference Example 7 and N,N-diethylpropane-1,3-diamine.

LC/MS 506 (M+H).

Example 11

Production of 3-methoxy-N-(3-morpholin-4-ylpropyl)-4-oxo-5-(2-oxo-2-phenylethyl)-4,5-dihydrothieno[3,2-c]quinoline-2-carboxamide trifluoroacetate

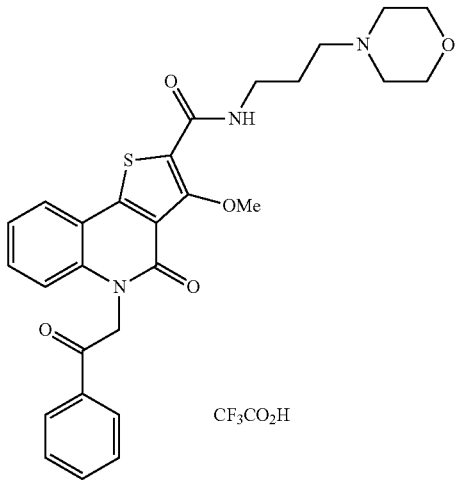 [SMILES: COc1c(C(=O)NCCCN2CCOCC2)sc2c1c(=O)n(CC(=O)c1ccccc1)c1ccccc21 ; "CF3CO2H"]

In the same manner as in Example 5, the title compound was obtained from the compound of Reference Example 7 and 3-morpholin-4-ylpropan-1-amine.

LC/MS 520 (M+H).

Example 12

Production of 3-methoxy-N-[3-(4-methylpiperazin-1-yl)propyl]-4-oxo-5-(2-oxo-2-phenylethyl)-4,5-dihydrothieno[3,2-c]quinoline-2-carboxamide ditrifluoroacetate

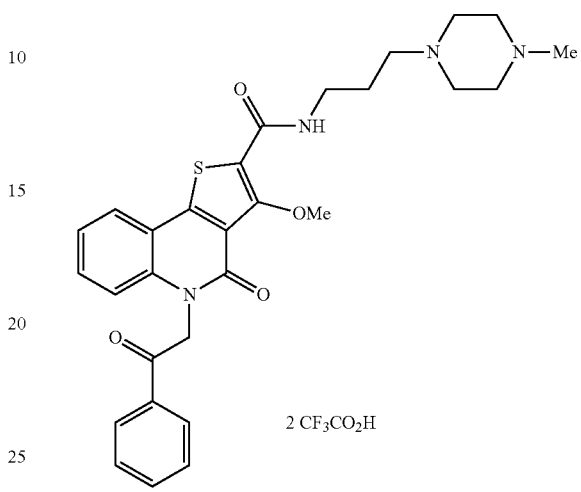

In the same manner as in Example 5, the title compound was obtained from the compound of Reference Example 7 and 3-(4-methylpiperazin-1-yl)propan-1-amine.

LC/MS 533 (M+H).

Example 13

Production of N-[4-(diethylamino)-1-methylbutyl]-3-methoxy-4-oxo-5-(2-oxo-2-phenylethyl)-4,5-dihydrothieno[3,2-c]quinoline-2-carboxamide trifluoroacetate

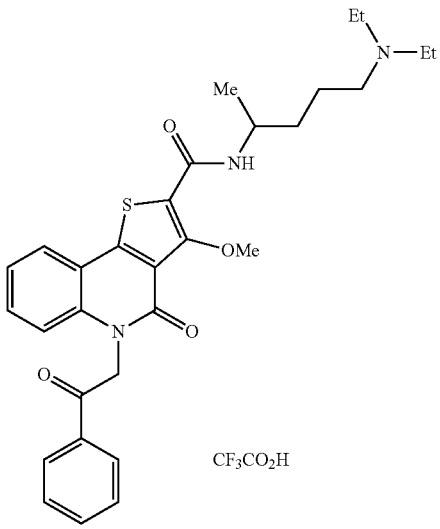 [SMILES: CCN(CC)CCCC(C)NC(=O)c1sc2c(c1OC)c(=O)n(CC(=O)c1ccccc1)c1ccccc21 ; "CF3CO2H"]

In the same manner as in Example 5, the title compound was obtained from the compound of Reference Example 7 and $N^1,N^1$-diethylpentane-1,4-diamine.

LC/MS 534 (M+H).

Example 14

Production of N-(1-benzylpyrrolidin-3-yl)-3-methoxy-4-oxo-5-(2-oxo-2-phenylethyl)-4,5-dihydrothieno[3,2-c]quinoline-2-carboxamide trifluoroacetate

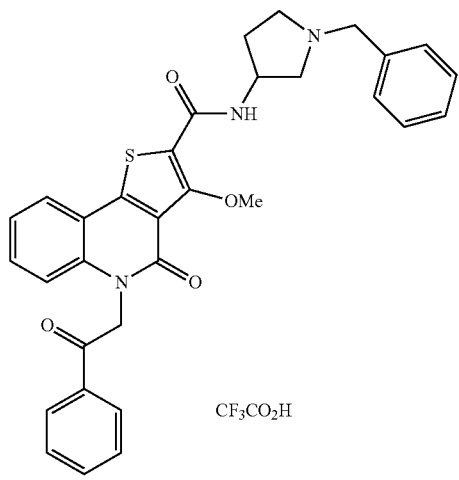 [SMILES: COc1c(C(=O)NC2CCN(Cc3ccccc3)C2)sc2c1c(=O)n(CC(=O)c1ccccc1)c1ccccc21 ; "CF3CO2H"]

In the same manner as in Example 5, the title compound was obtained from the compound of Reference Example 7 and 1-benzylpyrrolidin-3-amine.

LC/MS 552 (M+H).

Example 15

Production of N-(1-benzylpiperidin-4-yl)-3-methoxy-4-oxo-5-(2-oxo-2-phenylethyl)-4,5-dihydrothieno[3,2-c]quinoline-2-carboxamide trifluoroacetate

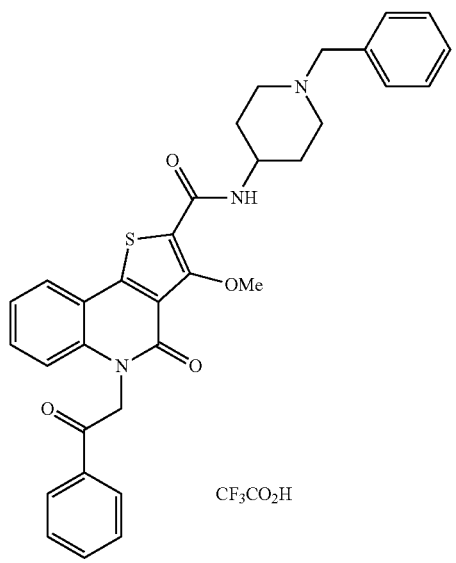 [SMILES: COc1c(C(=O)NC2CCN(Cc3ccccc3)CC2)sc2c1c(=O)n(CC(=O)c1ccccc1)c1ccccc21 ; "CF3CO2H"]

In the same manner as in Example 5, the title compound was obtained from the compound of Reference Example 7 and 1-benzylpiperidin-4-amine.

LC/MS 566 (M+H).

Example 16

Production of 3-methoxy-N-methyl-N-(1-methylpyrrolidin-3-yl)-4-oxo-5-(2-oxo-2-phenylethyl)-4,5-dihydrothieno[3,2-c]quinoline-2-carboxamide trifluoroacetate

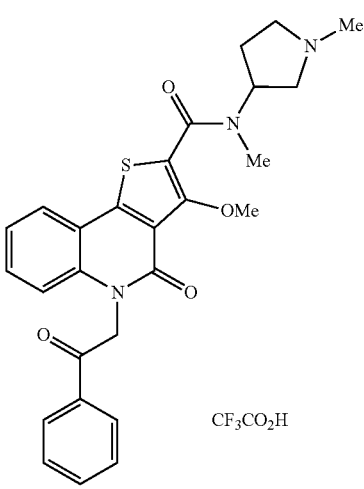 [SMILES: COc1c(C(=O)N(C)C2CCN(C)C2)sc2c1c(=O)n(CC(=O)c1ccccc1)c1ccccc21 ; "CF3CO2H"]

In the same manner as in Example 5, the title compound was obtained from the compound of Reference Example 7 and N,1-dimethylpyrrolidin-3-amine.

LC/MS 490 (M+H).

Example 17

Production of 3-methoxy-2-[(4-methyl-1,4-diazepan-1-yl)carbonyl]-5-(2-oxo-2-phenylethyl)thieno[3,2-c]quinolin-4(5H)-one trifluoroacetate

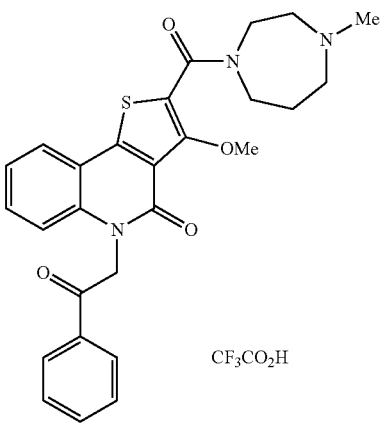 [SMILES: COc1c(C(=O)N2CCCN(C)CC2)sc2c1c(=O)n(CC(=O)c1ccccc1)c1ccccc21 ; "CF3CO2H"]

In the same manner as in Example 5, the title compound was obtained from the compound of Reference Example 7 and 1-methyl-1,4-diazepane.

LC/MS 490 (M+H).

Example 18

Production of 2-[(4-ethylpiperazin-1-yl)carbonyl]-3-methoxy-5-(2-oxo-2-phenylethyl)thieno[3,2-c]quinolin-4(5H)-one trifluoroacetate

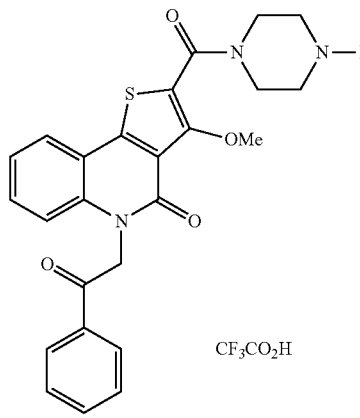

In the same manner as in Example 5, the title compound was obtained from the compound of Reference Example 7 and 1-ethylpiperazine.

LC/MS 490 (M+H).

Example 19

Production of N-[2-(diethylamino)ethyl]-3-methoxy-N-methyl-4-oxo-5-(2-oxo-2-phenylethyl)-4,5-dihydrothieno[3,2-c]quinoline-2-carboxamide trifluoroacetate

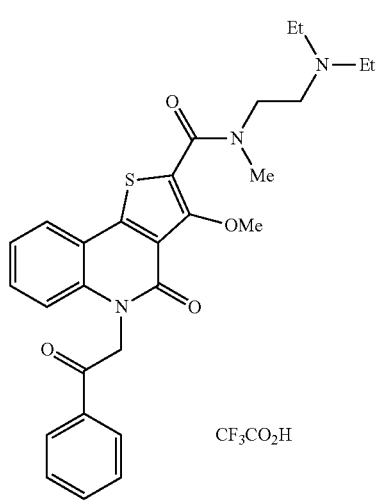 [SMILES: CCN(CC)CCN(C)C(=O)c1sc2c(c1OC)c(=O)n(CC(=O)c1ccccc1)c1ccccc21 ; "CF3CO2H"]

In the same manner as in Example 5, the title compound was obtained from the compound of Reference Example 7 and N,N-diethyl-N'-methylethane-1,2-diamine.

LC/MS 506 (M+H).

Example 20

Production of 3-methoxy-5-(2-oxo-2-phenylethyl)-2-{[(2S)-2-(pyrrolidin-1-ylmethyl)pyrrolidin-1-yl]carbonyl}thieno[3,2-c]quinolin-4(5H)-one trifluoroacetate

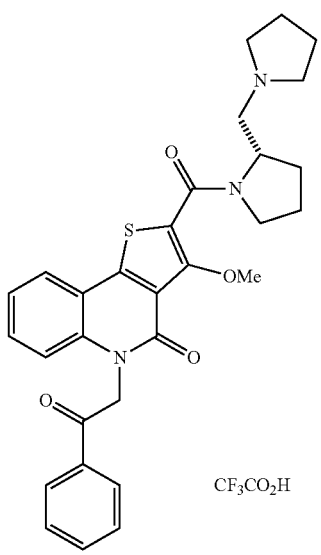 [SMILES: COc1c(C(=O)N2CCC[C@H]2CN2CCCC2)sc2c1c(=O)n(CC(=O)c1ccccc1)c1ccccc21 ; "CF3CO2H"]

In the same manner as in Example 5, the title compound was obtained from the compound of Reference Example 7 and 1-[(2S)-pyrrolidin-2-ylmethyl]pyrrolidine.

LC/MS 530 (M+H).

Example 21

Production of 3-methoxy-5-(2-oxo-2-phenylethyl)-2-[(4-pyrrolidin-1-ylpiperidin-1-yl)carbonyl]thieno[3,2-c]quinolin-4(5H)-one trifluoroacetate

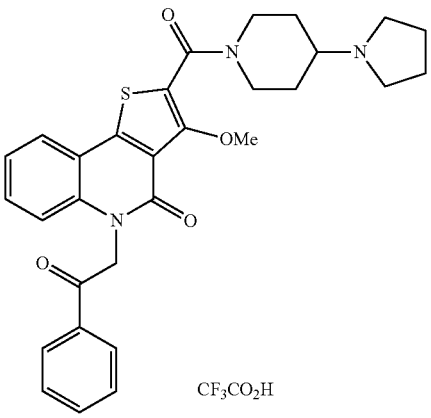 [SMILES: COc1c(C(=O)N2CCC(N3CCCC3)CC2)sc2c1c(=O)n(CC(=O)c1ccccc1)c1ccccc21 ; "CF3CO2H"]

In the same manner as in Example 5, the title compound was obtained from the compound of Reference Example 7 and 4-pyrrolidin-1-ylpiperidine.

LC/MS 530 (M+H).

Example 22

Production of N-(2-cyanoethyl)-3-methoxy-4-oxo-5-(2-oxo-2-phenylethyl)-N-(pyridin-3-ylmethyl)-4,5-dihydrothieno[3,2-c]quinoline-2-carboxamide trifluoroacetate

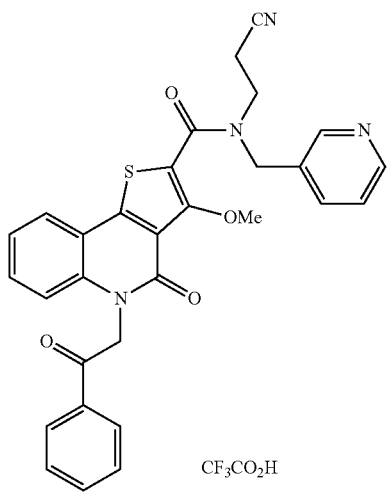 [SMILES: COc1c(C(=O)N(CCC#N)Cc2cccnc2)sc2c1c(=O)n(CC(=O)c1ccccc1)c1ccccc21 ; "CF3CO2H"]

In the same manner as in Example 5, the title compound was obtained from the compound of Reference Example 7 and 3-[(pyridin-3-ylmethyl)amino]propanenitrile.
LC/MS 537 (M+H).

Example 23

Production of 2-{[4-(1,3-benzodioxol-5-ylmethyl)piperazin-1-yl]carbonyl}-3-methoxy-5-(2-oxo-2-phenylethyl)thieno[3,2-c]quinolin-4(5H)-one trifluoroacetate

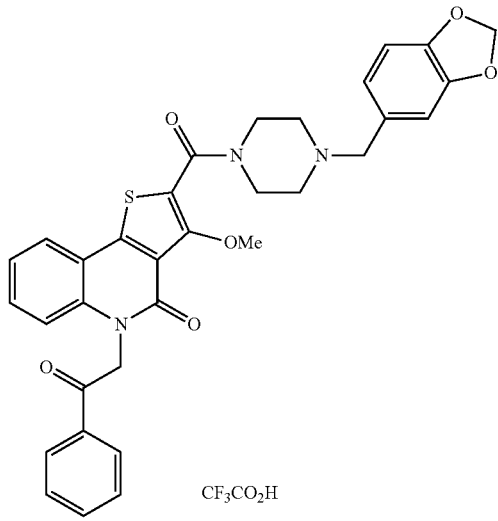 [SMILES: COc1c(C(=O)N2CCN(Cc3ccc4c(c3)OCO4)CC2)sc2c1c(=O)n(CC(=O)c1ccccc1)c1ccccc21 ; "CF3CO2H"]

In the same manner as in Example 5, the title compound was obtained from the compound of Reference Example 7 and 1-(1,3-benzodioxol-5-ylmethyl)piperazine.
LC/MS 596 (M+H).

Example 24

Production of N-[2-(diethylamino)ethyl]-3-(2-ethoxyethoxy)-4-oxo-5-(2-oxo-2-phenylethyl)-4,5-dihydrothieno[3,2-c]quinoline-2-carboxamide trifluoroacetate

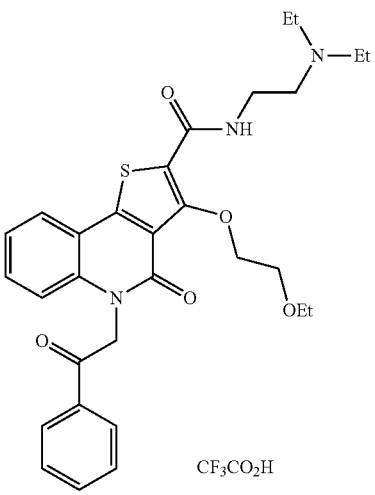 [SMILES: CCOCCOc1c(C(=O)NCCN(CC)CC)sc2c1c(=O)n(CC(=O)c1ccccc1)c1ccccc21 ; "CF3CO2H"]

In the same manner as in Example 5, the title compound was obtained from the compound of Reference Example 21 and N,N-diethylethane-1,2-diamine.
LC/MS 550 (M+H).

Example 25

Production of N,N-diethyl-3-methoxy-4-oxo-5-(2-oxo-2-phenylethyl)-4,5-dihydrothieno[3,2-c]quinoline-2-carboxamide

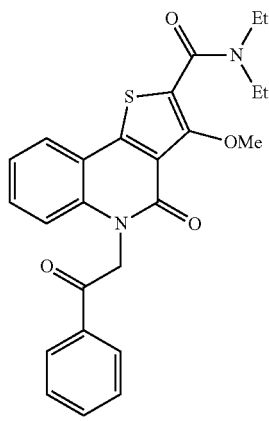 [SMILES: CCN(CC)C(=O)c1sc2c(c1OC)c(=O)n(CC(=O)c1ccccc1)c1ccccc21]

To a solution of the compound of Reference Example 7 (130 mg, 0.33 mmol), diethylamine (36 mg, 0.49 mmol) and HOBt (67 mg, 0.49 mmol) in DMF (4 mL) was added WSCD (94 mg, 0.49 mmol) under ice-cooling, and the mixture was stirred at room temperature for 18 hr. The reaction mixture was diluted with saturated aqueous sodium hydrogen carbonate solution, and extracted twice with ethyl acetate. The extract was combined, washed with saturated brine, dried over magnesium sulfate, and concentrated under reduced pressure. The residue was purified by silica gel chromatography (eluate; ethyl acetate), and the obtained oil was recrystallized from ethyl acetate-diethyl ether to give the title compound (104 mg, 70%) as white crystals.

$^1$H-NMR (300 MHz, DMSO-d$_6$) δ:1.15 (6H, t, J=7.1 Hz), 3.39-3.50 (4H, m), 3.87 (3H, s), 5.98 (2H, s), 7.33 (1H, t, J=7.5 Hz), 7.48 (1H, d, J=7.8 Hz), 7.56 (1H, td, J=8.7, 1.2 Hz), 7.64 (2H, t, J=7.5 Hz), 7.75 (1H, d, J=7.5 Hz), 7.96 (1H, dd, J=7.8, 1.2 Hz), 8.18 (2H, d, J=7.5 Hz).

Example 26

Production of 3-methoxy-4-oxo-5-(2-oxo-2-phenyl-ethyl)-N-phenyl-4,5-dihydrothieno[3,2-c]quinoline-2-carboxamide

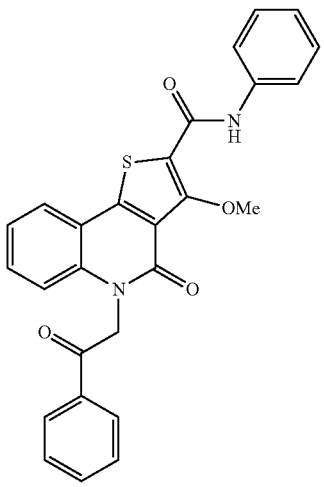 [SMILES: COc1c(C(=O)Nc2ccccc2)sc2c1c(=O)n(CC(=O)c1ccccc1)c1ccccc21]

In the same manner as in Example 25, the title compound (163 mg, 63%) was obtained as pale-orange crystals from the compound of Reference Example 7 (200 mg, 0.51 mmol) and aniline (48 μL, 0.51 mmol).

$^1$H-NMR (300 MHz, DMSO-d$_6$) δ:4.15 (3H, s), 6.02 (2H, s), 7.12-7.21 (1H, m), 7.32-7.44 (3H, m), 7.48-7.55 (1H, m), 7.56-7.70 (3H, m), 7.71-7.82 (3H, m), 8.09 (1H, dd, J=7.9, 1.3 Hz), 8.14-8.24 (2H, m), 9.74 (1H, s).

Example 27

Production of 3-methoxy-N-methyl-4-oxo-5-(2-oxo-2-phenylethyl)-N-(2-oxo-2-pyrrolidin-1-ylethyl)-4,5-dihydrothieno[3,2-c]quinoline-2-carboxamide

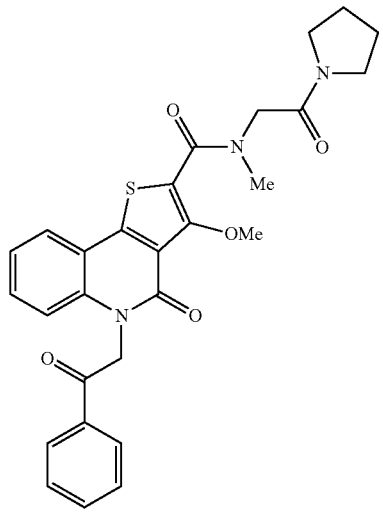 [SMILES: COc1c(C(=O)N(C)CC(=O)N2CCCC2)sc2c1c(=O)n(CC(=O)c1ccccc1)c1ccccc21]

A mixed solution of the compound of Example 120 (400 mg, 0.81 mmol) and a 2N aqueous sodium hydroxide solution (10 mL) in THF (10 mL)-ethanol (5 mL) was stirred at room temperature for 2 hr. The reaction mixture was neutralized with 2N hydrochloric acid (10 mL), and concentrated under reduced pressure. The residue was partitioned between saturated brine and ethyl acetate, and the aqueous phase was extracted with ethyl acetate. The organic phase was combined, dried over magnesium sulfate, and concentrated under reduced pressure to give N-{[3-methoxy-4-oxo-5-(2-oxo-2-phenylethyl)-4,5-dihydrothieno[3,2-c]quinolin-2-yl]carbonyl}-N-methylglycine (380 mg, 100%) as a white solid.

The title compound (84 mg, 40%) was obtained as white crystals from the thus-obtained N-{[3-methoxy-4-oxo-5-(2-oxo-2-phenylethyl)-4,5-dihydrothieno[3,2-c]quinolin-2-yl]carbonyl}-N-methylglycine (190 mg, 0.41 mmol) and pyrrolidine (44 mg, 0.61 mmol) by a method similar to that in Example 25.

$^1$H-NMR (300 MHz, CDCl$_3$) δ:1.75-2.05 (4H, m), 3.20 (1H, s), 3.27 (2H, s), 3.45-3.56 (4H, m), 4.01 (1H, s), 4.13 (2H, s), 4.23 (0.6H, br s), 4.29 (1.4H, s), 5.86 (2H, s), 7.03 (1H, d, J=8.4 Hz), 7.23-7.28 (1H, m), 7.45 (1H, t, J=8.0 Hz), 7.55 (2H, t, J=7.5 Hz), 7.67 (1H, t, J=7.2 Hz), 7.82 (1H, dd, J=8.1, 1.2 Hz), 8.10-8.12 (2H, m).

Example 28

Production of 3-methoxy-4-oxo-5-(2-oxo-2-phenylethyl)-N-(2-pyrrolidin-1-ylethyl)-4,5-dihydrothieno[3,2-c]quinoline-2-carboxamide

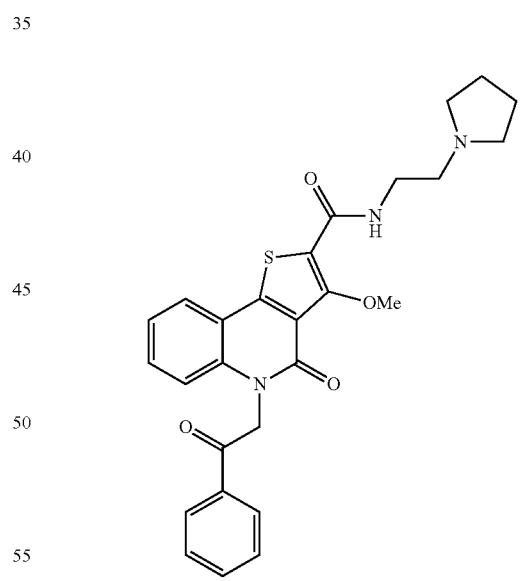

In the same manner as in Example 25, the title compound (1.54 g, 67%) was obtained as white crystals from the compound of Reference Example 7 (1.85 g, 4.69 mmol) and 1-(2-aminoethyl)pyrrolidine (642 mg, 5.63 mmol).

$^1$H-NMR (300 MHz, DMSO-d$_6$) δ:1.72 (4H, br s), 2.45-2.60 (4H, br), 2.64 (2H, t, J=6.3 Hz), 3.44 (2H, t, J=5.9 Hz), 4.01 (3H, s), 6.00 (2H, s), 7.35 (1H, t, J=7.8 Hz), 7.49 (1H, d, J=8.1 Hz), 7.55-7.67 (3H, m), 7.70 (1H, t, J=7.5 Hz), 8.05 (1H, dd, J=8.1, 1.5 Hz), 8.16-8.19 (3H, m).

Example 29

Production of N-[2-(diethylamino)-2-oxoethyl]-3-methoxy-N-methyl-4-oxo-5-(2-oxo-2-phenylethyl)-4,5-dihydrothieno[3,2-c]quinoline-2-carboxamide

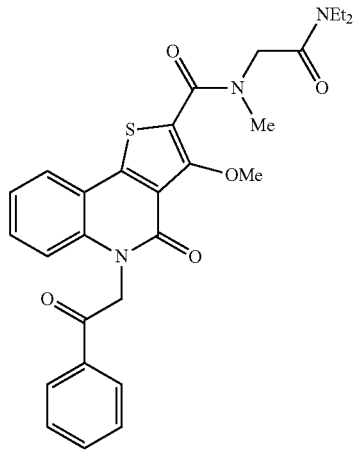

In the same manner as in Example 25, the title compound (124 mg, 58%) was obtained as white crystals from N-{[3-methoxy-4-oxo-5-(2-oxo-2-phenylethyl)-4,5-dihydrothieno[3,2-c]quinolin-2-yl]carbonyl}-N-methylglycine (190 mg, 0.41 mmol) obtained in Example 27 and diethylamine (45 mg, 0.61 mmol).

$^1$H-NMR (300 MHz, CDCl$_3$) δ:1.05-1.31 (6H, m), 3.18 (1.2H, s), 3.26 (1.8H, s), 3.34-3.47 (4H, m), 4.01 (1.2H, s), 4.10 (1.8H, s), 4.30 (0.8H, s), 4.36 (1.2H, s), 5.85 (2H, s), 7.03 (1H, d, J=8.4 Hz), 7.23-7.28 (1H, m), 7.46 (1H, t, J=7.4 Hz), 7.55 (2H, t, J=7.5 Hz), 7.67 (1H, t, J=7.4 Hz), 7.82 (1H, d, J=6.9 Hz), 8.11 (2H, d, J=7.2 Hz).

Example 30

Production of 3-methoxy-4-oxo-5-(2-oxo-2-phenylethyl)-N-(2-pyrrolidin-1-ylethyl)-4,5-dihydrothieno[3,2-c]quinoline-2-carboxamide hydrochloride

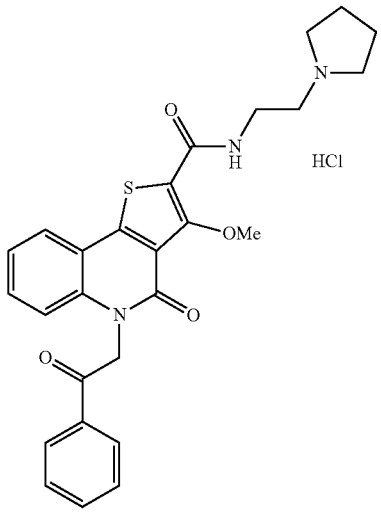 [SMILES: COc1c(C(=O)NCCN2CCCC2)sc2c1c(=O)n(CC(=O)c1ccccc1)c1ccccc21 ; Cl]

To a solution of the compound of Example 28 (200 mg, 0.41 mmol) in ethyl acetate (25 mL) was added 4N hydrogen chloride ethyl acetate solution (0.11 mL). The precipitate was collected by filtration, washed with ethyl acetate, and dried under reduced pressure to give the title compound (162 mg, 75%) as a white powder.

$^1$H-NMR (300 MHz, DMSO-d$_6$) δ:1.77-2.10 (4H, m), 2.95-3.10 (2H, br), 3.29-3.40 (2H, m), 3.55-3.75 (4H, m), 4.07 (3H, s), 6.00 (2H, s), 7.36 (1H, t, J=7.4 Hz), 7.51 (1H, d, J=8.4 Hz), 7.57-7.67 (3H, m), 7.78 (1H, t, J=7.4 Hz), 8.06 (1H, dd, J=7.8, 1.2 Hz), 8.16-8.19 (2H, m), 8.31 (1H, t, J=6.0 Hz), 10.33 (1H, br s).

Example 31

Production of 3-methoxy-4-oxo-5-(2-oxo-2-phenylethyl)-N-(2-pyrrolidin-1-ylethyl)-4,5-dihydrothieno[3,2-c]quinoline-2-carboxamide methanesulfonate

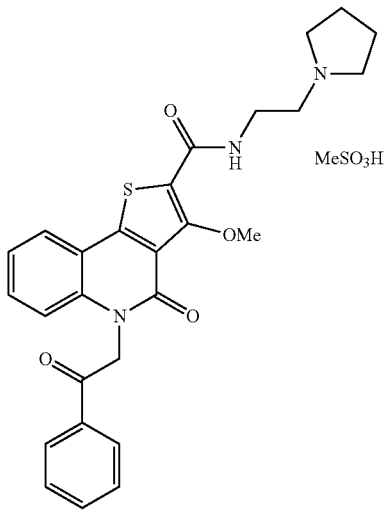 [SMILES: "MeSO3H" ; COc1c(C(=O)NCCN2CCCC2)sc2c1c(=O)n(CC(=O)c1ccccc1)c1ccccc21]

To a solution of the compound of Example 28 (200 mg, 0.41 mmol) in ethyl acetate (25 mL) was added a solution of methanesulfonic acid (39 mg, 0.41 mmol) in ethyl acetate (5 mL). The precipitate was collected by filtration, washed with ethyl acetate, and dried under reduced pressure to give the title compound (197 mg, 82%) as a white powder.

$^1$H-NMR (300 MHz, DMSO-d$_6$) δ:1.65-2.10 (4H, m), 2.30 (3H, s), 3.00-3.20 (2H, br), 3.35-3.45 (2H, br), 3.60-3.75 (4H, m), 4.06 (3H, s), 6.00 (2H, s), 7.36 (1H, t, J=7.2 Hz), 7.51 (1H, d, J=8.4 Hz), 7.57-7.67 (3H, m), 7.78 (1H, t, J=7.5 Hz), 8.06 (1H, dd, J=7.8, 1.2 Hz), 8.16-8.19 (2H, m), 8.29 (1H, t, J=5.9 Hz), 9.30-9.45 (1H, br).

Example 32

Production of N-(2-hydroxyethyl)-3-methoxy-4-oxo-5-(2-oxo-2-phenylethyl)-4,5-dihydrothieno[3,2-c]quinoline-2-carboxamide

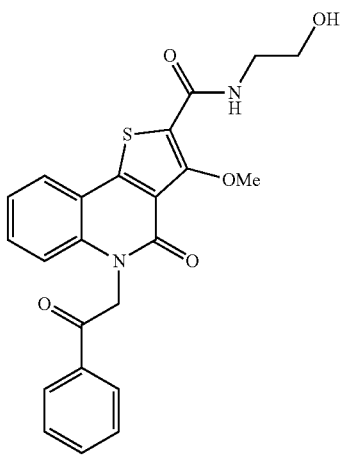 [SMILES: COc1c(C(=O)NCCO)sc2c1c(=O)n(CC(=O)c1ccccc1)c1ccccc21]

In the same manner as in Example 25, the title compound (65.8 mg, 67%) was obtained as a white powder from the compound of Reference Example 7 (89.0 mg, 0.226 mmol) and 2-aminoethanol (16.3 μL, 0.271 mmol).

$^1$H-NMR (300 MHz, DMSO-d$_6$) δ:3.40-3.46 (2H, m), 3.54-3.59 (2H, m), 4.03 (3H, s), 4.87 (1H, t, J=5.3 Hz), 5.99 (2H, s), 7.32-7.38 (1H, m), 7.48-7.67 (4H, m), 7.74-7.79 (1H, m), 8.00-8.06 (2H, m), 8.16-8.19 (2H, m).

Example 33

Production of N-cyclopropyl-3-methoxy-5-methyl-4-oxo-4,5-dihydrothieno[3,2-c]quinoline-2-carboxamide

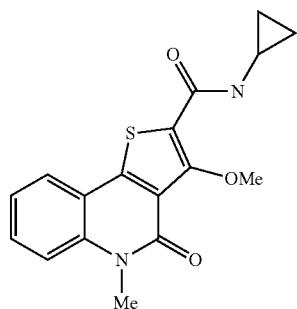 [SMILES: COc1c(C(=O)NC2CC2)sc2c1c(=O)n(C)c1ccccc21]

In the same manner as in Example 1, the title compound was obtained from the compound of Reference Example 84 and cyclopropanamine.

LC/MS 329 (M+H).

Example 34

Production of N-[2-(diethylamino)ethyl]-3-methoxy-4-oxo-5-(2-oxo-2-phenylethyl)-4,5-dihydrothieno[3,2-c]quinoline-2-carboxamide

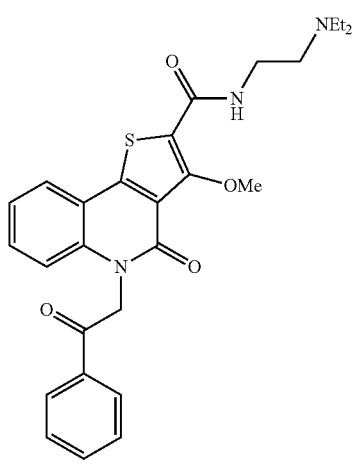

In the same manner as in Example 25, the title compound (500 mg, 80%) was obtained as white crystals from the compound of Reference Example 7 (500 mg, 1.27 mmol) and N,N-diethylethylenediamine (220 mg, 1.90 mmol).

$^1$H-NMR (300 MHz, DMSO-d$_6$) δ:1.00 (6H, t, J=7.1 Hz), 2.50-2.62 (6H, m), 3.37-3.42 (2H, m), 4.03 (3H, s), 6.00 (2H, s), 7.35 (1H, t, J=7.4 Hz), 7.49 (1H, d, J=8.4 Hz), 7.55-7.67 (3H, m), 7.77 (1H, t, J=7.5 Hz), 8.05 (1H, dd, J=7.8, 1.5 Hz), 8.12 (1H, t, J=5.1 Hz), 8.16-8.19 (2H, m).

Example 35

Production of N-benzyl-3-methoxy-5-methyl-4-oxo-4,5-dihydrothieno[3,2-c]quinoline-2-carboxamide

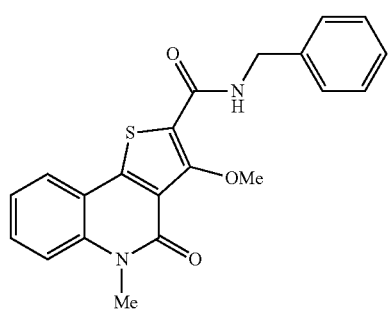 [SMILES: COc1c(C(=O)NCc2ccccc2)sc2c1c(=O)n(C)c1ccccc21]

In the same manner as in Example 1, the title compound was obtained from the compound of Reference Example 84 and 1-phenylmethanamine.

LC/MS 379 (M+H).

Example 36

Production of 3-methoxy-5-methyl-4-oxo-N-(3-phenylpropyl)-4,5-dihydrothieno[3,2-c]quinoline-2-carboxamide

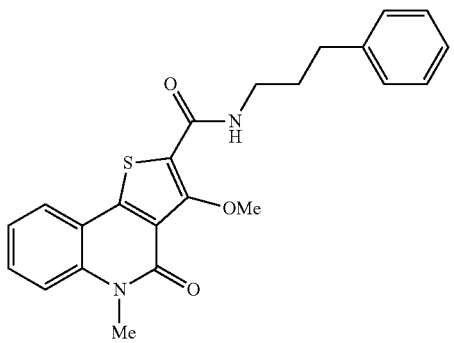 [SMILES: COc1c(C(=O)NCCCc2ccccc2)sc2c1c(=O)n(C)c1ccccc21]

In the same manner as in Example 1, the title compound was obtained from the compound of Reference Example 84 and 3-phenylpropan-1-amine.

LC/MS 407 (M+H).

Example 37

Production of 3-methoxy-N-(2-methoxyethyl)-5-methyl-4-oxo-4,5-dihydrothieno[3,2-c]quinoline-2-carboxamide

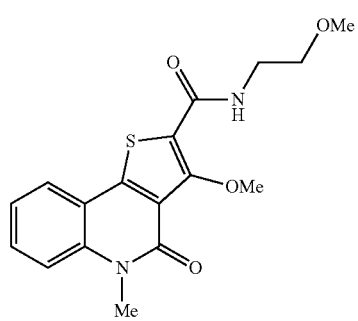 [SMILES: COCCNC(=O)c1sc2c(c1OC)c(=O)n(C)c1ccccc21]

In the same manner as in Example 1, the title compound was obtained from the compound of Reference Example 84 and 2-methoxyethanamine.

LC/MS 347 (M+H).

Example 38

Production of 3-methoxy-5-methyl-4-oxo-N-(tetrahydrofuran-2-ylmethyl)-4,5-dihydrothieno[3,2-c]quinoline-2-carboxamide

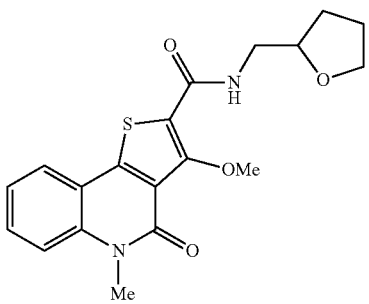 [SMILES: COc1c(C(=O)NCC2CCCO2)sc2c1c(=O)n(C)c1ccccc21]

In the same manner as in Example 1, the title compound was obtained from the compound of Reference Example 84 and 1-(tetrahydrofuran-2-yl)methanamine.

LC/MS 373 (M+H).

Example 39

Production of 3-methoxy-4-oxo-5-(2-oxo-2-phenylethyl)-N-(2-pyrrolidin-1-ylethyl)-4,5-dihydrofuro[3,2-c]quinoline-2-carboxamide

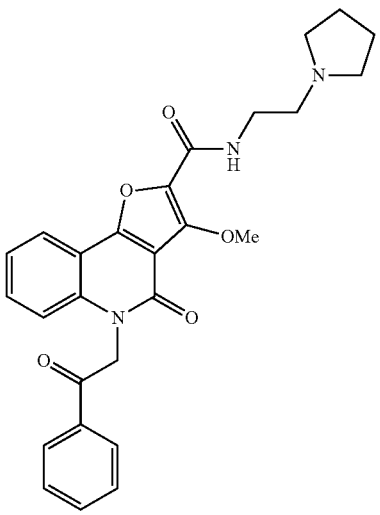 [SMILES: COc1c(C(=O)NCCN2CCCC2)oc2c1c(=O)n(CC(=O)c1ccccc1)c1ccccc21]

In the same manner as in Example 25, the title compound (125 mg, 66%) was obtained as a white powder from the compound of Reference Example 24 (150 mg, 0.397 mmol) and 1-(2-aminoethyl)pyrrolidine (65.4 μL, 0.516 mmol).

$^1$H-NMR (300 MHz, DMSO-$d_6$) δ:1.69-1.73 (4H, m), 2.49-2.51 (4H, m), 2.61 (2H, t, J=6.6 Hz), 3.40-3.46 (2H, m), 4.15 (3H, s), 6.00 (2H, s), 7.43 (1H, t, J=8.1 Hz), 7.54 (1H, d, J=8.4 Hz), 7.60-7.67 (3H, m), 7.74-7.79 (1H, m), 8.06 (1H, t, J=8.6 Hz), 8.15-8.19 (3H, m).

Example 40

Production of 3-methoxy-1-methyl-4-oxo-5-(2-oxo-2-phenylethyl)-N-(2-pyrrolidin-1-ylethyl)-4,5-dihydro-1H-pyrrolo[3,2-c]quinoline-2-carboxamide

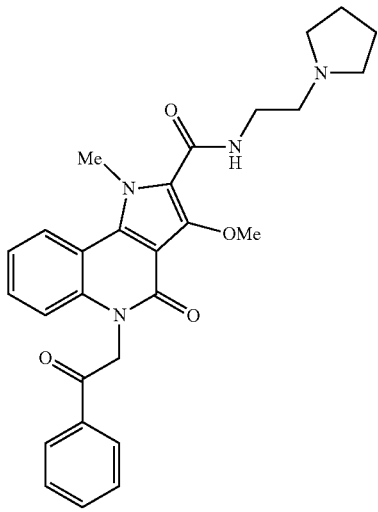

In the same manner as in Example 25, the title compound mg, 78%) was obtained as a white powder from the compound of Reference Example 28 (150 mg, 0.384 mmol) and 1-(2-aminoethyl)pyrrolidine (63.3 μL, 0.499 mmol).

$^1$H-NMR (300 MHz, DMSO-d$_6$) δ:1.65-1.75 (4H, m), 2.48-2.55 (4H, m), 2.62 (2H, t, J=6.2 Hz), 3.39-3.45 (2H, m), 3.97 (3H, s), (3H, s), 5.97 (2H, s), 7.29-7.39 (2H, m), 7.45-7.50 (1H, m), 7.61-7.66 (2H, m), 7.73-7.78 (1H, m), 8.16-8.18 (3H, m), (1H, dd, J=8.1, 1.2 Hz).

Example 41

Production of 5-(cyclopropylmethyl)-N-[2-(diethylamino)ethyl]-3-methoxy-N-methyl-4-oxo-4,5-dihydrothieno[3,2-c]quinoline-2-carboxamide

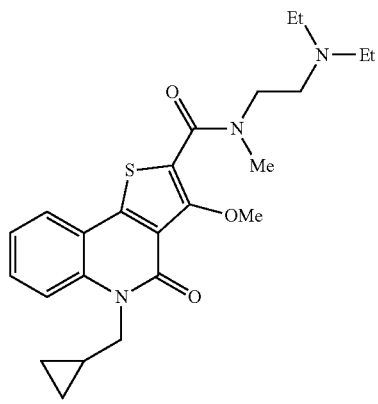 [SMILES: CCN(CC)CCN(C)C(=O)c1sc2c(c1OC)c(=O)n(CC1CC1)c1ccccc21]

To a solution of the compound of Example 121 (400 mg, 1.03 mmol) in DMF (5 mL) was added sodium hydride (60% in oil, 45.4 mg, 1.14 mmol) under ice-cooling, and the mixture was stirred for 15 min. Cyclopropylmethylbromide (120 μL, 1.24 mmol) was added to the obtained mixture under ice-cooling, and the mixture was stirred for 15 hr. The reaction mixture was added to water, and the mixture was extracted with ethyl acetate. The extract was washed with saturated brine, dried over magnesium sulfate, and concentrated under reduced pressure. The residue was purified by aminosilica gel chromatography (eluate; ethyl acetate/hexane=3/7) to give the title compound (320 mg, 70%) as a colorless oil.

$^1$H-NMR (300 MHz, DMSO-d$_6$) δ:0.45-0.50 (4H, m), 0.70-1.05 (6H, br), 1.23-1.31 (1H, m), 2.25-2.70 (6H, br), 3.06 (3H, s), 3.40-3.60 (2H, br), 3.89 (3H, s), 4.27 (2H, d, J=6.9 Hz), 7.30-7.35 (1H, m), 7.62-7.68 (1H, m), 7.76 (1H, d, J=8.4 Hz), 7.91 (1H, dd, J=7.8, 1.2 Hz).

Example 42

Production of N-[2-(diethylamino)ethyl]-3-methoxy-N-methyl-4-oxo-5-(2-oxo-2-phenylethyl)-4,5-dihydrofuro[3,2-c]quinoline-2-carboxamide

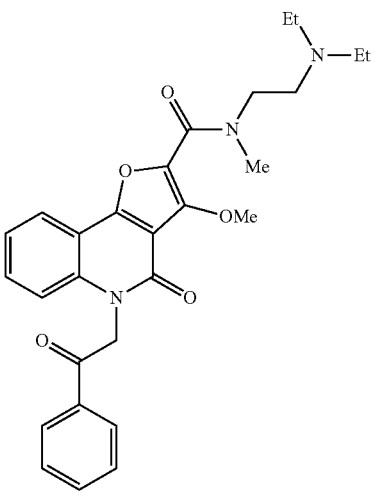 [SMILES: CCN(CC)CCN(C)C(=O)c1oc2c(c1OC)c(=O)n(CC(=O)c1ccccc1)c1ccccc21]

In the same manner as in Example 25, the title compound (130 mg, 80%) was obtained as a colorless oil from the compound of Reference Example 24 (130 mg, 0.344 mmol) and N,N-diethyl-N'-methylethylenediamine (72.3 μL, 0.477 mmol).

$^1$H-NMR (300 MHz, DMSO-d$_6$) δ:0.75-0.90 (3H, br), 0.90-1.05 (3H, br), 2.25-2.40 (2H, br), 2.45-2.70 (4H, br), 2.95-3.30 (3H, br), 3.52 (2H, t, J=6.5 Hz), 4.04 (3H, s), 5.99

(2H, s), 7.37-7.42 (1H, m), 7.52 (1H, d, J=8.7 Hz), 7.57-7.67 (3H, m), 7.74-7.79 (1H, m), 8.04 (1H, d, J=7.5 Hz), 8.16-8.19 (2H, m).

Example 43

Production of 3-ethoxy-4-oxo-5-(2-oxo-2-phenylethyl)-N-(2-pyrrolidin-1-ylethyl)-4,5-dihydrothieno[3,2-c]quinoline-2-carboxamide

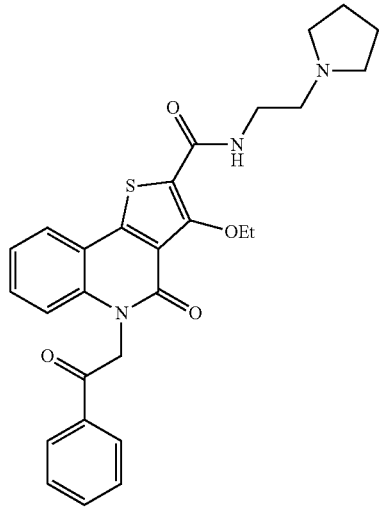 [SMILES: CCOc1c(C(=O)NCCN2CCCC2)sc2c1c(=O)n(CC(=O)c1ccccc1)c1ccccc21]

In the same manner as in Example 25, the title compound (126 mg, 67%) was obtained as white crystals from the compound of Reference Example 9 (150 mg, 0.37 mmol) and 1-(2-aminoethyl)pyrrolidine (63 mg, 0.55 mmol).

$^1$H-NMR (300 MHz, DMSO-$d_6$) δ:1.39 (3H, t, J=7.0 Hz), 1.72 (4H, br s), 2.40-2.60 (4H, br), 2.63 (2H, t, J=6.0 Hz), 3.40-3.47 (2H, m), 4.31 (2H, q, J=7.0 Hz), 5.99 (2H, s), 7.35 (1H, t, J=7.8 Hz), 7.48 (1H, d, J=8.4 Hz), 7.56 (1H, dd, J=7.2, 1.5 Hz), 7.64 (2H, t, J=8.4 Hz), 7.77 (1H, t, J=7.2 Hz), 8.05 (1H, dd, J=8.1, 1.5 Hz), 8.10 (1H, br t), 8.16-8.19 (2H, m).

Example 44

Production of N-[2-(diethylamino)ethyl]-N-ethyl-3-methoxy-4-oxo-5-(2-oxo-2-phenylethyl)-4,5-dihydrothieno[3,2-c]quinoline-2-carboxamide

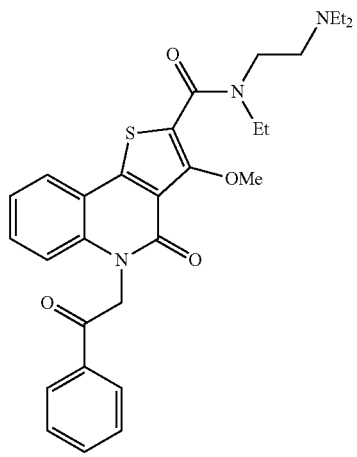

In the same manner as in Example 25, the title compound (150 mg, 56%) was obtained as white crystals from the compound of Reference Example 7 (200 mg, 0.51 mmol) and N,N,N'-triethylethylenediamine (110 mg, 0.76 mmol).

$^1$H-NMR (300 MHz, DMSO-$d_6$) δ:0.70-1.10 (6H, br), 1.14 (3H, br t), 2.20-2.70 (6H, br), 3.40-3.60 (4H, br), 3.87 (3H, s), 5.98 (2H, s), 7.33 (1H, t, J=7.5 Hz), 7.47 (1H, d, J=8.1 Hz), 7.55 (1H, td, J=7.8, 1.5 Hz), 7.64 (2H, t, J=7.5 Hz), 7.77 (1H, t, J=7.5 Hz), 7.95 (1H, dd, J=7.8, 1.5 Hz), 8.16-8.19 (2H, m).

Example 45

Production of N-[2-(diethylamino)ethyl]-3-ethoxy-N-methyl-4-oxo-5-(2-oxo-2-phenylethyl)-4,5-dihydrothieno[3,2-c]quinoline-2-carboxamide hydrochloride

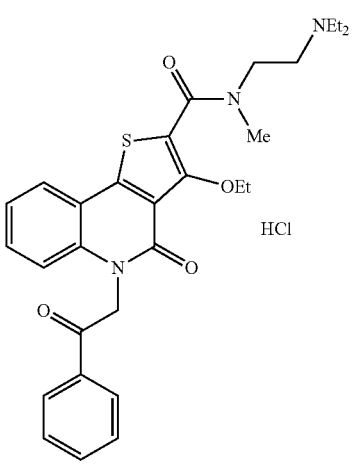

To a solution of the compound of Reference Example 9 (150 mg, 0.37 mmol), N,N-diethyl-N'-methylethylenediamine (72 mg, 0.55 mmol) and HOBt (74 mg, 0.55 mmol) in DMF (5 mL) was added WSCD (105 mg, 0.55 mmol) under ice-cooling, and the mixture was stirred at room temperature for 18 hr. The reaction mixture was diluted with saturated aqueous sodium hydrogen carbonate solution, and extracted twice with ethyl acetate. The extract was combined, washed with saturated brine, dried over magnesium sulfate, and concentrated under reduced pressure. The residue was purified by silica gel chromatography (eluate; ethyl acetate/hexane=1/1) to give a white non-crystalline solid (180 mg).

To a solution of the white non-crystalline solid (180 mg) in ethyl acetate (5 mL) was added 4N hydrogen chloride ethyl acetate solution (0.1 mL). The precipitate was collected by filtration, washed with ethyl acetate, and dried under reduced pressure to give the title compound (173 mg, 83%) as a white powder.

$^1$H-NMR (300 MHz, DMSO-$d_6$) δ:1.15-1.35 (9H, m), 3.12-3.40 (9H, br), 3.84 (2H, t, J=7.2 Hz), 4.14 (2H, q, J=7.0 Hz), 5.99 (2H, s), 7.35 (1H, t, J=7.5 Hz), 7.49 (1H, d, J=8.1 Hz), 7.55-7.67 (3H, m), 7.75-7.80 (1H, m), 7.98 (1H, dd, J=8.1, 1.5 Hz), 8.16-8.19 (2H, m), 9.85-10.10 (1H, br).

Example 46

Production of N-[2-(diethylamino)ethyl]-3-methoxy-N-(1-methylethyl)-4-oxo-5-(2-oxo-2-phenylethyl)-4,5-dihydrothieno[3,2-c]quinoline-2-carboxamide hydrochloride

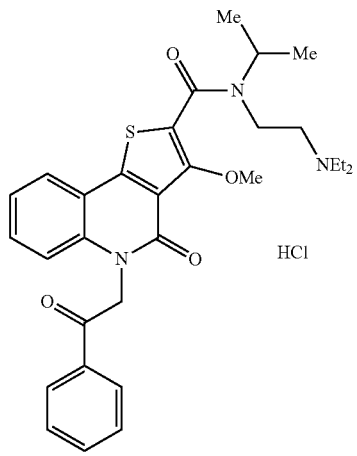

In the same manner as in Example 45, the title compound mg, 56%) was obtained as a white powder from the compound of Reference Example 7 (200 mg, 0.51 mmol) and N,N-diethyl-N'-isopropylethylenediamine (120 mg, 0.76 mmol).

$^1$H-NMR (300 MHz, DMSO-$d_6$) δ:1.20-1.35 (12H, m), 3.15-3.40 (6H, br), 3.65-3.80 (2H, m), 3.89 (3H, s), 4.10-4.30 (1H, br), 5.99 (2H, s), 7.33 (1H, t, J=7.5 Hz), 7.49-7.67 (4H, m), 7.77 (1H, t, J=7.5 Hz), 7.97 (1H, dd, J=7.2, 1.2 Hz), 8.16-8.19 (2H, m), 9.95-10.10 (1H, br).

Example 47

Production of N-(1-ethylpropyl)-3-methoxy-5-methyl-4-oxo-4,5-dihydrothieno[3,2-c]quinoline-2-carboxamide

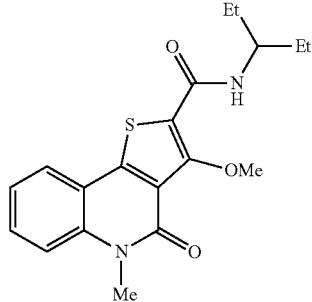 [SMILES: CCC(CC)NC(=O)c1sc2c(c1OC)c(=O)n(C)c1ccccc21]

In the same manner as in Example 1, the title compound was obtained from the compound of Reference Example 84 and pentan-3-amine.

LC/MS 359 (M+H).

Example 48

Production of N-[2-(diethylamino)ethyl]-3-methoxy-5-(4-methoxybenzyl)-N-methyl-4-oxo-4,5-dihydrothieno[3,2-c] quinoline-2-carboxamide hydrochloride

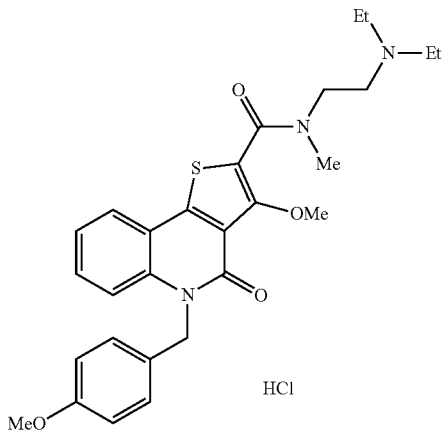 [SMILES: CCN(CC)CCN(C)C(=O)c1sc2c(c1OC)c(=O)n(Cc1ccc(OC)cc1)c1ccccc21 ; Cl]

In the same manner as in Example 25, N-[2-(diethylamino)ethyl]-3-methoxy-5-(4-methoxybenzyl)-N-methyl-4-oxo-4,5-dihydrothieno[3,2-c]quinoline-2-carboxamide (4.90 g, 85%) was obtained as a colorless oil from the compound of Reference Example 13 (4.50 g, 11.4 mmol) and N,N-diethyl-N'-methylethylenediamine (2.40 mL, 14.8 mmol).

The title compound (490 mg, 91%) was obtained as a white powder from the thus-obtained N-[2-(diethylamino)ethyl]-3-methoxy-5-(4-methoxybenzyl)-N-methyl-4-oxo-4,5-dihydrothieno[3,2-c]quinoline-2-carboxamide (500 mg, 0.985 mmol) by a method similar to that in Example 30.

$^1$H-NMR (300 MHz, DMSO-$d_6$) δ:1.15-1.35 (6H, br), 3.13 (3H, s), 3.10-3.40 (6H, br), 3.70 (3H, s), 3.87 (2H, t, J=6.6 Hz), 3.96 (3H, s), 5.52 (2H, s), 6.87 (2H, d, J=8.6 Hz), 7.20 (2H, d, J=8.6 Hz), 7.30 (1H, t, J=7.2 Hz), 7.49-7.58 (2H, m), 7.92 (1H, d, J=7.8 Hz), 10.55 (1H, s).

Example 49

Production of N-[2-(diethylamino)ethyl]-3-methoxy-N-methyl-4-oxo-5-(2-phenylethyl)-4,5-dihydrothieno[3,2-c]quinoline-2-carboxamide

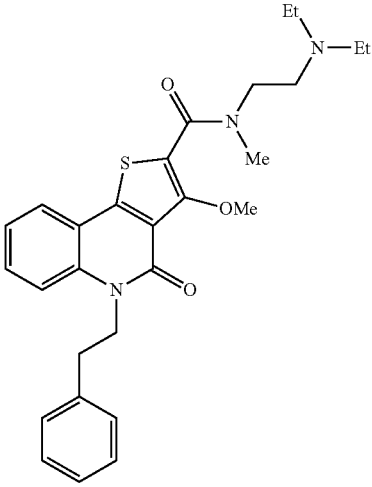 [SMILES: CCN(CC)CCN(C)C(=O)c1sc2c(c1OC)c(=O)n(CCc1ccccc1)c1ccccc21]

In the same manner as in Example 41, the title compound (45.1 mg, 28%) was obtained as a colorless oil from the compound of Example 121 (125 mg, 0.323 mmol) and (2-bromoethyl)benzene (53.5 μL, 0.387 mmol).

$^1$H-NMR (300 MHz, DMSO-d$_6$) δ:0.75-1.05 (6H, br), 2.25-2.70 (6H, br), 2.92-2.97 (2H, m), 3.05 (3H, s), 3.40-3.55 (2H, br), 3.88 (3H, s), 4.50 (2H, t, J=6.5 Hz), 7.20-7.26 (1H, m), 7.30-7.36 (5H, m), 7.63-7.75 (2H, m), 7.92 (1H, dd, J=7.8, 1.5 Hz).

Example 50

Production of N-[2-(diethylamino)ethyl]-5-(3,3-dimethyl-2-oxobutyl)-3-methoxy-N-methyl-4-oxo-4,5-dihydrothieno[3,2-c]quinoline-2-carboxamide

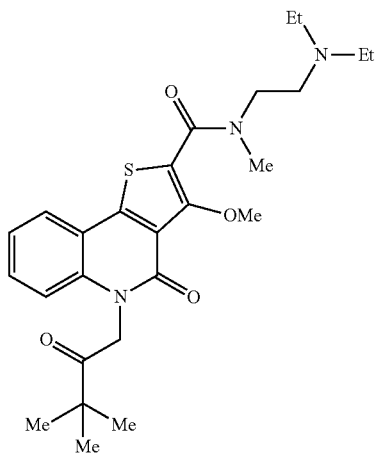 [SMILES: CCN(CC)CCN(C)C(=O)c1sc2c(c1OC)c(=O)n(CC(=O)C(C)(C)C)c1ccccc21]

In the same manner as in Example 41, the title compound (45.1 mg, 28%) was obtained as a colorless oil from the compound of Example 121 (125 mg, 0.323 mmol) and 1-bromo-3,3-dimethylbutan-2-one (57.9 μL, 0.441 mmol).

$^1$H-NMR (300 MHz, DMSO-d$_6$) δ:0.70-1.10 (6H, br), 1.30 (9H, s), 2.20-2.40 (6H, br), 3.06 (3H, s), 3.40-3.60 (2H, br), 3.87 (3H, s), 5.47 (2H, s), 7.28-7.34 (2H, m), 7.55-7.61 (1H, m), 7.92 (1H, dd, J=7.8, 1.2 Hz).

Example 51

Production of N-[2-(diethylamino)ethyl]-3-methoxy-N-methyl-4-oxo-5-(2-phenoxyethyl)-4,5-dihydrothieno[3,2-c]quinoline-2-carboxamide

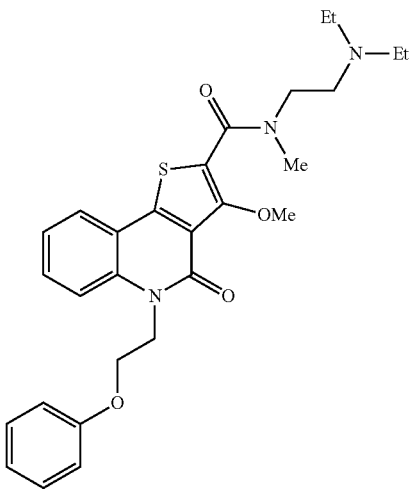 [SMILES: CCN(CC)CCN(C)C(=O)c1sc2c(c1OC)c(=O)n(CCOc1ccccc1)c1ccccc21]

In the same manner as in Example 41, the title compound (75.1 mg, 43%) was obtained as a colorless oil from the compound of Example 121 (135 mg, 0.348 mmol) and (2-bromoethoxy)benzene (105 mg, 0.522 mmol).

$^1$H-NMR (300 MHz, DMSO-d$_6$) δ:0.70-1.10 (6H, br), 2.20-2.70 (6H, br), 3.05 (3H, s), 3.40-3.60 (2H, br), 3.91 (3H, s), 4.30 (2H, t, J=5.9 Hz), 4.73 (2H, t, J=5.9 Hz), 6.88-6.93 (3H, m), 7.22-7.36 (3H, m), 7.65 (1H, t, J=8.0 Hz), 7.83 (1H, d, J=8.7 Hz), 7.91 (1H, d, J=7.8 Hz).

Example 52

Production of N-[2-(diethylamino)ethyl]-3-methoxy-N-methyl-4-oxo-5-[2-oxo-2-(phenylamino)ethyl]-4,5-dihydrothieno[3,2-c]quinoline-2-carboxamide hydrochloride

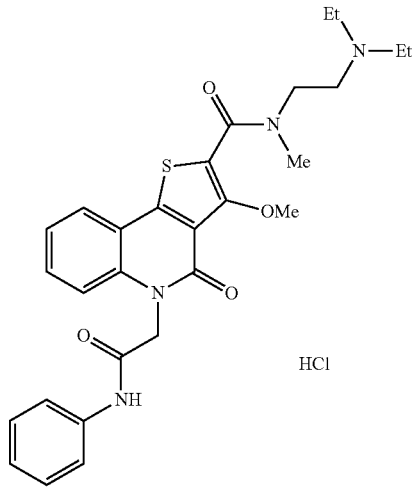 [SMILES: CCN(CC)CCN(C)C(=O)c1sc2c(c1OC)c(=O)n(CC(=O)Nc1ccccc1)c1ccccc21 ; Cl]

To a solution of the compound of Example 122 (150 mg, 0.336 mmol), aniline (39.8 mg, 0.437 mmol) and HOBt (68.2 mg, 0.505 mmol) in DMF (3 mL) was added WSCD (96.8 mg, 0.505 mmol) under ice-cooling, and the mixture was stirred at room temperature for 15 hr. The reaction mixture was diluted with saturated aqueous sodium hydrogen carbonate solution, and extracted twice with ethyl acetate. The extract was combined, washed with saturated brine, dried over magnesium sulfate, and concentrated under reduced pressure. The residue was purified by aminosilica gel chromatography (eluate; ethyl acetate/hexane=1/1) to give N-[2-(diethylamino)ethyl]-3-methoxy-N-methyl-4-oxo-5-[2-oxo-2-(phenylamino) ethyl]-4,5-dihydrothieno[3,2-c]quinoline-2-carboxamide as a colorless oil.

The title compound (65.2 mg, 35%) was obtained as a white powder from the thus-obtained N-[2-(diethylamino) ethyl]-3-methoxy-N-methyl-4-oxo-5-[2-oxo-2-(phenylamino)ethyl]-4,5-dihydrothieno[3,2-c]quinoline-2-carboxamide by a method similar to that in Example 30.

$^1$H-NMR (300 MHz, DMSO-d$_6$) δ:1.10-1.35 (6H, br), 3.12 (3H, s), 3.15-3.40 (6H, br), 3.75-3.90 (2H, br), 3.92 (3H, s), 5.22 (2H, s), 7.07 (1H, t, J=7.5 Hz), 7.29-7.38 (3H, m), 7.53-7.66 (4H, m), 7.96 (1H, dd, J=7.5, 1.4 Hz), 9.76 (1H, s), 10.51 (1H, s).

Example 53

Production of ethyl[2-{[2-(diethylamino)ethyl](methyl)carbamoyl}-3-methoxy-4-oxothieno[3,2-c]quinolin-5(4H)-yl]acetate

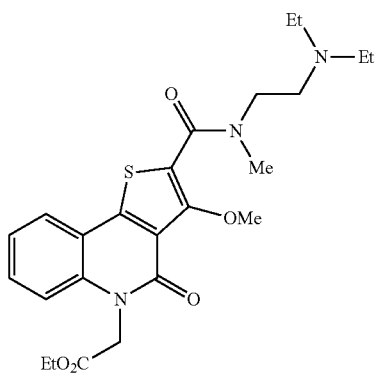

In the same manner as in Example 41, the title compound (680 mg, 83%) was obtained as a colorless oil from the compound of Example 121 (670 mg, 1.73 mmol) and ethyl bromoacetate (229 μL, 2.08 mmol).

$^1$H-NMR (300 MHz, DMSO-d$_6$) δ:0.70-1.10 (6H, br), 1.23 (3H, t, J=7.1 Hz), 2.25-2.70 (6H, m), 3.06 (3H, s), 3.40-3.60 (2H, br), 3.89 (3H, s), 4.18 (2H, q, J=7.1 Hz), 5.16 (2H, s), 7.34 (1H, t, J=7.7 Hz), 7.51 (1H, d, J=8.1 Hz), 7.61 (1H, t, J=8.1 Hz), 7.94 (1H, d, J=7.7 Hz).

Example 54

Production of 3-methoxy-5-methyl-4-oxo-N-prop-2-yn-1-yl-4,5-dihydrothieno[3,2-c]quinoline-2-carboxamide

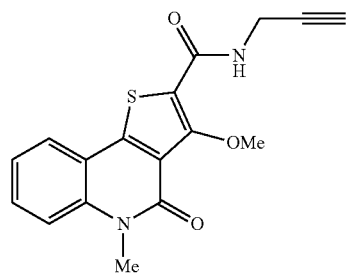 [SMILES: C#CCNC(=O)c1sc2c(c1OC)c(=O)n(C)c1ccccc21]

In the same manner as in Example 1, the title compound was obtained from the compound of Reference Example 84 and prop-2-yn-1-amine.

LC/MS 327 (M+H).

Example 55

Production of N-[2-(dimethylamino)ethyl]-3-methoxy-1-methyl-4-oxo-5-(2-oxo-2-phenylethyl)-4,5-dihydro-1H-pyrrolo[3,2-c]quinoline-2-carboxamide

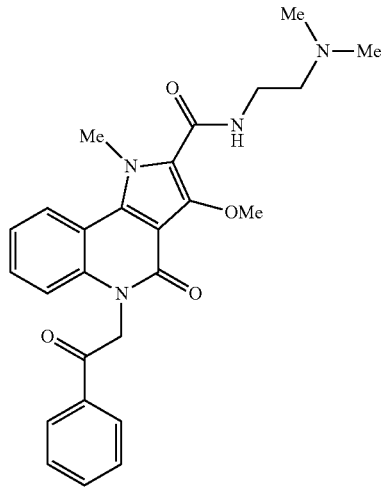 [SMILES: COc1c(C(=O)NCCN(C)C)n(C)c2c1c(=O)n(CC(=O)c1ccccc1)c1ccccc21]

In the same manner as in Example 25, the title compound (65.0 mg, 61%) was obtained as a white powder from the compound of Reference Example 28 (90.0 mg, 0.231 mmol) and N,N-dimethylethylenediamine (25.2 μL, 0.300 mmol).

$^1$H-NMR (300 MHz, DMSO-d$_6$) δ:2.22 (6H, s), 2.44 (2H, t, J=6.2 Hz), 3.37-3.43 (2H, m), 3.98 (3H, s), 4.38 (3H, s), 5.97 (2H, s), 7.29-7.39 (2H, m), 7.45-7.51 (1H, m), 7.63 (2H, t, J=7.7 Hz), 7.73-7.79 (1H, m), 8.11-8.19 (3H, m), 8.38 (1H, dd, J=8.4, 1.2 Hz).

Example 56

Production of N-[2-(diethylamino)ethyl]-3-methoxy-N,1-dimethyl-4-oxo-5-(2-oxo-2-phenylethyl)-4,5-dihydro-1H-pyrrolo[3,2-c]quinoline-2-carboxamide hydrochloride

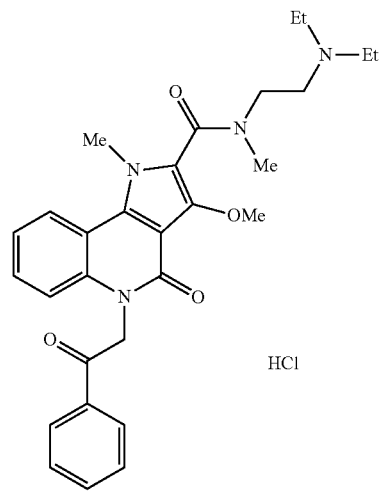 [SMILES: CCN(CC)CCN(C)C(=O)c1c(OC)c2c(=O)n(CC(=O)c3ccccc3)c3ccccc3c2n1C ; Cl]

In the same manner as in Example 25, N-[2-(diethylamino)ethyl]-3-methoxy-N,1-dimethyl-4-oxo-5-(2-oxo-2-phenylethyl)-4,5-dihydro-1H-pyrrolo[3,2-c]quinoline-2-carboxamide was obtained as a colorless oil from the compound of Reference Example 28 (90.0 mg, 0.231 mmol) and N,N-diethyl-N'-methylethylenediamine (48.6 µL, 0.300 mmol).

The title compound (75.1 mg, 60%) was obtained as a white powder from the thus-obtained N-[2-(diethylamino)ethyl]-3-methoxy-N,1-dimethyl-4-oxo-5-(2-oxo-2-phenylethyl)-4,5-dihydro-1H-pyrrolo[3,2-c]quinoline-2-carboxamide by a method similar to that in Example 30.

$^1$H-NMR (300 MHz, DMSO-$d_6$) δ:1.15-1.31 (6H, br), 2.95-3.40 (9H, br), 3.80-3.95 (5H, m), 4.03 (3H, s), 5.98 (2H, s), 7.29-7.50 (3H, m), 7.64 (2H, t, J=7.5 Hz), 7.73-7.79 (1H, m), 8.16-8.19 (2H, m), 8.34 (1H, dd, J=8.3, 1.1 Hz), 9.80-10.15 (1H, br).

Example 57

Production of N-[2-(3,4-dimethoxyphenyl)ethyl]-3-methoxy-5-methyl-4-oxo-4,5-dihydrothieno[3,2-c]quinoline-2-carboxamide

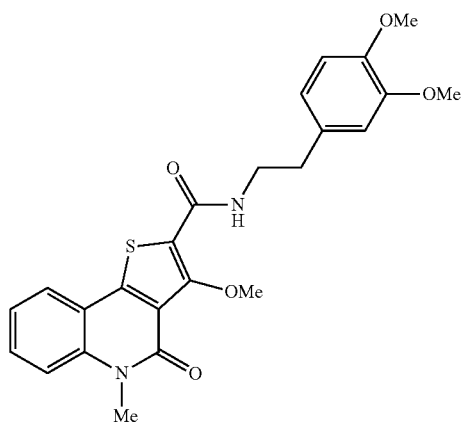 [SMILES: COc1ccc(CCNC(=O)c2sc3c(c2OC)c(=O)n(C)c2ccccc32)cc1OC]

In the same manner as in Example 1, the title compound was obtained from the compound of Reference Example 84 and 2-(3,4-dimethoxyphenyl)ethanamine.
LC/MS 453 (M+H).

Example 58

Production of N-[2-(diethylamino)ethyl]-3-methoxy-4-oxo-5-(2-oxo-2-phenylethyl)-N-(2,2,2-trifluoroethyl)-4,5-dihydrothieno[3,2-c]quinoline-2-carboxamide hydrochloride

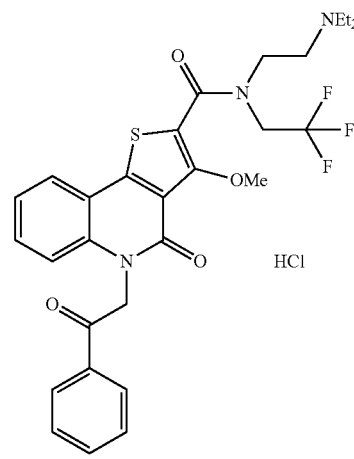

In the same manner as in Example 45, the title compound (12 mg, 7%) was obtained as a white powder from the compound of Reference Example 7 (116 mg, 0.29 mmol) and N,N-diethyl-N'-(2,2,2-trifluoroethyl)ethylenediamine (70 mg, 0.35 mmol).

$^1$H-NMR (300 MHz, CDCl$_3$) δ:0.80-1.10 (6H, br), 2.30-2.70 (6H, br), 3.75 (2H, t, J=5.6 Hz), 4.02 (3H, s), 4.44 (2H, br d, J=7.8 Hz), 5.86 (2H, s), 7.04 (1H, d, J=8.4 Hz), 7.26 (1H, t, J=7.8 Hz), 7.47 (1H, td, J=8.7, 1.5 Hz), 7.56 (2H, t, J=7.5 Hz), 7.65-7.70 (1H, m), 7.83 (1H, dd, J=7.8, 1.5 Hz), 8.11 (2H, d, J=7.2 Hz).

Example 59

Production of 3-methoxy-5-methyl-N-[3-(1-methylethoxy)propyl]-4-oxo-4,5-dihydrothieno[3,2-c]quinoline-2-carboxamide

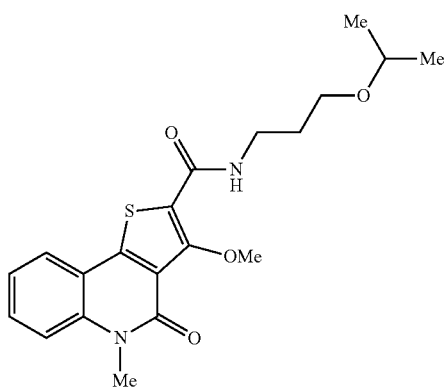 [SMILES: COc1c(C(=O)NCCCOC(C)C)sc2c1c(=O)n(C)c1ccccc21]

In the same manner as in Example 1, the title compound was obtained from the compound of Reference Example 84 and 3-(1-methylethoxy)propan-1-amine.
LC/MS 389 (M+H).

Example 60

Production of 3-methoxy-5-methyl-4-oxo-N-[3-(2-oxopyrrolidin-1-yl)propyl]-4,5-dihydrothieno[3,2-c]quinoline-2-carboxamide

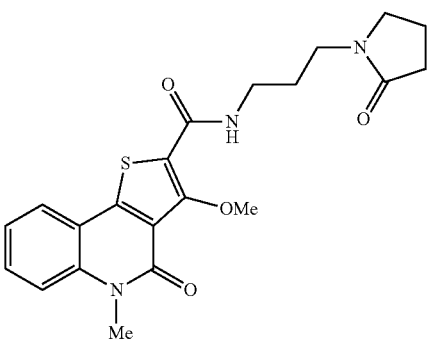 [SMILES: COc1c(C(=O)NCCCN2CCCC2=O)sc2c1c(=O)n(C)c1ccccc21]

In the same manner as in Example 1, the title compound was obtained from the compound of Reference Example 84 and 1-(3-aminopropyl)pyrrolidin-2-one.
LC/MS 414 (M+H).

Example 61

Production of N-(2-aminoethyl)-3-methoxy-4-oxo-5-(2-oxo-2-phenylethyl)-4,5-dihydrothieno[3,2-c]quinoline-2-carboxamide hydrochloride

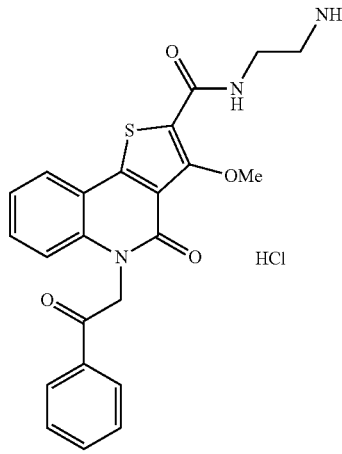

A solution of the compound of Example 64 (90 mg, 0.17 mmol) and 4N hydrogen chloride ethyl acetate solution (10 mL) in ethyl acetate (20 mL) was stirred at room temperature for 5 hr. The precipitate was collected by filtration, washed with ethyl acetate and diethyl ether, and dried under reduced pressure to give the title compound (78 mg, 97%) as a white powder.

$^1$H-NMR (300 MHz, DMSO-d$_6$) δ:3.02 (2H, t, J=6.0 Hz), 3.62 (2H, q, J=6.0 Hz), 4.06 (3H, s), 6.00 (2H, s), 7.36 (1H, t, J=7.4 Hz), 7.50 (1H, d, J=8.4 Hz), 7.57-7.59 (3H, m), 7.65 (1H, t, J=7.5 Hz), 7.94 (3H, br s), 8.06 (1H, dd, J=8.1, 1.5 Hz), 8.16-8.23 (3H, m).

Example 62

Production of N-(3-aminopropyl)-3-methoxy-4-oxo-5-(2-oxo-2-phenylethyl)-4,5-dihydrothieno[3,2-c]quinoline-2-carboxamide hydrochloride

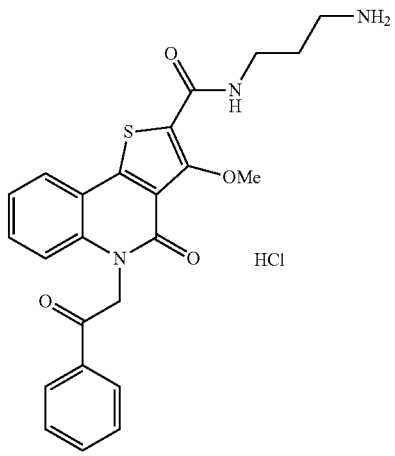 [SMILES: COc1c(C(=O)NCCCN)sc2c1c(=O)n(CC(=O)c1ccccc1)c1ccccc21 ; Cl]

In the same manner as in Example 61, the title compound (121 mg, 100%) was obtained as a white powder from the compound of Example 65 (130 mg, 0.24 mmol).

$^1$H-NMR (300 MHz, DMSO-d$_6$) δ:1.80-1.90 (2H, m), 2.85 (2H, t, J=7.4 Hz), 3.33-3.49 (2H, m), 4.04 (3H, s), 6.00 (2H, s), 7.36 (1H, t, J=7.4 Hz), 7.50 (1H, d, J=8.1 Hz), 7.56-7.67 (3H, m), 7.75-7.80 (4H, m), 8.05 (1H, dd, J=7.8, 1.2 Hz), 8.16-8.23 (3H, m).

Example 63

Production of N-(3-amino-2,2-dimethylpropyl)-3-methoxy-4-oxo-5-(2-oxo-2-phenylethyl)-4,5-dihydrothieno[3,2-c]quinoline-2-carboxamide hydrochloride

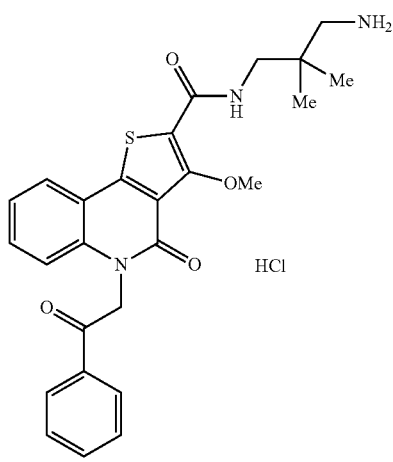 [SMILES: COc1c(C(=O)NCC(C)(C)CN)sc2c1c(=O)n(CC(=O)c1ccccc1)c1ccccc21 ; Cl]

In the same manner as in Example 61, the title compound (123 mg, 92%) was obtained as a white powder from the compound of Example 66 (150 mg, 0.26 mmol).

$^1$H-NMR (300 MHz, DMSO-d$_6$) δ:1.01 (6H, s), 2.69 (2H, q, J=6.0 Hz), 3.32 (2H, d, J=6.6 Hz), 4.08 (3H, s), 6.01 (2H, s), 7.34 (1H, t, J=7.8 Hz), 7.51 (1H, d, J=8.1 Hz), 7.57-7.67 (3H, m), 7.78 (1H, t, J=7.2 Hz), 7.90 (3H, br s), 8.06 (1H, dd, J=8.1, 1.5 Hz), 8.17-8.19 (3H, m).

Example 64

Production of tert-butyl[2-({[3-methoxy-4-oxo-5-(2-oxo-2-phenylethyl)-4,5-dihydrothieno[3,2-c]quinolin-2-yl]carbonyl}amino)ethyl]carbamate

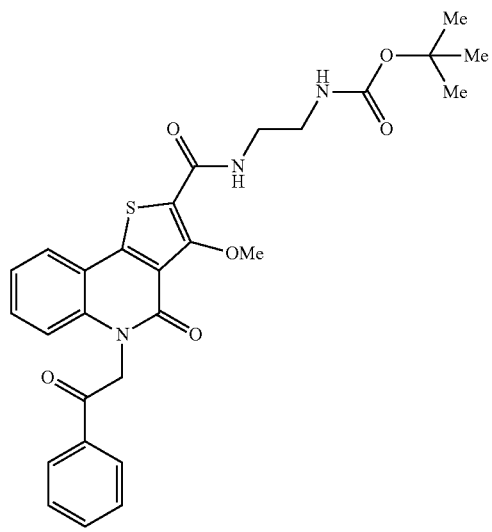 [SMILES: COc1c(C(=O)NCCNC(=O)OC(C)(C)C)sc2c1c(=O)n(CC(=O)c1ccccc1)c1ccccc21]

In the same manner as in Example 25, the title compound (136 mg, 50%) was obtained as white crystals from the compound of Reference Example 7 (200 mg, 0.51 mmol) and tert-butyl N-(2-aminoethyl)carbamate (122 mg, 0.76 mmol).

$^1$H-NMR (300 MHz, DMSO-$d_6$) δ:1.37 (9H, s), 3.10-3.20 (2H, m), 3.37-3.41 (2H, m), 4.04 (3H, s), 6.00 (2H, s), 6.99 (1H, br t), 7.35 (1H, t, J=7.4 Hz), 7.49 (1H, d, J=8.4 Hz), 7.55-7.67 (3H, m), 7.77 (1H, t, J=7.5 Hz), 8.04-8.07 (2H, m), 8.16-8.19 (2H, m).

Example 65

Production of tert-butyl[3-({[3-methoxy-4-oxo-5-(2-oxo-2-phenylethyl)-4,5-dihydrothieno[3,2-c]quinolin-2-yl]carbonyl}amino)propyl]carbamate

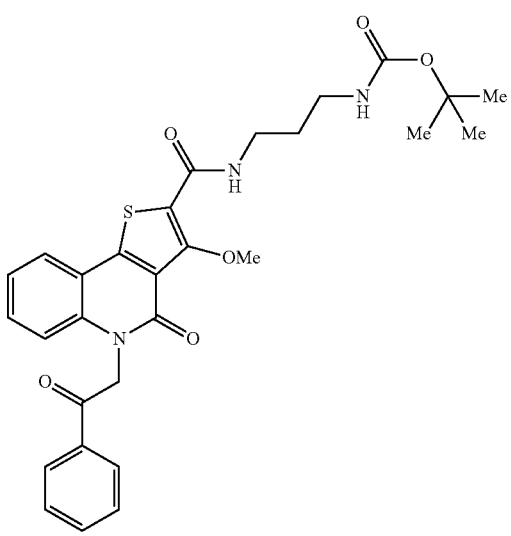 [SMILES: COc1c(C(=O)NCCCNC(=O)OC(C)(C)C)sc2c1c(=O)n(CC(=O)c1ccccc1)c1ccccc21]

In the same manner as in Example 25, the title compound (136 mg, 50%) was obtained as white crystals from the compound of Reference Example 7 (200 mg, 0.51 mmol) and tert-butyl N-(3-aminopropyl)carbamate (133 mg, 0.76 mmol).

$^1$H-NMR (300 MHz, DMSO-$d_6$) δ:1.32 (9H, s), 1.60-1.70 (2H, m), 2.90-3.00 (2H, m), 3.25-3.35 (2H, m), 4.05 (3H, s), 6.00 (2H, s), 6.91 (1H, br t), 7.35 (1H, t, J=7.5 Hz), 7.49 (1H, d, J=8.4 Hz), 7.55-7.67 (3H, m), 7.77 (1H, t, J=7.2 Hz), 8.05 (1H, dd, J=7.8, 1.2 Hz), 8.17-8.19 (3H, m).

Example 66

Production of tert-butyl[3-({[3-methoxy-4-oxo-5-(2-oxo-2-phenylethyl)-4,5-dihydrothieno[3,2-c]quinolin-2-yl]carbonyl}amino)-2,2-dimethylpropyl]carbamate

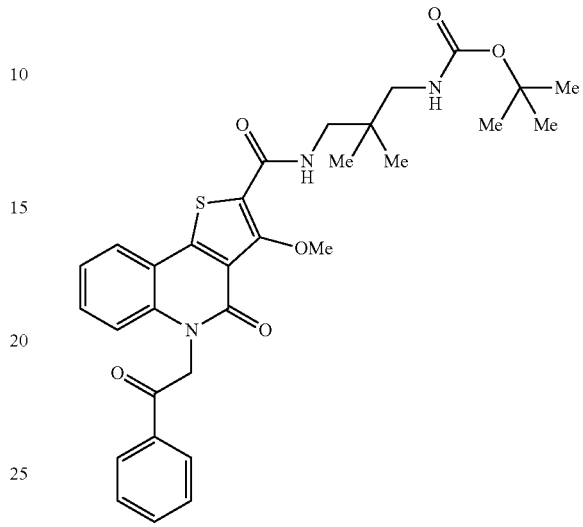

In the same manner as in Example 25, the title compound (205 mg, 69%) was obtained as white crystals from the compound of Reference Example 7 (200 mg, 0.51 mmol) and 1-Boc-amino-2,2-dimethyl-1,3-propanediamine (154 mg, 0.76 mmol).

$^1$H-NMR (300 MHz, DMSO-$d_6$) δ:1.42 (9H, s), 2.81 (2H, d, J=6.3 Hz), 3.13 (2H, d, J=6.3 Hz), 4.09 (3H, s), 6.00 (2H, s), 7.11 (1H, br t), 7.35 (1H, t, J=7.5 Hz), 7.50 (1H, d, J=8.4 Hz), 7.56-7.67 (3H, m), 7.77 (1H, t, J=7.5 Hz), 8.05 (1H, dd, J=8.1, 1.5 Hz), 8.16-8.19 (2H, m), 8.37 (1H, br t).

Example 67

Production of N-[2-(dimethylamino)ethyl]-3-methoxy-N-methyl-4-oxo-5-(2-oxo-2-phenylethyl)-4,5-dihydrothieno[3,2-c]quinoline-2-carboxamide hydrochloride

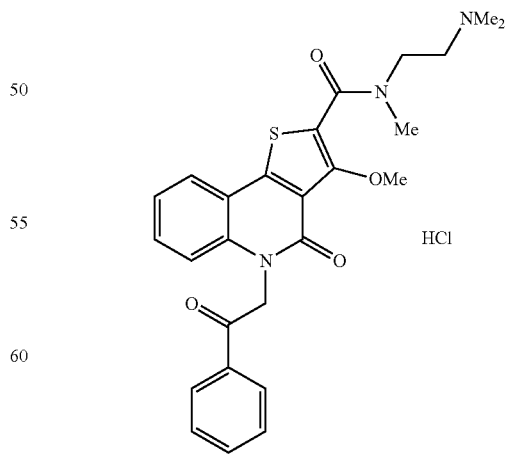

To a solution of the compound of Reference Example 7 (200 mg, 0.51 mmol), N,N,N'-trimethylethylenediamine (78 mg, 0.76 mmol) and HOBt (103 mg, 0.76 mmol) in DMF (5 mL) was added WSCD (145 mg, 0.76 mmol) under ice-cooling, and the mixture was stirred at room temperature for 24 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by silica gel chromatography (eluate; ethyl acetate/hexane=2/1) to give N-[2-(dimethylamino)ethyl]-3-methoxy-N-methyl-4-oxo-5-(2-oxo-2-phenylethyl)-4,5-dihydrothieno[3,2-c]quinoline-2-carboxamide (180 mg) as a colorless amorphous substance.

To a solution of the N-[2-(dimethylamino)ethyl]-3-methoxy-N-methyl-4-oxo-5-(2-oxo-2-phenylethyl)-4,5-dihydrothieno[3,2-c]quinoline-2-carboxamide (180 mg, 0.38 mmol) in ethyl acetate (10 mL) was added 4N hydrogen chloride ethyl acetate solution (0.1 mL), and the obtained precipitate was collected by filtration, washed with diethyl ether, and dried under reduced pressure to give the title compound (144 mg, 55%) as a white powder.

$^1$H-NMR (300 MHz, DMSO-$d_6$) δ:1.15 (6H, t, J=7.1 Hz), 3.10 (3H, s), 3.39-3.50 (4H, m), 3.87 (3H, s), 5.98 (2H, s), 7.33 (1H, t, J=7.5 Hz), 7.48 (1H, d, J=7.8 Hz), 7.56 (1H, td, J=8.7, 1.2 Hz), 7.64 (2H, t, J=7.5 Hz), 7.75 (1H, d, J=7.5 Hz), 7.96 (1H, dd, J=7.8, 1.2 Hz), 8.18 (2H, d, J=7.5 Hz).

Example 68

Production of 3-ethoxy-1-methyl-4-oxo-5-(2-oxo-2-phenylethyl)-N-(2-pyrrolidin-1-ylethyl)-4,5-dihydro-1H-pyrrolo[3,2-c]quinoline-2-carboxamide

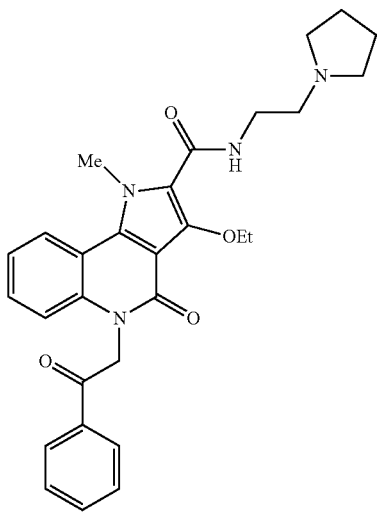 [SMILES: CCOc1c(C(=O)NCCN2CCCC2)n(C)c2c1c(=O)n(CC(=O)c1ccccc1)c1ccccc21]

In the same manner as in Example 25, the title compound (44.0 mg, 18%) was obtained as a white powder from the compound of Reference Example 30 (200 mg, 0.495 mmol) and 1-(2-aminoethyl)pyrrolidine (82.1 μL, 0.644 mmol).

$^1$H-NMR (300 MHz, DMSO-$d_6$) δ:1.32 (3H, t, J=7.0 Hz), 1.65-1.75 (4H, br), 2.40-2.55 (4H, br), 2.62 (2H, t, J=6.0 Hz), 3.05-3.47 (2H, m), 4.29 (2H, q, J=7.0 Hz), 4.39 (3H, s), 5.96 (2H, s), 7.29-7.39 (2H, m), 7.48 (1H, t, J=7.8 Hz), 7.63 (2H, t, J=7.7 Hz), 7.76 (1H, t, J=7.4 Hz), 8.12-8.19 (3H, m), 8.38 (1H, d, J=8.4 Hz).

Example 69

Production of N-[2-(4-hydroxypiperidin-1-yl)ethyl]-3-methoxy-1-methyl-4-oxo-5-(2-oxo-2-phenylethyl)-4,5-dihydro-1H-pyrrolo[3,2-c]quinoline-2-carboxamide

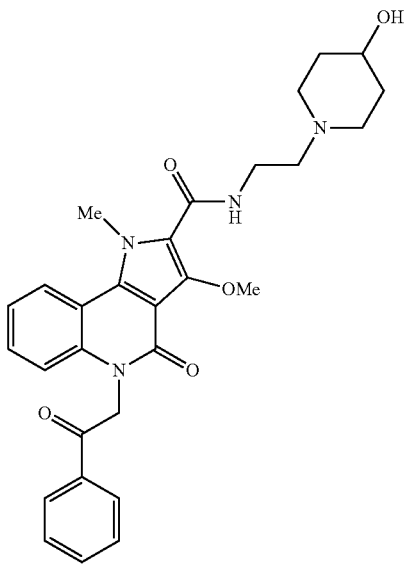 [SMILES: COc1c(C(=O)NCCN2CCC(O)CC2)n(C)c2c1c(=O)n(CC(=O)c1ccccc1)c1ccccc21]

In the same manner as in Example 25, the title compound (210 mg, 79%) was obtained as a white powder from the compound of Reference Example 28 (200 mg, 0.512 mmol) and 4-(2-aminoethyl)cyclohexanol (96.0 mg, 0.606 mmol).

$^1$H-NMR (300 MHz, DMSO-$d_6$) δ:1.35-1.50 (2H, br), 1.70-1.80 (2H, br), 2.00-2.15 (2H, br), 2.45-2.55 (2H, br), 2.70-2.85 (2H, br), 3.35-3.50 (3H, m), 4.01 (3H, s), 4.38 (3H, s), 4.56 (1H, d, J=4.5 Hz), 5.97 (2H, s), 7.29-7.40 (2H, m), 7.48 (1H, t, J=7.8 Hz), 7.64 (2H, t, J=7.7 Hz), 7.76 (1H, t, J=7.2 Hz), 8.12-8.19 (3H, m), 8.38 (1H, d, J=8.4 Hz).

Example 70

Production of 3-methoxy-1-methyl-4-oxo-5-(2-oxo-2-phenylethyl)-N-(2-piperidin-1-ylethyl)-4,5-dihydro-1H-pyrrolo[3,2-c]quinoline-2-carboxamide

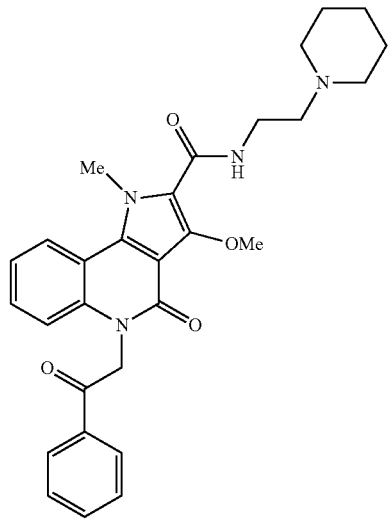 [SMILES: COc1c(C(=O)NCCN2CCCCC2)n(C)c2c1c(=O)n(CC(=O)c1ccccc1)c1ccccc21]

In the same manner as in Example 25, the title compound (230 mg, 90%) was obtained as a white powder from the compound of Reference Example 28 (200 mg, 0.512 mmol) and 1-(2-aminoethyl)piperidine (94.9 μL, 0.666 mmol).

¹H-NMR (300 MHz, DMSO-d₆) δ:1.30-1.65 (6H, br), 2.30-2.60 (6H, br), 3.40-3.45 (2H, m), 4.01 (3H, s), 4.38 (3H, s), 5.97 (2H, s), 7.29-7.39 (2H, m), 7.45-7.51 (1H, m), 7.63 (2H, t, J=7.5 Hz), 7.73-7.78 (1H, m), 8.11-8.19 (3H, m), 8.38 (1H, dd, J=8.4, 1.2 Hz).

Example 71

Production of 3-methoxy-1-methyl-N-(2-morpholin-4-ylethyl)-4-oxo-5-(2-oxo-2-phenylethyl)-4,5-dihydro-1H-pyrrolo[3,2-c]quinoline-2-carboxamide

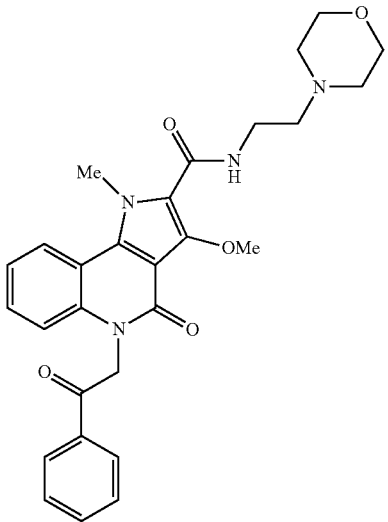 [SMILES: COc1c(C(=O)NCCN2CCOCC2)n(C)c2c1c(=O)n(CC(=O)c1ccccc1)c1ccccc21]

In the same manner as in Example 25, the title compound (210 mg, 82%) was obtained as a white powder from the compound of Reference Example 28 (200 mg, 0.512 mmol) and 1-(2-aminoethyl)morpholine (87.4 μL, 0.666 mmol).

¹H-NMR (300 MHz, DMSO-d₆) δ:2.40-2.55 (6H, br), 3.40-3.50 (2H, br), 3.61 (4H, t, J=4.2 Hz), 4.01 (3H, s), 4.37 (3H, s), 5.97 (2H, s), 7.29-7.40 (2H, m), 7.48 (1H, t, J=7.7 Hz), 7.64 (2H, t, J=7.4 Hz), 7.76 (1H, t, J=7.4 Hz), 8.12-8.19 (3H, m), 8.38 (1H, d, J=8.4 Hz).

Example 72

Production of N-[3-(dimethylamino)propyl]-3-methoxy-1-methyl-4-oxo-5-(2-oxo-2-phenylethyl)-4,5-dihydro-1H-pyrrolo[3,2-c]quinoline-2-carboxamide

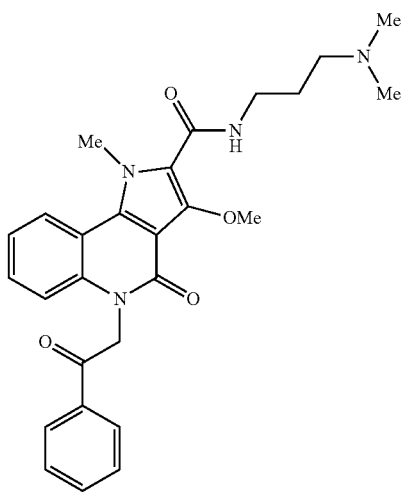 [SMILES: COc1c(C(=O)NCCCN(C)C)n(C)c2c1c(=O)n(CC(=O)c1ccccc1)c1ccccc21]

In the same manner as in Example 25, the title compound (163 mg, 67%) was obtained as a white powder from the compound of Reference Example 28 (200 mg, 0.512 mmol) and N,N-dimethylpropane-1,3-diamine (80.0 μL, 0.666 mmol).

¹H-NMR (300 MHz, DMSO-d₆) δ:1.75-1.84 (2H, m), 2.43 (6H, s), 2.65 (2H, t, J=7.2 Hz), 3.34-3.41 (2H, m), 4.00 (3H, s), 4.32 (3H, s), 5.97 (2H, s), 7.29-7.40 (2H, m), 7.45-7.51 (1H, m), 7.63 (2H, t, J=7.7 Hz), 7.74-7.78 (1H, m), 8.11-8.19 (3H, m), 8.37 (1H, dd, J=8.4, 1.2 Hz).

Example 73

Production of 2-{[2-(aminomethyl)piperidin-1-yl]carbonyl}-3-methoxy-5-(2-oxo-2-phenylethyl)thieno[3,2-c]quinolin-4(5H)-one hydrochloride

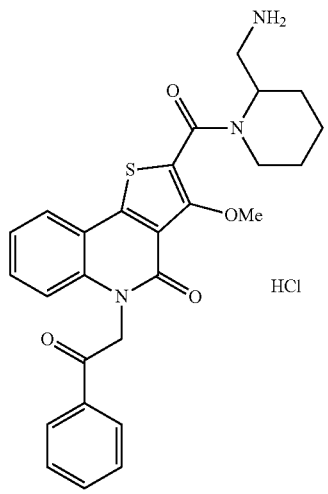 [SMILES: COc1c(C(=O)N2CCCCC2CN)sc2c1c(=O)n(CC(=O)c1ccccc1)c1ccccc21 ; Cl]

To a solution of the compound of Reference Example 7 (150 mg, 0.38 mmol), 2-(Boc-aminomethyl)piperidine (122 mg, 0.58 mmol) and HOBt (77 mg, 0.58 mmol) in DMF (5 mL) was added WSCD (109 mg, 0.58 mmol) under ice-cooling, and the mixture was stirred at room temperature for 3 days. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by silica gel chromatography (eluate; ethyl acetate/hexane=1/1 to 2/1) to give tert-butyl[(1-{[3-methoxy-4-oxo-5-(2-oxo-2-phenylethyl)-4,5-dihydrothieno[3,2-c]quinolin-2-yl]carbonyl}piperidin-2-yl)methyl]carbamate (150 mg) as a colorless oil.

A solution of the obtained tert-butyl[(1-{[3-methoxy-4-oxo-5-(2-oxo-2-phenylethyl)-4,5-dihydrothieno[3,2-c]quinolin-2-yl]carbonyl}piperidin-2-yl)methyl]carbamate (150 mg) and 4N hydrochloride ethyl acetate solution (8 mL) in ethyl acetate (15 mL) was stirred at room temperature for 18 hr. The obtained precipitate was collected by filtration, washed with diethyl ether, and dried under reduced pressure to give the title compound (133 mg, 67%) as a white powder.

¹H-NMR (300 MHz, DMSO-d₆) δ:1.40-1.90 (6H, m), 3.00-3.15 (2H, m), 3.20-3.30 (1H, m), 3.60-3.80 (1H, m), 3.90 (3H, s), 4.75-4.90 (1H, br), 5.99 (2H, s), 7.35 (1H, t,

J=7.4 Hz), 7.48-7.67 (4H, m), 7.77 (1H, t, J=7.4 Hz), 7.85-8.00 (4H, m), 8.16-8.19 (2H, m).

Example 74

Production of 3-methoxy-4-oxo-5-(2-oxo-2-phenylethyl)-N-(piperidin-2-ylmethyl)-4,5-dihydrothieno[3,2-c]quinoline-2-carboxamide hydrochloride

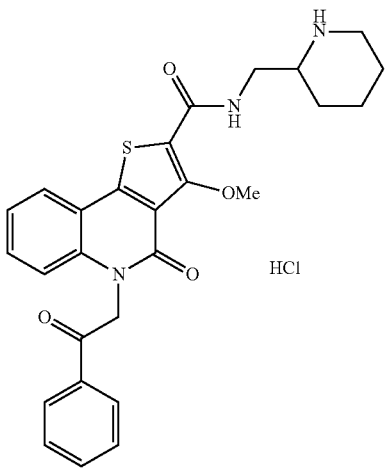 [SMILES: COc1c(C(=O)NCC2CCCCN2)sc2c1c(=O)n(CC(=O)c1ccccc1)c1ccccc21 ; Cl]

In the same manner as in Example 73, the title compound (95 mg, 53%) was obtained as a white powder from the compound of Reference Example 7 (150 mg, 0.38 mmol) and 2-aminomethyl-N-Boc-piperidine (122 mg, 0.57 mmol).

$^1$H-NMR (300 MHz, DMSO-d$_6$) δ:1.44-1.91 (6H, m), 2.85 (1H, q, J=12.0 Hz), 3.26 (2H, d, J=12.0 Hz), 3.47-3.55 (1H, m), 3.62-3.69 (1H, m), 4.06 (3H, s), 6.01 (2H, s), 7.36 (1H, t, J=7.5 Hz), 7.51 (1H, d, J=8.1 Hz), 7.57-7.67 (3H, m), 7.78 (1H, t, J=7.4 Hz), 8.07 (1H, dd, J=7.8, 1.2 Hz), 8.18 (2H, d, J=8.4 Hz), 8.27 (1H, t, J=6.2 Hz), 8.50-8.70 (1H, m), 8.70-8.85 (1H, m).

Example 75

Production of 3-methoxy-4-oxo-5-(2-oxo-2-phenylethyl)-N-(pyrrolidin-2-ylmethyl)-4,5-dihydrothieno[3,2-c]quinoline-2-carboxamide hydrochloride

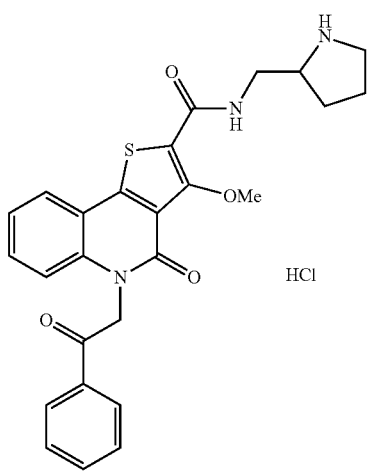 [SMILES: COc1c(C(=O)NCC2CCCN2)sc2c1c(=O)n(CC(=O)c1ccccc1)c1ccccc21 ; Cl]

In the same manner as in Example 73, the title compound (126 mg, 65%) was obtained as a white powder from the compound of Reference Example 7 (150 mg, 0.38 mmol) and 2-aminomethyl-N-Boc-pyrrolidine (122 mg, 0.57 mmol).

$^1$H-NMR (300 MHz, DMSO-d$_6$) δ:1.63-1.75 (1H, m), 1.83-2.10 (3H, m), 3.11-3.27 (2H, m), 3.61-3.76 (3H, m), 4.08 (3H, s), 6.01 (2H, s), 7.36 (1H, t, J=7.5 Hz), 7.51 (1H, d, J=8.4 Hz), 7.57-7.67 (3H, m), 7.78 (1H, t, J=7.5 Hz), 8.07 (1H, dd, J=7.8, 1.2 Hz), 8.16-8.19 (2H, m), 8.40 (1H, t, J=5.9 Hz), 8.80-9.20 (2H, br).

Example 76

Production of 3-methoxy-N-[3-(3-methyl-1H-pyrazol-1-yl)propyl]-4-oxo-5-(2-oxo-2-phenylethyl)-4,5-dihydrothieno[3,2-c]quinoline-2-carboxamide

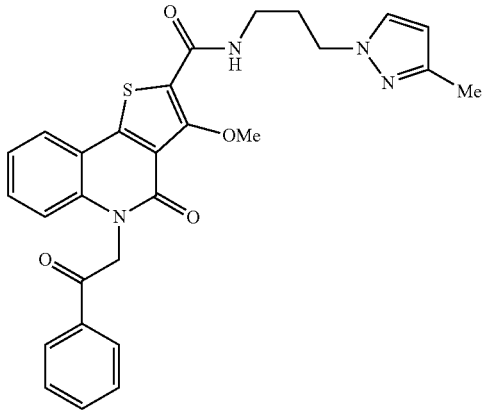 [SMILES: COc1c(C(=O)NCCCn2ccc(C)n2)sc2c1c(=O)n(CC(=O)c1ccccc1)c1ccccc21]

In the same manner as in Example 25, the title compound (113 mg, 58%) was obtained as a white powder from the compound of Reference Example 7 (150 mg, 0.38 mmol) and (3-methylpyrazol-1-yl)propanamine (79 mg, 0.57 mmol).

$^1$H-NMR (300 MHz, DMSO-d$_6$) δ:2.02 (2H, t, J=6.9 Hz), 2.15 (3H, s), 3.26-3.35 (2H, m), 4.04 (3H, s), 4.09 (2H, t, J=6.9 Hz), 5.99 (2H, s), 7.35 (1H, t, J=7.5 Hz), 7.49 (1H, d, J=8.4 Hz), 7.55-7.67 (4H, m), 7.77 (1H, t, J=7.5 Hz), 8.05 (1H, dd, J=8.1, 1.2 Hz), 8.03-8.19 (4H, m).

Example 77

Production of 3-methoxy-1-methyl-4-oxo-5-(2-oxo-2-phenylethyl)-N-piperidin-4-yl-4,5-dihydro-1H-pyrrolo[3,2-c]quinoline-2-carboxamide

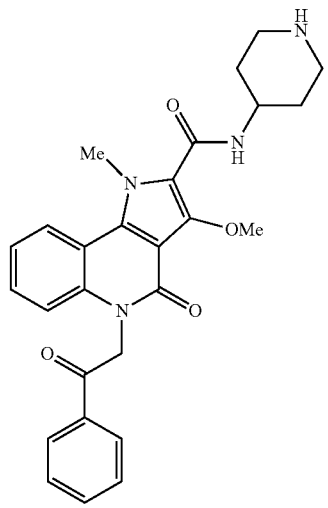 [SMILES: COc1c(C(=O)NC2CCNCC2)n(C)c2c1c(=O)n(CC(=O)c1ccccc1)c1ccccc21]

In the same manner as in Example 25, tert-butyl 4-({[3-methoxy-1-methyl-4-oxo-5-(2-oxo-2-phenylethyl)-4,5-dihydro-1H-pyrrolo[3,2-c]quinolin-2-yl]carbonyl}amino)piperidine-1-carboxylate (615 mg) was obtained as a white powder from the compound of Reference Example 28 (404 mg, 1.00 mmol) and 4-amino-1-Boc-piperidine (260 mg, 1.33 mmol).

The thus-obtained tert-butyl 4-({[3-methoxy-1-methyl-4-oxo-5-(2-oxo-2-phenylethyl)-4,5-dihydro-1H-pyrrolo[3,2-c]quinolin-2-yl]carbonyl}amino)piperidine-1-carboxylate (610 mg) and trifluoroacetic acid (5 mL) were stirred at room temperature for 2 hr. The reaction mixture was concentrated under reduced pressure, saturated sodium hydrogen carbonate solution was added, and the mixture was extracted with ethyl acetate. The extract was washed with brine, dried over magnesium sulfate, and concentrated under reduced pressure. The residue was purified by aminosilica gel chromatography (eluate; ethyl acetate/methanol=20/1), and the obtained solid was recrystallized from ethyl acetate-ethanol to give the title compound (430 mg, 85%) as white crystals.

$^1$H-NMR (300 MHz, DMSO-$d_6$) δ:1.34-1.46 (2H, m), 1.78-1.84 (2H, m), 1.90-2.20 (1H, br), 2.50-2.60 (2H, m), 2.85-3.00 (2H, br), 3.80-3.95 (1H, m), 3.98 (3H, s), 4.32 (3H, s), 5.97 (2H, s), 7.29-7.39 (2H, m), 7.45-7.50 (1H, m), 7.63 (2H, t, J=7.5 Hz), 7.76 (1H, t, J=7.5 Hz), 7.86 (1H, d, J=7.8 Hz), 8.16-8.18 (2H, m), 8.37 (1H, dd, J=8.4, 1.2 Hz).

Example 78

Production of 3-methoxy-1-methyl-4-oxo-5-(2-oxo-2-phenylethyl)-N-pyridin-3-yl-4,5-dihydro-1H-pyrrolo[3,2-c]quinoline-2-carboxamide

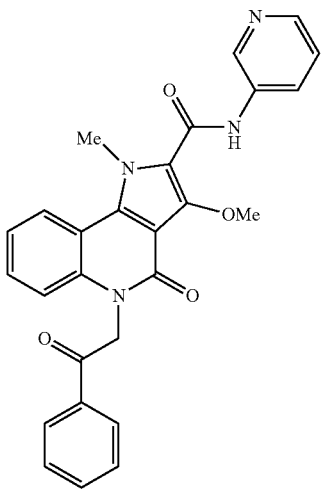 [SMILES: COc1c(C(=O)Nc2cccnc2)n(C)c2c1c(=O)n(CC(=O)c1ccccc1)c1ccccc21]

A mixture of the compound of Reference Example 28 (200 mg, 0.512 mmol), 3-aminopyridine (60.6 mg, 0.644 mmol), HATU (245 mg, 0.644 mmol), N,N'-diisopropylethylamine (336 μL, 1.93 mmol), and DMF (5 mL) was stirred at room temperature for 15 hr. The reaction mixture was diluted with water, and extracted twice with ethyl acetate. The extract was combined, washed with brine, dried over magnesium sulfate, and concentrated under reduced pressure. The residue was purified by aminosilica gel chromatography (eluate; ethyl acetate), and the obtained solid was recrystallized from THF to give the title compound (83.0 mg, 36%) as white crystals.

$^1$H-NMR (300 MHz, DMSO-$d_6$) δ:4.07 (3H, s), 4.33 (3H, s), 6.00 (2H, s), 7.32-7.44 (3H, m), 7.49-7.54 (1H, m), 7.64 (2H, t, J=7.5 Hz), 7.77 (1H, t, J=7.5 Hz), 8.17-8.22 (3H, m), 8.33 (1H, dd, J=8.3, 1.1 Hz), 8.41 (1H, dd, J=8.3, 1.1 Hz), 8.91 (1H, d, J=2.1 Hz), 10.31 (1H, s).

Example 79

Production of N-[1-(2-hydroxyethyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

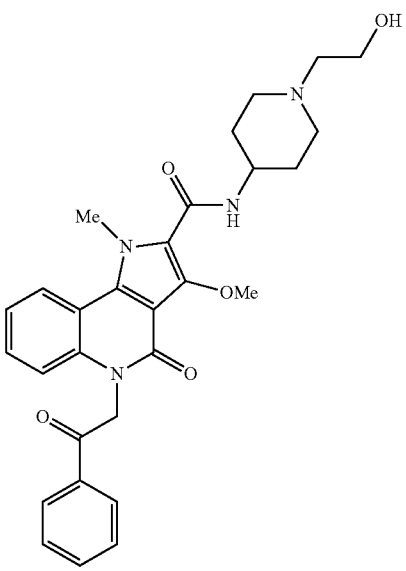 [SMILES: COc1c(C(=O)NC2CCN(CCO)CC2)n(C)c2c1c(=O)n(CC(=O)c1ccccc1)c1ccccc21]

1) A mixture of the compound of Example 77 (200 mg, 0.399 mmol), 2-bromoethanol (42.5 μL, 0.599 mmol), potassium carbonate (248 mg, 1.80 mmol) and DMF (5 mL) was stirred at 100° C. for 15 hr. The reaction mixture was diluted with water, and extracted twice with ethyl acetate. The extract was combined, washed with brine, dried over magnesium sulfate, and concentrated under reduced pressure. The residue was purified by aminosilica gel chromatography (eluate; ethyl acetate), and the obtained solid was recrystallized from ethyl acetate-ethanol to give the title compound (68.0 mg, 33%) as white crystals.

$^1$H-NMR (300 MHz, DMSO-$d_6$) δ:1.51-1.62 (2H, m), 1.75-1.90 (2H, br), 2.18 (2H, t, J=10.5 Hz), 2.40 (2H, t, J=5.9 Hz), 2.70-2.85 (2H, br), 3.47-3.52 (2H, m), 3.75-3.90 (1H, br), 3.98 (3H, s), 4.32-4.38 (4H, m), 5.97 (2H, s), 7.29-7.39 (2H, m), 7.47 (1H, t, J=7.6 Hz), 7.63 (2H, t, J=7.6 Hz), 7.76 (1H, t, J=7.1 Hz), 7.87 (1H, d, J=7.5 Hz), 8.17 (2H, d, J=7.6 Hz), 8.37 (1H, d, J=8.4 Hz).

2) The white powder was recrystallized from ethanol-water to give the title compound as white crystals. melting point: 202° C.

Example 80

Production of 3-methoxy-1-methyl-4-oxo-5-(2-oxo-2-phenylethyl)-N-(pyridin-2-ylmethyl)-4,5-dihydro-1H-pyrrolo[3,2-c]quinoline-2-carboxamide hydrochloride

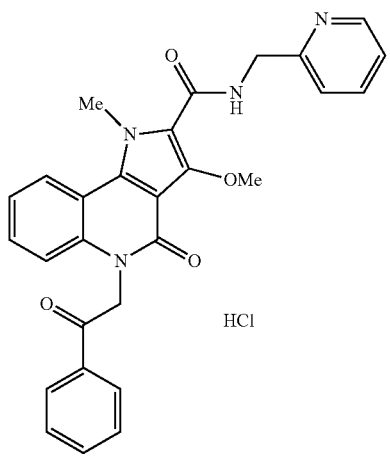 [SMILES: COc1c(C(=O)NCc2ccccn2)n(C)c2c1c(=O)n(CC(=O)c1ccccc1)c1ccccc21 ; Cl]

In the same manner as in Example 25, 3-methoxy-1-methyl-4-oxo-5-(2-oxo-2-phenylethyl)-N-(pyridin-2-ylmethyl)-4,5-dihydro-1H-pyrrolo[3,2-c]quinoline-2-carboxamide was obtained as a white powder from the compound of Reference Example 28 (200 mg, 0.512 mmol) and 2-(aminomethyl)pyridine (69.6 mg, 0.644 mmol).

The title compound (222 mg, 87%) was obtained as a white powder from the thus-obtained 3-methoxy-1-methyl-4-oxo-5-(2-oxo-2-phenylethyl)-N-(pyridin-2-ylmethyl)-4,5-dihydro-1H-pyrrolo[3,2-c]quinoline-2-carboxamide by a method similar to that in Example 30.

$^1$H-NMR (300 MHz, DMSO-$d_6$) δ:4.08 (3H, s), 4.34 (3H, s), 4.85 (2H, d, J=5.7 Hz), 5.98 (2H, s), 7.30-7.42 (2H, m), 7.47-7.52 (1H, m), 7.64 (2H, t, J=7.5 Hz), 7.74-7.85 (3H, m), 8.16-8.19 (2H, m), 8.31-8.40 (2H, m), 8.77-8.84 (2H, m).

Example 81

Production of 3-methoxy-1-methyl-4-oxo-5-(2-oxo-2-phenylethyl)-N-(piperidin-2-ylmethyl)-4,5-dihydro-1H-pyrrolo[3,2-c]quinoline-2-carboxamide hydrochloride

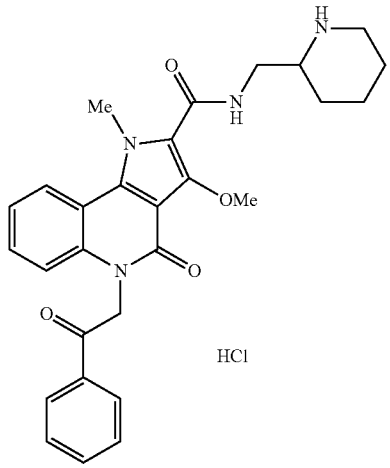 [SMILES: COc1c(C(=O)NCC2CCCCN2)n(C)c2c1c(=O)n(CC(=O)c1ccccc1)c1ccccc21 ; Cl]

In the same manner as in Example 73, the title compound (230 mg, 89%) was obtained as a white powder from the compound of Reference Example 28 (200 mg, 0.512 mmol) and 2-(aminomethyl)-1-N-Boc-piperidine (138 mg, 0.644 mmol).

$^1$H-NMR (300 MHz, DMSO-$d_6$) δ:1.40-1.95 (6H, br), 2.70-2.95 (1H, br), 3.15-3.35 (2H, br), 3.46-3.69 (2H, m), 4.03 (3H, s), 4.36 (3H, s), 5.98 (2H, s), 7.30-7.41 (2H, m), 7.47-7.52 (1H, m), 7.64 (2H, t, J=7.7 Hz), 7.76 (1H, t, J=7.5 Hz), 8.16-8.25 (3H, m), 8.39 (1H, dd, J=8.3, 1.1 Hz), 8.55-8.75 (1H, br), 8.75-8.90 (1H, br).

Example 82

Production of 3-methoxy-4-oxo-5-(2-oxo-2-phenylethyl)-N-(2-pyrrolidin-1-ylethyl)-4,5-dihydrothieno[3,2-c]quinolin-2-yl]carboxamide hydrochloride

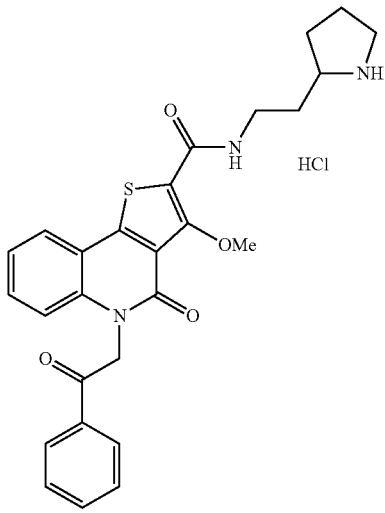 [SMILES: COc1c(C(=O)NCCC2CCCN2)sc2c1c(=O)n(CC(=O)c1ccccc1)c1ccccc21 ; Cl]

In the same manner as in Example 73, the title compound (114 mg, 47%) was obtained as a white powder from the compound of Reference Example 7 (150 mg, 0.38 mmol) and 2-aminoethyl-N-Boc-pyrrolidine (122 mg, 0.57 mmol).

$^1$H-NMR (300 MHz, DMSO-$d_6$) δ:1.50-1.65 (1H, m), 1.80-2.10 (5H, m), 2.14-2.25 (1H, m), 3.10-3.20 (2H, m), 3.35-3.60 (2H, m), 4.05 (3H, s), 6.00 (2H, s), 7.35 (1H, t, J=7.5 Hz), 7.50 (1H, d, J=8.7 Hz), 7.56-7.67 (3H, m), 7.77 (1H, t, J=7.5 Hz), 8.05 (1H, dd, J=7.8, 1.2 Hz), 8.16-8.20 (3H, m), 8.50-9.50 (2H, br).

Example 83

Production of 3-methoxy-4-oxo-5-(2-oxo-2-phenyl-ethyl)-N-(2-piperidin-1-ylethyl)-4,5-dihydrothieno[3,2-c]quinoline-2-carboxamide hydrochloride

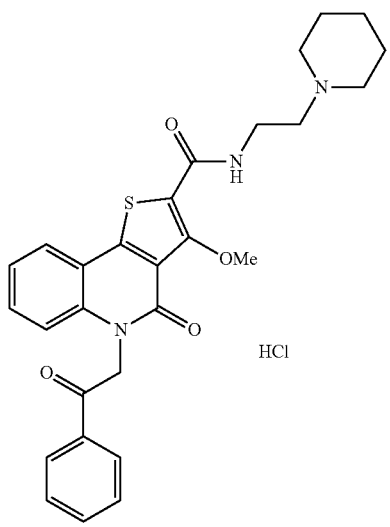 [SMILES: COc1c(C(=O)NCCN2CCCCC2)sc2c1c(=O)n(CC(=O)c1ccccc1)c1ccccc21 ; Cl]

In the same manner as in Example 67, the title compound (147 mg, 53%) was obtained as a white powder from the compound of Reference Example 7 (200 mg, 0.51 mmol) and 1-(2-aminoethyl)piperidine (98 mg, 0.76 mmol).

$^1$H-NMR (300 MHz, DMSO-d$_6$) δ:1.30-1.50 (1H, m), 1.65-1.80 (5H, m), 2.85-3.00 (2H, m), 3.26 (2H, br d, J=5.1 Hz), 3.53 (2H, br d, J=11.1 Hz), 3.73 (2H, q, J=5.7 Hz), 4.06 (3H, s), 6.00 (2H, s), 7.36 (1H, t, J=7.5 Hz), 7.50 (1H, d, J=8.4 Hz), 7.57-7.67 (3H, m), 7.77 (1H, t, J=7.5 Hz), 8.06 (1H, dd, J=8.1, 1.5 Hz), 8.16 (1H, d, J=1.5 Hz), 8.19 (1H, s), 8.40 (1H, t, J=5.7 Hz), 9.80-9.90 (1H, br).

Example 84

Production of 3-methoxy-1-methyl-4-oxo-5-(2-oxo-2-phenylethyl)-N-piperidin-3-yl-4,5-dihydro-1H-pyrrolo[3,2-c]quinoline-2-carboxamide hydrochloride

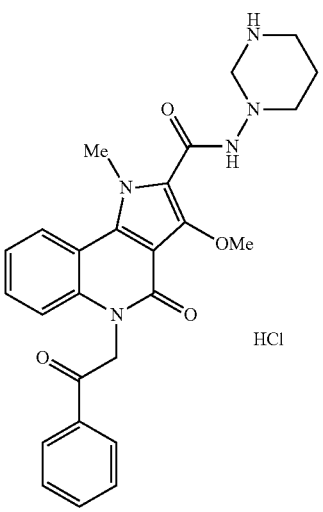 [SMILES: COc1c(C(=O)NN2CCCNC2)n(C)c2c1c(=O)n(CC(=O)c1ccccc1)c1ccccc21 ; Cl]

In the same manner as in Example 73, the title compound (67.1 mg, 27%) was obtained as a white powder from the compound of Reference Example 28 (200 mg, 0.512 mmol) and 3-amino-1-N-Boc-piperidine (129 mg, 0.644 mmol).

$^1$H-NMR (300 MHz, DMSO-d$_6$) δ:1.55-2.05 (4H, m), 2.75-3.00 (2H, m), 3.20 (1H, d, J=13.2 Hz), 3.25-3.40 (1H, br), 3.99 (3H, s), 4.20-4.30 (1H, br), 4.31 (3H, s), 5.98 (2H, s), 7.30-7.41 (2H, m), 7.46-7.52 (1H, m), 7.64 (2H, t, J=7.7 Hz), 7.73-7.79 (1H, m), 8.05 (1H, d, J=8.1 Hz), 8.16-8.19 (2H, m), 8.38 (1H, dd, J=8.3, 1.4 Hz), 8.85-9.05 (2H, br).

Example 85

Production of N-[trans-2-aminocyclohexyl]-3-methoxy-1-methyl-4-oxo-5-(2-oxo-2-phenylethyl)-4,5-dihydro-1H-pyrrolo[3,2-c]quinoline-2-carboxamide

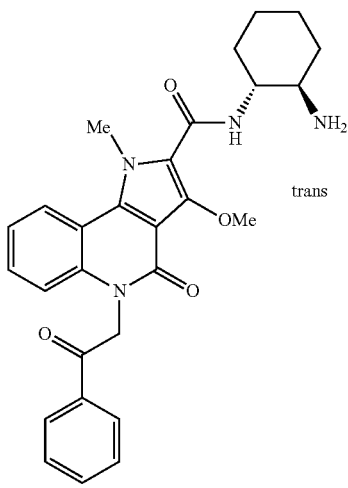 [SMILES: COc1c(C(=O)N[C@@H]2CCCC[C@H]2N)n(C)c2c1c(=O)n(CC(=O)c1ccccc1)c1ccccc21 ; "trans"]

In the same manner as in Example 73, N-[trans-2-aminocyclohexyl]-3-methoxy-1-methyl-4-oxo-5-(2-oxo-2-phenylethyl)-4,5-dihydro-1H-pyrrolo[3,2-c]quinoline-2-carboxamide hydrochloride was obtained from the compound of Reference Example 28 (200 mg, 0.512 mmol) and N-Boc-trans-1,2-diaminocyclohexane (138 mg, 0.644 mmol).

To the thus-obtained N-[trans-2-aminocyclohexyl]-3-methoxy-1-methyl-4-oxo-5-(2-oxo-2-phenylethyl)-4,5-dihydro-1H-pyrrolo[3,2-c]quinoline-2-carboxamide hydrochloride was added saturated sodium hydrogen carbonate solution, and the mixture was extracted with ethyl acetate. The extract was washed with brine, dried over magnesium sulfate, and concentrated under reduced pressure. The residue was purified by aminosilica gel chromatography (eluate; ethyl acetate/methanol=20/1), and the obtained solid was recrystallized from ethyl acetate-ethanol to give the title compound (80.0 mg, 33%) as white crystals.

$^1$H-NMR (300 MHz, DMSO-d$_6$) δ:1.10-1.40 (4H, br), 1.50-1.75 (4H, br), 1.70-1.90 (1H, br), 1.90-2.05 (1H, br), 2.45-2.60 (1H, br), 3.45-3.60 (1H, br), 3.97 (3H, s), 4.30 (3H, s), 5.97 (2H, s), 7.29-7.39 (2H, m), 7.47 (1H, t, J=7.7 Hz), 7.63 (2H, t, J=7.7 Hz), 7.76 (1H, t, J=7.4 Hz), 7.90 (1H, d, J=7.8 Hz), 8.17 (2H, d, J=7.7 Hz), 8.37 (1H, d, J=8.1 Hz).

Example 86

Production of 3-methoxy-1-methyl-4-oxo-5-(2-oxo-2-phenylethyl)-N-pyrrolidin-3-yl-4,5-dihydro-1H-pyrrolo[3,2-c]quinoline-2-carboxamide hydrochloride

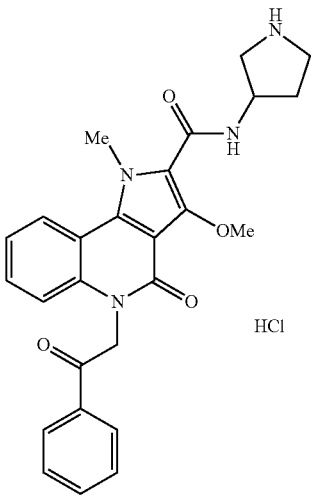 [SMILES: COc1c(C(=O)NC2CCNC2)n(C)c2c1c(=O)n(CC(=O)c1ccccc1)c1ccccc21 ; Cl]

In the same manner as in Example 73, the title compound (122 mg, 50%) was obtained as a white powder from the compound of Reference Example 28 (200 mg, 0.512 mmol) and 3-amino-1-N-Boc-pyrrolidine (120 mg, 0.644 mmol).

$^1$H-NMR (300 MHz, DMSO-$d_6$) δ:1.94-2.05 (1H, m), 2.20-2.32 (1H, m), 3.17-3.49 (4H, m), 4.00 (3H, s), 4.30 (3H, s), 4.58-4.69 (1H, m), 5.98 (2H, s), 7.30-7.40 (2H, m), 7.46-7.52 (1H, m), 7.64 (2H, t, J=7.5 Hz), 7.73-7.79 (1H, m), 8.16-8.19 (2H, m), 8.26 (1H, d, J=6.9 Hz), 8.38 (1H, dd, J=8.3, 1.1 Hz), 9.10-9.30 (2H, br).

Example 87

Production of N-[3-(dimethylamino)-2,2-dimethylpropyl]-3-methoxy-1-methyl-4-oxo-5-(2-oxo-2-phenylethyl)-4,5-dihydro-1H-pyrrolo[3,2-c]quinoline-2-carboxamide hydrochloride

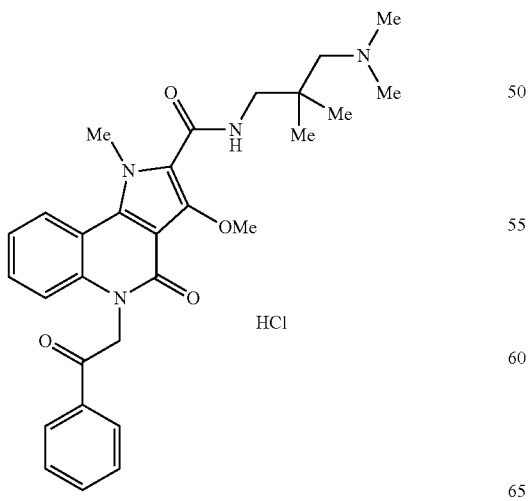

In the same manner as in Example 25, N-[3-(dimethylamino)-2,2-dimethylpropyl]-3-methoxy-1-methyl-4-oxo-5-(2-oxo-2-phenylethyl)-4,5-dihydro-1H-pyrrolo[3,2-c]quinoline-2-carboxamide was obtained as a white powder from the compound of Reference Example 28 (200 mg, 0.512 mmol).

The title compound (203 mg, 76%) was obtained as a white powder from the thus-obtained N-[3-(dimethylamino)-2,2-dimethylpropyl]-3-methoxy-1-methyl-4-oxo-5-(2-oxo-2-phenylethyl)-4,5-dihydro-1H-pyrrolo[3,2-c]quinoline-2-carboxamide by a method similar to that in Example 30.

$^1$H-NMR (300 MHz, DMSO-$d_6$) δ:1.12 (6H, s), 2.86 (3H, s), 2.87 (3H, s), 3.03-3.07 (2H, br), 3.33-3.40 (2H, br), 4.04 (3H, s), 4.30 (3H, s), 5.99 (2H, s), 7.30-7.41 (2H, m), 7.46-7.52 (1H, m), 7.64 (2H, t, J=7.5 Hz), 7.76 (1H, t, J=7.4 Hz), 8.16-8.21 (3H, m), 8.38 (1H, dd, J=8.3, 1.1 Hz), 9.50-9.70 (1H, br).

Example 88

Production of N-(4-aminocyclohexyl)-3-methoxy-1-methyl-4-oxo-5-(2-oxo-2-phenylethyl)-4,5-dihydro-1H-pyrrolo[3,2-c]quinoline-2-carboxamide hydrochloride

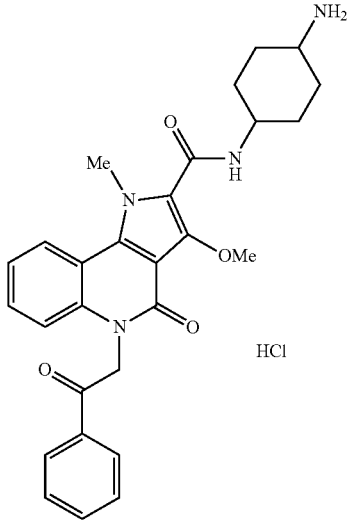 [SMILES: COc1c(C(=O)NC2CCC(N)CC2)n(C)c2c1c(=O)n(CC(=O)c1ccccc1)c1ccccc21 ; Cl]

In the same manner as in Example 73, the title compound (121 mg, 47%) was obtained as a white powder from the compound of Reference Example 28 (200 mg, 0.512 mmol) and tert-butyl (4-aminocyclohexyl)carbamate (138 mg, 0.644 mmol).

$^1$H-NMR (300 MHz, DMSO-$d_6$) δ:1.18-1.34 (1H, br), 1.55-1.75 (1H, br), 1.75-1.90 (2H, br), 1.95-2.20 (1H, br), 2.60-2.81 (2H, m), 3.15-3.45 (3H, m), 4.01 (3H, s), 4.30 (3H, s), 5.98 (2H, s), 7.30-7.40 (2H, m), 7.46-7.51 (1H, m), 7.64 (2H, t, J=7.5 Hz), 7.74-7.79 (1H, m), 8.16-8.20 (3H, m), 8.38 (1H, dd, J=8.3, 1.4 Hz), 8.65-8.95 (2H, br).

Example 89

Production of 2-{[(3R)-3-aminopyrrolidin-1-yl]carbonyl}-3-methoxy-1-methyl-5-(2-oxo-2-phenylethyl)-1,5-dihydro-4H-pyrrolo[3,2-c]quinolin-4-one hydrochloride

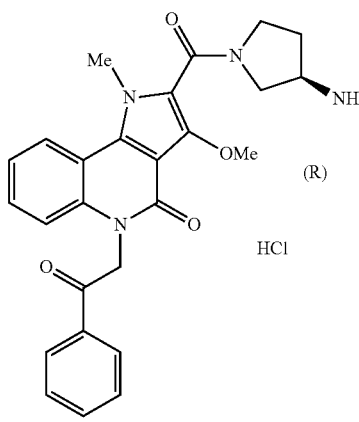

In the same manner as in Example 73, the title compound (190 mg, 78%) was obtained as a white powder from the compound of Reference Example 28 (200 mg, 0.512 mmol) and tert-butyl (3R)-pyrrolidin-3-ylcarbamate (120 mg, 0.644 mmol).

$^1$H-NMR (300 MHz, DMSO-$d_6$) δ:1.95-2.15 (1H, m), 2.15-2.40 (1H, m), 3.57-3.92 (8H, m), 4.03-4.10 (3H, br), 5.98 (2H, s), 7.28-7.40 (2H, m), 7.44-7.49 (1H, m), 7.63 (2H, t, J=7.5 Hz), 7.76 (1H, t, J=7.4 Hz), 8.16-8.19 (2H, m), 8.30-8.50 (4H, br).

Example 90

Production of 2-{[(3S)-3-aminopiperidin-1-yl]carbonyl}-3-methoxy-1-methyl-5-(2-oxo-2-phenylethyl)-1,5-dihydro-4H-pyrrolo[3,2-c]quinolin-4-one hydrochloride

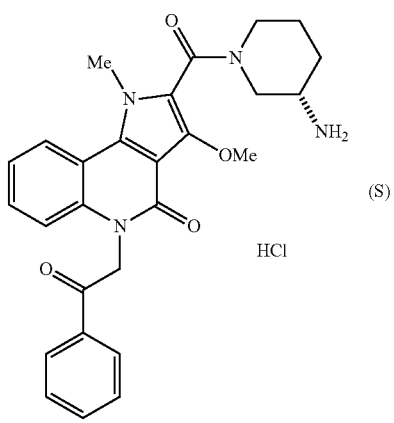 [SMILES: COc1c(C(=O)N2CCC[C@H](N)C2)n(C)c2c1c(=O)n(CC(=O)c1ccccc1)c1ccccc21 ; Cl ; "(S)"]

In the same manner as in Example 73, the title compound (190 mg, 78%) was obtained as a white powder from the compound of Reference Example 28 (200 mg, 0.512 mmol) and tert-butyl (3S)-piperidin-3-ylcarbamate (120 mg, 0.644 mmol).

$^1$H-NMR (300 MHz, DMSO-$d_6$) δ:1.45-2.00 (3H, br), 2.00-2.15 (1H, br), 2.75-3.30 (4H, br), 3.65-3.85 (0.5H, br), 3.91 (3H, s), 4.03 (3H, s), 4.40-4.75 (0.5H, br), 5.97 (2H, s), 7.29-7.40 (2H, m), 7.44-7.49 (1H, m), 7.64 (2H, t, J=7.5 Hz), 7.76 (1H, t, J=7.4 Hz), 8.10-8.20 (5H, br), 8.34 (1H, d, J=7.8 Hz).

Example 91

Production of 2-{[3-(aminomethyl)piperidin-1-yl]carbonyl}-3-methoxy-1-methyl-5-(2-oxo-2-phenylethyl)-1,5-dihydro-4H-pyrrolo[3,2-c]quinolin-4-one hydrochloride

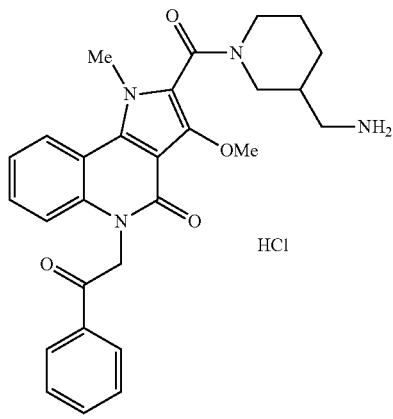 [SMILES: COc1c(C(=O)N2CCCC(CN)C2)n(C)c2c1c(=O)n(CC(=O)c1ccccc1)c1ccccc21 ; Cl]

In the same manner as in Example 73, the title compound (170 mg, 66%) was obtained as a white powder from the compound of Reference Example 28 (200 mg, 0.512 mmol) and tert-butyl (piperidin-3-ylmethyl)carbamate (143 mg, 0.644 mmol).

$^1$H-NMR (300 MHz, DMSO-$d_6$) δ:1.20-1.60 (2H, br), 1.60-2.00 (3H, br), 2.55-3.05 (3H, br), 3.10-3.30 (1H, br), 3.60-3.80 (1H, br), 3.90 (3H, s), 4.01 (3H, s), 4.25-4.60 (1H, br), 5.98 (2H, s), 7.28-7.39 (2H, m), 7.46 (1H, t, J=7.7 Hz), 7.64 (2H, t, J=7.7 Hz), 7.76 (1H, t, J=7.1 Hz), 7.90-8.25 (5H, br), 8.33 (1H, d, J=8.1 Hz).

Example 92

Production of N-[2-(dimethylamino)-1-methylethyl]-3-methoxy-1-methyl-4-oxo-5-(2-oxo-2-phenylethyl)-4,5-dihydro-1H-pyrrolo[3,2-c]quinoline-2-carboxamide

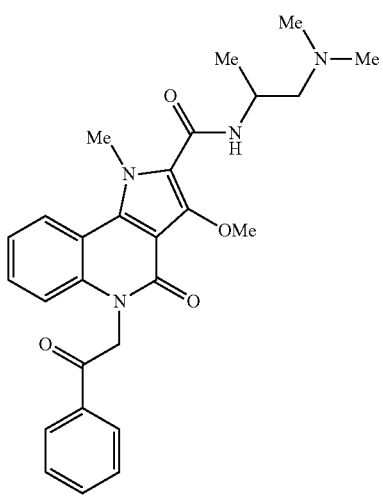 [SMILES: COc1c(C(=O)NC(C)CN(C)C)n(C)c2c1c(=O)n(CC(=O)c1ccccc1)c1ccccc21]

In the same manner as in Example 25, the title compound (67.0 mg, 29%) was obtained as a white powder from the compound of Reference Example 28 (440 mg, 1.01 mmol) and 1-(dimethylamino)isopropylamine (68.1 mg, 0.666 mmol).

¹H-NMR (300 MHz, DMSO-d₆) δ:1.20 (3H, d, J=6.0 Hz), 2.20 (6H, s), 2.20-2.27 (1H, m), 2.39-2.46 (1H, m), 3.97 (3H, s), 3.98-4.10 (1H, m), 4.36 (3H, s), 5.97 (2H, s), 7.29-7.39 (2H, m), 7.45-7.51 (1H, m), 7.63 (2H, t, J=7.5 Hz), 7.73-7.79 (1H, m), 7.96 (1H, d, J=6.6 Hz), 8.16-8.19 (2H, m), 8.38 (1H, dd, J=8.1, 1.2 Hz).

Example 93

Production of 2-{[(3R)-3-aminopiperidin-1-yl]carbonyl}-3-methoxy-1-methyl-5-(2-oxo-2-phenylethyl)-1,5-dihydro-4H-pyrrolo[3,2-c]quinolin-4-one hydrochloride

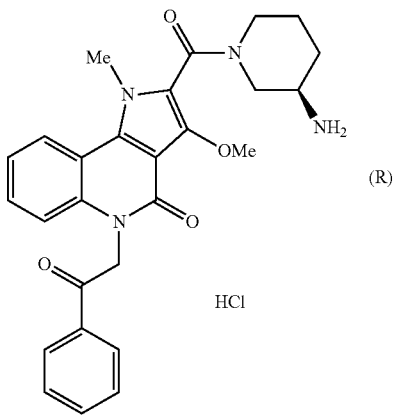 [SMILES: COc1c(C(=O)N2CCC[C@@H](N)C2)n(C)c2c1c(=O)n(CC(=O)c1ccccc1)c1ccccc21 ; Cl ; "(R)"]

In the same manner as in Example 73, the title compound (190 mg, 75%) was obtained as a white powder from the compound of Reference Example 28 (200 mg, 0.512 mmol) and tert-butyl (3R)-piperidin-3-ylcarbamate (133 mg, 0.666 mmol).

¹H-NMR (300 MHz, DMSO-d₆) δ:1.45-2.00 (3H, br), 2.00-2.15 (1H, br), 2.75-3.30 (4H, br), 3.65-3.85 (0.5H, br), 3.91 (3H, s), 4.03 (3H, s), 4.40-4.75 (0.5H, br), 5.97 (2H, s), 7.29-7.40 (2H, m), 7.44-7.49 (1H, m), 7.64 (2H, t, J=7.7 Hz), 7.76 (1H, t, J=7.4 Hz), 8.10-8.30 (5H, br), 8.34 (1H, d, J=8.1 Hz).

Example 94

Production of 3-methoxy-N-methyl-4-oxo-5-(2-oxo-2-phenylethyl)-N-(2-piperidin-1-ylethyl)-4,5-dihydrothieno[3,2-c]quinoline-2-carboxamide hydrochloride

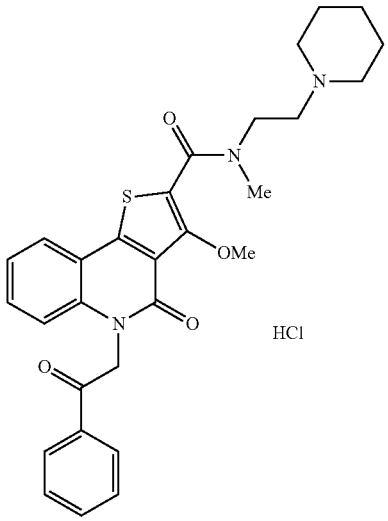 [SMILES: COc1c(C(=O)N(C)CCN2CCCCC2)sc2c1c(=O)n(CC(=O)c1ccccc1)c1ccccc21 ; Cl]

In the same manner as in Example 67, the title compound (154 mg, 73%) was obtained as a white powder from the compound of Reference Example 7 (150 mg, 0.38 mmol) and 1-(2-N'-methylaminoethyl)piperidine (108 mg, 0.76 mmol).

¹H-NMR (300 MHz, CDCl₃) δ:1.25-1.45 (1H, m), 1.60-1.90 (4H, m), 2.80-3.00 (2H, br), 3.11 (3H, s), 3.35-3.40 (2H, m), 3.40-3.65 (2H, br), 3.80-3.90 (5H, m), 5.99 (2H, s), 7.35 (1H, t, J=7.5 Hz), 7.48-7.67 (4H, m), 7.77 (1H, t, J=7.5 Hz), 7.98 (1H, dd, J=7.8, 1.2 Hz), 8.16-8.19 (3H, m), 9.75-9.90 (1H, br).

Example 95

Production of 3-methoxy-N-methyl-4-oxo-5-(2-oxo-2-phenylethyl)-N-(2-pyrrolidin-1-ylethyl)-4,5-dihydrothieno[3,2-c]quinoline-2-carboxamide hydrochloride

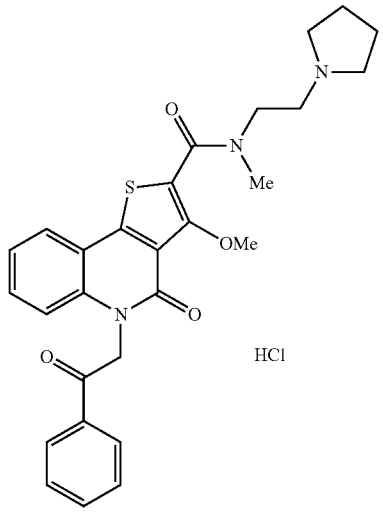 [SMILES: COc1c(C(=O)N(C)CCN2CCCC2)sc2c1c(=O)n(CC(=O)c1ccccc1)c1ccccc21 ; Cl]

In the same manner as in Example 67, the title compound (153 mg, 74%) was obtained as a white powder from the compound of Reference Example 7 (150 mg, 0.38 mmol) and 1-(2-N'-methylaminoethyl)pyrrolidine (98 mg, 0.76 mmol).

¹H-NMR (300 MHz, CDCl₃) δ:1.75-2.10 (4H, m), 2.90-3.15 (5H, m), 3.35-3.50 (2H, m), 3.50-3.80 (2H, br), 3.83-3.90 (5H, m), 5.99 (2H, s), 7.35 (1H, t, J=7.5 Hz), 7.48-7.67 (4H, m), 7.77 (1H, t, J=7.5 Hz), 7.97 (1H, dd, J=7.8, 1.2 Hz), 8.16-8.19 (2H, m), 10.35-10.65 (1H, br).

Example 96

Production of 3-methoxy-4-oxo-5-(2-oxo-2-phenylethyl)-N-[(2S)-piperidine-2-ylmethyl]-4,5-dihydrothieno[3,2-c]quinoline-2-carboxamide hydrochloride

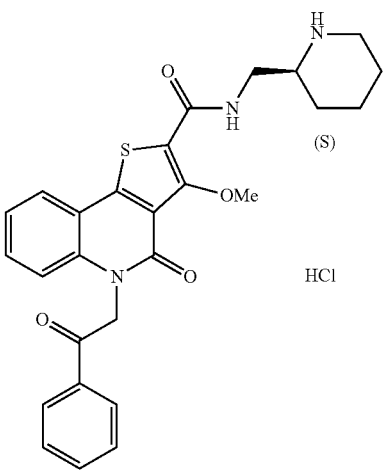

In the same manner as in Example 73, the title compound (80 mg, 57%) was obtained as a white powder from the compound of Reference Example 7 (107 mg, 0.27 mmol) and (S)-2-(Boc-aminomethyl)piperidine (58 mg, 0.27 mmol).

¹H-NMR (300 MHz, CDCl₃) δ:1.35-1.90 (6H, m), 3.00-3.40 (4H, m), 3.90 (3H, s), 4.70-4.90 (1H, br), 5.99 (2H, s), 7.35 (1H, t, J=7.5 Hz), 7.48-7.67 (4H, m), 7.77 (1H, t, J=7.5 Hz), 7.95-8.19 (6H, m).

Example 97

Production of 3-methoxy-N-{2-[(1-methylethyl)amino]ethyl}-4-oxo-5-(2-oxo-2-phenylethyl)-4,5-dihydrothieno[3,2-c]quinoline-2-carboxamide

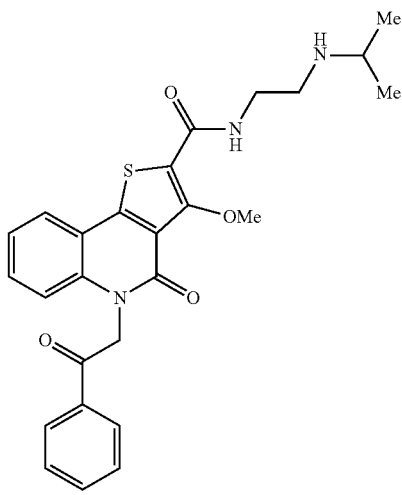 [SMILES: COc1c(C(=O)NCCNC(C)C)sc2c1c(=O)n(CC(=O)c1ccccc1)c1ccccc21]

To a mixed solution of the compound of Example 61 (150 mg, 0.32 mmol) and acetone (0.2 mL) in methanol (5 mL)-DMF (5 mL) was added sodium cyanoborohydride (20 mg, 0.32 mmol), and the mixture was stirred at room temperature for 24 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by aminosilica gel chromatography (eluate; ethyl acetate), and the obtained white solid was recrystallized from ethyl acetate-hexane to give the title compound (69 mg, 45%) as white crystals.

¹H-NMR (300 MHz, CDCl₃) δ:1.09 (6H, d, J=6.3 Hz), 2.83-2.89 (3H, m), 3.57 (2H, q, J=5.7 Hz), 4.16 (3H, s), 5.87 (2H, s), 7.02 (1H, d, J=8.4 Hz), 7.26-7.28 (1H, m), 7.44-7.50 (1H, m), 7.56 (2H, t, J=7.5 Hz), 7.66 (1H, t, J=7.5 Hz), 7.91 (1H, dd, J=8.1, 1.2 Hz), 8.10-8.13 (3H, m).

Example 98

Production of 3-methoxy-N-{3-[(1-methylethyl)amino]propyl}-4-oxo-5-(2-oxo-2-phenylethyl)-4,5-dihydrothieno[3,2-c]quinoline-2-carboxamide

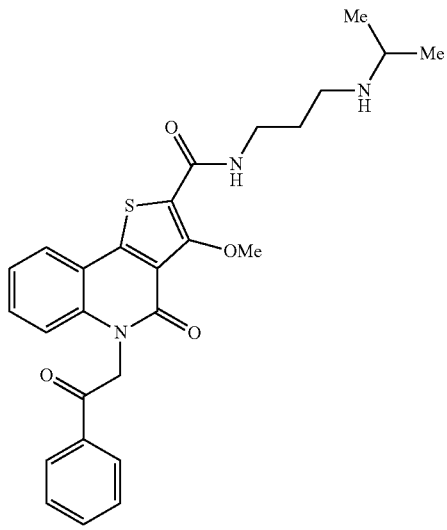 [SMILES: COc1c(C(=O)NCCCNC(C)C)sc2c1c(=O)n(CC(=O)c1ccccc1)c1ccccc21]

In the same manner as in Example 97, the title compound (9 mg, 5%) was obtained as a white powder from the compound of Example 62 (190 mg, 0.38 mmol).

¹H-NMR (300 MHz, CDCl₃) δ:1.08 (6H, d, J=6.3 Hz), 1.75-1.88 (2H, m), 2.73 (2H, t, J=6.9 Hz), 2.76-2.85 (1H, m), 3.58 (2H, q, J=6.4 Hz), 4.14 (3H, s), 5.87 (2H, s), 7.02 (1H, d, J=8.7 Hz), 7.20-7.28 (1H, m), 7.44-7.50 (1H, m), 7.56 (2H, t, J=7.5 Hz), 7.65-7.68 (1H, m), 7.80 (1H, br t), 7.91 (1H, dd, J=7.8, 1.2 Hz), 8.10-8.13 (2H, m).

Example 99

Production of 3-methoxy-1-methyl-4-oxo-5-(2-oxo-2-phenylethyl)-N-(piperidin-3-ylmethyl)-4,5-dihydro-1H-pyrrolo[3,2-c]quinoline-2-carboxamide hydrochloride

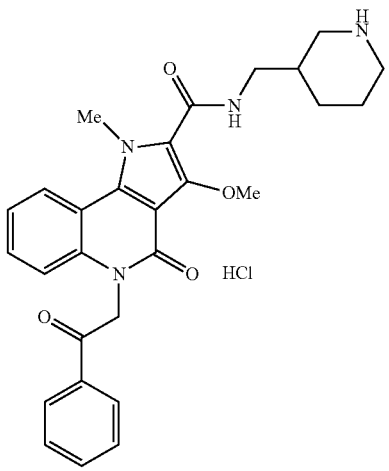 [SMILES: COc1c(C(=O)NCC2CCCNC2)n(C)c2c1c(=O)n(CC(=O)c1ccccc1)c1ccccc21 ; Cl]

In the same manner as in Example 73, the title compound (190 mg, 75%) was obtained as a white powder from the compound of Reference Example 28 (200 mg, 0.512 mmol) and tert-butyl 3-(aminomethyl)piperidine-1-carboxylate (143 mg, 0.666 mmol).

¹H-NMR (300 MHz, DMSO-d₆) δ:1.15-1.35 (1H, br), 1.50-1.90 (3H, br), 1.95-2.15 (1H, br), 2.64 (1H, t, J=6.2 Hz), 2.78 (1H, t, J=5.7 Hz), 3.15-3.45 (4H, br), 4.01 (3H, s), 4.30 (3H, s), 5.98 (2H, s), 7.29-7.41 (2H, m), 7.48 (1H, t, J=7.6 Hz), 7.64 (2H, t, J=7.6 Hz), 7.76 (1H, t, J=7.4 Hz), 8.16-8.19 (3H, m), 8.37 (1H, d, J=8.1 Hz), 8.55-8.85 (2H, br).

Example 100

Production of N-[(1-aminocyclohexyl)methyl]-3-methoxy-1-methyl-4-oxo-5-(2-oxo-2-phenylethyl)-4,5-dihydro-1H-pyrrolo[3,2-c]quinoline-2-carboxamide hydrochloride

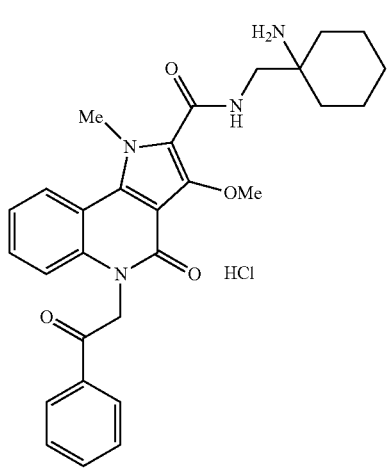 [SMILES: COc1c(C(=O)NCC2(N)CCCCC2)n(C)c2c1c(=O)n(CC(=O)c1ccccc1)c1ccccc21 ; Cl]

In the same manner as in Example 73, the title compound (80.0 mg, 30%) was obtained as a white powder from the compound of Reference Example 28 (200 mg, 0.512 mmol) and tert-butyl[1-(aminomethyl)cyclohexyl]carbamate (147 mg, 0.644 mmol).

¹H-NMR (300 MHz, DMSO-d₆) δ:1.25-1.70 (10H, br), 3.61 (2H, d, J=6.3 Hz), 4.04 (3H, s), 4.34 (3H, s), 5.98 (2H, s), 7.31-7.42 (2H, m), 7.50 (1H, t, J=7.6 Hz), 7.64 (2H, t, J=7.6 Hz), 7.77 (1H, t, J=7.5 Hz), 7.80-8.00 (3H, br), 8.16-8.22 (3H, m), 8.39 (1H, d, J=8.4 Hz).

Example 101

Production of N-{[1-(2-hydroxyethyl)piperidin-2-yl]methyl}-3-methoxy-1-methyl-4-oxo-5-(2-oxo-2-phenylethyl)-4,5-dihydro-1H-pyrrolo[3,2-c]quinoline-2-carboxamide

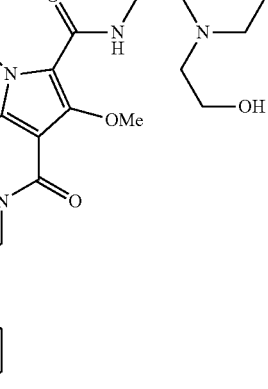

In the same manner as in Example 79, the title compound (47.1 mg, 39%) was obtained as a white powder from the compound of Example 81 (200 mg, 0.399 mmol) and 2-bromoethanol (24.2 µL, 0.341 mmol).

¹H-NMR (300 MHz, DMSO-d₆) δ:1.20-1.75 (6H, br), 2.20-3.10 (5H, br), 3.40-3.65 (4H, br), 3.98-4.05 (3H, br), 4.15-4.50 (4H, br), 5.98 (2H, s), 7.29-7.40 (2H, m), 7.45-7.51 (1H, m), 7.64 (2H, t, J=7.7 Hz), 7.76 (1H, t, J=7.5 Hz), 8.00-8.20 (3H, m), 8.39 (1H, dd, J=8.3, 1.1 Hz).

Example 102

Production of N-{[1-(2-hydroxyethyl)piperidin-3-yl]methyl}-3-methoxy-1-methyl-4-oxo-5-(2-oxo-2-phenylethyl)-4,5-dihydro-1H-pyrrolo[3,2-c]quinoline-2-carboxamide

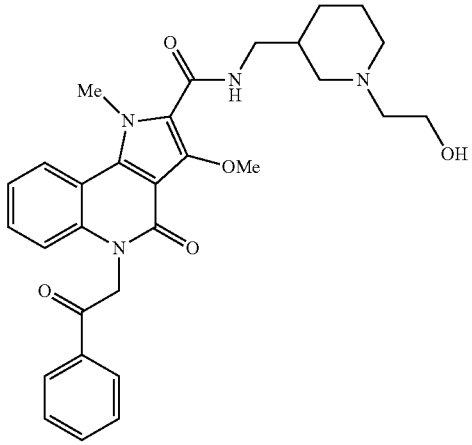 [SMILES: COc1c(C(=O)NCC2CCCN(CCO)C2)n(C)c2c1c(=O)n(CC(=O)c1ccccc1)c1ccccc21]

In the same manner as in Example 79, the title compound (85.2 mg, 50%) was obtained as a white powder from the compound of Example 99 (160 mg, 0.306 mmol) and 2-bromoethanol (65.0 µL, 0.918 mmol).

¹H-NMR (300 MHz, DMSO-d₆) δ:0.90-1.10 (1H, br), 1.35-1.55 (1H, br), 1.55-1.90 (4H, br), 1.96 (1H, t, J=7.1 Hz), 2.36 (2H, t, J=6.3 Hz), 2.72 (1H, d, J=9.9 Hz), 2.83 (1H, d, J=7.5 Hz), 3.15-3.30 (2H, br), 3.45-3.51 (2H, m), 3.99 (3H, s), 4.30-4.34 (4H, m), 5.97 (2H, s), 7.29-7.39 (2H, m), 7.47 (1H, t, J=7.7 Hz), 7.63 (2H, t, J=7.7 Hz), 7.76 (1H, t, J=7.5 Hz), 8.02 (1H, t, J=6.0 Hz), 8.17 (2H, d, J=7.7 Hz), 8.37 (1H, d, J=8.1 Hz).

Example 103

Production of N-(2-aminoethyl)-3-methoxy-N-methyl-4-oxo-5-(2-oxo-2-phenylethyl)-4,5-dihydrothieno[3,2-c]quinoline-2-carboxamide hydrochloride

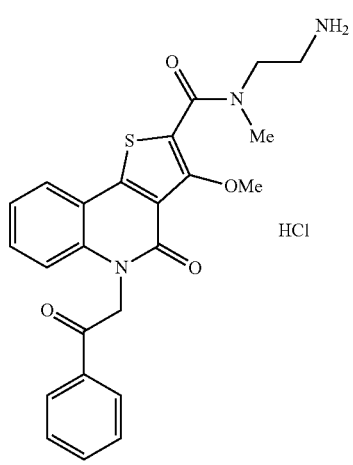 [SMILES: COc1c(C(=O)N(C)CCN)sc2c1c(=O)n(CC(=O)c1ccccc1)c1ccccc21 ; Cl]

To a solution of the compound of Reference Example 7 (300 mg, 0.760 mmol), 1-Boc-amino-2-methylaminoethane hydrochloride (321 mg, 1.52 mmol), triethylamine (154 mg, 1.52 mmol) and HOBt (206 mg, 1.52 mmol) in DMF (10 mL) was added WSCD (290 mg, 1.52 mmol) under ice-cooling, and the mixture was stirred at room temperature for 18 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by silica gel chromatography (eluate; ethyl acetate/hexane=2/1) to give tert-butyl {2-[{[3-methoxy-4-oxo-5-(2-oxo-2-phenylethyl)-4,5-dihydrothieno[3,2-c]quinolin-2-yl]carbonyl}(methyl)amino]ethyl}carbamate (230 mg) as a colorless oil.

A solution of the obtained tert-butyl {2-[{[3-methoxy-4-oxo-5-(2-oxo-2-phenylethyl)-4,5-dihydrothieno[3,2-c]quinolin-2-yl]carbonyl}(methyl)amino]ethyl}carbamate (230 mg) and 4N hydrogen chloride ethyl acetate solution (8 mL) in ethyl acetate (15 mL) was stirred at room temperature for 2 hr. The obtained precipitate was collected by filtration, washed with diethyl ether, and dried under reduced pressure to give the title compound (178 mg, 48%) as a white powder.

¹H-NMR (300 MHz, DMSO-d₆) δ:3.00-3.10 (5H, m), 3.60-3.75 (2H, m), 3.89 (3H, s), 5.99 (2H, s), 7.35 (1H, t, J=7.5 Hz), 7.49 (1H, d, J=8.7 Hz), 7.56 (1H, d, J=7.2 Hz), 7.64 (2H, t, J=7.5 Hz), 7.77 (1H, t, J=7.2 Hz), 7.80-7.98 (4H, m), 8.17 (2H, d, J=7.5 Hz).

Example 104

Production of N-(3-aminopropyl)-3-methoxy-N-methyl-4-oxo-5-(2-oxo-2-phenylethyl)-4,5-dihydrothieno[3,2-c]quinoline-2-carboxamide hydrochloride

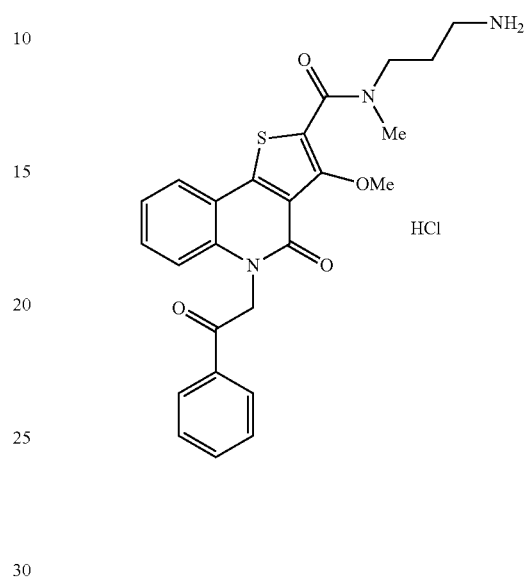

To a solution of the compound of Reference Example 7 (300 mg, 0.760 mmol), 1-Boc-amino-3-methylaminopropane (286 mg, 1.52 mmol) and HOBt (206 mg, 1.52 mmol) in DMF (10 mL) was added WSCD (290 mg, 1.52 mmol) under ice-cooling, and the mixture was stirred at room temperature for 18 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by silica gel chromatography (eluate; ethyl acetate/hexane=2/1) to give tert-butyl {3-[{[3-methoxy-4-oxo-5-(2-oxo-2-phenylethyl)-4,5-dihydrothieno[3,2-c]quinolin-2-yl]carbonyl}(methyl)amino]propyl}carbamate (230 mg) as a white non-crystalline solid.

A solution of the obtained tert-butyl {3-[{[3-methoxy-4-oxo-5-(2-oxo-2-phenylethyl)-4,5-dihydrothieno[3,2-c]quinolin-2-yl]carbonyl}(methyl)amino]propyl}carbamate (230 mg) and 4N hydrogen chloride ethyl acetate solution (8 mL) in ethyl acetate (15 mL) was stirred at room temperature for 2 hr. The obtained precipitate was collected by filtration, washed with diethyl ether, and dried under reduced pressure to give the title compound (216 mg, 54%) as a white powder.

¹H-NMR (300 MHz, CDCl₃) δ:1.80-2.00 (2H, m), 2.70-2.90 (2H, br), 3.06 (3H, s), 3.45-3.60 (2H, m), 3.89 (3H, s), 5.99 (2H, s), 7.35 (1H, t, J=7.5 Hz), 7.48-7.67 (4H, m), 7.75-7.79 (4H, m), 7.97 (1H, d, J=7.8 Hz), 8.17-8.19 (2H, m).

Example 105

Production of 3-methoxy-4-oxo-5-(2-oxo-2-phenyl-ethyl)-N-piperidin-4-yl-4,5-dihydrothieno[3,2-c]quinoline-2-carboxamide hydrochloride

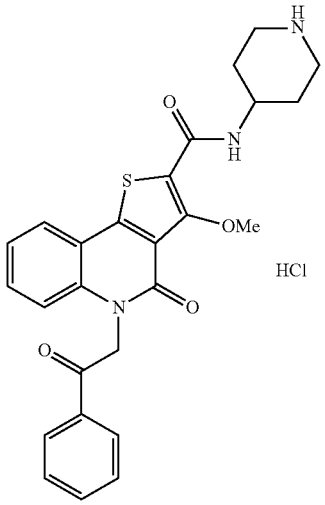 [SMILES: COc1c(C(=O)NC2CCNCC2)sc2c1c(=O)n(CC(=O)c1ccccc1)c1ccccc21 ; Cl]

In the same manner as in Example 73, the title compound (222 mg, 57%) was obtained as a white powder from the compound of Reference Example 7 (300 mg, 0.760 mmol) and 4-amino-1-Boc-piperidine (305 mg, 1.52 mmol).

$^1$H-NMR (300 MHz, DMSO-$d_6$) δ:1.70-1.95 (2H, m), 2.05 (2H, d, J=11.1 Hz), 3.04 (2H, t, J=11.1 Hz), 3.29 (2H, d, J=14.7 Hz), 4.03-4.12 (4H, m), 6.00 (2H, s), 7.35 (1H, t, J=7.5 Hz), 7.49 (1H, d, J=8.4 Hz), 7.59-7.67 (3H, m), 7.77 (1H, t, J=7.5 Hz), 7.90 (1H, d, J=7.2 Hz), 8.05 (1H, dd, J=8.1, 1.2 Hz), 8.18 (2H, d, J=7.5 Hz), 8.70-8.85 (2H, br).

Example 106

Production of N-(2-hydroxyethyl)-3-methoxy-N-methyl-4-oxo-5-(2-oxo-2-phenylethyl)-4,5-dihydrothieno[3,2-c]quinoline-2-carboxamide

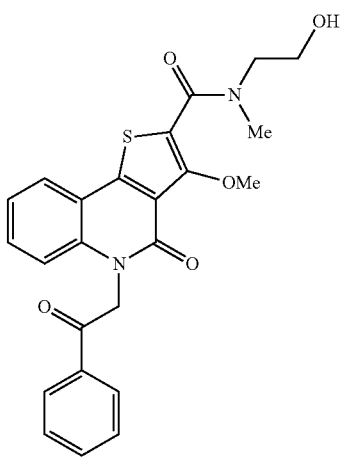 [SMILES: COc1c(C(=O)N(C)CCO)sc2c1c(=O)n(CC(=O)c1ccccc1)c1ccccc21]

In the same manner as in Example 25, the title compound (1.16 g, 68%) was obtained as white crystals from the compound of Reference Example 7 (1.50 g, 3.80 mmol) and N-methyl-2-aminoethanol (428 mg, 5.70 mmol).

$^1$H-NMR (300 MHz, CDCl$_3$) δ:3.00-3.10 (1H, br), 3.21 (3H, s), 3.65-3.80 (2H, br), 3.80-4.00 (2H, br), 4.04 (3H, s), 5.86 (2H, s), 7.03 (1H, d, J=8.4 Hz), 7.26 (1H, t, J=7.5 Hz), 7.47 (1H, td, J=7.8, 1.5 Hz), 7.53-7.59 (2H, m), 7.65-7.71 (1H, m), 7.83 (1H, dd, J=9.0, 1.2 Hz), 8.10-8.13 (2H, m).

Example 107

Production of N-{[1-(2-hydroxyethyl)piperidin-2-yl]methyl}-3-methoxy-4-oxo-5-(2-oxo-2-phenylethyl)-4,5-dihydrothieno[3,2-c]quinoline-2-carboxamide

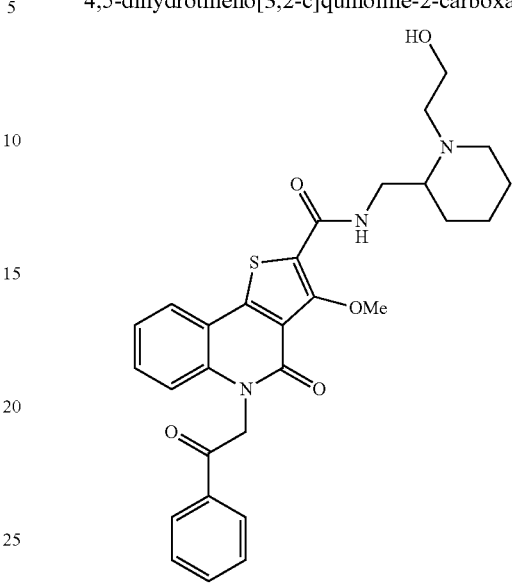

In the same manner as in Example 101, the title compound (29 mg, 29%) was obtained as a white powder from the compound of Example 74 (100 mg, 0.19 mmol).

$^1$H-NMR (300 MHz, DMSO-$d_6$) δ:1.20-1.50 (3H, m), 1.50-1.80 (3H, m), 2.27 (1H, t, J=9.5 Hz), 2.35-2.60 (3H, m), 2.75-2.90 (1H, m), 2.95 (2H, d, J=12.0 Hz), 3.45-3.60 (4H, m), 4.44 (1H, t, J=5.4 Hz), 6.00 (2H, s), 7.35 (1H, t, J=7.5 Hz), 7.49 (1H, d, J=8.4 Hz), 7.57 (1H, d, J=7.2 Hz), 7.64 (2H, t, J=7.5 Hz), 7.77 (1H, t, J=7.5 Hz), 8.05 (1H, d, J=7.2 Hz), 8.10 (1H, t, J=4.2 Hz), 8.18 (2H, d, J=7.2 Hz).

Example 108

Production of N-[1-(2-hydroxyethyl)piperidin-4-yl]-3-methoxy-4-oxo-5-(2-oxo-2-phenylethyl)-4,5-dihydrothieno[3,2-c]quinoline-2-carboxamide

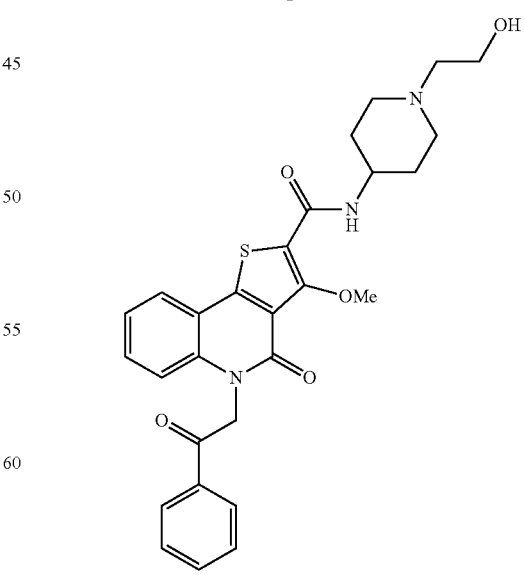

In the same manner as in Example 101, the title compound (41 mg, 27%) was obtained as a white powder from the compound of Example 105 (150 mg, 0.29 mmol).

¹H-NMR (300 MHz, DMSO-d₆) δ:1.55-1.75 (2H, m), 1.84 (2H, d, J=9.6 Hz), 2.18 (2H, t, J=10.2 Hz), 2.37-2.44 (2H, m), 2.77 (2H, d, J=10.8 Hz), 3.46-3.52 (2H, m), 3.75-3.85 (1H, m), 4.04 (3H, s), 4.38 (1H, t, J=5.4 Hz), 6.00 (2H, s), 7.35 (1H, t, J=7.5 Hz), 7.49 (1H, d, J=8.4 Hz), 7.57 (1H, dd, J=7.2, 1.5 Hz), 7.64 (2H, t, J=7.5 Hz), 7.71-7.80 (2H, m), 8.05 (1H, dd, J=7.2, 1.2 Hz), 8.16-8.19 (2H, m).

Example 109

Production of N-(3-hydroxy-2,2-dimethylpropyl)-3-methoxy-1-methyl-4-oxo-5-(2-oxo-2-phenylethyl)-4,5-dihydro-1H-pyrrolo[3,2-c]quinoline-2-carboxamide

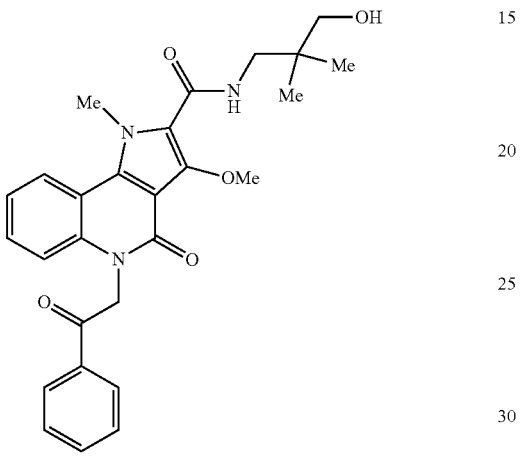

In the same manner as in Example 25, the title compound (190 mg, 62%) was obtained as a white powder from the compound of Reference Example 28 (200 mg, 0.512 mmol) and 3-amino-2,2-dimethyl-1-propanol (66.4 mg, 0.644 mmol).

¹H-NMR (300 MHz, DMSO-d₆) δ:0.88 (6H, s), 3.22-3.24 (4H, m), 4.02 (3H, s), 4.34 (3H, s), 4.78 (1H, t, J=8.3 Hz), 5.98 (2H, s), 7.29-7.40 (2H, m), 7.45-7.51 (1H, m), 7.63 (2H, t, J=7.5 Hz), 7.73-7.79 (1H, m), 8.10-8.19 (3H, m), 8.38 (1H, dd, J=8.4, 1.2 Hz).

Example 110

Production of N-(3-hydroxy-2,2-dimethylpropyl)-3-methoxy-4-oxo-5-(2-oxo-2-phenylethyl)-4,5-dihydrothieno[3,2-c]quinoline-2-carboxamide

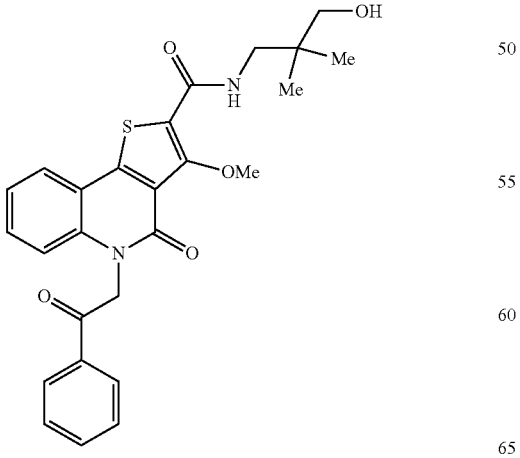

In the same manner as in Example 25, the title compound (251 mg, 69%) was obtained as white crystals from the compound of Reference Example 7 (300 mg, 0.76 mmol) and 3-amino-2,2-dimethyl-1-propanol (118 mg, 1.14 mmol).

¹H-NMR (300 MHz, CDCl₃) δ:0.89 (6H, s), 3.25-3.35 (4H, m), 4.04 (3H, s), 4.99 (1H, t, J=4.8 Hz), 6.00 (2H, s), 7.35 (1H, t, J=7.5 Hz), 7.49 (1H, d, J=8.4 Hz), 7.57 (1H, dd, J=7.2, 1.2 Hz), 7.64 (2H, t, J=7.5 Hz), 7.77 (1H, t, J=7.5 Hz), 8.05 (1H, dd, J=7.2, 1.2 Hz), 8.16-8.19 (2H, m), 8.29 (1H, t, J=5.7 Hz).

Example 111

Production of N-[1-(2-hydroxyethyl)piperidin-4-yl]-3-methoxy-1-methyl-4-oxo-5-(2-oxo-2-phenylethyl)-4,5-dihydro-1H-pyrrolo[3,2-c]quinoline-2-carboxamide hydrochloride

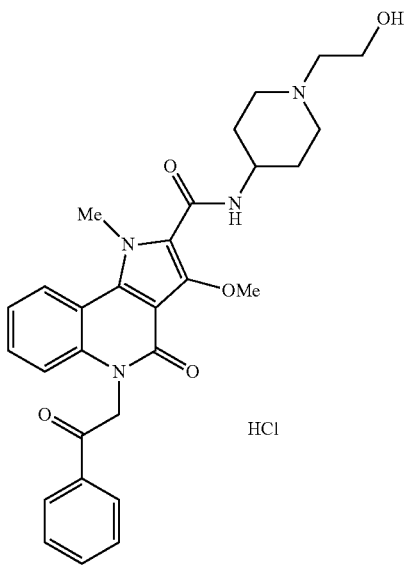 [SMILES: COc1c(C(=O)NC2CCN(CCO)CC2)n(C)c2c1c(=O)n(CC(=O)c1ccccc1)c1ccccc21 ; Cl]

To a solution of the compound of Example 79 (150 mg, 0.290 mmol) in ethyl acetate (4 mL)/ethanol (6 mL) was added 4N hydrogen chloride ethyl acetate solution (80.0 μL). The precipitate was collected by filtration, washed with ethyl acetate, and dried under reduced pressure to give the title compound (72 mg, 45%) as a white powder.

¹H-NMR (300 MHz, DMSO-d₆) δ:1.88-2.20 (4H, br), 3.05-3.65 (6H, br), 3.74-3.82 (2H, br), 3.90-4.15 (4H, br), 4.28 (3H, s), 5.30-5.45 (1H, m), 5.98 (2H, s), 7.29-7.40 (2H, m), 7.46-7.51 (1H, m), 7.64 (2H, t, J=7.5 Hz), 7.76 (1H, t, J=7.4 Hz), 8.09-8.19 (3H, m), 8.37 (1H, d, J=7.5 Hz), 9.75-10.10 (1H, br).

Example 112

Production of N-[2-(diethylamino)ethyl]-3-methoxy-N-methyl-4-oxo-5-(2-oxo-2-phenylethyl)-4,5-dihydrothieno[3,2-c]quinoline-2-carboxamide hydrochloride

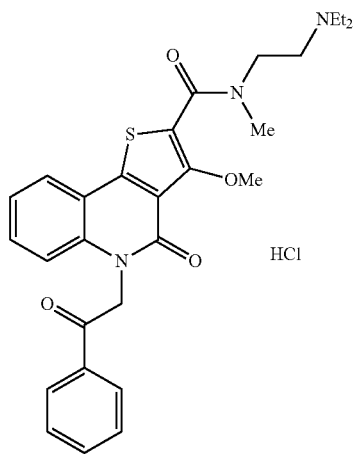

In the same manner as in Example 30, the title compound (289 mg, 82%) was obtained as a white powder from the compound of Reference Example 7 (330 mg, 0.65 mmol) and N,N-diethyl-N'-methylethylenediamine (149 mg, 1.14 mmol).

$^1$H-NMR (300 MHz, DMSO-d$_6$) δ:1.20-1.40 (6H, br), 3.10-3.40 (6H, m), 3.58 (3H, s), 3.84-3.90 (5H, m), 5.99 (2H, s), 7.35 (1H, t, J=7.5 Hz), 7.49 (1H, d, J=8.4 Hz), 7.56 (1H, dd, J=7.2, 1.2 Hz), 7.60-7.67 (2H, m), 7.77 (1H, t, J=7.5 Hz), 7.97 (1H, dd, J=7.2, 1.2 Hz), 8.16-8.19 (2H, m), 10.35-10.60 (1H, br).

Example 113

Production of 3-methoxy-4-oxo-5-(2-oxo-2-phenylethyl)-N-[(2R)-piperidin-2-ylmethyl]-4,5-dihydrothieno[3,2-c]quinoline-2-carboxamide hydrochloride

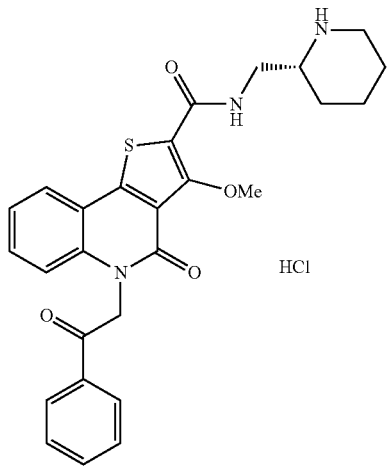 [SMILES: COc1c(C(=O)NC[C@H]2CCCCN2)sc2c1c(=O)n(CC(=O)c1ccccc1)c1ccccc21 ; Cl]

In the same manner as in Example 73, the title compound (166 mg, 60%) was obtained as a white powder from the compound of Reference Example 7 (200 mg, 0.51 mmol) and (R)-2-aminomethyl-1-N-Boc-piperidine (163 mg, 0.76 mmol).

$^1$H-NMR (300 MHz, DMSO-d$_6$) δ:1.40-1.95 (6H, m), 2.75-3.00 (1H, m), 3.25 (2H, d, J=10.8 Hz), 3.49-3.57 (1H, m), 3.63-3.70 (1H, m), 4.07 (3H, s), 6.01 (2H, s), 7.36 (1H, t, J=7.5 Hz), 7.50 (1H, d, J=8.7 Hz), 7.57-7.67 (3H, m), 7.77 (1H, t, J=7.5 Hz), 8.06 (1H, dd, J=7.2, 1.2 Hz), 8.16-8.19 (2H, m), 8.27 (1H, t, J=6.0 Hz), 8.70-8.90 (2H, m).

Example 114

Production of N-(2-hydroxy-2-methylpropyl)-3-methoxy-4-oxo-5-(2-oxo-2-phenylethyl)-4,5-dihydrothieno[3,2-c]quinoline-2-carboxamide

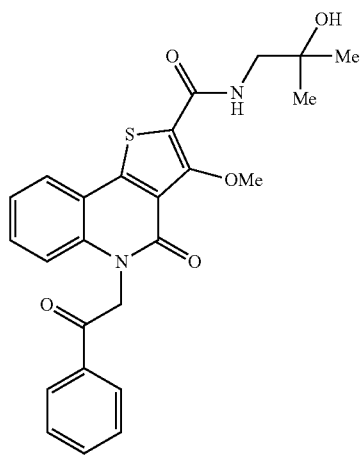 [SMILES: COc1c(C(=O)NCC(C)(C)O)sc2c1c(=O)n(CC(=O)c1ccccc1)c1ccccc21]

In the same manner as in Example 73, the title compound (108 mg, 47%) was obtained as white crystals from the compound of Reference Example 7 (200 mg, 0.51 mmol) and 1-amino-2-methyl-2-propanol (68 mg, 0.76 mmol).

$^1$H-NMR (300 MHz, DMSO-d$_6$) δ:1.16 (6H, s), 3.31 (2H, s), 4.06 (3H, s), 4.77 (1H, s), 6.00 (2H, s), 7.35 (1H, t, J=7.5 Hz), 7.50 (1H, d, J=8.4 Hz), 7.57-7.67 (3H, m), 7.77 (1H, t, J=7.5 Hz), 7.98 (1H, t, J=2.4 Hz), 8.05 (1H, d, J=7.8 Hz), 8.18 (2H, d, J=7.2 Hz).

Example 115

Production of 3-methoxy-N-methyl-N-{2-[(1-methylethyl)amino]ethyl}-4-oxo-5-(2-oxo-2-phenylethyl)-4,5-dihydrothieno[3,2-c]quinoline-2-carboxamide hydrochloride

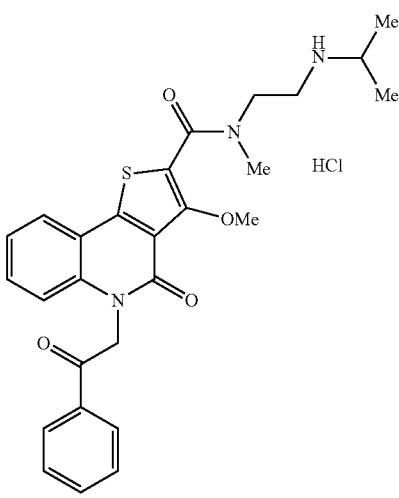 [SMILES: COc1c(C(=O)N(C)CCNC(C)C)sc2c1c(=O)n(CC(=O)c1ccccc1)c1ccccc21 ; Cl]

To a solution of the compound of Example 103 (130 mg, 0.27 mmol), acetone (155 mg, 2.67 mmol) and acetic acid (0.1 mL) in THF (5 mL) was added sodium triacetoxyborohydride (113 mg, 0.54 mmol), and the mixture was stirred at room temperature for 18 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by aminosilica gel chromatography (eluate; ethyl acetate) to give a colorless oil (0.09 g). To a solution of the obtained colorless oil in ethyl acetate (5 mL) was added 4N hydrogen chloride ethyl acetate solution (0.1 mL). The precipitate was collected by filtration, washed with ethyl acetate, and dried under reduced pressure to give the title compound (73.0 mg, 52%) as a white powder.

$^1$H-NMR (300 MHz, DMSO-$d_6$) δ:1.15-1.35 (6H, br), 3.05-3.25 (5H, m), 3.30-3.40 (1H, m), 3.76 (2H, br t, J=6.6 Hz), 3.90 (3H, s), 5.99 (2H, s), 7.35 (1H, t, J=7.5 Hz), 7.49 (1H, t, J=8.1 Hz), 7.56 (1H, dd, J=7.2, 1.2 Hz), 7.60-7.67 (2H, m), 7.77 (1H, t, J=7.5 Hz), 7.98 (1H, dd, J=7.2, 1.2 Hz), 8.16-8.19 (2H, m), 8.50-8.80 (2H, br).

Example 116

Production of 3-methoxy-N-methyl-N-{3-[(1-methylethyl)amino]propyl}-4-oxo-5-(2-oxo-2-phenylethyl)-4,5-dihydrothieno[3,2-c]quinoline-2-carboxamide hydrochloride

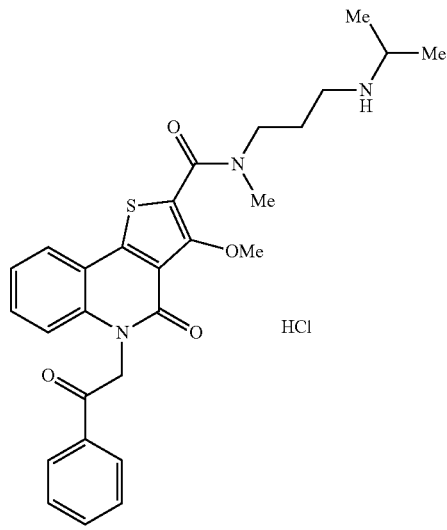 [SMILES: COc1c(C(=O)N(C)CCCNC(C)C)sc2c1c(=O)n(CC(=O)c1ccccc1)c1ccccc21 ; Cl]

In the same manner as in Example 115, the title compound (118 mg, 73%) was obtained as a white powder from the compound of Example 104 (150 mg, 0.30 mmol).

$^1$H-NMR (300 MHz, DMSO-$d_6$) δ:1.10-1.35 (6H, br), 1.85-2.05 (2H, br), 2.70-3.00 (2H, br), 3.07 (3H, s), 3.20-3.40 (1H, m), 3.45-3.60 (2H, m), 3.90 (3H, s), 5.99 (2H, s), 7.35 (1H, t, J=7.5 Hz), 7.49 (1H, d, J=8.4 Hz), 7.56 (1H, dd, J=6.9, 1.2 Hz), 7.62-7.67 (2H, m), 7.77 (1H, t, J=7.5 Hz), 7.97 (1H, dd, J=7.2, 1.2 Hz), 8.16-8.19 (2H, m), 8.65-8.80 (2H, br).

Example 117

Production of N-{2-[ethyl(2-hydroxyethyl)amino]ethyl}-3-methoxy-N-methyl-4-oxo-5-(2-oxo-2-phenylethyl)-4,5-dihydrothieno[3,2-c]quinoline-2-carboxamide hydrochloride

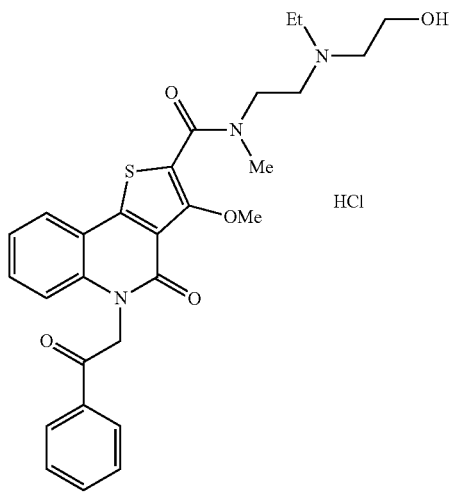 [SMILES: CCN(CCO)CCN(C)C(=O)c1sc2c(c1OC)c(=O)n(CC(=O)c1ccccc1)c1ccccc21 ; Cl]

To a solution of the compound of Example 106 (1.0 g, 2.21 mmol) and triethylamine (269 mg, 2.66 mmol) in dichloromethane (20 mL) was added methanesulfonyl chloride (279 mg, 2.44 mmol) under ice-cooling, and the mixture was stirred at room temperature for 18 hr. The reaction mixture was diluted with water, and extracted with ethyl acetate. The extract was washed with brine, dried over magnesium sulfate, and concentrated under reduced pressure to give N-(2-chloroethyl)-3-methoxy-N-methyl-4-oxo-5-(2-oxo-2-phenylethyl)-4,5-dihydrothieno[3,2-c]quinoline-2-carboxamide (1.01 g) as a white non-crystalline solid.

A solution of the obtained N-(2-chloroethyl)-3-methoxy-N-methyl-4-oxo-5-(2-oxo-2-phenylethyl)-4,5-dihydrothieno[3,2-c]quinoline-2-carboxamide (200 mg, 0.43 mmol), N-ethylaminoethanol (228 mg, 2.55 mmol), diisopropylethylamine (330 mg, 2.55 mmol) and sodium iodide (64 mg, 0.43 mmol) in 1-butanol (5 mL) was stirred at 110° C. for 18 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by aminosilica gel chromatography (eluate; ethyl acetate to ethyl acetate/methanol=20/1) to give N-{2-[ethyl(2-hydroxyethyl)amino]ethyl}-3-methoxy-N-methyl-4-oxo-5-(2-oxo-2-phenylethyl)-4,5-dihydrothieno[3,2-c]quinoline-2-carboxamide (0.08 g) as a white non-crystalline solid.

$^1$H-NMR (300 MHz, CDCl$_3$) δ:1.00-1.15 (0.75H, br), 1.20-1.35 (2.25H, m), 2.20-2.90 (4H, m), 3.16 (0.75H, s), 3.20 (2.25H, s), 3.50-3.95 (6H, m), 4.02-4.04 (3H, m), 5.85 (2H, s), 7.03 (1H, d, J=8.4 Hz), 7.23-7.28 (1H, m), 7.45 (1H, t, J=7.5 Hz), 7.55 (2H, t, J=7.5 Hz), 7.64-7.69 (1H, m), 7.80-7.84 (1H, m), 8.09-8.12 (2H, m).

To a solution of the obtained white non-crystalline solid in ethyl acetate (5 mL) was added 4N hydrogen chloride ethyl acetate solution (0.1 mL). The precipitate was collected by filtration, washed with ethyl acetate, and dried under reduced pressure to give the title compound (7 mg, 5%) as a white powder.

Example 118

Production of N-(trans-4-hydroxycyclohexyl)-3-methoxy-1-methyl-4-oxo-5-(2-oxo-2-phenylethyl)-4,5-dihydro-1H-pyrrolo[3,2-c]quinoline-2-carboxamide

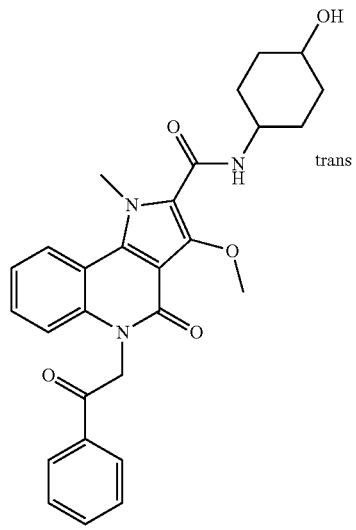

In the same manner as in Example 25, the title compound (230 mg, 95%) was obtained as a white powder from the compound of Reference Example 28 (200 mg, 0.512 mmol) and trans-4-aminocyclohexanol (74.2 mg, 0.644 mmol).

$^1$H-NMR (300 MHz, DMSO-$d_6$) δ:1.22-1.44 (4H, m), 1.83-1.92 (4H, m), 3.40-3.55 (1H, br), 3.68-3.85 (1H, br), 3.96 (3H, s), 4.30 (3H, s), 4.57 (1H, d, J=4.2 Hz), 5.96 (2H, s), 7.28-7.38 (2H, m), 7.44-7.50 (1H, m), 7.63 (2H, t, J=7.5 Hz), 7.73-7.79 (2H, m), 8.15-8.18 (2H, m), 8.36 (1H, dd, J=8.3, 1.1 Hz).

Example 119

Production of N-(1-benzylpiperidin-4-yl)-3-methoxy-5-(4-methoxybenzyl)-4-oxo-4,5-dihydrothieno[3,2-c]quinoline-2-carboxamide

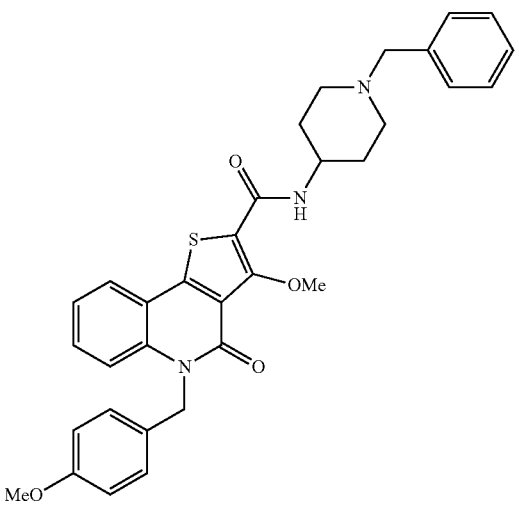 [SMILES: COc1ccc(Cn2c(=O)c3c(OC)c(C(=O)NC4CCN(Cc5ccccc5)CC4)sc3c3ccccc32)cc1]

In the same manner as in Example 25, the title compound (1.17 g, 82%) was obtained as white crystals from the compound of Reference Example 13 (1.0 g, 2.52 mmol) and 4-amino-1-benzylpiperidine (720 mg, 3.78 mmol).

$^1$H-NMR (300 MHz, DMSO-$d_6$) δ:1.55-1.75 (2H, m), 1.80-1.95 (2H, br d), 2.17 (2H, t, J=10.2 Hz), 2.65-2.80 (2H, br d), 3.50 (2H, s), 3.70 (3H, s), 3.80-3.90 (1H, br), 4.08 (3H, s), 5.53 (2H, br s), 6.85-6.88 (2H, m), 7.20 (2H, d, J=8.7 Hz), 7.25-7.34 (5H, m), 7.49-7.56 (2H, m), 7.74 (1H, d, J=7.8 Hz), 8.00 (1H, dd, J=8.1, 1.2 Hz).

Example 120

Production of N-{[3-methoxy-4-oxo-5-(2-oxo-2-phenylethyl)-4,5-dihydrothieno[3,2-c]quinolin-2-yl]carbonyl}-N-methylglycine ethyl ester

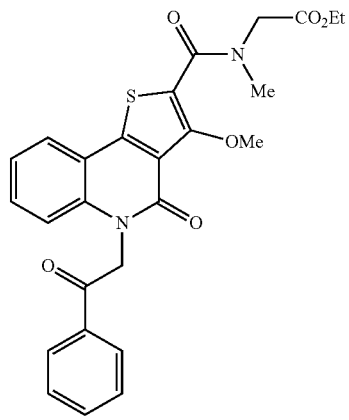 [SMILES: CCOC(=O)CN(C)C(=O)c1sc2c(c1OC)c(=O)n(CC(=O)c1ccccc1)c1ccccc21]

In the same manner as in Example 25, the title compound (400 mg, 91%) was obtained as a white solid from the compound of Example 7 (350 mg, 0.89 mmol) and sarcosine ethyl ester hydrochloride (204 mg, 1.33 mmol).

$^1$H-NMR (300 MHz, CDCl$_3$) δ:1.24-1.35 (3H, m), 3.19 (1.2H, br s), 3.24 (1.8H, s), 3.98 (1.2H, br s), 4.08 (1.8H, s), 4.15-4.30 (4H, m), 5.86 (2H, s), 7.03 (1H, d, J=8.7 Hz), 7.24-7.29 (1H, m), 7.43-7.49 (1H, m), 7.53-7.58 (2H, m), 7.65-7.70 (1H, m), 7.83 (1H, dd, J=7.8, 1.2 Hz), 8.10-8.13 (2H, m).

Example 121

Production of N-[2-(diethylamino)ethyl]-3-methoxy-N-methyl-4-oxo-4,5-dihydrothieno[3,2-c]quinoline-2-carboxamide

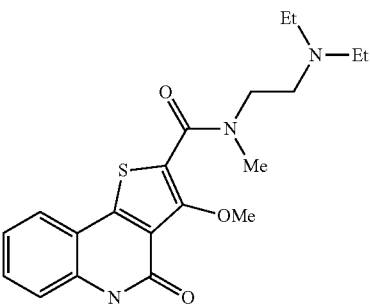

A mixture of the compound of Example 48 (4.10 g, 8.08 mol), trifluoroacetic acid (34 mL) and trifluoromethanesulfonic acid (6.6 mL) was stirred at room temperature for 5 hr and at 80° C. for 2.5 hr. After cooling, the reaction mixture was concentrated under reduced pressure, and ethyl acetate and 1N aqueous sodium hydroxide solution were added to the residue. The mixture was extracted with ethyl acetate and the extract was washed successively with water and brine, dried over magnesium sulfate, and concentrated under reduced pressure. The residue was purified by aminosilica gel chromatography (eluate; ethyl acetate/hexane=1/2) to give the title compound (1.50 g, 48%) as a white powder.

$^1$H-NMR (300 MHz, DMSO-$d_6$) δ:0.70-1.10 (6H, br), 2.20-2.70 (6H, br), 3.05 (3H, s), 3.40-3.60 (2H, br), 3.91 (3H, s), 7.21-7.26 (1H, m), 7.38-7.41 (1H, m), 7.49-7.55 (1H, m), 7.82-7.85 (1H, m), 11.75 (1H, s).

Example 122

Production of [2-{[2-(diethylamino)ethyl](methyl)carbamoyl}-3-methoxy-4-oxothieno[3,2-c]quinolin-5(4H)-yl]acetic acid

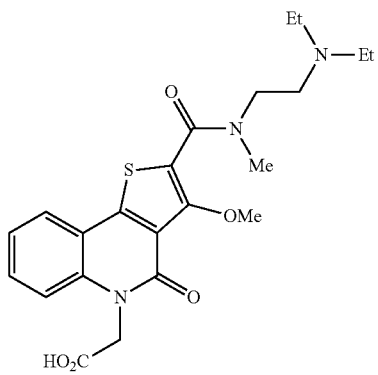 [SMILES: CCN(CC)CCN(C)C(=O)c1sc2c(c1OC)c(=O)n(CC(=O)O)c1ccccc21]

A solution of the compound of Example 53 (670 mg, 1.41 mmol) and 8N aqueous sodium hydroxide solution (1.0 mL) in ethanol (7.0 mL) was stirred at room temperature for 15 hr. The reaction mixture was neutralized with 1N hydrochloric acid, and concentrated under reduced pressure. THF was added to the residue and, after filtration, the filtrate was concentrated under reduced pressure to give the title compound (580 mg, 92%) as a pale-yellow solid.

$^1$H-NMR (300 MHz, DMSO-$d_6$) δ:1.10-1.35 (6H, br), 2.70-3.30 (9H, m), 3.70-3.85 (2H, br), 3.91 (3H, s), 5.06 (2H, s), 7.34 (1H, t, J=7.7 Hz), 7.48 (1H, d, J=8.2 Hz), 7.62 (1H, t, J=8.2 Hz), 7.94 (1H, d, J=7.7 Hz).

Example 123

Production of 2-[4-({[3-methoxy-1-methyl-4-oxo-5-(2-oxo-2-phenylethyl)-4,5-dihydro-1H-pyrrolo[3,2-c]quinolin-2-yl]carbonyl}amino)piperidin-1-yl]-2-oxoethyl acetate

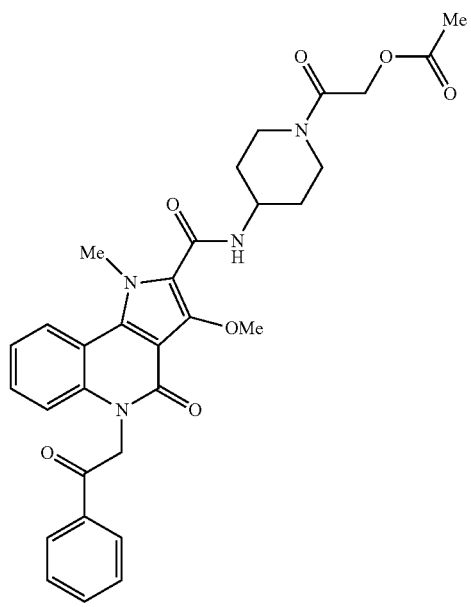 [SMILES: COc1c(C(=O)NC2CCN(C(=O)COC(C)=O)CC2)n(C)c2c1c(=O)n(CC(=O)c1ccccc1)c1ccccc21]

To a mixture of the compound of Example 77 (200 mg, 0.423 mmol), triethylamine (122 μL, 0.880 mmol) and THF (10 mL) was added acetoxyacetyl chloride (47.3 μL, 0.440 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate), and the obtained solid was recrystallized from ethyl acetate-THF to give the title compound (171 mg, 75%) as a white powder.

$^1$H-NMR (300 MHz, DMSO-$d_6$) δ:1.35-1.70 (2H, m), 1.80-2.00 (2H, m), 2.08 (3H, s), 2.80-3.00 (1H, m), 3.10-3.25 (1H, m), 3.60-3.80 (1H, m), 3.97 (3H, s), 4.00-4.25 (2H, m), 4.31 (3H, s), 4.80 (2H, d, J=1.8 Hz), 5.97 (2H, s), 7.29-7.39 (2H, m), 7.45-7.50 (1H, m), 7.63 (2H, t, J=7.5 Hz), 7.73-7.79 (1H, m), 7.98 (1H, d, J=7.8 Hz), 8.16-8.18 (2H, m), 8.37 (1H, dd, J=8.4, 1.2 Hz).

Example 124

Production of N-[1-(hydroxyacetyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

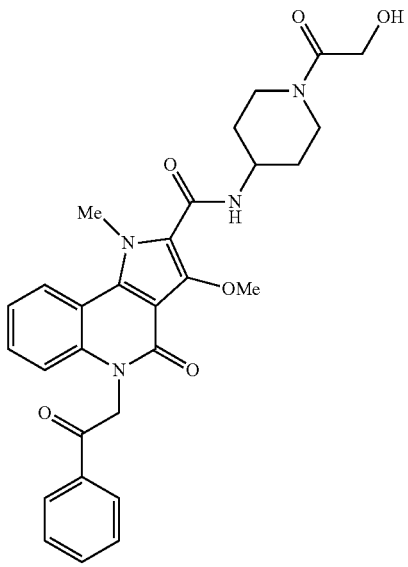 [SMILES: COc1c(C(=O)NC2CCN(C(=O)CO)CC2)n(C)c2c1c(=O)n(CC(=O)c1ccccc1)c1ccccc21]

1) A mixed solution of the compound of Example 123 (125 mg, 0.218 mmol) and 8N aqueous sodium hydroxide solution (1 mL) in THF (2 mL)-ethanol (7 mL) was stirred at room temperature for 2 hr. The reaction mixture was diluted with water, acidified with 6N hydrochloric acid (1.5 mL), and extracted twice with ethyl acetate. The extract was combined, washed with saturated brine, dried over magnesium sulfate and concentrated under reduced pressure. The residue was purified by aminosilica gel chromatography (eluate; ethyl acetate), and the obtained solid was recrystallized from ethyl acetate-THF to give the title compound (59.2 mg, 51%) as white crystals.

$^1$H-NMR (300 MHz, DMSO-$d_6$) δ:1.35-1.65 (2H, m), 1.80-2.00 (2H, m), 2.85-3.00 (1H, m), 3.05-3.25 (1H, m), 3.60-3.75 (1H, m), 3.97 (3H, s), 4.00-4.30 (4H, m), 4.31 (3H, s), 4.51 (1H, t, J=5.3 Hz), 5.97 (2H, s), 7.29-7.39 (2H, m), 7.48 (1H, t, J=7.6 Hz), 7.63 (2H, t, J=7.6 Hz), 7.76 (1H, t, J=7.4 Hz), 7.95 (1H, d, J=8.4 Hz), 8.17 (2H, d, J=7.6 Hz), 8.37 (1H, d, J=8.1 Hz)

2) The white powder was recrystallized from ethanol-water to give the title compound as white crystals. melting point: 224° C. .

Example 125

Production of tert-butyl 4-({[3-methoxy-1,6-dimethyl-4-oxo-5-(2-oxo-2-phenylethyl)-4,5-dihydro-1H-pyrrolo[3,2-c]pyridin-2-yl]carbonyl}amino)piperidine-1-carboxylate

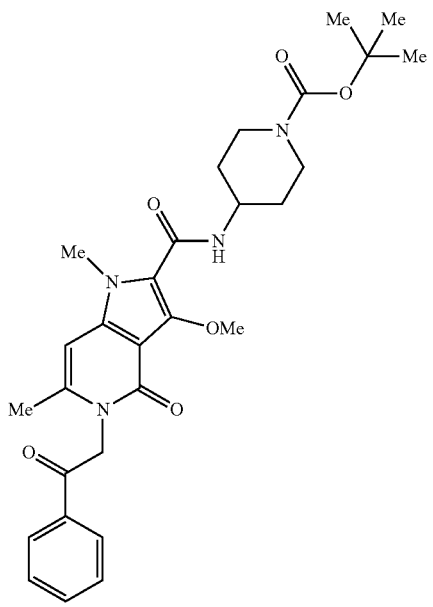 [SMILES: COc1c(C(=O)NC2CCN(C(=O)OC(C)(C)C)CC2)n(C)c2cc(C)n(CC(=O)c3ccccc3)c(=O)c12]

In the same manner as in Example 25, the title compound (315 mg, 72%) was obtained as a white powder from the compound of Reference Example 35 (290 mg, 0.818 mmol) and 4-amino-1-Boc-piperidine (212 mg, 1.06 mmol).

$^{1}$H-NMR (300 MHz, DMSO-$d_6$) δ:1.29-1.51 (11H, m), 1.75-1.90 (2H, m), 2.28 (3H, s), 2.86-3.05 (2H, m), 3.77-3.90 (5H, m), 3.92-4.04 (4H, m), 5.62 (2H, s), 6.58 (1H, s), 7.55-7.66 (3H, m), 7.73 (1H, d, J=6.6 Hz), 8.11 (2H, d, J=7.7 Hz).

Example 126

Production of 3-methoxy-1,6-dimethyl-4-oxo-5-(2-oxo-2-phenylethyl)-N-piperidin-4-yl-4,5-dihydro-1H-pyrrolo[3,2-C]pyridine-2-carboxamide hydrochloride

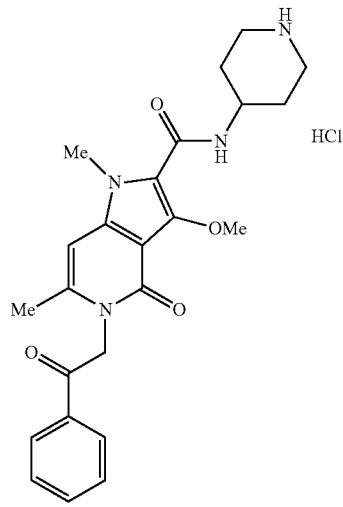 [SMILES: COc1c(C(=O)NC2CCNCC2)n(C)c2cc(C)n(CC(=O)c3ccccc3)c(=O)c12 ; Cl]

To a mixture of the compound of Example 125 (300 mg, 0.559 mmol) and ethyl acetate (4 mL) was added 4N hydrogen chloride ethyl acetate solution (4 mL), and the mixture was stirred at room temperature for 2 hr. The precipitated solid was collected by filtration, and washed with ethyl acetate to give the title compound (240 mg, 91%) as a white powder.

$^{1}$H-NMR (300 MHz, DMSO-$d_6$) δ:1.61-1.84 (2H, m), 1.95-2.11 (2H, m), 2.28 (3H, s), 2.92-3.12 (2H, m), 3.20-3.32 (2H, m), 3.83 (3H, s), 3.94-4.15 (4H, m), 5.62 (2H, s), 6.59 (1H, s), 7.61 (2H, t, J=7.6 Hz), 7.68-7.81 (2H, m), 8.04-8.19 (2H, m), 8.64 (1H, br s), 8.87 (1H, br s).

Example 127

Production of 2-[4-({[3-methoxy-1,6-dimethyl-4-oxo-5-(2-oxo-2-phenylethyl)-4,5-dihydro-1H-pyrrolo[3,2-c]pyridin-2-yl]carbonyl}amino)piperidin-1-yl]-2-oxoethyl acetate

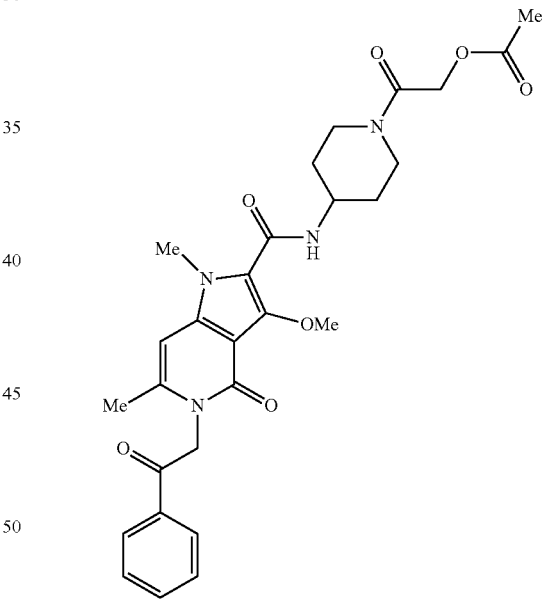

In the same manner as in Example 123, the title compound (210 mg, 82%) was obtained as a white powder from the compound of Example 126 (225 mg, 0.476 mmol) and acetoxyacetyl chloride (61.4 μL, 0.571 mmol).

$^{1}$H-NMR (300 MHz, DMSO-$d_6$) δ:1.26-1.64 (2H, m), 1.78-1.97 (2H, m), 2.09 (3H, s), 2.28 (3H, s), 2.79-2.97 (1H, m), 3.09-3.25 (1H, m), 3.58-3.74 (1H, m), 3.86 (3H, s), 3.95-4.20 (5H, m), 4.79 (2H, s), 5.62 (2H, s), 6.58 (1H, s), 7.55-7.68 (3H, m), 7.69-7.78 (1H, m), 8.06-8.15 (2H, m).

Example 128

Production of N-[1-(hydroxyacetyl)piperidin-4-yl]-3-methoxy-1,6-dimethyl-4-oxo-5-(2-oxo-2-phenylethyl)-4,5-dihydro-1H-pyrrolo[3,2-c]pyridine-2-carboxamide

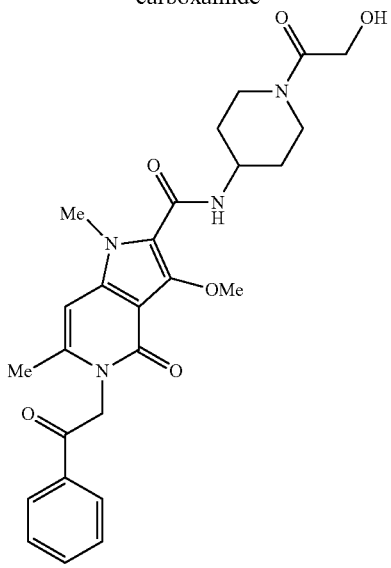

In the same manner as in Example 124, the title compound (156 mg, 85%) was obtained as a white powder from the compound of Example 127 (200 mg, 0.373 mmol), 8N aqueous sodium hydroxide solution (0.5 mL), THF (2.5 mL) and ethanol (5 mL).

$^1$H-NMR (300 MHz, DMSO-d$_6$) δ:1.32-1.61 (2H, m), 1.79-1.93 (2H, m), 2.28 (3H, s), 2.82-2.98 (1H, m), 3.04-3.20 (1H, m), 3.57-3.71 (1H, m), 3.86 (3H, s), 3.96-4.25 (7H, m), 4.50 (1H, d, J=5.3 Hz), 5.61 (2H, s), 6.58 (1H, s), 7.55-7.67 (3H, m), 7.69-7.78 (1H, m), 8.07-8.16 (2H, m).

Example 129

Production of tert-butyl 4-({[6-ethyl-3-methoxy-1-methyl-4-oxo-5-(2-oxo-2-phenylethyl)-4,5-dihydro-1H-pyrrolo[3,2-c]pyridin-2-yl]carbonyl}amino)piperidine-1-carboxylate

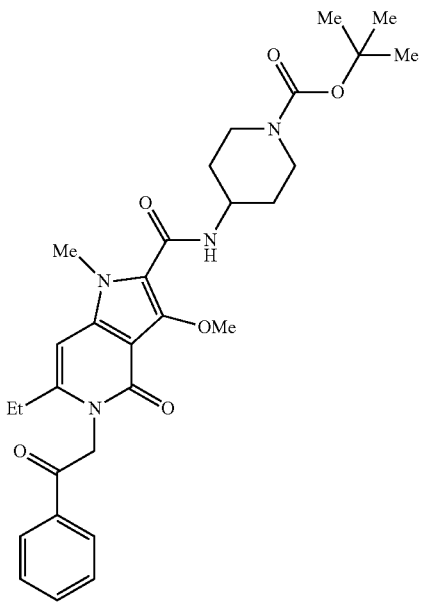 [SMILES: CCc1cc2c(c(OC)c(C(=O)NC3CCN(C(=O)OC(C)(C)C)CC3)n2C)c(=O)n1CC(=O)c1ccccc1]

In the same manner as in Example 25, the title compound (126 mg, 84%) was obtained as a white powder from the compound of Reference Example 42 (100 mg, 0.271 mmol) and 4-amino-1-Boc-piperidine (70.7 mg, 0.353 mmol).

$^1$H-NMR (300 MHz, DMSO-d$_6$) δ:1.18 (3H, t, J=7.3 Hz), 1.32-1.51 (11H, m), 1.74-1.89 (2H, m), 2.58 (2H, q, J=7.5 Hz), 2.85-3.04 (2H, m), 3.77-3.91 (5H, m), 3.91-4.05 (4H, m), 5.59 (2H, s), 6.49 (1H, s), 7.55-7.67 (3H, m), 7.69-7.79 (1H, m), 8.06-8.16 (2H, m).

Example 130

Production of 6-ethyl-3-methoxy-1-methyl-4-oxo-5-(2-oxo-2-phenylethyl)-N-piperidin-4-yl-4,5-dihydro-1H-pyrrolo[3,2-c]pyridine-2-carboxamide hydrochloride

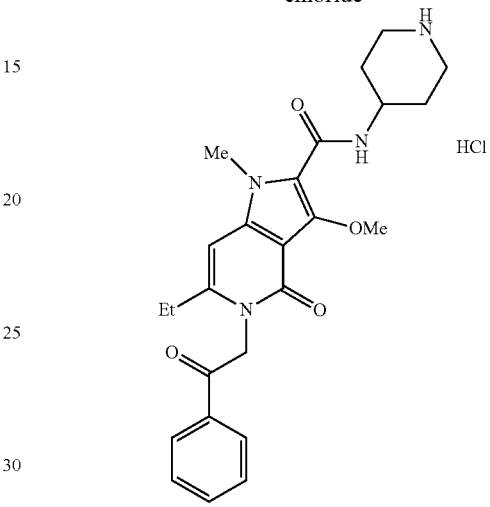

A solution of the compound of Example 129 (115 mg, 0.209 mmol) and 4N hydrogen chloride ethyl acetate solution (4 mL) in ethyl acetate (4 mL) was stirred at room temperature for 3 hr. The precipitated solid was collected by filtration, and washed with ethyl acetate to give the title compound.

Example 131

Production of 6-ethyl-N-[1-(hydroxyacetyl)piperidin-4-yl]-3-methoxy-1-methyl-4-oxo-5-(2-oxo-2-phenylethyl)-4,5-dihydro-1H-pyrrolo[3,2-c]pyridine-2-carboxamide

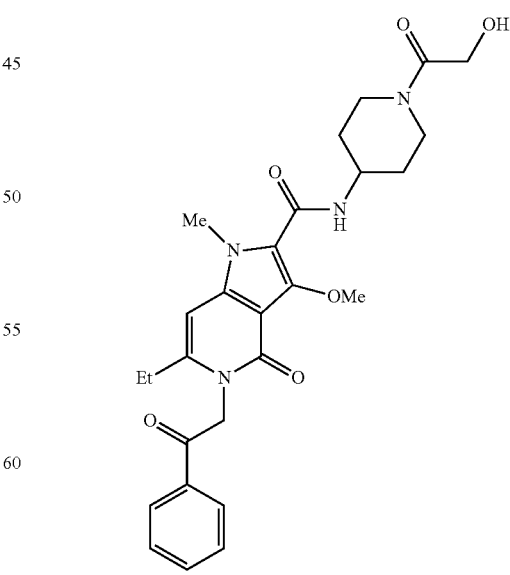

To a mixture of the compound of Example 130 (90.0 mg, 0.185 mmol), triethylamine (76.9 μL, 0.555 mmol) and THF (5 mL) was added acetoxyacetyl chloride (23.8 μL, 0.221 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate), and the obtained solid was dissolved in THF (1.2 mL)-ethanol (2.5 mL). 8N Aqueous sodium hydroxide solution (250 μL) was added, and the mixture was stirred at room temperature for 2 hr. The reaction mixture was diluted with water, acidified with 6N hydrochloric acid (0.5 mL), and extracted twice with ethyl acetate. The extract was combined, washed with saturated brine, dried over magnesium sulfate and concentrated under reduced pressure. The residue was purified by aminosilica gel chromatography (eluate; ethyl acetate/methanol=10/0-9/1), and the obtained solid was recrystallized from ethyl acetate to give the title compound (61.2 mg, 65%) as white crystals.

$^1$H-NMR (300 MHz, DMSO-$d_6$) δ:1.13-1.23 (3H, m), 1.31-1.59 (2H, m), 1.80-1.94 (2H, m), 2.58 (2H, q, J=7.4 Hz), 2.83-2.99 (1H, m), 3.04-3.21 (1H, m), 3.59-3.70 (1H, m), 3.89 (3H, s), 3.97-4.26 (7H, m), 4.49 (1H, t, J=5.4 Hz), 5.59 (2H, s), 6.49 (1H, s), 7.56-7.67 (3H, m), 7.70-7.78 (1H, m), 8.06-8.15 (2H, m).

Example 132

Production of 3-ethoxy-N-(2-hydroxy-2-methylpropyl)-1,6-dimethyl-4-oxo-5-(2-oxo-2-phenylethyl)-4,5-dihydro-1H-pyrrolo[3,2-c]pyridine-2-carboxamide

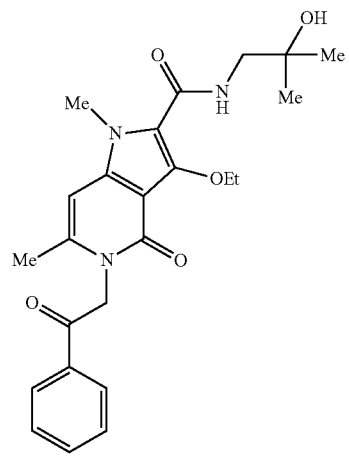 [SMILES: CCOc1c(C(=O)NCC(C)(C)O)n(C)c2cc(C)n(CC(=O)c3ccccc3)c(=O)c12]

In the same manner as in Example 25, the title compound (65.8 mg, 67%) was obtained as a white powder from the compound of Reference Example 44 (100 mg, 0.271 mmol) and 1-amino-2-methylpropan-2-ol (31.5 mg, 0.353 mmol).

$^1$H-NMR (300 MHz, DMSO-$d_6$) δ:1.13 (6H, s), 1.31 (3H, t, J=7.0 Hz), 2.28 (3H, s), 3.24 (2H, d, J=5.5 Hz), 3.90 (3H, s), 4.35 (2H, q, J=7.0 Hz), 4.66 (1H, s), 5.61 (2H, s), 6.59 (1H, S), 7.61 (2H, t, J=7.6 Hz), 7.69-7.79 (1H, m), 7.93 (1H, t, J=5.6 Hz), 8.06-8.15 (2H, m).

Example 133

Production of 3-ethoxy-1,6-dimethyl-4-oxo-5-(2-oxo-2-phenylethyl)-N-piperidin-4-yl-4,5-dihydro-1H-pyrrolo[3,2-c]pyridine-2-carboxamide hydrochloride

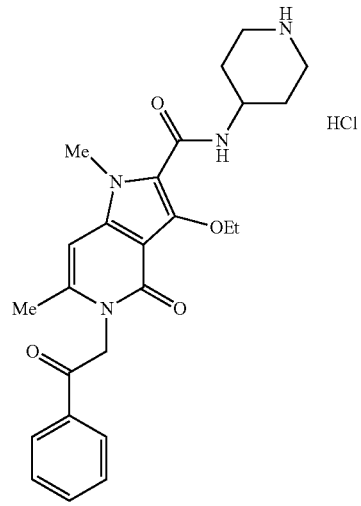 [SMILES: CCOc1c(C(=O)NC2CCNCC2)n(C)c2cc(C)n(CC(=O)c3ccccc3)c(=O)c12 ; Cl]

In the same manner as in Example 73, the title compound (303 mg, 95%) was obtained as a white powder from the compound of Reference Example 44 (250 mg, 0.679 mmol) and 4-amino-1-Boc-piperidine (177 mg, 0.882 mmol).

$^1$H-NMR (300 MHz, DMSO-$d_6$) δ:1.28 (3H, t, J=7.1 Hz), 1.61-1.81 (2H, m), 1.97-2.12 (2H, m), 2.28 (3H, s), 2.94-3.10 (2H, m), 3.21-3.32 (2H, m), 3.85 (3H, s), 3.97-4.14 (1H, m), 4.34 (2H, q, J=7.0 Hz), 5.62 (2H, s), 6.59 (1H, s), 7.61 (2H, t, J=7.6 Hz), 7.69-7.81 (2H, m), 8.04-8.17 (2H, m), 8.85 (2H, br s).

Example 134

Production of N-(2-hydroxy-2-methylpropyl)-3-methoxy-1,6-dimethyl-4-oxo-5-(2-oxo-2-phenylethyl)-4,5-dihydro-1H-pyrrolo[3,2-c]pyridine-2-carboxamide

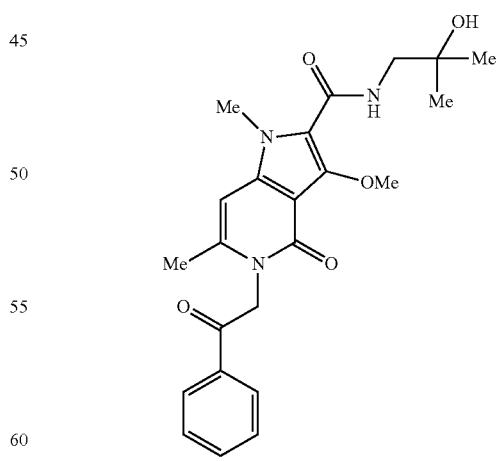

In the same manner as in Example 25, the title compound (201 mg, 84%) was obtained as a white powder from the compound of Reference Example 35 (200 mg, 0.564 mmol) and 1-amino-2-methylpropan-2-ol (65.4 mg, 0.734 mmol).

$^1$H-NMR (300 MHz, DMSO-$d_6$) δ:1.13 (6H, s), 2.29 (3H, s), 3.24 (2H, d, J=5.7 Hz), 3.89 (3H, s), 4.02 (3H, s), 4.65 (1H, s), 5.62 (2H, s), 6.59 (1H, s), 7.56-7.66 (2H, m), 7.69-7.78 (1H, m), 7.85 (1H, t, J=5.7 Hz), 8.06-8.15 (2H, m).

Example 135

Production of 3-methoxy-1,6-dimethyl-4-oxo-5-(2-oxo-2-phenylethyl)-N-(1-pyridin-4-ylpiperidin-4-yl)-4,5-dihydro-1H-pyrrolo[3,2-c]pyridine-2-carboxamide

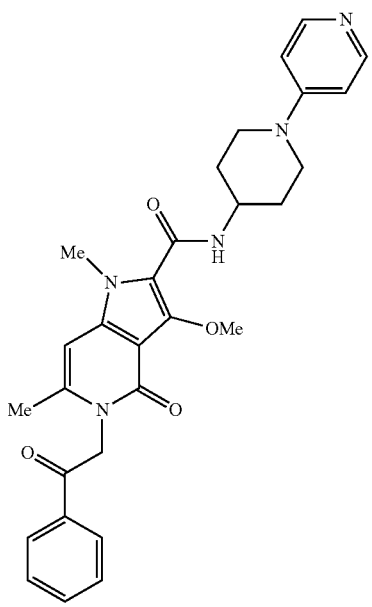 [SMILES: COc1c(C(=O)NC2CCN(c3ccncc3)CC2)n(C)c2cc(C)n(CC(=O)c3ccccc3)c(=O)c12]

In the same manner as in Example 25, the title compound (656 mg, 91%) was obtained as a white powder from the compound of Reference Example 35 (500 mg, 1.41 mmol) and 1-pyridin-4-ylpiperidin-4-amine (388 mg, 1.55 mmol).

$^1$H-NMR (300 MHz, DMSO-$d_6$) δ:1.48-1.65 (2H, m), 1.85-1.97 (2H, m), 2.28 (3H, s), 2.98-3.14 (2H, m), 3.77-3.90 (5H, m), 3.98 (3H, s), 4.01-4.15 (1H, m), 5.61 (2H, s), 6.58 (1H, s), 6.82 (2H, d, J=1.5 Hz), 7.56-7.68 (3H, m), 7.70-7.78 (1H, m), 8.05-8.20 (4H, m).

Example 136

Production of 3-ethoxy-N-[1-(hydroxyacetyl)piperidin-4-yl]-1,6-dimethyl-4-oxo-5-(2-oxo-2-phenylethyl)-4,5-dihydro-1H-pyrrolo[3,2-c]pyridine-2-carboxamide

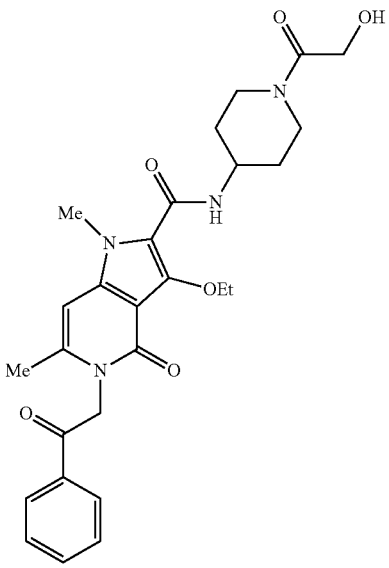 [SMILES: CCOc1c(C(=O)NC2CCN(C(=O)CO)CC2)n(C)c2cc(C)n(CC(=O)c3ccccc3)c(=O)c12]

To a mixture of the compound of Example 133 (200 mg, 0.423 mmol), triethylamine (122 μL, 0.880 mmol) and THF (10 mL) was added acetoxyacetyl chloride (47.3 μL, 0.440 mmol) at 0° C., and the mixture was stirred at room temperature for 15 hr. The reaction mixture was diluted with ethyl acetate, washed with water and brine, dried over magnesium sulfate, and concentrated under reduced pressure. The residue was dissolved in ethanol (7 mL) and THF (2 mL), 8N aqueous sodium hydroxide solution (1 mL) was added, and the mixture was stirred at room temperature for 2 hr. The reaction mixture was diluted with water, acidified with 6N hydrochloric acid (1.5 mL), and extracted twice with ethyl acetate. The extract was combined, washed with brine, dried over magnesium sulfate and concentrated under reduced pressure. The residue was purified by aminosilica gel chromatography (eluate; ethyl acetate), and the obtained solid was recrystallized from ethyl acetate-hexane to give the title compound (102 mg, 65%) as white crystals.

$^1$H-NMR (300 MHz, DMSO-$d_6$) δ:1.25 (3H, t, J=7.1 Hz), 1.31-1.57 (2H, m), 1.82-1.96 (2H, m), 2.28 (3H, s), 2.80-2.95 (1H, m), 3.03-3.19 (1H, m), 3.87 (3H, s), 3.95-4.13 (3H, m), 4.18-4.28 (1H, m), 4.34 (2H, q, J=7.0 Hz), 4.50 (1H, t, J=5.4 Hz), 5.61 (2H, s), 6.58 (1H, s), 7.55-7.78 (4H, m), 8.06-8.14 (2H, m).

Example 137

Production of N-[1-(hydroxyacetyl)piperidin-4-yl]-1,6-dimethyl-4-oxo-5-(2-oxo-2-phenylethyl)-3-propoxy-4,5-dihydro-1H-pyrrolo[3,2-c]pyridine-2-carboxamide

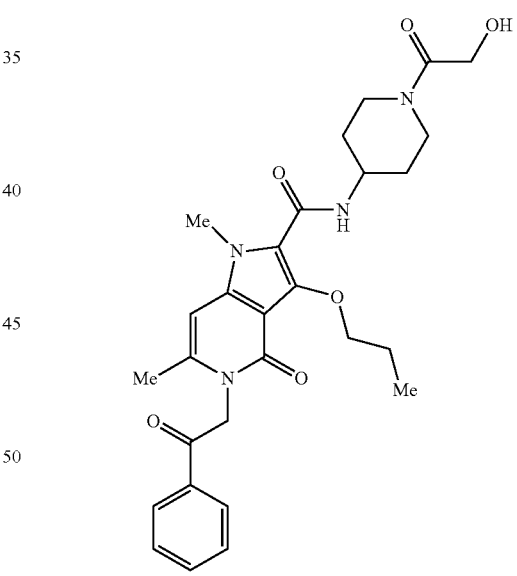

In the same manner as in Example 25, the title compound (45.2 mg, 33%) was obtained as a white powder from the compound of Reference Example 46 (100 mg, 0.262 mmol), 2-(4-aminopiperidin-1-yl)-2-oxoethanol hydrochloride (61.1 mg, 0.314 mmol) and triethylamine (43.5 μL, 0.314 mmol).

$^1$H-NMR (300 MHz, DMSO-$d_6$) δ:0.92 (3H, t, J=7.4 Hz), 1.22-1.53 (2H, m), 1.60-1.75 (2H, m), 1.85-1.95 (2H, m), 2.27 (3H, s), 2.77-2.92 (1H, m), 3.00-3.17 (1H, m), 3.60-3.74 (1H, m), 3.86 (3H, s), 3.95-4.13 (3H, m), 4.25 (3H, t, J=6.7 Hz), 4.50 (1H, t, J=5.4 Hz), 5.62 (2H, s), 6.57 (1H, s), 7.55-7.67 (3H, m), 7.69-7.78 (1H, m), 8.05-8.16 (2H, m).

Example 138

Production of 3-ethoxy-N-[1-(2-hydroxyethyl)piperidin-4-yl]-1,6-dimethyl-4-oxo-5-(2-oxo-2-phenylethyl)-4,5-dihydro-1H-pyrrolo[3,2-c]pyridine-2-carboxamide

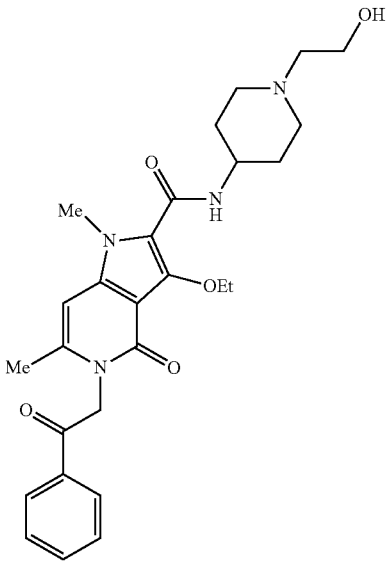 [SMILES: CCOc1c(C(=O)NC2CCN(CCO)CC2)n(C)c2cc(C)n(CC(=O)c3ccccc3)c(=O)c12]

In the same manner as in Example 79, the title compound (78.5 mg, 57%) was obtained as a white powder from the compound of Example 133 (135 mg, 0.277 mmol) and 2-bromoethanol (58.9 µL, 0.832 mmol).

$^1$H-NMR (300 MHz, DMSO-d$_6$) δ:1.28 (3H, t, J=7.1 Hz), 1.39-1.57 (2H, m), 1.78-1.91 (2H, m), 2.09-2.22 (2H, m), 2.28 (3H, s), 2.38 (2H, t, J=6.3 Hz), 2.67-2.81 (2H, m,), 3.48 (2H, q, J=6.2 Hz), 3.70-3.83 (1H, m), 3.87 (3H, s), 4.29-4.41 (3H, m), 5.61 (2H, s), 6.58 (1H, s), 7.56-7.68 (3H, m), 7.70-7.78 (1H, m), 8.06-8.15 (2H, m).

Example 139

Production of 3-ethoxy-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

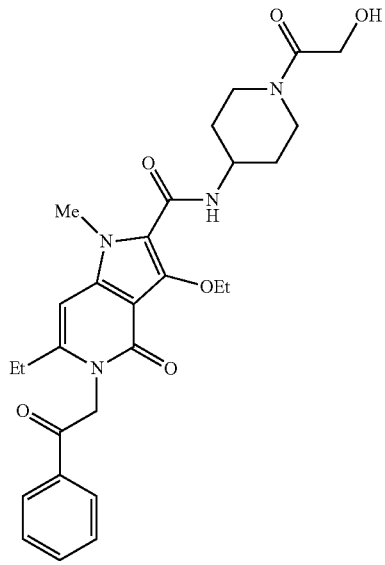 [SMILES: CCOc1c(C(=O)NC2CCN(C(=O)CO)CC2)n(C)c2cc(CC)n(CC(=O)c3ccccc3)c(=O)c12]

1) To a solution of the compound of Reference Example 48 (74.0 mg, 0.194 mmol), 2-(4-aminopiperidin-1-yl)-2-oxoethanol hydrochloride (49.1 mg, 0.252 mmol), HOBt (39.2 mg, 0.290 mmol) and triethylamine (34.9 µL, 0.252 mmol) in DMF (3 mL) was added WSCD (55.6 mg, 0.290 mmol) under ice-cooling, and the mixture was stirred at room temperature for 15 hr. The reaction mixture was diluted with water, and extracted twice with ethyl acetate. The extract was combined, washed with water and brine, dried over magnesium sulfate, and concentrated under reduced pressure. The residue was purified by aminosilica gel chromatography (eluate; ethyl acetate), and the obtained solid was recrystallized from ethyl acetate to give the title compound (61.2 mg, 60%) as white crystals.

$^1$H-NMR (300 MHz, DMSO-d$_6$) δ:1.13-1.29 (6H, m), 1.32-1.56 (2H, m), 1.83-1.96 (2H, m), 2.57 (2H, q, J=7.4 Hz), 2.80-2.94 (1H, m), 3.04-3.19 (1H, m), 3.59-3.72 (1H, m), 3.90 (3H, s), 3.95-4.14 (3H, m), 4.17-4.27 (1H, m), 4.34 (2H, q, J=7.2 Hz), 4.51 (1H, t, J=5.4 Hz), 5.59 (2H, s), 6.49 (1H, s), 7.56-7.65 (2H, m), 7.66-7.77 (2H, m), 8.07-8.14 (2H, m).

2) The white crystals were recrystallized from ethanol-water to give the title compound as white crystals. melting point: 204° C.

Example 140

Production of N-[1-(hydroxyacetyl)piperidin-4-yl]-1,6-dimethyl-4-oxo-5-(2-oxo-2-phenylethyl)-3-(2,2,2-trifluoroethoxy)-4,5-dihydro-1H-pyrrolo[3,2-c]pyridine-2-carboxamide

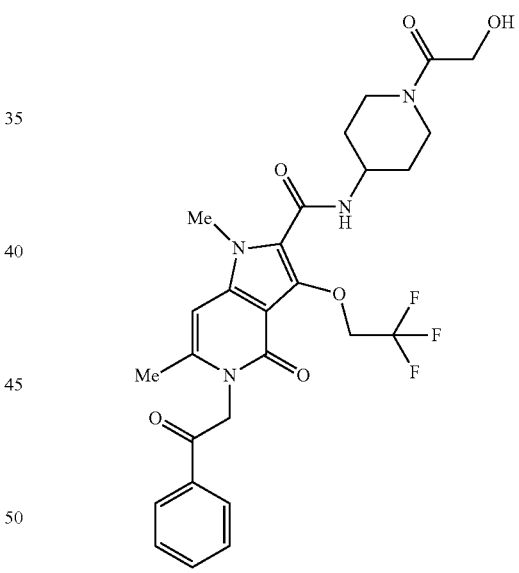

1) To a solution of the compound of Reference Example 50 (70.0 mg, 0.166 mmol), 2-(4-aminopiperidin-1-yl)-2-oxoethanol hydrochloride (42.0 mg, 0.216 mmol), HOBt (33.6 mg, 0.249 mmol) and triethylamine (29.9 µL, 0.216 mmol) in DMF (3 mL) was added WSCD (55.6 mg, 0.290 mmol) under ice-cooling, and the mixture was stirred at room temperature for 15 hr. The reaction mixture was diluted with water, and extracted twice with ethyl acetate. The extract was combined, washed with water and brine, dried over magnesium sulfate, and concentrated under reduced pressure. The residue was purified by aminosilica gel chromatography (eluate; ethyl acetate), and the obtained solid was recrystallized from ethyl acetate to give the title compound (51.3 mg, 55%) as white crystals.

$^1$H-NMR (300 MHz, DMSO-d$_6$) δ:1.22-1.50 (2H, m), 1.81-1.94 (2H, m), 2.29 (3H, s), 2.74-2.91 (1H, m), 3.01-3.16 (1H, m), 3.63-3.75 (1H, m), 3.83 (3H, s), 3.95-4.13 (3H, m), 4.20-4.32 (1H, m), 4.53 (1H, t, J=5.5 Hz), 5.06 (2H, q, J=9.3 Hz), 5.65 (2H, s), 6.64 (1H, s), 7.51 (1H, d, J=7.7 Hz), 7.57-7.66 (2H, m), 7.70-7.79 (1H, m), 8.07-8.15 (2H, m).

2) The white crystals were recrystallized from ethanol-water to give the title compound as white crystals. melting point: 132° C.

Example 141

Production of 3-ethoxy-N-[1-(hydroxyacetyl)piperidin-4-yl]-1-methyl-4-oxo-5-(2-oxo-2-phenylethyl)-6-propyl-4,5-dihydro-1H-pyrrolo[3,2-c]pyridine-2-carboxamide

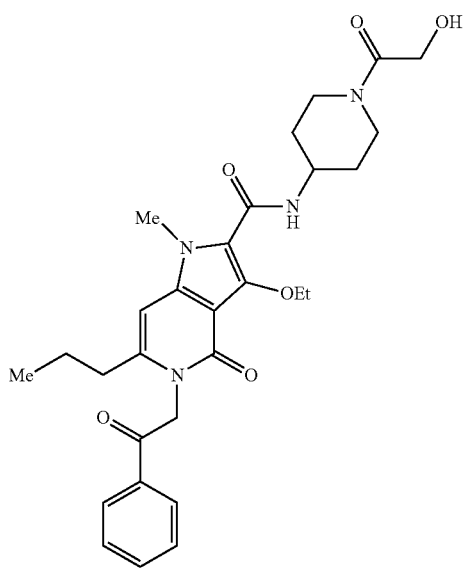 [SMILES: CCCc1cc2c(c(OCC)c(C(=O)NC3CCN(C(=O)CO)CC3)n2C)c(=O)n1CC(=O)c1ccccc1]

To a solution of the compound of Reference Example 57 (200 mg, 0.504 mmol), 2-(4-aminopiperidin-1-yl)-2-oxoethanol hydrochloride (128 mg, 0.656 mmol), HOBt (102 mg, 0.757 mmol) and triethylamine (90.8 μL, 0.656 mmol) in DMF (5 mL) was added WSCD (145 mg, 0.757 mmol) under ice-cooling, and the mixture was stirred at room temperature for 15 hr. The reaction mixture was diluted with water, and extracted twice with ethyl acetate. The extract was combined, washed with water and brine, dried over magnesium sulfate, and concentrated under reduced pressure. The residue was purified by aminosilica gel chromatography (eluate; ethyl acetate), and the obtained solid was recrystallized from THF-ethyl acetate to give the title compound (224 mg, 83%) as white crystals.

$^1$H-NMR (300 MHz, DMSO-d$_6$) δ:0.93 (3H, t, J=7.3 Hz), 1.25 (3H, t, J=7.1 Hz), 1.31-1.66 (4H, m), 1.84-1.95 (2H, m), 2.51-2.59 (2H, m), 2.81-2.95 (1H, m), 3.04-3.18 (1H, m), 3.61-3.71 (1H, m), 3.89 (3H, s), 3.96-4.14 (3H, m), 4.18-4.27 (1H, m), 4.33 (2H, q, J=7.0 Hz), 4.51 (1H, t, J=5.1 Hz), 5.55 (2H, s), 6.51 (1H, s), 7.56-7.77 (4H, m), 8.08-8.14 (2H, m).

Example 142

Production of 6-ethyl-3-(2-fluoroethoxy)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

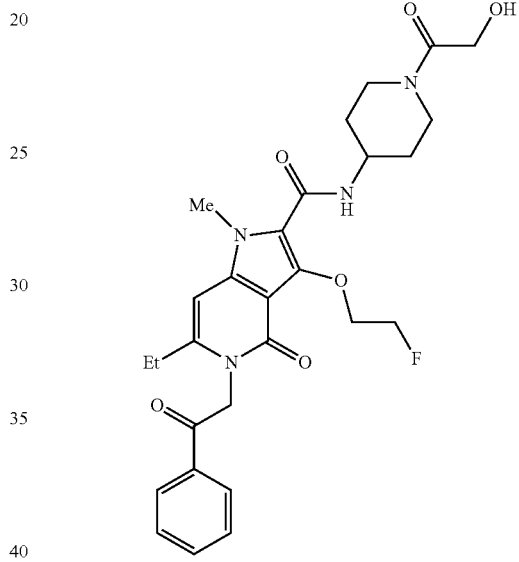

To a solution of the compound of Reference Example 59 (202 mg, 0.504 mmol), 2-(4-aminopiperidin-1-yl)-2-oxoethanol hydrochloride (128 mg, 0.656 mmol), HOBt (102 mg, 0.757 mmol) and triethylamine (90.8 μL, 0.656 mmol) in DMF (5 mL) was added WSCD (145 mg, 0.757 mmol) under ice-cooling, and the mixture was stirred at room temperature for 15 hr. The reaction mixture was diluted with water, and extracted twice with ethyl acetate. The extract was combined, washed with water and saturated brine, dried over magnesium sulfate, and concentrated under reduced pressure. The residue was purified by aminosilica gel chromatography (eluate; ethyl acetate), and the obtained solid was recrystallized from THF-ethyl acetate to give the title compound (219 mg, 80%) as white crystals.

$^1$H-NMR (300 MHz, DMSO-d$_6$) δ:1.19 (3H, t, J=7.4 Hz), 1.26-1.48 (2H, m), 1.87 (2H, s), 2.59 (2H, q, J=7.4 Hz), 2.76-2.91 (1H, m), 3.01-3.17 (1H, m), 3.57-3.73 (1H, m), 3.92 (3H, s), 3.97-4.13 (3H, m), 4.18-4.32 (1H, m), 4.45-4.81

(5H, m), 5.59 (2H, s), 6.49-6.56 (1H, m), 7.55-7.66 (3H, m), 7.69-7.78 (1H, m), 8.06-8.16 (2H, m).

Example 143

Production of 6-ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide

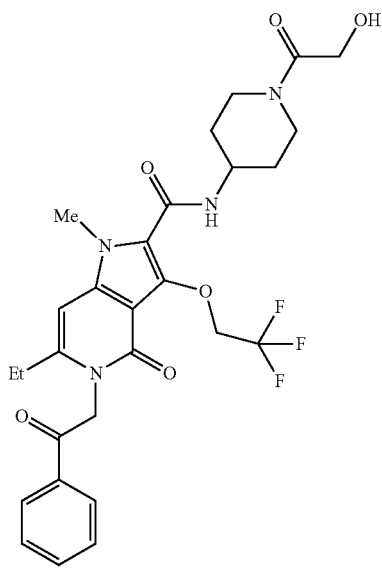 [SMILES: CCc1cc2c(c(OCC(F)(F)F)c(C(=O)NC3CCN(C(=O)CO)CC3)n2C)c(=O)n1CC(=O)c1ccccc1]

1) To a solution of the compound of Reference Example 61 (230 mg, 0.527 mmol), 2-(4-aminopiperidin-1-yl)-2-oxoethanol hydrochloride (133 mg, 0.685 mmol), HOBt (107 mg, 0.791 mmol) and triethylamine (95.0 μL, 0.685 mmol) in DMF (4 mL) was added WSCD (152 mg, 0.791 mmol) under ice-cooling, and the mixture was stirred at room temperature for 15 hr. The reaction mixture was diluted with water, and extracted twice with ethyl acetate. The extract was combined, washed with water and saturated brine, dried over magnesium sulfate, and concentrated under reduced pressure. The residue was purified by aminosilica gel chromatography (eluate; ethyl acetate/hexane=1/3-1/0), and the obtained solid was recrystallized from ethyl acetate-hexane to give the title compound (146 mg, 48%) as white crystals.

$^1$H-NMR (300 MHz, DMSO-$d_6$) δ:1.13-1.49 (5H, m), 1.82-1.94 (2H, m), 2.59 (2H, q, J=7.2 Hz), 2.76-2.88 (1H, m), 3.02-3.15 (1H, m), 3.64-3.75 (1H, m), 3.86 (3H, s), 3.96-4.16 (3H, m), 4.20-4.33 (1H, m), 4.53 (1H, t, J=5.4 Hz), 5.05 (2H, q, J=9.3 Hz), 5.63 (2H, s), 6.54 (1H, s), 7.51 (1H, d, J=7.7 Hz), 7.61 (2H, t, J=7.6 Hz), 7.70-7.78 (1H, m), 8.08-8.14 (2H, m).

2) The white crystals were recrystallized from ethanol-water to give the title compound as white crystals. melting point: 159° C.

Example 144

Production of N-[2-(diethylamino)ethyl]-3-methoxy-N-methyl-4-oxo-5-(2-oxo-2-phenylethyl)-4,5,6,7,8,9-hexahydrothieno[3,2-c]quinoline-2-carboxamide

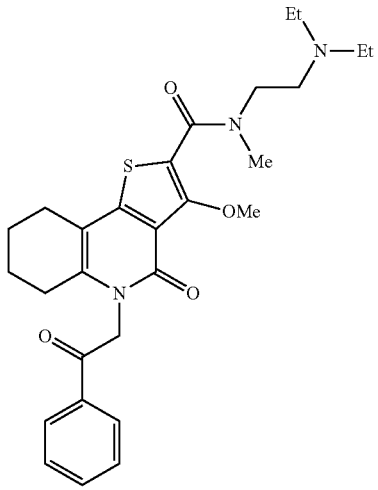 [SMILES: CCN(CC)CCN(C)C(=O)c1sc2c3c(n(CC(=O)c4ccccc4)c(=O)c2c1OC)CCCC3]

In the same manner as in Example 25, the title compound (54.0 mg, 28%) was obtained as a colorless oil from the compound of Reference Example 66 (150 mg, 0.377 mmol) and N,N-diethyl-N'-methylethane-1,2-diamine (79.3 μL, 0.490 mmol).

$^1$H-NMR (300 MHz, DMSO-$d_6$) δ:0.74-1.05 (6H, m), 1.67-1.85 (4H, m), 2.19-2.65 (10H, m), 3.03 (3H, s), 3.40-3.56 (2H, m), 3.82 (3H, s), 5.65 (2H, s), 7.61 (2H, t, J=7.6 Hz), 7.70-7.78 (1H, m), 8.07-8.16 (2H, m).

Example 145

Production of N-[2-(diethylamino)ethyl]-3-ethoxy-N,6-dimethyl-4-oxo-4,5-dihydrothieno[3,2-c]pyridine-2-carboxamide

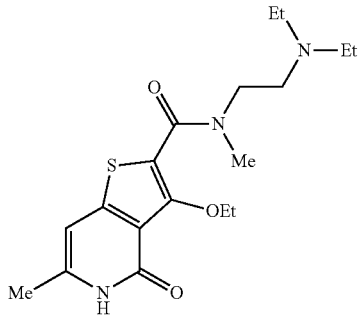 [SMILES: CCOc1c(C(=O)N(C)CCN(CC)CC)sc2cc(C)[nH]c(=O)c12]

A mixture of the compound of Reference Example 70 (2.50 g, 6.51 mmol), 6N hydrochloric acid (15 mL) and DMF (15 mL) was stirred for 15 hr under refluxing conditions. After cooling, the reaction mixture was concentrated under reduced pressure, and water (20 mL) was added to the residue. The mixture was neutralized with saturated sodium hydrogen carbonate solution, and extracted with ethyl acetate. The extract was washed successively with water and brine, dried over magnesium sulfate, and concentrated under reduced pressure.

The residue was purified by aminosilica gel chromatography (eluate; ethyl acetate) to give the title compound (568 mg, 24%) as a colorless oil.
$^1$H-NMR (300 MHz, DMSO-d$_6$) δ:0.70-1.05 (6H, m), 1.21 (3H, t, J=7.0 Hz), 2.21 (3H, s), 2.25-2.65 (6H, m), 3.01 (3H, s), 3.40-3.55 (2H, m), 4.13 (2H, q, J=7.0 Hz), 6.54 (1H, s), 11.41 (1H, s).

Example 146

Production of N-[2-(diethylamino)ethyl]-3-ethoxy-N,6-dimethyl-4-oxo-5-(2-oxo-2-phenylethyl)-4,5-dihydrothieno[3,2-c]pyridine-2-carboxamide

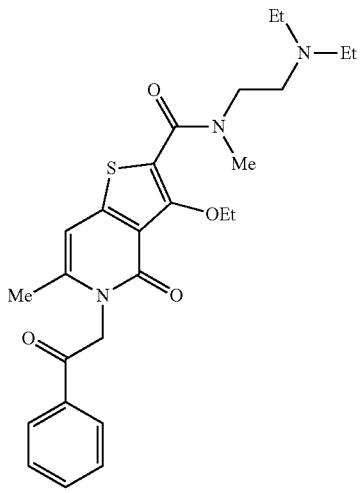 [SMILES: CCOc1c(C(=O)N(C)CCN(CC)CC)sc2cc(C)n(CC(=O)c3ccccc3)c(=O)c12]

A mixture of the compound of Example 145 (300 mg, 0.821 mmol), phenacyl bromide (196 mg, 0.985 mmol), potassium carbonate (272 mg, 1.97 mmol) and DMF (5 mL) was stirred at 60° C. for 15 hr. After cooling, the mixture was diluted with water (10 mL), and extracted with ethyl acetate. The extract was washed successively with water and brine, dried over magnesium sulfate, and concentrated under reduced pressure. The residue was purified by aminosilica gel chromatography (eluate; ethyl acetate/hexane=1/9 to 10/0) to give the title compound (51.2 mg, 13%) as a colorless oil.
$^1$H-NMR (300 MHz, DMSO-d$_6$) δ:0.70-1.05 (6H, m), 1.15-1.20 (3H, m), 2.25-2.65 (9H, m), 3.02 (3H, br s), 3.40-3.55 (2H, m), 4.05 (2H, q, J=6.9 Hz), 5.66 (2H, s), 6.80-6.81 (1H, m), 7.62 (2H, t, J=7.7 Hz), 7.72-7.78 (1H, m), 8.10-8.13 (2H, m).

Example 147

Production of N-[2-(diethylamino)ethyl]-3-ethoxy-N,6,7-trimethyl-4-oxo-4,5-dihydrothieno[3,2-c]pyridine-2-carboxamide

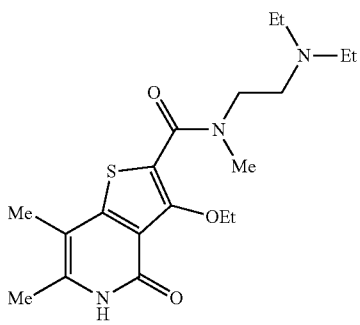 [SMILES: CCOc1c(C(=O)N(C)CCN(CC)CC)sc2c(C)c(C)[nH]c(=O)c12]

In the same manner as in Example 145, the title compound (60 mg, 29%) was obtained as a white solid from the compound of Reference Example 74 (220 mg, 0.55 mmol).

$^1$H-NMR (300 MHz, DMSO-d$_6$) δ:0.80-1.10 (6H, m), 1.37 (3H, t, J=6.9 Hz), 2.17 (3H, s), 2.41 (3H, s), 2.48-2.73 (6H, m), 3.17 (3H, s), 3.61 (2H, br s), 4.27 (2H, q, J=7.1 Hz), 12.31 (1H, br s).

Example 148

Production of N-[2-(diethylamino)ethyl]-3-ethoxy-N,6,7-trimethyl-4-oxo-5-(2-oxo-2-phenylethyl)-4,5-dihydrothieno[3,2-c]pyridine-2-carboxamide

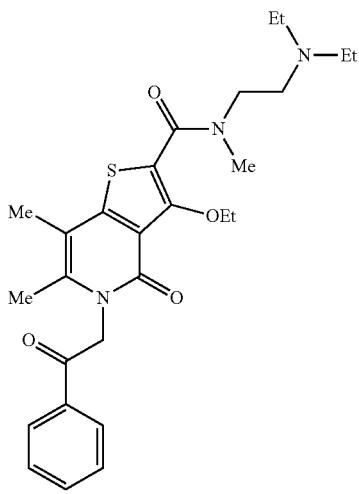 [SMILES: CCOc1c(C(=O)N(C)CCN(CC)CC)sc2c(C)c(C)n(CC(=O)c3ccccc3)c(=O)c12]

In the same manner as in Example 146, the title compound (10 mg, 12%) was obtained as a pale-yellow oil from the compound of Example 147 (60 mg, 0.16 mmol) and phenacyl bromide (196 mg, 0.985 mmol).
$^1$H-NMR (300 MHz, CDCl$_3$) δ: 0.80-1.15 (6H, m), 1.34 (3H, t, J=7.1 Hz), 2.21-2.80 (12H, m), 3.16 (3H, s), 3.62 (2H, br s), 4.22 (2H, q, J=7.1 Hz), 5.67 (2H, s), 7.54 (2H, t, J=7.5 Hz), 7.66 (1H, t, J=7.5 Hz), 8.08 (2H, dd, J=8.1, 1.5 Hz).

Example 149

Production of N-[1-(hydroxyacetyl)piperidin-4-yl]-3-methoxy-6-methyl-4-oxo-5-(2-oxo-2-phenylethyl)-4,5-dihydrothieno[3,2-c]pyridine-2-carboxamide

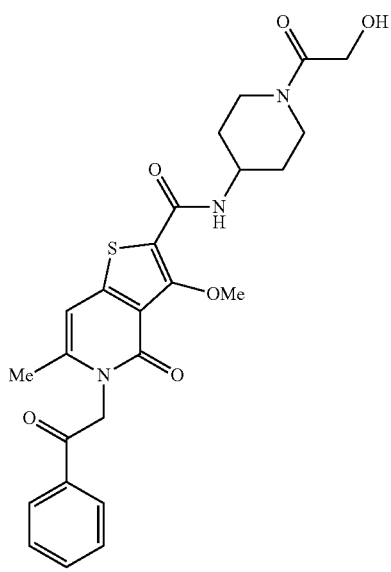 [SMILES: COc1c(C(=O)NC2CCN(C(=O)CO)CC2)sc2cc(C)n(CC(=O)c3ccccc3)c(=O)c12]

In the same manner as in Example 25, the title compound (224 mg, 80%) was obtained as a white powder from the compound of Reference Example 78 (200 mg, 0.560 mmol), 2-(4-aminopiperidin-1-yl)-2-oxoethanol hydrochloride (142 mg, 0.727 mmol) and triethylamine (101 μL, 0.727 mmol).

¹H-NMR (300 MHz, DMSO-d₆) δ: 1.38-1.66 (2H, m), 1.79-1.92 (2H, m), 2.26-2.35 (3H, m), 2.78-2.94 (1H, m), 3.03-3.18 (1H, m), 3.58-3.71 (1H, m), 3.94-4.14 (6H, m), 4.18-4.30 (1H, m), 4.51 (1H, t, J=5.3 Hz), 5.68 (2H, s), 6.86 (1H, s), 7.56-7.69 (3H, m), 7.71-7.80 (1H, m), 8.07-8.16 (2H, m).

Example 150

Production of 3-ethoxy-N-[1-(hydroxyacetyl)piperidin-4-yl]-6-methyl-4-oxo-5-(2-oxo-2-phenylethyl)-4,5-dihydrothieno[3,2-c]pyridine-2-carboxamide

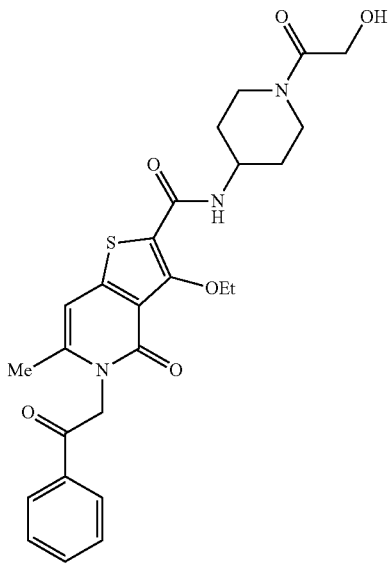 [SMILES: CCOc1c(C(=O)NC2CCN(C(=O)CO)CC2)sc2cc(C)n(CC(=O)c3ccccc3)c(=O)c12]

In the same manner as in Example 25, the title compound (178 mg, 65%) was obtained as a white powder from the compound of Reference Example 79 (200 mg, 0.538 mmol), 2-(4-aminopiperidin-1-yl)-2-oxoethanol hydrochloride (142 mg, 0.727 mmol) and triethylamine (101 μL, 0.727 mmol).

¹H-NMR (300 MHz, DMSO-d₆) δ: 1.30 (3H, t, J=7.1 Hz), 1.37-1.61 (2H, m), 1.84-1.95 (2H, m), 2.30 (3H, s), 2.76-2.91 (1H, m), 3.02-3.18 (1H, m), 3.59-3.73 (1H, m), 3.95-4.13 (3H, m), 4.21-4.33 (3H, m), 4.51 (1H, t, J=5.4 Hz), 5.68 (2H, s), 6.86 (1H, s), 7.57-7.70 (3H, m), 7.71-7.79 (1H, m), 8.07-8.17 (2H, m).

Example 151

Production of 3-methoxy-5-methyl-2-(piperidin-1-ylcarbonyl)thieno[3,2-c]quinolin-4(5H)-one

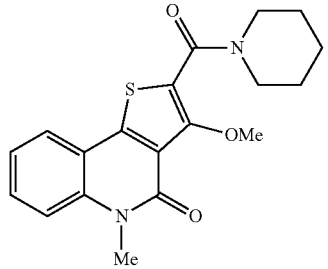 [SMILES: COc1c(C(=O)N2CCCCC2)sc2c1c(=O)n(C)c1ccccc21]

In the same manner as in Example 1, the title compound was obtained from the compound of Reference Example 84 and piperidine.

LC/MS 357 (M+H).

Example 152

Production of 2-[(2,6-dimethylmorpholin-4-yl)carbonyl]-3-methoxy-5-methylthieno[3,2-c]quinolin-4(5H)-one

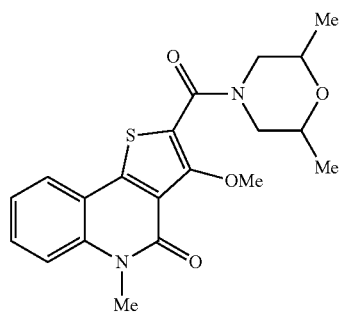 [SMILES: COc1c(C(=O)N2CC(C)OC(C)C2)sc2c1c(=O)n(C)c1ccccc21]

In the same manner as in Example 1, the title compound was obtained from the compound of Reference Example 84 and 2,6-dimethylmorpholine.

LC/MS 387 (M+H).

Example 153

Production of 2-[(4-benzylpiperidin-1-yl)carbonyl]-3-methoxy-5-methylthieno[3,2-c]quinolin-4(5H)-one

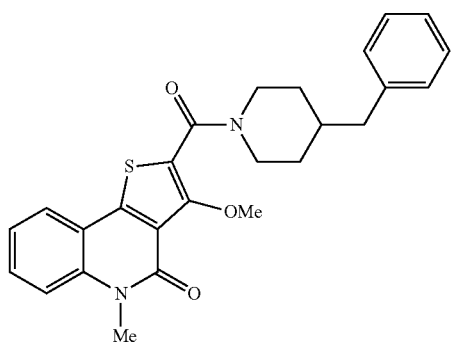 [SMILES: COc1c(C(=O)N2CCC(Cc3ccccc3)CC2)sc2c1c(=O)n(C)c1ccccc21]

In the same manner as in Example 1, the title compound was obtained from the compound of Reference Example 84 and 4-benzylpiperidine.

LC/MS 447 (M+H).

Example 154

Production of N-[2-(3,4-dimethoxyphenyl)ethyl]-3-methoxy-N,5-dimethyl-4-oxo-4,5-dihydrothieno[3,2-c]quinoline-2-carboxamide

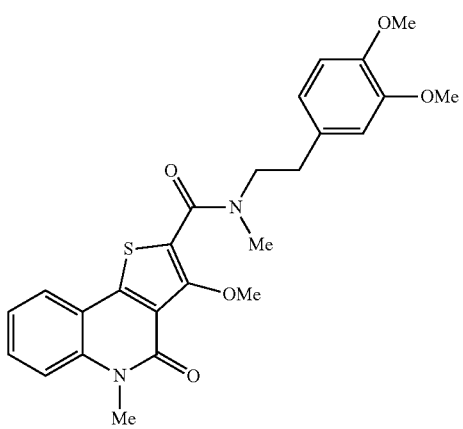 [SMILES: COc1ccc(CCN(C)C(=O)c2sc3c(c2OC)c(=O)n(C)c2ccccc32)cc1OC]

In the same manner as in Example 1, the title compound was obtained from the compound of Reference Example 84 and 2-(3,4-dimethoxyphenyl)-N-methylethanamine.
LC/MS 467 (M+H).

Example 155

Production of 3-methoxy-N,N-bis(2-methoxyethyl)-5-methyl-4-oxo-4,5-dihydrothieno[3,2-c]quinoline-2-carboxamide

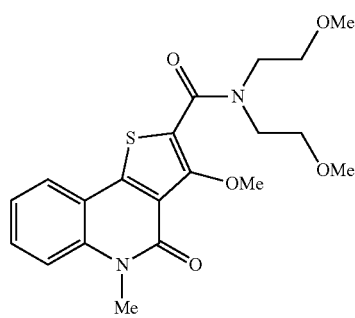 [SMILES: COCCN(CCOC)C(=O)c1sc2c(c1OC)c(=O)n(C)c1ccccc21]

In the same manner as in Example 1, the title compound was obtained from the compound of Reference Example 84 and 2-methoxy-N-(2-methoxyethyl)ethanamine.
LC/MS 405 (M+H).

Example 156

Production of 3-methoxy-5-methyl-2-(octahydroisoquinoline-2(1H)-ylcarbonyl)thieno[3,2-c]quinolin-4(5H)-one

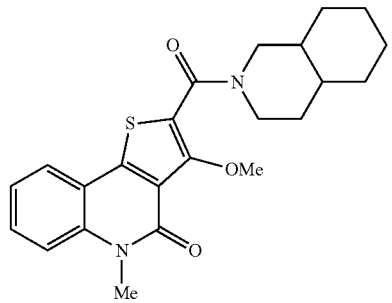 [SMILES: COc1c(C(=O)N2CCC3CCCCC3C2)sc2c1c(=O)n(C)c1ccccc21]

In the same manner as in Example 1, the title compound was obtained from the compound of Reference Example 84 and decahydroisoquinoline.
LC/MS 411 (M+H).

Example 157

Production of N-ethyl-N-{1-[(3-methoxy-5-methyl-4-oxo-4,5-dihydrothieno[3,2-c]quinolin-2-yl)carbonyl]pyrrolidin-3-yl}acetamide

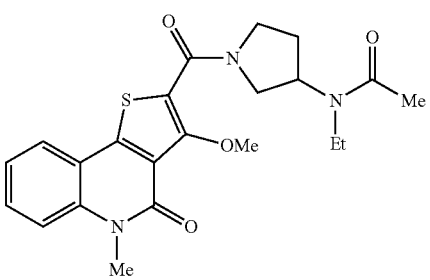 [SMILES: CCN(C(C)=O)C1CCN(C(=O)c2sc3c(c2OC)c(=O)n(C)c2ccccc32)C1]

In the same manner as in Example 1, the title compound was obtained from the compound of Reference Example 84 and N-ethyl-N-pyrrolidin-3-ylacetamide.
LC/MS 428 (M+H).

Example 158

Production of N-{1-[(3-methoxy-5-methyl-4-oxo-4,5-dihydrothieno[3,2-c]quinolin-2-yl)carbonyl]pyrrolidin-3-yl}acetamide

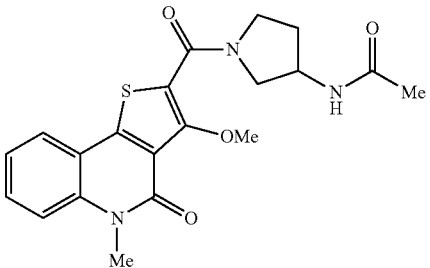 [SMILES: COc1c(C(=O)N2CCC(NC(C)=O)C2)sc2c1c(=O)n(C)c1ccccc21]

In the same manner as in Example 1, the title compound was obtained from the compound of Reference Example 84 and N-pyrrolidin-3-ylacetamide.
LC/MS 400 (M+H).

Example 159

Production of N-cyclohexyl-N-ethyl-3-methoxy-5-methyl-4-oxo-4,5-dihydrothieno[3,2-c]quinoline-2-carboxamide

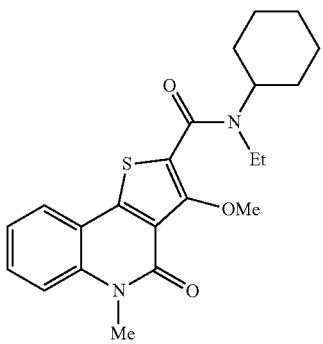 [SMILES: CCN(C(=O)c1sc2c(c1OC)c(=O)n(C)c1ccccc21)C1CCCCC1]

In the same manner as in Example 1, the title compound was obtained from the compound of Reference Example 84 and N-ethylcyclohexanamine.

LC/MS 399 (M+H).

Example 160

Production of N-(3,3-diphenylpropyl)-3-methoxy-5-methyl-4-oxo-4,5-dihydrothieno[3,2-c]quinoline-2-carboxamide

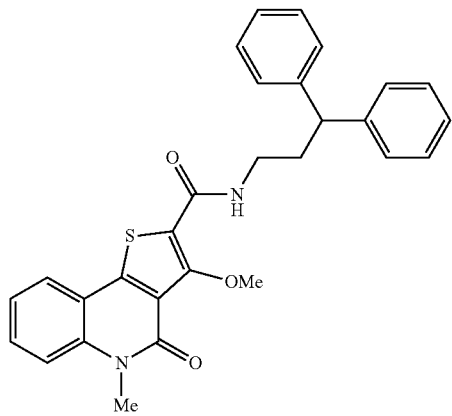 [SMILES: COc1c(C(=O)NCCC(c2ccccc2)c2ccccc2)sc2c1c(=O)n(C)c1ccccc21]

A solution of the compound of Reference Example 84 in DMF (0.10 M, 0.601 mL, 60 µmol) was diluted with DMF (0.200 mL), and a solution of 3,3-diphenylpropan-1-amine in DMF (1.0 M, 0.062 mL, 62 µmol) and a solution of HOBt and WSCD in 1:1 mixture in DMF (0.50 M, 0.134 mL, 67 µmol) were added. The obtained mixture was agitated at room temperature for 16 hr. Dichloromethane (2 mL) and water (1 mL) were added to the reaction mixture. After agitating for 2.5 hr, sodium hydrogen carbonate (7 mg) was added and the mixture was agitated. The organic layer was filtered through a Teflon (registered trade mark) filter to separate the aqueous layer, and concentrated under reduced pressure. The residue was purified by preparative HPLC to give the title compound (21.9 mg, 76%).

LC/MS 483 (M+H).

Example 161

Production of 5-butyl-N-cyclopropyl-3-methoxy-4-oxo-4,5-dihydrothieno[3,2-c]quinoline-2-carboxamide

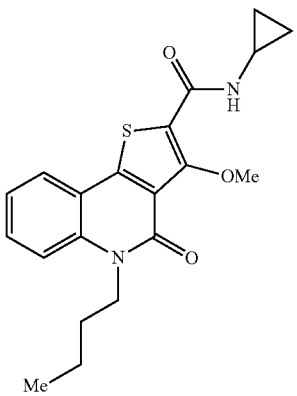 [SMILES: CCCCn1c(=O)c2c(OC)c(C(=O)NC3CC3)sc2c2ccccc21]

In the same manner as in Example 1, the title compound was obtained from the compound of Reference Example 103 and cyclopropanamine.

LC/MS 371 (M+H).

Example 162

Production of N-benzyl-5-butyl-3-methoxy-4-oxo-4,5-dihydrothieno[3,2-c]quinoline-2-carboxamide

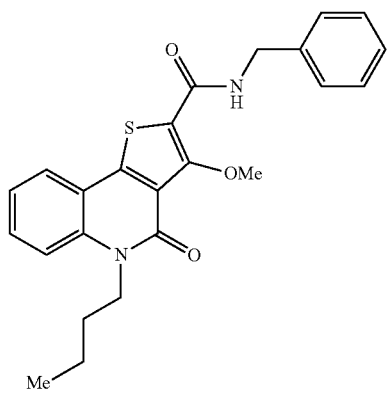 [SMILES: CCCCn1c(=O)c2c(OC)c(C(=O)NCc3ccccc3)sc2c2ccccc21]

In the same manner as in Example 1, the title compound was obtained from the compound of Reference Example 103 and 1-phenylmethanamine.

LC/MS 421 (M+H).

Example 163

Production of N-(1,3-benzodioxol-5-ylmethyl)-5-butyl-3-methoxy-4-oxo-4,5-dihydrothieno[3,2-c]quinoline-2-carboxamide

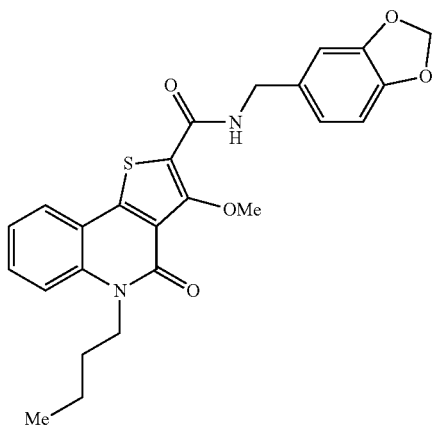 [SMILES: CCCCn1c(=O)c2c(OC)c(C(=O)NCc3ccc4c(c3)OCO4)sc2c2ccccc21]

In the same manner as in Example 1, the title compound was obtained from the compound of Reference Example 103 and 1-(1,3-benzodioxol-5-yl)methanamine.

LC/MS 465 (M+H).

Example 165

Production of 5-butyl-3-methoxy-N-(2-methoxyethyl)-4-oxo-4,5-dihydrothieno[3,2-c]quinoline-2-carboxamide

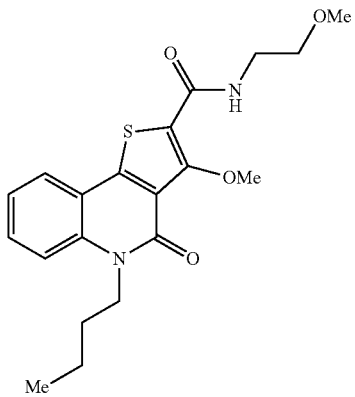

In the same manner as in Example 1, the title compound was obtained from the compound of Reference Example 103 and 2-methoxyethanamine.

LC/MS 389 (M+H).

Example 164

Production of 5-butyl-3-methoxy-4-oxo-N-(3-phenylpropyl)-4,5-dihydrothieno[3,2-c]quinoline-2-carboxamide

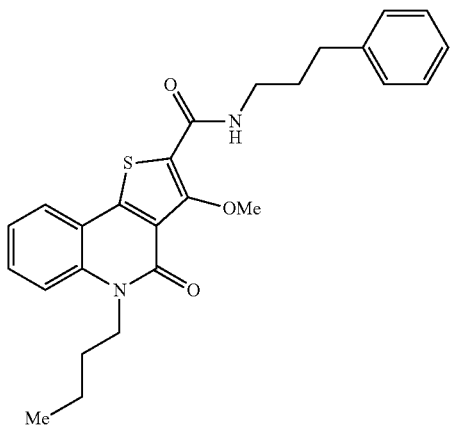 [SMILES: CCCCn1c(=O)c2c(OC)c(C(=O)NCCCc3ccccc3)sc2c2ccccc21]

In the same manner as in Example 1, the title compound was obtained from the compound of Reference Example 103 and 3-phenylpropan-1-amine.

LC/MS 449 (M+H).

Example 166

Production of 5-butyl-3-methoxy-4-oxo-N-(tetrahydrofuran-2-ylmethyl)-4,5-dihydrothieno[3,2-c]quinoline-2-carboxamide

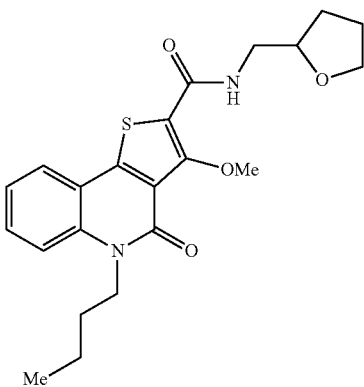 [SMILES: CCCCn1c(=O)c2c(OC)c(C(=O)NCC3CCCO3)sc2c2ccccc21]

In the same manner as in Example 1, the title compound was obtained from the compound of Reference Example 103 and 1-(tetrahydrofuran-2-yl)methanamine.

LC/MS 415 (M+H).

Example 167

Production of 5-butyl-N-(1-ethylpropyl)-3-methoxy-4-oxo-4,5-dihydrothieno[3,2-c]quinoline-2-carboxamide

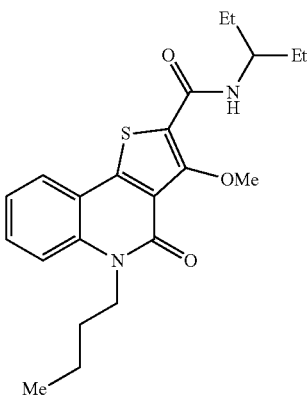 [SMILES: CCCCn1c(=O)c2c(OC)c(C(=O)NC(CC)CC)sc2c2ccccc21]

In the same manner as in Example 1, the title compound was obtained from the compound of Reference Example 103 and pentan-3-amine.

LC/MS 401 (M+H).

Example 168

Production of 5-butyl-3-methoxy-4-oxo-N-prop-2-yn-1-yl-4,5-dihydrothieno[3,2-c]quinoline-2-carboxamide

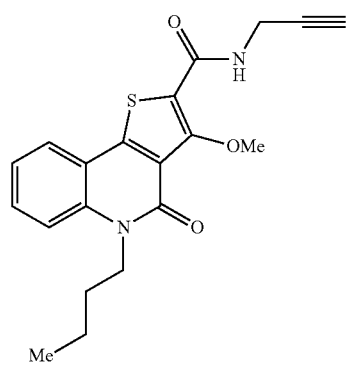 [SMILES: C#CCNC(=O)c1sc2c(c1OC)c(=O)n(CCCC)c1ccccc21]

In the same manner as in Example 1, the title compound was obtained from the compound of Reference Example 103 and prop-2-yn-1-amine.

LC/MS 369 (M+H).

Example 169

Production of 5-butyl-N-[2-(3,4-dimethoxyphenyl)ethyl]-3-methoxy-4-oxo-4,5-dihydrothieno[3,2-c]quinoline-2-carboxamide

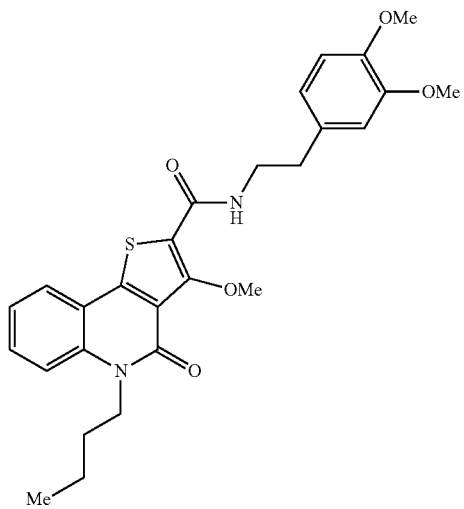 [SMILES: CCCCn1c(=O)c2c(OC)c(C(=O)NCCc3ccc(OC)c(OC)c3)sc2c2ccccc21]

In the same manner as in Example 1, the title compound was obtained from the compound of Reference Example 103 and 2-(3,4-dimethoxyphenyl)ethanamine.

LC/MS 495 (M+H).

Example 170

Production of 5-butyl-3-methoxy-N-[3-(1-methylethoxy)propyl]-4-oxo-4,5-dihydrothieno[3,2-c]quinoline-2-carboxamide

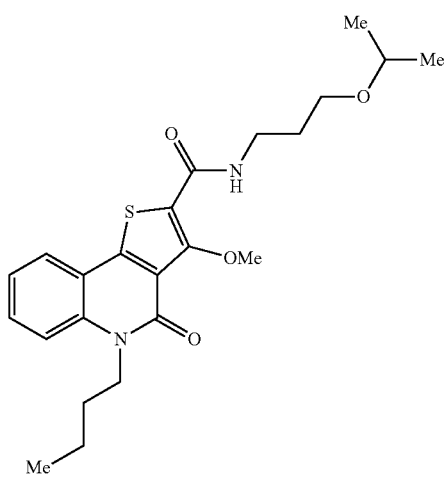 [SMILES: CCCCn1c(=O)c2c(OC)c(C(=O)NCCCOC(C)C)sc2c2ccccc21]

In the same manner as in Example 1, the title compound was obtained from the compound of Reference Example 103 and 3-(1-methylethoxy)propan-1-amine.

LC/MS 431 (M+H).

Example 171

Production of 5-butyl-N-(furan-2-ylmethyl)-3-methoxy-4-oxo-4,5-dihydrothieno[3,2-c]quinoline-2-carboxamide

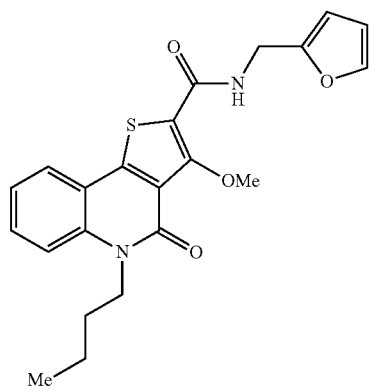 [SMILES: CCCCn1c(=O)c2c(OC)c(C(=O)NCc3ccco3)sc2c2ccccc21]

In the same manner as in Example 1, the title compound was obtained from the compound of Reference Example 103 and 1-furan-2-ylmethanamine.

LC/MS 411 (M+H).

Example 172

Production of 5-butyl-3-methoxy-4-oxo-N-[3-(2-oxopyrrolidin-1-yl)propyl]-4,5-dihydrothieno[3,2-c]quinoline-2-carboxamide

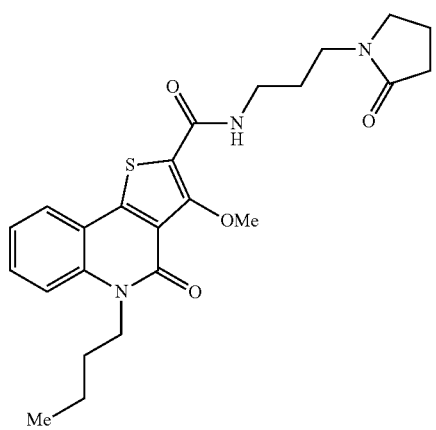 [SMILES: CCCCn1c(=O)c2c(OC)c(C(=O)NCCCN3CCCC3=O)sc2c2ccccc21]

In the same manner as in Example 1, the title compound was obtained from the compound of Reference Example 103 and 1-(3-aminopropyl)pyrrolidin-2-one.

LC/MS 456 (M+H).

Example 173

Production of 5-butyl-3-methoxy-2-(piperidin-1-ylcarbonyl)thieno[3,2-c]quinolin-4(5H)-one

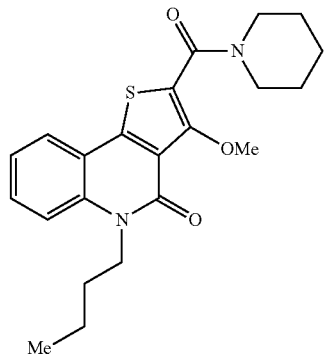 [SMILES: CCCCn1c(=O)c2c(OC)c(C(=O)N3CCCCC3)sc2c2ccccc21]

In the same manner as in Example 1, the title compound was obtained from the compound of Reference Example 103 and piperidine.

LC/MS 399 (M+H).

Example 174

Production of 5-butyl-2-[(2,6-dimethylmorpholin-4-yl)carbonyl]-3-methoxythieno[3,2-c]quinolin-4(5H)-one

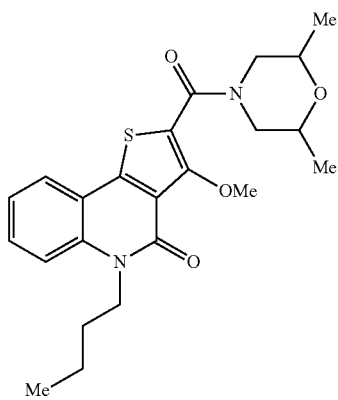 [SMILES: CCCCn1c(=O)c2c(OC)c(C(=O)N3CC(C)OC(C)C3)sc2c2ccccc21]

In the same manner as in Example 1, the title compound was obtained from the compound of Reference Example 103 and 2,6-dimethylmorpholine.

LC/MS 429 (M+H).

Example 175

Production of 2-[(4-benzylpiperidin-1-yl)carbonyl]-5-butyl-3-methoxythieno[3,2-c]quinolin-4(5H)-one

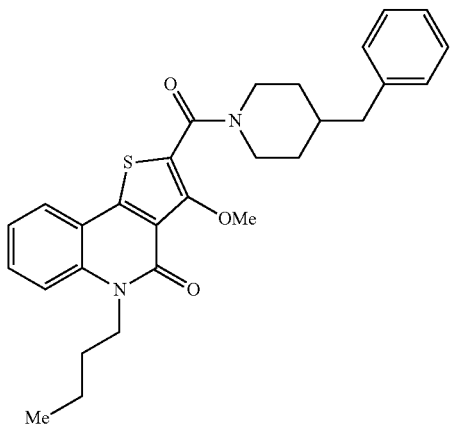 [SMILES: CCCCn1c(=O)c2c(OC)c(C(=O)N3CCC(Cc4ccccc4)CC3)sc2c2ccccc21]

In the same manner as in Example 1, the title compound was obtained from the compound of Reference Example 103 and 4-benzylpiperidine.

LC/MS 489 (M+H).

Example 176

Production of 5-butyl-N-[2-(3,4-dimethoxyphenyl)ethyl]-3-methoxy-N-methyl-4-oxo-4,5-dihydrothieno[3,2-c]quinoline-2-carboxamide

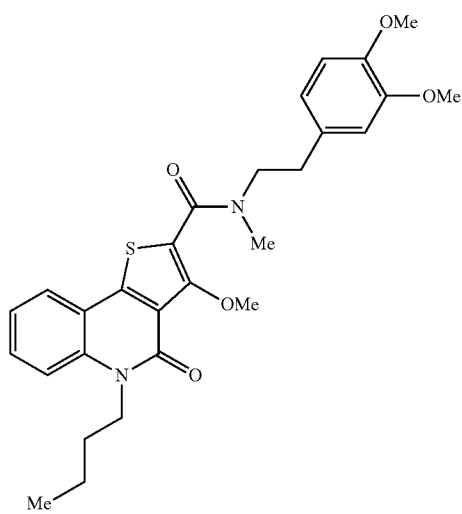 [SMILES: CCCCn1c(=O)c2c(OC)c(C(=O)N(C)CCc3ccc(OC)c(OC)c3)sc2c2ccccc21]

In the same manner as in Example 1, the title compound was obtained from the compound of Reference Example 103 and 2-(3,4-dimethoxyphenyl)-N-methylethanamine.

LC/MS 509 (M+H).

Example 177

Production of 5-butyl-3-methoxy-N,N-bis(2-methoxyethyl)-4-oxo-4,5-dihydrothieno[3,2-c]quinoline-2-carboxamide

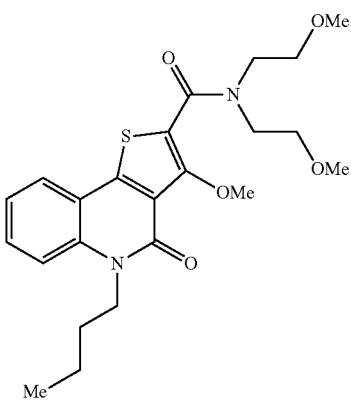 [SMILES: CCCCn1c(=O)c2c(OC)c(C(=O)N(CCOC)CCOC)sc2c2ccccc21]

In the same manner as in Example 1, the title compound was obtained from the compound of Reference Example 103 and 2-methoxy-N-(2-methoxyethyl)ethanamine.

LC/MS 447 (M+H).

Example 178

Production of 5-butyl-3-methoxy-2-(octahydroisoquinoline-2(1H)-ylcarbonyl)thieno[3,2-c]quinolin-4(5H)-one

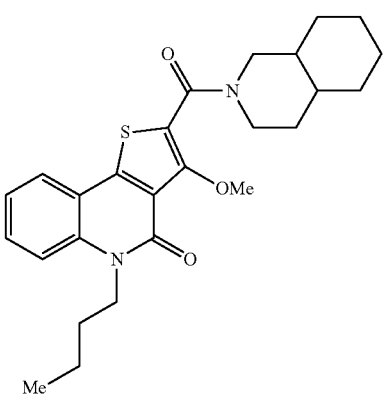 [SMILES: CCCCn1c(=O)c2c(OC)c(C(=O)N3CCC4CCCCC4C3)sc2c2ccccc21]

In the same manner as in Example 1, the title compound was obtained from the compound of Reference Example 103 and decahydroisoquinoline.

LC/MS 453 (M+H).

Example 179

Production of N-{1-[(5-butyl-3-methoxy-4-oxo-4,5-dihydrothieno[3,2-c]quinolin-2-yl)carbonyl]pyrrolidin-3-yl}-N-ethylacetamide

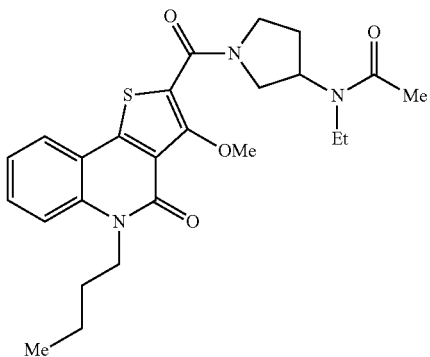 [SMILES: CCCCn1c(=O)c2c(OC)c(C(=O)N3CCC(N(CC)C(C)=O)C3)sc2c2ccccc21]

In the same manner as in Example 1, the title compound was obtained from the compound of Reference Example 103 and N-ethyl-N-pyrrolidin-3-ylacetamide.

LC/MS 470 (M+H)

Example 180

Production of N-{1-[(5-butyl-3-methoxy-4-oxo-4,5-dihydrothieno[3,2-c]quinolin-2-yl)carbonyl]pyrrolidin-3-yl}acetamide

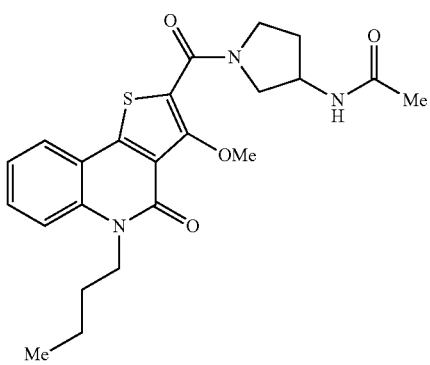 [SMILES: CCCCn1c(=O)c2c(OC)c(C(=O)N3CCC(NC(C)=O)C3)sc2c2ccccc21]

In the same manner as in Example 1, the title compound was obtained from the compound of Reference Example 103 and N-pyrrolidin-3-ylacetamide.

LC/MS 442 (M+H).

Example 181

Production of 5-butyl-N-cyclohexyl-N-ethyl-3-methoxy-4-oxo-4,5-dihydrothieno[3,2-c]quinoline-2-carboxamide

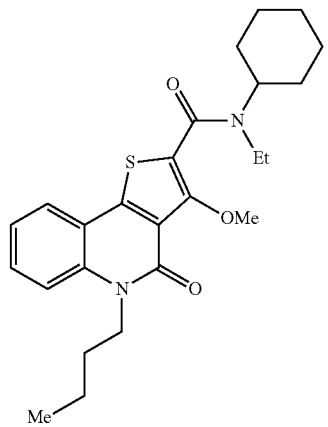 [SMILES: CCCCn1c(=O)c2c(OC)c(C(=O)N(CC)C3CCCCC3)sc2c2ccccc21]

In the same manner as in Example 1, the title compound was obtained from the compound of Reference Example 103 and N-ethylcyclohexanamine.

LC/MS 441 (M+H).

Example 182

Production of 5-butyl-N-(3,3-diphenylpropyl)-3-methoxy-4-oxo-4,5-dihydrothieno[3,2-c]quinoline-2-carboxamide

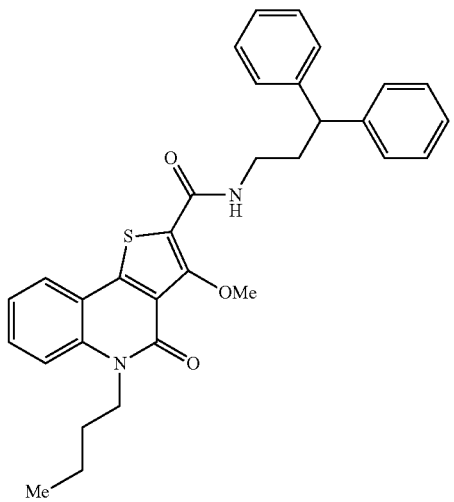 [SMILES: CCCCn1c(=O)c2c(OC)c(C(=O)NCCC(c3ccccc3)c3ccccc3)sc2c2ccccc21]

In the same manner as in Example 160, the title compound was obtained from the compound of Reference Example 103 and 3,3-diphenylpropan-1-amine.

LC/MS 525 (M+H).

Example 183

Production of N-benzyl-3-methoxy-4-oxo-5-(pyridin-2-ylmethyl)-4,5-dihydrothieno[3,2-c]quinoline-2-carboxamide trifluoroacetate

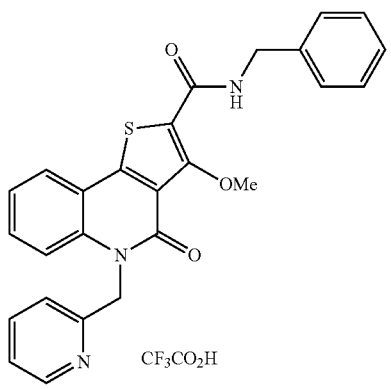 [SMILES: COc1c(C(=O)NCc2ccccc2)sc2c1c(=O)n(Cc1ccccn1)c1ccccc21 ; "CF3CO2H"]

In the same manner as in Example 1, the title compound was obtained from the compound of Reference Example 19 and 1-phenylmethanamine.

LC/MS 456 (M+H).

Example 184

Production of N-(1,3-benzodioxol-5-ylmethyl)-3-methoxy-4-oxo-5-(pyridin-2-ylmethyl)-4,5-dihydrothieno[3,2-c]quinoline-2-carboxamide trifluoroacetate

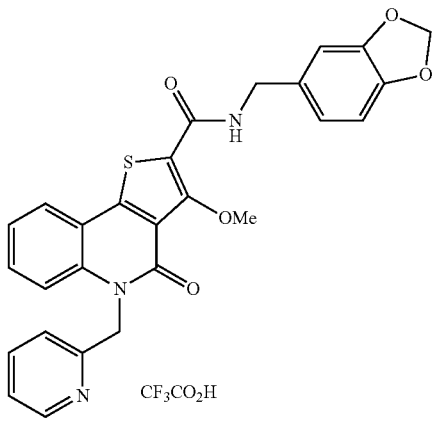 [SMILES: COc1c(C(=O)NCc2ccc3c(c2)OCO3)sc2c1c(=O)n(Cc1ccccn1)c1ccccc21 ; "CF3CO2H"]

In the same manner as in Example 1, the title compound was obtained from the compound of Reference Example 19 and 1-(1,3-benzodioxol-5-yl)methanamine.

LC/MS 500 (M+H).

Example 185

Production of 3-methoxy-4-oxo-N-(3-phenylpropyl)-5-(pyridin-2-ylmethyl)-4,5-dihydrothieno[3,2-c]quinoline-2-carboxamide trifluoroacetate

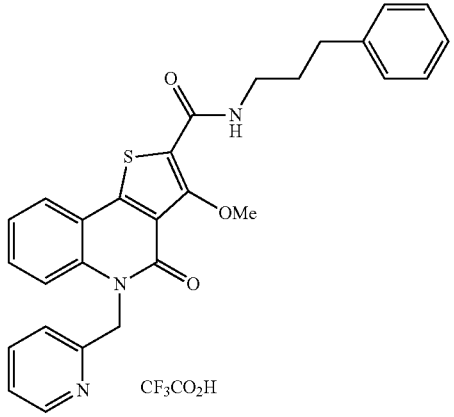 [SMILES: COc1c(C(=O)NCCCc2ccccc2)sc2c1c(=O)n(Cc1ccccn1)c1ccccc21 ; "CF3CO2H"]

In the same manner as in Example 1, the title compound was obtained from the compound of Reference Example 19 and 3-phenylpropan-1-amine.

LC/MS 484 (M+H).

Example 186

Production of 3-methoxy-N-(2-methoxyethyl)-4-oxo-5-(pyridin-2-ylmethyl)-4,5-dihydrothieno[3,2-c]quinoline-2-carboxamide trifluoroacetate

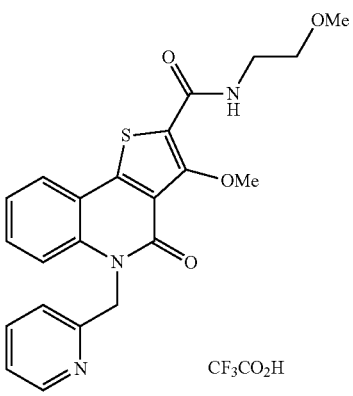 [SMILES: COCCNC(=O)c1sc2c(c1OC)c(=O)n(Cc1ccccn1)c1ccccc21 ; "CF3CO2H"]

In the same manner as in Example 1, the title compound was obtained from the compound of Reference Example 19 and 2-methoxyethanamine.

LC/MS 424 (M+H).

Example 187

Production of 3-methoxy-4-oxo-5-(pyridin-2-ylmethyl)-N-(tetrahydrofuran-2-ylmethyl)-4,5-dihydrothieno[3,2-c]quinoline-2-carboxamide trifluoroacetate

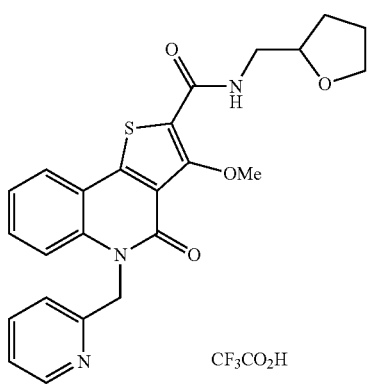 [SMILES: COc1c(C(=O)NCC2CCCO2)sc2c1c(=O)n(Cc1ccccn1)c1ccccc21 ; "CF3CO2H"]

In the same manner as in Example 1, the title compound was obtained from the compound of Reference Example 19 and 1-(tetrahydrofuran-2-yl)methanamine.

LC/MS 450 (M+H).

Example 188

Production of N-(1-ethylpropyl)-3-methoxy-4-oxo-5-(pyridin-2-ylmethyl)-4,5-dihydrothieno[3,2-c]quinoline-2-carboxamide trifluoroacetate

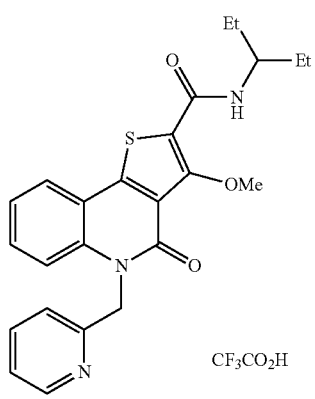 [SMILES: CCC(CC)NC(=O)c1sc2c(c1OC)c(=O)n(Cc1ccccn1)c1ccccc21 ; "CF3CO2H"]

In the same manner as in Example 1, the title compound was obtained from the compound of Reference Example 19 and pentan-3-amine.

LC/MS 436 (M+H).

Example 189

Production of N-cyclohexyl-3-methoxy-4-oxo-5-(pyridin-2-ylmethyl)-4,5-dihydrothieno[3,2-c]quinoline-2-carboxamide trifluoroacetate

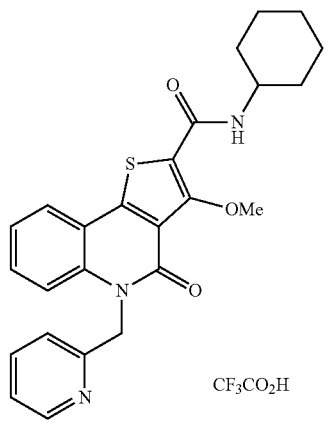 [SMILES: COc1c(C(=O)NC2CCCCC2)sc2c1c(=O)n(Cc1ccccn1)c1ccccc21 ; "CF3CO2H"]

In the same manner as in Example 1, the title compound was obtained from the compound of Reference Example 19 and cyclohexanamine.

LC/MS 448 (M+H).

Example 190

Production of 3-methoxy-4-oxo-N-prop-2-yn-1-yl-5-(pyridin-2-ylmethyl)-4,5-dihydrothieno[3,2-c]quinoline-2-carboxamide trifluoroacetate

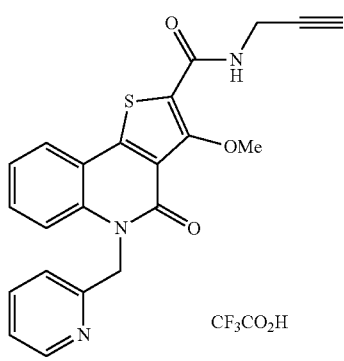 [SMILES: C#CCNC(=O)c1sc2c(c1OC)c(=O)n(Cc1ccccn1)c1ccccc21 ; "CF3CO2H"]

In the same manner as in Example 1, the title compound was obtained from the compound of Reference Example 19 and prop-2-yn-1-amine.

LC/MS 404 (M+H).

Example 191

Production of N-[2-(3,4-dimethoxyphenyl)ethyl]-3-methoxy-4-oxo-5-(pyridin-2-ylmethyl)-4,5-dihydrothieno[3,2-c]quinoline-2-carboxamide trifluoroacetate

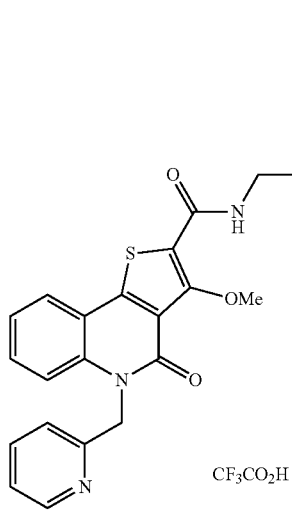

In the same manner as in Example 1, the title compound was obtained from the compound of Reference Example 19 and 2-(3,4-dimethoxyphenyl)ethanamine.

LC/MS 530 (M+H).

Example 192

Production of 3-methoxy-N-[3-(1-methylethoxy)propyl]-4-oxo-5-(pyridin-2-ylmethyl)-4,5-dihydrothieno[3,2-c]quinoline-2-carboxamide trifluoroacetate

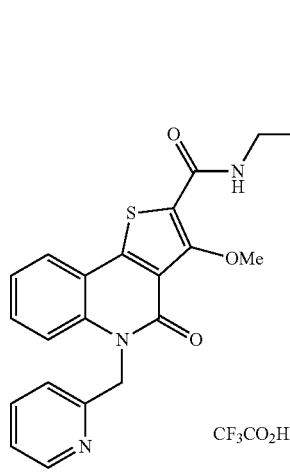

In the same manner as in Example 1, the title compound was obtained from the compound of Reference Example 19 and 3-(1-methylethoxy)propan-1-amine.

LC/MS 466 (M+H).

Example 193

Production of 3-methoxy-4-oxo-N-(2-oxoazepan-3-yl)-5-(pyridin-2-ylmethyl)-4,5-dihydrothieno[3,2-c]quinoline-2-carboxamide trifluoroacetate

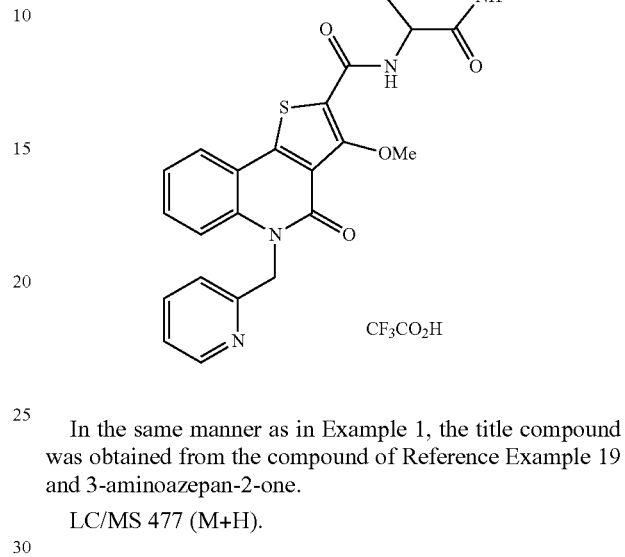

In the same manner as in Example 1, the title compound was obtained from the compound of Reference Example 19 and 3-aminoazepan-2-one.

LC/MS 477 (M+H).

Example 194

Production of 3-methoxy-4-oxo-N-[3-(2-oxopyrrolidin-1-yl)propyl]-5-(pyridin-2-ylmethyl)-4,5-dihydrothieno[3,2-c]quinoline-2-carboxamide trifluoroacetate

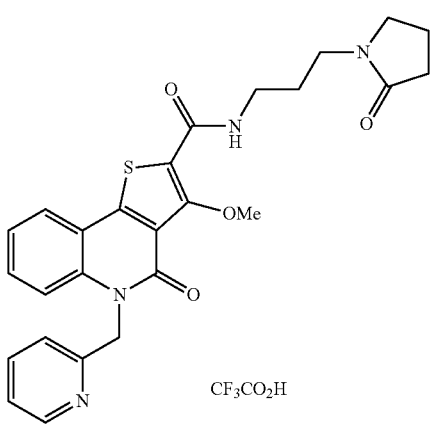 [SMILES: COc1c(C(=O)NCCCN2CCCC2=O)sc2c1c(=O)n(Cc1ccccn1)c1ccccc21 ; "CF3CO2H"]

In the same manner as in Example 1, the title compound was obtained from the compound of Reference Example 19 and 1-(3-aminopropyl)pyrrolidin-2-one.

LC/MS 491 (M+H).

Example 195

Production of 3-methoxy-2-(piperidin-1-ylcarbonyl)-5-(pyridin-2-ylmethyl)thieno[3,2-c]quinolin-4(5H)-one trifluoroacetate

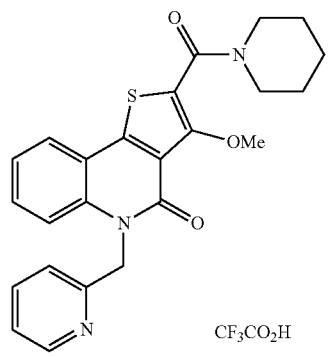 [SMILES: COc1c(C(=O)N2CCCCC2)sc2c1c(=O)n(Cc1ccccn1)c1ccccc21 ; "CF3CO2H"]

In the same manner as in Example 1, the title compound was obtained from the compound of Reference Example 19 and piperidine.

LC/MS 434 (M+H).

Example 196

Production of 2-[(2,6-dimethylmorpholin-4-yl)carbonyl]-3-methoxy-5-(pyridin-2-ylmethyl)thieno[3,2-c]quinolin-4(5H)-one trifluoroacetate

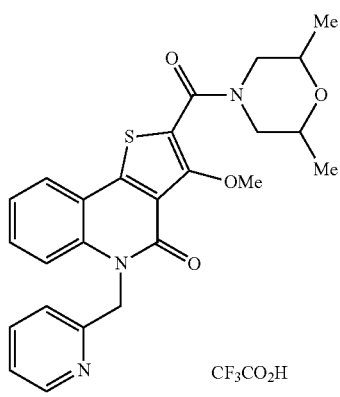 [SMILES: COc1c(C(=O)N2CC(C)OC(C)C2)sc2c1c(=O)n(Cc1ccccn1)c1ccccc21 ; "CF3CO2H"]

In the same manner as in Example 1, the title compound was obtained from the compound of Reference Example 19 and 2,6-dimethylmorpholine.

LC/MS 464 (M+H).

Example 197

Production of 2-[(4-benzylpiperidin-1-yl)carbonyl]-3-methoxy-5-(pyridin-2-ylmethyl)thieno[3,2-c]quinolin-4(5H)-one trifluoroacetate

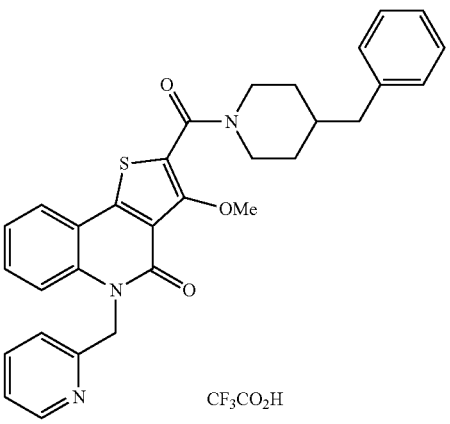 [SMILES: COc1c(C(=O)N2CCC(Cc3ccccc3)CC2)sc2c1c(=O)n(Cc1ccccn1)c1ccccc21 ; "CF3CO2H"]

In the same manner as in Example 1, the title compound was obtained from the compound of Reference Example 19 and 4-benzylpiperidine.

LC/MS 524 (M+H).

Example 198

Production of N-[2-(3,4-dimethoxyphenyl)ethyl]-3-methoxy-N-methyl-4-oxo-5-(pyridin-2-ylmethyl)-4,5-dihydrothieno[3,2-c]quinoline-2-carboxamide trifluoroacetate

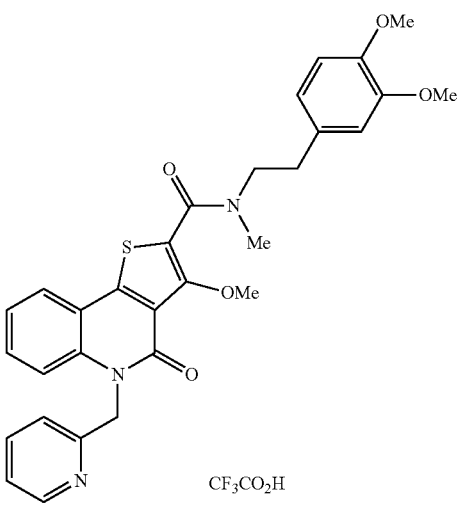 [SMILES: COc1ccc(CCN(C)C(=O)c2sc3c(c2OC)c(=O)n(Cc2ccccn2)c2ccccc32)cc1OC ; "CF3CO2H"]

In the same manner as in Example 1, the title compound was obtained from the compound of Reference Example 19 and 2-(3,4-dimethoxyphenyl)-N-methylethanamine.

LC/MS 544 (M+H).

Example 199

Production of 3-methoxy-N,N-bis(2-methoxyethyl)-4-oxo-5-(pyridin-2-ylmethyl)-4,5-dihydrothieno[3,2-c]quinoline-2-carboxamide trifluoroacetate

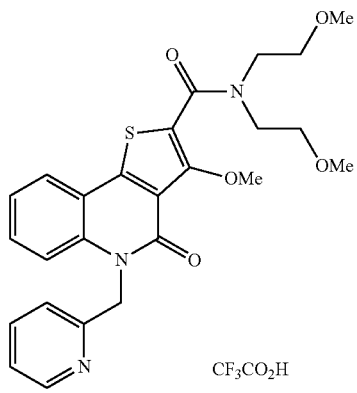 [SMILES: COCCN(CCOC)C(=O)c1sc2c(c1OC)c(=O)n(Cc1ccccn1)c1ccccc21 ; "CF3CO2H"]

In the same manner as in Example 1, the title compound was obtained from the compound of Reference Example 19 and 2-methoxy-N-(2-methoxyethyl)ethanamine.

LC/MS 482 (M+H).

Example 200

Production of 3-methoxy-2-(octahydroisoquinolin-2(1H)-ylcarbonyl)-5-(pyridin-2-ylmethyl)thieno[3,2-c]quinolin-4(5H)-one trifluoroacetate

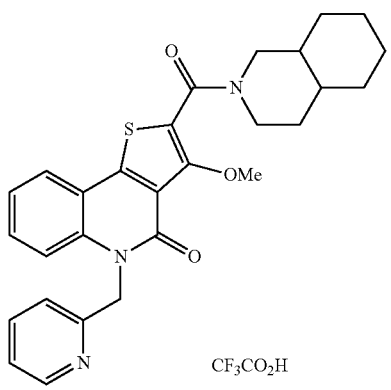 [SMILES: COc1c(C(=O)N2CCC3CCCCC3C2)sc2c1c(=O)n(Cc1ccccn1)c1ccccc21 ; "CF3CO2H"]

In the same manner as in Example 1, the title compound was obtained from the compound of Reference Example 19 and decahydroisoquinoline.

LC/MS 488 (M+H).

Example 201

Production of N-ethyl-N-(1-{[3-methoxy-4-oxo-5-(pyridin-2-ylmethyl)-4,5-dihydrothieno[3,2-c]quinolin-2-yl]carbonyl}pyrrolidin-3-yl)acetamide trifluoroacetate

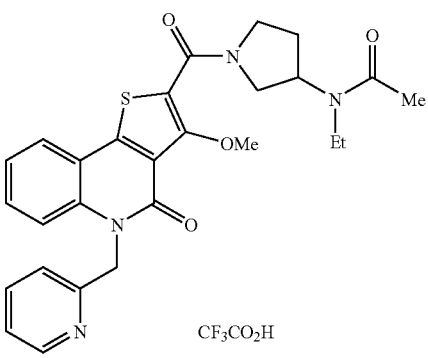 [SMILES: CCN(C(C)=O)C1CCN(C(=O)c2sc3c(c2OC)c(=O)n(Cc2ccccn2)c2ccccc32)C1 ; "CF3CO2H"]

In the same manner as in Example 1, the title compound was obtained from the compound of Reference Example 19 and N-ethyl-N-pyrrolidin-3-ylacetamide.

LC/MS 505 (M+H).

Example 202

Production of N-(1-{[3-methoxy-4-oxo-5-(pyridin-2-ylmethyl)-4,5-dihydrothieno[3,2-c]quinolin-2-yl]carbonyl}pyrrolidin-3-yl)acetamide trifluoroacetate

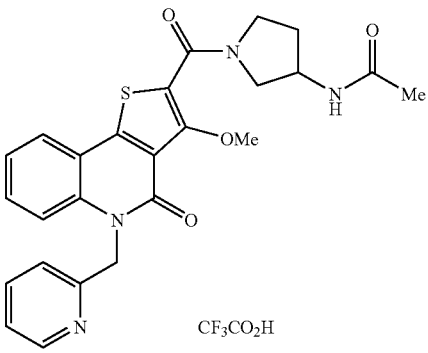 [SMILES: COc1c(C(=O)N2CCC(NC(C)=O)C2)sc2c1c(=O)n(Cc1ccccn1)c1ccccc21 ; "CF3CO2H"]

In the same manner as in Example 1, the title compound was obtained from the compound of Reference Example 19 and N-pyrrolidin-3-ylacetamide.

LC/MS 477 (M+H).

Example 203

Production of N-cyclohexyl-N-ethyl-3-methoxy-4-oxo-5-(pyridin-2-ylmethyl)-4,5-dihydrothieno[3,2-c]quinoline-2-carboxamide trifluoroacetate

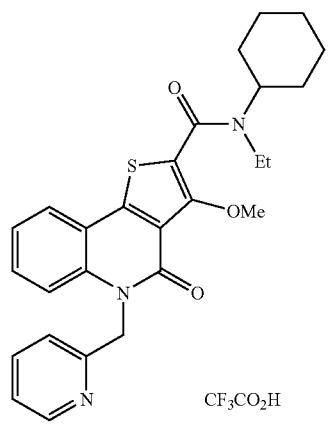 [SMILES: CCN(C(=O)c1sc2c(c1OC)c(=O)n(Cc1ccccn1)c1ccccc21)C1CCCCC1 ; "CF3CO2H"]

In the same manner as in Example 1, the title compound was obtained from the compound of Reference Example 19 and N-ethylcyclohexanamine.

LC/MS 476 (M+H).

Example 204

Production of N-(3,3-diphenylpropyl)-3-methoxy-4-oxo-5-(pyridin-2-ylmethyl)-4,5-dihydrothieno[3,2-c]quinoline-2-carboxamide trifluoroacetate

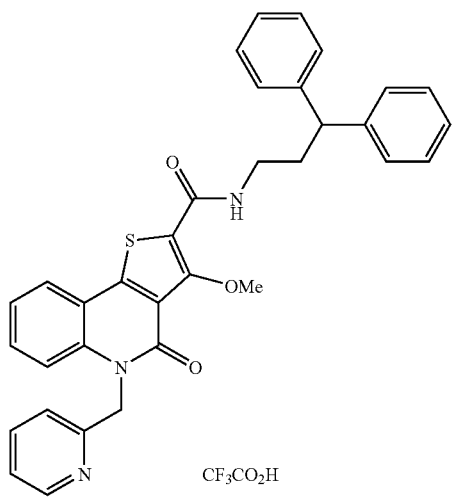 [SMILES: COc1c(C(=O)NCCC(c2ccccc2)c2ccccc2)sc2c1c(=O)n(Cc1ccccn1)c1ccccc21 ; "CF3CO2H"]

In the same manner as in Example 160, the title compound was obtained from the compound of Reference Example 19 and 3,3-diphenylpropan-1-amine.

LC/MS 560 (M+H).

Example 205

Production of N-benzyl-3-methoxy-4-oxo-5-(2-oxo-2-phenylethyl)-4,5-dihydrothieno[3,2-c]quinoline-2-carboxamide

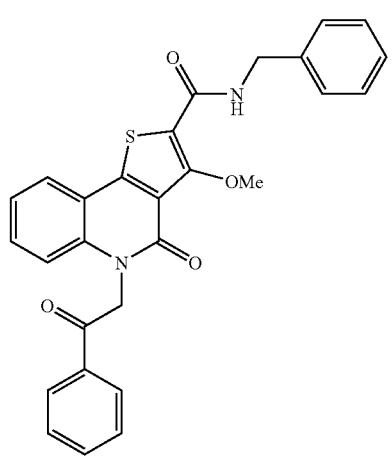 [SMILES: COc1c(C(=O)NCc2ccccc2)sc2c1c(=O)n(CC(=O)c1ccccc1)c1ccccc21]

In the same manner as in Example 1, the title compound was obtained from the compound of Reference Example 7 and 1-phenylmethanamine.

LC/MS 483 (M+H).

Example 206

Production of N-(1,3-benzodioxol-5-ylmethyl)-3-methoxy-4-oxo-5-(2-oxo-2-phenylethyl)-4,5-dihydrothieno[3,2-c]quinoline-2-carboxamide

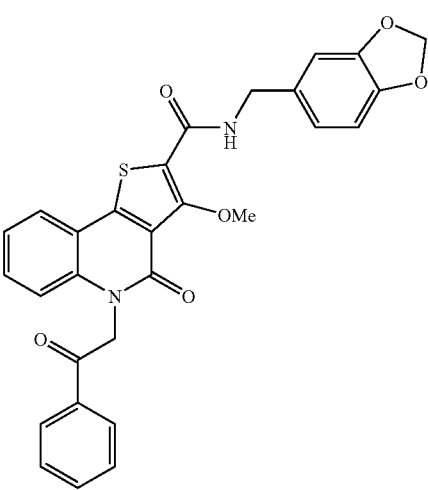 [SMILES: COc1c(C(=O)NCc2ccc3c(c2)OCO3)sc2c1c(=O)n(CC(=O)c1ccccc1)c1ccccc21]

In the same manner as in Example 1, the title compound was obtained from the compound of Reference Example 7 and 1-(1,3-benzodioxol-5-yl)methanamine.

LC/MS 527 (M+H).

Example 207

Production of 3-methoxy-4-oxo-5-(2-oxo-2-phenyl-ethyl)-N-(3-phenylpropyl)-4,5-dihydrothieno[3,2-c]quinoline-2-carboxamide

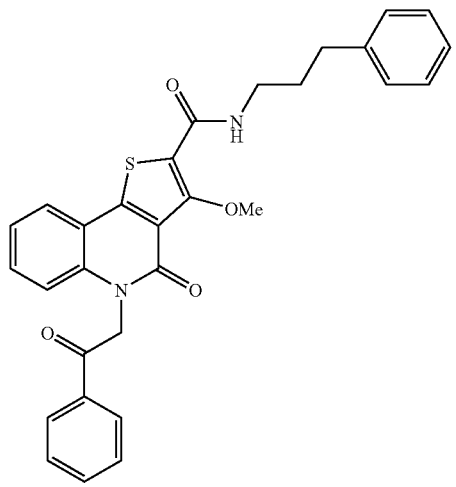 [SMILES: COc1c(C(=O)NCCCc2ccccc2)sc2c1c(=O)n(CC(=O)c1ccccc1)c1ccccc21]

In the same manner as in Example 1, the title compound was obtained from the compound of Reference Example 7 and 3-phenylpropan-1-amine.

LC/MS 511 (M+H).

Example 208

Production of 3-methoxy-N-(2-methoxyethyl)-4-oxo-5-(2-oxo-2-phenylethyl)-4,5-dihydrothieno[3,2-c]quinoline-2-carboxamide

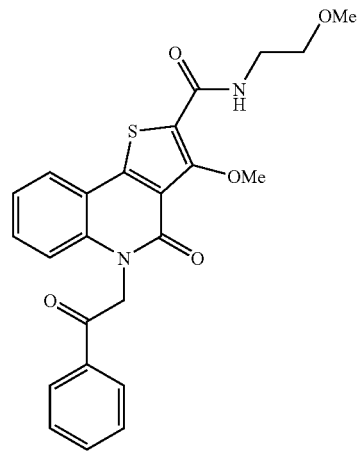

In the same manner as in Example 1, the title compound was obtained from the compound of Reference Example 7 and 2-methoxyethanamine.

LC/MS 451 (M+H).

Example 209

Production of N-(1-ethylpropyl)-3-methoxy-4-oxo-5-(2-oxo-2-phenylethyl)-4,5-dihydrothieno[3,2-c]quinoline-2-carboxamide

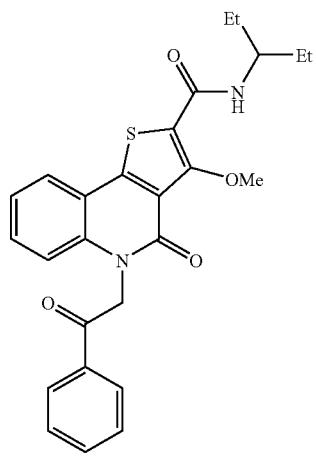 [SMILES: CCC(CC)NC(=O)c1sc2c(c1OC)c(=O)n(CC(=O)c1ccccc1)c1ccccc21]

In the same manner as in Example 1, the title compound was obtained from the compound of Reference Example 7 and pentan-3-amine.

LC/MS 463 (M+H).

Example 210

Production of N-cyclohexyl-3-methoxy-4-oxo-5-(2-oxo-2-phenylethyl)-4,5-dihydrothieno[3,2-c]quinoline-2-carboxamide

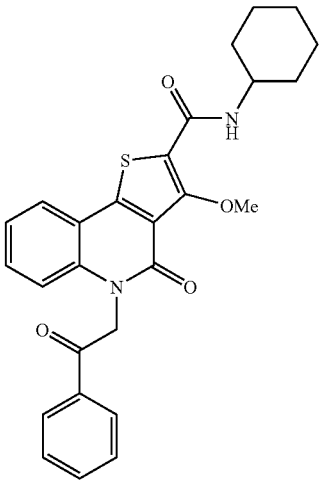 [SMILES: COc1c(C(=O)NC2CCCCC2)sc2c1c(=O)n(CC(=O)c1ccccc1)c1ccccc21]

In the same manner as in Example 1, the title compound was obtained from the compound of Reference Example 7 and cyclohexanamine.

LC/MS 475 (M+H).

Example 211

Production of 3-methoxy-4-oxo-5-(2-oxo-2-phenyl-ethyl)-N-prop-2-yn-1-yl-4,5-dihydrothieno[3,2-c]quinoline-2-carboxamide

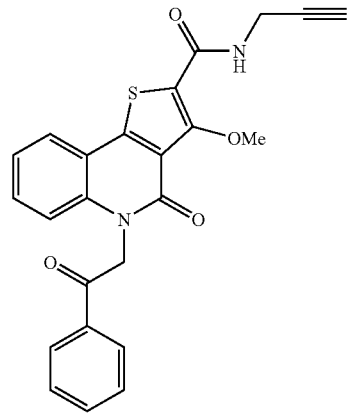 [SMILES: C#CCNC(=O)c1sc2c(c1OC)c(=O)n(CC(=O)c1ccccc1)c1ccccc21]

In the same manner as in Example 1, the title compound was obtained from the compound of Reference Example 7 and prop-2-yn-1-amine.

LC/MS 431 (M+H).

Example 212

Production of 3-methoxy-N-[3-(1-methylethoxy)propyl]-4-oxo-5-(2-oxo-2-phenylethyl)-4,5-dihydrothieno[3,2-c]quinoline-2-carboxamide

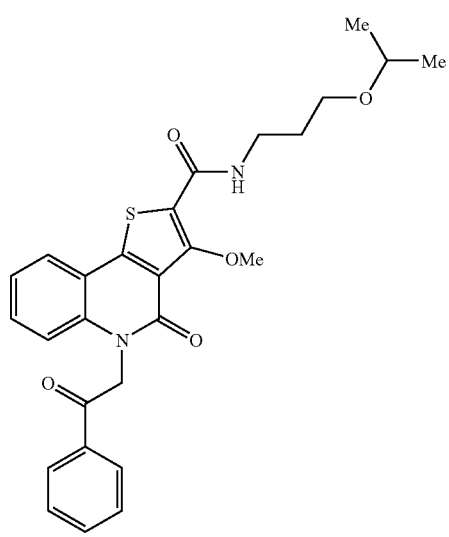 [SMILES: COc1c(C(=O)NCCCOC(C)C)sc2c1c(=O)n(CC(=O)c1ccccc1)c1ccccc21]

In the same manner as in Example 1, the title compound was obtained from the compound of Reference Example 7 and 3-(1-methylethoxy)propan-1-amine.

LC/MS 493 (M+H).

Example 213

Production of 3-methoxy-4-oxo-N-(2-oxoazepan-3-yl)-5-(2-oxo-2-phenylethyl)-4,5-dihydrothieno[3,2-c]quinoline-2-carboxamide

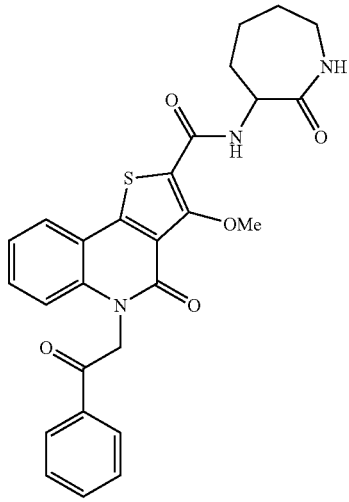 [SMILES: COc1c(C(=O)NC2CCCCNC2=O)sc2c1c(=O)n(CC(=O)c1ccccc1)c1ccccc21]

In the same manner as in Example 1, the title compound was obtained from the compound of Reference Example 7 and 3-aminoazepan-2-one.

LC/MS 504 (M+H).

Example 214

Production of N-(furan-2-ylmethyl)-3-methoxy-4-oxo-5-(2-oxo-2-phenylethyl)-4,5-dihydrothieno[3,2-c]quinoline-2-carboxamide

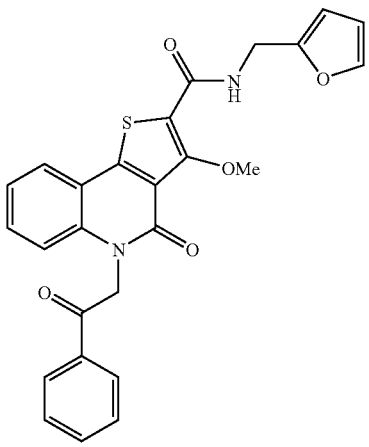 [SMILES: COc1c(C(=O)NCc2ccco2)sc2c1c(=O)n(CC(=O)c1ccccc1)c1ccccc21]

In the same manner as in Example 1, the title compound was obtained from the compound of Reference Example 7 and 1-furan-2-ylmethanamine.

LC/MS 473 (M+H).

Example 215

Production of 3-methoxy-4-oxo-5-(2-oxo-2-phenyl-ethyl)-N-[3-(2-oxopyrrolidin-1-yl)propyl]-4,5-dihydrothieno[3,2-c]quinoline-2-carboxamide

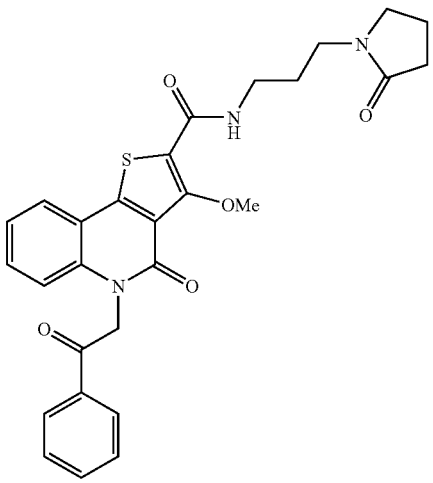 [SMILES: COc1c(C(=O)NCCCN2CCCC2=O)sc2c1c(=O)n(CC(=O)c1ccccc1)c1ccccc21]

In the same manner as in Example 1, the title compound was obtained from the compound of Reference Example 7 and 1-(3-aminopropyl)pyrrolidin-2-one.

LC/MS 518 (M+H).

Example 216

Production of 2-[(2,6-dimethylmorpholin-4-yl)carbonyl]-3-methoxy-5-(2-oxo-2-phenylethyl)thieno[3,2-c]quinolin-4(5H)-one

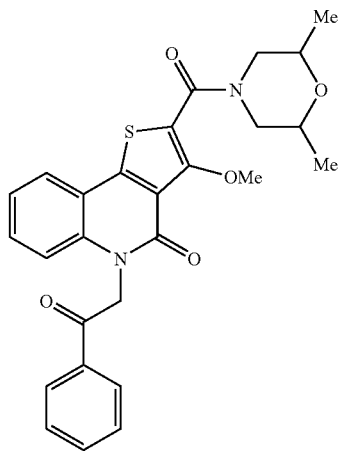 [SMILES: COc1c(C(=O)N2CC(C)OC(C)C2)sc2c1c(=O)n(CC(=O)c1ccccc1)c1ccccc21]

In the same manner as in Example 1, the title compound was obtained from the compound of Reference Example 7 and 2,6-dimethylmorpholine.

LC/MS 491 (M+H).

Example 217

Production of 2-[(4-benzylpiperidin-1-yl)carbonyl]-3-methoxy-5-(2-oxo-2-phenylethyl)thieno[3,2-c]quinolin-4(5H)-one

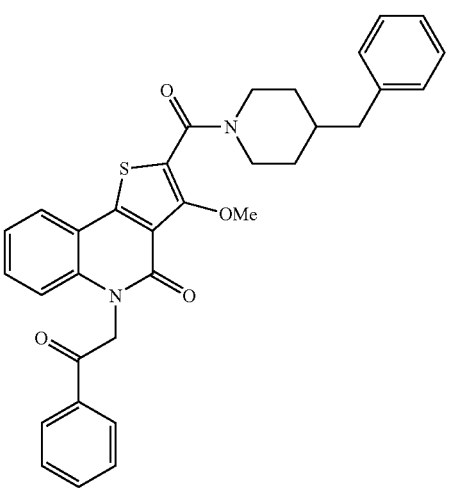 [SMILES: COc1c(C(=O)N2CCC(Cc3ccccc3)CC2)sc2c1c(=O)n(CC(=O)c1ccccc1)c1ccccc21]

In the same manner as in Example 1, the title compound was obtained from the compound of Reference Example 7 and 4-benzylpiperidine.

LC/MS 551 (M+H).

Example 218

Production of N-[2-(3,4-dimethoxyphenyl)ethyl]-3-methoxy-N-methyl-4-oxo-5-(2-oxo-2-phenylethyl)-4,5-dihydrothieno[3,2-c]quinoline-2-carboxamide

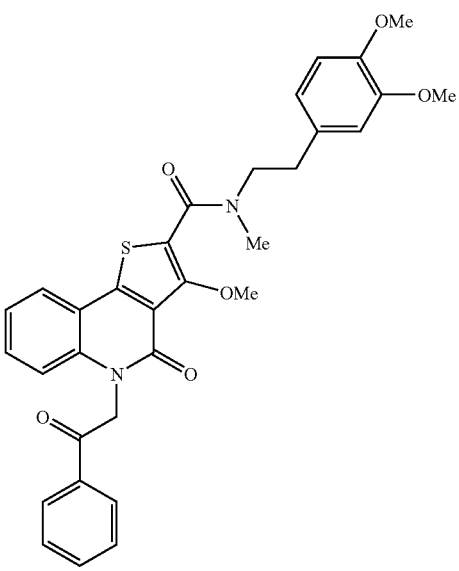 [SMILES: COc1ccc(CCN(C)C(=O)c2sc3c(c2OC)c(=O)n(CC(=O)c2ccccc2)c2ccccc32)cc1OC]

In the same manner as in Example 1, the title compound was obtained from the compound of Reference Example 7 and 2-(3,4-dimethoxyphenyl)-N-methylethanamine.

LC/MS 571 (M+H).

Example 219

Production of 3-methoxy-N,N-bis(2-methoxyethyl)-4-oxo-5-(2-oxo-2-phenylethyl)-4,5-dihydrothieno[3,2-c]quinoline-2-carboxamide

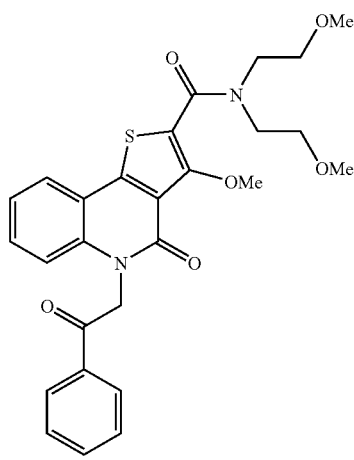 [SMILES: COCCN(CCOC)C(=O)c1sc2c(c1OC)c(=O)n(CC(=O)c1ccccc1)c1ccccc21]

In the same manner as in Example 1, the title compound was obtained from the compound of Reference Example 7 and 2-methoxy-N-(2-methoxyethyl)ethanamine.

LC/MS 509 (M+H).

Example 220

Production of 2-(3,4-dihydroisoquinolin-2(1H)-yl-carbonyl)-3-methoxy-5-(2-oxo-2-phenylethyl)thieno[3,2-c]quinolin-4(5H)-one

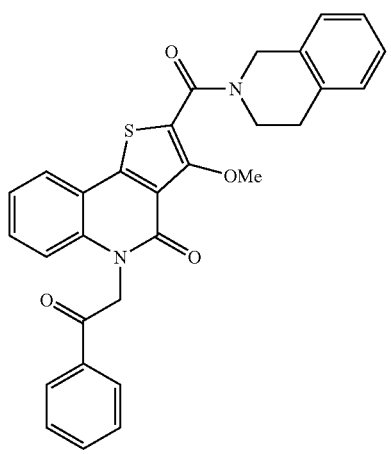 [SMILES: COc1c(C(=O)N2CCc3ccccc3C2)sc2c1c(=O)n(CC(=O)c1ccccc1)c1ccccc21]

In the same manner as in Example 1, the title compound was obtained from the compound of Reference Example 7 and 1,2,3,4-tetrahydroisoquinoline.

LC/MS 509 (M+H).

Example 221

Production of 3-methoxy-2-(octahydroisoquinolin-2(1H)-ylcarbonyl)-5-(2-oxo-2-phenylethyl)thieno[3,2-c]quinolin-4(5H)-one

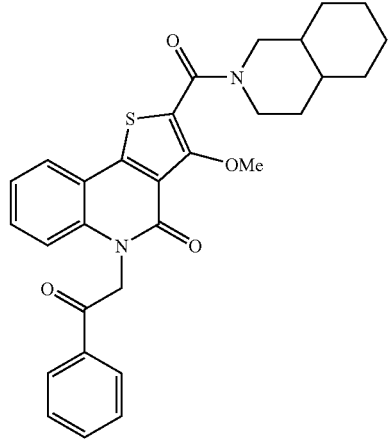 [SMILES: COc1c(C(=O)N2CCC3CCCCC3C2)sc2c1c(=O)n(CC(=O)c1ccccc1)c1ccccc21]

In the same manner as in Example 1, the title compound was obtained from the compound of Reference Example 7 and decahydroisoquinoline.

LC/MS 515 (M+H).

Example 222

Production of N-(1-{[3-methoxy-4-oxo-5-(2-oxo-2-phenylethyl)-4,5-dihydrothieno[3,2-c]quinolin-2-yl]carbonyl}pyrrolidin-3-yl)acetamide

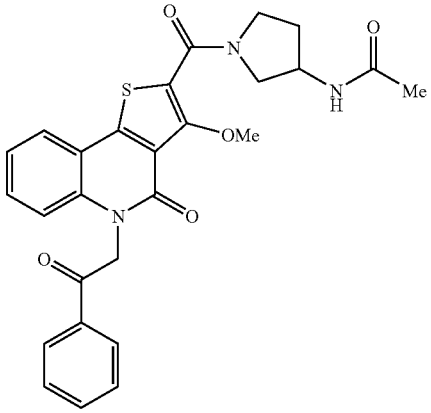 [SMILES: COc1c(C(=O)N2CCC(NC(C)=O)C2)sc2c1c(=O)n(CC(=O)c1ccccc1)c1ccccc21]

In the same manner as in Example 1, the title compound was obtained from the compound of Reference Example 7 and N-pyrrolidin-3-ylacetamide.

LC/MS 504 (M+H).

Example 223

Production of N-cyclohexyl-N-ethyl-3-methoxy-4-oxo-5-(2-oxo-2-phenylethyl)-4,5-dihydrothieno[3,2-c]quinoline-2-carboxamide

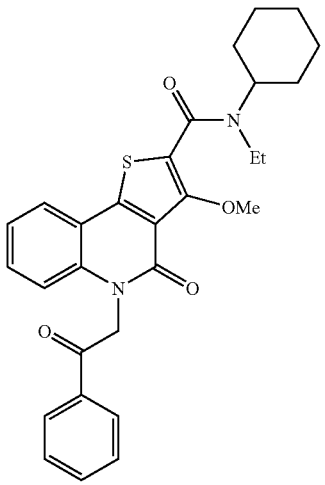 [SMILES: CCN(C(=O)c1sc2c(c1OC)c(=O)n(CC(=O)c1ccccc1)c1ccccc21)C1CCCCC1]

In the same manner as in Example 1, the title compound was obtained from the compound of Reference Example 7 and N-ethylcyclohexanamine.

LC/MS 503 (M+H).

Example 224

Production of N-(3,3-diphenylpropyl)-3-methoxy-4-oxo-5-(2-oxo-2-phenylethyl)-4,5-dihydrothieno[3,2-c]quinoline-2-carboxamide

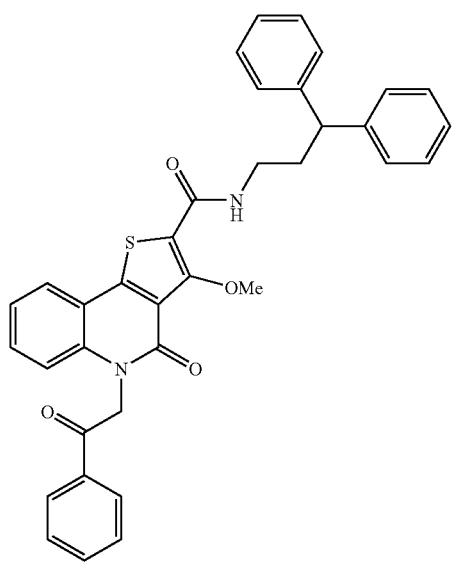 [SMILES: COc1c(C(=O)NCCC(c2ccccc2)c2ccccc2)sc2c1c(=O)n(CC(=O)c1ccccc1)c1ccccc21]

In the same manner as in Example 160, the title compound was obtained from the compound of Reference Example 7 and 3,3-diphenylpropan-1-amine.

LC/MS 587 (M+H).

Example 225

Production of N-[2-(dimethylamino)ethyl]-3-methoxy-5-methyl-4-oxo-4,5-dihydrothieno[3,2-c]quinoline-2-carboxamide trifluoroacetate

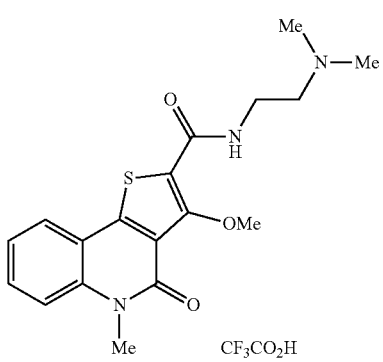 [SMILES: COc1c(C(=O)NCCN(C)C)sc2c1c(=O)n(C)c1ccccc21 ; "CF3CO2H"]

In the same manner as in Example 5, the title compound was obtained from the compound of Reference Example 84 and N,N-dimethylethane-1,2-diamine.

LC/MS 360 (M+H).

Example 226

Production of 3-methoxy-5-methyl-4-oxo-N-(pyridin-2-ylmethyl)-4,5-dihydrothieno[3,2-c]quinoline-2-carboxamide trifluoroacetate

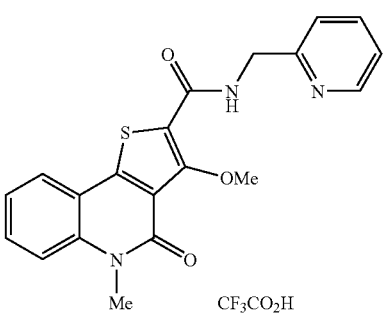 [SMILES: COc1c(C(=O)NCc2ccccn2)sc2c1c(=O)n(C)c1ccccc21 ; "CF3CO2H"]

In the same manner as in Example 5, the title compound was obtained from the compound of Reference Example 84 and 1-pyridin-2-ylmethanamine.

LC/MS 380 (M+H).

Example 227

Production of 3-methoxy-5-methyl-4-oxo-N-(pyridin-4-ylmethyl)-4,5-dihydrothieno[3,2-c]quinoline-2-carboxamide trifluoroacetate

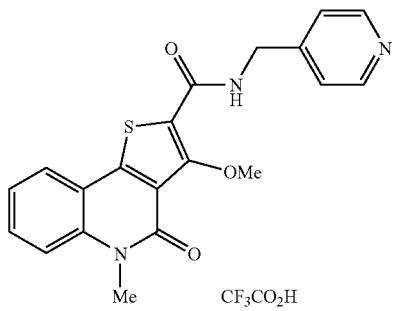 [SMILES: COc1c(C(=O)NCc2ccncc2)sc2c1c(=O)n(C)c1ccccc21 ; "CF3CO2H"]

In the same manner as in Example 5, the title compound was obtained from the compound of Reference Example 84 and 1-pyridin-4-ylmethanamine.

LC/MS 380 (M+H).

Example 228

Production of 3-methoxy-5-methyl-4-oxo-N-(2-pyrrolidin-1-ylethyl)-4,5-dihydrothieno[3,2-c]quinoline-2-carboxamide trifluoroacetate

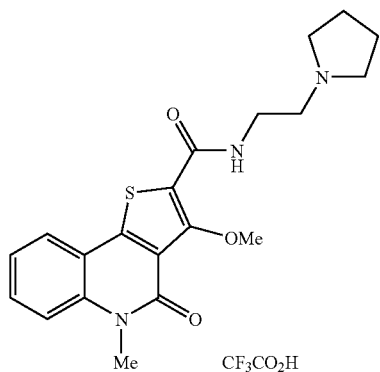 [SMILES: COc1c(C(=O)NCCN2CCCC2)sc2c1c(=O)n(C)c1ccccc21 ; "CF3CO2H"]

In the same manner as in Example 5, the title compound was obtained from the compound of Reference Example 84 and 2-pyrrolidin-1-ylethanamine.

LC/MS 386 (M+H).

Example 229

Production of 3-methoxy-5-methyl-4-oxo-N-(2-pyridin-3-ylethyl)-4,5-dihydrothieno[3,2-c]quinoline-2-carboxamide trifluoroacetate

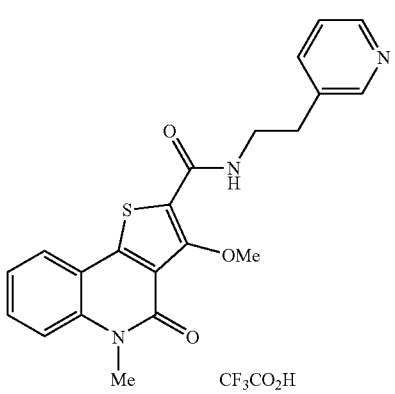 [SMILES: COc1c(C(=O)NCCc2cccnc2)sc2c1c(=O)n(C)c1ccccc21 ; "CF3CO2H"]

In the same manner as in Example 5, the title compound was obtained from the compound of Reference Example 84 and 2-pyridin-3-ylethanamine.

LC/MS 394 (M+H).

Example 230

Production of 3-methoxy-5-methyl-N-[(5-methylpyrazin-2-yl)methyl]-4-oxo-4,5-dihydrothieno[3,2-c]quinoline-2-carboxamide trifluoroacetate

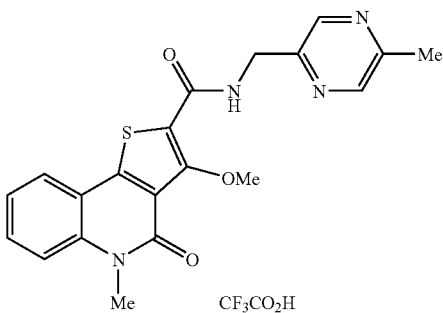 [SMILES: COc1c(C(=O)NCc2cnc(C)cn2)sc2c1c(=O)n(C)c1ccccc21 ; "CF3CO2H"]

In the same manner as in Example 5, the title compound was obtained from the compound of Reference Example 84 and 1-(5-methylpyrazin-2-yl)methanamine.

LC/MS 395 (M+H).

Example 231

Production of N-[3-(1H-imidazol-1-yl)propyl]-3-methoxy-5-methyl-4-oxo-4,5-dihydrothieno[3,2-c]quinoline-2-carboxamide trifluoroacetate

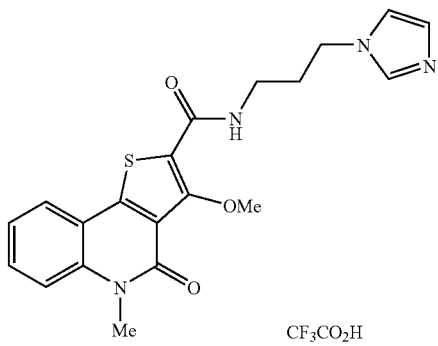 [SMILES: COc1c(C(=O)NCCCn2ccnc2)sc2c1c(=O)n(C)c1ccccc21 ; "CF3CO2H"]

In the same manner as in Example 5, the title compound was obtained from the compound of Reference Example 84 and 3-(1H-imidazol-1-yl)propan-1-amine.

LC/MS 397 (M+H).

Example 232

Production of 3-methoxy-5-methyl-N-[2-(1-methylpyrrolidin-2-yl)ethyl]-4-oxo-4,5-dihydrothieno[3,2-c]quinoline-2-carboxamide trifluoroacetate

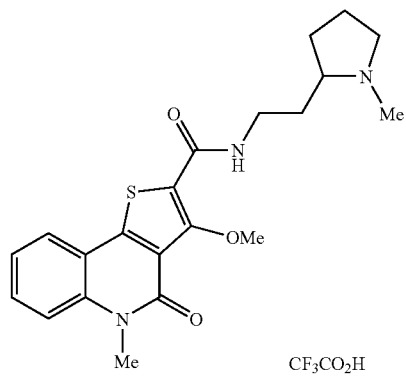 [SMILES: COc1c(C(=O)NCCC2CCCN2C)sc2c1c(=O)n(C)c1ccccc21 ; "CF3CO2H"]

In the same manner as in Example 5, the title compound was obtained from the compound of Reference Example 84 and 2-(1-methylpyrrolidin-2-yl)ethanamine.

LC/MS 400 (M+H).

Example 233

Production of 3-methoxy-5-methyl-4-oxo-N-(2-piperidin-1-ylethyl)-4,5-dihydrothieno[3,2-c]quinoline-2-carboxamide trifluoroacetate

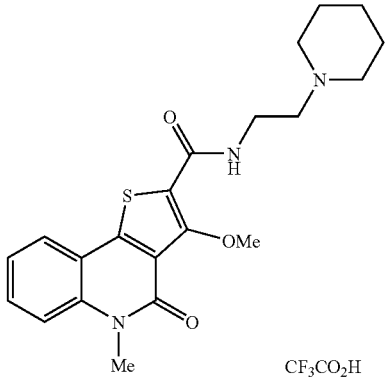 [SMILES: COc1c(C(=O)NCCN2CCCCC2)sc2c1c(=O)n(C)c1ccccc21 ; "CF3CO2H"]

In the same manner as in Example 5, the title compound was obtained from the compound of Reference Example 84 and 2-piperidin-1-ylethanamine.

LC/MS 400 (M+H).

Example 234

Production of N-[3-(diethylamino)propyl]-3-methoxy-5-methyl-4-oxo-4,5-dihydrothieno[3,2-c]quinoline-2-carboxamide trifluoroacetate

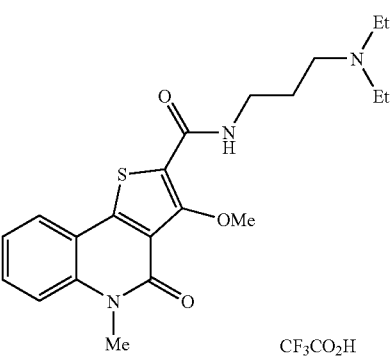 [SMILES: CCN(CC)CCCNC(=O)c1sc2c(c1OC)c(=O)n(C)c1ccccc21 ; "CF3CO2H"]

In the same manner as in Example 5, the title compound was obtained from the compound of Reference Example 84 and N,N-diethylpropane-1,3-diamine.

LC/MS 402 (M+H).

Example 235

Production of 3-methoxy-5-methyl-N-(3-morpholin-4-ylpropyl)-4-oxo-4,5-dihydrothieno[3,2-c]quinoline-2-carboxamide trifluoroacetate

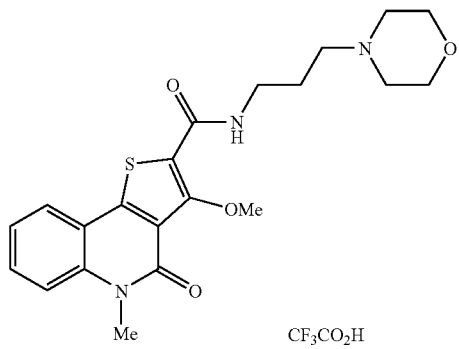 [SMILES: COc1c(C(=O)NCCCN2CCOCC2)sc2c1c(=O)n(C)c1ccccc21 ; "CF3CO2H"]

In the same manner as in Example 5, the title compound was obtained from the compound of Reference Example 84 and 3-morpholin-4-ylpropan-1-amine.

LC/MS 416 (M+H).

Example 236

Production of 3-methoxy-5-methyl-N-[3-(4-methylpiperazin-1-yl)propyl]-4-oxo-4,5-dihydrothieno[3,2-c]quinoline-2-carboxamide ditrifluoroacetate

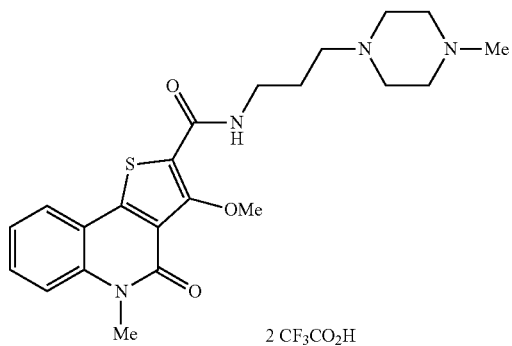 [SMILES: COc1c(C(=O)NCCCN2CCN(C)CC2)sc2c1c(=O)n(C)c1ccccc21 ; "2 CF3CO2H"]

In the same manner as in Example 5, the title compound was obtained from the compound of Reference Example 84 and 3-(4-methylpiperazin-1-yl)propan-1-amine.

LC/MS 429 (M+H).

Example 237

Production of N-[4-(diethylamino)-1-methylbutyl]-3-methoxy-5-methyl-4-oxo-4,5-dihydrothieno[3,2-c]quinoline-2-carboxamide trifluoroacetate

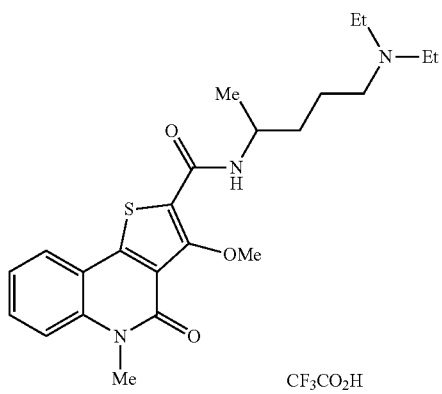 [SMILES: CCN(CC)CCCC(C)NC(=O)c1sc2c(c1OC)c(=O)n(C)c1ccccc21 ; "CF3CO2H"]

In the same manner as in Example 5, the title compound was obtained from the compound of Reference Example 84 and $N^1,N^1$-diethylpentane-1,4-diamine.

LC/MS 430 (M+H).

Example 238

Production of N-(1-benzylpyrrolidin-3-yl)-3-methoxy-5-methyl-4-oxo-4,5-dihydrothieno[3,2-c]quinoline-2-carboxamide trifluoroacetate

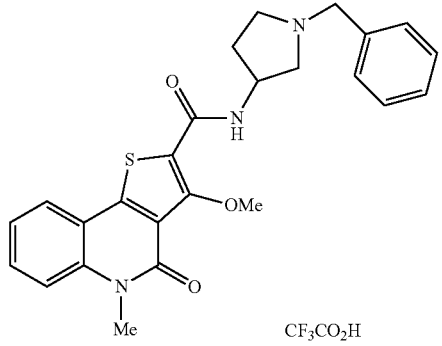 [SMILES: COc1c(C(=O)NC2CCN(Cc3ccccc3)C2)sc2c1c(=O)n(C)c1ccccc21 ; "CF3CO2H"]

In the same manner as in Example 5, the title compound was obtained from the compound of Reference Example 84 and 1-benzylpyrrolidin-3-amine.

LC/MS 448 (M+H).

Example 239

Production of N-(1-benzylpiperidin-4-yl)-3-methoxy-5-methyl-4-oxo-4,5-dihydrothieno[3,2-c]quinoline-2-carboxamide trifluoroacetate

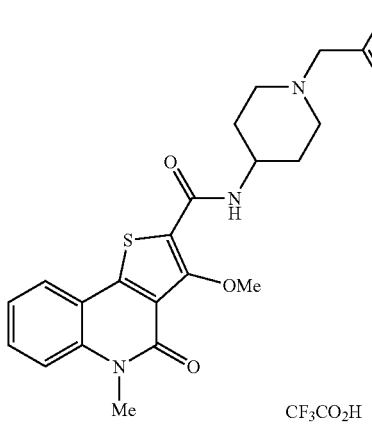

In the same manner as in Example 5, the title compound was obtained from the compound of Reference Example 84 and 1-benzylpiperidin-4-amine.
LC/MS 462 (M+H).

Example 240

Production of 3-methoxy-N,5-dimethyl-N-(1-methylpyrrolidin-3-yl)-4-oxo-4,5-dihydrothieno[3,2-c]quinoline-2-carboxamide trifluoroacetate

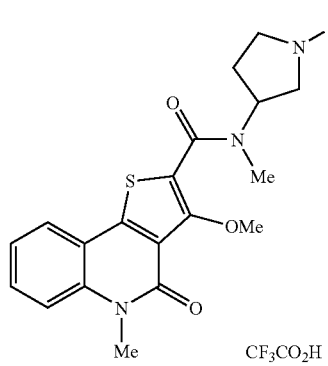

In the same manner as in Example 5, the title compound was obtained from the compound of Reference Example 84 and N,1-dimethylpyrrolidin-3-amine.
LC/MS 386 (M+H).

Example 241

Production of 3-methoxy-5-methyl-2-[(4-methyl-1,4-diazepan-1-yl)carbonyl]thieno[3,2-c]quinolin-4(5H)-one trifluoroacetate

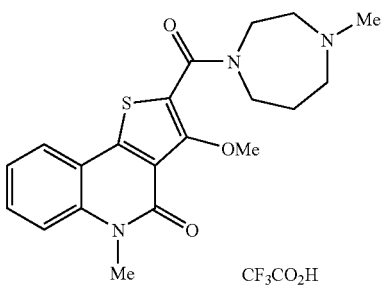 [SMILES: COc1c(C(=O)N2CCCN(C)CC2)sc2c1c(=O)n(C)c1ccccc21 ; "CF3CO2H"]

In the same manner as in Example 5, the title compound was obtained from the compound of Reference Example 84 and 1-methyl-1,4-diazepane.
LC/MS 386 (M+H).

Example 242

Production of 2-[(4-ethylpiperazin-1-yl)carbonyl]-3-methoxy-5-methylthieno[3,2-c]quinolin-4(5H)-one trifluoroacetate

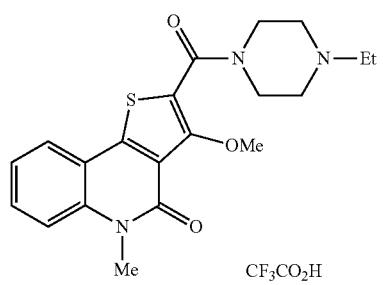 [SMILES: CCN1CCN(C(=O)c2sc3c(c2OC)c(=O)n(C)c2ccccc32)CC1 ; "CF3CO2H"]

In the same manner as in Example 5, the title compound was obtained from the compound of Reference Example 84 and 1-ethylpiperazine.
LC/MS 386 (M+H).

Example 243

Production of N-[2-(diethylamino)ethyl]-3-methoxy-N,5-dimethyl-4-oxo-4,5-dihydrothieno[3,2-c]quinoline-2-carboxamide trifluoroacetate

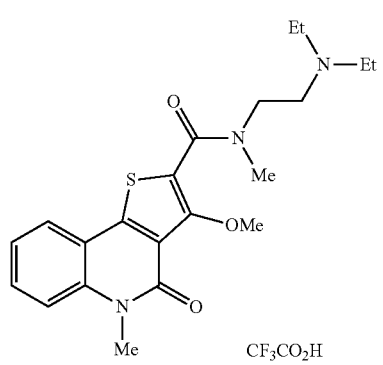 [SMILES: CCN(CC)CCN(C)C(=O)c1sc2c(c1OC)c(=O)n(C)c1ccccc21 ; "CF3CO2H"]

In the same manner as in Example 5, the title compound was obtained from the compound of Reference Example 84 and N,N-diethyl-N'-methylethane-1,2-diamine. LC/MS 402 (M+H).

Example 244

Production of 3-methoxy-5-methyl-2-{[(2S)-2-(pyrrolidin-1-ylmethyl)pyrrolidin-1-yl]carbonyl}thieno[3,2-c]quinolin-4(5H)-one trifluoroacetate

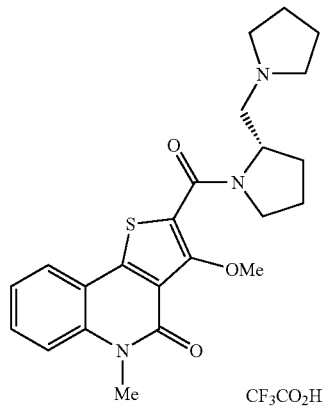 [SMILES: COc1c(C(=O)N2CCC[C@H]2CN2CCCC2)sc2c1c(=O)n(C)c1ccccc21 ; "CF3CO2H"]

In the same manner as in Example 5, the title compound was obtained from the compound of Reference Example 84 and 1-[(2S)-pyrrolidin-2-ylmethyl]pyrrolidine.
LC/MS 426 (M+H).

Example 245

Production of 3-methoxy-5-methyl-2-[(4-pyrrolidin-1-ylpiperidin-1-yl)carbonyl]thieno[3,2-c]quinolin-4(5H)-one trifluoroacetate

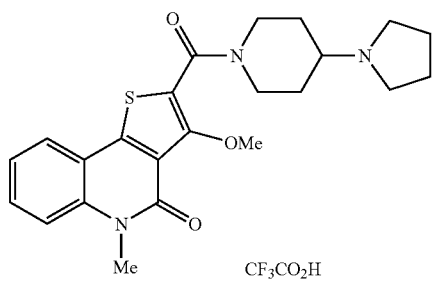 [SMILES: COc1c(C(=O)N2CCC(N3CCCC3)CC2)sc2c1c(=O)n(C)c1ccccc21 ; "CF3CO2H"]

In the same manner as in Example 5, the title compound was obtained from the compound of Reference Example 84 and 4-pyrrolidin-1-ylpiperidine.
LC/MS 426 (M+H).

Example 246

Production of 3-methoxy-5-methyl-2-[(4-phenylpiperazin-1-yl)carbonyl]thieno[3,2-c]quinolin-4(5H)-one trifluoroacetate

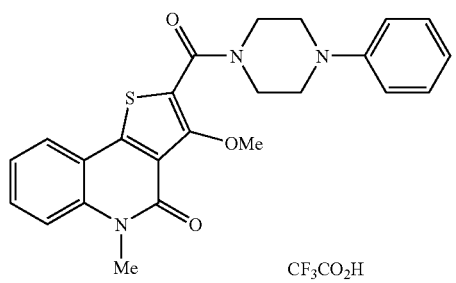 [SMILES: COc1c(C(=O)N2CCN(c3ccccc3)CC2)sc2c1c(=O)n(C)c1ccccc21 ; "CF3CO2H"]

In the same manner as in Example 5, the title compound was obtained from the compound of Reference Example 84 and 1-phenylpiperazine.
LC/MS 434 (M+H).

Example 247

Production of N-(2-cyanoethyl)-3-methoxy-5-methyl-4-oxo-N-(pyridin-3-ylmethyl)-4,5-dihydrothieno[3,2-c]quinoline-2-carboxamide trifluoroacetate

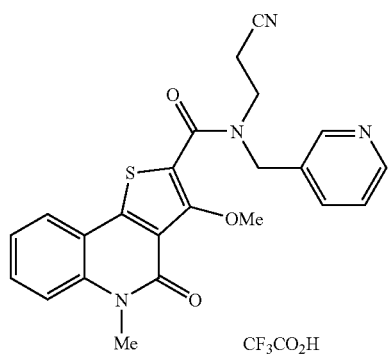 [SMILES: COc1c(C(=O)N(CCC#N)Cc2cccnc2)sc2c1c(=O)n(C)c1ccccc21 ; "CF3CO2H"]

In the same manner as in Example 5, the title compound was obtained from the compound of Reference Example 84 and 3-[(pyridin-3-ylmethyl)amino]propanenitrile.
LC/MS 433 (M+H).

Example 248

Production of 2-{[4-(1,3-benzodioxol-5-ylmethyl)piperazin-1-yl]carbonyl}-3-methoxy-5-methylthieno[3,2-c]quinolin-4(5H)-one trifluoroacetate

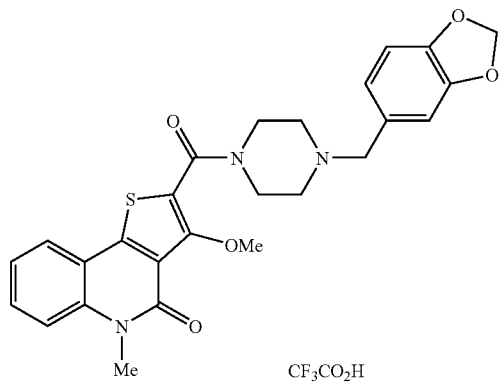 [SMILES: COc1c(C(=O)N2CCN(Cc3ccc4c(c3)OCO4)CC2)sc2c1c(=O)n(C)c1ccccc21 ; "CF3CO2H"]

In the same manner as in Example 5, the title compound was obtained from the compound of Reference Example 84 and 1-(1,3-benzodioxol-5-ylmethyl)piperazine.
LC/MS 492 (M+H).

Example 249

Production of 5-butyl-N-[2-(dimethylamino)ethyl]-3-methoxy-4-oxo-4,5-dihydrothieno[3,2-c]quinoline-2-carboxamide trifluoroacetate

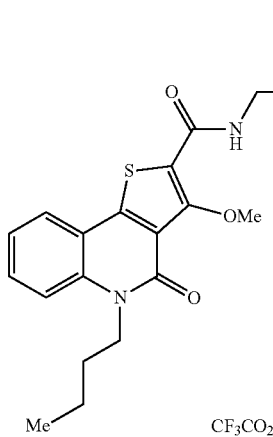

In the same manner as in Example 5, the title compound was obtained from the compound of Reference Example 103 and N,N-dimethylethane-1,2-diamine.

LC/MS 402 (M+H).

Example 250

Production of 5-butyl-3-methoxy-4-oxo-N-(pyridin-2-ylmethyl)-4,5-dihydrothieno[3,2-c]quinoline-2-carboxamide trifluoroacetate

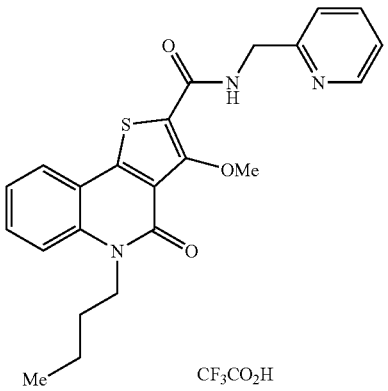 [SMILES: CCCCn1c(=O)c2c(OC)c(C(=O)NCc3ccccn3)sc2c2ccccc21 ; "CF3CO2H"]

In the same manner as in Example 5, the title compound was obtained from the compound of Reference Example 103 and 1-pyridin-2-ylmethanamine.

LC/MS 422 (M+H).

Example 251

Production of 5-butyl-3-methoxy-4-oxo-N-(pyridin-4-ylmethyl)-4,5-dihydrothieno[3,2-c]quinoline-2-carboxamide trifluoroacetate

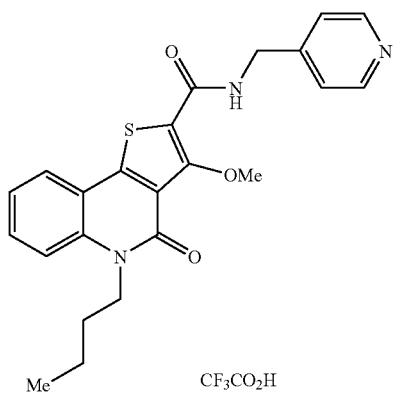 [SMILES: CCCCn1c(=O)c2c(OC)c(C(=O)NCc3ccncc3)sc2c2ccccc21 ; "CF3CO2H"]

In the same manner as in Example 5, the title compound was obtained from the compound of Reference Example 103 and 1-pyridin-4-ylmethanamine.

LC/MS 422 (M+H).

Example 252

Production of 5-butyl-3-methoxy-4-oxo-N-(2-pyrrolidin-1-ylethyl)-4,5-dihydrothieno[3,2-c]quinoline-2-carboxamide trifluoroacetate

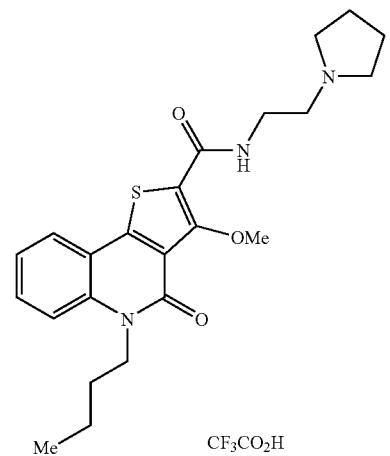 [SMILES: CCCCn1c(=O)c2c(OC)c(C(=O)NCCN3CCCC3)sc2c2ccccc21 ; "CF3CO2H"]

In the same manner as in Example 5, the title compound was obtained from the compound of Reference Example 103 and 2-pyrrolidin-1-ylethanamine.

LC/MS 428 (M+H).

Example 253

Production of 5-butyl-3-methoxy-4-oxo-N-(2-pyridin-3-ylethyl)-4,5-dihydrothieno[3,2-c]quinoline-2-carboxamide trifluoroacetate

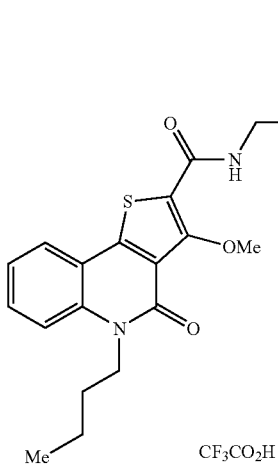

In the same manner as in Example 5, the title compound was obtained from the compound of Reference Example 103 and 2-pyridin-3-ylethanamine.

LC/MS 436 (M+H).

Example 254

Production of 5-butyl-3-methoxy-N-[(5-methylpyrazin-2-yl)methyl]-4-oxo-4,5-dihydrothieno[3,2-c]quinoline-2-carboxamide trifluoroacetate

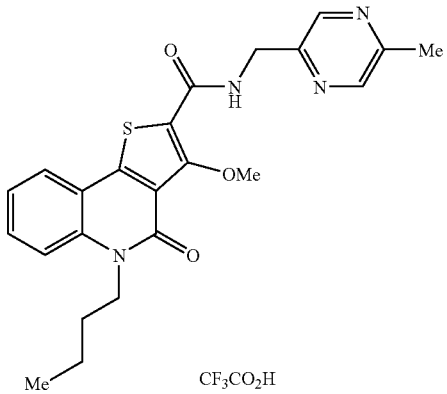 [SMILES: CCCCn1c(=O)c2c(OC)c(C(=O)NCc3cnc(C)cn3)sc2c2ccccc21 ; "CF3CO2H"]

In the same manner as in Example 5, the title compound was obtained from the compound of Reference Example 103 and 1-(5-methylpyrazin-2-yl)methanamine.

LC/MS 437 (M+H).

Example 255

Production of 5-butyl-N-[3-(1H-imidazol-1-yl)propyl]-3-methoxy-4-oxo-4,5-dihydrothieno[3,2-c]quinoline-2-carboxamide trifluoroacetate

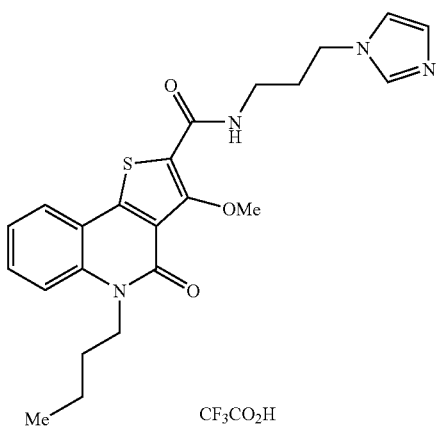 [SMILES: CCCCn1c(=O)c2c(OC)c(C(=O)NCCCn3ccnc3)sc2c2ccccc21 ; "CF3CO2H"]

In the same manner as in Example 5, the title compound was obtained from the compound of Reference Example 103 and 3-(1H-imidazol-1-yl)propan-1-amine.

LC/MS 439 (M+H).

Example 256

Production of 5-butyl-3-methoxy-N-[2-(1-methylpyrrolidin-2-yl)ethyl]-4-oxo-4,5-dihydrothieno[3,2-c]quinoline-2-carboxamide trifluoroacetate

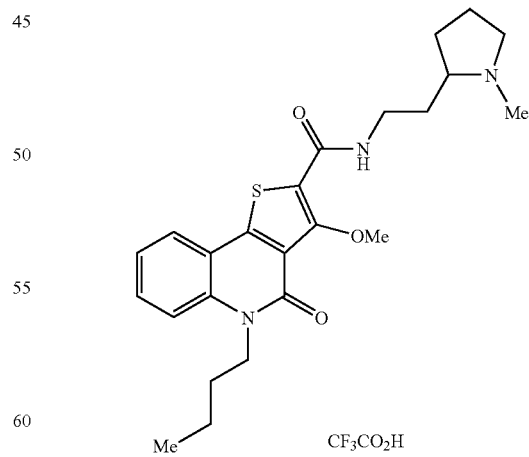

In the same manner as in Example 5, the title compound was obtained from the compound of Reference Example 103 and 2-(1-methylpyrrolidin-2-yl)ethanamine.

LC/MS 442 (M+H).

Example 257

Production of 5-butyl-3-methoxy-4-oxo-N-(2-piperidin-1-ylethyl)-4,5-dihydrothieno[3,2-c]quinoline-2-carboxamide trifluoroacetate

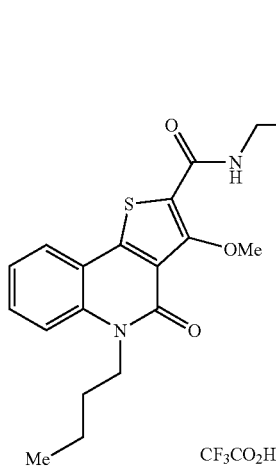

In the same manner as in Example 5, the title compound was obtained from the compound of Reference Example 103 and 2-piperidin-1-ylethanamine.
LC/MS 442 (M+H).

Example 258

Production of 5-butyl-N-[3-(diethylamino)propyl]-3-methoxy-4-oxo-4,5-dihydrothieno[3,2-c]quinoline-2-carboxamide trifluoroacetate

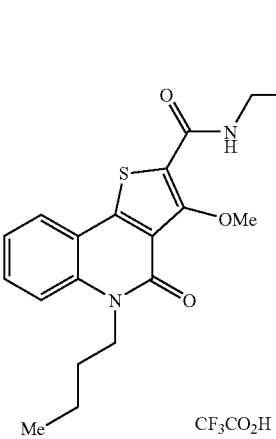

In the same manner as in Example 5, the title compound was obtained from the compound of Reference Example 103 and N,N-diethylpropane-1,3-diamine.
LC/MS 444 (M+H).

Example 259

Production of 5-butyl-3-methoxy-N-(3-morpholin-4-ylpropyl)-4-oxo-4,5-dihydrothieno[3,2-c]quinoline-2-carboxamide trifluoroacetate

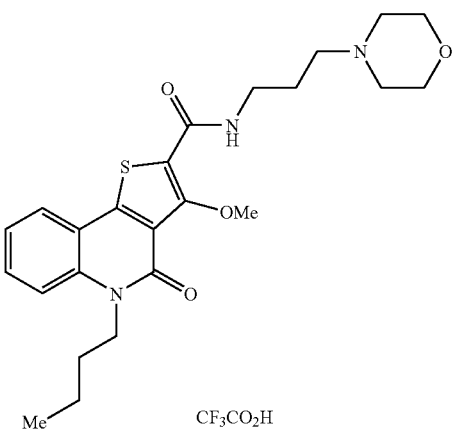 [SMILES: CCCCn1c(=O)c2c(OC)c(C(=O)NCCCN3CCOCC3)sc2c2ccccc21 ; "CF3CO2H"]

In the same manner as in Example 5, the title compound was obtained from the compound of Reference Example 103 and 3-morpholin-4-ylpropan-1-amine.
LC/MS 458 (M+H).

Example 260

Production of 5-butyl-3-methoxy-N-[3-(4-methylpiperazin-1-yl)propyl]-4-oxo-4,5-dihydrothieno[3,2-c]quinoline-2-carboxamide ditrifluoroacetate

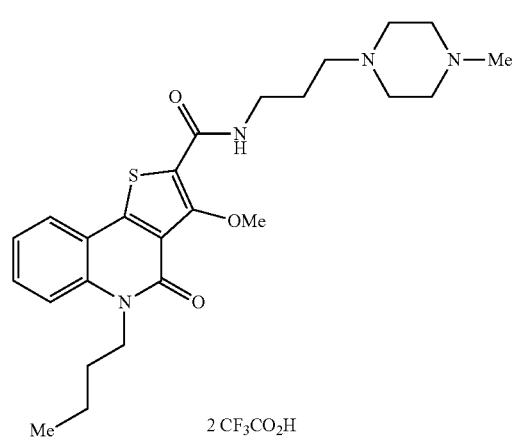 [SMILES: CCCCn1c(=O)c2c(OC)c(C(=O)NCCCN3CCN(C)CC3)sc2c2ccccc21 ; "2 CF3CO2H"]

In the same manner as in Example 5, the title compound was obtained from the compound of Reference Example 103 and 3-(4-methylpiperazin-1-yl)propan-1-amine.
LC/MS 471 (M+H).

Example 261

Production of 5-butyl-N-[4-(diethylamino)-1-methylbutyl]-3-methoxy-4-oxo-4,5-dihydrothieno[3,2-c]quinoline-2-carboxamide trifluoroacetate

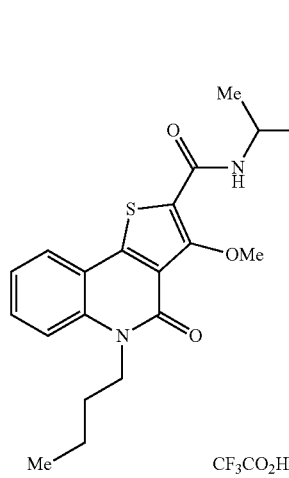

In the same manner as in Example 5, the title compound was obtained from the compound of Reference Example 103 and $N^1,N^1$-diethylpentane-1,4-diamine.

LC/MS 472 (M+H).

Example 262

Production of N-(1-benzylpyrrolidin-3-yl)-5-butyl-3-methoxy-4-oxo-4,5-dihydrothieno[3,2-c]quinoline-2-carboxamide trifluoroacetate

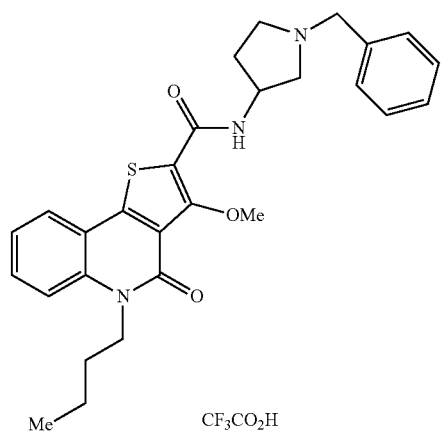 [SMILES: CCCCn1c(=O)c2c(OC)c(C(=O)NC3CCN(Cc4ccccc4)C3)sc2c2ccccc21 ; "CF3CO2H"]

In the same manner as in Example 5, the title compound was obtained from the compound of Reference Example 103 and 1-benzylpyrrolidin-3-amine.

LC/MS 490 (M+H).

Example 263

Production of N-(1-benzylpiperidin-4-yl)-5-butyl-3-methoxy-4-oxo-4,5-dihydrothieno[3,2-c]quinoline-2-carboxamide trifluoroacetate

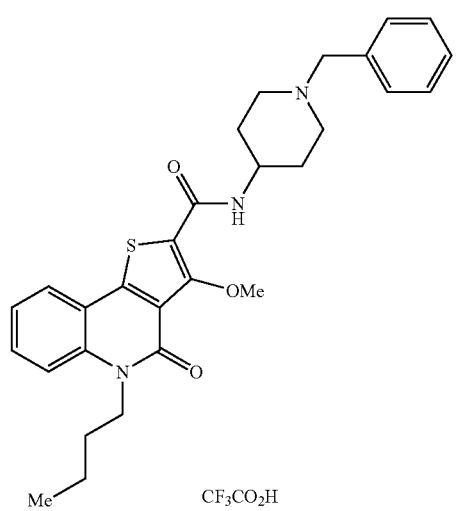 [SMILES: CCCCn1c(=O)c2c(OC)c(C(=O)NC3CCN(Cc4ccccc4)CC3)sc2c2ccccc21 ; "CF3CO2H"]

In the same manner as in Example 5, the title compound was obtained from the compound of Reference Example 103 and 1-benzylpiperidin-4-amine.

LC/MS 504 (M+H).

Example 264

Production of 5-butyl-3-methoxy-N-methyl-N-(1-methylpyrrolidin-3-yl)-4-oxo-4,5-dihydrothieno[3,2-c]quinoline-2-carboxamide trifluoroacetate

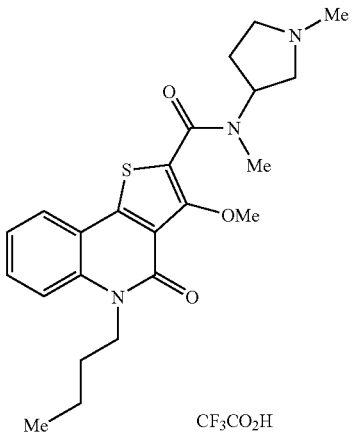 [SMILES: CCCCn1c(=O)c2c(OC)c(C(=O)N(C)C3CCN(C)C3)sc2c2ccccc21 ; "CF3CO2H"]

In the same manner as in Example 5, the title compound was obtained from the compound of Reference Example 103 and N,1-dimethylpyrrolidin-3-amine.

LC/MS 428 (M+H).

Example 265

Production of 5-butyl-3-methoxy-2-[(4-methyl-1,4-diazepan-1-yl)carbonyl]thieno[3,2-c]quinolin-4(5H)-one trifluoroacetate

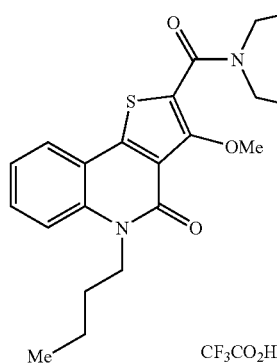

In the same manner as in Example 5, the title compound was obtained from the compound of Reference Example 103 and 1-methyl-1,4-diazepane.

LC/MS 428 (M+H).

Example 266

Production of 5-butyl-2-[(4-ethylpiperazin-1-yl)carbonyl]-3-methoxythieno[3,2-c]quinolin-4(5H)-one trifluoroacetate

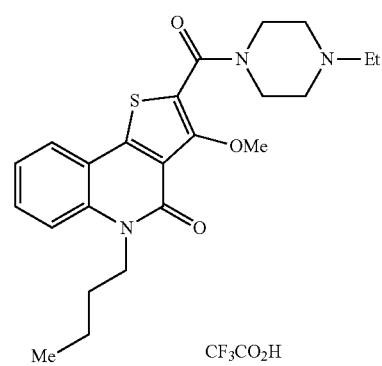 [SMILES: CCCCn1c(=O)c2c(OC)c(C(=O)N3CCN(CC)CC3)sc2c2ccccc21 ; "CF3CO2H"]

In the same manner as in Example 5, the title compound was obtained from the compound of Reference Example 103 and 1-ethylpiperazine.

LC/MS 428 (M+H).

Example 267

Production of 5-butyl-N-[2-(diethylamino)ethyl]-3-methoxy-N-methyl-4-oxo-4,5-dihydrothieno[3,2-c]quinoline-2-carboxamide trifluoroacetate

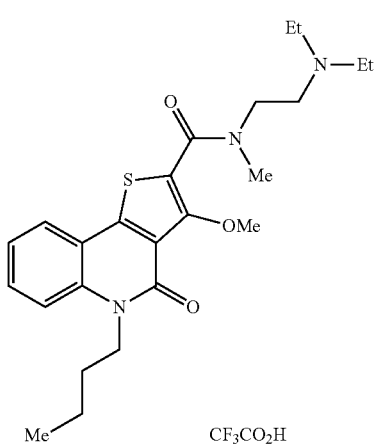 [SMILES: CCCCn1c(=O)c2c(OC)c(C(=O)N(C)CCN(CC)CC)sc2c2ccccc21 ; "CF3CO2H"]

In the same manner as in Example 5, the title compound was obtained from the compound of Reference Example 103 and N,N-diethyl-N'-methylethane-1,2-diamine.

LC/MS 444 (M+H).

Example 268

Production of 5-butyl-3-methoxy-2-{[(2S)-2-(pyrrolidin-1-ylmethyl)pyrrolidin-1-yl]carbonyl}thieno[3,2-c]quinolin-4(5H)-one trifluoroacetate

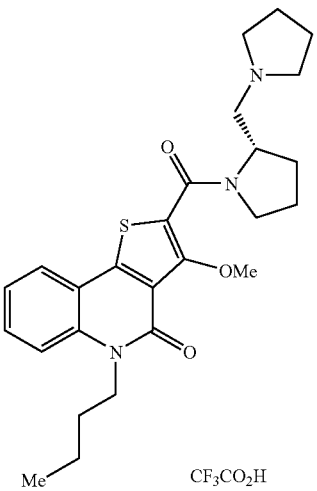 [SMILES: CCCCn1c(=O)c2c(OC)c(C(=O)N3CCC[C@H]3CN3CCCC3)sc2c2ccccc21 ; "CF3CO2H"]

In the same manner as in Example 5, the title compound was obtained from the compound of Reference Example 103 and 1-[(2S)-pyrrolidin-2-ylmethyl]pyrrolidine.

LC/MS 468 (M+H).

Example 269

Production of 5-butyl-3-methoxy-2-[(4-pyrrolidin-1-ylpiperidin-1-yl)carbonyl]thieno[3,2-c]quinolin-4(5H)-one trifluoroacetate

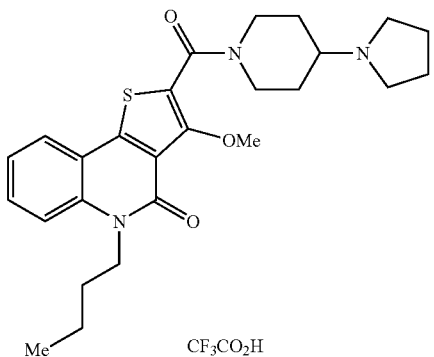 [SMILES: CCCCn1c(=O)c2c(OC)c(C(=O)N3CCC(N4CCCC4)CC3)sc2c2ccccc21 ; "CF3CO2H"]

In the same manner as in Example 5, the title compound was obtained from the compound of Reference Example 103 and 4-pyrrolidin-1-ylpiperidine.
LC/MS 468 (M+H).

Example 270

Production of 5-butyl-3-methoxy-2-[(4-phenylpiperazin-1-yl)carbonyl]thieno[3,2-c]quinolin-4(5H)-one trifluoroacetate

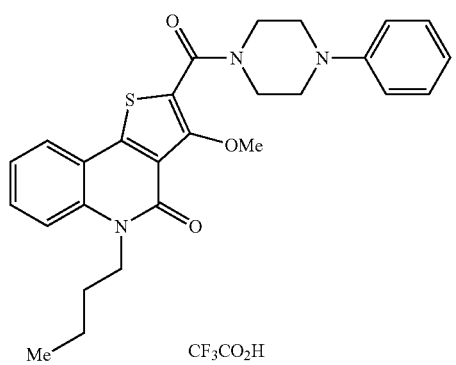 [SMILES: CCCCn1c(=O)c2c(OC)c(C(=O)N3CCN(c4ccccc4)CC3)sc2c2ccccc21 ; "CF3CO2H"]

In the same manner as in Example 5, the title compound was obtained from the compound of Reference Example 103 and 1-phenylpiperazine.
LC/MS 476 (M+H).

Example 271

Production of 5-butyl-N-(2-cyanoethyl)-3-methoxy-4-oxo-N-(pyridin-3-ylmethyl)-4,5-dihydrothieno[3,2-c]quinoline-2-carboxamide trifluoroacetate

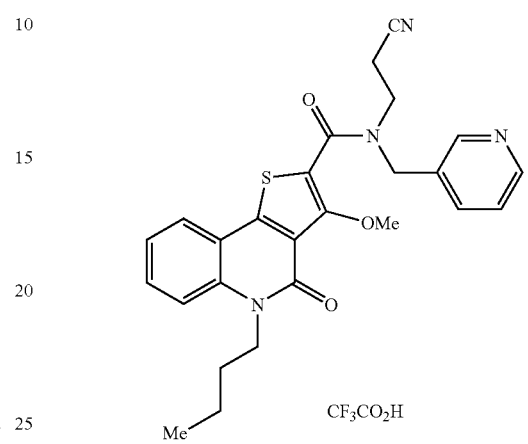

In the same manner as in Example 5, the title compound was obtained from the compound of Reference Example 103 and 3-[(pyridin-3-ylmethyl)amino]propanenitrile.
LC/MS 475 (M+H).

Example 272

Production of 2-{[4-(1,3-benzodioxol-5-ylmethyl)piperazin-1-yl]carbonyl}-5-butyl-3-methoxythieno[3,2-c]quinolin-4(5H)-one trifluoroacetate

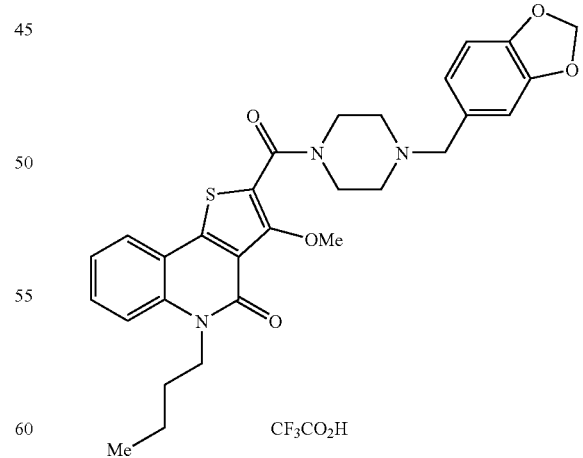

In the same manner as in Example 5, the title compound was obtained from the compound of Reference Example 103 and 1-(1,3-benzodioxol-5-ylmethyl)piperazine.
LC/MS 534 (M+H).

Example 273

Production of N-[2-(dimethylamino)ethyl]-3-methoxy-4-oxo-5-(pyridin-2-ylmethyl)-4,5-dihydrothieno[3,2-c]quinoline-2-carboxamide ditrifluoroacetate

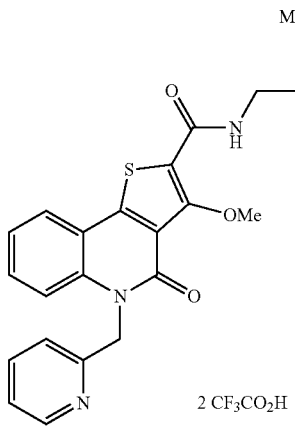

In the same manner as in Example 3, the title compound was obtained from the compound of Reference Example 19 and N,N-dimethylethane-1,2-diamine.

LC/MS 437 (M+H).

Example 274

Production of 3-methoxy-4-oxo-N,5-bis(pyridin-2-ylmethyl)-4,5-dihydrothieno[3,2-c]quinoline-2-carboxamide ditrifluoroacetate

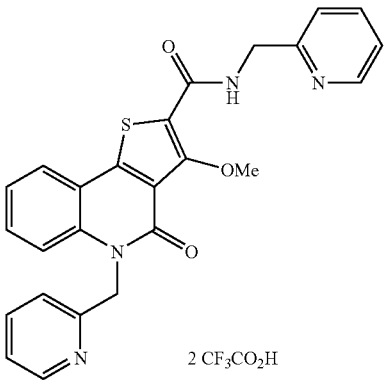 [SMILES: COc1c(C(=O)NCc2ccccn2)sc2c1c(=O)n(Cc1ccccn1)c1ccccc21 ; "2 CF3CO2H"]

In the same manner as in Example 3, the title compound was obtained from the compound of Reference Example 19 and 1-pyridin-2-ylmethanamine.

LC/MS 457 (M+H).

Example 275

Production of 3-methoxy-4-oxo-5-(pyridin-2-ylmethyl)-N-(pyridin-4-ylmethyl)-4,5-dihydrothieno[3,2-c]quinoline-2-carboxamide ditrifluoroacetate

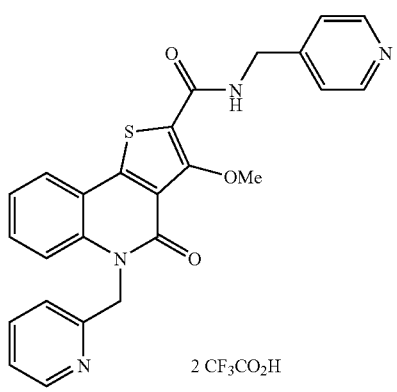 [SMILES: COc1c(C(=O)NCc2ccncc2)sc2c1c(=O)n(Cc1ccccn1)c1ccccc21 ; "2 CF3CO2H"]

In the same manner as in Example 3, the title compound was obtained from the compound of Reference Example 19 and 1-pyridin-4-ylmethanamine.

LC/MS 457 (M+H).

Example 276

Production of 3-methoxy-4-oxo-5-(pyridin-2-ylmethyl)-N-(2-pyrrolidin-1-ylethyl)-4,5-dihydrothieno[3,2-c]quinoline-2-carboxamide ditrifluoroacetate

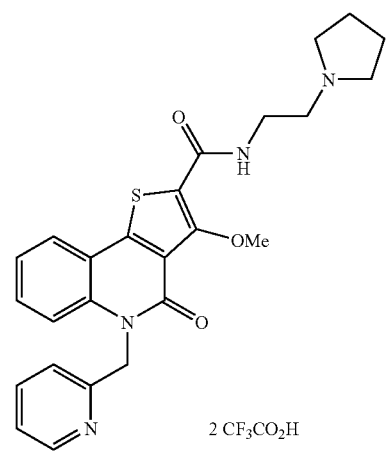 [SMILES: COc1c(C(=O)NCCN2CCCC2)sc2c1c(=O)n(Cc1ccccn1)c1ccccc21 ; "2 CF3CO2H"]

In the same manner as in Example 3, the title compound was obtained from the compound of Reference Example 19 and 2-pyrrolidin-1-ylethanamine.

LC/MS 463 (M+H).

Example 277

Production of 3-methoxy-4-oxo-N-(2-pyridin-3-yl-ethyl)-5-(pyridin-2-ylmethyl)-4,5-dihydrothieno[3,2-c]quinoline-2-carboxamide ditrifluoroacetate

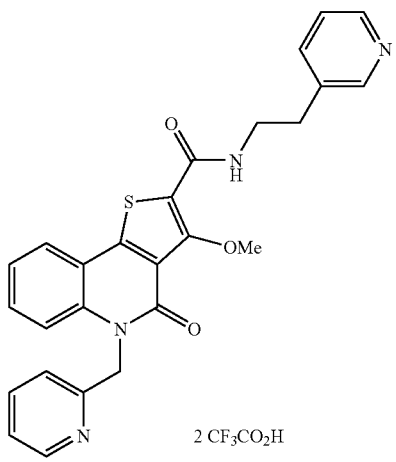 [SMILES: COc1c(C(=O)NCCc2cccnc2)sc2c1c(=O)n(Cc1ccccn1)c1ccccc21 ; "2 CF3CO2H"]

In the same manner as in Example 3, the title compound was obtained from the compound of Reference Example 19 and 2-pyridin-3-ylethanamine.

LC/MS 471 (M+H).

Example 278

Production of 3-methoxy-N-[(5-methylpyrazin-2-yl)methyl]-4-oxo-5-(pyridin-2-ylmethyl)-4,5-dihydrothieno[3,2-c]quinoline-2-carboxamide ditrifluoroacetate

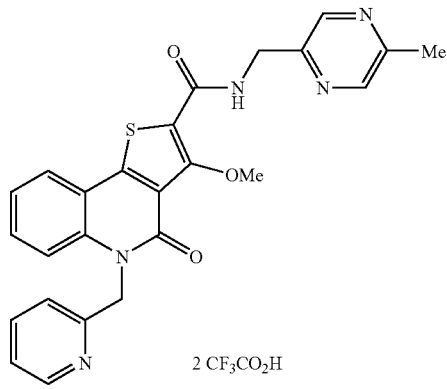 [SMILES: COc1c(C(=O)NCc2cnc(C)cn2)sc2c1c(=O)n(Cc1ccccn1)c1ccccc21 ; "2 CF3CO2H"]

In the same manner as in Example 3, the title compound was obtained from the compound of Reference Example 19 and 1-(5-methylpyrazin-2-yl)methanamine.

LC/MS 472 (M+H).

Example 279

Production of N-[3-(1H-imidazol-1-yl)propyl]-3-methoxy-4-oxo-5-(pyridin-2-ylmethyl)-4,5-dihydrothieno[3,2-c]quinoline-2-carboxamide ditrifluoroacetate

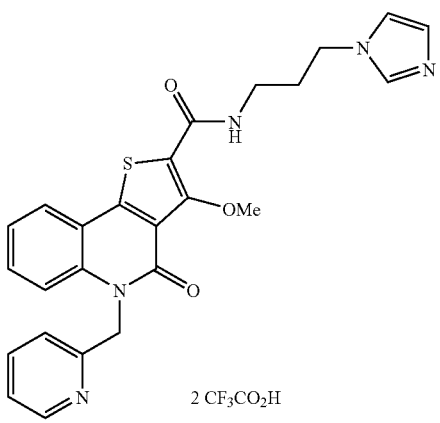 [SMILES: COc1c(C(=O)NCCCn2ccnc2)sc2c1c(=O)n(Cc1ccccn1)c1ccccc21 ; "2 CF3CO2H"]

In the same manner as in Example 3, the title compound was obtained from the compound of Reference Example 19 and 3-(1H-imidazol-1-yl)propan-1-amine.

LC/MS 474 (M+H).

Example 280

Production of 3-methoxy-N-[2-(1-methylpyrrolidin-2-yl)ethyl]-4-oxo-5-(pyridin-2-ylmethyl)-4,5-dihydrothieno[3,2-c]quinoline-2-carboxamide ditrifluoroacetate

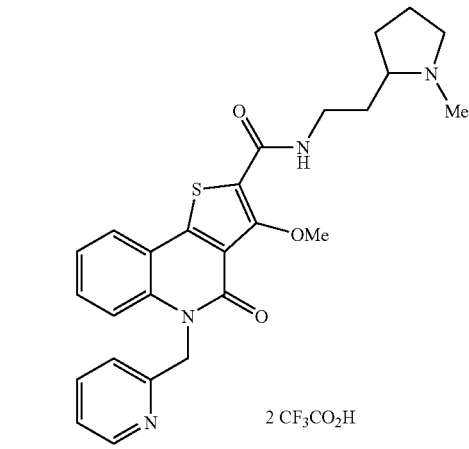 [SMILES: COc1c(C(=O)NCCC2CCCN2C)sc2c1c(=O)n(Cc1ccccn1)c1ccccc21 ; "2 CF3CO2H"]

In the same manner as in Example 3, the title compound was obtained from the compound of Reference Example 19 and 2-(1-methylpyrrolidin-2-yl)ethanamine.

LC/MS 477 (M+H).

Example 281

Production of 3-methoxy-4-oxo-N-(2-piperidin-1-ylethyl)-5-(pyridin-2-ylmethyl)-4,5-dihydrothieno[3,2-c]quinoline-2-carboxamide ditrifluoroacetate

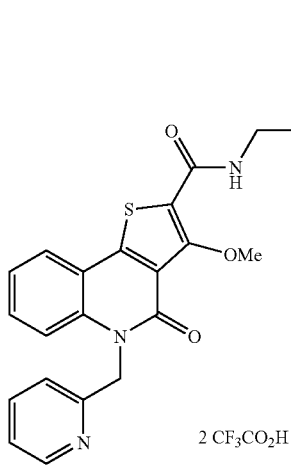

2 CF$_3$CO$_2$H

In the same manner as in Example 3, the title compound was obtained from the compound of Reference Example 19 and 2-piperidin-1-ylethanamine.

LC/MS 477 (M+H).

Example 282

Production of N-[3-(diethylamino)propyl]-3-methoxy-4-oxo-5-(pyridin-2-ylmethyl)-4,5-dihydrothieno[3,2-c]quinoline-2-carboxamide ditrifluoroacetate

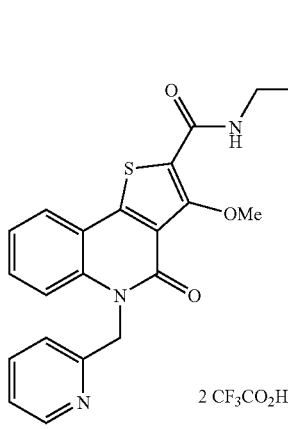

2 CF$_3$CO$_2$H

In the same manner as in Example 3, the title compound was obtained from the compound of Reference Example 19 and N,N-diethylpropane-1,3-diamine.

LC/MS 479 (M+H).

Example 283

Production of 3-methoxy-N-(3-morpholin-4-ylpropyl)-4-oxo-5-(pyridin-2-ylmethyl)-4,5-dihydrothieno[3,2-c]quinoline-2-carboxamide ditrifluoroacetate

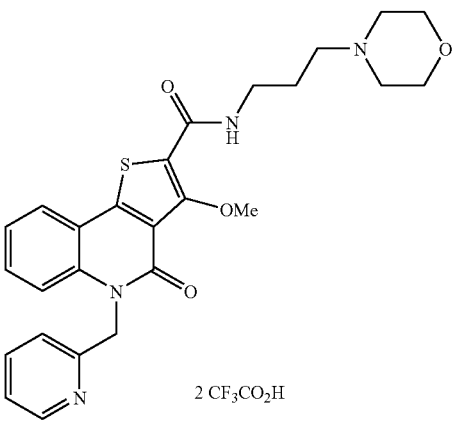 [SMILES: COc1c(C(=O)NCCCN2CCOCC2)sc2c1c(=O)n(Cc1ccccn1)c1ccccc21 ; "2 CF3CO2H"]

2 CF$_3$CO$_2$H

In the same manner as in Example 3, the title compound was obtained from the compound of Reference Example 19 and 3-morpholin-4-ylpropan-1-amine.

LC/MS 493 (M+H).

Example 284

Production of 3-methoxy-N-[3-(4-methylpiperazin-1-yl)propyl]-4-oxo-5-(pyridin-2-ylmethyl)-4,5-dihydrothieno[3,2-c] quinoline-2-carboxamide tritrifluoroacetate

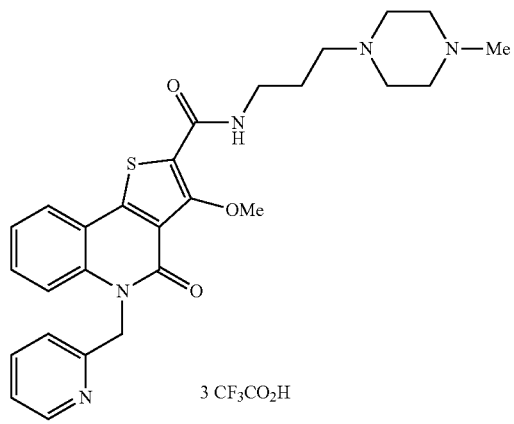 [SMILES: COc1c(C(=O)NCCCN2CCN(C)CC2)sc2c1c(=O)n(Cc1ccccn1)c1ccccc21 ; "3 CF3CO2H"]

3 CF$_3$CO$_2$H

In the same manner as in Example 3, the title compound was obtained from the compound of Reference Example 19 and 3-(4-methylpiperazin-1-yl)propan-1-amine.

Example 285

Production of N-[4-(diethylamino)-1-methylbutyl]-3-methoxy-4-oxo-5-(pyridin-2-ylmethyl)-4,5-dihydrothieno[3,2-c]quinoline-2-carboxamide ditrifluoroacetate

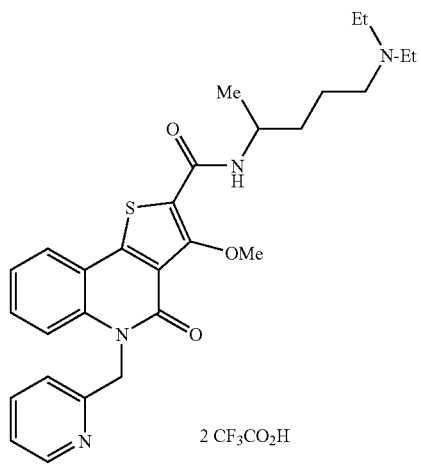

In the same manner as in Example 3, the title compound was obtained from the compound of Reference Example 19 and $N^1,N^1$-diethylpentane-1,4-diamine.

LC/MS 507 (M+H).

Example 286

Production of N-(1-benzylpyrrolidin-3-yl)-3-methoxy-4-oxo-5-(pyridin-2-ylmethyl)-4,5-dihydrothieno[3,2-c]quinoline-2-carboxamide ditrifluoroacetate

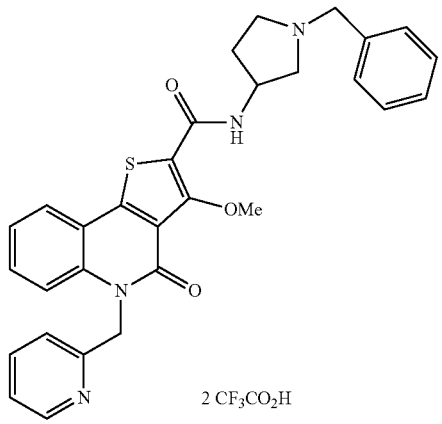 [SMILES: COc1c(C(=O)NC2CCN(Cc3ccccc3)C2)sc2c1c(=O)n(Cc1ccccn1)c1ccccc21 ; "2 CF3CO2H"]

In the same manner as in Example 3, the title compound was obtained from the compound of Reference Example 19 and 1-benzylpyrrolidin-3-amine.

LC/MS 525 (M+H).

Example 287

Production of N-(1-benzylpiperidin-4-yl)-3-methoxy-4-oxo-5-(pyridin-2-ylmethyl)-4,5-dihydrothieno[3,2-c]quinoline-2-carboxamide ditrifluoroacetate

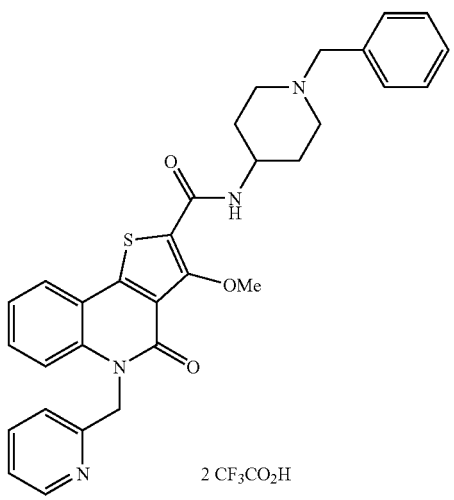 [SMILES: COc1c(C(=O)NC2CCN(Cc3ccccc3)CC2)sc2c1c(=O)n(Cc1ccccn1)c1ccccc21 ; "2 CF3CO2H"]

In the same manner as in Example 3, the title compound was obtained from the compound of Reference Example 19 and 1-benzylpiperidin-4-amine.

LC/MS 539 (M+H).

Example 288

Production of 3-methoxy-N-methyl-N-(1-methylpyrrolidin-3-yl)-4-oxo-5-(pyridin-2-ylmethyl)-4,5-dihydrothieno[3,2-c]quinoline-2-carboxamide ditrifluoroacetate

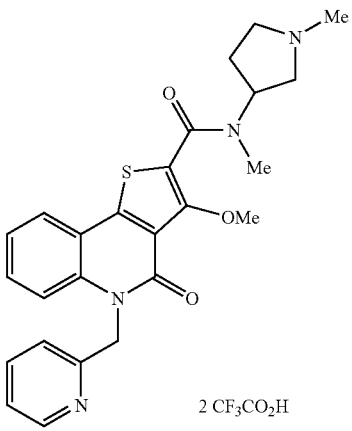 [SMILES: COc1c(C(=O)N(C)C2CCN(C)C2)sc2c1c(=O)n(Cc1ccccn1)c1ccccc21 ; "2 CF3CO2H"]

In the same manner as in Example 3, the title compound was obtained from the compound of Reference Example 19 and N,1-dimethylpyrrolidin-3-amine.

Example 289

Production of 3-methoxy-2-[(4-methyl-1,4-diazepan-1-yl)carbonyl]-5-(pyridin-2-ylmethyl)thieno[3,2-c]quinolin-4(5H)-one ditrifluoroacetate

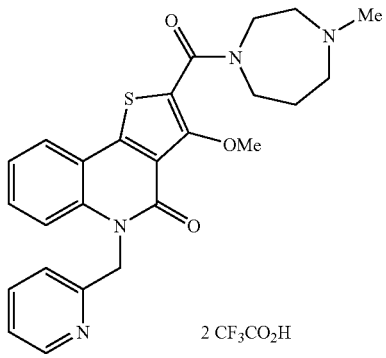 [SMILES: COc1c(C(=O)N2CCCN(C)CC2)sc2c1c(=O)n(Cc1ccccn1)c1ccccc21 ; "2 CF3CO2H"]

In the same manner as in Example 3, the title compound was obtained from the compound of Reference Example 19 and 1-methyl-1,4-diazepane.

Example 290

Production of 2-[(4-ethylpiperazin-1-yl)carbonyl]-3-methoxy-5-(pyridin-2-ylmethyl)thieno[3,2-c]quinolin-4(5H)-one ditrifluoroacetate

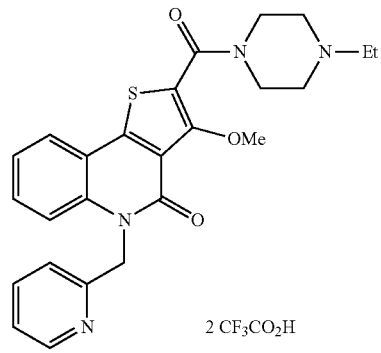 [SMILES: CCN1CCN(C(=O)c2sc3c(c2OC)c(=O)n(Cc2ccccn2)c2ccccc32)CC1 ; "2 CF3CO2H"]

In the same manner as in Example 3, the title compound was obtained from the compound of Reference Example 19 and 1-ethylpiperazine.

Example 291

Production of 3-methoxy-5-(pyridin-2-ylmethyl)-2-{[(2S)-2-(pyrrolidin-1-ylmethyl)pyrrolidin-1-yl]carbonyl}thieno[3,2-c]quinolin-4(5H)-one ditrifluoroacetate

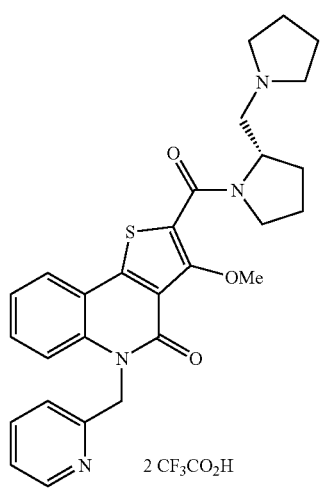 [SMILES: COc1c(C(=O)N2CCC[C@H]2CN2CCCC2)sc2c1c(=O)n(Cc1ccccn1)c1ccccc21 ; "2 CF3CO2H"]

In the same manner as in Example 3, the title compound was obtained from the compound of Reference Example 19 and 1-[(2S)-pyrrolidin-2-ylmethyl]pyrrolidine.

LC/MS 503 (M+H).

Example 292

Production of 3-methoxy-5-(pyridin-2-ylmethyl)-2-[(4-pyrrolidin-1-ylpiperidin-1-yl)carbonyl]thieno[3,2-c]quinolin-4(5H)-one ditrifluoroacetate

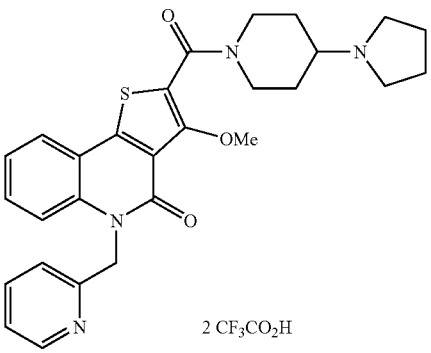 [SMILES: COc1c(C(=O)N2CCC(N3CCCC3)CC2)sc2c1c(=O)n(Cc1ccccn1)c1ccccc21 ; "2 CF3CO2H"]

In the same manner as in Example 3, the title compound was obtained from the compound of Reference Example 19 and 4-pyrrolidin-1-ylpiperidine.

LC/MS 503 (M+H).

Example 293

Production of 3-methoxy-2-[(4-phenylpiperazin-1-yl)carbonyl]-5-(pyridin-2-ylmethyl)thieno[3,2-c]quinolin-4(5H)-one ditrifluoroacetate

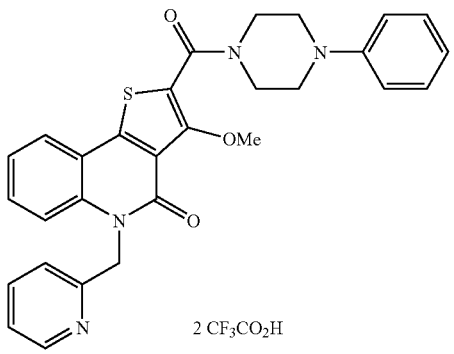 [SMILES: COc1c(C(=O)N2CCN(c3ccccc3)CC2)sc2c1c(=O)n(Cc1ccccn1)c1ccccc21 ; "2 CF3CO2H"]

In the same manner as in Example 3, the title compound was obtained from the compound of Reference Example 19 and 1-phenylpiperazine.

LC/MS 511 (M+H).

Example 294

Production of N-(2-cyanoethyl)-3-methoxy-4-oxo-5-(pyridin-2-ylmethyl)-N-(pyridin-3-ylmethyl)-4,5-dihydrothieno[3,2-c]quinoline-2-carboxamide ditrifluoroacetate

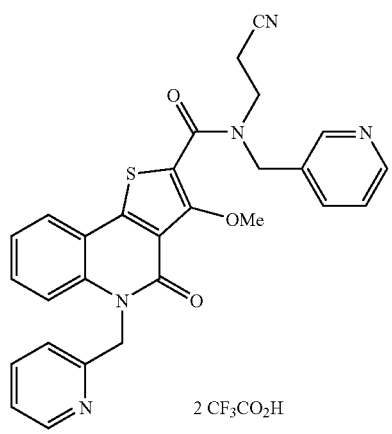 [SMILES: COc1c(C(=O)N(CCC#N)Cc2cccnc2)sc2c1c(=O)n(Cc1ccccn1)c1ccccc21 ; "2 CF3CO2H"]

In the same manner as in Example 3, the title compound was obtained from the compound of Reference Example 19 and 3-[(pyridin-3-ylmethyl)amino]propanenitrile.

LC/MS 510 (M+H).

Example 295

Production of 3-methoxy-4-oxo-5-(2-oxo-2-phenylethyl)-N-(pyridin-2-ylmethyl)-4,5-dihydrothieno[3,2-c]quinoline-2-carboxamide trifluoroacetate

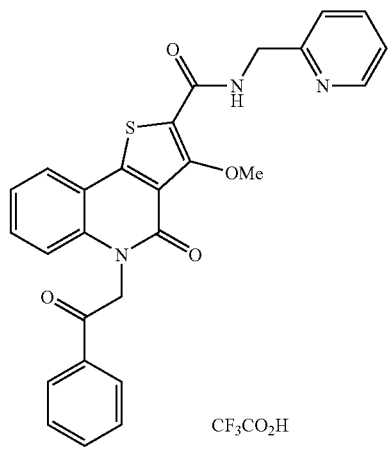 [SMILES: COc1c(C(=O)NCc2ccccn2)sc2c1c(=O)n(CC(=O)c1ccccc1)c1ccccc21 ; "CF3CO2H"]

In the same manner as in Example 5, the title compound was obtained from the compound of Reference Example 7 and 1-pyridin-2-ylmethanamine.

LC/MS 484 (M+H).

Example 296

Production of 3-methoxy-4-oxo-5-(2-oxo-2-phenylethyl)-N-(pyridin-4-ylmethyl)-4,5-dihydrothieno[3,2-c]quinoline-2-carboxamide trifluoroacetate

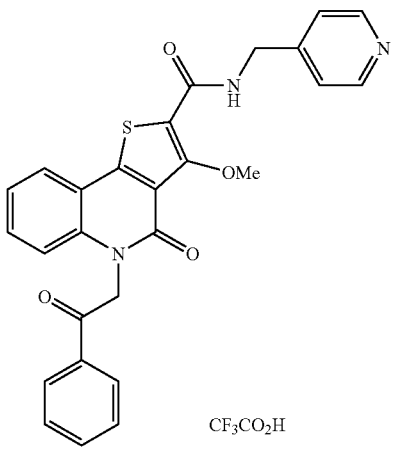 [SMILES: COc1c(C(=O)NCc2ccncc2)sc2c1c(=O)n(CC(=O)c1ccccc1)c1ccccc21 ; "CF3CO2H"]

In the same manner as in Example 5, the title compound was obtained from the compound of Reference Example 7 and 1-pyridin-4-ylmethanamine.

LC/MS 484 (M+H).

Example 297

Production of 3-methoxy-4-oxo-5-(2-oxo-2-phenyl-ethyl)-N-(2-pyridin-3-ylethyl)-4,5-dihydrothieno[3,2-c]quinoline-2-carboxamide trifluoroacetate

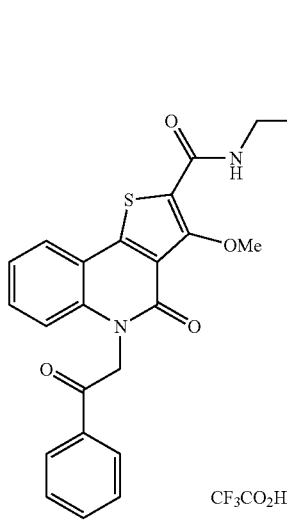

In the same manner as in Example 5, the title compound was obtained from the compound of Reference Example 7 and 2-pyridin-3-ylethanamine.
LC/MS 498 (M+H).

Example 298

Production of 3-methoxy-N-[(5-methylpyrazin-2-yl)methyl]-4-oxo-5-(2-oxo-2-phenylethyl)-4,5-dihydrothieno[3,2-c]quinoline-2-carboxamide trifluoroacetate

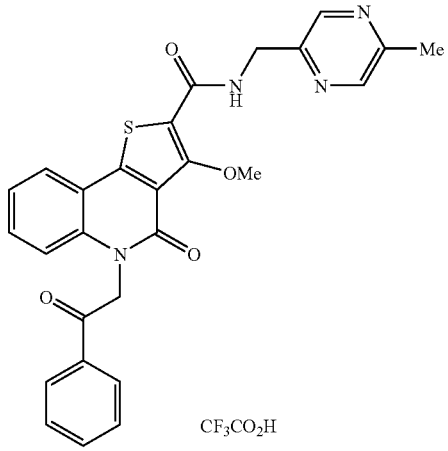 [SMILES: COc1c(C(=O)NCc2cnc(C)cn2)sc2c1c(=O)n(CC(=O)c1ccccc1)c1ccccc21 ; "CF3CO2H"]

In the same manner as in Example 5, the title compound was obtained from the compound of Reference Example 7 and 1-(5-methylpyrazin-2-yl)methanamine.
LC/MS 499 (M+H).

Example 299

Production of 3-methoxy-5-(2-oxo-2-phenylethyl)-2-[(4-phenylpiperazin-1-yl)carbonyl]thieno[3,2-c]quinolin-4(5H)-one trifluoroacetate

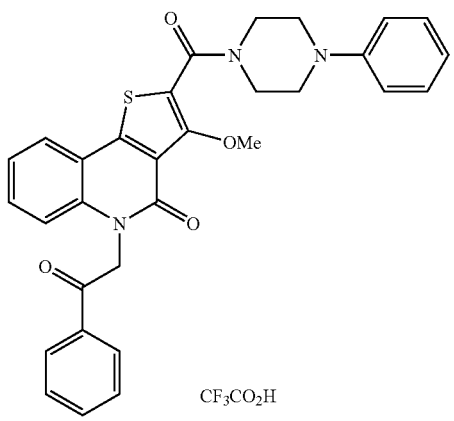 [SMILES: COc1c(C(=O)N2CCN(c3ccccc3)CC2)sc2c1c(=O)n(CC(=O)c1ccccc1)c1ccccc21 ; "CF3CO2H"]

In the same manner as in Example 5, the title compound was obtained from the compound of Reference Example 7 and 1-phenylpiperazine.
LC/MS 538 (M+H).

Example 300

Production of 3-(benzyloxy)-N,5-dimethyl-4-oxo-4,5-dihydrothieno[3,2-c]quinoline-2-carboxamide

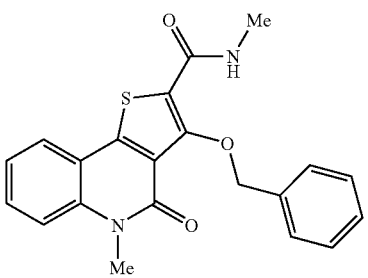 [SMILES: CNC(=O)c1sc2c(c1OCc1ccccc1)c(=O)n(C)c1ccccc21]

To a solution (0.15 M, 0.40 mL, 60 μmol) of the compound of Reference Example 91 in DMF were added a solution (0.66 M, 0.10 mL, 66 μmol) of methanamine (2.0 M THF solution) in DMF and a solution (0.39 M, 0.20 mL, 78 μmol) of HOBt and WSCD in 1:1 mixture in DMF. The obtained mixture was agitated at room temperature for 14 hr. Dichloromethane (2 mL) and saturated aqueous sodium hydrogen carbonate solution (1 mL) were added to the reaction mixture, the organic layer was filtered through a Teflon (registered trade mark) filter to separate the aqueous layer, and the filtrate was concentrated under reduced pressure. The residue was purified by preparative HPLC to give the title compound (12.4 mg, 55%).
LC/MS 379 (M+H).

Example 301

Production of 3-(benzyloxy)-N-butyl-5-methyl-4-oxo-4,5-dihydrothieno[3,2-c]quinoline-2-carboxamide

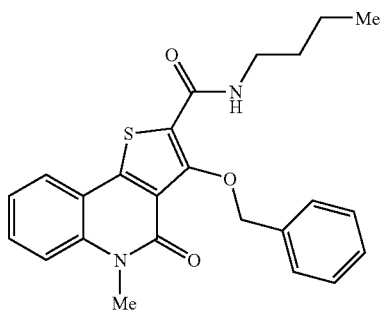 [SMILES: CCCCNC(=O)c1sc2c(c1OCc1ccccc1)c(=O)n(C)c1ccccc21]

In the same manner as in Example 5, the title compound was obtained from the compound of Reference Example 91 and butan-1-amine.
LC/MS 421 (M+H).

Example 302

Production of 3-(benzyloxy)-N-(furan-2-ylmethyl)-5-methyl-4-oxo-4,5-dihydrothieno[3,2-c]quinoline-2-carboxamide

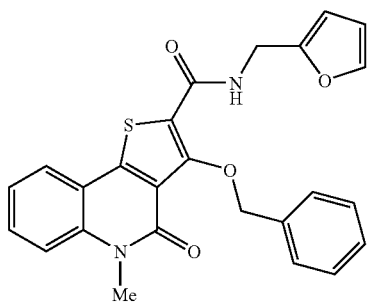 [SMILES: Cn1c(=O)c2c(OCc3ccccc3)c(C(=O)NCc3ccco3)sc2c2ccccc21]

In the same manner as in Example 5, the title compound was obtained from the compound of Reference Example 91 and 1-furan-2-ylmethanamine.
LC/MS 445 (M+H).

Example 303

Production of 3-(benzyloxy)-5-methyl-4-oxo-N-(tetrahydrofuran-2-ylmethyl)-4,5-dihydrothieno[3,2-c]quinoline-2-carboxamide

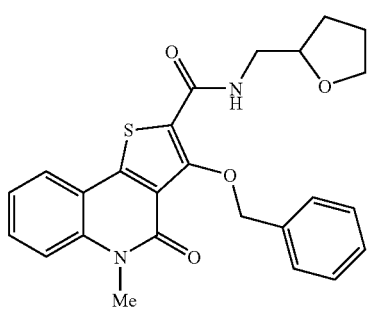 [SMILES: Cn1c(=O)c2c(OCc3ccccc3)c(C(=O)NCC3CCCO3)sc2c2ccccc21]

In the same manner as in Example 5, the title compound was obtained from the compound of Reference Example 91 and 1-(tetrahydrofuran-2-yl)methanamine.
LC/MS 449 (M+H).

Example 304

Production of 3-(benzyloxy)-5-methyl-4-oxo-N-(2-phenylethyl)-4,5-dihydrothieno[3,2-c]quinoline-2-carboxamide

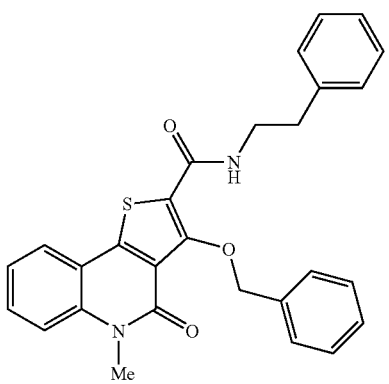 [SMILES: Cn1c(=O)c2c(OCc3ccccc3)c(C(=O)NCCc3ccccc3)sc2c2ccccc21]

In the same manner as in Example 5, the title compound was obtained from the compound of Reference Example 91 and 2-phenylethanamine.
LC/MS 469 (M+H).

Example 305

Production of 3-(benzyloxy)-N-(2-methoxybenzyl)-5-methyl-4-oxo-4,5-dihydrothieno[3,2-c]quinoline-2-carboxamide

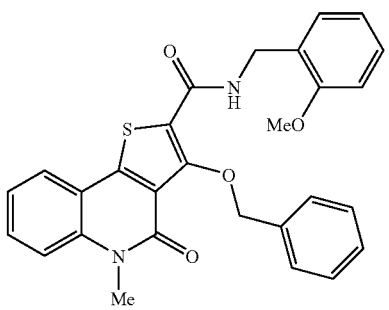 [SMILES: COc1ccccc1CNC(=O)c1sc2c(c1OCc1ccccc1)c(=O)n(C)c1ccccc21]

In the same manner as in Example 5, the title compound was obtained from the compound of Reference Example 91 and 1-(2-methoxyphenyl)methanamine.
LC/MS 485 (M+H).

Example 306

Production of 3-(benzyloxy)-5-methyl-4-oxo-N-(1,2,3,4-tetrahydronaphthalen-1-yl)-4,5-dihydrothieno[3,2-c]quinoline-2-carboxamide

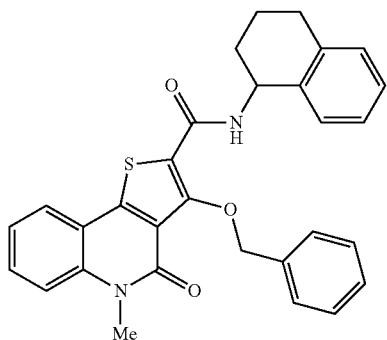 [SMILES: Cn1c(=O)c2c(OCc3ccccc3)c(C(=O)NC3CCCc4ccccc43)sc2c2ccccc21]

In the same manner as in Example 5, the title compound was obtained from the compound of Reference Example 91 and 1,2,3,4-tetrahydronaphthalen-1-amine.
LC/MS 495 (M+H).

Example 307

Production of N-(1,3-benzodioxol-5-ylmethyl)-3-(benzyloxy)-5-methyl-4-oxo-4,5-dihydrothieno[3,2-c]quinoline-2-carboxamide

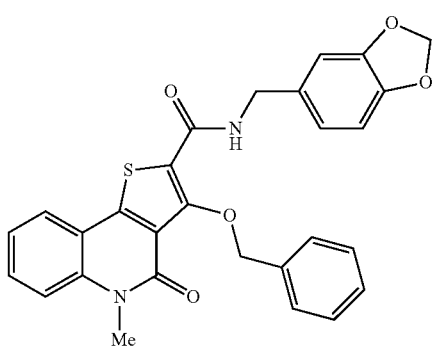 [SMILES: Cn1c(=O)c2c(OCc3ccccc3)c(C(=O)NCc3ccc4c(c3)OCO4)sc2c2ccccc21]

In the same manner as in Example 5, the title compound was obtained from the compound of Reference Example 91 and 1-(1,3-benzodioxol-5-yl)methanamine.
LC/MS 499 (M+H).

Example 308

Production of 3-(benzyloxy)-N,N-diethyl-5-methyl-4-oxo-4,5-dihydrothieno[3,2-c]quinoline-2-carboxamide

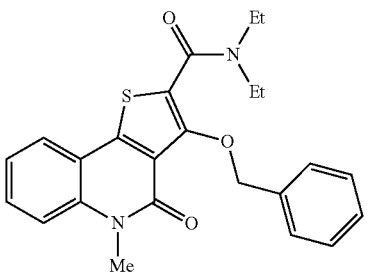 [SMILES: CCN(CC)C(=O)c1sc2c(c1OCc1ccccc1)c(=O)n(C)c1ccccc21]

In the same manner as in Example 5, the title compound was obtained from the compound of Reference Example 91 and N-ethylethanamine.
LC/MS 421 (M+H).

Example 309

Production of 3-(benzyloxy)-5-methyl-2-(piperidin-1-ylcarbonyl)thieno[3,2-c]quinolin-4(5H)-one

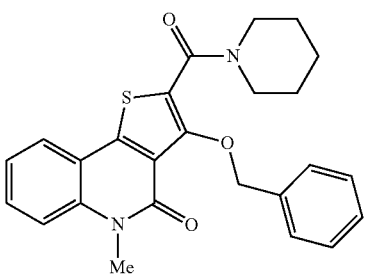 [SMILES: Cn1c(=O)c2c(OCc3ccccc3)c(C(=O)N3CCCCC3)sc2c2ccccc21]

In the same manner as in Example 5, the title compound was obtained from the compound of Reference Example 91 and piperidine.
LC/MS 433 (M+H).

Example 310

Production of 3-(benzyloxy)-N-(2-methoxyethyl)-N,5-dimethyl-4-oxo-4,5-dihydrothieno[3,2-c]quinoline-2-carboxamide

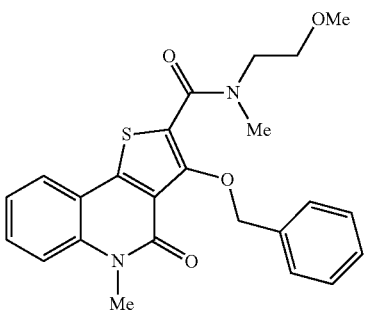 [SMILES: COCCN(C)C(=O)c1sc2c(c1OCc1ccccc1)c(=O)n(C)c1ccccc21]

In the same manner as in Example 5, the title compound was obtained from the compound of Reference Example 91 and 2-methoxy-N-methylethanamine.
LC/MS 437 (M+H).

Example 311

Production of 3-(benzyloxy)-N-methoxy-N,5-dimethyl-4-oxo-4,5-dihydrothieno[3,2-c]quinoline-2-carboxamide

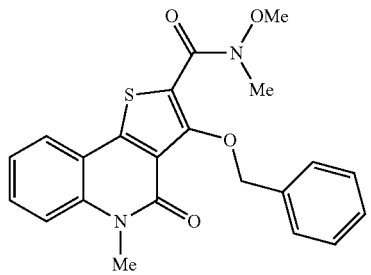 [SMILES: CON(C)C(=O)c1sc2c(c1OCc1ccccc1)c(=O)n(C)c1ccccc21]

In the same manner as in Example 335, the title compound was obtained from the compound of Reference Example 91 and N-methoxymethanamine hydrochloride.
LC/MS 409 (M+H).

Example 312

Production of 3-(benzyloxy)-5-methyl-2-(thiomorpholin-4-ylcarbonyl)thieno[3,2-c]quinolin-4(5H)-one

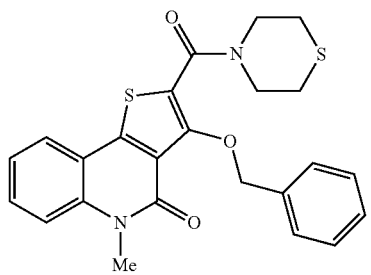 [SMILES: Cn1c(=O)c2c(OCc3ccccc3)c(C(=O)N3CCSCC3)sc2c2ccccc21]

In the same manner as in Example 5, the title compound was obtained from the compound of Reference Example 91 and thiomorpholine.
LC/MS 451 (M+H).

Example 313

Production of 3-(benzyloxy)-2-{[(2R)-2-(methoxymethyl)pyrrolidin-1-yl]carbonyl}-5-methylthieno[3,2-c]quinolin-4(5H)-one

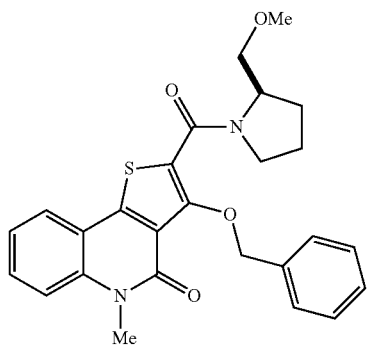 [SMILES: COC[C@H]1CCCN1C(=O)c1sc2c(c1OCc1ccccc1)c(=O)n(C)c1ccccc21]

In the same manner as in Example 5, the title compound was obtained from the compound of Reference Example 91 and (2R)-2-(methoxymethyl)pyrrolidine.
LC/MS 463 (M+H).

Example 314

Production of N-benzyl-3-(benzyloxy)-N,5-dimethyl-4-oxo-4,5-dihydrothieno[3,2-c]quinoline-2-carboxamide

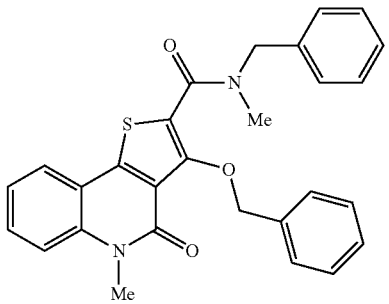 [SMILES: CN(Cc1ccccc1)C(=O)c1sc2c(c1OCc1ccccc1)c(=O)n(C)c1ccccc21]

In the same manner as in Example 5, the title compound was obtained from the compound of Reference Example 91 and N-methyl-1-phenylmethanamine.
LC/MS 469 (M+H).

Example 315

Production of 3-(benzyloxy)-5-methyl-N,N-bis(2-methylpropyl)-4-oxo-4,5-dihydrothieno[3,2-c]quinoline-2-carboxamide

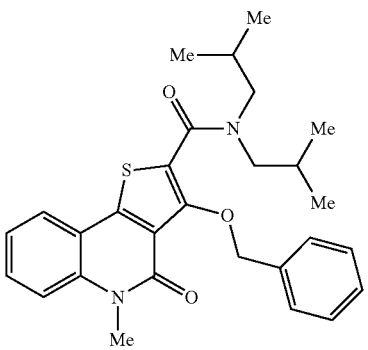 [SMILES: CC(C)CN(CC(C)C)C(=O)c1sc2c(c1OCc1ccccc1)c(=O)n(C)c1ccccc21]

In the same manner as in Example 335, the title compound was obtained from the compound of Reference Example 91 and 2-methyl-N-(2-methylpropyl)propan-1-amine hydrochloride.
LC/MS 477 (M+H).

Example 316

Production of 3-(benzyloxy)-N-[3-(dimethylamino)propyl]-5-methyl-4-oxo-4,5-dihydrothieno[3,2-c]quinoline-2-carboxamide trifluoroacetate

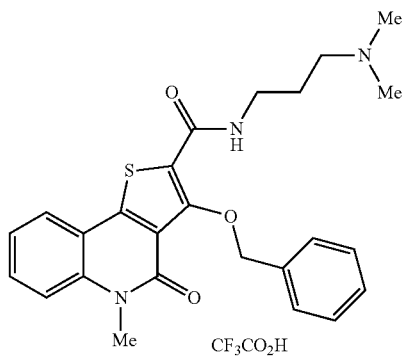 [SMILES: CN(C)CCCNC(=O)c1sc2c(c1OCc1ccccc1)c(=O)n(C)c1ccccc21 ; "CF3CO2H"]

In the same manner as in Example 5, the title compound was obtained from the compound of Reference Example 91 and N,N-dimethylpropane-1,3-diamine.
LC/MS 450 (M+H).

Example 317

Production of 3-(benzyloxy)-N-[2-(diethylamino)ethyl]-5-methyl-4-oxo-4,5-dihydrothieno[3,2-c]quinoline-2-carboxamide trifluoroacetate

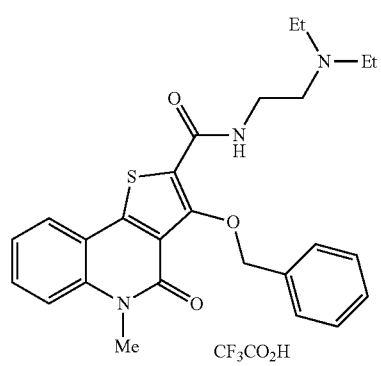 [SMILES: CCN(CC)CCNC(=O)c1sc2c(c1OCc1ccccc1)c(=O)n(C)c1ccccc21 ; "CF3CO2H"]

In the same manner as in Example 5, the title compound was obtained from the compound of Reference Example 91 and N,N-diethylethane-1,2-diamine.
LC/MS 464 (M+H).

Example 318

Production of 3-(benzyloxy)-N-[3-(1H-imidazol-1-yl)propyl]-5-methyl-4-oxo-4,5-dihydrothieno[3,2-c]quinoline-2-carboxamide trifluoroacetate

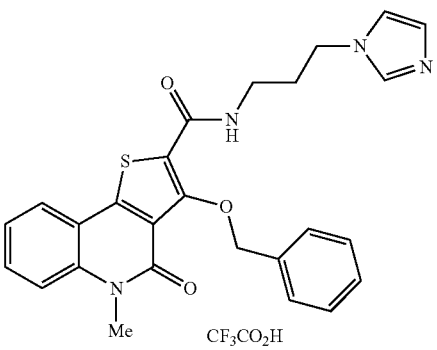 [SMILES: Cn1c(=O)c2c(OCc3ccccc3)c(C(=O)NCCCn3ccnc3)sc2c2ccccc21 ; "CF3CO2H"]

In the same manner as in Example 5, the title compound was obtained from the compound of Reference Example 91 and 3-(1H-imidazol-1-yl)propan-1-amine.
LC/MS 473 (M+H).

Example 319

Production of 3-(benzyloxy)-N-{2-[bis(1-methylethyl)amino]ethyl}-5-methyl-4-oxo-4,5-dihydrothieno[3,2-c]quinoline-2-carboxamide trifluoroacetate

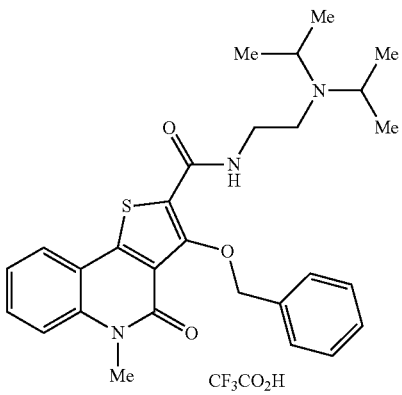 [SMILES: CC(C)N(CCNC(=O)c1sc2c(c1OCc1ccccc1)c(=O)n(C)c1ccccc21)C(C)C ; "CF3CO2H"]

In the same manner as in Example 5, the title compound was obtained from the compound of Reference Example 91 and N,N-bis(1-methylethyl)ethane-1,2-diamine.
LC/MS 492 (M+H).

Example 320

Production of 3-(benzyloxy)-5-methyl-2-[(4-methylpiperazin-1-yl)carbonyl]thieno[3,2-c]quinolin-4(5H)-one trifluoroacetate

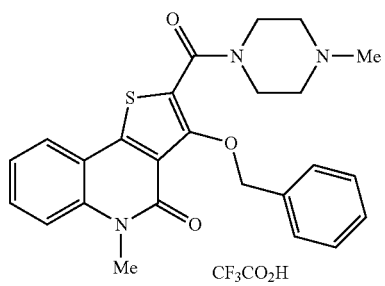 [SMILES: CN1CCN(C(=O)c2sc3c(c2OCc2ccccc2)c(=O)n(C)c2ccccc32)CC1 ; "CF3CO2H"]

In the same manner as in Example 5, the title compound was obtained from the compound of Reference Example 91 and 1-methylpiperazine.

LC/MS 448 (M+H).

Example 321

Production of 3-(benzyloxy)-N,5-dimethyl-N-(1-methylpyrrolidin-3-yl)-4-oxo-4,5-dihydrothieno[3,2-c]quinoline-2-carboxamide trifluoroacetate

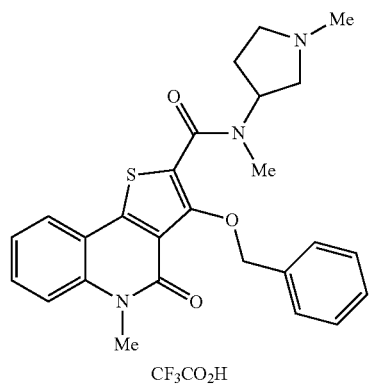 [SMILES: CN1CCC(N(C)C(=O)c2sc3c(c2OCc2ccccc2)c(=O)n(C)c2ccccc32)C1 ; "CF3CO2H"]

In the same manner as in Example 5, the title compound was obtained from the compound of Reference Example 91 and N,1-dimethylpyrrolidin-3-amine.

LC/MS 462 (M+H).

Example 322

Production of 3-(benzyloxy)-N-[2-(diethylamino)ethyl]-N,5-dimethyl-4-oxo-4,5-dihydrothieno[3,2-c]quinoline-2-carboxamide trifluoroacetate

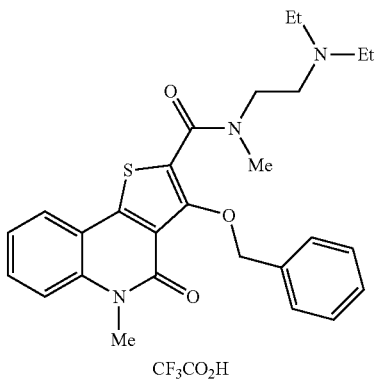 [SMILES: CCN(CC)CCN(C)C(=O)c1sc2c(c1OCc1ccccc1)c(=O)n(C)c1ccccc21 ; "CF3CO2H"]

In the same manner as in Example 5, the title compound was obtained from the compound of Reference Example 91 and N,N-diethyl-N'-methylethane-1,2-diamine.

LC/MS 478 (M+H).

Example 323

Production of 3-(benzyloxy)-5-methyl-2-[(4-pyridin-2-ylpiperazin-1-yl)carbonyl]thieno[3,2-c]quinolin-4(5H)-one trifluoroacetate

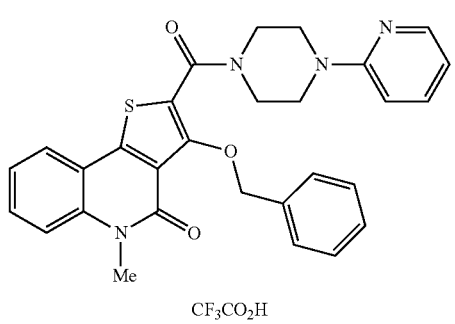 [SMILES: Cn1c(=O)c2c(OCc3ccccc3)c(C(=O)N3CCN(c4ccccn4)CC3)sc2c2ccccc21 ; "CF3CO2H"]

In the same manner as in Example 5, the title compound was obtained from the compound of Reference Example 91 and 1-pyridin-2-ylpiperazine.

LC/MS 511 (M+H).

Example 324

Production of 3-butoxy-N,5-dimethyl-4-oxo-4,5-dihydrothieno[3,2-c]quinoline-2-carboxamide

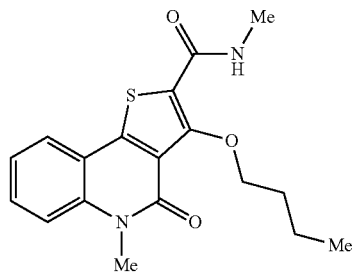 [SMILES: CCCCOc1c(C(=O)NC)sc2c1c(=O)n(C)c1ccccc21]

In the same manner as in Example 300, the title compound was obtained from the compound of Reference Example 92 and methanamine (2.0 M THF solution).
LC/MS 345 (M+H).

Example 325

Production of 3-butoxy-N-butyl-5-methyl-4-oxo-4,5-dihydrothieno[3,2-c]quinoline-2-carboxamide

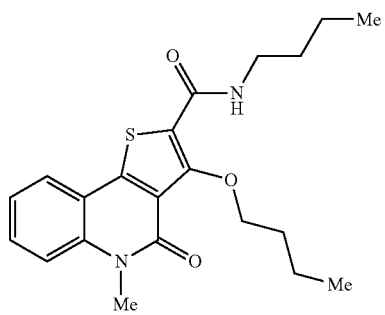 [SMILES: CCCCNC(=O)c1sc2c(c1OCCCC)c(=O)n(C)c1ccccc21]

In the same manner as in Example 5, the title compound was obtained from the compound of Reference Example 92 and butan-1-amine.
LC/MS 387 (M+H).

Example 326

Production of 3-butoxy-N-(furan-2-ylmethyl)-5-methyl-4-oxo-4,5-dihydrothieno[3,2-c]quinoline-2-carboxamide

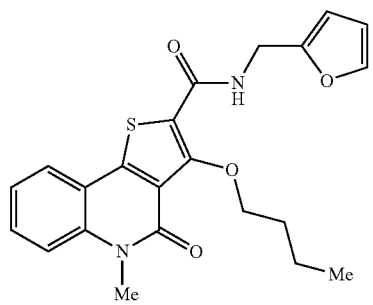 [SMILES: CCCCOc1c(C(=O)NCc2ccco2)sc2c1c(=O)n(C)c1ccccc21]

In the same manner as in Example 5, the title compound was obtained from the compound of Reference Example 92 and 1-furan-2-ylmethanamine.
LC/MS 411 (M+H).

Example 327

Production of 3-butoxy-5-methyl-4-oxo-N-(tetrahydrofuran-2-ylmethyl)-4,5-dihydrothieno[3,2-c]quinoline-2-carboxamide

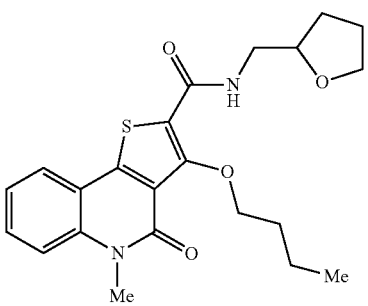 [SMILES: CCCCOc1c(C(=O)NCC2CCCO2)sc2c1c(=O)n(C)c1ccccc21]

In the same manner as in Example 5, the title compound was obtained from the compound of Reference Example 92 and 1-(tetrahydrofuran-2-yl)methanamine.
LC/MS 415 (M+H).

Example 328

Production of 3-butoxy-5-methyl-4-oxo-N-(2-phenylethyl)-4,5-dihydrothieno[3,2-c]quinoline-2-carboxamide

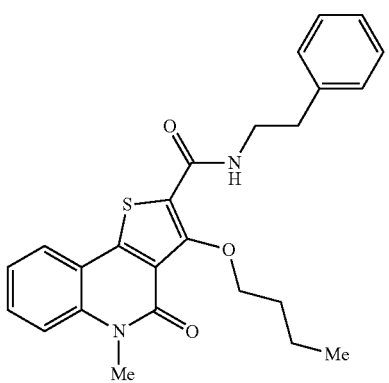 [SMILES: CCCCOc1c(C(=O)NCCc2ccccc2)sc2c1c(=O)n(C)c1ccccc21]

In the same manner as in Example 5, the title compound was obtained from the compound of Reference Example 92 and 2-phenylethanamine.
LC/MS 435 (M+H).

Example 329

Production of 3-butoxy-N-(2-methoxybenzyl)-5-methyl-4-oxo-4,5-dihydrothieno[3,2-c]quinoline-2-carboxamide

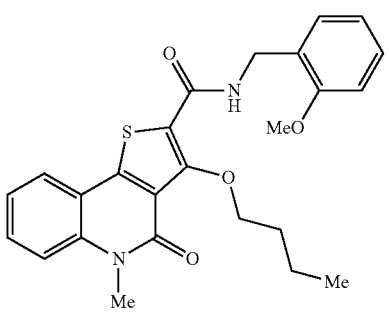 [SMILES: CCCCOc1c(C(=O)NCc2ccccc2OC)sc2c1c(=O)n(C)c1ccccc21]

In the same manner as in Example 5, the title compound was obtained from the compound of Reference Example 92 and 1-(2-methoxyphenyl)methanamine.
LC/MS 451 (M+H).

Example 330

Production of 3-butoxy-5-methyl-4-oxo-N-(1,2,3,4-tetrahydronaphthalen-1-yl)-4,5-dihydrothieno[3,2-c]quinoline-2-carboxamide

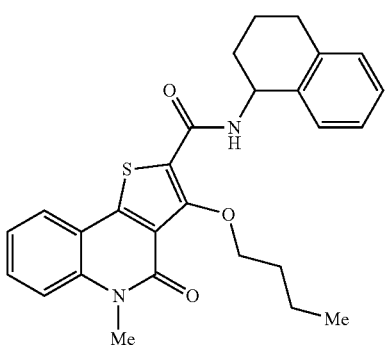 [SMILES: CCCCOc1c(C(=O)NC2CCCc3ccccc32)sc2c1c(=O)n(C)c1ccccc21]

In the same manner as in Example 5, the title compound was obtained from the compound of Reference Example 92 and 1,2,3,4-tetrahydronaphthalen-1-amine.
LC/MS 461 (M+H).

Example 331

Production of N-(1,3-benzodioxol-5-ylmethyl)-3-butoxy-5-methyl-4-oxo-4,5-dihydrothieno[3,2-c]quinoline-2-carboxamide

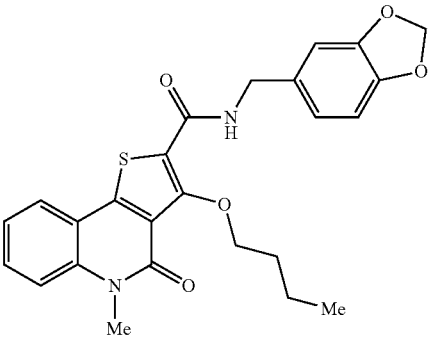 [SMILES: CCCCOc1c(C(=O)NCc2ccc3c(c2)OCO3)sc2c1c(=O)n(C)c1ccccc21]

In the same manner as in Example 5, the title compound was obtained from the compound of Reference Example 92 and 1-(1,3-benzodioxol-5-yl)methanamine.
LC/MS 465 (M+H).

Example 332

Production of 3-butoxy-N,N-diethyl-5-methyl-4-oxo-4,5-dihydrothieno[3,2-c]quinoline-2-carboxamide

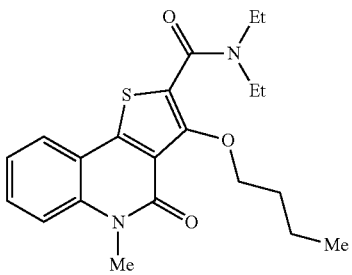 [SMILES: CCCCOc1c(C(=O)N(CC)CC)sc2c1c(=O)n(C)c1ccccc21]

In the same manner as in Example 5, the title compound was obtained from the compound of Reference Example 92 and N-ethylethanamine.
LC/MS 387 (M+H).

Example 333

Production of 3-butoxy-5-methyl-2-(piperidin-1-ylcarbonyl)thieno[3,2-c]quinolin-4(5H)-one

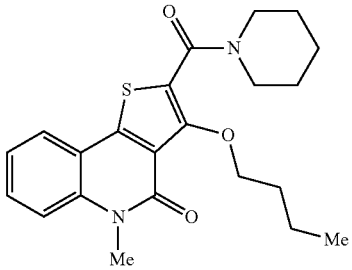 [SMILES: CCCCOc1c(C(=O)N2CCCCC2)sc2c1c(=O)n(C)c1ccccc21]

In the same manner as in Example 5, the title compound was obtained from the compound of Reference Example 92 and piperidine.
LC/MS 399 (M+H).

Example 334

Production of 3-butoxy-N-(2-methoxyethyl)-N,5-dimethyl-4-oxo-4,5-dihydrothieno[3,2-c]quinoline-2-carboxamide

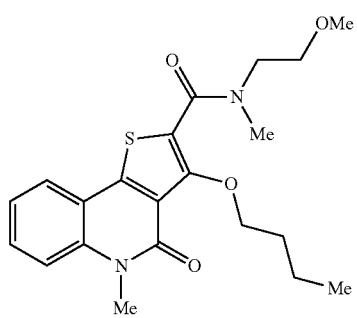 [SMILES: CCCCOc1c(C(=O)N(C)CCOC)sc2c1c(=O)n(C)c1ccccc21]

In the same manner as in Example 5, the title compound was obtained from the compound of Reference Example 92 and 2-methoxy-N-methylethanamine.

LC/MS 403 (M+H).

Example 335

Production of 3-butoxy-N-methoxy-N,5-dimethyl-4-oxo-4,5-dihydrothieno[3,2-c]quinoline-2-carboxamide

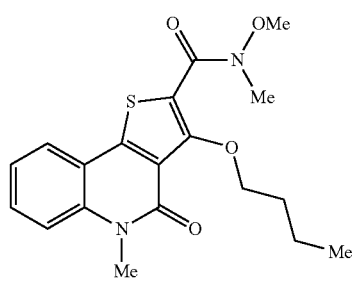 [SMILES: CCCCOc1c(C(=O)N(C)OC)sc2c1c(=O)n(C)c1ccccc21]

To a solution (0.15 M, 0.40 mL, 60 μmol) of the compound of Reference Example 92 in DMF were added a mixture of a suspension (0.66 M, 0.111 mL, 73 μmol) of N-methoxymethanamine hydrochloride in DMF and triethylamine (10.9 μL, 78 μmol), and a solution (0.39 M, 0.20 mL, 78 μmol) of HOBt and WSCD in 1:1 mixture in DMF. The obtained mixture was shaken at room temperature for 14 hr. Dichloromethane (2 mL) and saturated aqueous sodium hydrogen carbonate solution (1 mL) were added to the reaction mixture, the organic layer was filtered through a Teflon (registered trade mark) filter to separate the aqueous layer, and the filtrate was concentrated under reduced pressure. The residue was purified by preparative HPLC to give the title compound (16.6 mg, 74%).

LC/MS 375 (M+H).

Example 336

Production of 3-butoxy-5-methyl-2-(thiomorpholin-4-ylcarbonyl)thieno[3,2-c]quinolin-4(5H)-one

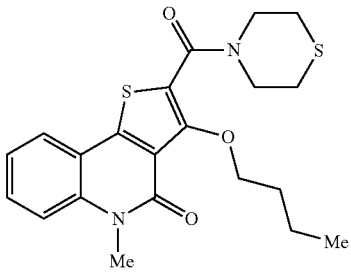 [SMILES: CCCCOc1c(C(=O)N2CCSCC2)sc2c1c(=O)n(C)c1ccccc21]

In the same manner as in Example 5, the title compound was obtained from the compound of Reference Example 92 and thiomorpholine.

LC/MS 417 (M+H).

Example 337

Production of 3-butoxy-2-{[(2R)-2-(methoxymethyl)pyrrolidin-1-yl]carbonyl}-5-methylthieno[3,2-c]quinolin-4(5H)-one

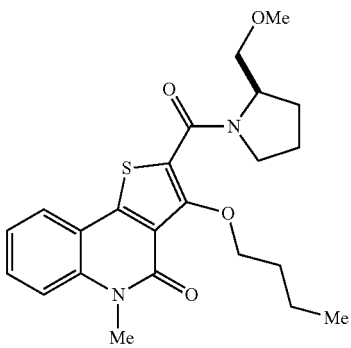 [SMILES: CCCCOc1c(C(=O)N2CCC[C@@H]2COC)sc2c1c(=O)n(C)c1ccccc21]

In the same manner as in Example 5, the title compound was obtained from the compound of Reference Example 92 and (2R)-2-(methoxymethyl)pyrrolidine.

LC/MS 429 (M+H)

Example 338

Production of N-benzyl-3-butoxy-N,5-dimethyl-4-oxo-4,5-dihydrothieno[3,2-c]quinoline-2-carboxamide

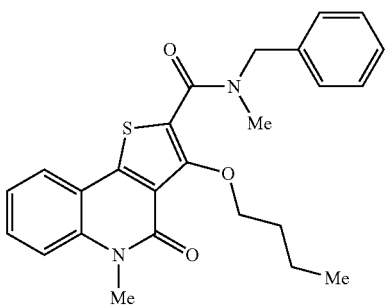 [SMILES: CCCCOc1c(C(=O)N(C)Cc2ccccc2)sc2c1c(=O)n(C)c1ccccc21]

In the same manner as in Example 5, the title compound was obtained from the compound of Reference Example 92 and N-methyl-1-phenylmethanamine.

LC/MS 435 (M+H).

Example 339

Production of 3-butoxy-5-methyl-N,N-bis(2-methyl-propyl)-4-oxo-4,5-dihydrothieno[3,2-c]quinoline-2-carboxamide

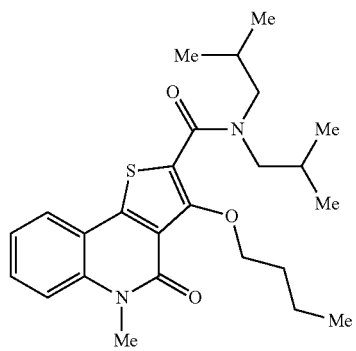 [SMILES: CCCCOc1c(C(=O)N(CC(C)C)CC(C)C)sc2c1c(=O)n(C)c1ccccc21]

In the same manner as in Example 335, the title compound was obtained from the compound of Reference Example 92 and 2-methyl-N-(2-methylpropyl)propan-1-amine hydrochloride.

LC/MS 443 (M+H).

Example 340

Production of 3-butoxy-N-[3-(dimethylamino)propyl]-5-methyl-4-oxo-4,5-dihydrothieno[3,2-c]quinoline-2-carboxamide trifluoroacetate

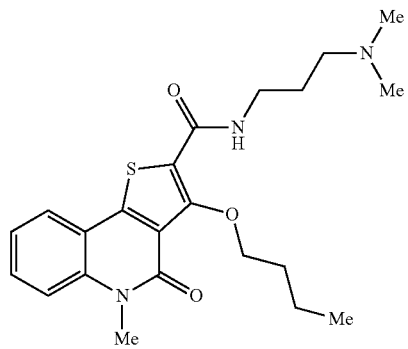

In the same manner as in Example 5, the title compound was obtained from the compound of Reference Example 92 and N,N-dimethylpropane-1,3-diamine.

LC/MS 416 (M+H).

Example 341

Production of 3-butoxy-N-[2-(diethylamino)ethyl]-5-methyl-4-oxo-4,5-dihydrothieno[3,2-c]quinoline-2-carboxamide trifluoroacetate

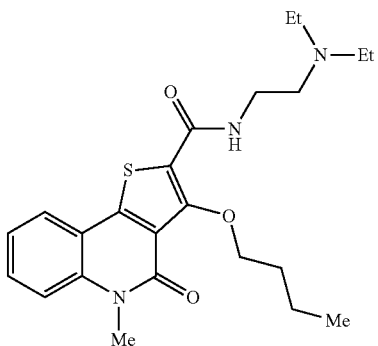

In the same manner as in Example 5, the title compound was obtained from the compound of Reference Example 92 and N,N-diethylethane-1,2-diamine.

LC/MS 430 (M+H).

Example 342

Production of 3-butoxy-N-[3-(1H-imidazol-1-yl)propyl]-5-methyl-4-oxo-4,5-dihydrothieno[3,2-c]quinoline-2-carboxamide trifluoroacetate

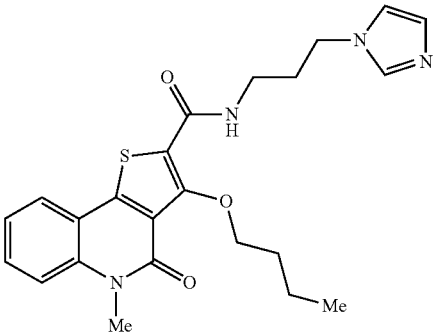

In the same manner as in Example 5, the title compound was obtained from the compound of Reference Example 92 and 3-(1H-imidazol-1-yl)propan-1-amine.

LC/MS 439 (M+H).

Example 343

Production of N-{2-[bis(1-methylethyl)amino]ethyl}-3-butoxy-5-methyl-4-oxo-4,5-dihydrothieno[3,2-c]quinoline-2-carboxamide trifluoroacetate

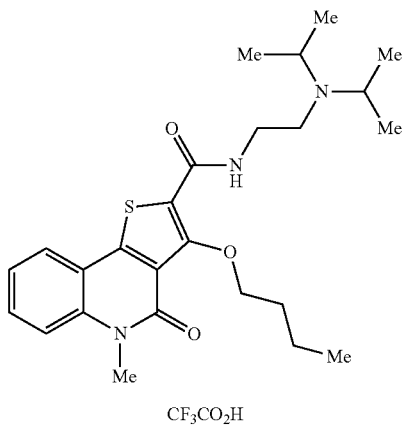 [SMILES: CCCCOc1c(C(=O)NCCN(C(C)C)C(C)C)sc2c1c(=O)n(C)c1ccccc21 ; "CF3CO2H"]

In the same manner as in Example 5, the title compound was obtained from the compound of Reference Example 92 and N,N-bis(1-methylethyl)ethane-1,2-diamine.

LC/MS 458 (M+H).

Example 344

Production of 3-butoxy-5-methyl-2-[(4-methylpiperazin-1-yl)carbonyl]thieno[3,2-c]quinolin-4(5H)-one trifluoroacetate

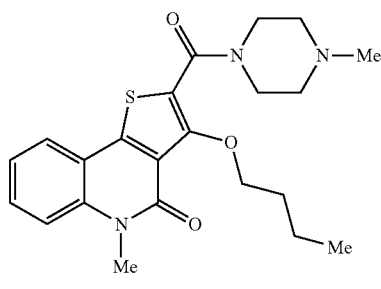

In the same manner as in Example 5, the title compound was obtained from the compound of Reference Example 92 and 1-methylpiperazine.

LC/MS 414 (M+H).

Example 345

Production of 3-butoxy-N,5-dimethyl-N-(1-methylpyrrolidin-3-yl)-4-oxo-4,5-dihydrothieno[3,2-c]quinoline-2-carboxamide trifluoroacetate

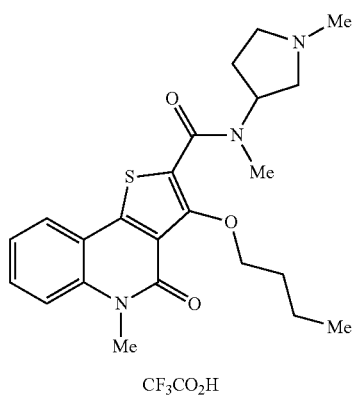 [SMILES: CCCCOc1c(C(=O)N(C)C2CCN(C)C2)sc2c1c(=O)n(C)c1ccccc21 ; "CF3CO2H"]

In the same manner as in Example 5, the title compound was obtained from the compound of Reference Example 92 and N,1-dimethylpyrrolidin-3-amine.

LC/MS 428 (M+H).

Example 346

Production of 3-butoxy-N-[2-(diethylamino)ethyl]-N,5-dimethyl-4-oxo-4,5-dihydrothieno[3,2-c]quinoline-2-carboxamide trifluoroacetate

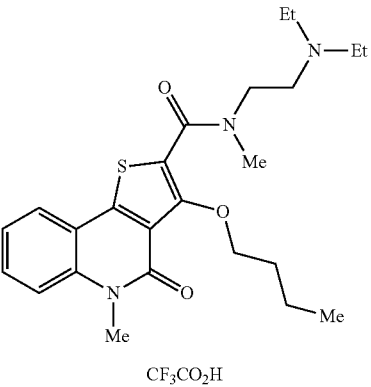 [SMILES: CCCCOc1c(C(=O)N(C)CCN(CC)CC)sc2c1c(=O)n(C)c1ccccc21 ; "CF3CO2H"]

In the same manner as in Example 5, the title compound was obtained from the compound of Reference Example 92 and N,N-diethyl-N'-methylethane-1,2-diamine.

LC/MS 444 (M+H).

Example 347

Production of 3-butoxy-5-methyl-2-[(4-pyridin-2-ylpiperazin-1-yl)carbonyl]thieno[3,2-c]quinolin-4(5H)-one trifluoroacetate

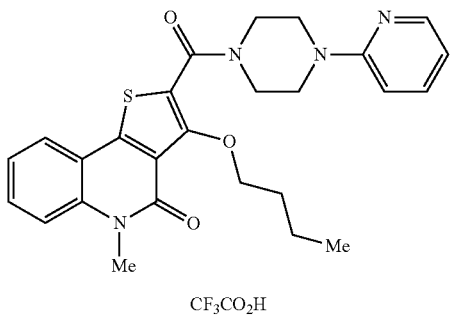 [SMILES: CCCCOc1c(C(=O)N2CCN(c3ccccn3)CC2)sc2c1c(=O)n(C)c1ccccc21 ; "CF3CO2H"]

In the same manner as in Example 5, the title compound was obtained from the compound of Reference Example 92 and 1-pyridin-2-ylpiperazine.

LC/MS 477 (M+H).

Example 348

Production of N,5-dimethyl-4-oxo-3-(pyridin-4-ylmethoxy)-4,5-dihydrothieno[3,2-c]quinoline-2-carboxamide trifluoroacetate

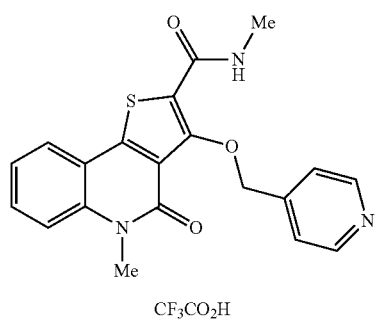 [SMILES: CNC(=O)c1sc2c(c1OCc1ccncc1)c(=O)n(C)c1ccccc21 ; "CF3CO2H"]

To a solution (0.10 M, 0.40 mL, 40 μmol) of the compound of Reference Example 93 in DMF were added a solution (0.66 M, 0.10 mL, 66 μmol) of methanamine (2.0 M THF solution) in DMF and a solution (0.39 M, 0.20 mL, 78 μmol) of HOBt and WSCD in 1:1 mixture in DMF. The obtained mixture was shaken at room temperature for 14 hr. Dichloromethane (2 mL) and saturated aqueous sodium hydrogen carbonate solution (1 mL) were added to the reaction mixture, the organic layer was filtered through a Teflon (registered trade mark) filter to separate the aqueous layer, and the filtrate was concentrated under reduced pressure. The residue was purified by preparative HPLC to give the title compound (13.2 mg, 67%).

LC/MS 380 (M+H).

Example 349

Production of N-butyl-5-methyl-4-oxo-3-(pyridin-4-ylmethoxy)-4,5-dihydrothieno[3,2-c]quinoline-2-carboxamide trifluoroacetate

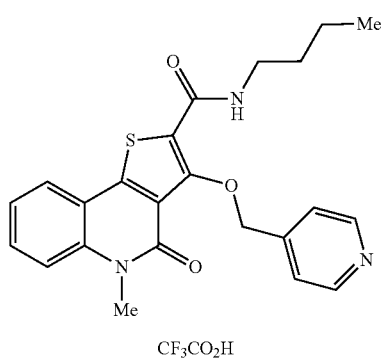 [SMILES: CCCCNC(=O)c1sc2c(c1OCc1ccncc1)c(=O)n(C)c1ccccc21 ; "CF3CO2H"]

To a solution (0.10 M, 0.40 mL, 40 μmol) of the compound of Reference Example 93 in DMF were added a solution (0.66 M, 0.10 mL, 66 μmol) of butan-1-amine in DMF and a solution (0.39 M, 0.20 mL, 78 μmol) of HOBt and WSCD in 1:1 mixture in DMF. The obtained mixture was shaken at room temperature for 14 hr. Dichloromethane (2 mL) and saturated aqueous sodium hydrogen carbonate solution (1 mL) were added to the reaction mixture, the organic layer was filtered through a Teflon (registered trade mark) filter to separate the aqueous layer, and the filtrate was concentrated under reduced pressure. The residue was purified by preparative HPLC to give the title compound (13.5 mg, 63%).

LC/MS 422 (M+H).

Example 350

Production of N-(furan-2-ylmethyl)-5-methyl-4-oxo-3-(pyridin-4-ylmethoxy)-4,5-dihydrothieno[3,2-c]quinoline-2-carboxamide trifluoroacetate

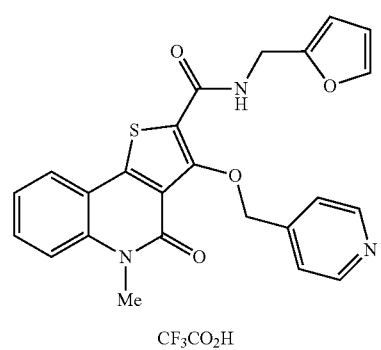 [SMILES: Cn1c(=O)c2c(OCc3ccncc3)c(C(=O)NCc3ccco3)sc2c2ccccc21 ; "CF3CO2H"]

In the same manner as in Example 349, the title compound was obtained from the compound of Reference Example 93 and 1-furan-2-ylmethanamine.

LC/MS 446 (M+H).

Example 351

Production of 5-methyl-4-oxo-3-(pyridin-4-yl-methoxy)-N-(tetrahydrofuran-2-ylmethyl)-4,5-dihydrothieno[3,2-c]quinoline-2-carboxamide trifluoroacetate

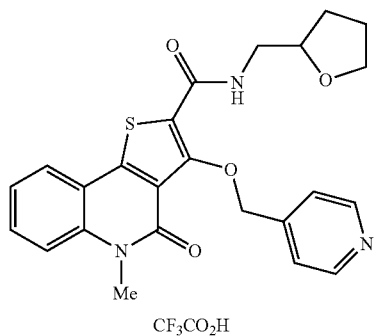 [SMILES: Cn1c(=O)c2c(OCc3ccncc3)c(C(=O)NCC3CCCO3)sc2c2ccccc21 ; "CF3CO2H"]

In the same manner as in Example 349, the title compound was obtained from the compound of Reference Example 93 and 1-(tetrahydrofuran-2-yl)methanamine.

LC/MS 450 (M+H).

Example 352

Production of 5-methyl-4-oxo-N-(2-phenylethyl)-3-(pyridin-4-ylmethoxy)-4,5-dihydrothieno[3,2-c]quinoline-2-carboxamide trifluoroacetate

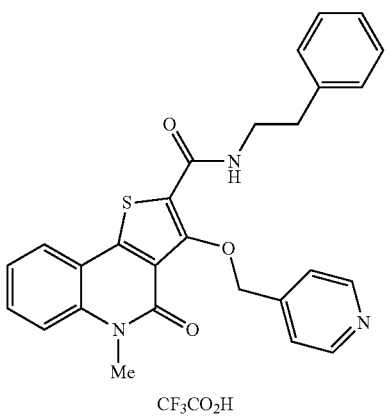 [SMILES: Cn1c(=O)c2c(OCc3ccncc3)c(C(=O)NCCc3ccccc3)sc2c2ccccc21 ; "CF3CO2H"]

In the same manner as in Example 349, the title compound was obtained from the compound of Reference Example 93 and 2-phenylethanamine.

LC/MS 470 (M+H).

Example 353

Production of N-(2-methoxybenzyl)-5-methyl-4-oxo-3-(pyridin-4-ylmethoxy)-4,5-dihydrothieno[3,2-c]quinoline-2-carboxamide trifluoroacetate

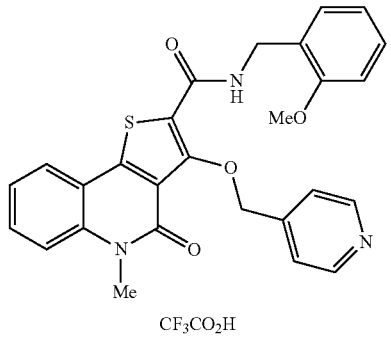 [SMILES: COc1ccccc1CNC(=O)c1sc2c(c1OCc1ccncc1)c(=O)n(C)c1ccccc21 ; "CF3CO2H"]

In the same manner as in Example 349, the title compound was obtained from the compound of Reference Example 93 and 1-(2-methoxyphenyl)methanamine.

LC/MS 486 (M+H).

Example 354

Production of 5-methyl-4-oxo-3-(pyridin-4-yl-methoxy)-N-(1,2,3,4-tetrahydronaphthalen-1-yl)-4,5-dihydrothieno[3,2-c]quinoline-2-carboxamide trifluoroacetate

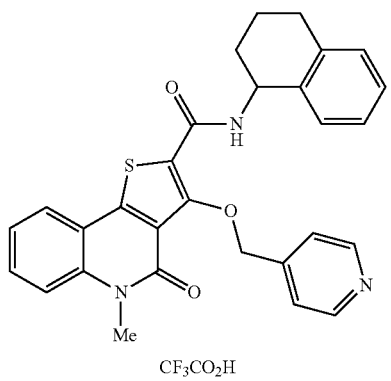 [SMILES: Cn1c(=O)c2c(OCc3ccncc3)c(C(=O)NC3CCCc4ccccc43)sc2c2ccccc21 ; "CF3CO2H"]

In the same manner as in Example 349, the title compound was obtained from the compound of Reference Example 93 and 1,2,3,4-tetrahydronaphthalen-1-amine.

LC/MS 496 (M+H).

Example 355

Production of N-(1,3-benzodioxol-5-ylmethyl)-5-methyl-4-oxo-3-(pyridin-4-ylmethoxy)-4,5-dihydrothieno[3,2-c]quinoline-2-carboxamide trifluoroacetate

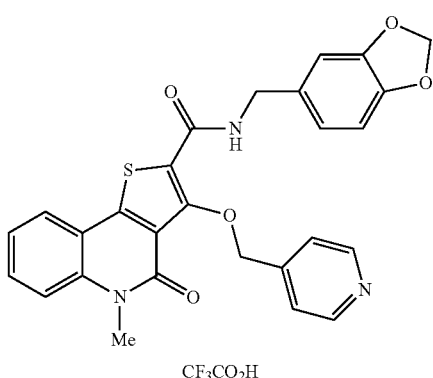

CF₃CO₂H

In the same manner as in Example 349, the title compound was obtained from the compound of Reference Example 93 and 1-(1,3-benzodioxol-5-yl)methanamine.

LC/MS 500 (M+H).

Example 356

Production of N,N-diethyl-5-methyl-4-oxo-3-(pyridin-4-ylmethoxy)-4,5-dihydrothieno[3,2-c]quinoline-2-carboxamide trifluoroacetate

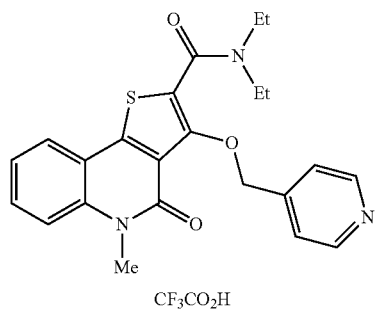 [SMILES: CCN(CC)C(=O)c1sc2c(c1OCc1ccncc1)c(=O)n(C)c1ccccc21 ; "CF3CO2H"]

CF₃CO₂H

In the same manner as in Example 349, the title compound was obtained from the compound of Reference Example 93 and N-ethylethanamine.

LC/MS 422 (M+H).

Example 357

Production of 5-methyl-2-(piperidin-1-ylcarbonyl)-3-(pyridin-4-ylmethoxy)thieno[3,2-c]quinolin-4(5H)-one trifluoroacetate

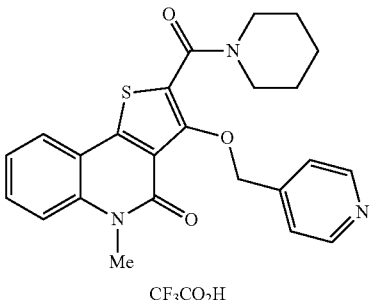

CF₃CO₂H

In the same manner as in Example 349, the title compound was obtained from the compound of Reference Example 93 and piperidine.

LC/MS 434 (M+H).

Example 358

Production of N-(2-methoxyethyl)-N,5-dimethyl-4-oxo-3-(pyridin-4-ylmethoxy)-4,5-dihydrothieno[3,2-c]quinoline-2-carboxamide trifluoroacetate

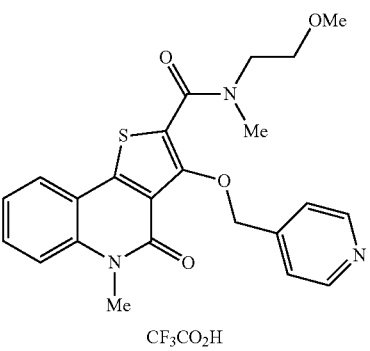 [SMILES: COCCN(C)C(=O)c1sc2c(c1OCc1ccncc1)c(=O)n(C)c1ccccc21 ; "CF3CO2H"]

CF₃CO₂H

In the same manner as in Example 349, the title compound was obtained from the compound of Reference Example 93 and 2-methoxy-N-methylethanamine.

LC/MS 438 (M+H).

Example 359

Production of N-methoxy-N,5-dimethyl-4-oxo-3-(pyridin-4-ylmethoxy)-4,5-dihydrothieno[3,2-c]quinoline-2-carboxamide trifluoroacetate

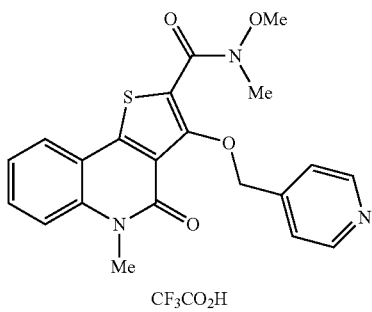 [SMILES: CON(C)C(=O)c1sc2c(c1OCc1ccncc1)c(=O)n(C)c1ccccc21 ; "CF3CO2H"]

To a solution (0.10 M, 0.40 mL, 40 μmol) of the compound of Reference Example 93 in DMF were added a mixture of a suspension (0.66 M, 0.111 mL, 73 mmol) of N-methoxymethanamine hydrochloride in DMF and triethylamine (10.9 μL, 78 μmol), and a solution (0.39 M, 0.20 mL, 78 μmol) of HOBt and WSCD in 1:1 mixture in DMF. The obtained mixture was shaken at room temperature for 14 hr. Dichloromethane (2 mL) and saturated aqueous sodium hydrogen carbonate solution (1 mL) were added to the reaction mixture, the organic layer was filtered through a Teflon (registered trade mark) filter to separate the aqueous layer, and the filtrate was concentrated under reduced pressure. The residue was purified by preparative HPLC to give the title compound (12.3 mg, 59%).

LC/MS 410 (M+H).

Example 360

Production of 5-methyl-3-(pyridin-4-ylmethoxy)-2-(thiomorpholin-4-ylcarbonyl)thieno[3,2-c]quinolin-4(5H)-one trifluoroacetate

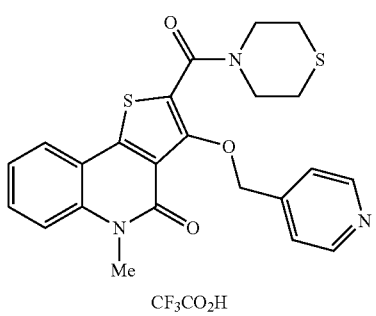 [SMILES: Cn1c(=O)c2c(OCc3ccncc3)c(C(=O)N3CCSCC3)sc2c2ccccc21 ; "CF3CO2H"]

In the same manner as in Example 349, the title compound was obtained from the compound of Reference Example 93 and thiomorpholine.

LC/MS 452 (M+H).

Example 361

Production of 2-{[(2R)-2-(methoxymethyl)pyrrolidin-1-yl]carbonyl}-5-methyl-3-(pyridin-4-ylmethoxy)thieno[3,2-c]quinolin-4(5H)-one trifluoroacetate

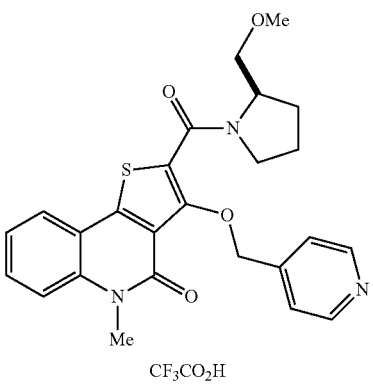 [SMILES: COC[C@H]1CCCN1C(=O)c1sc2c(c1OCc1ccncc1)c(=O)n(C)c1ccccc21 ; "CF3CO2H"]

In the same manner as in Example 349, the title compound was obtained from the compound of Reference Example 93 and (2R)-2-(methoxymethyl)pyrrolidine.

LC/MS 464 (M+H).

Example 362

Production of N-benzyl-N,5-dimethyl-4-oxo-3-(pyridin-4-ylmethoxy)-4,5-dihydrothieno[3,2-c]quinoline-2-carboxamide trifluoroacetate

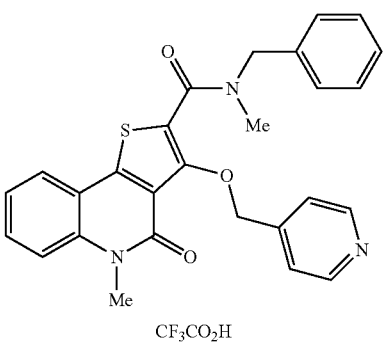 [SMILES: CN(Cc1ccccc1)C(=O)c1sc2c(c1OCc1ccncc1)c(=O)n(C)c1ccccc21 ; "CF3CO2H"]

In the same manner as in Example 349, the title compound was obtained from the compound of Reference Example 93 and N-methyl-1-phenylmethanamine.

LC/MS 470 (M+H).

Example 363

Production of 5-methyl-N,N-bis(2-methylpropyl)-4-oxo-3-(pyridin-4-ylmethoxy)-4,5-dihydrothieno[3,2-c]quinoline-2-carboxamide trifluoroacetate

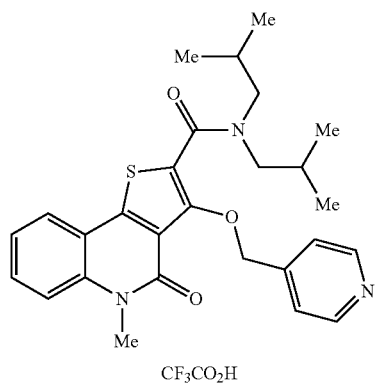 [SMILES: CC(C)CN(CC(C)C)C(=O)c1sc2c(c1OCc1ccncc1)c(=O)n(C)c1ccccc21 ; "CF3CO2H"]

In the same manner as in Example 359, the title compound was obtained from the compound of Reference Example 93 and 2-methyl-N-(2-methylpropyl)propan-1-amine hydrochloride.

LC/MS 478 (M+H).

Example 364

Production of N-[3-(dimethylamino)propyl]-5-methyl-4-oxo-3-(pyridin-4-ylmethoxy)-4,5-dihydrothieno[3,2-c]quinoline-2-carboxamide ditrifluoroacetate

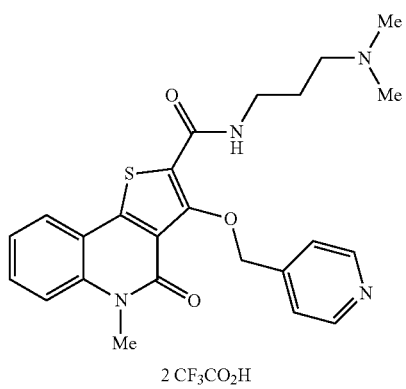 [SMILES: CN(C)CCCNC(=O)c1sc2c(c1OCc1ccncc1)c(=O)n(C)c1ccccc21 ; "2 CF3CO2H"]

In the same manner as in Example 349, the title compound was obtained from the compound of Reference Example 93 and N,N-dimethylpropane-1,3-diamine.

LC/MS 451 (M+H).

Example 365

Production of N-[2-(diethylamino)ethyl]-5-methyl-4-oxo-3-(pyridin-4-ylmethoxy)-4,5-dihydrothieno[3,2-c]quinoline-2-carboxamide ditrifluoroacetate

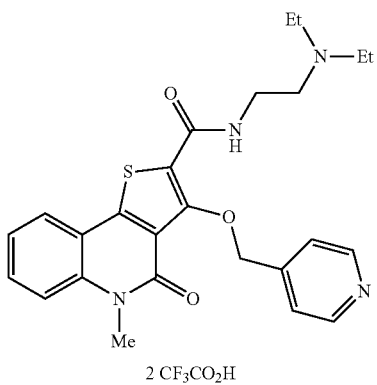 [SMILES: CCN(CC)CCNC(=O)c1sc2c(c1OCc1ccncc1)c(=O)n(C)c1ccccc21 ; "2 CF3CO2H"]

In the same manner as in Example 349, the title compound was obtained from the compound of Reference Example 93 and N,N-diethylethane-1,2-diamine.

LC/MS 465 (M+H).

Example 366

Production of N-[3-(1H-imidazol-1-yl)propyl]-5-methyl-4-oxo-3-(pyridin-4-ylmethoxy)-4,5-dihydrothieno[3,2-c]quinoline-2-carboxamide ditrifluoroacetate

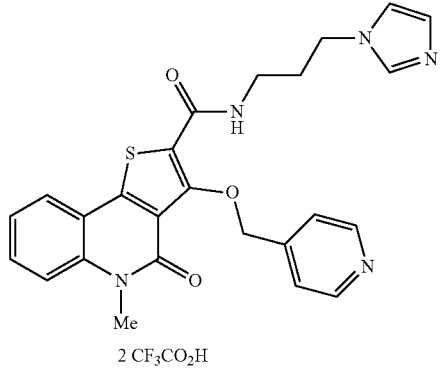 [SMILES: Cn1c(=O)c2c(OCc3ccncc3)c(C(=O)NCCCn3ccnc3)sc2c2ccccc21 ; "2 CF3CO2H"]

In the same manner as in Example 349, the title compound was obtained from the compound of Reference Example 93 and 3-(1H-imidazol-1-yl)propan-1-amine.

LC/MS 474 (M+H).

Example 367

Production of N-{2-[bis(1-methylethyl)amino]ethyl}-5-methyl-4-oxo-3-(pyridin-4-ylmethoxy)-4,5-dihydrothieno[3,2-c]quinoline-2-carboxamide ditrifluoroacetate

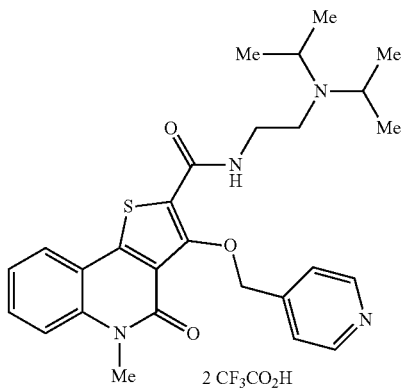 [SMILES: CC(C)N(CCNC(=O)c1sc2c(c1OCc1ccncc1)c(=O)n(C)c1ccccc21)C(C)C ; "2 CF3CO2H"]

In the same manner as in Example 349, the title compound was obtained from the compound of Reference Example 93 and N,N-bis(1-methylethyl)ethane-1,2-diamine.
LC/MS 493 (M+H).

Example 368

Production of 5-methyl-2-[(4-methylpiperazin-1-yl)carbonyl]-3-(pyridin-4-ylmethoxy)thieno[3,2-c]quinolin-4(5H)-one ditrifluoroacetate

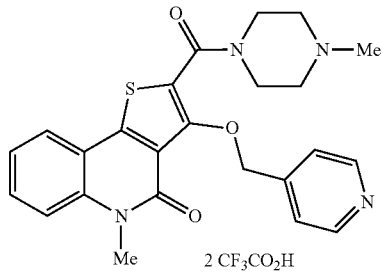 [SMILES: CN1CCN(C(=O)c2sc3c(c2OCc2ccncc2)c(=O)n(C)c2ccccc32)CC1 ; "2 CF3CO2H"]

In the same manner as in Example 349, the title compound was obtained from the compound of Reference Example 93 and 1-methylpiperazine.

Example 369

Production of N,5-dimethyl-N-(1-methylpyrrolidin-3-yl)-4-oxo-3-(pyridin-4-ylmethoxy)-4,5-dihydrothieno[3,2-c]quinoline-2-carboxamide ditrifluoroacetate

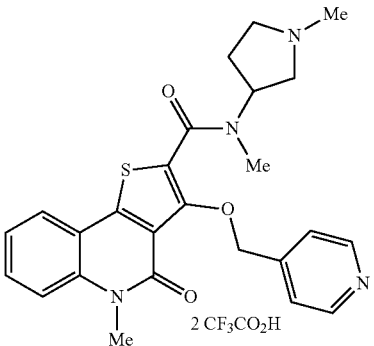 [SMILES: CN1CCC(N(C)C(=O)c2sc3c(c2OCc2ccncc2)c(=O)n(C)c2ccccc32)C1 ; "2 CF3CO2H"]

In the same manner as in Example 349, the title compound was obtained from the compound of Reference Example 93 and N,1-dimethylpyrrolidin-3-amine.

Example 370

Production of N-[2-(diethylamino)ethyl]-N,5-dimethyl-4-oxo-3-(pyridin-4-ylmethoxy)-4,5-dihydrothieno[3,2-c]quinoline-2-carboxamide ditrifluoroacetate

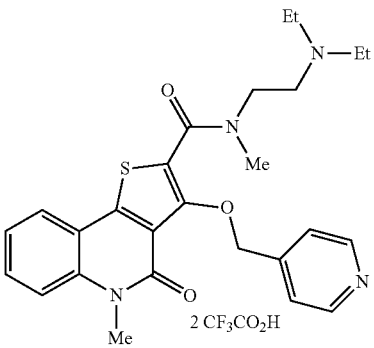 [SMILES: CCN(CC)CCN(C)C(=O)c1sc2c(c1OCc1ccncc1)c(=O)n(C)c1ccccc21 ; "2 CF3CO2H"]

In the same manner as in Example 349, the title compound was obtained from the compound of Reference Example 93 and N,N-diethyl-N'-methylethane-1,2-diamine.

Example 371

Production of 5-methyl-3-(pyridin-4-ylmethoxy)-2-[(4-pyridin-2-ylpiperazin-1-yl)carbonyl]thieno[3,2-c]quinolin-4(5H)-one 2 trifluoroacetate

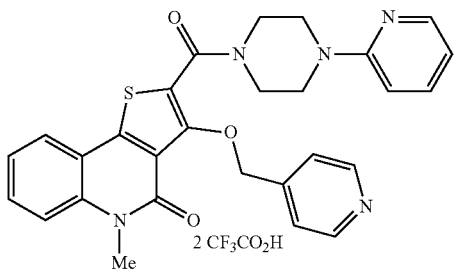 [SMILES: Cn1c(=O)c2c(OCc3ccncc3)c(C(=O)N3CCN(c4ccccn4)CC3)sc2c2ccccc21 ; "2 CF3CO2H"]

In the same manner as in Example 349, the title compound was obtained from the compound of Reference Example 93 and 1-pyridin-2-ylpiperazine.

LC/MS 512 (M+H).

Example 372

Production of N,5-dimethyl-3-(2-morpholin-4-ylethoxy)-4-oxo-4,5-dihydrothieno[3,2-c]quinoline-2-carboxamide trifluoroacetate

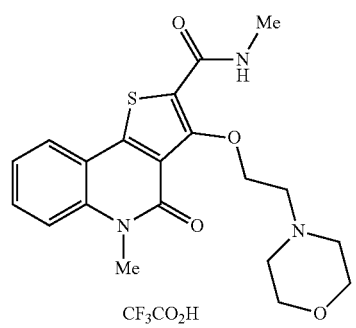 [SMILES: CNC(=O)c1sc2c(c1OCCN1CCOCC1)c(=O)n(C)c1ccccc21 ; "CF3CO2H"]

In the same manner as in Example 349, the title compound was obtained from the compound of Reference Example 94 and methanamine (2.0 M THF solution).

LC/MS 402 (M+H).

Example 373

Production of N-butyl-5-methyl-3-(2-morpholin-4-ylethoxy)-4-oxo-4,5-dihydrothieno[3,2-c]quinoline-2-carboxamide trifluoroacetate

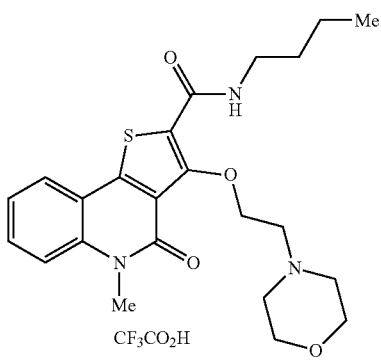 [SMILES: CCCCNC(=O)c1sc2c(c1OCCN1CCOCC1)c(=O)n(C)c1ccccc21 ; "CF3CO2H"]

In the same manner as in Example 349, the title compound was obtained from the compound of Reference Example 94 and butan-1-amine.

LC/MS 444 (M+H).

Example 374

Production of N-(furan-2-ylmethyl)-5-methyl-3-(2-morpholin-4-ylethoxy)-4-oxo-4,5-dihydrothieno[3,2-c]quinoline-2-carboxamide trifluoroacetate

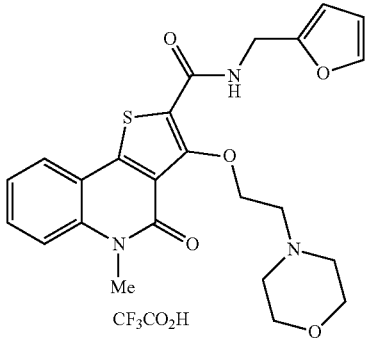 [SMILES: Cn1c(=O)c2c(OCCN3CCOCC3)c(C(=O)NCc3ccco3)sc2c2ccccc21 ; "CF3CO2H"]

In the same manner as in Example 349, the title compound was obtained from the compound of Reference Example 94 and 1-furan-2-ylmethanamine.

LC/MS 468 (M+H).

Example 375

Production of 5-methyl-3-(2-morpholin-4-ylethoxy)-4-oxo-N-(tetrahydrofuran-2-ylmethyl)-4,5-dihydrothieno[3,2-c]quinoline-2-carboxamide trifluoroacetate

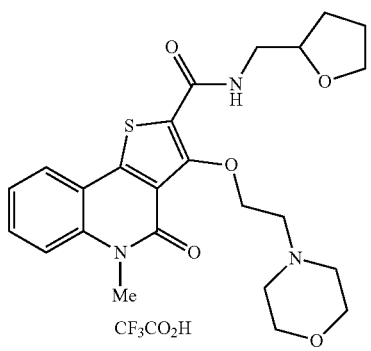 [SMILES: Cn1c(=O)c2c(OCCN3CCOCC3)c(C(=O)NCC3CCCO3)sc2c2ccccc21 ; "CF3CO2H"]

In the same manner as in Example 349, the title compound was obtained from the compound of Reference Example 94 and 1-(tetrahydrofuran-2-yl)methanamine.

LC/MS 472 (M+H).

Example 376

Production of 5-methyl-3-(2-morpholin-4-ylethoxy)-4-oxo-N-(2-phenylethyl)-4,5-dihydrothieno[3,2-c]quinoline-2-carboxamide trifluoroacetate

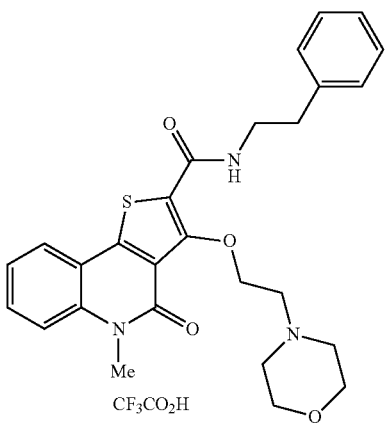 [SMILES: Cn1c(=O)c2c(OCCN3CCOCC3)c(C(=O)NCCc3ccccc3)sc2c2ccccc21 ; "CF3CO2H"]

In the same manner as in Example 349, the title compound was obtained from the compound of Reference Example 94 and 2-phenylethanamine.

LC/MS 492 (M+H).

Example 377

Production of N-(2-methoxybenzyl)-5-methyl-3-(2-morpholin-4-ylethoxy)-4-oxo-4,5-dihydrothieno[3,2-c]quinoline-2-carboxamide trifluoroacetate

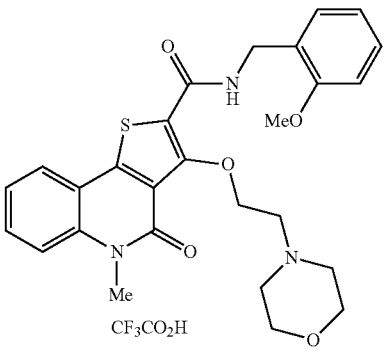 [SMILES: COc1ccccc1CNC(=O)c1sc2c(c1OCCN1CCOCC1)c(=O)n(C)c1ccccc21 ; "CF3CO2H"]

In the same manner as in Example 349, the title compound was obtained from the compound of Reference Example 94 and 1-(2-methoxyphenyl)methanamine.

LC/MS 508 (M+H).

Example 378

Production of 5-methyl-3-(2-morpholin-4-ylethoxy)-4-oxo-N-(1,2,3,4-tetrahydronaphthalen-1-yl)-4,5-dihydrothieno[3,2-c]quinoline-2-carboxamide trifluoroacetate

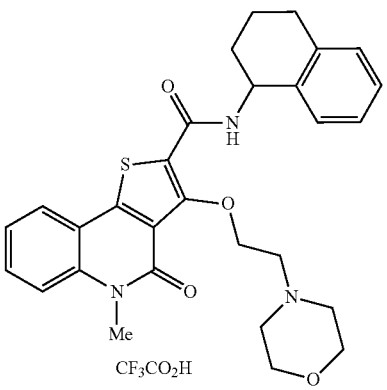 [SMILES: Cn1c(=O)c2c(OCCN3CCOCC3)c(C(=O)NC3CCCc4ccccc43)sc2c2ccccc21 ; "CF3CO2H"]

In the same manner as in Example 349, the title compound was obtained from the compound of Reference Example 94 and 1,2,3,4-tetrahydronaphthalen-1-amine.

LC/MS 518 (M+H).

Example 379

Production of N-(1,3-benzodioxol-5-ylmethyl)-5-methyl-3-(2-morpholin-4-ylethoxy)-4-oxo-4,5-dihydrothieno[3,2-c]quinoline-2-carboxamide trifluoroacetate

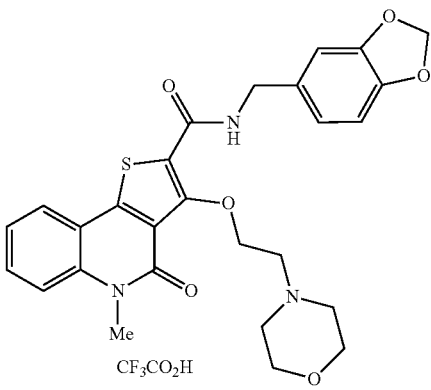 [SMILES: Cn1c(=O)c2c(OCCN3CCOCC3)c(C(=O)NCc3ccc4c(c3)OCO4)sc2c2ccccc21 ; "CF3CO2H"]

In the same manner as in Example 349, the title compound was obtained from the compound of Reference Example 94 and 1-(1,3-benzodioxol-5-yl)methanamine.

LC/MS 522 (M+H).

Example 380

Production of N,N-diethyl-5-methyl-3-(2-morpholin-4-ylethoxy)-4-oxo-4,5-dihydrothieno[3,2-c]quinoline-2-carboxamide trifluoroacetate

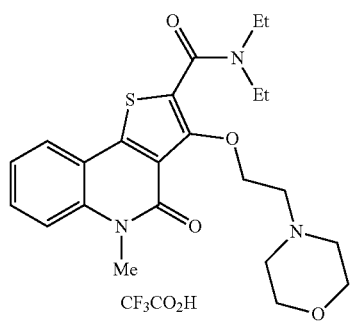 [SMILES: CCN(CC)C(=O)c1sc2c(c1OCCN1CCOCC1)c(=O)n(C)c1ccccc21 ; "CF3CO2H"]

In the same manner as in Example 349, the title compound was obtained from the compound of Reference Example 94 and N-ethylethanamine.

LC/MS 444 (M+H).

Example 381

Production of 5-methyl-3-(2-morpholin-4-ylethoxy)-2-(piperidin-1-ylcarbonyl)thieno[3,2-c]quinolin-4(5H)-one trifluoroacetate

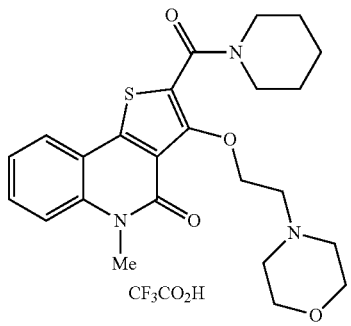 [SMILES: Cn1c(=O)c2c(OCCN3CCOCC3)c(C(=O)N3CCCCC3)sc2c2ccccc21 ; "CF3CO2H"]

In the same manner as in Example 349, the title compound was obtained from the compound of Reference Example 94 and piperidine.

LC/MS 456 (M+H).

Example 382

Production of N-(2-methoxyethyl)-N,5-dimethyl-3-(2-morpholin-4-ylethoxy)-4-oxo-4,5-dihydrothieno[3,2-c]quinoline-2-carboxamide trifluoroacetate

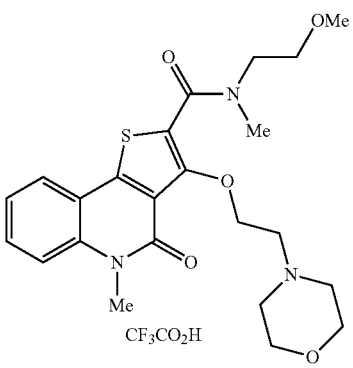 [SMILES: COCCN(C)C(=O)c1sc2c(c1OCCN1CCOCC1)c(=O)n(C)c1ccccc21 ; "CF3CO2H"]

In the same manner as in Example 349, the title compound was obtained from the compound of Reference Example 94 and 2-methoxy-N-methylethanamine.

LC/MS 460 (M+H).

Example 383

Production of N-methoxy-N,5-dimethyl-3-(2-morpholin-4-ylethoxy)-4-oxo-4,5-dihydrothieno[3,2-c]quinoline-2-carboxamide trifluoroacetate

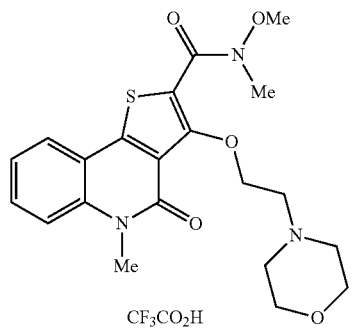 [SMILES: CON(C)C(=O)c1sc2c(c1OCCN1CCOCC1)c(=O)n(C)c1ccccc21 ; "CF3CO2H"]

In the same manner as in Example 359, the title compound was obtained from the compound of Reference Example 94 and N-methoxymethanamine hydrochloride.

LC/MS 432 (M+H).

Example 384

Production of 5-methyl-3-(2-morpholin-4-ylethoxy)-2-(thiomorpholin-4-ylcarbonyl)thieno[3,2-c]quinolin-4(5H)-one trifluoroacetate

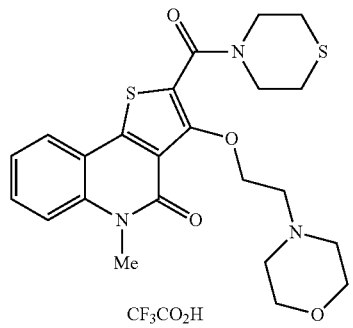 [SMILES: Cn1c(=O)c2c(OCCN3CCOCC3)c(C(=O)N3CCSCC3)sc2c2ccccc21 ; "CF3CO2H"]

In the same manner as in Example 349, the title compound was obtained from the compound of Reference Example 94 and thiomorpholine.

LC/MS 474 (M+H).

Example 385

Production of 2-{[(2R)-2-(methoxymethyl)pyrrolidin-1-yl]carbonyl}-5-methyl-3-(2-morpholin-4-ylethoxy)thieno[3,2-c]quinolin-4(5H)-one trifluoroacetate

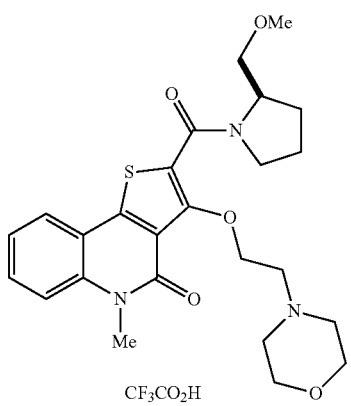 [SMILES: COC[C@H]1CCCN1C(=O)c1sc2c(c1OCCN1CCOCC1)c(=O)n(C)c1ccccc21 ; "CF3CO2H"]

In the same manner as in Example 349, the title compound was obtained from the compound of Reference Example 94 and (2R)-2-(methoxymethyl)pyrrolidine.

LC/MS 486 (M+H).

Example 386

Production of N-benzyl-N,5-dimethyl-3-(2-morpholin-4-ylethoxy)-4-oxo-4,5-dihydrothieno[3,2-c]quinoline-2-carboxamide trifluoroacetate

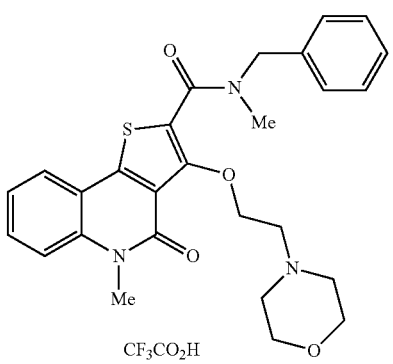 [SMILES: CN(Cc1ccccc1)C(=O)c1sc2c(c1OCCN1CCOCC1)c(=O)n(C)c1ccccc21 ; "CF3CO2H"]

In the same manner as in Example 349, the title compound was obtained from the compound of Reference Example 94 and N-methyl-1-phenylmethanamine.

LC/MS 492 (M+H).

Example 387

Production of 5-methyl-N,N-bis(2-methylpropyl)-3-(2-morpholin-4-ylethoxy)-4-oxo-4,5-dihydrothieno[3,2-c]quinoline-2-carboxamide trifluoroacetate

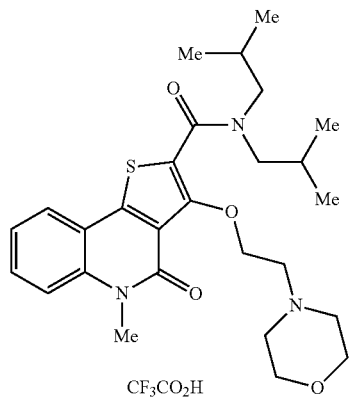 [SMILES: CC(C)CN(CC(C)C)C(=O)c1sc2c(c1OCCN1CCOCC1)c(=O)n(C)c1ccccc21 ; "CF3CO2H"]

In the same manner as in Example 359, the title compound was obtained from the compound of Reference Example 94 and 2-methyl-N-(2-methylpropyl)propan-1-amine hydrochloride.

LC/MS 500 (M+H).

Example 388

Production of N-[3-(dimethylamino)propyl]-5-methyl-3-(2-morpholin-4-ylethoxy)-4-oxo-4,5-dihydrothieno[3,2-c]quinoline-2-carboxamide ditrifluoroacetate

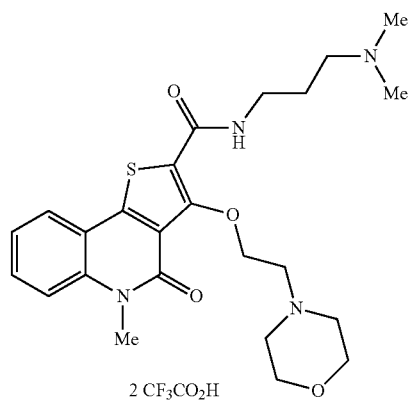 [SMILES: CN(C)CCCNC(=O)c1sc2c(c1OCCN1CCOCC1)c(=O)n(C)c1ccccc21 ; "2 CF3CO2H"]

In the same manner as in Example 349, the title compound was obtained from the compound of Reference Example 94 and N,N-dimethylpropane-1,3-diamine.

LC/MS 473 (M+H).

Example 389

Production of N-[2-(diethylamino)ethyl]-5-methyl-3-(2-morpholin-4-ylethoxy)-4-oxo-4,5-dihydrothieno[3,2-c]quinoline-2-carboxamide ditrifluoroacetate

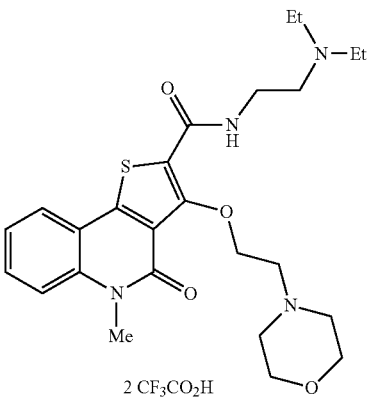 [SMILES: CCN(CC)CCNC(=O)c1sc2c(c1OCCN1CCOCC1)c(=O)n(C)c1ccccc21 ; "2 CF3CO2H"]

In the same manner as in Example 349, the title compound was obtained from the compound of Reference Example 94 and N,N-diethylethane-1,2-diamine.

LC/MS 487 (M+H).

Example 390

Production of N-[3-(1H-imidazol-1-yl)propyl]-5-methyl-3-(2-morpholin-4-ylethoxy)-4-oxo-4,5-dihydrothieno[3,2-c]quinoline-2-carboxamide ditrifluoroacetate

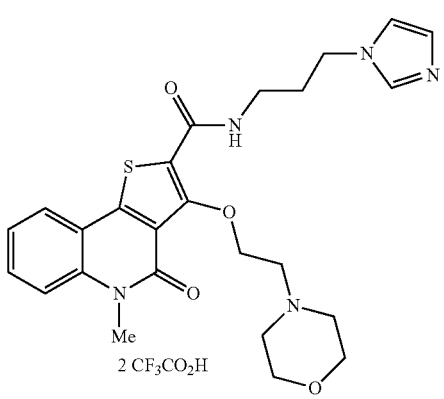 [SMILES: Cn1c(=O)c2c(OCCN3CCOCC3)c(C(=O)NCCCn3ccnc3)sc2c2ccccc21 ; "2 CF3CO2H"]

In the same manner as in Example 349, the title compound was obtained from the compound of Reference Example 94 and 3-(1H-imidazol-1-yl)propan-1-amine.

LC/MS 496 (M+H).

Example 391

Production of N-{2-[bis(1-methylethyl)amino]ethyl}-5-methyl-3-(2-morpholin-4-ylethoxy)-4-oxo-4,5-dihydrothieno[3,2-c]quinoline-2-carboxamide ditrifluoroacetate

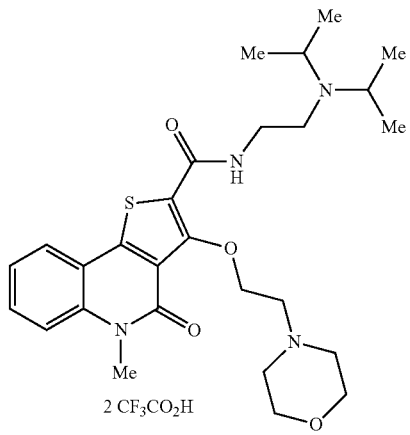 [SMILES: CC(C)N(CCNC(=O)c1sc2c(c1OCCN1CCOCC1)c(=O)n(C)c1ccccc21)C(C)C ; "2 CF3CO2H"]

In the same manner as in Example 349, the title compound was obtained from the compound of Reference Example 94 and N,N-bis(1-methylethyl)ethane-1,2-diamine.

LC/MS 515 (M+H).

Example 392

Production of 5-methyl-2-[(4-methylpiperazin-1-yl)carbonyl]-3-(2-morpholin-4-ylethoxy)thieno[3,2-c]quinolin-4(5H)-one ditrifluoroacetate

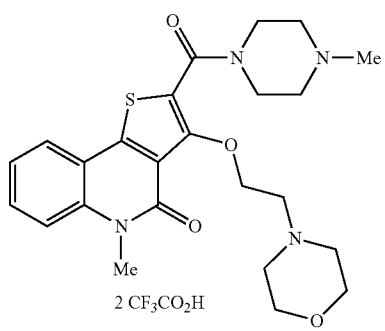 [SMILES: CN1CCN(C(=O)c2sc3c(c2OCCN2CCOCC2)c(=O)n(C)c2ccccc32)CC1 ; "2 CF3CO2H"]

In the same manner as in Example 349, the title compound was obtained from the compound of Reference Example 94 and 1-methylpiperazine.

Example 393

Production of N,5-dimethyl-N-(1-methylpyrrolidin-3-yl)-3-(2-morpholin-4-ylethoxy)-4-oxo-4,5-dihydrothieno[3,2-c]quinoline-2-carboxamide ditrifluoroacetate

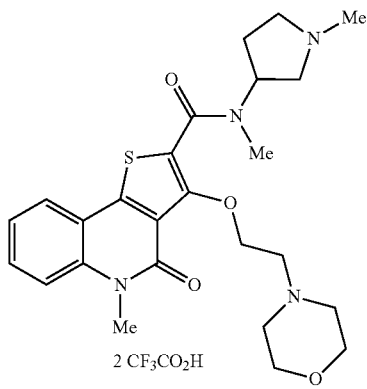 [SMILES: CN1CCC(N(C)C(=O)c2sc3c(c2OCCN2CCOCC2)c(=O)n(C)c2ccccc32)C1 ; "2 CF3CO2H"]

In the same manner as in Example 349, the title compound was obtained from the compound of Reference Example 94 and N,1-dimethylpyrrolidin-3-amine.

LC/MS 485 (M+H).

Example 394

Production of N-[2-(diethylamino)ethyl]-N,5-dimethyl-3-(2-morpholin-4-ylethoxy)-4-oxo-4,5-dihydrothieno[3,2-c]quinoline-2-carboxamide ditrifluoroacetate

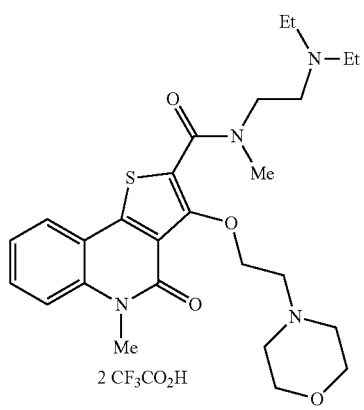 [SMILES: CCN(CC)CCN(C)C(=O)c1sc2c(c1OCCN1CCOCC1)c(=O)n(C)c1ccccc21 ; "2 CF3CO2H"]

In the same manner as in Example 349, the title compound was obtained from the compound of Reference Example 94 and N,N-diethyl-N'-methylethane-1,2-diamine.

LC/MS 501 (M+H).

Example 395

Production of 5-methyl-3-(2-morpholin-4-ylethoxy)-2-[(4-pyridin-2-ylpiperazin-1-yl)carbonyl]thieno[3,2-c]quinolin-4(5H)-one ditrifluoroacetate

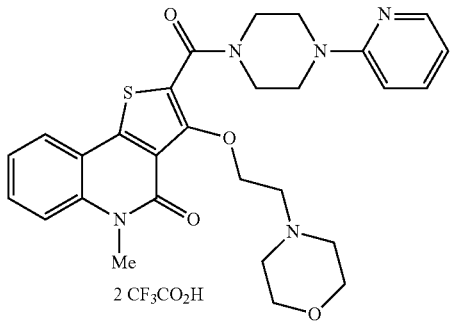 [SMILES: Cn1c(=O)c2c(OCCN3CCOCC3)c(C(=O)N3CCN(c4ccccn4)CC3)sc2c2ccccc21 ; "2 CF3CO2H"]

In the same manner as in Example 349, the title compound was obtained from the compound of Reference Example 94 and 1-pyridin-2-ylpiperazine.
LC/MS 534 (M+H).

Example 396

Production of N,5-dimethyl-4-oxo-3-(tetrahydrofuran-2-ylmethoxy)-4,5-dihydrothieno[3,2-c]quinoline-2-carboxamide

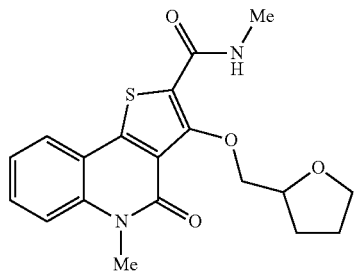 [SMILES: CNC(=O)c1sc2c(c1OCC1CCCO1)c(=O)n(C)c1ccccc21]

In the same manner as in Example 300, the title compound was obtained from the compound of Reference Example 95 and methanamine (2.0 M THF solution).
LC/MS 373 (M+H).

Example 397

Production of N-butyl-5-methyl-4-oxo-3-(tetrahydrofuran-2-ylmethoxy)-4,5-dihydrothieno[3,2-c]quinoline-2-carboxamide

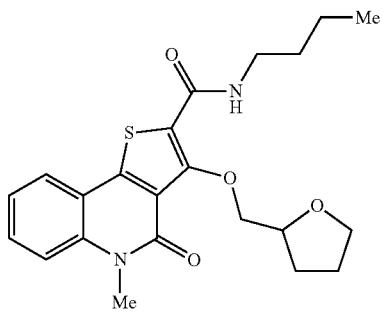 [SMILES: CCCCNC(=O)c1sc2c(c1OCC1CCCO1)c(=O)n(C)c1ccccc21]

In the same manner as in Example 5, the title compound was obtained from the compound of Reference Example 95 and butan-1-amine.
LC/MS 415 (M+H).

Example 398

Production of N-(furan-2-ylmethyl)-5-methyl-4-oxo-3-(tetrahydrofuran-2-ylmethoxy)-4,5-dihydrothieno[3,2-c]quinoline-2-carboxamide

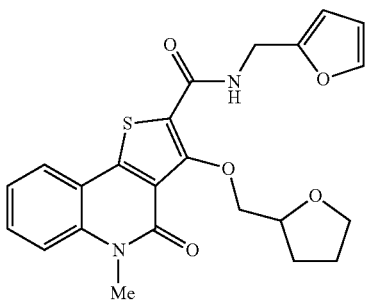 [SMILES: Cn1c(=O)c2c(OCC3CCCO3)c(C(=O)NCc3ccco3)sc2c2ccccc21]

In the same manner as in Example 5, the title compound was obtained from the compound of Reference Example 95 and 1-furan-2-ylmethanamine.
LC/MS 439 (M+H).

Example 399

Production of 5-methyl-4-oxo-3-(tetrahydrofuran-2-ylmethoxy)-N-(tetrahydrofuran-2-ylmethyl)-4,5-dihydrothieno[3,2-c]quinoline-2-carboxamide

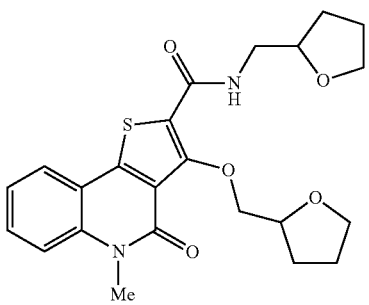 [SMILES: Cn1c(=O)c2c(OCC3CCCO3)c(C(=O)NCC3CCCO3)sc2c2ccccc21]

In the same manner as in Example 5, the title compound was obtained from the compound of Reference Example 95 and 1-(tetrahydrofuran-2-yl)methanamine.
LC/MS 443 (M+H).

Example 400

Production of 5-methyl-4-oxo-N-(2-phenylethyl)-3-(tetrahydrofuran-2-ylmethoxy)-4,5-dihydrothieno[3,2-c]quinoline-2-carboxamide

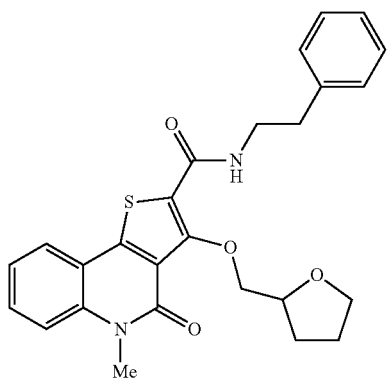 [SMILES: Cn1c(=O)c2c(OCC3CCCO3)c(C(=O)NCCc3ccccc3)sc2c2ccccc21]

In the same manner as in Example 5, the title compound was obtained from the compound of Reference Example 95 and 2-phenylethanamine.
LC/MS 463 (M+H).

Example 401

Production of N-(2-methoxybenzyl)-5-methyl-4-oxo-3-(tetrahydrofuran-2-ylmethoxy)-4,5-dihydrothieno[3,2-c]quinoline-2-carboxamide

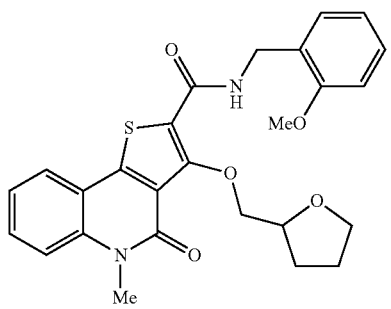 [SMILES: COc1ccccc1CNC(=O)c1sc2c(c1OCC1CCCO1)c(=O)n(C)c1ccccc21]

In the same manner as in Example 5, the title compound was obtained from the compound of Reference Example 95 and 1-(2-methoxyphenyl)methanamine.
LC/MS 479 (M+H).

Example 402

Production of 5-methyl-4-oxo-3-(tetrahydrofuran-2-ylmethoxy)-N-(1,2,3,4-tetrahydronaphthalen-1-yl)-4,5-dihydrothieno[3,2-c]quinoline-2-carboxamide

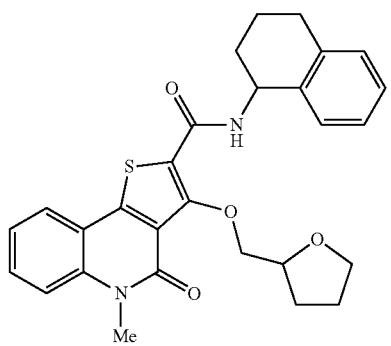 [SMILES: Cn1c(=O)c2c(OCC3CCCO3)c(C(=O)NC3CCCc4ccccc43)sc2c2ccccc21]

In the same manner as in Example 5, the title compound was obtained from the compound of Reference Example 95 and 1,2,3,4-tetrahydronaphthalen-1-amine.
LC/MS 489 (M+H).

Example 403

Production of N-(1,3-benzodioxol-5-ylmethyl)-5-methyl-4-oxo-3-(tetrahydrofuran-2-ylmethoxy)-4,5-dihydrothieno[3,2-c]quinoline-2-carboxamide

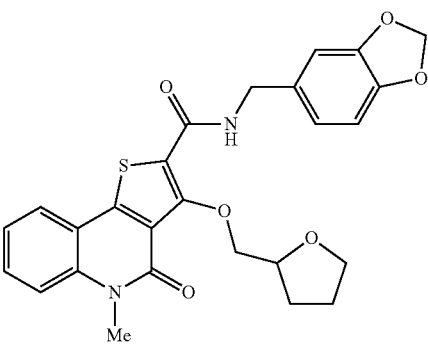 [SMILES: Cn1c(=O)c2c(OCC3CCCO3)c(C(=O)NCc3ccc4c(c3)OCO4)sc2c2ccccc21]

In the same manner as in Example 5, the title compound was obtained from the compound of Reference Example 95 and 1-(1,3-benzodioxol-5-yl)methanamine.
LC/MS 493 (M+H).

Example 404

Production of N,N-diethyl-5-methyl-4-oxo-3-(tetrahydrofuran-2-ylmethoxy)-4,5-dihydrothieno[3,2-c]quinoline-2-carboxamide

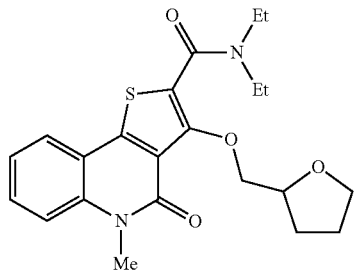 [SMILES: CCN(CC)C(=O)c1sc2c(c1OCC1CCCO1)c(=O)n(C)c1ccccc21]

In the same manner as in Example 5, the title compound was obtained from the compound of Reference Example 95 and N-ethylethanamine.
LC/MS 415 (M+H).

Example 405

Production of 5-methyl-2-(piperidin-1-ylcarbonyl)-3-(tetrahydrofuran-2-ylmethoxy)thieno[3,2-c]quinolin-4(5H)-one

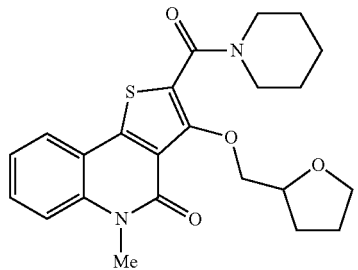 [SMILES: Cn1c(=O)c2c(OCC3CCCO3)c(C(=O)N3CCCCC3)sc2c2ccccc21]

In the same manner as in Example 5, the title compound was obtained from the compound of Reference Example 95 and piperidine.
LC/MS 427 (M+H).

Example 406

Production of N-(2-methoxyethyl)-N,5-dimethyl-4-oxo-3-(tetrahydrofuran-2-ylmethoxy)-4,5-dihydrothieno[3,2-c]quinoline-2-carboxamide

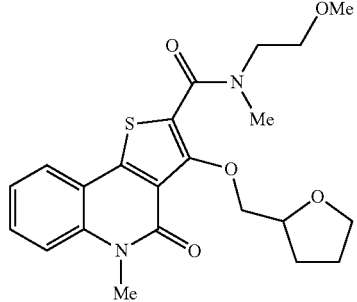 [SMILES: COCCN(C)C(=O)c1sc2c(c1OCC1CCCO1)c(=O)n(C)c1ccccc21]

In the same manner as in Example 5, the title compound was obtained from the compound of Reference Example 95 and 2-methoxy-N-methylethanamine.
LC/MS 461 (M+H).

Example 407

Production of N-methoxy-N,5-dimethyl-4-oxo-3-(tetrahydrofuran-2-ylmethoxy)-4,5-dihydrothieno[3,2-c]quinoline-2-carboxamide

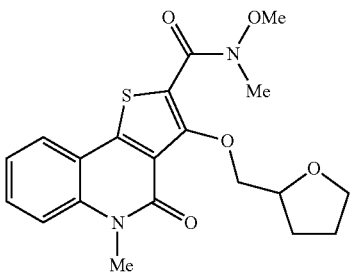 [SMILES: CON(C)C(=O)c1sc2c(c1OCC1CCCO1)c(=O)n(C)c1ccccc21]

In the same manner as in Example 335, the title compound was obtained from the compound of Reference Example 95 and N-methoxymethanamine hydrochloride.
LC/MS 403 (M+H).

Example 408

Production of 5-methyl-3-(tetrahydrofuran-2-ylmethoxy)-2-(thiomorpholin-4-ylcarbonyl)thieno[3,2-c]quinolin-4(5H)-one

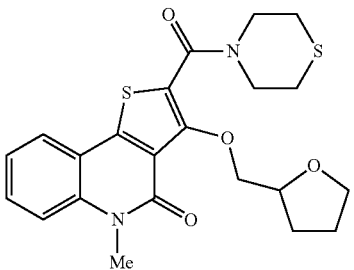 [SMILES: Cn1c(=O)c2c(OCC3CCCO3)c(C(=O)N3CCSCC3)sc2c2ccccc21]

In the same manner as in Example 5, the title compound was obtained from the compound of Reference Example 95 and thiomorpholine.
LC/MS 445 (M+H).

Example 409

Production of 2-{[(2R)-2-(methoxymethyl)pyrrolidin-1-yl]carbonyl}-5-methyl-3-(tetrahydrofuran-2-ylmethoxy)thieno[3,2-c]quinolin-4(5H)-one

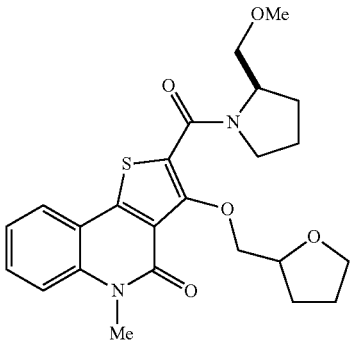 [SMILES: COC[C@H]1CCCN1C(=O)c1sc2c(c1OCC1CCCO1)c(=O)n(C)c1ccccc21]

In the same manner as in Example 5, the title compound was obtained from the compound of Reference Example 95 and (2R)-2-(methoxymethyl)pyrrolidine.
LC/MS 457 (M+H).

Example 410

Production of N-benzyl-N,5-dimethyl-4-oxo-3-(tetrahydrofuran-2-ylmethoxy)-4,5-dihydrothieno[3,2-c]quinoline-2-carboxamide

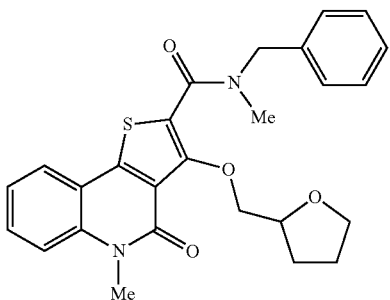 [SMILES: CN(Cc1ccccc1)C(=O)c1sc2c(c1OCC1CCCO1)c(=O)n(C)c1ccccc21]

In the same manner as in Example 5, the title compound was obtained from the compound of Reference Example 95 and N-methyl-1-phenylmethanamine.

LC/MS 463 (M+H).

Example 411

Production of 5-methyl-N,N-bis(2-methylpropyl)-4-oxo-3-(tetrahydrofuran-2-ylmethoxy)-4,5-dihydrothieno[3,2-c]quinoline-2-carboxamide

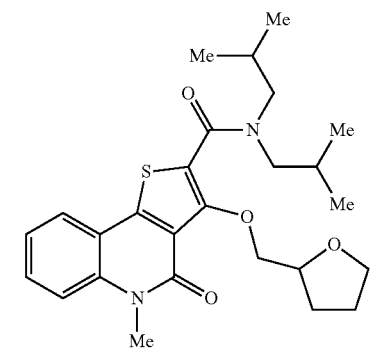 [SMILES: CC(C)CN(CC(C)C)C(=O)c1sc2c(c1OCC1CCCO1)c(=O)n(C)c1ccccc21]

In the same manner as in Example 335, the title compound was obtained from the compound of Reference Example 95 and 2-methyl-N-(2-methylpropyl)propan-1-amine hydrochloride.

LC/MS 471 (M+H).

Example 412

Production of N-[3-(dimethylamino)propyl]-5-methyl-4-oxo-3-(tetrahydrofuran-2-ylmethoxy)-4,5-dihydrothieno[3,2-c]quinoline-2-carboxamide trifluoroacetate

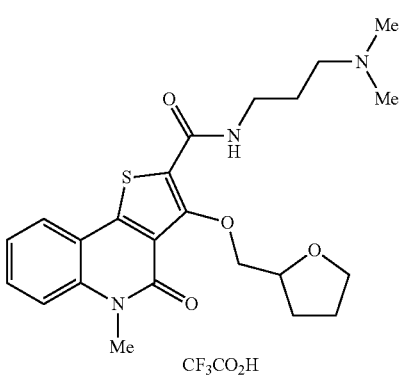 [SMILES: CN(C)CCCNC(=O)c1sc2c(c1OCC1CCCO1)c(=O)n(C)c1ccccc21 ; "CF3CO2H"]

In the same manner as in Example 5, the title compound was obtained from the compound of Reference Example 95 and N,N-dimethylpropane-1,3-diamine.

LC/MS 444 (M+H).

Example 413

Production of N-[2-(diethylamino)ethyl]-5-methyl-4-oxo-3-(tetrahydrofuran-2-ylmethoxy)-4,5-dihydrothieno[3,2-c]quinoline-2-carboxamide trifluoroacetate

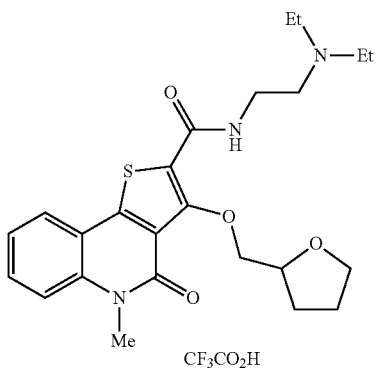 [SMILES: CCN(CC)CCNC(=O)c1sc2c(c1OCC1CCCO1)c(=O)n(C)c1ccccc21 ; "CF3CO2H"]

In the same manner as in Example 5, the title compound was obtained from the compound of Reference Example 95 and N,N-diethylethane-1,2-diamine.

LC/MS 458 (M+H).

Example 414

Production of N-[3-(1H-imidazol-1-yl)propyl]-5-methyl-4-oxo-3-(tetrahydrofuran-2-ylmethoxy)-4,5-dihydrothieno[3,2-c]quinoline-2-carboxamide trifluoroacetate

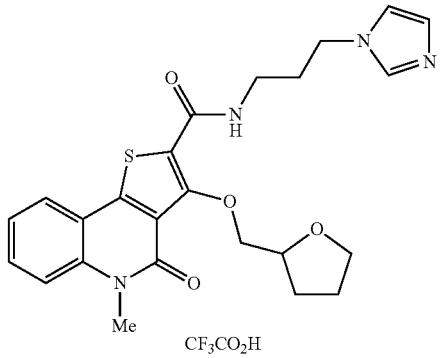 [SMILES: Cn1c(=O)c2c(OCC3CCCO3)c(C(=O)NCCCn3ccnc3)sc2c2ccccc21 ; "CF3CO2H"]

In the same manner as in Example 5, the title compound was obtained from the compound of Reference Example 95 and 3-(1H-imidazol-1-yl)propan-1-amine.

LC/MS 467 (M+H).

Example 415

Production of N-{2-[bis(1-methylethyl)amino]ethyl}-5-methyl-4-oxo-3-(tetrahydrofuran-2-ylmethoxy)-4,5-dihydrothieno[3,2-c]quinoline-2-carboxamide trifluoroacetate

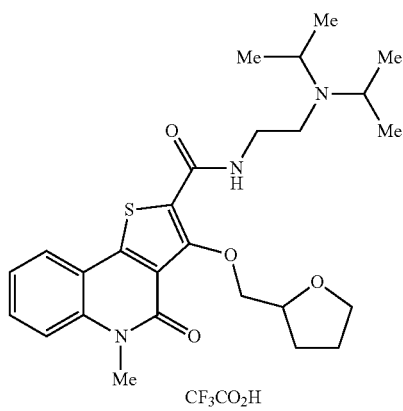 [SMILES: CC(C)N(CCNC(=O)c1sc2c(c1OCC1CCCO1)c(=O)n(C)c1ccccc21)C(C)C ; "CF3CO2H"]

In the same manner as in Example 5, the title compound was obtained from the compound of Reference Example 95 and N,N-bis(1-methylethyl)ethane-1,2-diamine.

LC/MS 486 (M+H).

Example 416

Production of 5-methyl-2-[(4-methylpiperazin-1-yl)carbonyl]-3-(tetrahydrofuran-2-ylmethoxy)thieno[3,2-c]quinolin-4(5H)-one trifluoroacetate

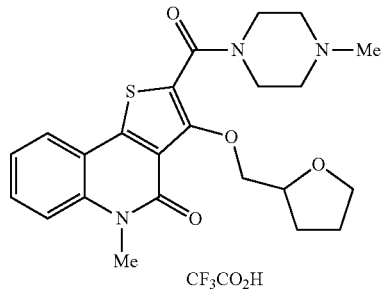 [SMILES: CN1CCN(C(=O)c2sc3c(c2OCC2CCCO2)c(=O)n(C)c2ccccc32)CC1 ; "CF3CO2H"]

In the same manner as in Example 5, the title compound was obtained from the compound of Reference Example 95 and 1-methylpiperazine.

LC/MS 442 (M+H).

Example 417

Production of N,5-dimethyl-N-(1-methylpyrrolidin-3-yl)-4-oxo-3-(tetrahydrofuran-2-ylmethoxy)-4,5-dihydrothieno[3,2-c]quinoline-2-carboxamide trifluoroacetate

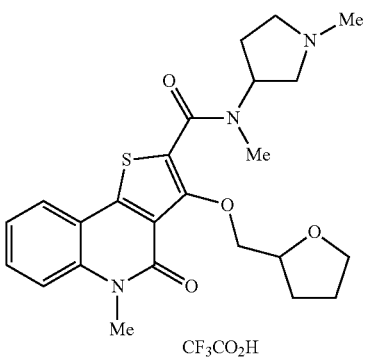 [SMILES: CN1CCC(N(C)C(=O)c2sc3c(c2OCC2CCCO2)c(=O)n(C)c2ccccc32)C1 ; "CF3CO2H"]

In the same manner as in Example 5, the title compound was obtained from the compound of Reference Example 95 and N,1-dimethylpyrrolidin-3-amine.

LC/MS 456 (M+H).

Example 418

Production of N-[2-(diethylamino)ethyl]-N,5-dimethyl-4-oxo-3-(tetrahydrofuran-2-ylmethoxy)-4,5-dihydrothieno[3,2-c]quinoline-2-carboxamide trifluoroacetate

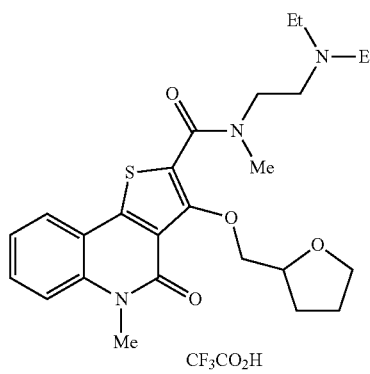

In the same manner as in Example 5, the title compound was obtained from the compound of Reference Example 95 and N,N-diethyl-N'-methylethane-1,2-diamine.
LC/MS 472 (M+H).

Example 419

Production of 5-methyl-2-[(4-pyridin-2-ylpiperazin-1-yl) carbonyl]-3-(tetrahydrofuran-2-ylmethoxy) thieno[3,2-c]quinolin-4(5H)-one trifluoroacetate

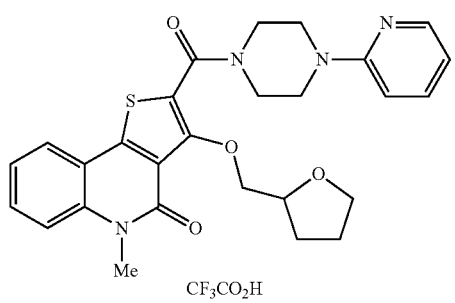 [SMILES: Cn1c(=O)c2c(OCC3CCCO3)c(C(=O)N3CCN(c4ccccn4)CC3)sc2c2ccccc21 ; "CF3CO2H"]

In the same manner as in Example 5, the title compound was obtained from the compound of Reference Example 95 and 1-pyridin-2-ylpiperazine.
LC/MS 505 (M+H).

Example 420

Production of 3-(2-ethoxyethoxy)-N,5-dimethyl-4-oxo-4,5-dihydrothieno[3,2-c]quinoline-2-carboxamide

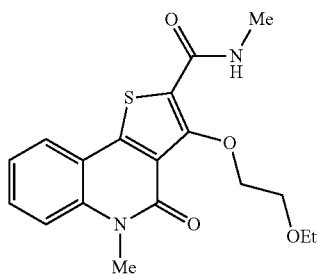 [SMILES: CCOCCOc1c(C(=O)NC)sc2c1c(=O)n(C)c1ccccc21]

In the same manner as in Example 300, the title compound was obtained from the compound of Reference Example 96 and methanamine (2.0 M THF solution).
LC/MS 361 (M+H).

Example 421

Production of N-butyl-3-(2-ethoxyethoxy)-5-methyl-4-oxo-4,5-dihydrothieno[3,2-c]quinoline-2-carboxamide

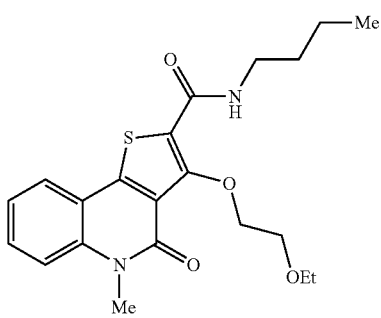 [SMILES: CCCCNC(=O)c1sc2c(c1OCCOCC)c(=O)n(C)c1ccccc21]

In the same manner as in Example 5, the title compound was obtained from the compound of Reference Example 96 and butan-1-amine.
LC/MS 403 (M+H).

Example 422

Production of 3-(2-ethoxyethoxy)-N-(furan-2-ylmethyl)-5-methyl-4-oxo-4,5-dihydrothieno[3,2-c]quinoline-2-carboxamide

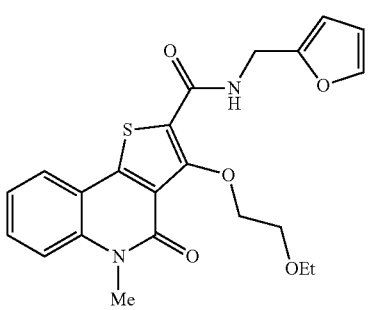 [SMILES: CCOCCOc1c(C(=O)NCc2ccco2)sc2c1c(=O)n(C)c1ccccc21]

In the same manner as in Example 5, the title compound was obtained from the compound of Reference Example 96 and 1-furan-2-ylmethanamine
LC/MS 427 (M+H).

Example 423

Production of 3-(2-ethoxyethoxy)-5-methyl-4-oxo-N-(tetrahydrofuran-2-ylmethyl)-4,5-dihydrothieno[3,2-c]quinoline-2-carboxamide

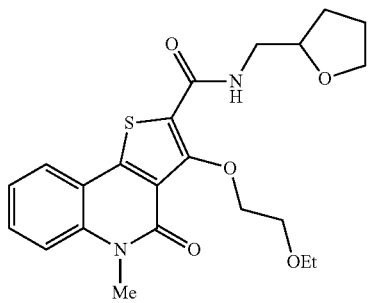 [SMILES: CCOCCOc1c(C(=O)NCC2CCCO2)sc2c1c(=O)n(C)c1ccccc21]

In the same manner as in Example 5, the title compound was obtained from the compound of Reference Example 96 and 1-(tetrahydrofuran-2-yl)methanamine.

LC/MS 431 (M+H).

Example 424

Production of 3-(2-ethoxyethoxy)-5-methyl-4-oxo-N-(2-phenylethyl)-4,5-dihydrothieno[3,2-c]quinoline-2-carboxamide

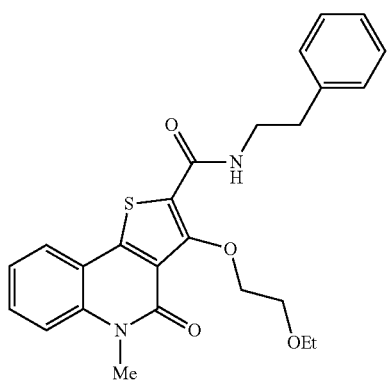 [SMILES: CCOCCOc1c(C(=O)NCCc2ccccc2)sc2c1c(=O)n(C)c1ccccc21]

In the same manner as in Example 5, the title compound was obtained from the compound of Reference Example 96 and 2-phenylethanamine.

LC/MS 451 (M+H).

Example 425

Production of 3-(2-ethoxyethoxy)-N-(2-methoxybenzyl)-5-methyl-4-oxo-4,5-dihydrothieno[3,2-c]quinoline-2-carboxamide

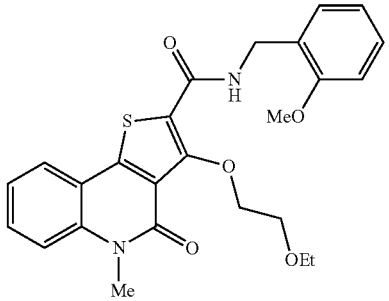 [SMILES: CCOCCOc1c(C(=O)NCc2ccccc2OC)sc2c1c(=O)n(C)c1ccccc21]

In the same manner as in Example 5, the title compound was obtained from the compound of Reference Example 96 and 1-(2-methoxyphenyl)methanamine.

LC/MS 467 (M+H).

Example 426

Production of 3-(2-ethoxyethoxy)-5-methyl-4-oxo-N-(1,2,3,4-tetrahydronaphthalen-1-yl)-4,5-dihydrothieno[3,2-c]quinoline-2-carboxamide

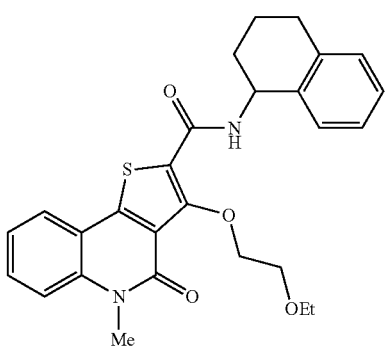 [SMILES: CCOCCOc1c(C(=O)NC2CCCc3ccccc32)sc2c1c(=O)n(C)c1ccccc21]

In the same manner as in Example 5, the title compound was obtained from the compound of Reference Example 96 and 1,2,3,4-tetrahydronaphthalen-1-amine.

LC/MS 477 (M+H).

Example 427

Production of N-(1,3-benzodioxol-5-ylmethyl)-3-(2-ethoxyethoxy)-5-methyl-4-oxo-4,5-dihydrothieno[3,2-c]quinoline-2-carboxamide

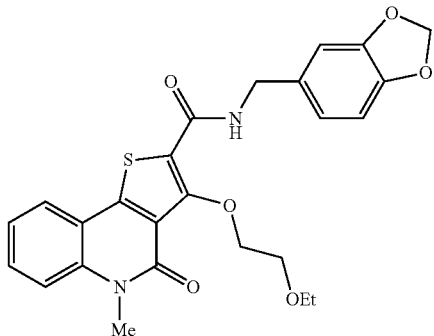 [SMILES: CCOCCOc1c(C(=O)NCc2ccc3c(c2)OCO3)sc2c1c(=O)n(C)c1ccccc21]

In the same manner as in Example 5, the title compound was obtained from the compound of Reference Example 96 and 1-(1,3-benzodioxol-5-yl)methanamine.
LC/MS 481 (M+H).

Example 428

Production of 3-(2-ethoxyethoxy)-N,N-diethyl-5-methyl-4-oxo-4,5-dihydrothieno[3,2-c]quinoline-2-carboxamide

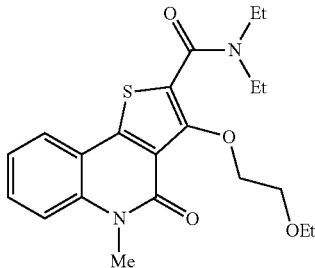 [SMILES: CCOCCOc1c(C(=O)N(CC)CC)sc2c1c(=O)n(C)c1ccccc21]

In the same manner as in Example 5, the title compound was obtained from the compound of Reference Example 96 and N-ethylethanamine.
LC/MS 403 (M+H).

Example 429

Production of 3-(2-ethoxyethoxy)-5-methyl-2-(piperidin-1-ylcarbonyl)thieno[3,2-c]quinolin-4(5H)-one

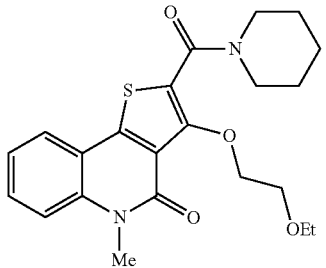 [SMILES: CCOCCOc1c(C(=O)N2CCCCC2)sc2c1c(=O)n(C)c1ccccc21]

In the same manner as in Example 5, the title compound was obtained from the compound of Reference Example 96 and piperidine.
LC/MS 415 (M+H).

Example 430

Production of 3-(2-ethoxyethoxy)-N-(2-methoxyethyl)-N,5-dimethyl-4-oxo-4,5-dihydrothieno[3,2-c]quinoline-2-carboxamide

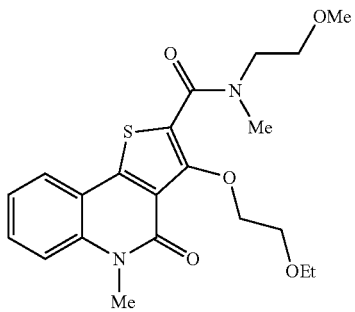 [SMILES: CCOCCOc1c(C(=O)N(C)CCOC)sc2c1c(=O)n(C)c1ccccc21]

In the same manner as in Example 5, the title compound was obtained from the compound of Reference Example 96 and 2-methoxy-N-methylethanamine.
LC/MS 419 (M+H).

Example 431

Production of 3-(2-ethoxyethoxy)-N-methoxy-N,5-dimethyl-4-oxo-4,5-dihydrothieno[3,2-c]quinoline-2-carboxamide

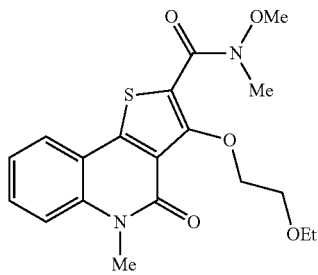 [SMILES: CCOCCOc1c(C(=O)N(C)OC)sc2c1c(=O)n(C)c1ccccc21]

In the same manner as in Example 335, the title compound was obtained from the compound of Reference Example 96 and N-methoxymethanamine hydrochloride.
LC/MS 391 (M+H).

Example 432

Production of 3-(2-ethoxyethoxy)-5-methyl-2-(thiomorpholin-4-ylcarbonyl)thieno[3,2-c]quinolin-4(5H)-one

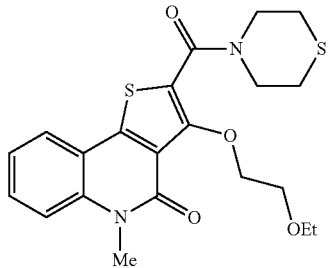 [SMILES: CCOCCOc1c(C(=O)N2CCSCC2)sc2c1c(=O)n(C)c1ccccc21]

In the same manner as in Example 5, the title compound was obtained from the compound of Reference Example 96 and thiomorpholine.
LC/MS 433 (M+H).

Example 433

Production of 3-(2-ethoxyethoxy)-2-{[(2R)-2-(methoxymethyl)pyrrolidin-1-yl]carbonyl}-5-methylthieno[3,2-c]quinolin-4(5H)-one

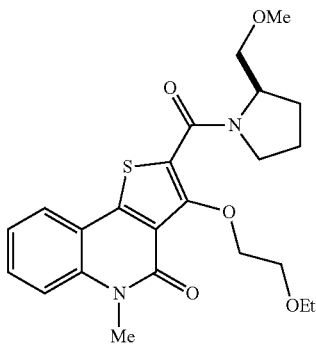 [SMILES: CCOCCOc1c(C(=O)N2CCC[C@@H]2COC)sc2c1c(=O)n(C)c1ccccc21]

In the same manner as in Example 5, the title compound was obtained from the compound of Reference Example 96 and (2R)-2-(methoxymethyl)pyrrolidine.

LC/MS 445 (M+H).

Example 434

Production of N-benzyl-3-(2-ethoxyethoxy)-N,5-dimethyl-4-oxo-4,5-dihydrothieno[3,2-c]quinoline-2-carboxamide

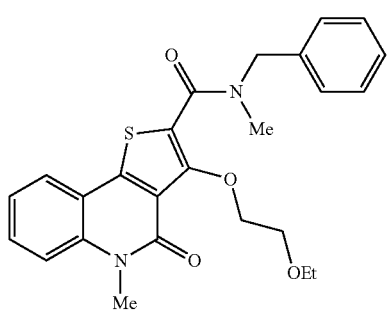 [SMILES: CCOCCOc1c(C(=O)N(C)Cc2ccccc2)sc2c1c(=O)n(C)c1ccccc21]

In the same manner as in Example 5, the title compound was obtained from the compound of Reference Example 96 and N-methyl-1-phenylmethanamine.

LC/MS 451 (M+H).

Example 435

Production of 3-(2-ethoxyethoxy)-5-methyl-N,N-bis(2-methylpropyl)-4-oxo-4,5-dihydrothieno[3,2-c]quinoline-2-carboxamide

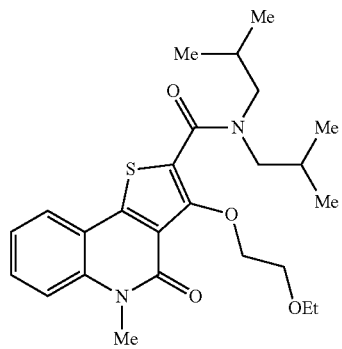 [SMILES: CCOCCOc1c(C(=O)N(CC(C)C)CC(C)C)sc2c1c(=O)n(C)c1ccccc21]

In the same manner as in Example 335, the title compound was obtained from the compound of Reference Example 96 and 2-methyl-N-(2-methylpropyl)propan-1-amine hydrochloride.

LC/MS 459 (M+H).

Example 436

Production of N-[3-(dimethylamino)propyl]-3-(2-ethoxyethoxy)-5-methyl-4-oxo-4,5-dihydrothieno[3,2-c]quinoline-2-carboxamide trifluoroacetate

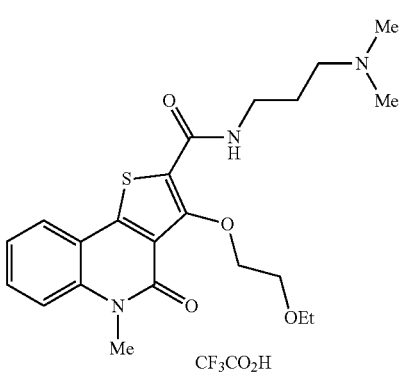 [SMILES: CCOCCOc1c(C(=O)NCCCN(C)C)sc2c1c(=O)n(C)c1ccccc21 ; "CF3CO2H"]

In the same manner as in Example 5, the title compound was obtained from the compound of Reference Example 96 and N,N-dimethylpropane-1,3-diamine.

LC/MS 432 (M+H).

Example 437

Production of N-[2-(diethylamino)ethyl]-3-(2-ethoxyethoxy)-5-methyl-4-oxo-4,5-dihydrothieno[3,2-c]quinoline-2-carboxamide trifluoroacetate

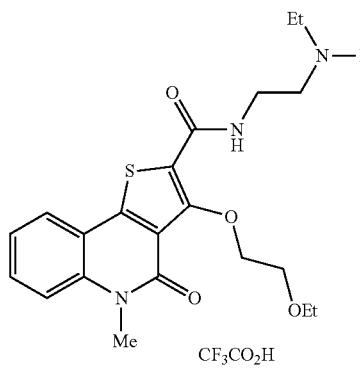

In the same manner as in Example 5, the title compound was obtained from the compound of Reference Example 96 and N,N-diethylethane-1,2-diamine.

LC/MS 446 (M+H).

Example 438

Production of 3-(2-ethoxyethoxy)-N-[3-(1H-imidazol-1-yl)propyl]-5-methyl-4-oxo-4,5-dihydrothieno[3,2-c]quinoline-2-carboxamide trifluoroacetate

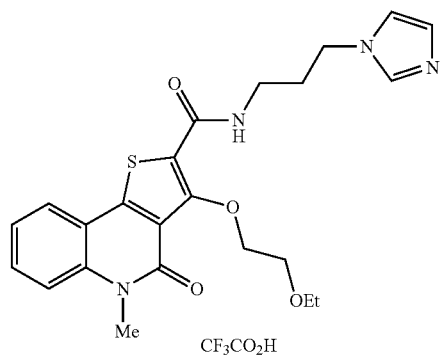 [SMILES: CCOCCOc1c(C(=O)NCCCn2ccnc2)sc2c1c(=O)n(C)c1ccccc21 ; "CF3CO2H"]

In the same manner as in Example 5, the title compound was obtained from the compound of Reference Example 96 and 3-(1H-imidazol-1-yl)propan-1-amine.

LC/MS 455 (M+H).

Example 439

Production of N-{2-[bis(1-methylethyl)amino]ethyl}-3-(2-ethoxyethoxy)-5-methyl-4-oxo-4,5-dihydrothieno[3,2-c]quinoline-2-carboxamide trifluoroacetate

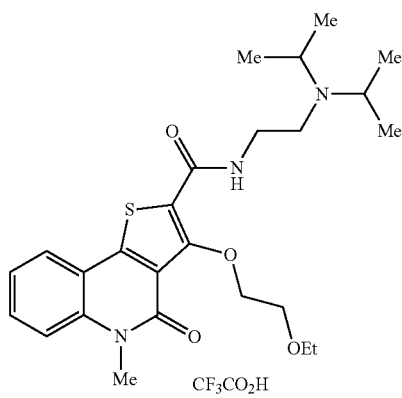 [SMILES: CCOCCOc1c(C(=O)NCCN(C(C)C)C(C)C)sc2c1c(=O)n(C)c1ccccc21 ; "CF3CO2H"]

In the same manner as in Example 5, the title compound was obtained from the compound of Reference Example 96 and N,N-bis(1-methylethyl)ethane-1,2-diamine.

LC/MS 474 (M+H).

Example 440

Production of 3-(2-ethoxyethoxy)-5-methyl-2-[(4-methylpiperazin-1-yl)carbonyl]thieno[3,2-c]quinolin-4(5H)-one trifluoroacetate

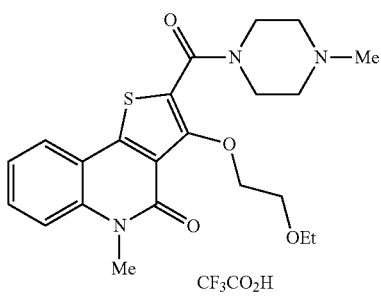 [SMILES: CCOCCOc1c(C(=O)N2CCN(C)CC2)sc2c1c(=O)n(C)c1ccccc21 ; "CF3CO2H"]

In the same manner as in Example 5, the title compound was obtained from the compound of Reference Example 96 and 1-methylpiperazine.

LC/MS 430 (M+H).

Example 441

Production of 3-(2-ethoxyethoxy)-N,5-dimethyl-N-(1-methylpyrrolidin-3-yl)-4-oxo-4,5-dihydrothieno[3,2-c]quinoline-2-carboxamide trifluoroacetate

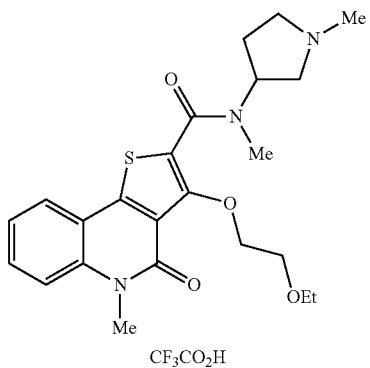 [SMILES: CCOCCOc1c(C(=O)N(C)C2CCN(C)C2)sc2c1c(=O)n(C)c1ccccc21 ; "CF3CO2H"]

In the same manner as in Example 5, the title compound was obtained from the compound of Reference Example 96 and N,1-dimethylpyrrolidin-3-amine.

LC/MS 444 (M+H).

Example 442

Production of N-[2-(diethylamino)ethyl]-3-(2-ethoxyethoxy)-N,5-dimethyl-4-oxo-4,5-dihydrothieno[3,2-c]quinoline-2-carboxamide trifluoroacetate

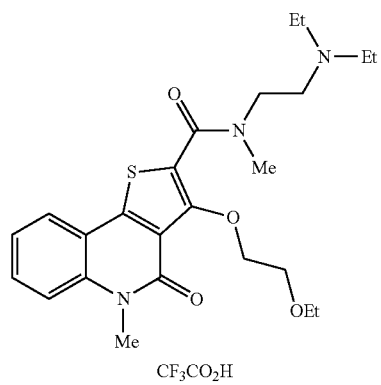 [SMILES: CCOCCOc1c(C(=O)N(C)CCN(CC)CC)sc2c1c(=O)n(C)c1ccccc21 ; "CF3CO2H"]

In the same manner as in Example 5, the title compound was obtained from the compound of Reference Example 96 and N,N-diethyl-N'-methylethane-1,2-diamine.

LC/MS 460 (M+H).

Example 443

Production of 3-(2-ethoxyethoxy)-5-methyl-2-[(4-pyridin-2-ylpiperazin-1-yl)carbonyl]thieno[3,2-c]quinolin-4(5H)-one trifluoroacetate

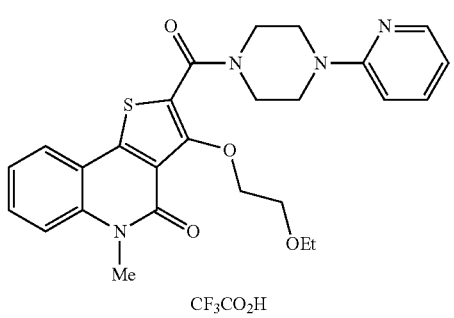 [SMILES: CCOCCOc1c(C(=O)N2CCN(c3ccccn3)CC2)sc2c1c(=O)n(C)c1ccccc21 ; "CF3CO2H"]

In the same manner as in Example 5, the title compound was obtained from the compound of Reference Example 96 and 1-pyridin-2-ylpiperazine.

LC/MS 493 (M+H).

Example 444

Production of 5-butyl-3-(2-ethoxyethoxy)-N-methyl-4-oxo-4,5-dihydrothieno[3,2-c]quinoline-2-carboxamide

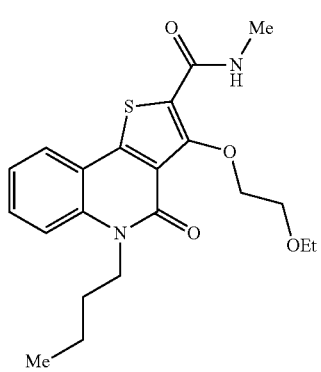 [SMILES: CCCCn1c(=O)c2c(OCCOCC)c(C(=O)NC)sc2c2ccccc21]

In the same manner as in Example 300, the title compound was obtained from the compound of Reference Example 104 and methanamine (2.0 M THF solution).

LC/MS 403 (M+H).

Example 445

Production of N,5-dibutyl-3-(2-ethoxyethoxy)-4-oxo-4,5-dihydrothieno[3,2-c]quinoline-2-carboxamide

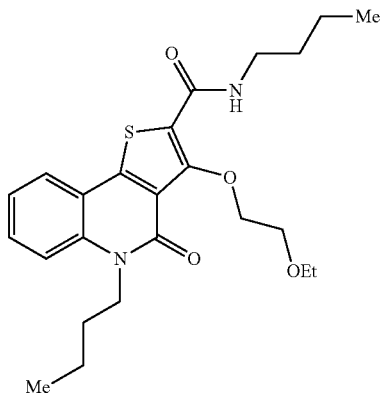 [SMILES: CCCCNC(=O)c1sc2c(c1OCCOCC)c(=O)n(CCCC)c1ccccc21]

In the same manner as in Example 5, the title compound was obtained from the compound of Reference Example 104 and butan-1-amine.

LC/MS 445 (M+H).

Example 446

Production of 5-butyl-3-(2-ethoxyethoxy)-N-(furan-2-ylmethyl)-4-oxo-4,5-dihydrothieno[3,2-c]quinoline-2-carboxamide

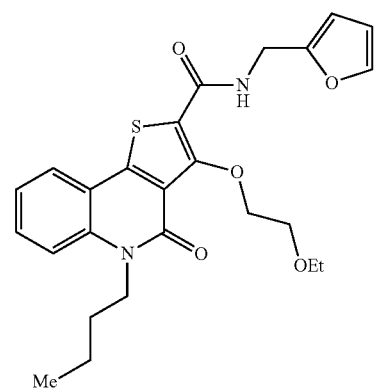 [SMILES: CCCCn1c(=O)c2c(OCCOCC)c(C(=O)NCc3ccco3)sc2c2ccccc21]

In the same manner as in Example 5, the title compound was obtained from the compound of Reference Example 104 and 1-furan-2-ylmethanamine.

LC/MS 469 (M+H).

Example 447

Production of 5-butyl-3-(2-ethoxyethoxy)-4-oxo-N-(tetrahydrofuran-2-ylmethyl)-4,5-dihydrothieno[3,2-c]quinoline-2-carboxamide

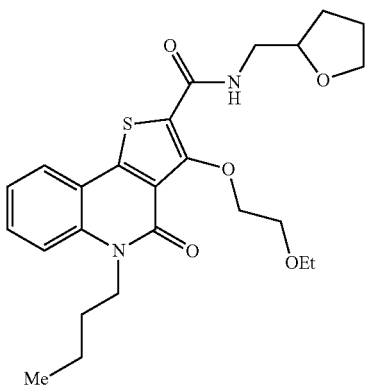 [SMILES: CCCCn1c(=O)c2c(OCCOCC)c(C(=O)NCC3CCCO3)sc2c2ccccc21]

In the same manner as in Example 5, the title compound was obtained from the compound of Reference Example 104 and 1-(tetrahydrofuran-2-yl)methanamine.

LC/MS 473 (M+H).

Example 448

Production of 5-butyl-3-(2-ethoxyethoxy)-4-oxo-N-(2-phenylethyl)-4,5-dihydrothieno[3,2-c]quinoline-2-carboxamide

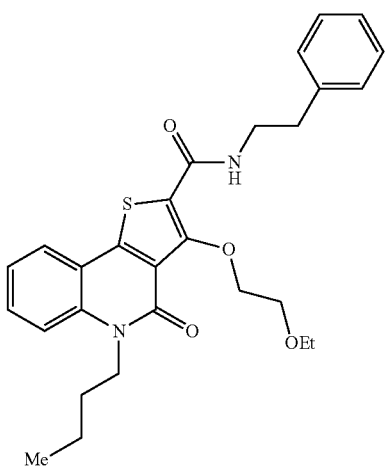 [SMILES: CCCCn1c(=O)c2c(OCCOCC)c(C(=O)NCCc3ccccc3)sc2c2ccccc21]

In the same manner as in Example 5, the title compound was obtained from the compound of Reference Example 104 and 2-phenylethanamine.

LC/MS 493 (M+H).

Example 449

Production of 5-butyl-3-(2-ethoxyethoxy)-N-(2-methoxybenzyl)-4-oxo-4,5-dihydrothieno[3,2-c]quinoline-2-carboxamide

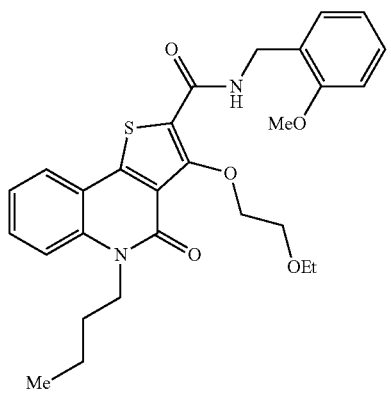 [SMILES: CCCCn1c(=O)c2c(OCCOCC)c(C(=O)NCc3ccccc3OC)sc2c2ccccc21]

In the same manner as in Example 5, the title compound was obtained from the compound of Reference Example 104 and 1-(2-methoxyphenyl)methanamine.

LC/MS 509 (M+H).

Example 450

Production of 5-butyl-3-(2-ethoxyethoxy)-4-oxo-N-(1,2,3,4-tetrahydronaphthalen-1-yl)-4,5-dihydrothieno[3,2-c]quinoline-2-carboxamide

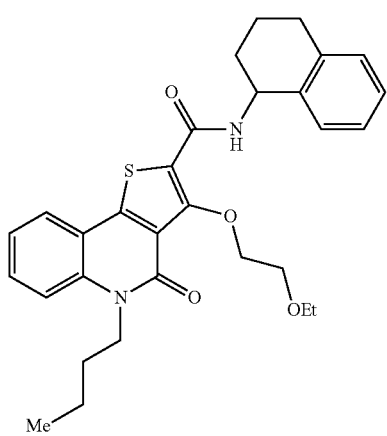 [SMILES: CCCCn1c(=O)c2c(OCCOCC)c(C(=O)NC3CCCc4ccccc43)sc2c2ccccc21]

In the same manner as in Example 5, the title compound was obtained from the compound of Reference Example 104 and 1,2,3,4-tetrahydronaphthalen-1-amine.

LC/MS 519 (M+H).

Example 451

Production of N-(1,3-benzodioxol-5-ylmethyl)-5-butyl-3-(2-ethoxyethoxy)-4-oxo-4,5-dihydrothieno[3,2-c]quinoline-2-carboxamide

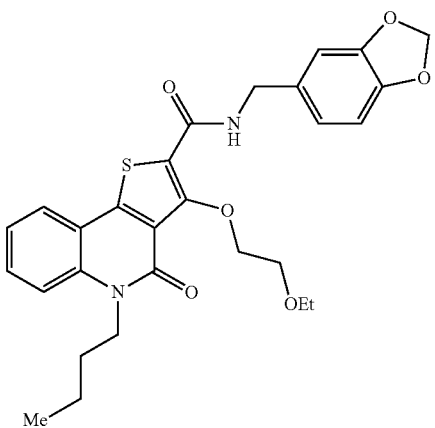 [SMILES: CCCCn1c(=O)c2c(OCCOCC)c(C(=O)NCc3ccc4c(c3)OCO4)sc2c2ccccc21]

In the same manner as in Example 5, the title compound was obtained from the compound of Reference Example 104 and 1-(1,3-benzodioxol-5-yl)methanamine.

LC/MS 523 (M+H).

Example 452

Production of 5-butyl-3-(2-ethoxyethoxy)-N,N-diethyl-4-oxo-4,5-dihydrothieno[3,2-c]quinoline-2-carboxamide

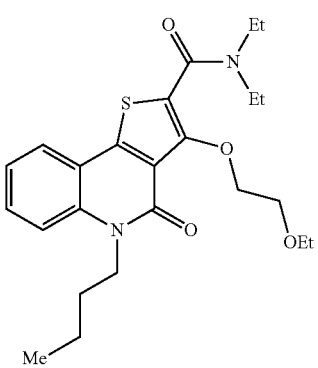 [SMILES: CCCCn1c(=O)c2c(OCCOCC)c(C(=O)N(CC)CC)sc2c2ccccc21]

In the same manner as in Example 5, the title compound was obtained from the compound of Reference Example 104 and N-ethylethanamine.

LC/MS 445 (M+H).

Example 453

Production of 5-butyl-3-(2-ethoxyethoxy)-2-(piperidin-1-ylcarbonyl)thieno[3,2-c]quinolin-4(5H)-one

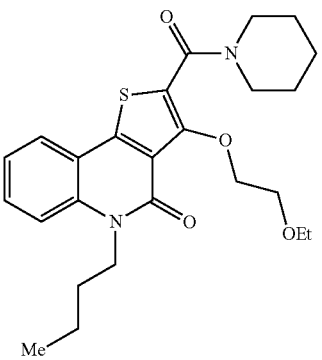 [SMILES: CCCCn1c(=O)c2c(OCCOCC)c(C(=O)N3CCCCC3)sc2c2ccccc21]

In the same manner as in Example 5, the title compound was obtained from the compound of Reference Example 104 and piperidine.
LC/MS 457 (M+H).

Example 454

Production of 5-butyl-3-(2-ethoxyethoxy)-N-(2-methoxyethyl)-N-methyl-4-oxo-4,5-dihydrothieno[3,2-c]quinoline-2-carboxamide

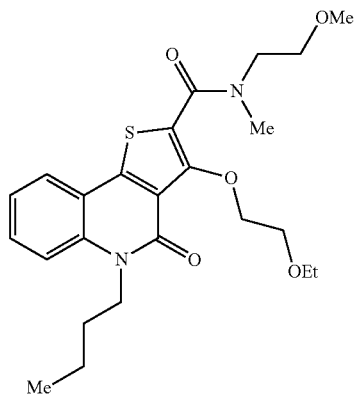 [SMILES: CCCCn1c(=O)c2c(OCCOCC)c(C(=O)N(C)CCOC)sc2c2ccccc21]

In the same manner as in Example 5, the title compound was obtained from the compound of Reference Example 104 and 2-methoxy-N-methylethanamine.
LC/MS 461 (M+H).

Example 455

Production of 5-butyl-3-(2-ethoxyethoxy)-N-methoxy-N-methyl-4-oxo-4,5-dihydrothieno[3,2-c]quinoline-2-carboxamide

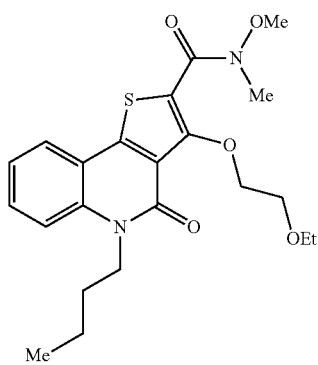 [SMILES: CCCCn1c(=O)c2c(OCCOCC)c(C(=O)N(C)OC)sc2c2ccccc21]

In the same manner as in Example 335, the title compound was obtained from the compound of Reference Example 104 and N-methoxymethanamine hydrochloride.
LC/MS 433 (M+H).

Example 456

Production of 5-butyl-3-(2-ethoxyethoxy)-2-(thiomorpholin-4-ylcarbonyl)thieno[3,2-c]quinolin-4(5H)-one

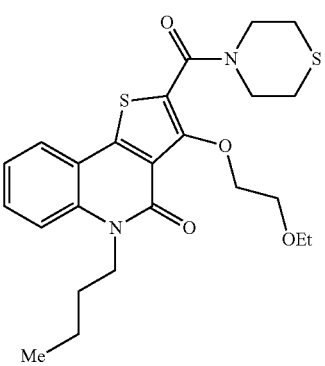 [SMILES: CCCCn1c(=O)c2c(OCCOCC)c(C(=O)N3CCSCC3)sc2c2ccccc21]

In the same manner as in Example 5, the title compound was obtained from the compound of Reference Example 104 and thiomorpholine.
LC/MS 475 (M+H).

Example 457

Production of 5-butyl-3-(2-ethoxyethoxy)-2-{[(2R)-2-(methoxymethyl)pyrrolidin-1-yl]carbonyl}thieno[3,2-c]quinolin-4(5H)-one

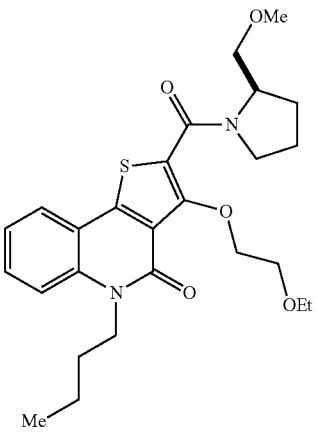 [SMILES: CCCCn1c(=O)c2c(OCCOCC)c(C(=O)N3CCC[C@@H]3COC)sc2c2ccccc21]

In the same manner as in Example 5, the title compound was obtained from the compound of Reference Example 104 and (2R)-2-(methoxymethyl)pyrrolidine.

LC/MS 487 (M+H).

Example 458

Production of N-benzyl-5-butyl-3-(2-ethoxyethoxy)-N-methyl-4-oxo-4,5-dihydrothieno[3,2-c]quinoline-2-carboxamide

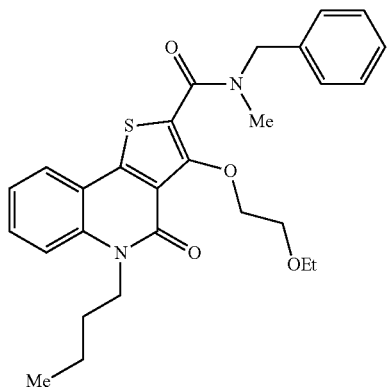 [SMILES: CCCCn1c(=O)c2c(OCCOCC)c(C(=O)N(C)Cc3ccccc3)sc2c2ccccc21]

In the same manner as in Example 5, the title compound was obtained from the compound of Reference Example 104 and N-methyl-1-phenylmethanamine.

LC/MS 493 (M+H).

Example 459

Production of 5-butyl-3-(2-ethoxyethoxy)-N,N-bis(2-methylpropyl)-4-oxo-4,5-dihydrothieno[3,2-c]quinoline-2-carboxamide

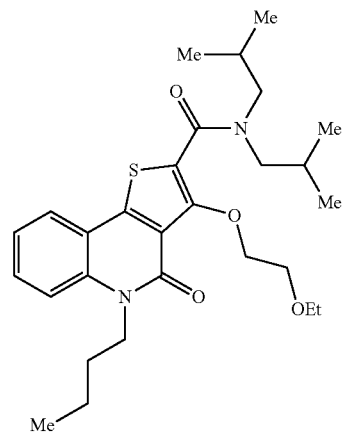 [SMILES: CCCCn1c(=O)c2c(OCCOCC)c(C(=O)N(CC(C)C)CC(C)C)sc2c2ccccc21]

In the same manner as in Example 335, the title compound was obtained from the compound of Reference Example 104 and 2-methyl-N-(2-methylpropyl)propan-1-amine hydrochloride.

LC/MS 501 (M+H).

Example 460

Production of 5-butyl-N-[3-(dimethylamino)propyl]-3-(2-ethoxyethoxy)-4-oxo-4,5-dihydrothieno[3,2-c]quinoline-2-carboxamide trifluoroacetate

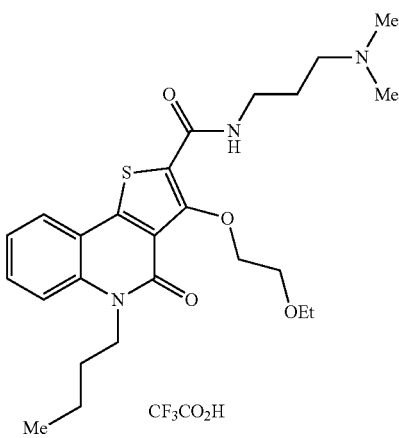 [SMILES: CCCCn1c(=O)c2c(OCCOCC)c(C(=O)NCCCN(C)C)sc2c2ccccc21 ; "CF3CO2H"]

In the same manner as in Example 5, the title compound was obtained from the compound of Reference Example 104 and N,N-dimethylpropane-1,3-diamine.

LC/MS 474 (M+H).

Example 461

Production of 5-butyl-N-[2-(diethylamino)ethyl]-3-(2-ethoxyethoxy)-4-oxo-4,5-dihydrothieno[3,2-c]quinoline-2-carboxamide trifluoroacetate

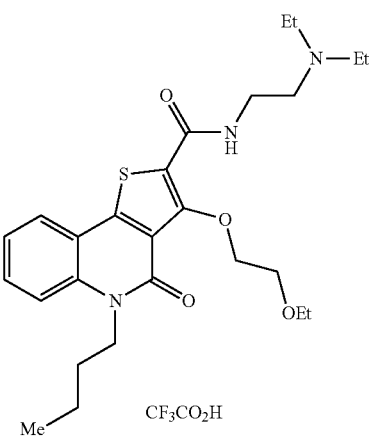 [SMILES: CCCCn1c(=O)c2c(OCCOCC)c(C(=O)NCCN(CC)CC)sc2c2ccccc21 ; "CF3CO2H"]

In the same manner as in Example 5, the title compound was obtained from the compound of Reference Example 104 and N,N-diethylethane-1,2-diamine.

LC/MS 488 (M+H).

Example 462

Production of 5-butyl-3-(2-ethoxyethoxy)-N-[3-(1H-imidazol-1-yl)propyl]-4-oxo-4,5-dihydrothieno[3,2-c]quinoline-2-carboxamide trifluoroacetate

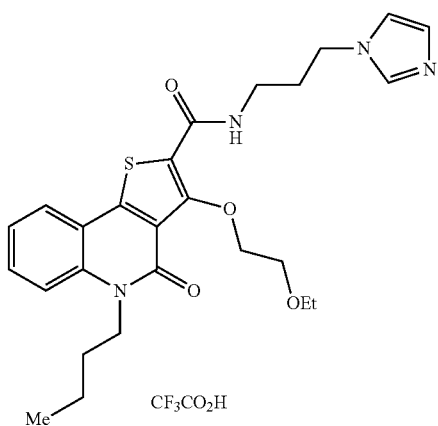 [SMILES: CCCCn1c(=O)c2c(OCCOCC)c(C(=O)NCCCn3ccnc3)sc2c2ccccc21 ; "CF3CO2H"]

In the same manner as in Example 5, the title compound was obtained from the compound of Reference Example 104 and 3-(1H-imidazol-1-yl)propan-1-amine.

LC/MS 497 (M+H).

Example 463

Production of N-{2-[bis(1-methylethyl)amino]ethyl}-5-butyl-3-(2-ethoxyethoxy)-4-oxo-4,5-dihydrothieno[3,2-c]quinoline-2-carboxamide trifluoroacetate

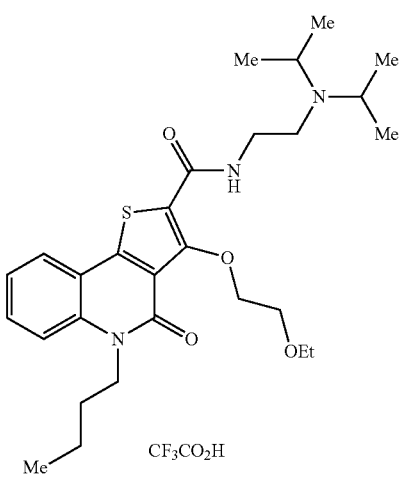 [SMILES: CCCCn1c(=O)c2c(OCCOCC)c(C(=O)NCCN(C(C)C)C(C)C)sc2c2ccccc21 ; "CF3CO2H"]

In the same manner as in Example 5, the title compound was obtained from the compound of Reference Example 104 and N,N-bis(1-methylethyl)ethane-1,2-diamine.

LC/MS 516 (M+H).

Example 464

Production of 5-butyl-3-(2-ethoxyethoxy)-2-[(4-methylpiperazin-1-yl)carbonyl]thieno[3,2-c]quinolin-4(5H)-one trifluoroacetate

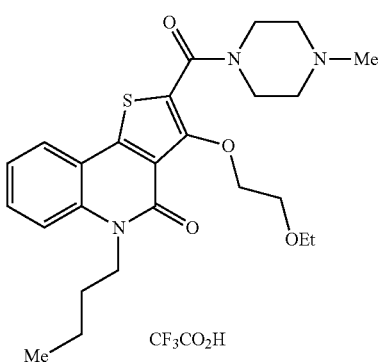 [SMILES: CCCCn1c(=O)c2c(OCCOCC)c(C(=O)N3CCN(C)CC3)sc2c2ccccc21 ; "CF3CO2H"]

In the same manner as in Example 5, the title compound was obtained from the compound of Reference Example 104 and 1-methylpiperazine.

LC/MS 472 (M+H).

Example 465

Production of 5-butyl-3-(2-ethoxyethoxy)-N-methyl-N-(1-methylpyrrolidin-3-yl)-4-oxo-4,5-dihydrothieno[3,2-c]quinoline-2-carboxamide trifluoroacetate

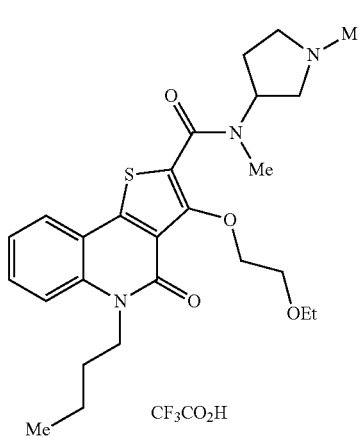

In the same manner as in Example 5, the title compound was obtained from the compound of Reference Example 104 and N,1-dimethylpyrrolidin-3-amine.

LC/MS 486 (M+H).

Example 466

Production of 5-butyl-N-[2-(diethylamino)ethyl]-3-(2-ethoxyethoxy)-N-methyl-4-oxo-4,5-dihydrothieno[3,2-c]quinoline-2-carboxamide trifluoroacetate

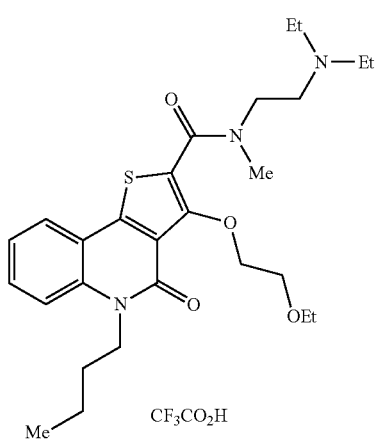 [SMILES: CCCCn1c(=O)c2c(OCCOCC)c(C(=O)N(C)CCN(CC)CC)sc2c2ccccc21 ; "CF3CO2H"]

In the same manner as in Example 5, the title compound was obtained from the compound of Reference Example 104 and N,N-diethyl-N'-methylethane-1,2-diamine.

LC/MS 502 (M+H).

Example 467

Production of 5-butyl-3-(2-ethoxyethoxy)-2-[(4-(pyridin-2-yl)piperazin-1-yl)carbonyl]thieno[3,2-c]quinolin-4(5H)-one trifluoroacetate

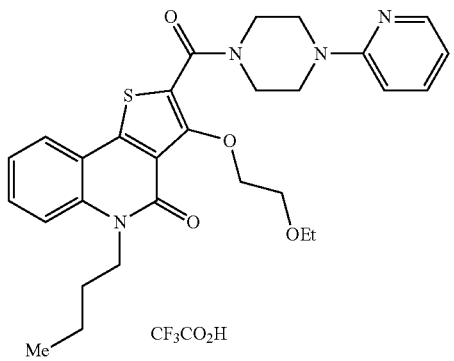 [SMILES: CCCCn1c(=O)c2c(OCCOCC)c(C(=O)N3CCN(c4ccccn4)CC3)sc2c2ccccc21 ; "CF3CO2H"]

In the same manner as in Example 5, the title compound was obtained from the compound of Reference Example 104 and 1-(pyridin-2-yl)piperazine.

LC/MS 535 (M+H).

Example 468

Production of 3-(2-ethoxyethoxy)-N-methyl-4-oxo-5-(2-oxo-2-phenylethyl)-4,5-dihydrothieno[3,2-c]quinoline-2-carboxamide

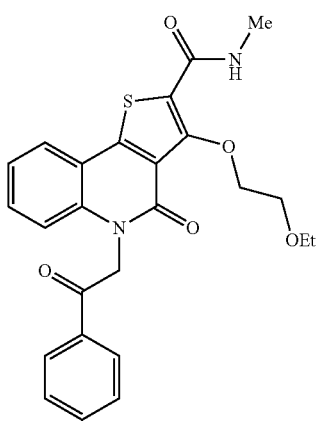 [SMILES: CCOCCOc1c(C(=O)NC)sc2c1c(=O)n(CC(=O)c1ccccc1)c1ccccc21]

In the same manner as in Example 300, the title compound was obtained from the compound of Reference Example 21 and methanamine (2.0 M THF solution).

LC/MS 465 (M+H).

Example 469

Production of N-butyl-3-(2-ethoxyethoxy)-4-oxo-5-(2-oxo-2-phenylethyl)-4,5-dihydrothieno[3,2-c]quinoline-2-carboxamide

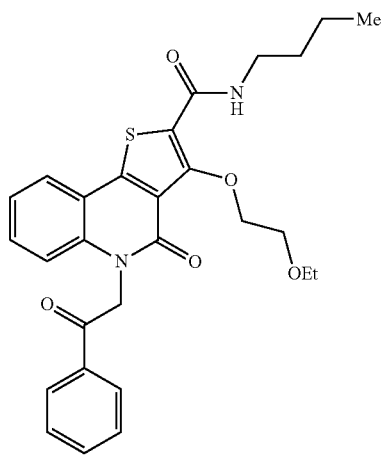 [SMILES: CCCCNC(=O)c1sc2c(c1OCCOCC)c(=O)n(CC(=O)c1ccccc1)c1ccccc21]

In the same manner as in Example 5, the title compound was obtained from the compound of Reference Example 21 and butan-1-amine.

LC/MS 507 (M+H).

Example 470

Production of 3-(2-ethoxyethoxy)-N-(furan-2-ylmethyl)-4-oxo-5-(2-oxo-2-phenylethyl)-4,5-dihydrothieno[3,2-c]quinoline-2-carboxamide

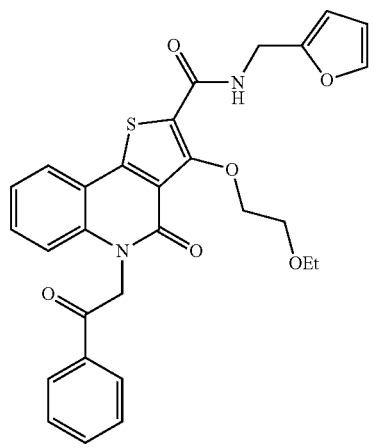 [SMILES: CCOCCOc1c(C(=O)NCc2ccco2)sc2c1c(=O)n(CC(=O)c1ccccc1)c1ccccc21]

In the same manner as in Example 5, the title compound was obtained from the compound of Reference Example 21 and 1-furan-2-ylmethanamine.

LC/MS 531 (M+H).

Example 471

Production of 3-(2-ethoxyethoxy)-4-oxo-5-(2-oxo-2-phenylethyl)-N-(tetrahydrofuran-2-ylmethyl)-4,5-dihydrothieno[3,2-c]quinoline-2-carboxamide

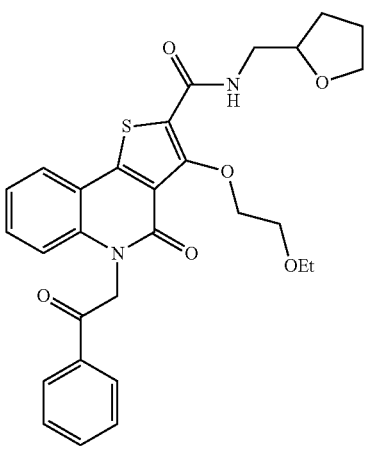 [SMILES: CCOCCOc1c(C(=O)NCC2CCCO2)sc2c1c(=O)n(CC(=O)c1ccccc1)c1ccccc21]

In the same manner as in Example 5, the title compound was obtained from the compound of Reference Example 21 and 1-(tetrahydrofuran-2-yl)methanamine.

LC/MS 535 (M+H).

Example 472

Production of 3-(2-ethoxyethoxy)-4-oxo-5-(2-oxo-2-phenylethyl)-N-(2-phenylethyl)-4,5-dihydrothieno[3,2-c]quinoline-2-carboxamide

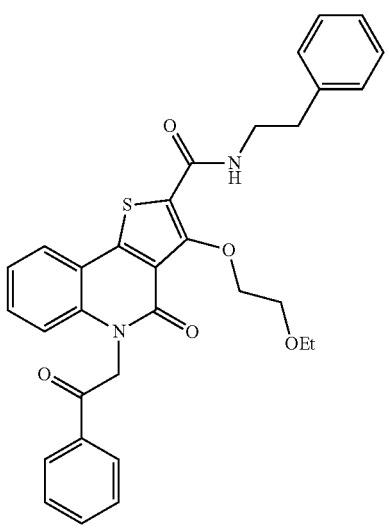 [SMILES: CCOCCOc1c(C(=O)NCCc2ccccc2)sc2c1c(=O)n(CC(=O)c1ccccc1)c1ccccc21]

In the same manner as in Example 5, the title compound was obtained from the compound of Reference Example 21 and 2-phenylethanamine.

LC/MS 555 (M+H).

Example 473

Production of 3-(2-ethoxyethoxy)-N-(2-methoxybenzyl)-4-oxo-5-(2-oxo-2-phenylethyl)-4,5-dihydrothieno[3,2-c]quinoline-2-carboxamide

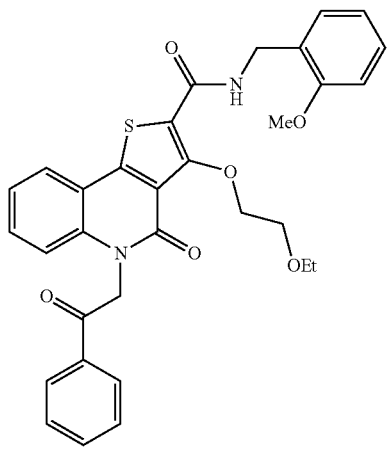 [SMILES: CCOCCOc1c(C(=O)NCc2ccccc2OC)sc2c1c(=O)n(CC(=O)c1ccccc1)c1ccccc21]

In the same manner as in Example 5, the title compound was obtained from the compound of Reference Example 21 and 1-(2-methoxyphenyl)methanamine.

LC/MS 571 (M+H).

Example 474

Production of 3-(2-ethoxyethoxy)-4-oxo-5-(2-oxo-2-phenylethyl)-N-(1,2,3,4-tetrahydronaphthalen-1-yl)-4,5-dihydrothieno[3,2-c]quinoline-2-carboxamide

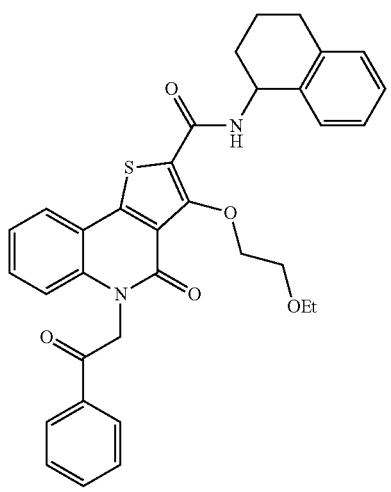 [SMILES: CCOCCOc1c(C(=O)NC2CCCc3ccccc32)sc2c1c(=O)n(CC(=O)c1ccccc1)c1ccccc21]

In the same manner as in Example 5, the title compound was obtained from the compound of Reference Example 21 and 1,2,3,4-tetrahydronaphthalen-1-amine.

LC/MS 581 (M+H).

Example 475

Production of N-(1,3-benzodioxol-5-ylmethyl)-3-(2-ethoxyethoxy)-4-oxo-5-(2-oxo-2-phenylethyl)-4,5-dihydrothieno[3,2-c]quinoline-2-carboxamide

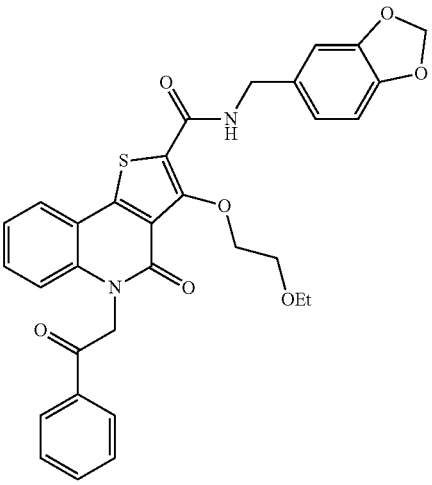 [SMILES: CCOCCOc1c(C(=O)NCc2ccc3c(c2)OCO3)sc2c1c(=O)n(CC(=O)c1ccccc1)c1ccccc21]

In the same manner as in Example 5, the title compound was obtained from the compound of Reference Example 21 and 1-(1,3-benzodioxol-5-yl)methanamine.

LC/MS 585 (M+H).

Example 476

Production of 3-(2-ethoxyethoxy)-N,N-diethyl-4-oxo-5-(2-oxo-2-phenylethyl)-4,5-dihydrothieno[3,2-c]quinoline-2-carboxamide

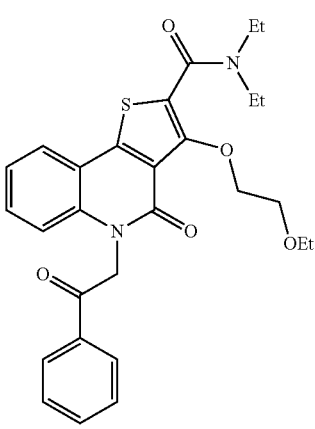 [SMILES: CCOCCOc1c(C(=O)N(CC)CC)sc2c1c(=O)n(CC(=O)c1ccccc1)c1ccccc21]

In the same manner as in Example 5, the title compound was obtained from the compound of Reference Example 21 and N-ethylethanamine.

LC/MS 507 (M+H).

Example 477

Production of 3-(2-ethoxyethoxy)-5-(2-oxo-2-phenylethyl)-2-(piperidin-1-ylcarbonyl)thieno[3,2-c]quinolin-4(5H)-one

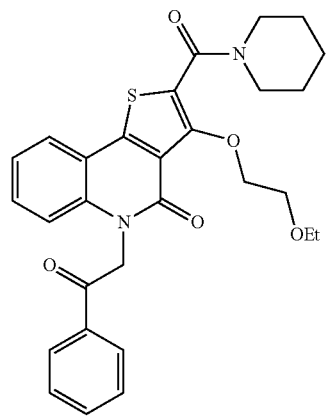 [SMILES: CCOCCOc1c(C(=O)N2CCCCC2)sc2c1c(=O)n(CC(=O)c1ccccc1)c1ccccc21]

In the same manner as in Example 5, the title compound was obtained from the compound of Reference Example 21 and piperidine.

LC/MS 519 (M+H).

Example 478

Production of 3-(2-ethoxyethoxy)-N-(2-methoxyethyl)-N-methyl-4-oxo-5-(2-oxo-2-phenylethyl)-4,5-dihydrothieno[3,2-c]quinoline-2-carboxamide

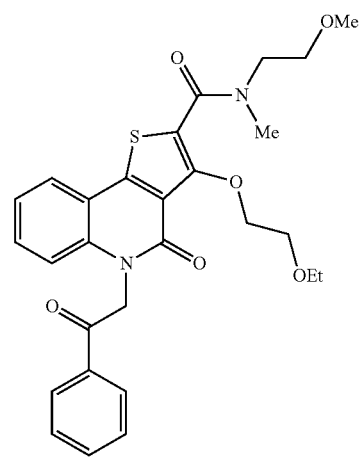 [SMILES: CCOCCOc1c(C(=O)N(C)CCOC)sc2c1c(=O)n(CC(=O)c1ccccc1)c1ccccc21]

In the same manner as in Example 5, the title compound was obtained from the compound of Reference Example 21 and 2-methoxy-N-methylethanamine.

LC/MS 523 (M+H).

Example 479

Production of 3-(2-ethoxyethoxy)-N-methoxy-N-methyl-4-oxo-5-(2-oxo-2-phenylethyl)-4,5-dihydrothieno[3,2-c]quinoline-2-carboxamide

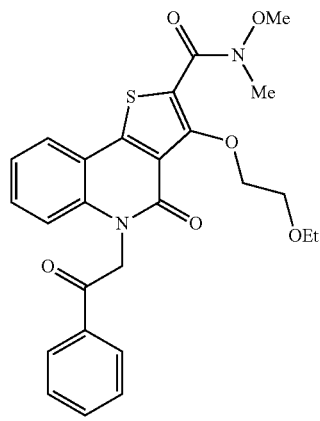 [SMILES: CCOCCOc1c(C(=O)N(C)OC)sc2c1c(=O)n(CC(=O)c1ccccc1)c1ccccc21]

In the same manner as in Example 335, the title compound was obtained from the compound of Reference Example 21 and N-methoxymethanamine hydrochloride.

LC/MS 495 (M+H).

Example 480

Production of 3-(2-ethoxyethoxy)-5-(2-oxo-2-phenylethyl)-2-(thiomorpholin-4-ylcarbonyl)thieno[3,2-c]quinolin-4(5H)-one

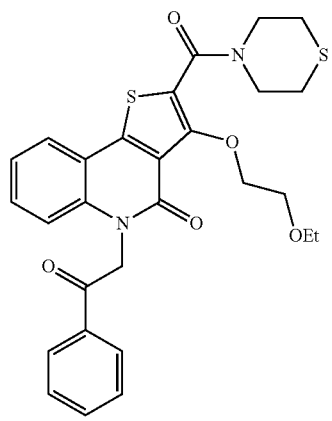 [SMILES: CCOCCOc1c(C(=O)N2CCSCC2)sc2c1c(=O)n(CC(=O)c1ccccc1)c1ccccc21]

In the same manner as in Example 5, the title compound was obtained from the compound of Reference Example 21 and thiomorpholine.

LC/MS 537 (M+H).

Example 481

Production of 3-(2-ethoxyethoxy)-2-{[(2R)-2-(methoxymethyl)pyrrolidin-1-yl]carbonyl}-5-(2-oxo-2-phenylethyl)thieno[3,2-c]quinolin-4(5H)-one

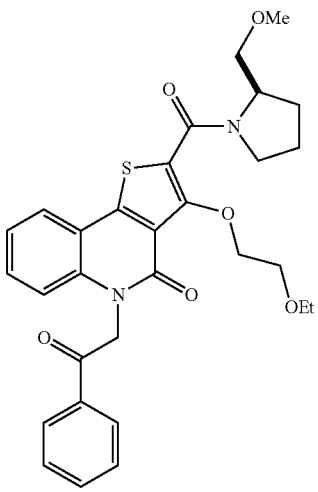 [SMILES: CCOCCOc1c(C(=O)N2CCC[C@@H]2COC)sc2c1c(=O)n(CC(=O)c1ccccc1)c1ccccc21]

In the same manner as in Example 5, the title compound was obtained from the compound of Reference Example 21 and (2R)-2-(methoxymethyl)pyrrolidine.

LC/MS 549 (M+H).

Example 482

Production of N-benzyl-3-(2-ethoxyethoxy)-N-methyl-4-oxo-5-(2-oxo-2-phenylethyl)-4,5-dihydrothieno[3,2-c]quinoline-2-carboxamide

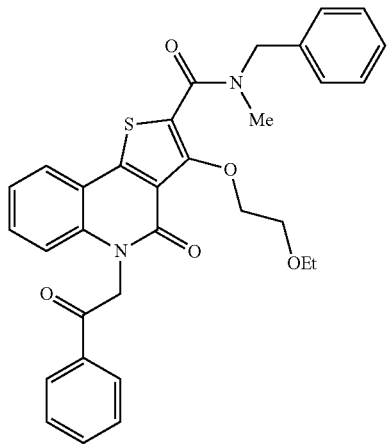 [SMILES: CCOCCOc1c(C(=O)N(C)Cc2ccccc2)sc2c1c(=O)n(CC(=O)c1ccccc1)c1ccccc21]

In the same manner as in Example 5, the title compound was obtained from the compound of Reference Example 21 and N-methyl-1-phenylmethanamine.

LC/MS 555 (M+H).

Example 483

Production of 3-(2-ethoxyethoxy)-N,N-bis(2-methylpropyl)-4-oxo-5-(2-oxo-2-phenylethyl)-4,5-dihydrothieno[3,2-c]quinoline-2-carboxamide

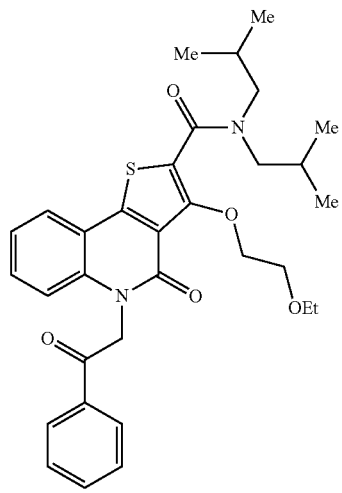 [SMILES: CCOCCOc1c(C(=O)N(CC(C)C)CC(C)C)sc2c1c(=O)n(CC(=O)c1ccccc1)c1ccccc21]

In the same manner as in Example 335, the title compound was obtained from the compound of Reference Example 21 and 2-methyl-N-(2-methylpropyl)propan-1-amine hydrochloride.

LC/MS 563 (M+H).

Example 484

Production of N-[3-(dimethylamino)propyl]-3-(2-ethoxyethoxy)-4-oxo-5-(2-oxo-2-phenylethyl)-4,5-dihydrothieno[3,2-c]quinoline-2-carboxamide trifluoroacetate

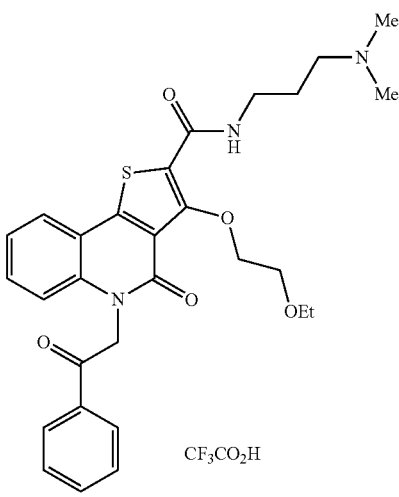 [SMILES: CCOCCOc1c(C(=O)NCCCN(C)C)sc2c1c(=O)n(CC(=O)c1ccccc1)c1ccccc21 ; "CF3CO2H"]

In the same manner as in Example 5, the title compound was obtained from the compound of Reference Example 21 and N,N-dimethylpropane-1,3-diamine.

LC/MS 536 (M+H).

Example 485

Production of 3-(2-ethoxyethoxy)-N-[3-(1H-imidazol-1-yl)propyl]-4-oxo-5-(2-oxo-2-phenylethyl)-4,5-dihydrothieno[3,2-c]quinoline-2-carboxamide trifluoroacetate

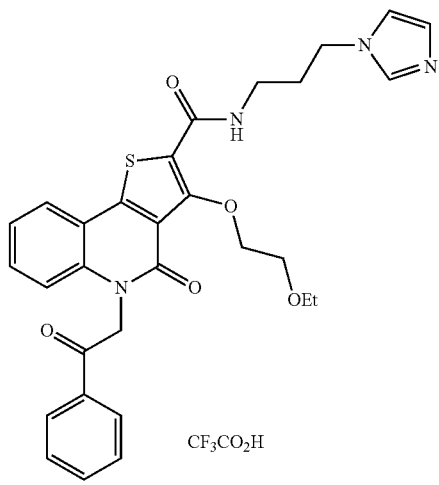 [SMILES: CCOCCOc1c(C(=O)NCCCn2ccnc2)sc2c1c(=O)n(CC(=O)c1ccccc1)c1ccccc21 ; "CF3CO2H"]

In the same manner as in Example 5, the title compound was obtained from the compound of Reference Example 21 and 3-(1H-imidazol-1-yl)propan-1-amine.

LC/MS 559 (M+H).

Example 486

Production of N-{2-[bis(1-methylethyl)amino]ethyl}-3-(2-ethoxyethoxy)-4-oxo-5-(2-oxo-2-phenylethyl)-4,5-dihydrothieno[3,2-c]quinoline-2-carboxamide trifluoroacetate

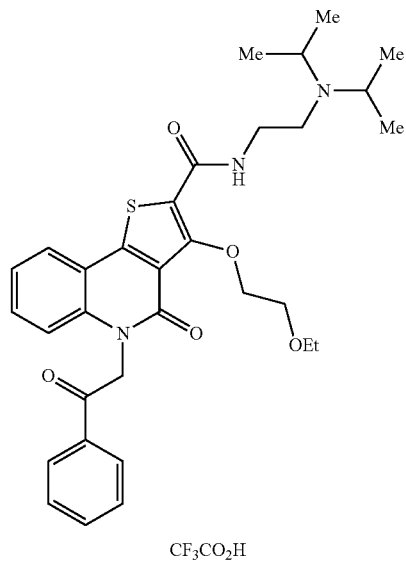

In the same manner as in Example 5, the title compound was obtained from the compound of Reference Example 21 and N,N-bis(1-methylethyl)ethane-1,2-diamine.

LC/MS 578 (M+H).

Example 487

Production of 3-(2-ethoxyethoxy)-2-[(4-methylpiperazin-1-yl)carbonyl]-5-(2-oxo-2-phenylethyl)thieno[3,2-c]quinolin-4(5H)-one trifluoroacetate

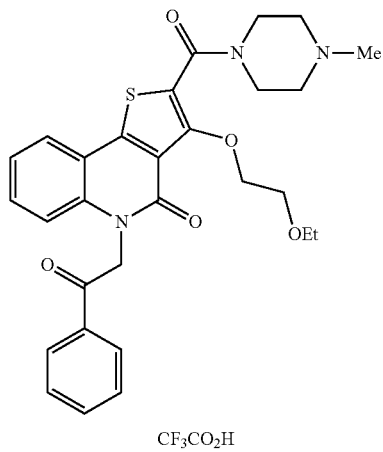

In the same manner as in Example 5, the title compound was obtained from the compound of Reference Example 21 and 1-methylpiperazine.

LC/MS 534 (M+H).

Example 488

Production of 3-(2-ethoxyethoxy)-N-methyl-N-(1-methylpyrrolidin-3-yl)-4-oxo-5-(2-oxo-2-phenylethyl)-4,5-dihydrothieno[3,2-c]quinoline-2-carboxamide trifluoroacetate

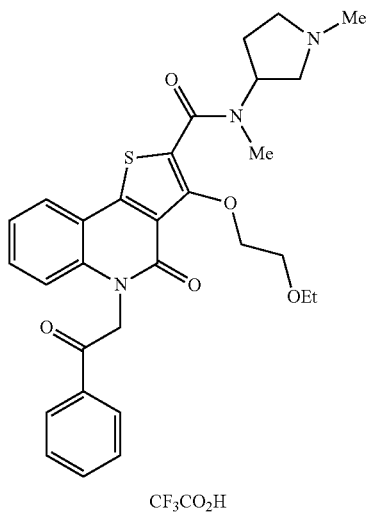

In the same manner as in Example 5, the title compound was obtained from the compound of Reference Example 21 and N,1-dimethylpyrrolidin-3-amine.

LC/MS 548 (M+H).

Example 489

Production of N-[2-(diethylamino)ethyl]-3-(2-ethoxyethoxy)-N-methyl-4-oxo-5-(2-oxo-2-phenylethyl)-4,5-dihydrothieno[3,2-c]quinoline-2-carboxamide trifluoroacetate

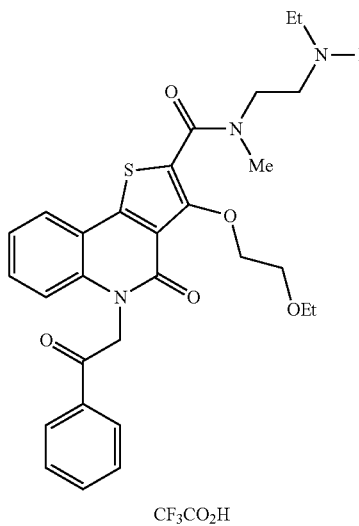

In the same manner as in Example 5, the title compound was obtained from the compound of Reference Example 21 and N,N-diethyl-N'-methylethane-1,2-diamine.
LC/MS 564 (M+H).

Example 490

Production of 3-(2-ethoxyethoxy)-5-(2-oxo-2-phenylethyl)-2-[(4-(pyridin-2-yl)piperazin-1-yl)carbonyl]thieno[3,2-c]quinolin-4(5H)-one trifluoroacetate

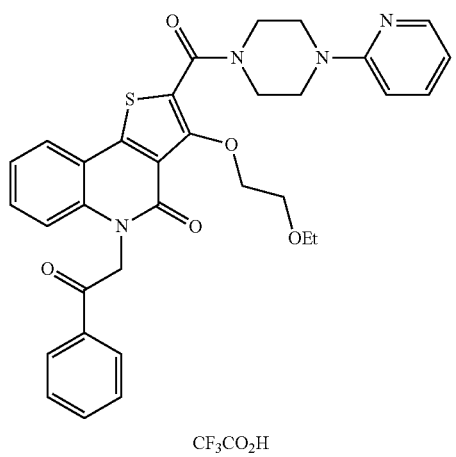 [SMILES: CCOCCOc1c(C(=O)N2CCN(c3ccccn3)CC2)sc2c1c(=O)n(CC(=O)c1ccccc1)c1ccccc21 ; "CF3CO2H"]

In the same manner as in Example 5, the title compound was obtained from the compound of Reference Example 21 and 1-(pyridin-2-yl)piperazine.
LC/MS 597 (M+H).

Example 491

Production of N-(2-amino-2-oxoethyl)-3-methoxy-4-oxo-5-(2-oxo-2-phenylethyl)-4,5-dihydrothieno[3,2-c]quinoline-2-carboxamide

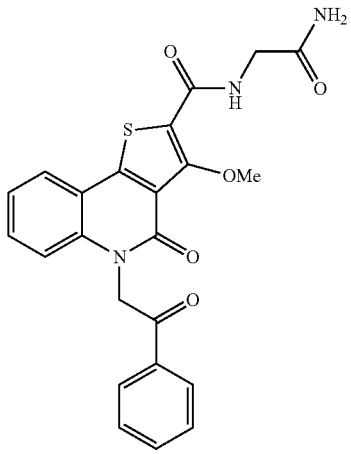 [SMILES: COc1c(C(=O)NCC(N)=O)sc2c1c(=O)n(CC(=O)c1ccccc1)c1ccccc21]

To a solution of the compound of Reference Example 7 (175 mg, 0.44 mmol), glycine amide (56 mg, 0.51 mmol), HOBt (89 mg, 0.66 mmol) and WSCD (126 mg, 0.66 mmol) in DMF (5.0 mL) was added triethylamine (0.16 ml, 1.2 mmol), and the mixture was stirred at room temperature for 25 hr. Water was added to the reaction mixture, and the precipitated solid was collected by filtration. The obtained solid was washed with water, ethanol and diethyl ether, and recrystallized from DMF to give the title compound (124 mg, 54%) as white crystals.

$^1$H-NMR (300 MHz, DMSO-d$_6$) δ:3.95 (2H, d, J=5.3 Hz), 4.06 (3H, s), 6.00 (2H, s), 7.19 (1H, s), 7.30-7.40 (1H, m), 7.45-7.69 (5H, m), 7.73-7.82 (1H, m), 8.06 (1H, dd, J=7.9, 1.3 Hz), 8.13-8.22 (2H, m), 8.28 (1H, t, J=5.3 Hz).

Example 492

Production of N-[2-(dimethylamino)ethyl]-3-methoxy-4-oxo-5-(2-oxo-2-phenylethyl)-4,5-dihydrothieno[3,2-c]quinoline-2-carboxamide

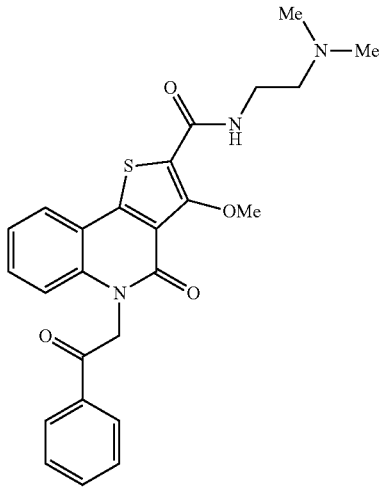 [SMILES: COc1c(C(=O)NCCN(C)C)sc2c1c(=O)n(CC(=O)c1ccccc1)c1ccccc21]

In the same manner as in Example 25, the title compound (124 mg, 81%) was obtained as a white powder from the compound of Reference Example 7 (130 mg, 0.33 mmol) and N,N-dimethylethylenediamine (44 mg, 0.49 mmol).

¹H-NMR (300 MHz, DMSO-d₆) δ:2.23 (6H, s), 2.45 (2H, d, J=6.2 Hz), 3.42 (2H, q, J=5.9 Hz), 4.02 (3H, s), 6.00 (2H, s), 7.35 (1H, t, J=7.5 Hz), 7.48 (1H, d, J=8.7 Hz), 7.57 (1H, dd, J=7.2, 1.5 Hz), 7.64 (2H, t, J=7.5 Hz), 7.76 (1H, t, J=7.5 Hz), 8.05 (1H, dd, J=8.1, 1.5 Hz), 8.13-8.19 (3H, m).

Example 493

Production of 3-methoxy-N-[2-(1-methylpyrrolidin-2-yl)ethyl]-4-oxo-5-(2-oxo-2-phenylethyl)-4,5-dihydrothieno[3,2-c]quinoline-2-carboxamide

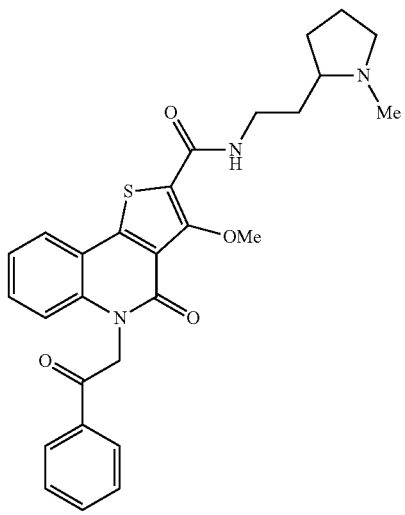 [SMILES: COc1c(C(=O)NCCC2CCCN2C)sc2c1c(=O)n(CC(=O)c1ccccc1)c1ccccc21]

In the same manner as in Example 25, the title compound (86 mg, 52%) was obtained as a white powder from the compound of Reference Example 7 (130 mg, 0.33 mmol) and 2-(2-aminoethyl)-1-methylpyrrolidine (63 mg, 0.49 mmol).

¹H-NMR (300 MHz, DMSO-d₆) δ:1.45-1.70 (4H, m), 1.78-2.15 (4H, m), 2.23 (3H, s), 2.90-2.97 (1H, m), 3.35-3.50 (2H, m), 4.01 (3H, s), 5.99 (2H, s), 7.35 (1H, t, J=7.5 Hz), 7.49 (1H, d, J=8.1 Hz), 7.56 (1H, dd, J=7.2, 1.5 Hz), 7.60-7.67 (2H, m), 7.77 (1H, t, J=7.5 Hz), 8.04 (1H, dd, J=7.8, 1.5 Hz), 8.16-8.22 (3H, m).

Example 494

Production of tert-butyl 2-[({[3-methoxy-4-oxo-5-(2-oxo-2-phenylethyl)-4,5-dihydrothieno[3,2-c]quinolin-2-yl]carbonyl}amino)methyl]piperidine-1-carboxylate

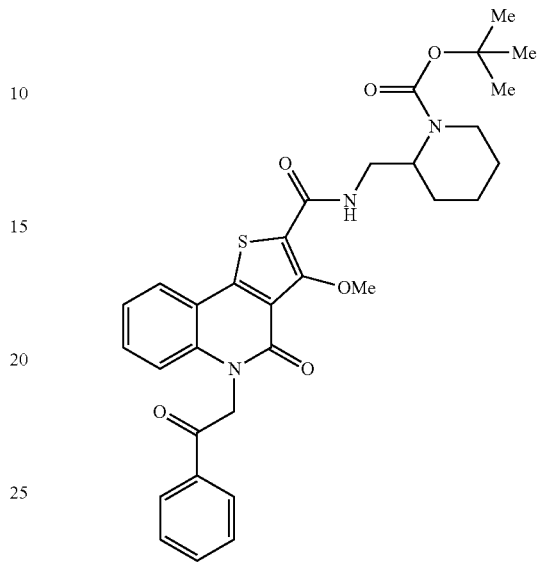

In the same manner as in Example 25, the title compound (190 mg, 85%) was obtained as a white powder from the compound of Reference Example 7 (150 mg, 0.38 mmol) and 2-aminomethyl-N-Boc-piperidine (122 mg, 0.57 mmol).

¹H-NMR (300 MHz, CDCl₃) δ:1.39 (9H, s), 1.40-1.60 (1H, m), 1.60-1.80 (5H, m), 2.94 (1H, t, J=12.6 Hz), 3.51-3.57 (1H, m), 3.70-3.90 (1H, br), 4.03 (1H, d, J=14.4 Hz), 4.15 (3H, s), 4.45-4.60 (1H, m), 5.86 (2H, s), 7.01 (1H, d, J=8.4 Hz), 7.26-7.28 (1H, m), 7.47 (1H, td, J=8.1, 1.5 Hz), 7.59 (2H, t, J=7.4 Hz), 7.65-7.70 (2H, m), 7.90 (1H, dd, J=7.8, 1.2 Hz), 8.10-8.13 (2H, m).

Example 495

Production of N-(2-hydroxy-2-methylpropyl)-3-methoxy-1-methyl-4-oxo-5-(2-oxo-2-phenylethyl)-4,5-dihydro-1H-pyrrolo[3,2-c]quinoline-2-carboxamide

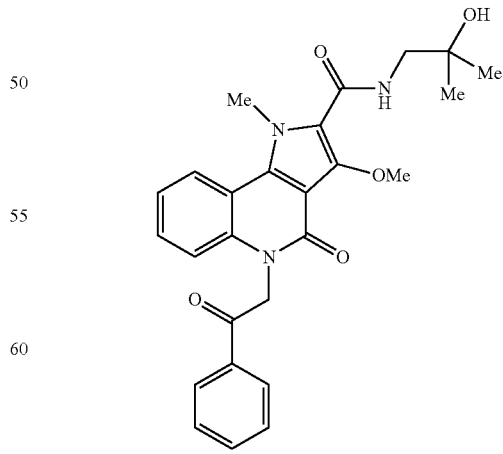

In the same manner as in Example 25, the title compound (215 mg, 91%) was obtained as a white powder from the compound of Reference Example 28 (200 mg, 0.512 mmol) and 1-amino-2-methylpropan-2-ol (59.3 mg, 0.666 mmol).

$^1$H-NMR (300 MHz, DMSO-d$_6$) δ:1.16 (6H, s), 3.29 (2H, d, J=5.7 Hz), 4.02 (3H, s), 4.38 (3H, s), 4.69 (1H, s), 5.98 (2H, s), 7.29-7.40 (2H, m), 7.46-7.51 (1H, m), 7.64 (2H, t, J=7.4 Hz), 7.73-7.79 (1H, m), 8.03 (1H, t, J=5.7 Hz), 8.16-8.19 (2H, m), 8.39 (1H, dd, J=8.3, 1.1 Hz).

Example 496

Production of 3-methoxy-1-methyl-4-oxo-5-(2-oxo-2-phenylethyl)-N-(tetrahydrofuran-2-ylmethyl)-4,5-dihydro-1H-pyrrolo[3,2-c]quinoline-2-carboxamide

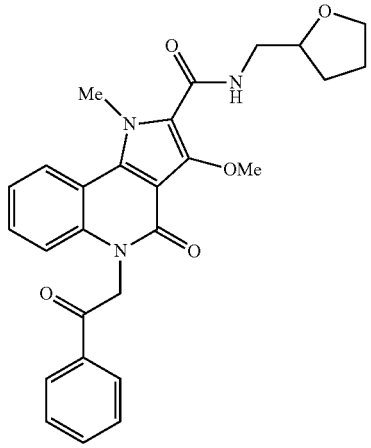 [SMILES: COc1c(C(=O)NCC2CCCO2)n(C)c2c1c(=O)n(CC(=O)c1ccccc1)c1ccccc21]

In the same manner as in Example 25, the title compound (199 mg, 82%) was obtained as a white powder from the compound of Reference Example 28 (200 mg, 0.512 mmol) and 1-(tetrahydrofuran-2-yl)methanamine (68.7 μL, 0.666 mmol).

$^1$H-NMR (300 MHz, DMSO-d$_6$) δ:1.56-1.67 (1H, m), 1.76-1.99 (3H, m), 3.36-3.48 (2H, m), 3.63-3.71 (1H, m), 3.79-3.86 (1H, m), 3.96-4.04 (4H, m), 4.36 (3H, s), 5.97 (2H, s), 7.29-7.40 (2H, m), 7.45-7.51 (1H, m), 7.63 (2H, t, J=7.5 Hz), 7.73-7.79 (1H, m), 8.03 (1H, t, J=5.7 Hz), 8.16-8.19 (2H, m), 8.38 (1H, dd, J=8.4, 1.2 Hz).

Example 497

Production of N-[trans-2-hydroxycyclohexyl]-3-methoxy-1-methyl-4-oxo-5-(2-oxo-2-phenylethyl)-4,5-dihydro-1H-pyrrolo[3,2-c]quinoline-2-carboxamide

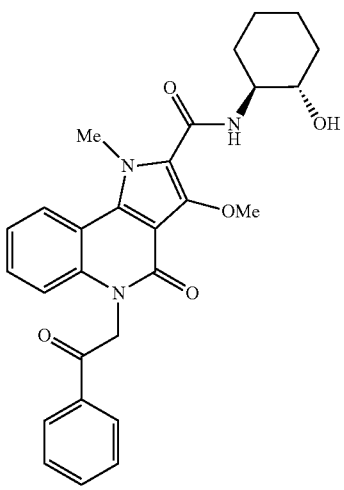 [SMILES: COc1c(C(=O)N[C@H]2CCCC[C@@H]2O)n(C)c2c1c(=O)n(CC(=O)c1ccccc1)c1ccccc21]

In the same manner as in Example 25, the title compound (168 mg, 67%) was obtained as a white powder from the compound of Reference Example 28 (200 mg, 0.512 mmol) and trans-2-aminocyclohexanol hydrochloride (101 mg, 0.666 mmol).

$^1$H-NMR (300 MHz, DMSO-d$_6$) δ:1.15-1.36 (4H, m), 1.55-1.70 (2H, m), 1.80-1.95 (1H, m), 1.95-2.10 (1H, m), 3.30-3.45 (1H, m), 3.55-3.70 (1H, m), 3.98 (3H, s), 4.36 (3H, s), 4.78 (1H, d, J=5.4 Hz), 5.97 (2H, s), 7.29-7.39 (2H, m), 7.45-7.50 (1H, m), 7.63 (2H, t, J=7.5 Hz), 7.73-7.79 (1H, m), 7.87 (1H, d, J=7.5 Hz), 8.16-8.19 (2H, m), 8.38 (1H, dd, J=8.4, 1.2 Hz).

Example 498

Production of N-[1-(2-hydroxyethyl)piperidin-4-yl]-3-methoxy-4-oxo-5-(pyridin-2-ylmethyl)-4,5-dihydrothieno[3,2-c]quinoline-2-carboxamide dihydrochloride

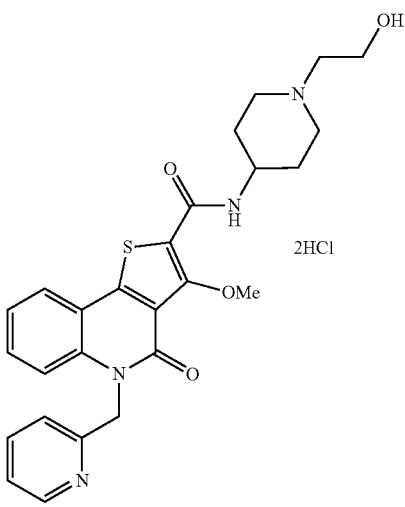 [SMILES: COc1c(C(=O)NC2CCN(CCO)CC2)sc2c1c(=O)n(Cc1ccccn1)c1ccccc21]

A mixture of the compound of Example 667 (60 mg, 0.15 mmol), 2-(chloromethyl)pyridine hydrochloride (37 mg, 0.22 mmol), potassium carbonate (52 mg, 0.37 mmol) and DMF (2 mL) was stirred at room temperature for 3 hr and at 40° C. for 1 hr. The reaction mixture was diluted with saturated aqueous sodium hydrogen carbonate solution, and extracted with ethyl acetate. The extract was washed with saturated brine, dried over magnesium sulfate, and concentrated under reduced pressure. The residue was purified by aminosilica gel chromatography (eluate; ethyl acetate, ethyl acetate/methanol=50/1 to 50/2) to give a white solid. To a solution of the white solid in ethyl acetate (2 mL) was added 4N hydrogen chloride ethyl acetate solution (0.1 mL), and precipitate was collected by filtration, washed with diethyl ether, and dried under reduced pressure to give the title compound (4.2 mg, 5%) as a white solid.

$^1$H-NMR (300 MHz, DMSO-d$_6$) δ:1.91-2.27 (4H, m), 3.05-3.30 (4H, m), 3.60-3.80 (4H, m), 4.07-4.10 (4H, m), 5.69 (2H, s), 7.28-7.34 (3H, m), 7.41-7.58 (2H, m), 7.77 (1H, t, J=8.6 Hz), 7.88 (1H, d, J=7.5 Hz), 8.02 (1H, d, J=8.1 Hz), 8.50 (1H, d, J=2.7 Hz), 9.40-9.55 (2H, br), 9.60-9.70 (1H, br).

Example 499

Production of 3-methoxy-1-methyl-4-oxo-5-(2-oxo-2-phenylethyl)-N-[1-(3,3,3-trifluoro-2-hydroxypropyl)piperidin-4-yl]-4,5-dihydro-1H-pyrrolo[3,2-c]quinoline-2-carboxamide

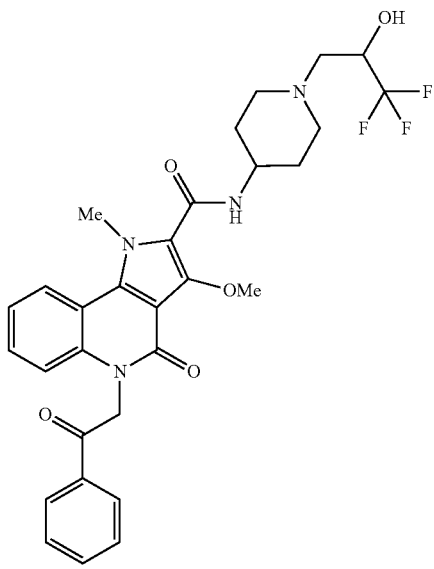 [SMILES: COc1c(C(=O)NC2CCN(CC(O)C(F)(F)F)CC2)n(C)c2c1c(=O)n(CC(=O)c1ccccc1)c1ccccc21]

In the same manner as in Example 79, the title compound (150 mg, 64%) was obtained as a white powder from the compound of Example 77 (200 mg, 0.400 mmol), 3-bromo-1,1,1-trifluoropropan-2-ol (62.2 μL, 0.600 mmol) and potassium carbonate (249 mg, 1.80 mmol).

$^1$H-NMR (300 MHz, DMSO-$d_6$) δ:1.50-1.70 (2H, m), 1.80-1.95 (2H, m), 2.15-2.35 (2H, m), 2.45-2.60 (2H, m), 2.75-2.90 (2H, m), 3.75-3.90 (1H, m), 3.98 (3H, s), 4.05-4.20 (1H, m), 4.31 (3H, s), 5.97 (2H, s), 6.09-6.16 (1H, m), 7.28-7.39 (2H, m), 7.45-7.50 (1H, m), 7.63 (2H, t, J=7.7 Hz), 7.73-7.79 (1H, m), 7.90 (1H, d, J=8.1 Hz), 8.16-8.18 (2H, m), 8.37 (1H, dd, J=8.3, 1.4 Hz).

Example 500

Production of 3-methoxy-N-{2-[(1-methylethyl)amino]ethyl}-4-oxo-5-(2-oxo-2-phenylethyl)-4,5-dihydrothieno[3,2-c]quinoline-2-carboxamide hydrochloride

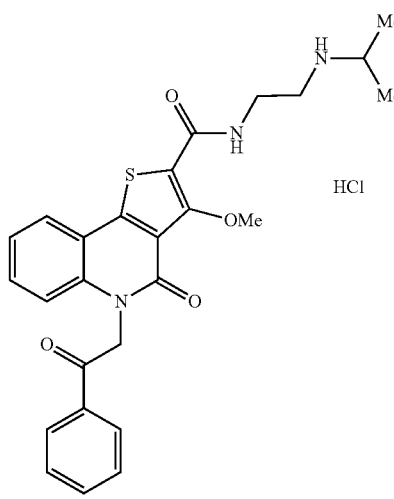

To a solution of the compound of Example 97 (150 mg, 0.30 mmol) in ethyl acetate (10 mL) was added 4N hydrogen chloride ethyl acetate solution (0.1 mL), and the resulting precipitate was collected by filtration, washed with ethyl acetate, and dried under reduced pressure to give the title compound (107 mg, 69%) as a white powder.

$^1$H-NMR (300 MHz, DMSO-$d_6$) δ:1.25 (6H, d, J=6.6 Hz), 3.13 (2H, br s), 3.30-3.45 (1H, m), 3.68 (2H, q, J=5.9 Hz), 4.07 (3H, s), 6.00 (2H, s), 7.36 (1H, t, J=7.5 Hz), 7.50 (1H, d, J=8.4 Hz), 7.57-7.67 (3H, m), 7.78 (1H, t, J=7.4 Hz), 8.06 (1H, dd, J=7.8, 1.2 Hz), 8.18 (2H, d, J=8.4 Hz), 8.29 (1H, t, J=5.9 Hz), 8.77 (2H, br s).

Example 501

Production of N-[1-(2-hydroxyethyl)piperidin-4-yl]-3-methoxy-5-(4-methoxybenzyl)-1-methyl-4-oxo-4,5-dihydro-1H-pyrrolo[3,2-c]quinoline-2-carboxamide

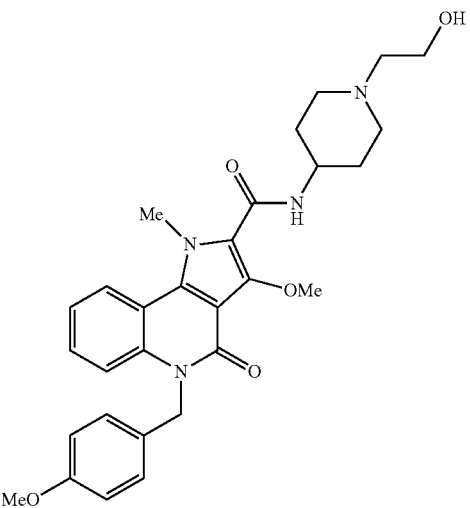 [SMILES: COc1ccc(Cn2c(=O)c3c(OC)c(C(=O)NC4CCN(CCO)CC4)n(C)c3c3ccccc32)cc1]

In the same manner as in Example 79, the title compound (1.91 g, 75%) was obtained as white crystals from the compound of Example 681 (2.50 g, 4.89 mmol).

$^1$H-NMR (300 MHz, DMSO-$d_6$) δ:1.58 (2H, q, J=9.9 Hz), 1.85 (2H, d, J=9.6 Hz), 2.18 (2H, t, J=9.9 Hz), 2.40 (2H, t, J=6.3 Hz), 2.78 (2H, d, J=11.4 Hz), 3.50 (2H, q, J=6.0 Hz), 3.69 (3H, s), 3.70-3.85 (1H, br), 4.04 (3H, s), 4.29 (3H, s), 4.35-4.40 (1H, m), 5.40-5.65 (2H, br), 6.86 (2H, d, J=8.7 Hz), 7.14 (2H, d, J=8.4 Hz), 7.24-7.30 (1H, m), 7.42-7.49 (2H, m), 7.91 (1H, d, J=7.8 Hz), 8.33 (1H, d, J=8.1 Hz).

Example 502

Production of N-[(1-hydroxycyclopropyl)methyl]-3-methoxy-1-methyl-4-oxo-5-(2-oxo-2-phenylethyl)-4,5-dihydro-1H-pyrrolo[3,2-c]quinoline-2-carboxamide

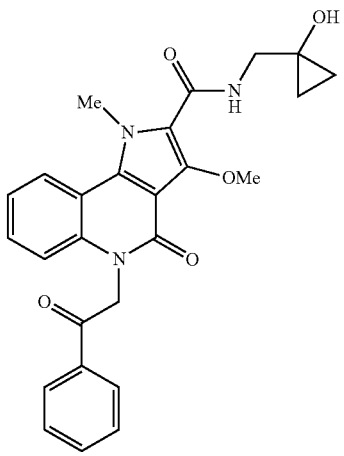 [SMILES: COc1c(C(=O)NCC2(O)CC2)n(C)c2c1c(=O)n(CC(=O)c1ccccc1)c1ccccc21]

In the same manner as in Example 25, the title compound (219 mg, 93%) was obtained as a white powder from the compound of Reference Example 28 (200 mg, 0.512 mmol) and 1-(aminomethyl)cyclopropanol (58.0 mg, 0.666 mmol).

$^1$H-NMR (300 MHz, DMSO-d$_6$) δ:0.55-0.65 (4H, m), 3.46 (2H, d, J=5.8 Hz), 4.01 (3H, s), 4.37 (3H, s), 5.50 (1H, s), 5.97 (2H, s), 7.29-7.40 (2H, m), 7.45-7.51 (1H, m), 7.64 (2H, t, J=7.5 Hz), 7.73-7.79 (1H, m), 8.10 (1H, t, J=5.8 Hz), 8.16-8.19 (2H, m), 8.38 (1H, dd, J=8.1, 1.2 Hz).

Example 503

Production of N-[(1-hydroxycyclohexyl)methyl]-3-methoxy-1-methyl-4-oxo-5-(2-oxo-2-phenylethyl)-4,5-dihydro-1H-pyrrolo[3,2-c]quinoline-2-carboxamide

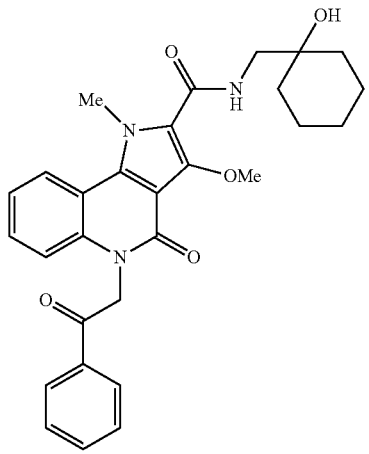 [SMILES: COc1c(C(=O)NCC2(O)CCCCC2)n(C)c2c1c(=O)n(CC(=O)c1ccccc1)c1ccccc21]

In the same manner as in Example 25, the title compound (235 mg, 92%) was obtained as a white powder from the compound of Reference Example 28 (200 mg, 0.512 mmol) and 1-(aminomethyl)cyclohexanol (110 mg, 0.666 mmol).

$^1$H-NMR (300 MHz, DMSO-d$_6$) δ:1.20-1.70 (10H, m), 3.25-3.40 (2H, m), 4.01 (3H, s), 4.38 (3H, s), 4.50 (1H, s), 5.97 (2H, s), 7.29-7.40 (2H, m), 7.45-7.51 (1H, m), 7.63 (2H, t, J=7.7 Hz), 7.73-7.79 (1H, m), 8.02 (1H, t, J=5.6 Hz), 8.16-8.19 (2H, m), 8.38 (1H, dd, J=8.4, 1.2 Hz).

Example 504

Production of 2-({2-[{[3-methoxy-4-oxo-5-(2-oxo-2-phenylethyl)-4,5-dihydrothieno[3,2-c]quinolin-2-yl]carbonyl}(methyl)amino]ethyl}amino)-2-oxoethyl acetate

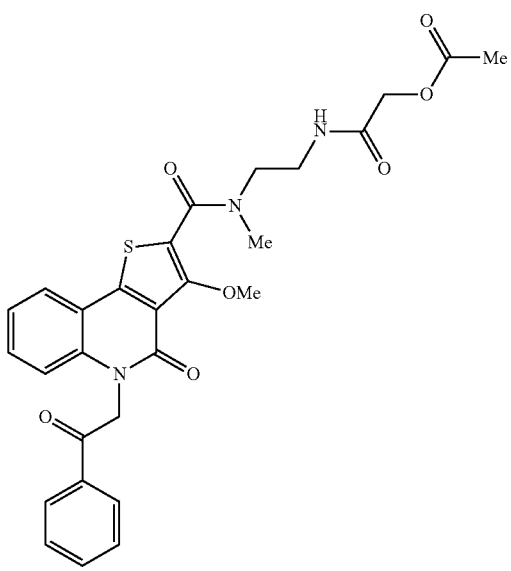 [SMILES: COc1c(C(=O)N(C)CCNC(=O)COC(C)=O)sc2c1c(=O)n(CC(=O)c1ccccc1)c1ccccc21]

To a solution of the compound of Example 103 (150 mg, 0.31 mmol) and triethylamine (69 mg, 0.68 mmol) in THF (10 mL) was added acetoxyacetyl chloride (46 mg, 0.34 mmol) under ice-cooling. After stirring at room temperature for 1 hr, the reaction mixture was diluted with saturated aqueous sodium hydrogen carbonate solution, and extracted with ethyl acetate. The extract was washed with saturated brine, dried over magnesium sulfate, and concentrated under reduced pressure. The residue was purified by silica gel chromatography (eluate; ethyl acetate to ethyl acetate/methanol=50/1) to give a white solid. Recrystallization of the white solid from ethyl acetate-hexane gave the title compound (140 mg, 82%) as white crystals.

$^1$H-NMR (300 MHz, CDCl$_3$) δ:2.28 (3H, s), 3.19 (3H, s), 3.62 (2H, br s), 3.77 (2H, br s), 4.02 (3H, s), 4.60 (2H, s), 5.87 (2H, s), 7.04 (1H, d, J=8.4 Hz), 7.20-7.28 (1H, m), 7.45-7.50 (2H, m), 7.56 (2H, t, J=7.5 Hz), 7.67 (1H, dd, J=7.5, 1.5 Hz), 7.84 (1H, dd, J=8.1, 1.2 Hz), 8.10-8.13 (2H, m).

Example 505

Production of 2-[4-({[3-methoxy-1-methyl-4-oxo-5-(2-oxo-2-phenylethyl)-4,5-dihydro-1H-pyrrolo[3,2-c]quinolin-2-yl]carbonyl}amino)piperidin-1-yl]-1,1-dimethyl-2-oxoethyl acetate

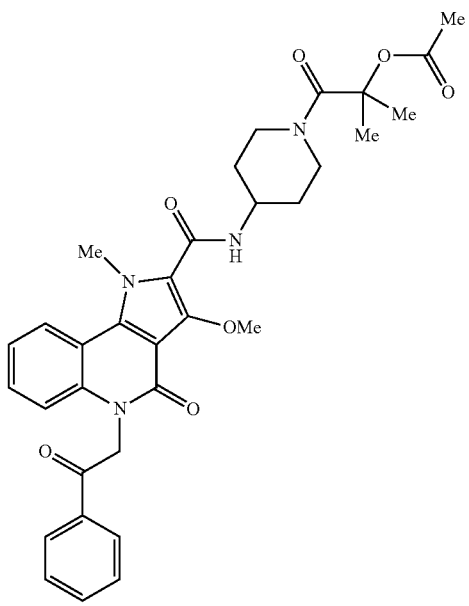 [SMILES: COc1c(C(=O)NC2CCN(C(=O)C(C)(C)OC(C)=O)CC2)n(C)c2c1c(=O)n(CC(=O)c1ccccc1)c1ccccc21]

In the same manner as in Example 504, the title compound was obtained as a colorless oil from the compound of Example 77 (200 mg, 0.423 mmol) and 2-chloro-1,1-dimethyl-2-oxoethyl acetate (63.0 μL, 0.440 mmol).

$^1$H-NMR (300 MHz, DMSO-$d_6$) δ:1.36-1.50 (10H, m), 1.80-1.95 (2H, m), 2.07 (3H, s), 2.75-3.40 (2H, m), 3.96 (3H, s), 4.00-4.25 (1H, m), 4.29 (3H, s), 5.97 (2H, s), 7.29-7.39 (2H, m), 7.45-7.50 (1H, m), 7.63 (2H, t, J=7.5 Hz), 7.73-7.79 (1H, m), 7.98 (1H, d, J=7.8 Hz), 8.16-8.18 (2H, m), 8.37 (1H, dd, J=8.3, 1.1 Hz).

Example 506

Production of N-[1-(2-hydroxy-2-methylpropanoyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

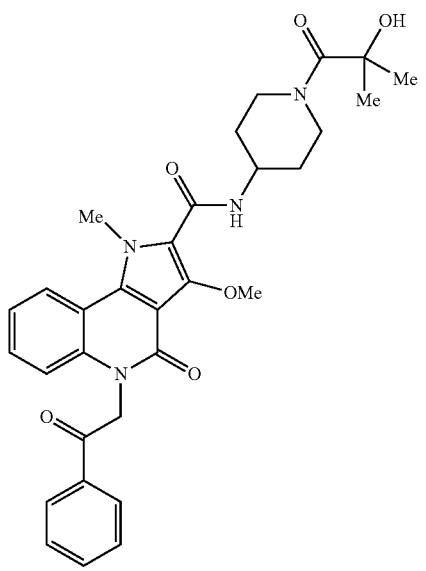 [SMILES: COc1c(C(=O)NC2CCN(C(=O)C(C)(C)O)CC2)n(C)c2c1c(=O)n(CC(=O)c1ccccc1)c1ccccc21]

In the same manner as in Example 508, the title compound (123 mg, 55%) was obtained as a white powder from the compound of Example 505, 8N aqueous sodium hydroxide solution (1.5 mL) and ethanol (12 mL).

$^1$H-NMR (300 MHz, DMSO-$d_6$) δ:1.33 (6H, s), 1.40-1.60 (2H, m), 1.80-1.95 (2H, m), 2.75-3.45 (2H, m), 3.97 (3H, s), 4.00-4.20 (1H, m), 4.31 (3H, s), 4.20-4.80 (2H, m), 5.39 (1H, s), 5.97 (2H, s), 7.29-7.39 (2H, m), 7.45-7.50 (1H, m), 7.63 (2H, t, J=7.5 Hz), 7.73-7.79 (1H, m), 7.93 (1H, d, J=8.1 Hz), 8.15-8.18 (2H, m), 8.37 (1H, d, J=8.3, 1.4 Hz).

Example 507

Production of 3-methoxy-N-{2-[(methoxyacetyl)amino]ethyl}-N-methyl-4-oxo-5-(2-oxo-2-phenylethyl)-4,5-dihydrothieno[3,2-c]quinoline-2-carboxamide

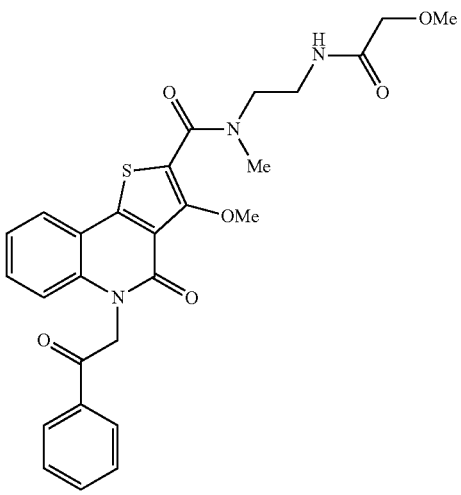 [SMILES: COCC(=O)NCCN(C)C(=O)c1sc2c(c1OC)c(=O)n(CC(=O)c1ccccc1)c1ccccc21]

To a solution of the compound of Example 103 (100 mg, 0.21 mmol) and triethylamine (46 mg, 0.45 mmol) in THF (10 mL) was added methoxyacetyl chloride (25 mg, 0.23 mmol) under ice-cooling. After stirring at room temperature for 2 hr, the reaction mixture was diluted with saturated aqueous sodium hydrogen carbonate solution, and extracted with ethyl acetate. The extract was washed with saturated brine, dried over magnesium sulfate, and concentrated under reduced pressure. The residue was purified by silica gel chromatography (eluate; ethyl acetate to ethyl acetate/methanol=50/1) to give a white solid. Recrystallization of the white solid from ethyl acetate-hexane gave the title compound (61 mg, 56%) as a white powder.

$^1$H-NMR (300 MHz, DMSO-$d_6$) δ:3.06 (3H, s), 3.30-3.50 (5H, m), 3.50-3.65 (2H, br), 3.70-3.95 (5H, m), 5.98 (2H, s), 7.34 (1H, t, J=7.4 Hz), 7.46-7.96 (7H, m), 8.18 (2H, d, J=7.5 Hz).

Example 508

Production of N-{2-[(hydroxyacetyl)amino]ethyl}-3-methoxy-N-methyl-4-oxo-5-(2-oxo-2-phenylethyl)-4,5-dihydrothieno[3,2-c]quinoline-2-carboxamide

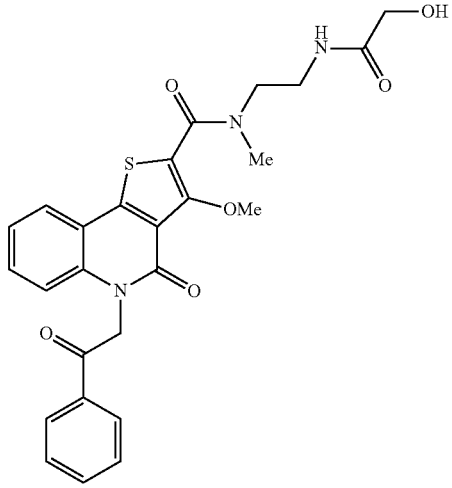 [SMILES: COc1c(C(=O)N(C)CCNC(=O)CO)sc2c1c(=O)n(CC(=O)c1ccccc1)c1ccccc21]

A mixed solution of the compound of Example 504 (120 mg, 0.22 mmol) and 4N aqueous sodium hydroxide solution (2 mL) in THF (4 mL)-methanol (4 mL) was stirred at room temperature for 2 hr, the reaction mixture was diluted with saturated aqueous sodium hydrogen carbonate solution, and the mixture was extracted with ethyl acetate. The extract was washed with saturated brine, dried over magnesium sulfate, and concentrated under reduced pressure. Recrystallization of the crude solid from ethyl acetate-hexane gave the title compound (65 mg, 58%) as white crystals.

$^1$H-NMR (300 MHz, DMSO-d$_6$) δ:3.06 (3H, s), 3.20-3.40 (2H, m), 3.45-3.60 (2H, br), 3.70-3.86 (5H, m), 5.40-5.55 (1H, br), 5.98 (2H, s), 7.34 (1H, t, J=7.5 Hz), 7.47 (1H, d, J=8.4 Hz), 7.55 (1H, t, J=7.2 Hz), 7.64 (2H, t, J=7.5 Hz), 7.77 (1H, t, J=7.5 Hz), 7.87-7.96 (2H, m), 8.16-8.19 (2H, m).

Example 509

Production of 2-[4-({[3-methoxy-4-oxo-5-(2-oxo-2-phenylethyl)-4,5-dihydrothieno[3,2-c]quinolin-2-yl]carbonyl}amino)piperidin-1-yl]-2-oxoethyl acetate

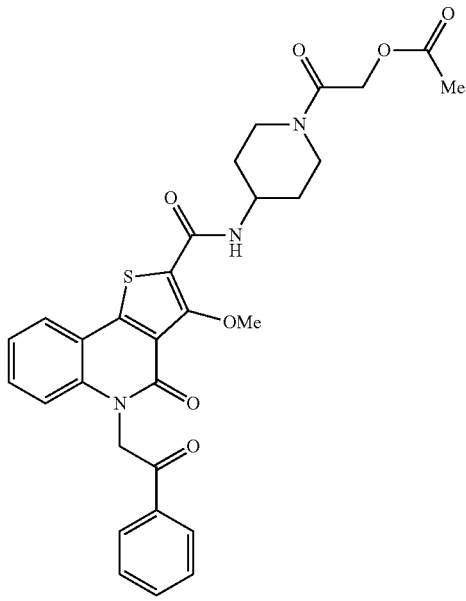 [SMILES: COc1c(C(=O)NC2CCN(C(=O)COC(C)=O)CC2)sc2c1c(=O)n(CC(=O)c1ccccc1)c1ccccc21]

In the same manner as in Example 123, the title compound (429 mg, 56%) was obtained as a white solid from the compound of Example 105 (620 mg, 1.20 mmol).

$^1$H-NMR (300 MHz, CDCl$_3$) δ:1.44-1.64 (2H, m), 2.01-2.28 (5H, m), 2.88-3.05 (1H, m), 3.17-3.34 (1H, m), 3.59-3.75 (1H, m), 4.15 (3H, s), 4.19-4.35 (1H, m), 4.41-4.54 (1H, m), 4.65-4.84 (2H, m), 5.87 (2H, s), 7.03 (1H, d, J=8.5 Hz), 7.28-7.35 (1H, m), 7.43-7.52 (1H, m), 7.52-7.63 (3H, m), 7.65-7.74 (1H, m), 7.91 (1H, dd, J=7.9, 1.3 Hz), 8.06-8.18 (2H, m).

Example 510

Production of 6-ethyl-N-[1-(hydroxyacetyl)piperidin-4-yl]-1-methyl-4-oxo-5-(2-oxo-2-phenylethyl)-3-propoxy-4,5-dihydro-1H-pyrrolo[3,2-c]pyridine-2-carboxamide

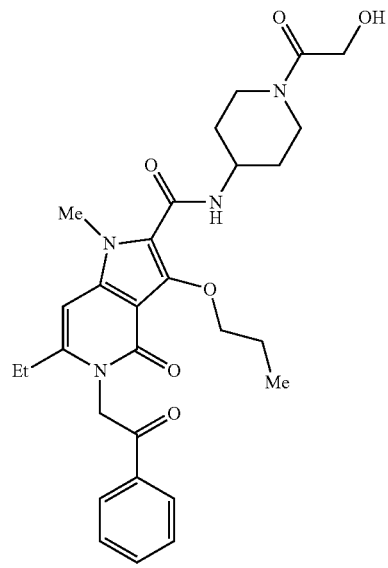 [SMILES: CCCOc1c(C(=O)NC2CCN(C(=O)CO)CC2)n(C)c2cc(CC)n(CC(=O)c3ccccc3)c(=O)c12]

In the same manner as in Example 140, the title compound (199 mg, 74%) was obtained as a white powder from the compound of Reference Example 173 (198 mg, 0.50 mmol).

$^1$H-NMR (300 MHz, DMSO-d$_6$) δ:0.92 (3H, t, J=7.4 Hz), 1.18 (3H, t, J=7.3 Hz), 1.26-1.55 (2H, m), 1.59-1.75 (2H, m), 1.83-1.97 (2H, m), 2.57 (2H, q, J=7.4 Hz), 2.77-2.91 (1H, m), 3.01-3.18 (1H, m), 3.60-3.75 (1H, m), 3.89 (3H, s), 3.97-4.14 (3H, m), 4.20-4.34 (3H, m), 4.51 (1H, t, J=5.4 Hz), 5.59 (2H, s), 6.48 (1H, s), 7.56-7.68 (3H, m), 7.69-7.78 (1H, m), 8.07-8.15 (2H, m).

Example 511

Production of N-[1-(hydroxyacetyl)piperidin-4-yl]-3-methoxy-4-oxo-5-(2-oxo-2-phenylethyl)-4,5-dihydrothieno[3,2-c]quinoline-2-carboxamide

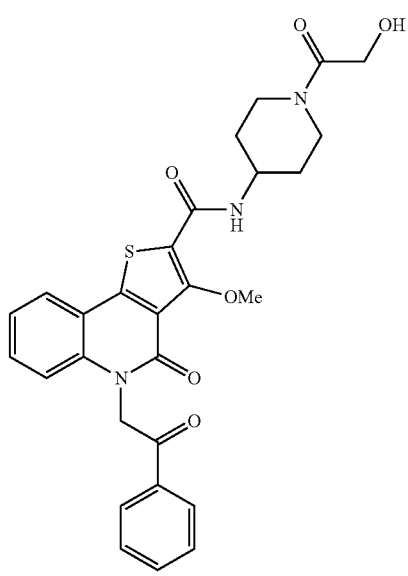 [SMILES: COc1c(C(=O)NC2CCN(C(=O)CO)CC2)sc2c1c(=O)n(CC(=O)c1ccccc1)c1ccccc21]

To a mixed solution of the compound of Example 509 (200 mg, 0.35 mmol) in THF (3.2 mL)-ethanol (11 mL) was added 8N aqueous sodium hydroxide solution (1.6 mL, 13 mmol), and the mixture was stirred at room temperature for 30 min. The reaction mixture was neutralized with 2N hydrochloric acid, and extracted with ethyl acetate-THF mixed solvent. The extract was combined, washed with saturated brine, dried over magnesium sulfate, and subjected to aminosilica gel filtration. The filtrate was concentrated under reduced pressure, the residue was recrystallized from THF-ethyl acetate to give the title compound (93 mg, 50%) as a white solid.

$^1$H-NMR (300 MHz, CDCl$_3$) δ:1.43-1.64 (2H, m), 2.07-2.24 (2H, m), 2.98-3.24 (2H, m), 3.44-3.58 (1H, m), 3.62 (1H, t, J=4.3 Hz), 4.15 (3H, s), 4.19 (2H, d, J=4.3 Hz), 4.22-4.35 (1H, m), 4.44-4.57 (1H, m), 5.86 (2H, s), 7.03 (1H, d, J=8.5 Hz), 7.28-7.34 (1H, m), 7.44-7.63 (4H, m), 7.64-7.73 (1H, m), 7.91 (1H, dd, J=7.8, 1.4 Hz), 8.06-8.16 (2H, m).

Example 512

Production of 2-{2-[({[3-methoxy-4-oxo-5-(2-oxo-2-phenylethyl)-4,5-dihydrothieno[3,2-c]quinolin-2-yl]carbonyl}amino)methyl]piperidin-1-yl}-2-oxoethyl acetate

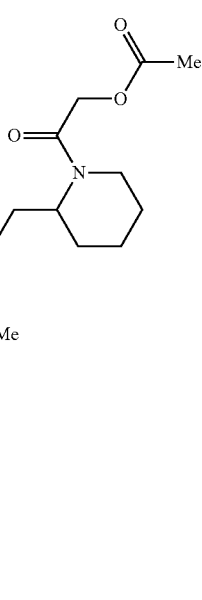

In the same manner as in Example 123, the title compound was obtained as a colorless oil from the compound of Example 84 (500 mg, 0.95 mmol) and acetoxyacetyl chloride (142 mg, 1.04 mmol).

$^1$H-NMR (300 MHz, DMSO-d$_6$) δ:1.10-1.80 (6H, m), 2.00 (3H, s), 2.81 (0.5H, t, J=13.1 Hz), 3.20-3.90 (3H, m), 3.99-4.04 (3.5H, m), 4.24 (0.5H, d, J=10.5 Hz), 4.65 (0.5H, d, J=14.7 Hz), 4.80-4.82 (2H, m), 5.99 (2H, s), 7.35 (1H, t, J=7.5 Hz), 7.49 (1H, d, J=8.7 Hz), 7.56-7.67 (3H, m), 7.77 (1H, t, J=7.2 Hz), 7.89 (0.5H, br t), 8.04 (1H, d, J=8.1 Hz), 8.17-8.19 (2H, m), 8.26 (0.5H, br s).

Example 513

Production of N-{[1-(hydroxyacetyl)piperidin-2-yl]methyl}-3-methoxy-4-oxo-5-(2-oxo-2-phenylethyl)-4,5-dihydrothieno[3,2-c]quinoline-2-carboxamide

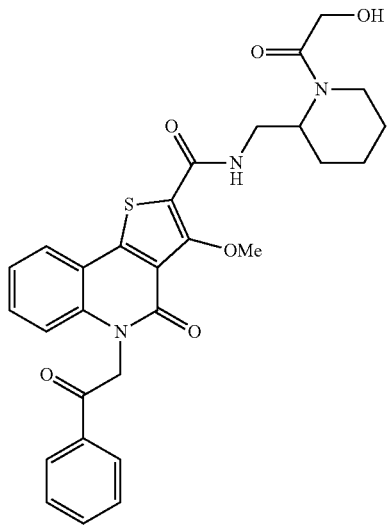 [SMILES: COc1c(C(=O)NCC2CCCCN2C(=O)CO)sc2c1c(=O)n(CC(=O)c1ccccc1)c1ccccc21]

In the same manner as in Example 508, the title compound (109 mg, 58%) was obtained as a white powder from the compound of Example 512 (200 mg, 0.34 mmol).

$^1$H-NMR (300 MHz, DMSO-$d_6$) δ:1.10-1.80 (6H, m), 2.86 (0.5H, t, J=12.9 Hz), 3.26 (0.5H, t, J=15.0 Hz), 3.35-3.48 (1.5H, m), 3.70-3.90 (0.5H, m), 3.90-4.05 (4H, m), 4.05-4.15 (1.5H, m), 4.25-4.40 (1.5H, m), 4.75-4.90 (0.5H, m), 5.99 (2H, s), 7.35 (1H, t, J=7.5 Hz), 7.49 (1H, d, J=8.4 Hz), 7.56-7.67 (3H, m), 7.77 (1H, t, J=7.5 Hz), 7.85-7.95 (0.5H, br), 8.04 (1H, dd, J=7.8, 1.2 Hz), 8.16-8.19 (2.5H, m).

Example 514

Production of 3-methoxy-N-[1-(methoxyacetyl)piperidin-4-yl]-1-methyl-4-oxo-5-(2-oxo-2-phenylethyl)-4,5-dihydro-1H-pyrrolo[3,2-c]quinoline-2-carboxamide

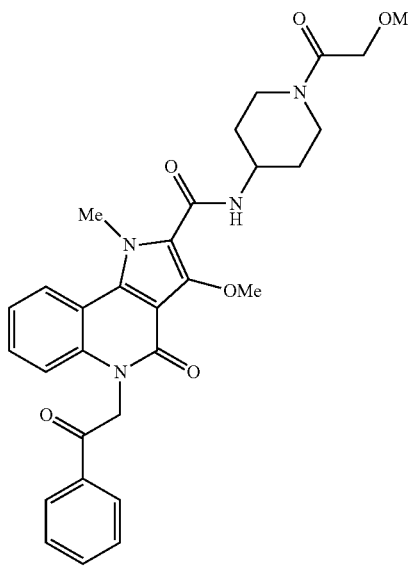

In the same manner as in Example 507, the title compound was obtained (159 mg, 73%) as a white powder from the compound of Example 77 (200 mg, 0.423 mmol) and methoxyacetyl chloride (40.3 µL, 0.440 mmol).

$^1$H-NMR (300 MHz, DMSO-$d_6$) δ: 1.35-1.65 (2H, m), 1.80-2.00 (2H, m), 2.80-2.95 (1H, m), 3.05-3.25 (1H, m), 3.30 (3H, s), 3.65-3.85 (1H, m), 3.97 (3H, s), 4.00-4.25 (4H, m), 4.31 (3H, s), 5.97 (2H, s), 7.29-7.39 (2H, m), 7.45-7.50 (1H, m), 7.63 (2H, t, J=7.7 Hz), 7.73-7.79 (1H, m), 7.95 (1H, d, J=8.1 Hz), 8.15-8.18 (2H, m), 8.37 (1H, dd, J=8.3, 1.1 Hz).

Example 515

Production of N-[1-(ethylcarbamoyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

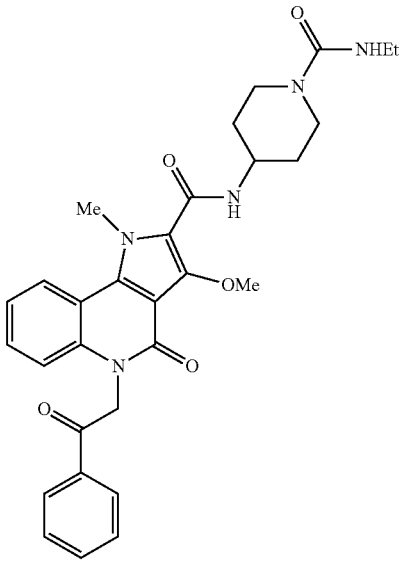

To a mixture of the compound of Example 77 (200 mg, 0.423 mmol) and THF (10 mL) was added ethyl isocyanate (101 µL, 1.27 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate). Recrystallization of the obtained solid from ethyl acetate-THF gave the title compound (172 mg, 75%) as a white powder.

$^1$H-NMR (300 MHz, DMSO-$d_6$) δ: 1.01 (3H, t, J=7.1 Hz), 1.35-1.50 (2H, m), 1.75-1.90 (2H, m), 2.80-3.10 (4H, m), 3.80-3.95 (2H, m), 3.96 (3H, s), 3.95-4.10 (1H, m), 4.30 (3H, s), 5.97 (2H, s), 6.48 (1H, t, J=5.4 Hz), 7.28-7.39 (2H, m), 7.44-7.50 (1H, m), 7.63 (2H, t, J=7.5 Hz), 7.73-7.79 (1H, m), 7.93 (1H, d, J=8.1 Hz), 8.15-8.18 (2H, m), 8.36 (1H, dd, J=8.3, 1.1 Hz).

Example 516

Production of 3-methoxy-1-methyl-N-[1-(methylsulfonyl)piperidin-4-yl]-4-oxo-5-(2-oxo-2-phenylethyl)-4,5-dihydro-1H-pyrrolo[3,2-c]quinoline-2-carboxamide

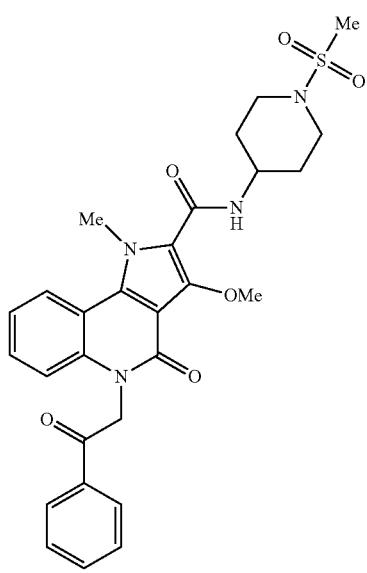 [SMILES: COc1c(C(=O)NC2CCN(S(C)(=O)=O)CC2)n(C)c2c1c(=O)n(CC(=O)c1ccccc1)c1ccccc21]

To a mixture of the compound of Example 77 (200 mg, 0.423 mmol), triethylamine (423 µL, 3.18 mmol) and THF (10 mL) was added methanesulfonyl chloride (98.3 µL, 1.27 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate). Recrystallization of the obtained solid from ethyl acetate gave the title compound (141 mg, 61%) as a white powder.

$^1$H-NMR (300 MHz, DMSO-d$_6$) δ: 1.60-1.75 (2H, m), 1.90-2.05 (2H, m), 2.85-3.05 (5H, m), 3.45-3.60 (2H, m), 3.90-4.05 (1H, m), 3.98 (3H, s), 4.30 (3H, s), 5.97 (2H, s), 7.29-7.39 (2H, m), 7.45-7.50 (1H, m), 7.63 (2H, t, J=7.5 Hz), 7.73-7.79 (1H, m), 8.00 (1H, d, J=7.8 Hz), 8.16-8.18 (2H, m), 8.37 (1H, dd, J=8.3, 1.1 Hz).

Example 517

Production of N-[1-(3-hydroxypropanoyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

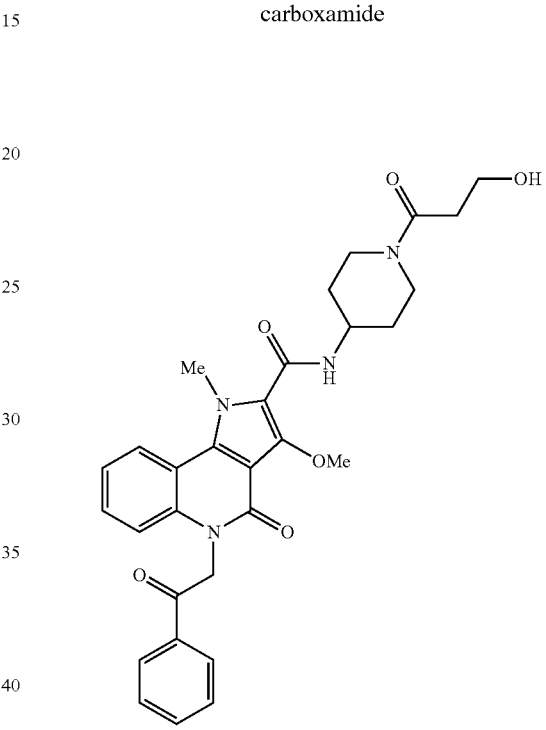

To a mixture of the compound of Example 77 (200 mg, 0.423 mmol), triethylamine (423 µL, 3.18 mmol) and THF (10 mL) was added β-propiolactone (39.9 µL, 0.635 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate). Recrystallization of the obtained solid from ethyl acetate gave the title compound (70.0 mg, 30%) as a white powder.

$^1$H-NMR (300 MHz, DMSO-d$_6$) δ: 1.30-1.60 (2H, m), 1.80-2.00 (2H, m), 2.45-2.55 (2H, m), 2.80-2.90 (1H, m), 3.15-3.25 (1H, m), 3.61-3.70 (2H, m), 3.80-3.95 (1H, m), 3.97 (3H, s), 4.00-4.15 (1H, m), 4.15-4.35 (1H, m), 4.31 (3H, s), 4.51 (1H, t, J=5.4 Hz), 5.97 (2H, s), 7.29-7.39 (2H, m), 7.45-7.50 (1H, m), 7.63 (2H, t, J=7.5 Hz), 7.73-7.79 (1H, m), 7.94 (1H, d, J=7.8 Hz), 8.15-8.22 (2H, m), 8.37 (1H, dd, J=8.4, 1.2 Hz).

Example 518

Production of 3-methoxy-1-methyl-N-{1-[(methylsulfonyl)acetyl]piperidin-4-yl}-4-oxo-5-(2-oxo-2-phenylethyl)-4,5-dihydro-1H-pyrrolo[3,2-c]quinoline-2-carboxamide

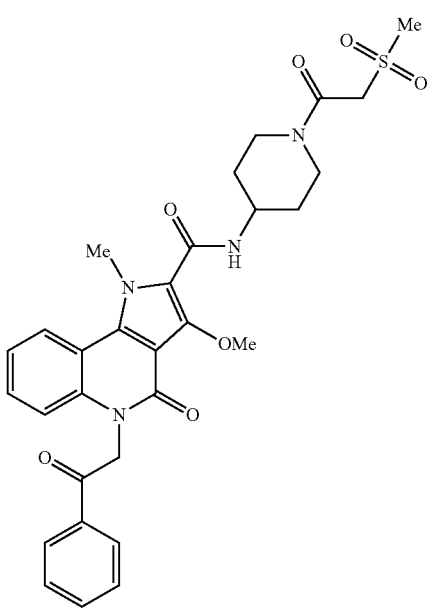 [SMILES: COc1c(C(=O)NC2CCN(C(=O)CS(C)(=O)=O)CC2)n(C)c2c1c(=O)n(CC(=O)c1ccccc1)c1ccccc21]

To a solution of the compound of Example 77 (200 mg, 0.423 mmol), (methylsulfonyl)acetic acid (76.0 mg, 0.550 mmol) and HOBt (85.8 mg, 0.635 mmol) in DMF (4 mL) was added WSCD (122 mg, 0.635 mmol) under ice-cooling, and the mixture was stirred at room temperature for 15 hr. The reaction mixture was diluted with saturated aqueous sodium hydrogen carbonate solution, and extracted twice with ethyl acetate. The extract was combined, washed with saturated brine, dried over magnesium sulfate, and concentrated under reduced pressure. The residue was purified by aminosilica gel chromatography (eluate; ethyl acetate). Recrystallization of the obtained solid from ethyl acetate gave the title compound (60.3 mg, 24%) as white crystals.

$^1$H-NMR (300 MHz, DMSO-$d_6$) δ: 1.35-1.70 (2H, m), 1.85-2.00 (2H, m), 2.90-3.05 (1H, m), 3.10 (3H, s), 3.20-3.35 (1H, m), 3.90-4.20 (5H, m), 4.20-4.35 (1H, m), 4.30 (3H, s), 4.50 (2H, s), 5.97 (2H, s), 7.29-7.39 (2H, m), 7.45-7.50 (1H, m), 7.63 (2H, t, J=7.7 Hz), 7.73-7.79 (1H, m), 7.98 (1H, d, J=7.8 Hz), 8.16-8.18 (2H, m), 8.37 (1H, dd, J=8.3, 1.1 Hz).

Example 519

Production of 3-methoxy-1-methyl-4-oxo-5-(2-oxo-2-phenylethyl)-N-[2-(2-oxopyrrolidin-1-yl)ethyl]-4,5-dihydro-1H-pyrrolo[3,2-c]quinoline-2-carboxamide

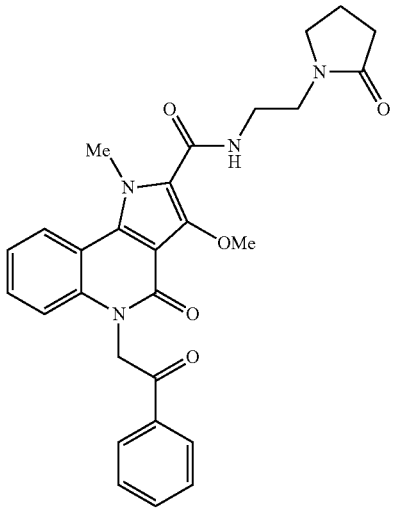 [SMILES: COc1c(C(=O)NCCN2CCCC2=O)n(C)c2c1c(=O)n(CC(=O)c1ccccc1)c1ccccc21]

In the same manner as in Example 25, the title compound (153 mg, 60%) was obtained as a pale-yellow solid from the compound of Reference Example 28 (200 mg, 0.51 mmol), 1-(2-aminoethyl)pyrrolidin-2-one (72 mg, 0.56 mmol), HOBt (89 mg, 0.66 mmol), WSCD (127 mg, 0.66 mmol) and DMF (6.0 mL).

$^1$H-NMR (300 MHz, CDCl$_3$) δ:1.97-2.14 (2H, m), 2.40 (2H, t, J=8.1 Hz), 3.44-3.59 (4H, m), 3.60-3.70 (2H, m), 4.18 (3H, s), 4.47 (3H, s), 5.88 (2H, s), 7.00-7.09 (1H, m), 7.21-7.33 (1H, m), 7.35-7.45 (1H, m), 7.49-7.59 (2H, m), 7.62-7.71 (1H, m), 7.81 (1H, t, J=5.4 Hz), 8.07-8.16 (2H, m), 8.25 (1H, dd, J=8.3, 1.3 Hz).

Example 520

Production of 2-{4-[{[3-methoxy-4-oxo-5-(2-oxo-2-phenylethyl)-4,5-dihydrothieno[3,2-c]quinolin-2-yl]carbonyl}(methyl)amino]piperidin-1-yl}-2-oxoethyl acetate

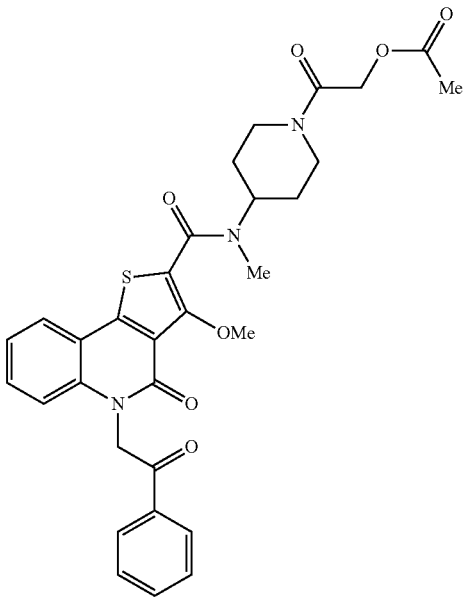 [SMILES: COc1c(C(=O)N(C)C2CCN(C(=O)COC(C)=O)CC2)sc2c1c(=O)n(CC(=O)c1ccccc1)c1ccccc21]

In the same manner as in Example 73, N-methyl-3-methoxy-4-oxo-5-(2-oxo-2-phenylethyl)-N-piperidin-4-yl-4,5- dihydrothieno[3,2-c]quinoline-2-carboxamide hydrochloride was obtained from the compound of Reference Example 7 (500 mg, 1.3 mmol) and tert-butyl 4-(methylamino)piperidine-1-carboxylate (327 mg, 1.5 mmol), and followed by the same manners as in Example 500 and 130 the title compound (182 mg, 24%) was obtained as a white solid.

$^1$H-NMR (300 MHz, DMSO-$d_6$) δ:1.59-1.91 (4H, m), 2.08 (3H, s), 2.57-2.77 (1H, m), 2.91 (3H, s), 2.99-3.17 (1H, m), 3.32 (1H, m), 3.69-3.90 (4H, m), 4.29-4.50 (1H, m), 4.78 (2H, s), 5.98 (2H, s), 7.30-7.38 (1H, m), 7.43-7.70 (4H, m), 7.73-7.82 (1H, m), 7.97 (1H, dd, J=7.9, 1.3 Hz), 8.11-8.22 (2H, m).

Example 521

Production of N-[1-(hydroxyacetyl)piperidin-4-yl]-3-methoxy-N-methyl-4-oxo-5-(2-oxo-2-phenylethyl)-4,5-dihydrothieno[3,2-c]quinoline-2-carboxamide

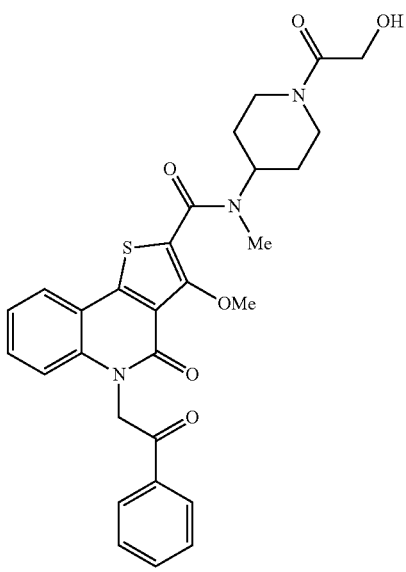 [SMILES: COc1c(C(=O)N(C)C2CCN(C(=O)CO)CC2)sc2c1c(=O)n(CC(=O)c1ccccc1)c1ccccc21]

In the same manner as in Example 511, the title compound (115 mg, 66%) was obtained as a white solid from the compound of Reference Example 520 (187 mg, 0.32 mmol), 8N aqueous sodium hydroxide solution (1.6 mL), THF (3.2 mL) and ethanol (11 mL).

$^1$H-NMR (300 MHz, CDCl$_3$) δ:1.64-1.98 (4H, m), 2.67-2.89 (1H, m), 3.00 (3H, s), 3.05-3.19 (1H, m), 3.52-3.66 (2H, m), 4.01 (3H, s), 4.10-4.26 (3H, m), 4.66-4.85 (1H, m), 5.87 (2H, s), 7.04 (1H, d, J=8.5 Hz), 7.23-7.32 (1H, m), 7.42-7.51 (1H, m), 7.52-7.62 (2H, m), 7.63-7.75 (1H, m), 7.84 (1H, dd, J=7.9, 1.3 Hz), 7.99-8.20 (2H, m).

Example 522

Production of 6-ethyl-N-[1-(hydroxyacetyl)piperidin-4-yl]-1-methyl-3-(1-methylethoxy)-4-oxo-5-(2-oxo-2-phenylethyl)-4,5-dihydro-1H-pyrrolo[3,2-c]pyridine-2-carboxamide

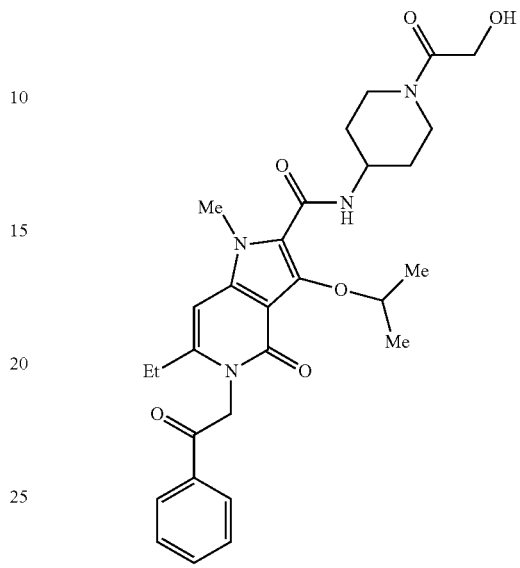

In the same manner as in Example 140, the title compound (237 mg, 88%) was obtained as a colorless powder from the compound of Reference Example 174 (188 mg, 0.50 mmol).

$^1$H-NMR (300 MHz, DMSO-$d_6$) δ:1.12-1.26 (9H, m), 1.26-1.57 (2H, m), 1.84-1.97 (2H, m), 2.57 (2H, q, J=7.4 Hz), 2.76-2.94 (1H, m), 3.02-3.20 (1H, m), 3.59-3.76 (1H, m), 3.91 (3H, s), 3.96-4.19 (3H, m), 4.21-4.34 (1H, m), 4.50 (1H, t, J=5.5 Hz), 4.94-5.09 (1H, m), 5.59 (2H, s), 6.48 (1H, s), 7.56-7.69 (3H, m), 7.69-7.78 (1H, m), 8.06-8.16 (2H, m).

Example 523

Production of tert-butyl 3-({[3-methoxy-1-methyl-4-oxo-5-(2-oxo-2-phenylethyl)-4,5-dihydro-1H-pyrrolo[3,2-c]quinolin-2-yl]carbonyl}amino)pyrrolidine-1-carboxylate

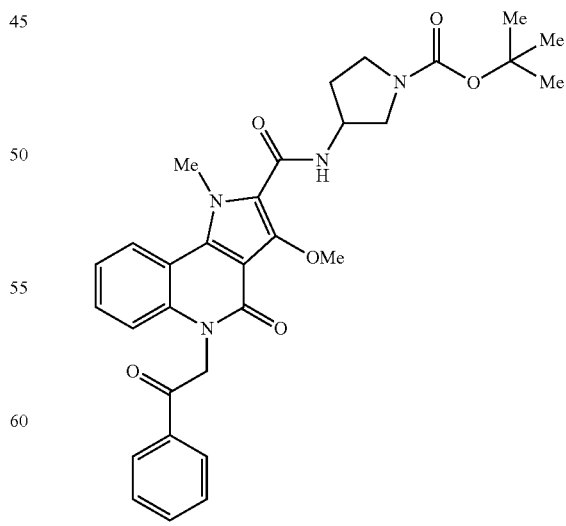

In the same manner as in Example 25, the title compound was obtained as a white powder from the compound of Reference Example 28 (400 mg, 1.02 mmol) and tert-butyl 3-aminopyrrolidine-1-carboxylate (248 mg, 1.33 mmol).

$^1$H-NMR (300 MHz, DMSO-d$_6$) δ: 1.41 (9H, s), 1.87-2.02 (1H, m), 2.05-2.19 (1H, m, J=14.7 Hz), 3.19-3.46 (3H, m), 3.48-3.61 (1H, m), 3.95 (3H, s), 4.30 (3H, s), 4.40-4.52 (1H, m), 5.97 (2H, s), 7.27-7.41 (2H, m), 7.44-7.53 (1H, m), 7.63 (2H, t, J=7.6 Hz), 7.72-7.80 (1H, m), 8.11-8.22 (3H, m), 8.37 (1H, dd, J=8.3, 1.1 Hz).

Example 524

Production of tert-butyl[4-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexyl]carbamate

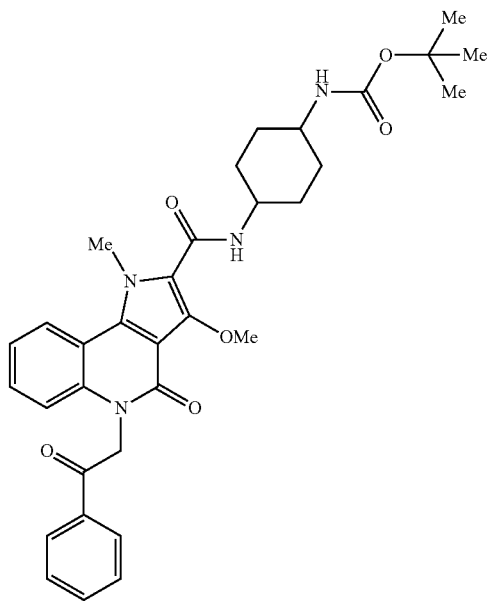 [SMILES: COc1c(C(=O)NC2CCC(NC(=O)OC(C)(C)C)CC2)n(C)c2c1c(=O)n(CC(=O)c1ccccc1)c1ccccc21]

In the same manner as in Example 25, the title compound was obtained as a white powder from the compound of Reference Example 28 (400 mg, 1.02 mmol) and tert-butyl (4-aminocyclohexyl)carbamate (285 mg, 1.33 mmol).

$^1$H-NMR (300 MHz, DMSO-d$_6$) δ: 1.16-1.69 (13H, m), 1.72-1.96 (4H, m), 3.16-3.29 (1H, m), 3.65-3.80 (1H, m, J=11.1 Hz), 3.95 (2.5H, s), 4.07 (0.5H, s), 4.30 (2.5H, s), 4.39 (0.5H, s), 5.97 (2H, s), 6.70-6.81 (0.8H, m), 6.85-6.94 (0.2H, m), 7.25-7.42 (2H, m), 7.43-7.53 (1H, m), 7.58-7.68 (2H, m), 7.72-7.86 (2H, m), 8.14-8.22 (2H, m), 8.36 (1H, dd, J=8.3, 1.1 Hz).

Example 525

Production of N-[1-(hydroxyacetyl)pyrrolidin-3-yl]-3-methoxy-1-methyl-4-oxo-5-(2-oxo-2-phenylethyl)-4,5-dihydro-1H-pyrrolo[3,2-c]quinoline-2-carboxamide

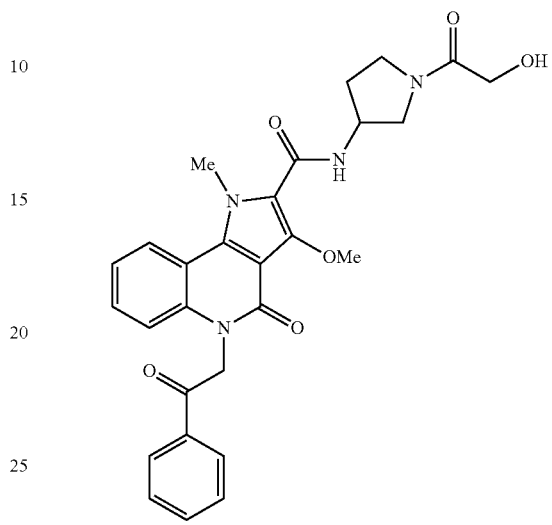

A mixture of the compound of Example 523, ethyl acetate (2 mL) and 4N hydrogen chloride ethyl acetate solution (2 mL) was stirred at room temperature for 1 hr. The mixture was concentrated under reduced pressure, saturated aqueous sodium hydrogen carbonate solution was added to the residue, and the mixture was extracted with ethyl acetate. The extract was combined, washed with saturated brine, dried over magnesium sulfate, and concentrated under reduced pressure to give 3-methoxy-1-methyl-4-oxo-5-(2-oxo-2-phenylethyl)-N-pyrrolidin-3-yl-4,5-dihydro-1H-pyrrolo[3,2-c]quinoline-2-carboxamide (153 mg, 27%) as a white powder.

To a mixture of the thus-obtained 3-methoxy-1-methyl-4-oxo-5-(2-oxo-2-phenylethyl)-N-pyrrolidin-3-yl-4,5-dihydro-1H-pyrrolo[3,2-c]quinoline-2-carboxamide (153 mg, 0.327 mmol), triethylamine (99.7 μL, 0.720 mmol) and THF (3 mL) was added acetoxyacetyl chloride (38.7 μL, 0.360 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate). The obtained oil was dissolved in THF (4 mL) and ethanol (12 mL), 8N aqueous sodium hydroxide solution (1 mL) was added and the mixture was stirred at room temperature for 1.5 hr. The reaction mixture was diluted with water, acidified with 1N hydrochloric acid (8.5 mL), and extracted twice with ethyl acetate. The extract was combined, washed with saturated brine, dried over magnesium sulfate and concentrated under reduced pressure. The residue was purified by aminosilica gel chromatography (eluate; ethyl acetate/methanol=10/0-9/1). Recrystallization of the obtained solid from ethyl acetate-THF gave the title compound (121 mg, 72%) as a white powder.

$^1$H-NMR (300 MHz, DMSO-d$_6$) δ: 1.86-2.31 (2H, m), 3.33-3.56 (3H, m), 3.58-3.72 (1H, m), 3.94 (3H, s), 4.02 (2H, dd, J=10.2, 5.7 Hz), 4.29 (3H, d, J=2.1 Hz), 4.40-4.64 (2H, m), 5.97 (2H, s), 7.27-7.41 (2H, m), 7.43-7.52 (1H, m), 7.63 (2H, t, J=7.6 Hz), 7.72-7.81 (1H, m), 8.12-8.23 (3H, m), 8.37 (1H, d, J=7.9 Hz).

7.23-7.40 (2H, m), 7.43-7.55 (2H, m), 7.63 (2H, t, J=7.6 Hz), 7.71-7.89 (2H, m), 8.11-8.23 (2H, m), 8.36 (1H, dd, J=8.3, 1.1 Hz).

Example 526

Production of N-{4-[(hydroxyacetyl)amino]cyclohexyl}-3-methoxy-1-methyl-4-oxo-5-(2-oxo-2-phenylethyl)-4,5-dihydro-1H-pyrrolo[3,2-c]quinoline-2-carboxamide

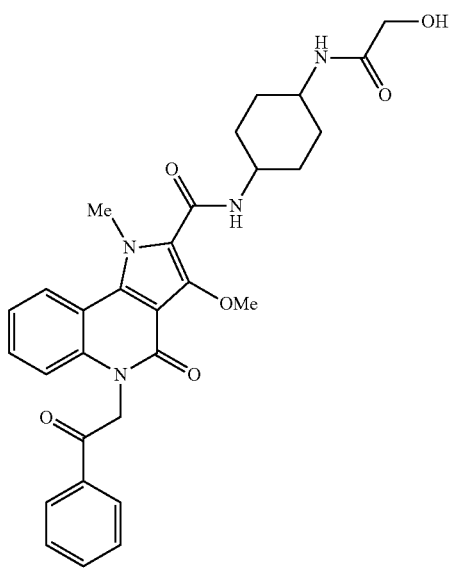 [SMILES: COc1c(C(=O)NC2CCC(NC(=O)CO)CC2)n(C)c2c1c(=O)n(CC(=O)c1ccccc1)c1ccccc21]

Example 527

Production of N-(1-glycylpiperidin-4-yl)-3-methoxy-1-methyl-4-oxo-5-(2-oxo-2-phenylethyl)-4,5-dihydro-1H-pyrrolo[3,2-c]quinoline-2-carboxamide hydrochloride

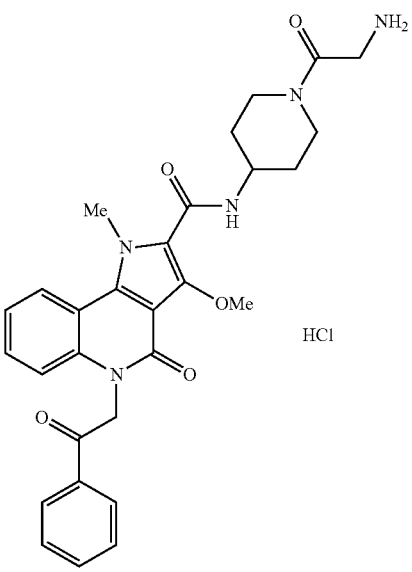 [SMILES: COc1c(C(=O)NC2CCN(C(=O)CN)CC2)n(C)c2c1c(=O)n(CC(=O)c1ccccc1)c1ccccc21 ; Cl]

To a mixture of the compound of Example 88 (190 mg, 0.363 mmol), triethylamine (151 μL, 1.09 mmol) and THF (7 mL) was added acetoxyacetyl chloride (46.9 μL, 0.436 mmol) at 0° C., and the mixture was stirred at room temperature for 15 hr. The reaction mixture was diluted with ethyl acetate, washed with water and saturated brine, dried over magnesium sulfate, and concentrated under reduced pressure. The residue was purified by aminosilica gel chromatography (eluate; ethyl acetate). The obtained oil was dissolved in THF (2.5 mL) and ethanol (5 mL), 8N aqueous sodium hydroxide solution (0.5 mL) was added and the mixture was stirred at room temperature for 1.5 hr. The reaction mixture was diluted with water, acidified with 1N hydrochloric acid (4.5 mL), and extracted twice with ethyl acetate. The extract was combined, washed with saturated brine, dried over magnesium sulfate and concentrated under reduced pressure. The residue was purified by aminosilica gel chromatography (eluate; ethyl acetate/THF=10/0-0/10). Recrystallization of the obtained solid from ethyl acetate-THF gave the title compound (91.1 mg, 46%) as a white powder.

$^1$H-NMR (300 MHz, DMSO-$d_6$) δ:1.44 (4H, t, J=10.1 Hz), 1.67-1.85 (2H, m), 1.88-2.02 (2H, m), 3.55-3.84 (4H, m), 3.96 (3H, s), 4.30 (3H, s), 5.43 (1H, t, J=5.8 Hz), 5.97 (2H, s),

To a solution of the compound of Example 77 (250 mg, 0.529 mmol), N-Boc-glycine (111 mg, 0.635 mmol) and HOBt (107 mg, 0.794 mmol) in DMF (5 mL) was added WSCD (152 mg, 0.794 mmol) under ice-cooling, and the mixture was stirred at room temperature for 15 hr. The reaction mixture was diluted with saturated aqueous sodium hydrogen carbonate solution, and extracted twice with ethyl acetate. The extract was combined, washed with saturated brine, dried over magnesium sulfate, and concentrated under reduced pressure. The residue was dissolved in ethyl acetate (2 mL), 4N hydrogen chloride ethyl acetate solution (2 mL) was added, and the mixture was stirred at room temperature for 1 hr. The precipitated solid was collected by filtration, washed with ethyl acetate, and recrystallized ethanol-ethyl acetate to give the title compound (236 mg, 79%) as white crystals.

$^1$H-NMR (300 MHz, DMSO-$d_6$) δ:1.35-1.70 (2H, m), 1.85-2.00 (2H, m), 2.95-3.10 (1H, m), 3.15-3.30 (1H, m), 3.60-3.75 (1H, m), 3.80-3.95 (2H, m), 3.97 (3H, s), 4.05-4.30 (2H, m), 4.31 (3H, s), 5.97 (2H, s), 7.29-7.40 (2H, m), 7.45-7.51 (1H, m), 7.63 (2H, t, J=7.5 Hz), 7.73-7.79 (1H, m), 7.99 (1H, d, J=7.8 Hz), 8.08-8.21 (5H, m), 8.37 (1H, dd, J=8.3, 1.1 Hz).

Example 528

Production of 2-{2-[2-({[3-methoxy-4-oxo-5-(2-oxo-2-phenylethyl)-4,5-dihydrothieno[3,2-c]quinolin-2-yl]carbonyl}amino)ethyl]pyrrolidin-1-yl}-2-oxoethyl acetate

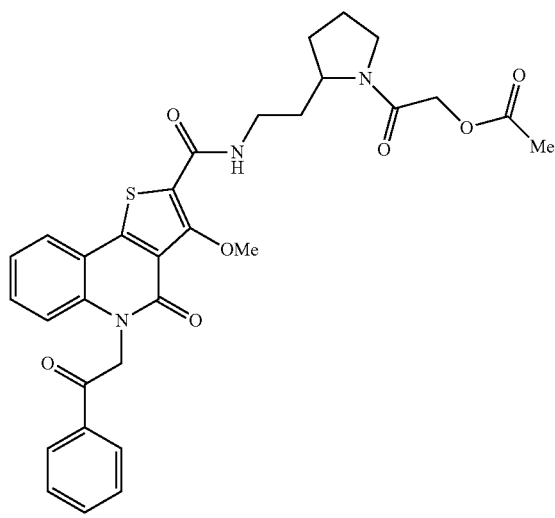 [SMILES: COc1c(C(=O)NCCC2CCCN2C(=O)COC(C)=O)sc2c1c(=O)n(CC(=O)c1ccccc1)c1ccccc21]

In the same manner as in Example 504, the title compound (200 mg, 89%) was obtained as a white solid from the compound of Example 82 (200 mg, 0.38 mmol) and acetoxyacetyl chloride (57 mg, 0.42 mmol).

$^1$H-NMR (300 MHz, DMSO-$d_6$) δ:1.50-2.00 (6H, m), 2.08 (3H, s), 2.90-3.10 (1H, m), 3.38-3.49 (2H, m), 3.50-3.65 (1H, m), 4.05 (3H, s), 4.10-4.20 (1H, m), 4.73 (2H, s), 5.99 (2H, s), 7.35 (1H, t, J=7.5 Hz), 7.49 (1H, d, J=8.4 Hz), 7.57 (1H, d, J=7.2 Hz), 7.64 (2H, t, J=7.5 Hz), 7.77 (1H, t, J=7.5 Hz), 8.04 (1H, d, J=7.8 Hz), 8.18 (2H, d, J=7.5 Hz), 8.45 (1H, t, J=6.0 Hz).

Example 529

Production of 2-{3-[({[3-methoxy-4-oxo-5-(2-oxo-2-phenylethyl)-4,5-dihydrothieno[3,2-c]quinolin-2-yl]carbonyl}amino)methyl]pyrrolidin-1-yl}-2-oxoethyl acetate

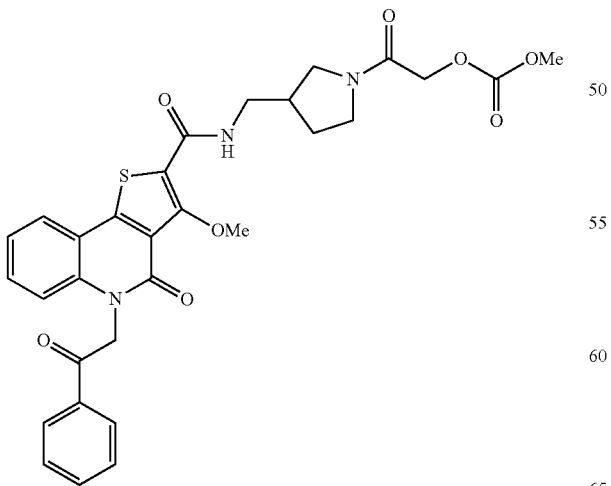

In the same manner as in Example 504, the title compound (160 mg, 71%) was obtained as a white solid from the compound of Example 669 (200 mg, 0.39 mmol) and acetoxyacetyl chloride (87 mg, 0.86 mmol).

$^1$H-NMR (300 MHz, DMSO-$d_6$) δ:1.60-1.78 (2H, m), 1.84-1.95 (1H, m), 2.07 (3H, s), 2.50-2.70 (1H, m), 3.07-3.57 (6H, m), 4.03 (1.5H, m), 4.04 (1.5H, s), 4.65 (2H, m), 6.00 (2H, s), 7.35 (1H, t, J=7.5 Hz), 7.49 (1H, d, J=8.4 Hz), 7.58-7.67 (3H, m), 7.77 (1H, t, J=7.5 Hz), 8.05 (1H, d, J=7.8 Hz), 8.16-8.23 (2H, m).

Example 530

Production of 2-{[trans-2-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexyl]amino}-2-oxoethyl acetate

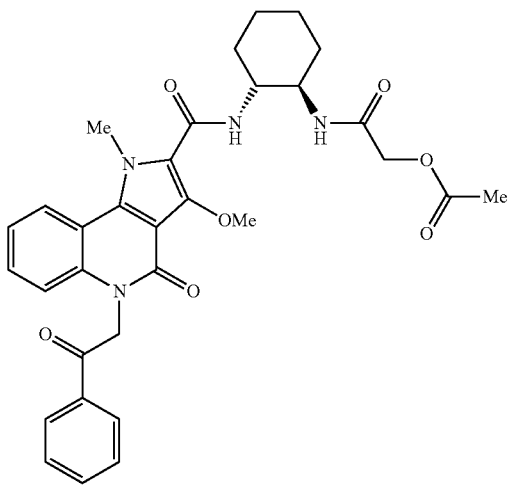

In the same manner as in Example 504, the title compound (190 mg, 85%) was obtained as a white solid from the compound of Example 85 (200 mg, 0.38 mmol) and acetoxyacetyl chloride (63 mg, 0.46 mmol).

$^1$H-NMR (300 MHz, DMSO-$d_6$) δ:1.20-1.41 (4H, m), 1.71 (2H, br s), 1.80-1.90 (1H, br d), 2.04 (3H, s), 2.41-2.45 (1H, m), 3.72-3.85 (2H, m), 3.95 (3H, s), 4.26 (3H, s), 4.40 (2H, s), 5.97 (2H, s), 7.29-7.40 (2H, m), 7.48 (1H, t, J=7.8 Hz), 7.64 (2H, t, J=7.5 Hz), 7.74-7.82 (2H, m), 7.95 (1H, d, J=8.1 Hz), 8.16-8.19 (2H, m), 8.38 (1H, d, J=6.9 Hz).

Example 531

Production of 2-[3-({[3-methoxy-1-methyl-4-oxo-5-(2-oxo-2-phenylethyl)-4,5-dihydro-1H-pyrrolo[3,2-c]quinolin-2-yl]carbonyl}amino)azetidin-1-yl]-2-oxoethyl acetate

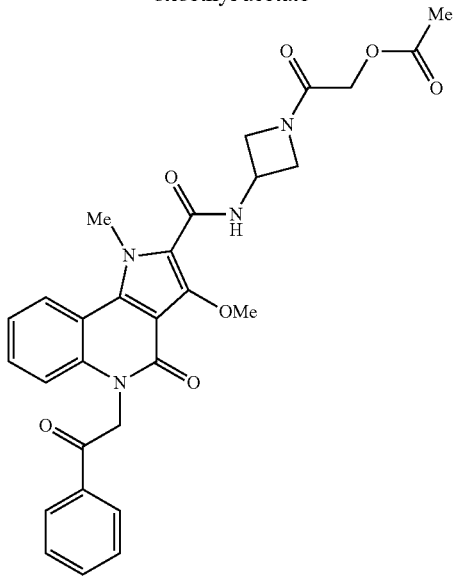

In the same manner as in Example 123, N-azetidin-3-yl-3-methoxy-1-methyl-4-oxo-5-(2-oxo-2-phenylethyl)-4,5-dihydro-1H-pyrrolo[3,2-c]quinoline-2-carboxamide hydrochloride (600 mg) was obtained as a white powder from the compound of Reference Example 670 (610 mg, 1.12 mmol). The title compound (121 mg, 17%) was obtained as a white solid from the thus-obtained white powder by a method similar to that in Example 504.

$^1$H-NMR (300 MHz, DMSO-$d_6$) δ:2.09 (3H, s), 3.30-3.50 (2H, m), 3.86 (3H, s), 4.16 (1H, s), 4.36 (3H, s), 4.40-4.42 (2H, m), 4.48 (2H, m), 5.97 (2H, s), 7.30-7.40 (2H, m), 7.48 (1H, d, J=8.3 Hz), 7.64 (2H, t, J=7.5 Hz), 7.76 (1H, t, J=7.5 Hz), 8.16-8.23 (3H, m), 8.40 (1H, d, J=7.5 Hz).

Example 532

Production of tert-butyl[3-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexyl]carbamate

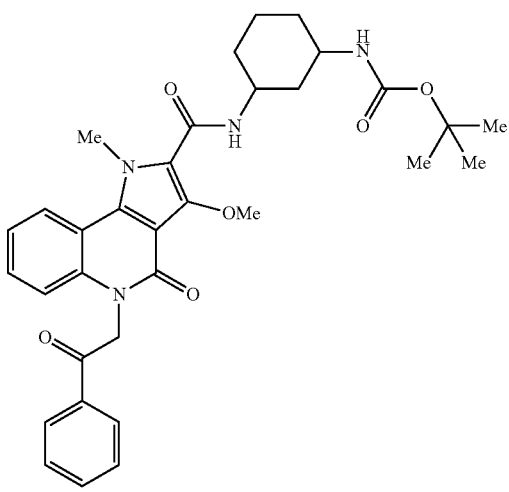 [SMILES: COc1c(C(=O)NC2CCCC(NC(=O)OC(C)(C)C)C2)n(C)c2c1c(=O)n(CC(=O)c1ccccc1)c1ccccc21]

In the same manner as in Example 25, the title compound (395 mg, 66%) was obtained as a white powder from the compound of Reference Example 7 (400 mg, 1.02 mmol) and tert-butyl (3-aminocyclohexyl)carbamate (285 mg, 1.33 mmol).

$^1$H-NMR (300 MHz, DMSO-$d_6$) δ: 0.98-1.46 (13H, m), 1.65-1.90 (3H, m), 2.00-2.12 (1H, m), 3.23-3.42 (1H, m), 3.73-3.88 (1H, m), 3.96 (2H, s), 4.04 (1H, s), 4.30 (2H, s), 4.35 (1H, s), 5.97 (2H, s), 6.76-6.94 (1H, m), 7.24-7.42 (2H, m), 7.43-7.53 (1H, m), 7.63 (2H, t, J=7.6 Hz), 7.71-7.80 (1H, m), 7.86 (1H, d, J=7.9 Hz), 8.12-8.22 (2H, m), 8.31-8.42 (1H, m).

Example 533

Production of N-(3-aminocyclohexyl)-3-methoxy-1-methyl-4-oxo-5-(2-oxo-2-phenylethyl)-4,5-dihydro-1H-pyrrolo[3,2-c]quinoline-2-carboxamide hydrochloride

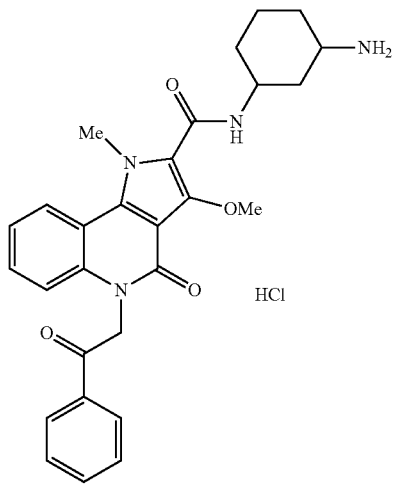 [SMILES: COc1c(C(=O)NC2CCCC(N)C2)n(C)c2c1c(=O)n(CC(=O)c1ccccc1)c1ccccc21 ; Cl]

To a mixture of the compound of Example 532 (380 mg, 0.648) and ethyl acetate (4 mL) was added 4N hydrogen chloride ethyl acetate solution (4 mL), and the mixture was stirred at room temperature for 2 hr. The precipitated solid was collected by filtration, and washed with ethyl acetate to give the title compound (305 mg, 90%) as a white powder.

$^1$H-NMR (300 MHz, DMSO-$d_6$) δ:1.09-2.03 (7H, m), 2.17-2.32 (1H, m), 3.05-3.24 (1H, m), 3.80-4.10 (4H, m), 4.28 (2.5H, s), 4.32 (0.5H, s), 5.97 (2H, s), 7.26-7.53 (3H, m), 7.63 (2H, t, J=7.4 Hz), 7.76 (1H, t, J=7.4 Hz), 7.95-8.22 (6H, m), 8.37 (1H, d, J=8.3 Hz).

Example 534

Production of 2-{[3-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexyl]amino}-2-oxoethyl acetate

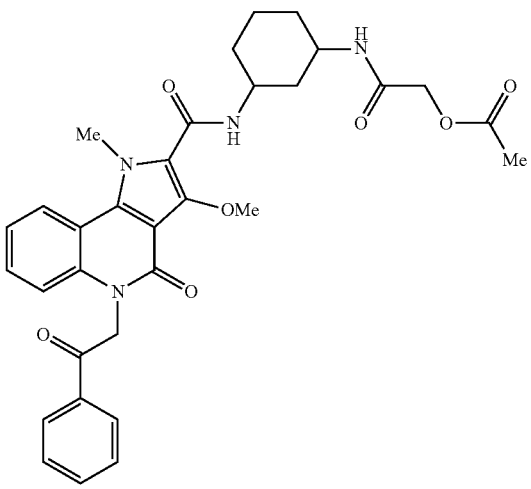 [SMILES: COc1c(C(=O)NC2CCCC(NC(=O)COC(C)=O)C2)n(C)c2c1c(=O)n(CC(=O)c1ccccc1)c1ccccc21]

In the same manner as in Example 504, the title compound (223 mg, 70%) was obtained as a white solid from the compound of Example 533 (285 mg, 0.546 mmol) and acetoxyacetyl chloride (70.4 μL, 0.655 mmol).

$^1$H-NMR (300 MHz, DMSO-$d_6$) δ:1.06-1.48 (4H, m), 1.67-1.93 (3H, m), 2.00-2.12 (4H, m), 3.59-3.76 (1H, m), 3.78-3.91 (1H, m), 3.95 (2.7H, s), 4.03 (0.3H, s), 4.29 (2.7H, s), 4.35 (0.3H, s), 4.41 (1.8H, s), 4.45 (0.2H, s), 5.97 (2H, s), 7.26-7.40 (2H, m), 7.43-7.52 (1H, m), 7.63 (2H, t, J=7.6 Hz), 7.72-7.80 (1H, m), 7.85-7.99 (2H, m), 8.11-8.23 (2H, m), 8.36 (1H, dd, J=8.4, 1.2 Hz).

Example 535

Production of N-{3-[(hydroxyacetyl)amino]cyclohexyl}-3-methoxy-1-methyl-4-oxo-5-(2-oxo-2-phenylethyl)-4,5-dihydro-1H-pyrrolo[3,2-c]quinoline-2-carboxamide

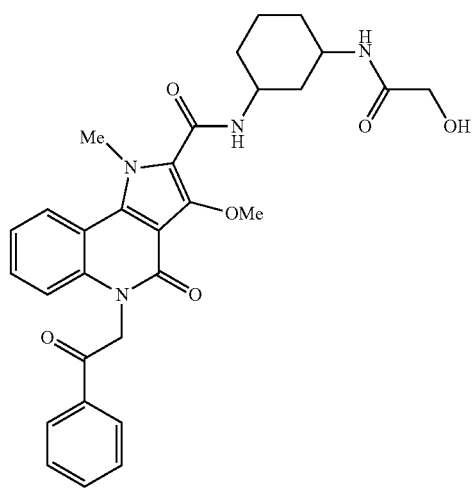 [SMILES: COc1c(C(=O)NC2CCCC(NC(=O)CO)C2)n(C)c2c1c(=O)n(CC(=O)c1ccccc1)c1ccccc21]

In the same manner as in Example 508, the title compound (173 mg, 93%) was obtained as a white powder from the compound of Example 534 (200 mg, 0.34 mmol), 8N aqueous sodium hydroxide solution (0.5 mL), THF (2.5 mL) and ethanol (5 mL).

$^1$H-NMR (300 MHz, DMSO-$d_6$) δ:1.12-1.50 (4H, m), 1.66-1.82 (2H, m), 1.84-1.94 (1H, m), 1.98-2.10 (1H, m), 3.65-3.91 (4H, m), 3.95 (2.7H, s), 4.06 (0.3H, s), 4.30 (2.7H, s), 4.35 (0.3H, s), 5.39 (1H, d, J=5.1 Hz), 5.98 (2H, s), 7.24-7.41 (2H, m), 7.46 (1H, d, J=7.8 Hz), 7.54-7.69 (3H, m), 7.76 (1H, t, J=0.3 Hz), 7.87 (1H, d, J=7.9 Hz), 8.17 (2H, d, J=7.7 Hz), 8.37 (1H, d, J=8.3 Hz).

Example 536

Production of methyl trans-4-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexanecarboxylate

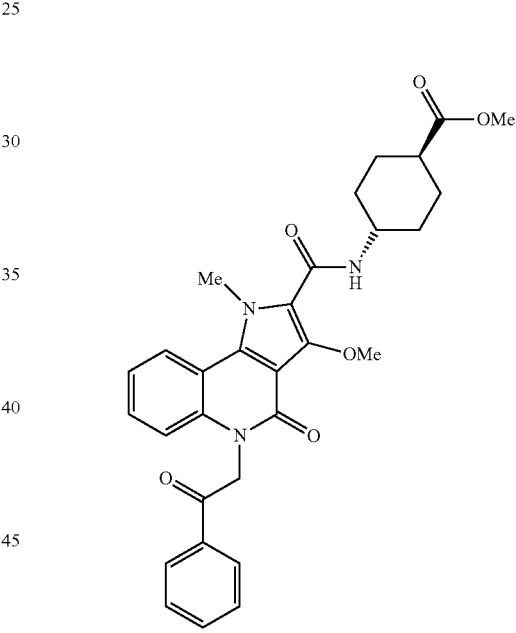

In the same manner as in Example 25, the title compound (535 mg, 79%) was obtained as a white powder from the compound of Reference Example 7 (500 mg, 1.28 mmol), triethylamine (230 μL, 1.66 mmol) and methyl trans-4-aminocyclohexanecarboxylate hydrochloride (321 mg, 1.66 mmol).

$^1$H-NMR (300 MHz, DMSO-$d_6$) δ: 1.27-1.60 (4H, m), 1.87-2.07 (4H, m), 2.25-2.41 (1H, m), 3.60 (3H, s), 3.69-3.86 (1H, m), 3.96 (3H, s), 4.30 (3H, s), 5.96 (2H, s), 7.25-7.41 (2H, m), 7.43-7.53 (1H, m), 7.63 (2H, t, J=7.6 Hz), 7.71-7.88 (2H, m), 8.11-8.23 (2H, m), 8.36 (1H, dd, J=8.3, 1.1 Hz).

Example 537

Production of trans-4-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexanecarboxylic acid

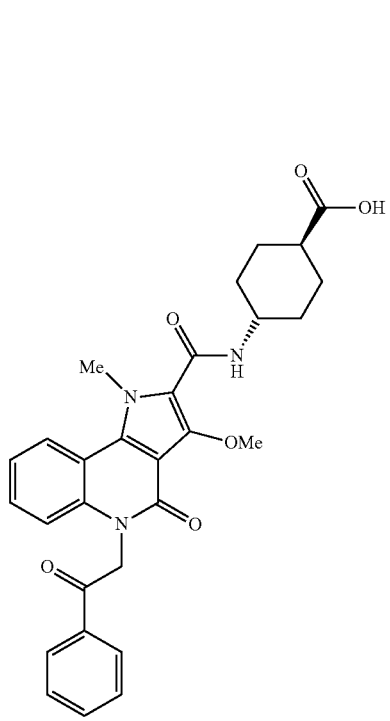

A mixture of the compound of Example 536 (300 mg, 0.566 mmol), 8N aqueous sodium hydroxide solution (1 mL) and ethanol (7 mL) was stirred at room temperature for 6 hr. The reaction mixture was acidified with 6N hydrochloric acid (1.5 mL), and the precipitated solid was collected by filtration. The obtained solid was washed with water, and dried under reduced pressure to give the title compound (225 mg, 81%) as a white powder.

$^1$H-NMR (300 MHz, DMSO-d$_6$) δ:1.25-1.57 (4H, m), 1.85-2.05 (4H, m), 2.10-2.26 (1H, m), 3.67-3.85 (1H, m), 3.98 (3H, s), 4.29 (3H, s), 5.97 (2H, s), 7.25-7.41 (2H, m), 7.42-7.52 (1H, m), 7.63 (2H, t, J=7.6 Hz), 7.71-7.88 (2H, m), 8.12-8.24 (2H, m), 8.37 (1H, dd, J=8.3, 1.1 Hz), 12.23 (1H, br s).

Example 538

Production of N-{trans-4-[(2-hydroxyethyl)carbamoyl]cyclohexyl}-3-methoxy-1-methyl-4-oxo-5-(2-oxo-2-phenylethyl)-4,5-dihydro-1H-pyrrolo[3,2-c]quinoline-2-carboxamide

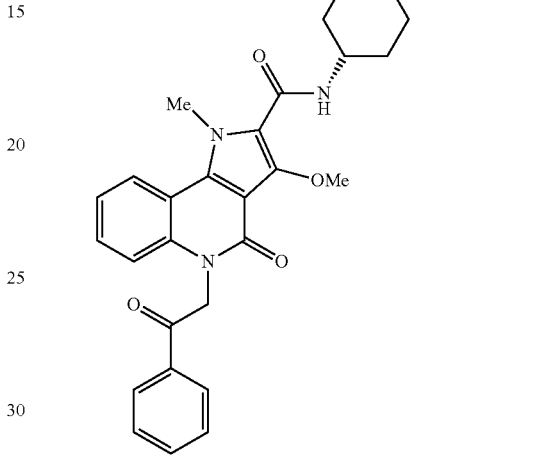

To a solution of the compound of Example 537 (215 mg, 0.417 mmol), 2-aminoethanol (32.5 μL, 0.542 mmol) and HOBt (84.6 mg, 0.626 mmol) in DMF (5 mL) was added WSCD (120 mg, 0.626 mmol) under ice-cooling, and the mixture was stirred at room temperature for 15 hr. The reaction mixture was diluted with saturated aqueous sodium hydrogen carbonate solution, and extracted twice with ethyl acetate. The extract was combined, washed with saturated brine, dried over magnesium sulfate, and concentrated under reduced pressure. The residue was purified by aminosilica gel chromatography (eluate; ethyl acetate/methanol=10/0-8/2). Recrystallization of the obtained solid from ethyl acetate-THF gave the title compound (131 mg, 56%) as a white powder.

$^1$H-NMR (300 MHz, DMSO-d$_6$) δ:1.22-1.58 (4H, m), 1.71-1.86 (2H, m), 1.90-2.03 (2H, m), 2.05-2.20 (1H, m), 3.03-3.18 (2H, m), 3.34-3.44 (2H, m), 3.65-3.84 (1H, m), 3.98 (3H, s), 4.30 (3H, s), 4.63 (1H, t, J=5.6 Hz), 5.97 (2H, s), 7.25-7.41 (2H, m), 7.47 (1H, t, J=7.7 Hz), 7.58-7.68 (2H, m), 7.70-7.88 (3H, m), 8.17 (2H, d, J=7.6 Hz), 8.37 (1H, d, J=8.1 Hz).

Example 539

Production of 2-[3-({[3-methoxy-1-methyl-4-oxo-5-(2-oxo-2-phenylethyl)-4,5-dihydro-1H-pyrrolo[3,2-c]quinolin-2-yl]carbonyl}amino)piperidin-1-yl]-2-oxoethyl acetate

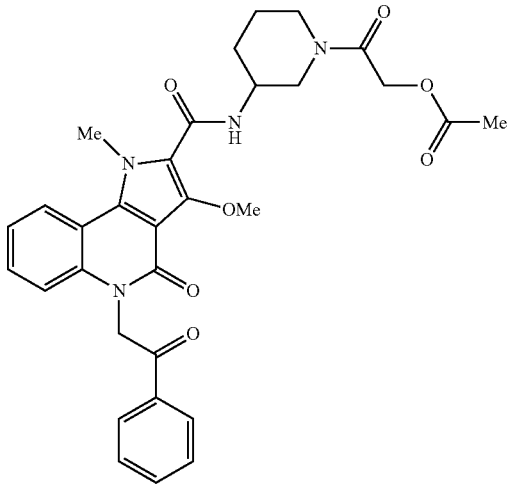 [SMILES: COc1c(C(=O)NC2CCCN(C(=O)COC(C)=O)C2)n(C)c2c1c(=O)n(CC(=O)c1ccccc1)c1ccccc21]

In the same manner as in Example 25, the title compound (284 mg, 39%) was obtained as a white solid from the compound of Reference Example 28 (500 mg, 1.3 mmol), tert-butyl 3-aminopiperidine-1-carboxylate (257 mg, 1.3 mmol), HOBt (203 mg, 1.5 mmol), WSCD (294 mg, 1.5 mmol), DMF (15 mL), 4N hydrogen chloride ethyl acetate solution (4.0 mL), THF (4.0 mL), methanol (4.0 mL), acetoxyacetyl chloride (0.098 mL, 0.91 mmol), triethylamine (0.28 mL, 2.0 mmol) and THF (16 mL).

$^1$H-NMR (300 MHz, CDCl$_3$) δ:1.64-1.88 (3H, m), 1.93-2.09 (1H, m), 2.16 (3H, s), 3.24-3.59 (2H, m), 3.67-3.82 (2H, m), 4.04-4.24 (4H, m), 4.47 (3H, s), 4.67-4.88 (2H, m), 5.79-5.97 (2H, m), 7.05 (1H, d, J=7.9 Hz), 7.20-7.34 (1H, m), 7.37-7.46 (1H, m), 7.55 (2H, t, J=7.6 Hz), 7.61-7.71 (1H, m), 7.82 (1H, d, J=7.0 Hz), 8.07-8.16 (2H, m), 8.26 (1H, dd, J=8.2, 1.4 Hz).

Example 540

Production of tert-butyl 4-[({[3-methoxy-1-methyl-4-oxo-5-(2-oxo-2-phenylethyl)-4,5-dihydro-1H-pyrrolo[3,2-c]quinolin-2-yl]carbonyl}amino)methyl]piperidine-1-carboxylate

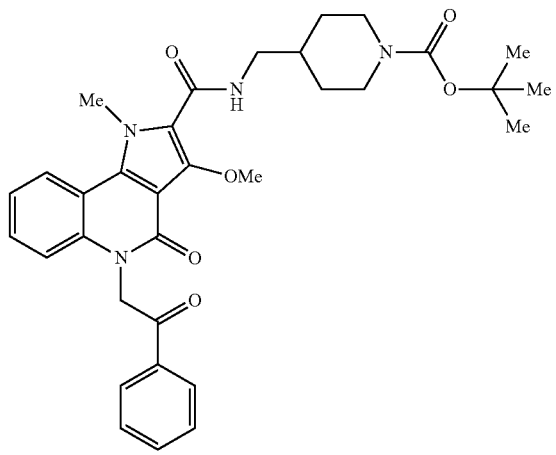 [SMILES: COc1c(C(=O)NCC2CCN(C(=O)OC(C)(C)C)CC2)n(C)c2c1c(=O)n(CC(=O)c1ccccc1)c1ccccc21]

In the same manner as in Example 25, the title compound (521 mg, 69%) was obtained as a white solid from the compound of Reference Example 28 (500 mg, 1.3 mmol), tert-butyl 4-(aminomethyl)piperidine-1-carboxylate (302 mg, 1.4 mmol), HOBt (208 mg, 1.5 mmol), WSC (294 mg, 1.5 mmol) and DMF (15 mL).

$^1$H-NMR (300 MHz, CDCl$_3$) δ:1.14-1.33 (2H, m), 1.41-1.51 (9H, m), 1.70-1.85 (3H, m), 2.63-2.80 (2H, m), 3.37 (2H, t, J=6.1 Hz), 4.03-4.25 (5H, m), 4.47 (3H, s), 5.89 (2H, s), 7.05 (1H, d, J=8.5 Hz), 7.21-7.31 (1H, m), 7.36-7.46 (1H, m), 7.50-7.60 (2H, m), 7.62-7.70 (1H, m), 7.76 (1H, t, J=5.9 Hz), 8.05-8.16 (2H, m), 8.26 (1H, dd, J=8.3, 1.3 Hz).

Example 541

Production of tert-butyl 4-[{[3-methoxy-1-methyl-4-oxo-5-(2-oxo-2-phenylethyl)-4,5-dihydro-1H-pyrrolo[3,2-c]quinolin-2-yl]carbonyl}(methyl)amino]piperidine-1-carboxylate

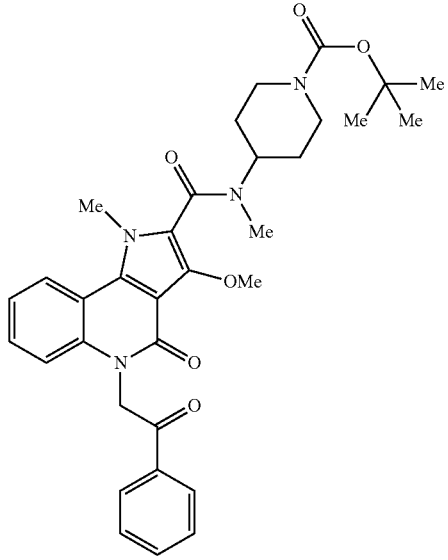 [SMILES: COc1c(C(=O)N(C)C2CCN(C(=O)OC(C)(C)C)CC2)n(C)c2c1c(=O)n(CC(=O)c1ccccc1)c1ccccc21]

In the same manner as in Example 25, the title compound (565 mg, 75%) was obtained as a white solid from the compound of Reference Example 28 (500 mg, 1.3 mmol), tert-butyl 4-(methylamino)piperidine-1-carboxylate (274 mg, 1.3 mmol), HOBt (208 mg, 1.5 mmol), WSCD (294 mg, 1.5 mmol) and DMF (15 mL).

$^1$H-NMR (300 MHz, CDCl$_3$) δ:1.42-1.52 (9H, m), 1.65-1.86 (4H, m), 2.56-2.97 (2H, m), 3.03 (3H, s), 3.97-4.20 (7H, m), 4.22-4.37 (1H, m), 4.61-4.81 (1H, m), 5.89 (2H, s), 7.05 (1H, d, J=8.5 Hz), 7.19-7.30 (1H, m), 7.33-7.43 (1H, m), 7.49-7.59 (2H, m), 7.60-7.70 (1H, m), 8.05-8.15 (2H, m), 8.18 (1H, d, J=7.4 Hz).

Example 542

Production of 3-methoxy-1-methyl-4-oxo-5-(2-oxo-2-phenylethyl)-N-(piperidin-4-ylmethyl)-4,5-dihydro-1H-pyrrolo[3,2-c]quinoline-2-carboxamide hydrochloride

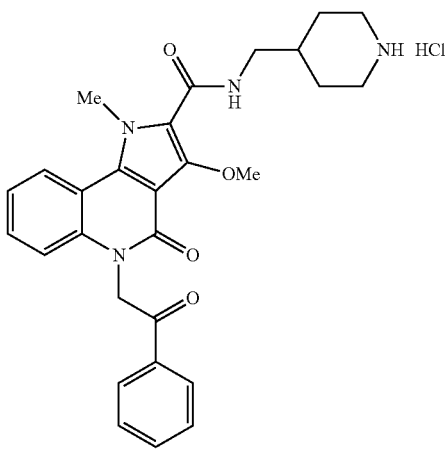 [SMILES: COc1c(C(=O)NCC2CCNCC2)n(C)c2c1c(=O)n(CC(=O)c1ccccc1)c1ccccc21 ; Cl]

A mixed solution of the compound of Example 540 (500 mg, 0.85 mmol) and 4N hydrogen chloride ethyl acetate solution (4.0 mL) in THF (4.0 mL)-methanol (4.0 mL) was stirred at room temperature for 2 hr. 4N hydrogen chloride ethyl acetate solution (4.0 mL) and methanol (8.0 mL) were added, and the mixture was stirred at room temperature for 1.5 hr. The reaction mixture was concentrated under reduced pressure, and recrystallized from methanol-diethyl ether to give the title compound (356 mg, 80%) as a pale-yellow solid.

$^1$H-NMR (300 MHz, DMSO-$d_6$) δ:1.29-1.48 (2H, m), 1.75-1.95 (3H, m), 2.78-2.94 (2H, m), 3.18-3.38 (4H, m), 4.00 (3H, s), 4.31 (3H, s), 5.98 (2H, s), 7.27-7.42 (2H, m), 7.44-7.53 (1H, m), 7.59-7.69 (2H, m), 7.72-7.81 (1H, m), 8.07-8.22 (3H, m), 8.38 (1H, dd, J=8.4, 1.2 Hz), 8.51 (2H, br s).

Example 543

Production of N-[1-(hydroxyacetyl)piperidin-3-yl]-3-methoxy-1-methyl-4-oxo-5-(2-oxo-2-phenylethyl)-4,5-dihydro-1H-pyrrolo[3,2-c]quinoline-2-carboxamide

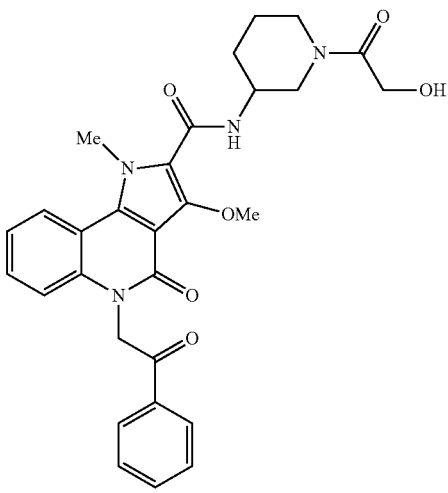 [SMILES: COc1c(C(=O)NC2CCCN(C(=O)CO)C2)n(C)c2c1c(=O)n(CC(=O)c1ccccc1)c1ccccc21]

In the same manner as in Example 511, the title compound (69 mg, 43%) was obtained as a white solid from the compound of Example 539 (174 mg, 0.30 mmol), 8N aqueous sodium hydroxide solution (1.6 mL), THF (3.2 mL) and ethanol (11 mL).

$^1$H-NMR (300 MHz, DMSO-$d_6$) δ:1.44-1.81 (3H, m), 1.84-1.96 (1H, m), 3.29-3.61 (3H, m), 3.80-3.90 (1H, m), 3.91-4.02 (4H, m), 4.04-4.17 (2H, m), 4.35 (3H, s), 4.54 (1H, t, J=5.4 Hz), 5.97 (2H, s), 7.27-7.42 (2H, m), 7.44-7.53 (1H, m), 7.59-7.69 (2H, m), 7.71-7.81 (1H, m), 7.89-8.01 (1H, m), 8.12-8.21 (2H, m), 8.38 (1H, dd, J=8.3, 1.1 Hz).

Example 544

Production of 2-{4-[({[3-methoxy-1-methyl-4-oxo-5-(2-oxo-2-phenylethyl)-4,5-dihydro-1H-pyrrolo[3,2-c]quinolin-2-yl]carbonyl}amino)methyl]piperidin-1-yl}-2-oxoethyl acetate

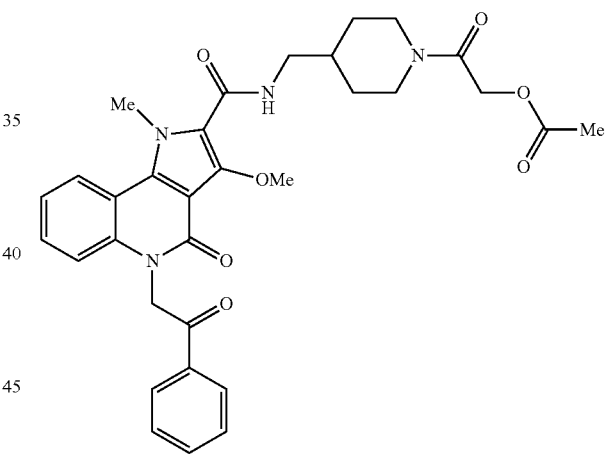

To a solution of the compound of Example 542 (400 mg, 0.76 mmol) and triethylamine (0.29 mL, 2.1 mmol) in THF (17 mL) was added acetoxyacetyl chloride (0.10 mL, 0.95 mmol) under ice-cooling, and the mixture was stirred at room temperature for 4 hr. The reaction mixture was diluted with saturated aqueous sodium hydrogen carbonate solution, and extracted twice with ethyl acetate. The extract was combined, washed with saturated brine, dried over magnesium sulfate, and filtered through aminosilica gel. The filtrate was concentrated, and the residue was recrystallized from ethanol-hexane to give the title compound (321 mg, 71%) as a white solid.

$^1$H-NMR (300 MHz, CDCl$_3$) δ:1.16-1.37 (2H, m), 1.78-1.99 (3H, m), 2.18 (3H, s), 2.58-2.71 (1H, m), 2.99-3.15 (1H, m), 3.31-3.43 (2H, m), 3.63-3.76 (1H, m), 4.17 (3H, s), 4.47 (3H, s), 4.57-4.66 (1H, m), 4.73 (2H, s), 5.89 (2H, s), 7.01-7.08 (1H, m), 7.20-7.33 (1H, m), 7.37-7.47 (1H, m), 7.50-7.60 (2H, m), 7.62-7.71 (1H, m), 7.79 (1H, t, J=5.9 Hz), 8.07-8.17 (2H, m), 8.26 (1H, dd, J=8.3, 1.3 Hz).

Example 545

Production of 2-{4-[{[3-methoxy-1-methyl-4-oxo-5-(2-oxo-2-phenylethyl)-4,5-dihydro-1H-pyrrolo[3,2-c]quinolin-2-yl]carbonyl}(methyl)amino]piperidin-1-yl}-2-oxoethyl acetate

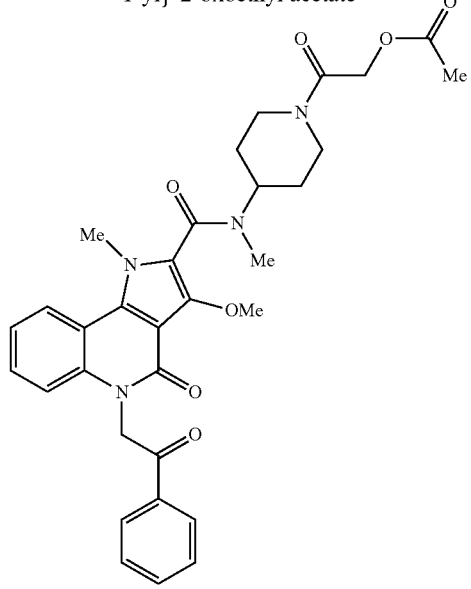

In the same manner as in Example 123, the title compound (226 mg, 40%) was obtained as a white solid from the compound of Example 541 (565 mg, 0.96 mmol), 4N hydrogen chloride ethyl acetate solution (4.0 mL), THF (4.0 mL), methanol (4.0 mL), acetoxyacetyl chloride (0.077 mL, 0.71 mmol), triethylamine (0.22 mL, 1.6 mmol) and THF (13 mL).

$^1$H-NMR (300 MHz, CDCl$_3$) δ:1.70-1.97 (4H, m), 2.15-2.24 (3H, m), 2.50-2.83 (1H, m), 3.03 (3H, s), 3.10-3.33 (1H, m), 3.63-3.86 (1H, m), 4.02 (3H, s), 4.04-4.11 (3H, m), 4.60-4.87 (4H, m), 5.89 (2H, s), 7.02-7.10 (1H, m), 7.17-7.32 (1H, m), 7.35-7.44 (1H, m), 7.47-7.60 (2H, m), 7.61-7.71 (1H, m), 8.07-8.15 (2H, m), 8.19 (1H, dd, J=8.1, 1.3 Hz).

Example 546

Production of N-{[1-(hydroxyacetyl)piperidin-4-yl]methyl}-3-methoxy-1-methyl-4-oxo-5-(2-oxo-2-phenylethyl)-4,5-dihydro-1H-pyrrolo[3,2-c]quinoline-2-carboxamide

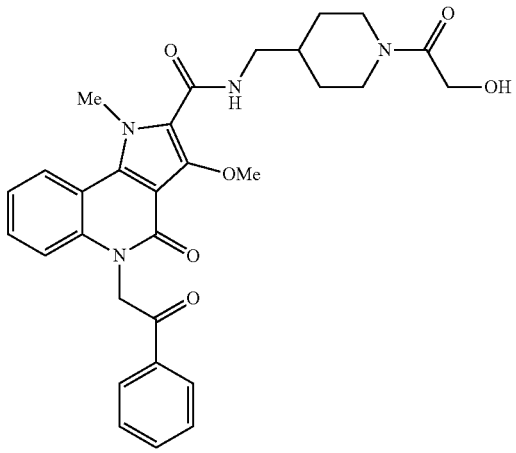 [SMILES: COc1c(C(=O)NCC2CCN(C(=O)CO)CC2)n(C)c2c1c(=O)n(CC(=O)c1ccccc1)c1ccccc21]

In the same manner as in Example 511, the title compound (77 mg, 41%) was obtained as a white solid from the compound of Example 544 (200 mg, 0.34 mmol), 8N aqueous sodium hydroxide solution (1.8 mL), THF (3.6 mL) and ethanol (13 mL).

$^1$H-NMR (300 MHz, DMSO-d$_6$) δ:0.99-1.26 (2H, m), 1.65-1.93 (3H, m), 2.57-2.71 (1H, m), 2.87-3.01 (1H, m), 3.18-3.27 (2H, m), 3.65-3.75 (1H, m), 3.98 (3H, s), 4.07 (2H, t, J=5.4 Hz), 4.27-4.40 (4H, m), 4.41-4.50 (1H, m), 5.97 (2H, s), 7.25-7.42 (2H, m), 7.44-7.53 (1H, m), 7.59-7.68 (2H, m), 7.71-7.81 (1H, m), 8.07 (1H, t, J=6.0 Hz), 8.13-8.21 (2H, m), 8.37 (1H, dd, J=8.3, 1.1 Hz).

Example 547

Production of N-[1-(hydroxyacetyl)piperidin-4-yl]-3-methoxy-N,1-dimethyl-4-oxo-5-(2-oxo-2-phenylethyl)-4,5-dihydro-1H-pyrrolo[3,2-c]quinoline-2-carboxamide

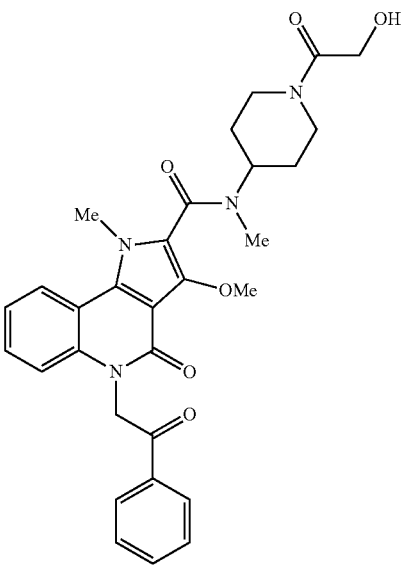 [SMILES: COc1c(C(=O)N(C)C2CCN(C(=O)CO)CC2)n(C)c2c1c(=O)n(CC(=O)c1ccccc1)c1ccccc21]

In the same manner as in Example 511, the title compound (117 mg, 62%) was obtained as a white solid from the compound of Example 545 (205 mg, 0.35 mmol), 8N aqueous sodium hydroxide solution (1.8 mL), THF (3.6 mL) and ethanol (13 mL).

$^1$H-NMR (300 MHz, CDCl$_3$) δ:1.65-2.01 (4H, m), 2.78-2.92 (1H, m), 2.99-3.09 (3H, m), 3.12-3.27 (1H, m), 3.48-3.69 (2H, m), 3.99-4.04 (3H, m), 4.04-4.11 (3H, m), 4.14-4.30 (2H, m), 4.61-4.88 (2H, m), 5.89 (2H, s), 7.06 (1H, d, J=8.7 Hz), 7.22-7.32 (1H, m), 7.35-7.44 (1H, m), 7.54 (2H, t, J=7.6 Hz), 7.62-7.72 (1H, m), 8.11 (2H, d, J=7.6 Hz), 8.19 (1H, dd, J=8.3, 1.3 Hz).

Example 548

Production of N-{trans-2-[(hydroxyacetyl)amino]cyclohexyl}-3-methoxy-4-oxo-5-(2-oxo-2-phenylethyl)-4,5-dihydrothieno[3,2-c]quinoline-2-carboxamide

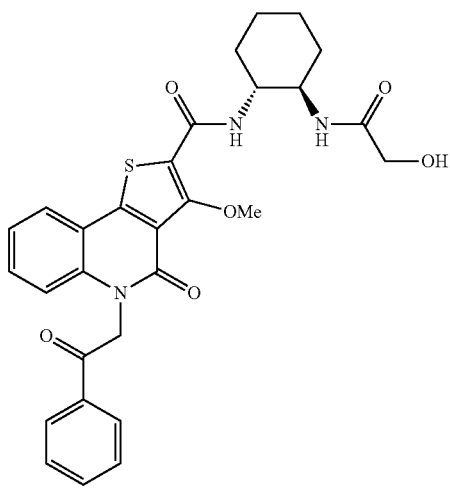 [SMILES: COc1c(C(=O)N[C@@H]2CCCC[C@H]2NC(=O)CO)sc2c1c(=O)n(CC(=O)c1ccccc1)c1ccccc21]

In the same manner as in Example 508, the title compound (88 mg, 58%) was obtained as white crystals from the compound of Example 530 (150 mg, 0.26 mmol).

$^1$H-NMR (300 MHz, DMSO-$d_6$) δ:1.20-1.50 (6H, m), 1.70 (2H, br s), 1.87 (1H, d, J=11.1 Hz), 2.05 (1H, d, J=9.6 Hz), 3.72-3.94 (7H, m), 4.31 (3H, s), 5.48 (1H, t, J=5.7 Hz), 5.97 (2H, s), 7.28-7.39 (2H, m), 7.47 (1H, t, J=7.8 Hz), 7.61-7.67 (3H, m), 7.76 (1H, t, J=7.5 Hz), 7.83 (1H, d, J=7.8 Hz), 8.15-8.18 (2H, m), 8.137 (1H, d, J=7.2 Hz).

Example 549

Production of N-{2-[1-(hydroxyacetyl)pyrrolidin-2-yl]ethyl}-3-methoxy-4-oxo-5-(2-oxo-2-phenylethyl)-4,5-dihydrothieno[3,2-c]quinoline-2-carboxamide

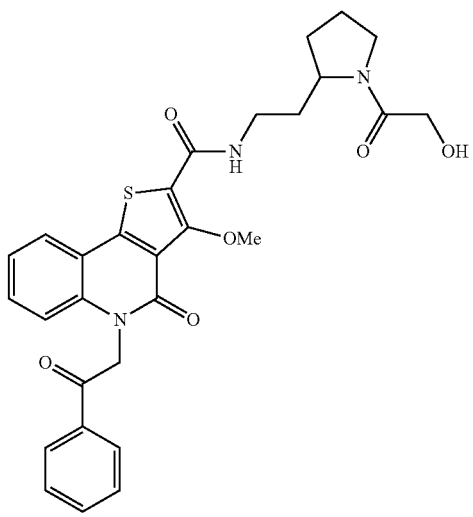 [SMILES: COc1c(C(=O)NCCC2CCCN2C(=O)CO)sc2c1c(=O)n(CC(=O)c1ccccc1)c1ccccc21]

In the same manner as in Example 508, the title compound (70 mg, 51%) was obtained as white crystals from the compound of Example 528 (150 mg, 0.25 mmol).

$^1$H-NMR (300 MHz, DMSO-$d_6$) δ:1.50-2.00 (7H, m), 3.00-3.15 (1H, m), 3.30-3.45 (1H, m), 3.55-3.70 (1H, m), 4.02-4.25 (7H, m), 4.52 (1H, t, J=5.3 Hz), 6.00 (2H, s), 7.35 (1H, t, J=7.5 Hz), 7.49 (1H, d, J=8.4 Hz), 7.56-7.67 (2H, m), 7.77 (1H, t, J=7.2 Hz), 8.05 (1H, d, J=7.8 Hz), 8.18 (2H, d, J=7.8 Hz), 8.46 (1H, t, J=5.3 Hz).

Example 550

Production of N-{[1-(hydroxyacetyl)pyrrolidin-3-yl]methyl}-3-methoxy-4-oxo-5-(2-oxo-2-phenylethyl)-4,5-dihydrothieno[3,2-c]quinoline-2-carboxamide

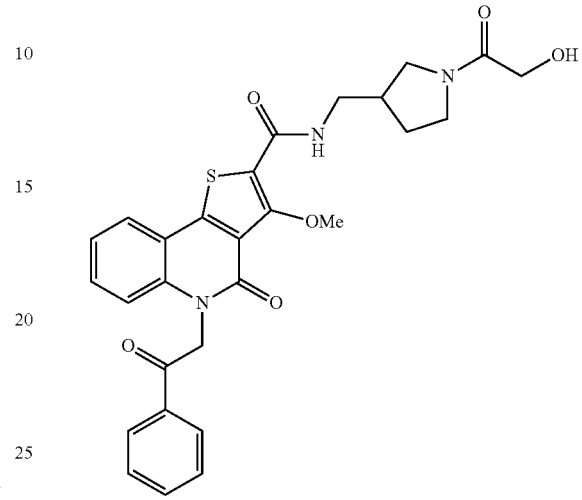

In the same manner as in Example 508, the title compound (31 mg, 29%) was obtained as white crystals from the compound of Example 529 (120 mg, 0.20 mmol).

$^1$H-NMR (300 MHz, DMSO-$d_6$) δ:1.58-1.76 (1H, m), 1.90-2.10 (1H, m), 2.50-2.65 (1H, m), 3.11-3.17 (1H, m), 3.30-3.65 (5H, m), 3.99 (2H, d, J=4.2 Hz), 4.03 (3H, d, J=0.9 Hz), 4.46 (1H, t, J=4.8 Hz), 6.00 (2H, s), 7.35 (1H, t, J=7.5 Hz), 7.49 (1H, d, J=8.4 Hz), 7.56-7.67 (3H, m), 7.77 (1H, t, J=7.5 Hz), 8.05 (1H, d, J=7.5 Hz), 8.18 (3H, d, J=7.5 Hz).

Example 551

Production of N-[1-(hydroxyacetyl)azetidin-3-yl]-3-methoxy-1-methyl-4-oxo-5-(2-oxo-2-phenylethyl)-4,5-dihydro-1H-pyrrolo[3,2-c]quinoline-2-carboxamide

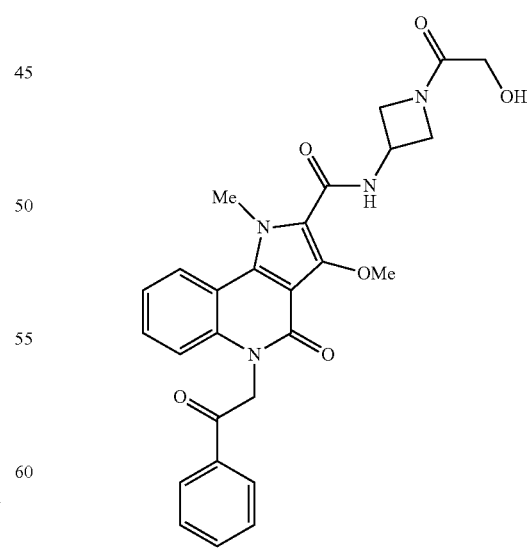

In the same manner as in Example 508, the title compound mg, 64%) was obtained as white crystals from the compound of Example 531 (100 mg, 0.18 mmol).

¹H-NMR (300 MHz, DMSO-d₆) δ:3.28-3.44 (2H, m), 3.84-3.86 (5H, tm), 4.22 (1H, t, J=6.3 Hz), 4.36 (3H, s), 4.39-4.43 (2H, m), 5.55 (1H, t, J=5.7 Hz), 5.96 (2H, s), 7.30-7.40 (2H, m), 7.48 (1H, t, J=7.5 Hz), 7.63 (2H, t, J=7.5 Hz), 7.76 (1H, t, J=7.5 Hz), 7.90 (1H, t, J=6.2 Hz), 8.16-8.19 (2H, m), 8.40 (1H, dd, J=8.1, 0.9 Hz).

Example 552

Production of 2-(1,4-dioxa-8-azaspiro[4.5]dec-8-ylcarbonyl)-3-methoxy-1-methyl-5-(2-oxo-2-phenylethyl)-1,5-dihydro-4H-pyrrolo[3,2-c]quinolin-4-one

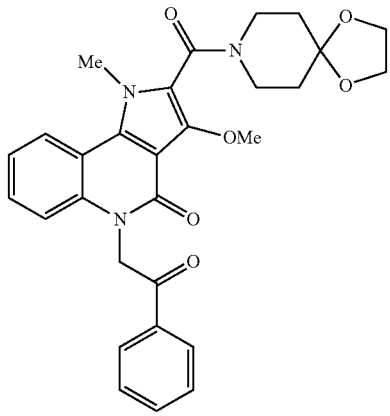 [SMILES: COc1c(C(=O)N2CCC3(CC2)OCCO3)n(C)c2c1c(=O)n(CC(=O)c1ccccc1)c1ccccc21]

In the same manner as in Example 25, the title compound (279 mg, 60%) was obtained as a white solid from the compound of Reference Example 28 (350 mg, 0.90 mmol), 1,4-dioxa-8-azaspiro[4.5]decane (154 mg, 1.1 mmol), HOBt (146 mg, 1.1 mmol), WSCD (206 mg, 1.1 mmol) and DMF (10 mL).

¹H-NMR (300 MHz, CDCl₃) δ:1.72-1.88 (4H, m), 3.64-3.77 (2H, m), 3.82-3.96 (2H, m), 3.98-4.02 (4H, m), 4.03 (3H, s), 4.09 (3H, s), 5.89 (2H, br s), 7.01-7.10 (1H, m), 7.19-7.30 (1H, m), 7.34-7.42 (1H, m), 7.49-7.58 (2H, m), 7.61-7.69 (1H, m), 8.06-8.14 (2H, m), 8.19 (1H, dd, J=8.3, 1.3 Hz).

Example 553

Production of 3-methoxy-1-methyl-5-(2-oxo-2-phenylethyl)-2-(piperazin-1-ylcarbonyl)-1,5-dihydro-4H-pyrrolo[3,2-c]quinolin-4-one hydrochloride

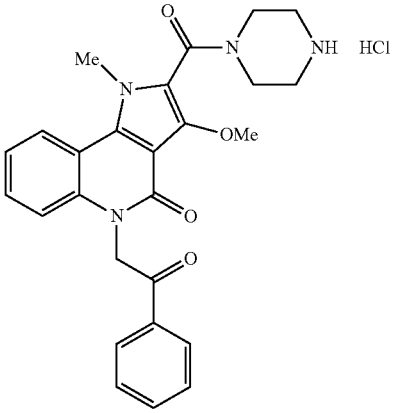 [SMILES: COc1c(C(=O)N2CCNCC2)n(C)c2c1c(=O)n(CC(=O)c1ccccc1)c1ccccc21 ; Cl]

In the same manner as in Example 542, the title compound (478 mg, 95%) was obtained as a pale-yellow solid from the compound of Example 680 (571 mg, 1.0 mmol), 4N hydrochloric acid ethyl acetate solution (11 mL), ethyl acetate (8.0 mL) and methanol (8.0 mL).

¹H-NMR (300 MHz, DMSO-d₆) δ:3.07-3.27 (4H, m), 3.65-3.78 (2H, m), 3.81-3.96 (5H, m), 4.05 (3H, s), 5.98 (2H, s), 7.24-7.52 (3H, m), 7.57-7.68 (2H, m), 7.71-7.81 (1H, m), 8.08-8.24 (2H, m), 8.35 (1H, dd, J=8.2, 1.0 Hz), 9.20 (2H, br s).

Example 554

Production of 2-(4-{[3-methoxy-1-methyl-4-oxo-5-(2-oxo-2-phenylethyl)-4,5-dihydro-1H-pyrrolo[3,2-c]quinolin-2-yl]carbonyl}piperazin-1-yl)-2-oxoethyl acetate

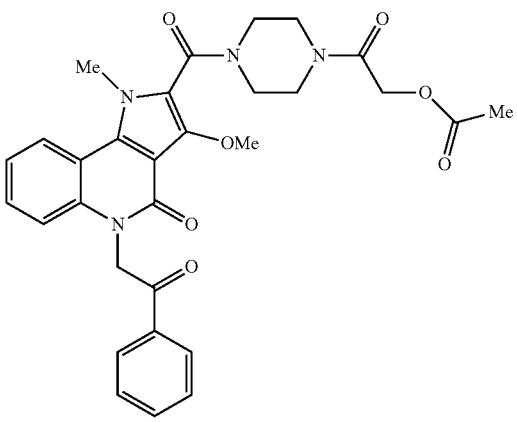 [SMILES: COc1c(C(=O)N2CCN(C(=O)COC(C)=O)CC2)n(C)c2c1c(=O)n(CC(=O)c1ccccc1)c1ccccc21]

In the same manner as in Example 544, the title compound (34 mg, 10%) was obtained as a white solid from the compound of Example 553 (300 mg, 0.61 mmol), acetoxyacetyl chloride (0.081 mL, 0.76 mmol), triethylamine (0.23 mL, 1.7 mmol) and THF (13 mL).

¹H-NMR (300 MHz, DMSO-d₆) δ:2.09 (3H, s), 3.43-3.79 (8H, m), 3.91 (3H, s), 4.03 (3H, s), 4.76-4.88 (2H, m), 5.98 (2H, s), 7.25-7.51 (3H, m), 7.59-7.68 (2H, m), 7.71-7.80 (1H, m), 8.13-8.22 (2H, m), 8.30-8.38 (1H, m).

Example 555

Production of 8-fluoro-3-methoxy-4-oxo-5-(2-oxo-2-phenylethyl)-N-piperidin-4-yl-4,5-dihydrothieno[3,2-c]quinoline-2-carboxamide hydrochloride

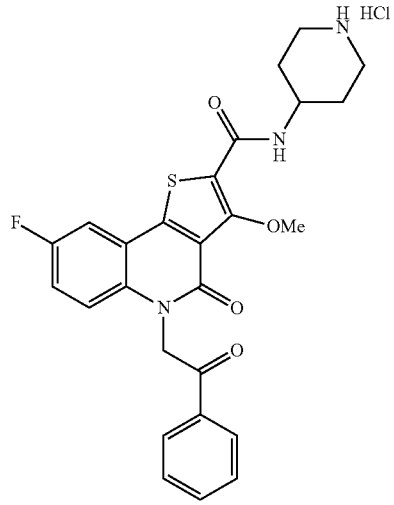 [SMILES: Cl ; COc1c(C(=O)NC2CCNCC2)sc2c1c(=O)n(CC(=O)c1ccccc1)c1ccc(F)cc21]

In the same manner as in Example 542, the title compound (335 mg, 83%) was obtained as a white solid from the compound of Example 673 (452 mg, 0.76 mmol), 4N hydrogen chloride ethyl acetate solution (6.0 mL), THF (4.0 mL) and methanol (4.0 mL).

¹H-NMR (300 MHz, DMSO-d₆) δ:1.70-1.91 (2H, m), 1.95-2.12 (2H, m), 2.93-3.13 (2H, m), 3.19-3.52 (2H, m), 3.95-4.22 (4H, m), 6.00 (2H, s), 7.41-7.52 (1H, m), 7.53-7.71 (3H, m), 7.72-7.84 (1H, m), 7.86-8.03 (2H, m), 8.11-8.25 (2H, m), 8.63 (2H, br s).

Example 556

Production of 2-[4-({[8-fluoro-3-methoxy-4-oxo-5-(2-oxo-2-phenylethyl)-4,5-dihydrothieno[3,2-c]quinolin-2-yl]carbonyl}amino)piperidin-1-yl]-2-oxoethyl acetate

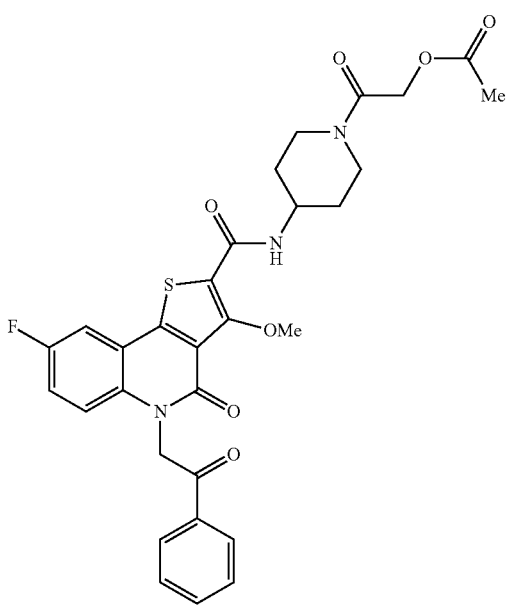 [SMILES: COc1c(C(=O)NC2CCN(C(=O)COC(C)=O)CC2)sc2c1c(=O)n(CC(=O)c1ccccc1)c1ccc(F)cc21]

In the same manner as in Example 544, the title compound (161 mg, 80%) was obtained as a white solid from the compound of Example 555 (180 mg, 0.34 mmol), acetoxyacetyl chloride (0.046 mL, 0.42 mmol), triethylamine (0.13 mL, 0.93 mmol) and THF (7.5 mL).

¹H-NMR (300 MHz, CDCl₃) δ:1.45-1.64 (2H, m), 2.01-2.26 (5H, m), 2.89-3.05 (1H, m), 3.15-3.34 (1H, m), 3.60-3.77 (1H, m), 4.15 (3H, s), 4.20-4.34 (1H, m), 4.41-4.54 (1H, m), 4.67-4.84 (2H, m), 5.85 (2H, s), 6.95-7.04 (1H, m), 7.16-7.24 (1H, m), 7.51-7.62 (4H, m), 7.64-7.74 (1H, m), 8.06-8.14 (2H, m).

Example 557

Production of 2-[4-({[5-(cyclohexylmethyl)-3-methoxy-1-methyl-4-oxo-4,5-dihydro-1H-pyrrolo[3,2-c]quinolin-2-yl]carbonyl}amino)piperidin-1-yl]-2-oxoethyl acetate

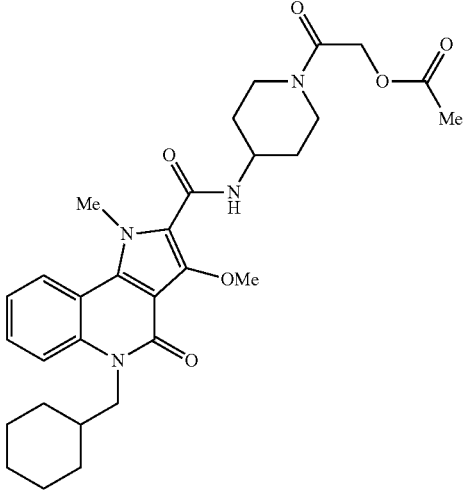 [SMILES: COc1c(C(=O)NC2CCN(C(=O)COC(C)=O)CC2)n(C)c2c1c(=O)n(CC1CCCCC1)c1ccccc21]

A mixture of the compound of Example 672 (110 mg, 0.24 mmol), bromomethylcyclohexane (108 mg, 0.60 mmol), potassium carbonate (72 mg, 0.60 mmol) and DMF (3 mL) was stirred at 80° C. for 24 hr. After cooling to room temperature, the reaction mixture was diluted with saturated aqueous sodium hydrogen carbonate solution and extracted with ethyl acetate. The extract was washed with saturated brine, dried over magnesium sulfate, and concentrated under reduced pressure. The residue was purified by silica gel chromatography (eluate: ethyl acetate) to give the title compound (34 mg, 16%) as a colorless oil.

¹H-NMR (300 MHz, DMSO-d₆) δ:1.05-1.20 (5H, m), 1.35-2.00 (9H, m), 2.09 (3H, s), 2.90 (1H, t, J=11.4 Hz), 3.19 (1H, t, J=12.2 Hz), 3.70 (1H, d, J=13.5 Hz), 3.97 (3H, s), 4.10-4.40 (8H, m), 4.80 (2H, d, J=2.1 Hz), 7.30 (1H, t, J=7.5 Hz), 7.54-7.62 (2H, m), 7.96 (1H, d, J=7.8 Hz), 8.32 (1H, d, J=7.8 Hz).

Example 558

Production of tert-butyl 4-({[3-methoxy-5-(4-methoxybenzyl)-1-methyl-4-oxo-4,5-dihydro-1H-pyrrolo[3,2-c]quinolin-2-yl]carbonyl}amino)piperidine-1-carboxylate

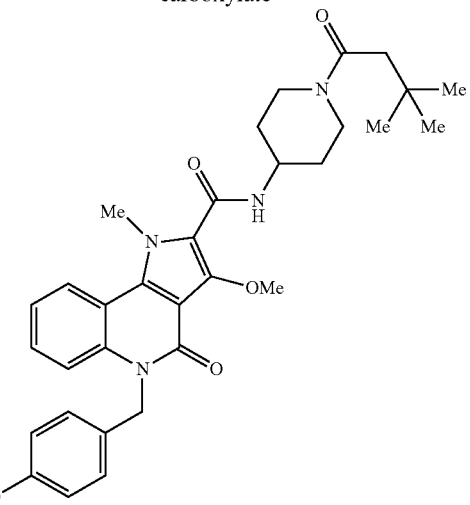

In the same manner as in Example 25, the title compound (6.09 g, 74%) was obtained as white crystals from the compound of Reference Example 107 (5.65 g, 14.4 mmol) and 1-Boc-4-aminopiperidine (5.77 g, 28.80 mmol).

$^1$H-NMR (300 MHz, DMSO-d$_6$) δ:1.32-1.53 (11H, m), 1.85 (2H, d, J=10.2 Hz), 2.85-3.10 (2H, m), 3.69 (3H, s), 3.88 (2H, d, J=13.2 Hz), 3.95-4.05 (4H, m), 4.27 (3H, s), 5.52 (2H, br s), 6.85 (2H, d, J=8.7 Hz), 7.14 (2H, d, J=8.7 Hz), 7.27 (1H, t, J=7.1 Hz), 7.41-7.48 (2H, m), 7.96 (1H, d, J=7.8 Hz), 8.32 (1H, d, J=8.1 Hz).

Example 559

Production of 2-[4-({[3-methoxy-5-(4-methoxybenzyl)-1-methyl-4-oxo-4,5-dihydro-1H-pyrrolo[3,2-c]quinolin-2-yl]carbonyl}amino)piperidin-1-yl]-2-oxoethyl acetate

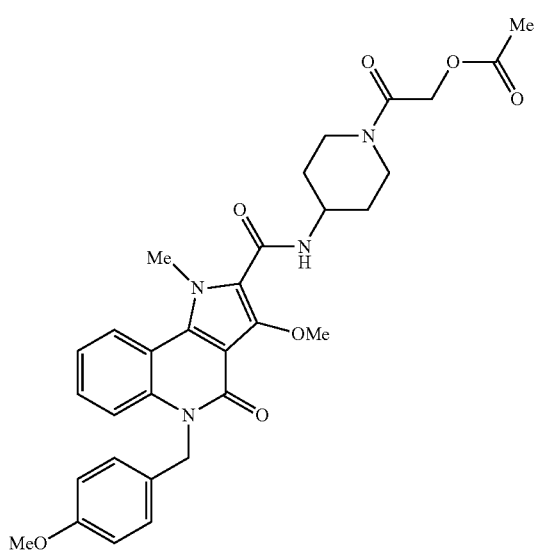 [SMILES: COc1ccc(Cn2c(=O)c3c(OC)c(C(=O)NC4CCN(C(=O)COC(C)=O)CC4)n(C)c3c3ccccc32)cc1]

In the same manner as in Example 123, the title compound mg, 73%) was obtained as a white solid from the compound of Example 681 (440 mg, 0.87 mmol).

$^1$H-NMR (300 MHz, DMSO-d$_6$) δ:1.35-1.65 (2H, m), 1.72-1.95 (2H, m), 2.09 (3H, s), 2.91 (1H, t, J=11.7 Hz), 3.20 (1H, t, J=12.0 Hz), 3.58-3.75 (4H, m), 4.00-4.20 (5H, m), 4.27 (3H, s), 4.80 (2H, d, J=2.4 Hz), 5.40-5.60 (2H, br), 6.86 (2H, d, J=8.7 Hz), 7.14 (2H, d, J=8.7 Hz), 7.27 (1H, td, J=7.1, 2.1 Hz), 7.41-7.49 (2H, m), 8.00 (1H, d, J=8.1 Hz), 8.33 (1H, d, J=8.1 Hz).

Example 560

Production of N-[1-(3-hydroxy-3-methylbutanoyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

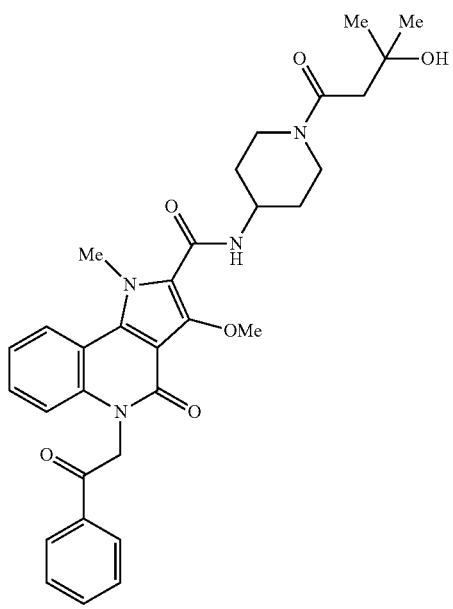 [SMILES: COc1c(C(=O)NC2CCN(C(=O)CC(C)(C)O)CC2)n(C)c2c1c(=O)n(CC(=O)c1ccccc1)c1ccccc21]

In the same manner as in Example 518, the title compound (109 mg, 60%) was obtained as a white powder from the compound of Example 77 (150 mg, 0.317 mmol) and 3-hydroxy-3-methylbutanoic acid (45.0 mg, 0.381 mmol).

$^1$H-NMR (300 MHz, DMSO-d$_6$) δ:1.18 (6H, s), 1.33-1.63 (2H, m), 1.79-1.97 (2H, m), 2.43-2.52 (2H, m), 2.81-2.96 (1H, m), 3.14-3.29 (1H, m), 3.90-4.00 (4H, m), 4.02-4.16 (1H, m), 4.22-4.36 (4H, m), 4.89 (1H, s), 5.97 (2H, s), 7.26-7.41 (2H, m), 7.48 (1H, t, J=7.6 Hz), 7.63 (2H, t, J=7.5 Hz), 7.72-7.81 (1H, m), 7.95 (1H, d, J=7.9 Hz), 8.17 (2H, d, J=7.7 Hz), 8.37 (1H, d, J=8.3 Hz).

Example 561

Production of 3-methoxy-1-methyl-4-oxo-5-(2-oxo-2-phenylethyl)-N-(1-propanoylpiperidin-4-yl)-4,5-dihydro-1H-pyrrolo[3,2-c]quinoline-2-carboxamide

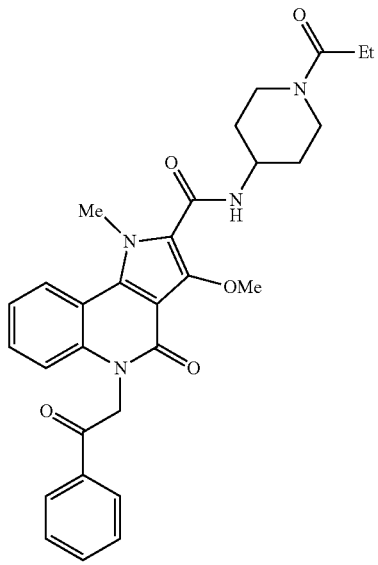 [SMILES: CCC(=O)N1CCC(NC(=O)c2c(OC)c3c(=O)n(CC(=O)c4ccccc4)c4ccccc4c3n2C)CC1]

In the same manner as in Example 123, the title compound (90.2, 81%) was obtained as a white powder from the compound of Example 77 (100 mg, 0.212 mmol) and propionyl chloride (20.2 µL, 0.233 mmol).

$^1$H-NMR (300 MHz, DMSO-d$_6$) δ:1.00 (3H, t, J=7.5 Hz), 1.31-1.61 (2H, m), 1.77-1.96 (2H, m), 2.34 (2H, q, J=7.4 Hz), 2.77-2.92 (1H, m), 3.10-3.25 (1H, m), 3.76-3.88 (1H, m), 3.97 (3H, s), 4.01-4.14 (1H, m), 4.19-4.29 (1H, m), 4.31 (3H, s), 5.97 (2H, s), 7.26-7.41 (2H, m), 7.43-7.52 (1H, m), 7.63 (2H, t, J=7.6 Hz), 7.71-7.81 (1H, m), 7.94 (1H, d, J=7.7 Hz), 8.12-8.22 (2H, m), 8.37 (1H, dd, J=8.3, 1.1 Hz).

Example 562

Production of 8-fluoro-N-[1-(hydroxyacetyl)piperidin-4-yl]-3-methoxy-4-oxo-5-(2-oxo-2-phenylethyl)-4,5-dihydrothieno[3,2-c]quinoline-2-carboxamide

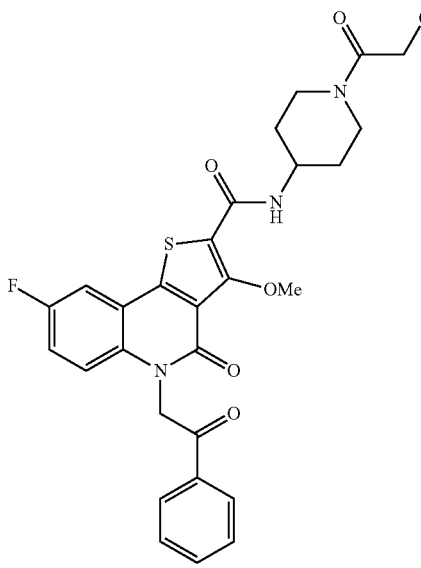

In the same manner as in Example 511, the title compound (59 mg, 39%) was obtained as a pale-yellow solid from the compound of Example 556 (164 mg, 0.28 mmol).

$^1$H-NMR (300 MHz, CDCl$_3$) δ:1.42-1.63 (2H, m), 2.08-2.25 (2H, m), 2.97-3.26 (2H, m), 3.47-3.59 (1H, m), 3.62 (1H, t, J=4.2 Hz), 4.14 (3H, s), 4.20 (2H, d, J=4.0 Hz), 4.23-4.34 (1H, m), 4.45-4.58 (1H, m), 5.85 (2H, s), 6.94-7.04 (1H, m), 7.15-7.25 (1H, m), 7.50-7.63 (4H, m), 7.64-7.77 (1H, m), 8.04-8.15 (2H, m).

Example 563

Production of 3-methoxy-1-methyl-4-oxo-5-(2-oxo-2-phenylethyl)-N-(1-pyridin-4-ylpiperidin-4-yl)-4,5-dihydro-1H-pyrrolo[3,2-c]quinoline-2-carboxamide

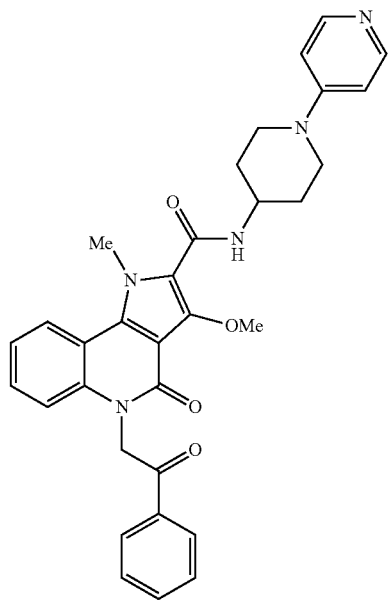 [SMILES: COc1c(C(=O)NC2CCN(c3ccncc3)CC2)n(C)c2c1c(=O)n(CC(=O)c1ccccc1)c1ccccc21]

To a solution of the compound of Reference Example 28 (200 mg, 0.51 mmol), 1-pyridin-4-ylpiperidin-4-amine hydrochloride (128 mg, 0.51 mmol) and HOBt (83 mg, 0.61 mmol) in DMF (5.0 mL) were added WSCD (118 mg, 0.61 mmol) and triethylamine (0.23 ml, 1.6 mmol) under ice-cooling, and the mixture was stirred at room temperature for 67 hr. The reaction mixture was diluted with brine, and extracted 4 times with ethyl acetate. The extracts were combined and concentrated under reduced pressure. The residue was purified by aminosilica gel chromatography (eluate; ethyl acetate/hexane=40/60-100/0) and recrystallized from THF to give the title compound (121 mg, 43%) as a pale-purple solid.

$^1$H-NMR (300 MHz, DMSO-d$_6$) δ:1.52-1.68 (2H, m), 1.87-1.98 (2H, m), 3.08 (2H, m), 3.89 (2H, m), 3.95 (3H, s), 4.04-4.17 (1H, m), 4.31 (3H, s), 5.97 (2H, s), 6.85 (2H, d, J=6.4 Hz), 7.26-7.41 (2H, m), 7.43-7.53 (1H, m), 7.63 (2H, m), 7.71-7.80 (1H, m), 7.98 (1H, d, J=7.7 Hz), 8.10-8.21 (4H, m), 8.37 (1H, d, J=7.4 Hz).

Example 564

Production of N-[1-(hydroxyacetyl)piperidin-4-yl]-3-methoxy-5-(3-methoxybenzyl)-1-methyl-4-oxo-4,5-dihydro-1H-pyrrolo[3,2-c]quinoline-2-carboxamide

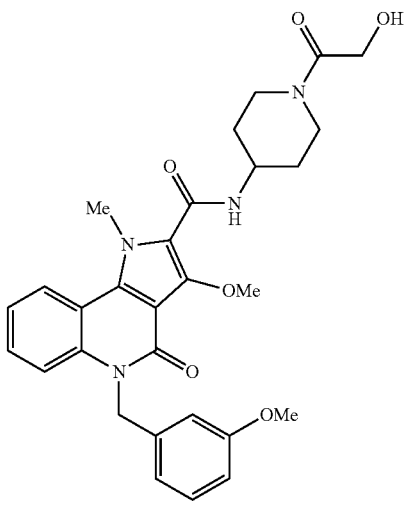 [SMILES: COc1cccc(Cn2c(=O)c3c(OC)c(C(=O)NC4CCN(C(=O)CO)CC4)n(C)c3c3ccccc32)c1]

A mixture of the compound of Example 672 (110 mg, 0.24 mmol), 3-methoxybenzyl chloride (150 mg, 0.96 mmol), potassium carbonate (55 mg, 0.40 mmol) and DMF (5 mL) was stirred at 80° C. for 5 hr. After cooling to room temperature, 2N aqueous sodium hydroxide solution (1 mL) was added, and the mixture was stirred at room temperature for 1 hr. The reaction mixture was diluted with saturated aqueous sodium hydrogen carbonate solution and extracted with ethyl acetate. The extract was washed with saturated brine, dried over magnesium sulfate, and concentrated under reduced pressure. The residue was purified by silica gel chromatography (eluate:ethyl acetate-ethyl acetate/methanol=10/1) and reprecipitated from ethyl acetate-hexane to give the title compound (14 mg, 10%) as a white powder.

$^1$H-NMR (300 MHz, DMSO-$d_6$) δ:1.40-1.65 (2H, m), 1.90 (2H, d, J=10.2 Hz), 2.93 (1H, t, J=10.2 Hz), 3.19 (1H, t, J=14.3 Hz), 3.60-3.70 (4H, m), 4.00-4.04 (4H, m), 4.04-4.10 (2H, m), 4.30-4.36 (4H, m), 4.52 (1H, t, J=5.4 Hz), 5.58 (2H, br s), 6.69 (1H, d, J=8.4 Hz), 6.79 (2H, d, J=6.3 Hz), 7.20 (1H, t, J=8.4 Hz), 7.28 (1H, t, J=6.3 Hz), 7.34-7.48 (2H, m), 7.89 (1H, d, J=8.1 Hz), 8.34 (1H, d, J=8.4 Hz).

Example 565

Production of 3-methoxy-1-methyl-4-oxo-5-(2-oxo-2-phenylethyl)-N-(2,2,6,6-tetramethylpiperidin-4-yl)-4,5-dihydro-1H-pyrrolo[3,2-c]quinoline-2-carboxamide

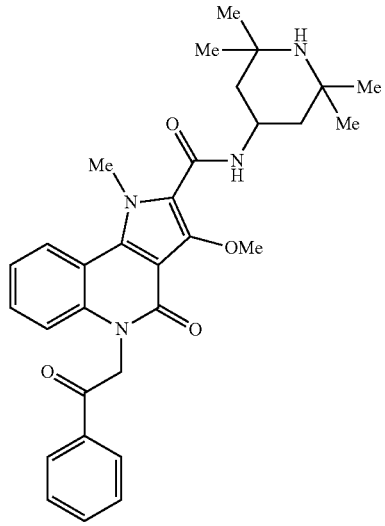 [SMILES: COc1c(C(=O)NC2CC(C)(C)NC(C)(C)C2)n(C)c2c1c(=O)n(CC(=O)c1ccccc1)c1ccccc21]

In the same manner as in Example 25, the title compound (410 mg, 76%) was obtained as a white solid from the compound of Reference Example 28 (400 mg, 1.02 mmol) and 4-amino-2,2,6,6-tetramethylpiperidine (320 mg, 2.04 mmol).

$^1$H-NMR (300 MHz, DMSO-$d_6$) δ: 0.86-1.24 (14H, m), 1.78 (2H, dd, J=12.6, 2.4 Hz), 3.96 (3H, s), 4.28-4.31 (4H, m), 5.97 (2H, s), 7.29-7.47 (3H, m), 7.63 (2H, t, J=7.5 Hz), 7.76 (2H, t, J=6.9 Hz), 8.17 (2H, d, J=7.5 Hz), 8.37 (1H, d, J=8.4 Hz).

Example 566

Production of 3-methoxy-1-methyl-5-(2-oxo-2-phenylethyl)-2-[(4-oxopiperidin-1-yl)carbonyl]-1,5-dihydro-4H-pyrrolo[3,2-c]quinolin-4-one

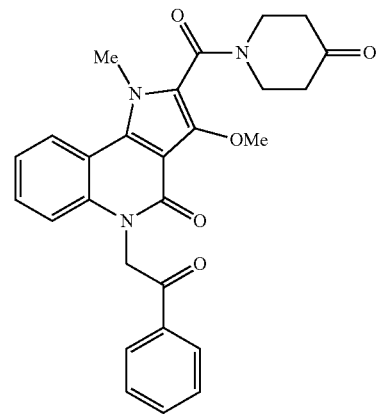 [SMILES: COc1c(C(=O)N2CCC(=O)CC2)n(C)c2c1c(=O)n(CC(=O)c1ccccc1)c1ccccc21]

A solution of the compound of Example 552 (285 mg, 0.55 mmol) and 5N hydrochloric acid (3.0 mL) in THF (6.0 mL) was stirred at room temperature for 2 hr. 5N Hydrochloric acid (1.5 mL) was added, and the mixture was stirred at room temperature for 2 hr. 5N Hydrochloric acid (1.5 mL) was added, and the mixture was stirred at room temperature for 3.5 hr and concentrated under reduced pressure. The residue was basified with saturated sodium hydrogen carbonate solution and extracted twice with ethyl acetate. The extracts were combined, washed with brine, and concentrated under reduced pressure. The residue was washed with water, and recrystallized from methanol-diethyl ether to give the title compound (123 mg, 47%) as a white solid.

$^1$H-NMR (300 MHz, CDCl$_3$) δ:1.78-1.93 (3H, m), 1.95-1.99 (1H, m), 3.58-3.73 (2H, m), 3.79-3.94 (2H, m), 4.03 (3H, s), 4.07-4.11 (3H, m), 5.90 (2H, s), 7.02-7.11 (1H, m), 7.19-7.30 (1H, m), 7.34-7.43 (1H, m), 7.49-7.58 (2H, m), 7.61-7.70 (1H, m), 8.07-8.14 (2H, m), 8.16-8.26 (1H, m).

Example 567

Production of N-[1-(N,N-dimethylglycyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

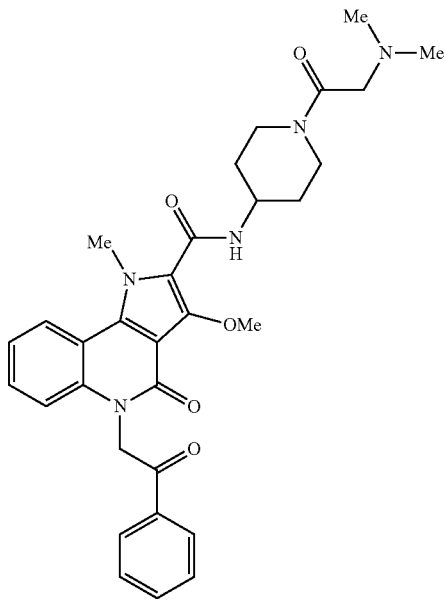 [SMILES: COc1c(C(=O)NC2CCN(C(=O)CN(C)C)CC2)n(C)c2c1c(=O)n(CC(=O)c1ccccc1)c1ccccc21]

In the same manner as in Example 25, the title compound (125 mg, 57%) was obtained as a pale-purple solid from the compound of Example 77 (200 mg, 0.39 mmol) and N,N-dimethylglycine (49 mg, 0.47 mmol).

$^1$H-NMR (300 MHz, CDCl$_3$) δ:1.40-1.64 (2H, m), 1.99-2.17 (2H, m), 2.31 (6H, s), 2.90-3.05 (1H, m), 3.08-3.21 (2H, m), 3.22-3.36 (1H, m), 3.99-4.11 (1H, m), 4.14 (3H, s), 4.18-4.29 (1H, m), 4.36-4.45 (1H, m), 4.47 (3H, s), 5.88 (2H, d, J=4.2 Hz), 7.05 (1H, d, J=7.7 Hz), 7.20-7.32 (1H, m), 7.37-7.46 (1H, m), 7.50-7.59 (2H, m), 7.62-7.73 (2H, m), 8.06-8.16 (2H, m), 8.26 (1H, dd, J=8.3, 1.3 Hz).

Example 568

Production of N-[1-(3-ethoxypropanoyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

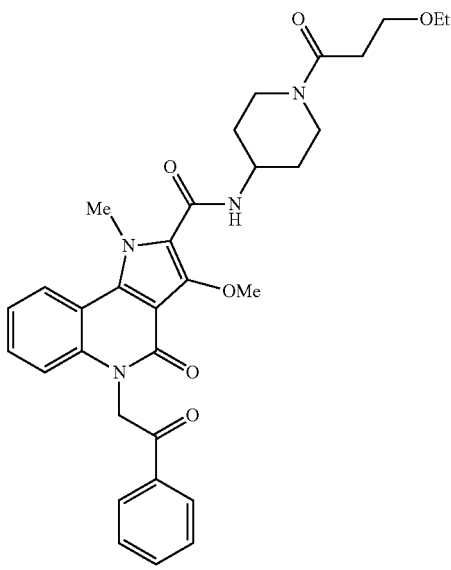 [SMILES: CCOCCC(=O)N1CCC(NC(=O)c2c(OC)c3c(=O)n(CC(=O)c4ccccc4)c4ccccc4c3n2C)CC1]

In the same manner as in Example 25, the title compound (159 mg, 70%) was obtained as a pale-purple solid from the compound of Example 77 (200 mg, 0.39 mmol) and 3-ethoxypropanoic acid (56 mg, 0.47 mmol).

$^1$H-NMR (300 MHz, DMSO-d$_6$) δ:1.09 (3H, t, J=7.0 Hz), 1.36-1.60 (2H, m), 1.80-1.96 (2H, m), 2.54-2.63 (2H, m), 2.78-2.92 (1H, m), 3.13-3.26 (1H, m), 3.42 (2H, q, J=6.9 Hz), 3.59 (2H, t, J=6.7 Hz), 3.81-3.91 (1H, m), 3.96 (3H, s), 4.02-4.14 (1H, m), 4.18-4.27 (1H, m), 4.31 (3H, s), 5.97 (2H, s), 7.26-7.41 (2H, m), 7.44-7.53 (1H, m), 7.58-7.68 (2H, m), 7.72-7.80 (1H, m), 7.94 (1H, d, J=7.9 Hz), 8.12-8.21 (2H, m), 8.37 (1H, dd, J=8.3, 1.3 Hz).

Example 569

Production of N-[1-(hydroxyacetyl)piperidin-4-yl]-3-methoxy-5-(2-methoxybenzyl)-1-methyl-4-oxo-4,5-dihydro-1H-pyrrolo[3,2-c]quinoline-2-carboxamide

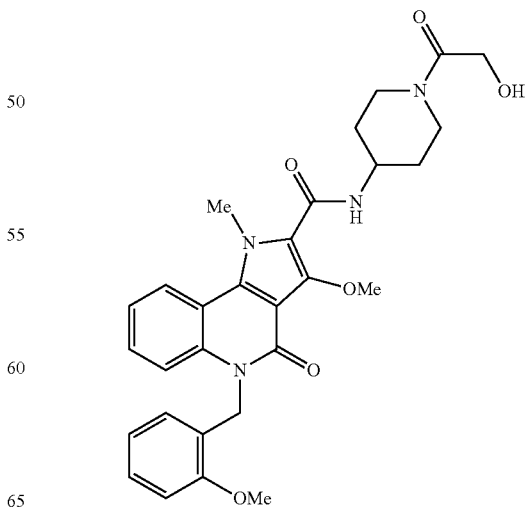

To a solution of the compound of Example 570 (40 mg, 0.07 mmol) in THF (1 mL)-methanol (1 ml) was added 2N sodium hydroxide solution (1 mL), and the mixture was stirred at room temperature for 1 hr. The reaction mixture was diluted with water, and extracted with ethyl acetate. The extract was washed with brine, dried over magnesium sulfate, and concentrated under reduced pressure. Recrystallization from ethyl acetate-hexane gave the title compound (30 mg, 80%) as white crystals.

¹H-NMR (300 MHz, DMSO-d₆) δ:1.50-1.60 (2H, m), 1.90 (2H, d, J=10.2 Hz), 2.93 (1H, t, J=12.5 Hz), 3.15 (1H, t, J=12.5 Hz), 3.67 (1H, d, J=13.2 Hz), 3.95 (3H, s), 4.00 (3H, s), 4.05-4.20 (3H, m), 4.20-4.30 (4H, m), 4.51 (1H, t, J=5.4 Hz), 5.47 (2H, s), 6.50 (1H, d, J=7.5 Hz), 6.75 (1H, t, J=7.5 Hz), 7.09 (1H, d, J=8.4 Hz), 7.21-7.31 (3H, m), 7.44 (1H, t, J=7.8 Hz), 7.97 (1H, d, J=7.8 Hz), 8.36 (1H, d, J=8.1 Hz).

Example 570

Production of 2-[4-({[3-methoxy-5-(2-methoxybenzyl)-1-methyl-4-oxo-4,5-dihydro-1H-pyrrolo[3,2-c]quinolin-2-yl]carbonyl}amino)piperidin-1-yl]-2-oxoethyl acetate

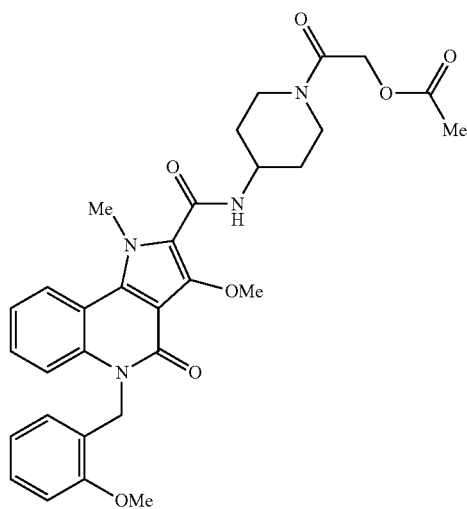 [SMILES: COc1ccccc1Cn1c(=O)c2c(OC)c(C(=O)NC3CCN(C(=O)COC(C)=O)CC3)n(C)c2c2ccccc21]

In the same manner as in Example 557, an amorphous solid (90 mg) was obtained from the compound of Example 672 (120 mg, 0.24 mmol), 2-methoxybenzyl chloride (50% dichloromethane solution; 0.1 mL, 0.79 mmol) and potassium carbonate (110 mg, 0.79 mmol). Recrystallization from ethyl acetate-diisopropyl ether gave the title compound (44 mg, 29%) as white crystals.

¹H-NMR (300 MHz, DMSO-d₆) δ:1.50-1.70 (2H, m), 2.07-2.28 (5H, m), 3.04 (1H, t, J=11.1 Hz), 3.29 (1H, t, J=11.1 Hz), 3.70 (1H, d, J=14.4 Hz), 3.99 (3H, s), 4.21-4.28 (4H, m), 4.40-4.56 (4H, m), 4.78 (2H, s), 5.62 (2H, br s), 6.77 (2H, d, J=4.2 Hz), 6.95 (1H, d, J=10.8 Hz), 7.19-7.42 (4H, m), 7.77 (1H, d, J=7.8 Hz), 8.25 (1H, dd, J=8.4, 1.2 Hz).

Example 571

Production of 3-methoxy-1-methyl-4-oxo-5-(2-oxo-2-phenylethyl)-N-(tetrahydro-2H-thiopyran-4-yl)-4,5-dihydro-1H-pyrrolo[3,2-c]quinoline-2-carboxamide

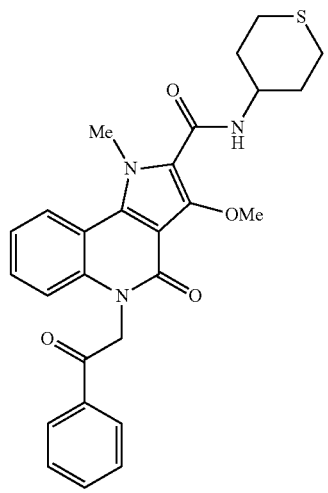 [SMILES: COc1c(C(=O)NC2CCSCC2)n(C)c2c1c(=O)n(CC(=O)c1ccccc1)c1ccccc21]

In the same manner as in Example 25, the title compound (2.51 g, 90%) was obtained as a white solid from the compound of Reference Example 28 (2.22 g, 5.69 mmol) and tetrahydrothiopyran-4-ylamine (1.0 g, 8.53 mmol).

¹H-NMR (300 MHz, DMSO-d₆) δ:1.63-1.77 (2H, m), 1.99-2.17 (2H, m), 2.66-2.78 (4H, m), 3.87-3.97 (4H, m), 4.30 (3H, s), 5.97 (2H, s), 7.28-7.39 (2H, m), 7.47 (1H, td, J=7.8, 1.2 Hz), 7.63 (2H, t, J=7.5 Hz), 7.76 (1H, t, J=8.1 Hz), 7.97 (1H, d, J=8.1 Hz), 8.16-8.18 (2H, m), 8.36 (1H, dd, J=8.4, 1.2 Hz).

Example 572

Production of 3-methoxy-1-methyl-N-(1-oxidotetrahydro-2H-thiopyran-4-yl)-4-oxo-5-(2-oxo-2-phenylethyl)-4,5-dihydro-1H-pyrrolo[3,2-c]quinoline-2-carboxamide

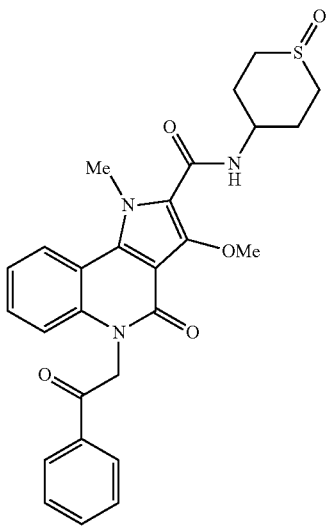 [SMILES: COc1c(C(=O)NC2CCS(=O)CC2)n(C)c2c1c(=O)n(CC(=O)c1ccccc1)c1ccccc21]

A solution of the compound of Example 571 (200 mg, 0.41 mmol) and mCPBA (70% containing water; 106 mg, 0.43 mmol) in ethyl acetate (25 mL) was stirred at 0° C. for 1 hr. The reaction mixture was diluted with saturated aqueous sodium hydrogen carbonate solution, and extracted with ethyl acetate. The extract was washed with saturated brine, dried over magnesium sulfate and concentrated under reduced pressure. Recrystallization of the residue from ethyl acetate-hexane gave the title compound (54 mg, 26%) as white crystals.

$^1$H-NMR (300 MHz, DMSO-$d_6$) δ: 1.88 (2H, d, J=12.9 Hz), 2.20 (2H, q, J=12.7 Hz), 2.70-3.00 (4H, m), 3.97-4.06 (4H, m), 4.29 (3H, s), 5.97 (2H, s), 7.29-7.40 (2H, m), 7.48 (1H, t, J=7.5 Hz), 7.63 (2H, t, J=7.5 Hz), 7.76 (1H, t, J=7.5 Hz), 8.05 (1H, d, J=8.1 Hz), 8.16-8.19 (2H, m), 8.37 (1H, d, J=7.5 Hz).

Example 573

Production of N-[1-(ethoxyacetyl)piperidin-4-yl]-3-methyl-1-methyl-4-oxo-5-(2-oxo-2-phenylethyl)-4,5-dihydro-1H-pyrrolo[3,2-c]quinoline-2-carboxamide

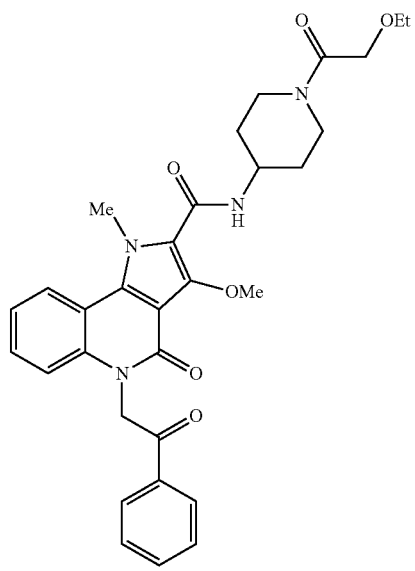 [SMILES: CCOCC(=O)N1CCC(NC(=O)c2c(OC)c3c(=O)n(CC(=O)c4ccccc4)c4ccccc4c3n2C)CC1]

In the same manner as in Example 25, the title compound (134 mg, 61%) was obtained as a white solid from the compound of Example 77 (200 mg, 0.39 mmol) and ethoxyacetic acid (0.045 mL, 0.47 mmol).

$^1$H-NMR (300 MHz, DMSO-$d_6$) δ:1.14 (3H, t, J=7.0 Hz), 1.35-1.64 (2H, m), 1.81-1.97 (2H, m), 2.81-2.95 (1H, m), 3.09-3.24 (1H, m), 3.42-3.55 (2H, m), 3.73-3.85 (1H, m), 3.96 (3H, s), 4.02-4.25 (4H, m), 4.31 (3H, s), 5.97 (2H, s), 7.26-7.41 (2H, m), 7.43-7.53 (1H, m), 7.58-7.68 (2H, m), 7.71-7.81 (1H, m), 7.95 (1H, d, J=7.7 Hz), 8.12-8.22 (2H, m), 8.37 (1H, dd, J=8.2, 1.2 Hz).

Example 574

Production of 3-methoxy-1-methyl-4-oxo-5-(2-oxo-2-phenylethyl)-N-(1-pyridin-4-ylpiperidin-4-yl)-4,5-dihydro-1H-pyrrolo[3,2-c]quinoline-2-carboxamide hydrochloride

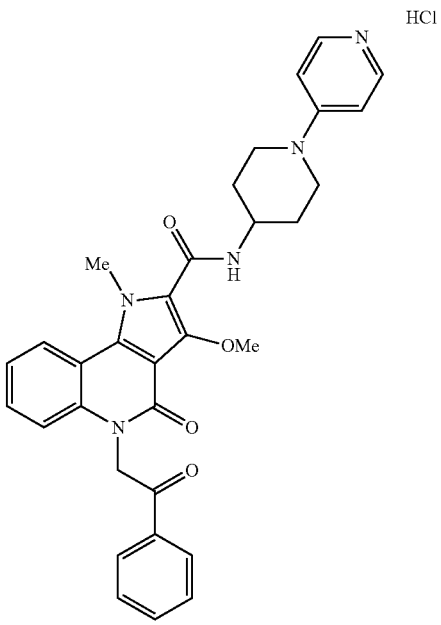 [SMILES: Cl ; COc1c(C(=O)NC2CCN(c3ccncc3)CC2)n(C)c2c1c(=O)n(CC(=O)c1ccccc1)c1ccccc21]

A solution of the compound of Example 563 (250 mg, 0.46 mmol) and 4N hydrogen chloride ethyl acetate solution (0.114 mL, 0.46 mmol) in methanol (3.0 mL)-ethyl acetate (3.0 mL) was stirred at room temperature for 10 min. The reaction mixture was concentrated under reduced pressure, and the residue was recrystallized from methanol-diethyl ether to give the title compound (45 mg, 17%) as a white solid.

$^1$H-NMR (300 MHz, DMSO-$d_6$) δ:1.54-1.74 (2H, m), 1.95-2.10 (2H, m), 3.36-3.48 (2H, m), 3.96 (3H, s), 4.11-4.36 (6H, m), 5.97 (2H, s), 7.17-7.27 (2H, m), 7.28-7.42 (2H, m), 7.43-7.53 (1H, m), 7.58-7.69 (2H, m), 7.71-7.82 (1H, m), 8.00 (1H, d, J=7.7 Hz), 8.12-8.19 (2H, m), 8.21-8.28 (2H, m), 8.38 (1H, dd, J=8.3, 1.1 Hz), 13.40 (1H, br s).

Example 575

Production of 3-methoxy-1-methyl-4-oxo-5-(2-oxo-2-phenylethyl)-N-(1-phenylpiperidin-4-yl)-4,5-dihydro-1H-pyrrolo[3,2-c]quinoline-2-carboxamide

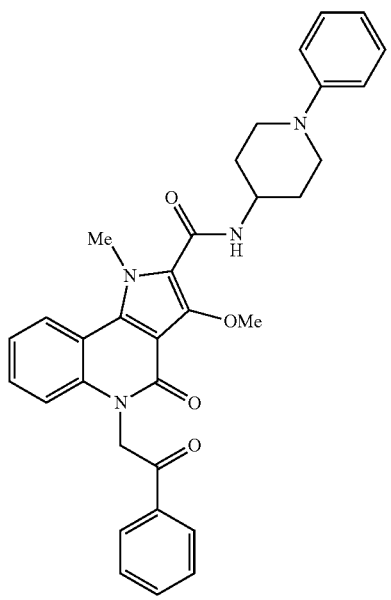 [SMILES: COc1c(C(=O)NC2CCN(c3ccccc3)CC2)n(C)c2c1c(=O)n(CC(=O)c1ccccc1)c1ccccc21]

A solution of the compound of Example 77 (200 mg, 0.42 mmol), iodobenzene (0.50 mL), tris(dibenzylideneacetone)dipalladium (0) (38 mg, 0.042 mmol), x-phos (40 mg, 0.085 mmol) and sodium tert-butoxide (102 mg, 1.1 mmol) in tert-butanol (4.0 mL) was stirred under microwave irradiation at 130° C. for 35 min. The reaction mixture was diluted with water, and extracted twice with ethyl acetate. The extracts were combined, dried over magnesium sulfate, and concentrated under reduced pressure. The residue was purified by aminosilica gel chromatography (eluate; ethyl acetate/hexane=30/70-100/0) and recrystallized from ethyl acetate to give the title compound (70 mg, 30%) as a white solid.

$^1$H-NMR (300 MHz, CDCl$_3$) δ:1.67-1.85 (2H, m), 2.09-2.25 (2H, m), 2.92-3.08 (2H, m), 3.53-3.69 (2H, m), 4.06-4.25 (4H, m), 4.48 (3H, s), 5.88 (2H, s), 6.82-6.92 (1H, m), 6.94-7.09 (3H, m), 7.20-7.32 (3H, m), 7.35-7.46 (1H, m), 7.49-7.59 (2H, m), 7.61-7.81 (2H, m), 8.03-8.16 (2H, m), 8.26 (1H, dd, J=8.3, 1.3 Hz).

Example 576

Production of 3-methoxy-1-methyl-4-oxo-5-(2-oxo-2-phenylethyl)-N-(1-prolylpiperidin-4-yl)-4,5-dihydro-1H-pyrrolo[3,2-c]quinoline-2-carboxamide hydrochloride

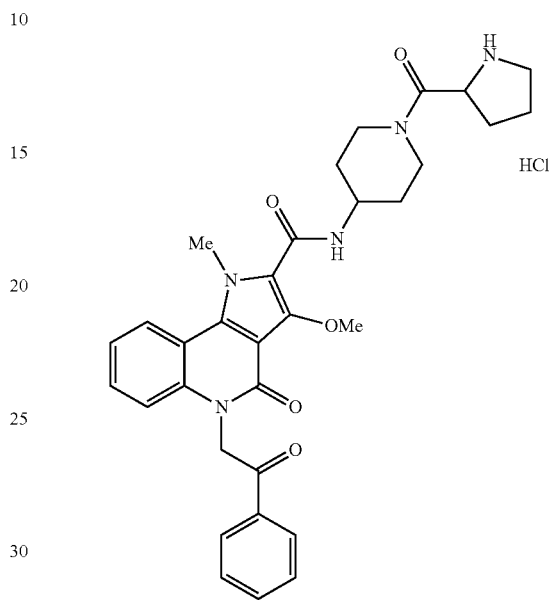

To a solution of the compound of Example 77 (300 mg, 0.59 mmol), 1-(tert-butoxycarbonyl)proline (152 mg, 0.71 mmol) and HOBt (96 mg, 0.71 mmol) in DMF (7.5 mL) were added WSCD (136 mg, 0.71 mmol) and triethylamine (0.18 ml, 1.3 mmol) under ice-cooling, and the mixture was stirred at room temperature for 17 hr. The reaction mixture was diluted with saturated sodium hydrogen carbonate solution, and extracted twice with ethyl acetate. The extracts were combined, dried over magnesium sulfate, and concentrated under reduced pressure. The residue was purified by aminosilica gel chromatography (eluate; ethyl acetate/hexane=20/80-100/0). The obtained compound was dissolved in methanol (4.5 mL), 4N hydrogen chloride ethyl acetate solution (4.5 mL) was added, and the mixture was stirred at room temperature for 7 hr. The reaction mixture was concentrated under reduced pressure and recrystallized from methanol-diethyl ether to give the title compound (234 mg, 65%) as a white solid.

$^1$H-NMR (300 MHz, DMSO-d$_6$) δ:1.37-1.69 (2H, m), 1.69-1.84 (1H, m), 1.84-2.05 (4H, m), 2.29-2.46 (1H, m), 2.91-3.27 (4H, m), 3.75-3.91 (1H, m), 3.97 (3H, d, J=1.5 Hz), 4.06-4.29 (2H, m), 4.32 (3H, d, J=3.2 Hz), 4.48-4.67 (1H, m), 5.97 (2H, s), 7.27-7.43 (2H, m), 7.44-7.54 (1H, m), 7.56-7.70 (2H, m), 7.70-7.83 (1H, m), 7.97 (1H, dd, J=11.8, 7.8 Hz), 8.08-8.26 (2H, m), 8.38 (1H, dd, J=8.3, 1.1 Hz), 8.93 (2H, br s).

Example 577

Production of 3-methoxy-1-methyl-4-oxo-5-(2-oxo-2-phenylethyl)-N-(1-pyridin-4-ylpiperidin-4-yl)-4,5-dihydro-1H-pyrrolo[3,2-c]quinoline-2-carboxamide methanesulfonate

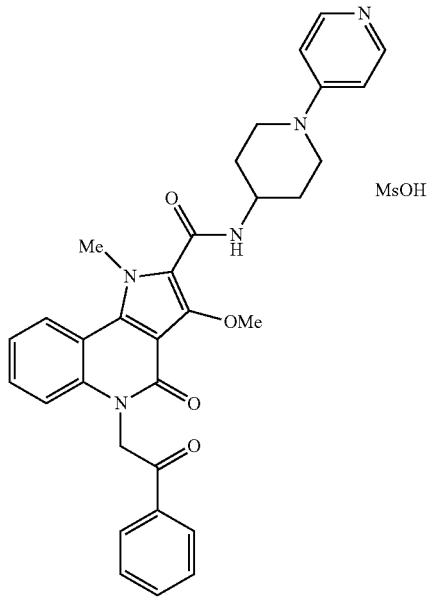 [SMILES: "MsOH" ; COc1c(C(=O)NC2CCN(c3ccncc3)CC2)n(C)c2c1c(=O)n(CC(=O)c1ccccc1)c1ccccc21]

In the same manner as in Example 574, the title compound (142 mg, 36%) was obtained as a pale-yellow solid from the compound of Example 563 (333 mg, 0.61 mmol), methanesulfonic acid (0.041 mL, 0.64 mmol).

$^1$H-NMR (300 MHz, DMSO-d$_6$) δ:1.55-1.73 (2H, m), 1.96-2.09 (2H, m), 2.30 (3H, s), 3.36-3.49 (2H, m), 3.96 (3H, s), 4.14-4.37 (6H, m), 5.97 (2H, s), 7.17-7.27 (2H, m), 7.28-7.42 (2H, m), 7.43-7.52 (1H, m), 7.57-7.68 (2H, m), 7.71-7.81 (1H, m), 8.00 (1H, d, J=7.9 Hz), 8.11-8.19 (2H, m), 8.21-8.28 (2H, m), 8.38 (1H, dd, J=8.2, 1.2 Hz), 13.22 (1H, br s).

Example 578

Production of 3-methoxy-1-methyl-4-oxo-5-(2-oxo-2-phenylethyl)-N-[1-(1,3-thiazol-2-yl)piperidin-4-yl]-4,5-dihydro-1H-pyrrolo[3,2-c]quinoline-2-carboxamide

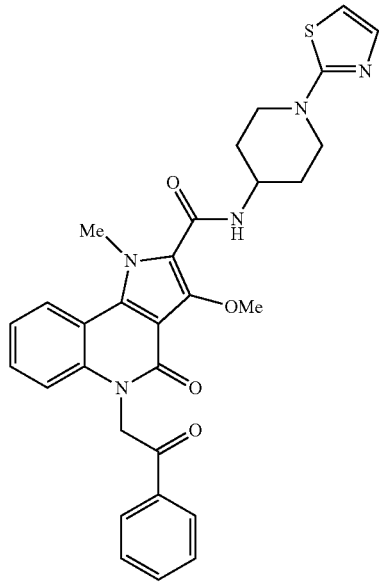 [SMILES: COc1c(C(=O)NC2CCN(c3nccs3)CC2)n(C)c2c1c(=O)n(CC(=O)c1ccccc1)c1ccccc21]

In the same manner as in Example 25, the title compound (152 mg, 53%) was obtained as a white solid from the compound of Reference Example 28 (200 mg, 0.51 mmol) and 1-(1,3-thiazol-2-yl)piperidin-4-amine hydrochloride (124 mg, 0.56 mmol).

$^1$H-NMR (300 MHz, DMSO-d$_6$) δ:1.58-1.79 (2H, m), 1.90-2.04 (2H, m), 3.15-3.28 (2H, m), 3.81-3.92 (2H, m), 3.96 (3H, s), 4.03-4.18 (1H, m), 4.31 (3H, s), 5.97 (2H, s), 6.83 (1H, d, J=3.6 Hz), 7.16 (1H, d, J=3.6 Hz), 7.27-7.41 (2H, m), 7.44-7.52 (1H, m), 7.58-7.68 (2H, m), 7.70-7.82 (1H, m), 8.00 (1H, d, J=7.9 Hz), 8.10-8.23 (2H, m), 8.37 (1H, dd, J=8.3, 1.3 Hz).

Example 579

Production of 8-fluoro-N-[1-(2-hydroxyethyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

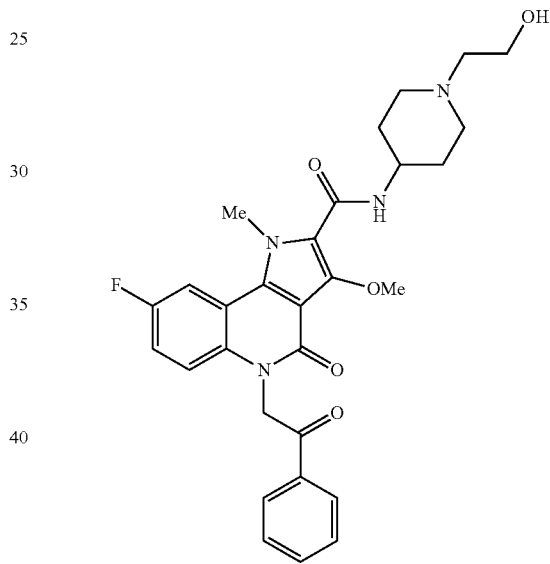

A solution of the compound of Example 675 (300 mg, 0.57 mmol), potassium carbonate (629 mg, 4.6 mmol) and triethylamine (0.11 mL, 0.76 mmol) in DMF (13 mL) was stirred at 100° C. for 5 min, and 2-bromoethanol (0.16 mL, 2.3=mol) was added. After stirring at 100° C. for 1.5 hr, the reaction mixture was concentrated under reduced pressure. The reaction mixture was diluted with water, and extracted 3 times with ethyl acetate. The extracts were combined, washed with saturated brine, dried over magnesium sulfate, and concentrated under reduced pressure. The residue was purified by aminosilica gel chromatography (eluate; methanol/ethyl acetate=0/100-5/95) and recrystallized from THF-diethyl ether to give the title compound (205 mg, 51%) as a white solid.

$^1$H-NMR (300 MHz, DMSO-d$_6$) δ:1.47-1.67 (2H, m), 1.75-1.89 (2H, m), 2.08-2.25 (2H, m), 2.40 (2H, t, J=6.3 Hz), 2.70-2.86 (2H, m), 3.49 (2H, q, J=6.1 Hz), 3.74-3.89 (1H, m), 3.97 (3H, s), 4.31 (3H, s), 4.38 (1H, t, J=5.4 Hz), 5.97 (2H, s), 7.28-7.40 (1H, m), 7.40-7.49 (1H, m), 7.58-7.68 (2H, m), 7.71-7.82 (1H, m), 7.92 (1H, d, J=7.7 Hz), 8.05-8.23 (3H, m).

Example 580

Production of 3-methoxy-1-methyl-4-oxo-5-(2-oxo-2-phenylethyl)-N-[1-(tetrahydrofuran-2-ylcarbonyl)piperidin-4-yl]-4,5-dihydro-1H-pyrrolo[3,2-c]quinoline-2-carboxamide

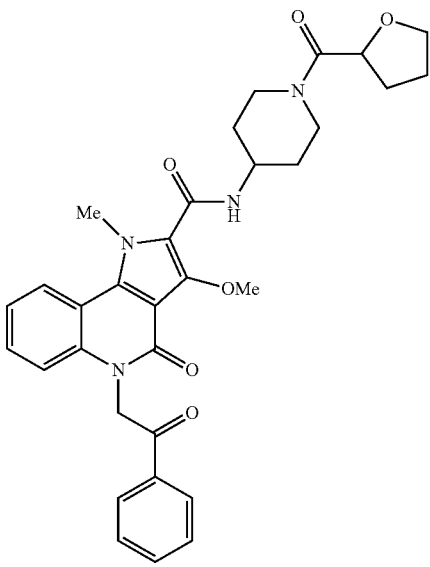 [SMILES: COc1c(C(=O)NC2CCN(C(=O)C3CCCO3)CC2)n(C)c2c1c(=O)n(CC(=O)c1ccccc1)c1ccccc21]

In the same manner as in Example 25, the title compound (41 mg, 17%) was obtained as a white solid from the compound of Reference Example 77 (200 mg, 0.42 mmol) and tetrahydrofuran-2-carboxylic acid (0.049 mL, 0.51 mmol).

$^1$H-NMR (300 MHz, DMSO-d$_6$) δ:1.34-1.63 (2H, m), 1.74-1.95 (4H, m), 1.96-2.12 (2H, m), 2.78-2.97 (1H, m), 3.09-3.28 (1H, m), 3.68-3.86 (2H, m), 3.88-4.02 (4H, m), 4.03-4.27 (2H, m), 4.28-4.35 (3H, m), 4.68 (1H, dd, J=7.4, 5.9 Hz), 5.97 (2H, s), 7.26-7.41 (2H, m), 7.43-7.53 (1H, m), 7.58-7.68 (2H, m), 7.71-7.81 (1H, m), 7.89-8.03 (1H, m), 8.12-8.22 (2H, m), 8.37 (1H, dd, J=8.3, 1.1 Hz).

Example 581

Production of 3-methoxy-1-methyl-N-{1-[4-(methylsulfonyl)phenyl]piperidin-4-yl}-4-oxo-5-(2-oxo-2-phenylethyl)-4,5-dihydro-1H-pyrrolo[3,2-c]quinoline-2-carboxamide

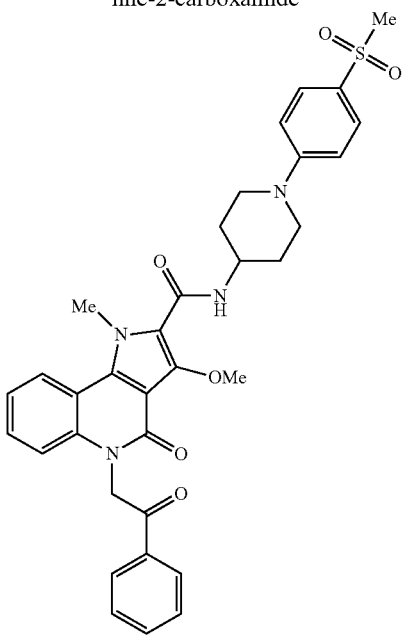

In the same manner as in Example 575, the title compound (28 mg, 8.0%) was obtained as a white solid from the compound of Example 77 (260 mg, 0.55 mmol) and 1-bromo-4-(methylsulfonyl)benzene (259 mg, 1.1 mmol).

$^1$H-NMR (300 MHz, DMSO-d$_6$) δ:1.54-1.72 (2H, m), 1.88-2.04 (2H, m), 3.05-3.20 (5H, m), 3.85-3.99 (5H, m), 4.04-4.22 (1H, m), 4.31 (3H, s), 5.97 (2H, s), 7.06-7.17 (2H, m), 7.26-7.41 (2H, m), 7.43-7.52 (1H, m), 7.57-7.71 (4H, m), 7.72-7.82 (1H, m), 7.99 (1H, d, J=7.9 Hz), 8.14-8.23 (2H, m), 8.37 (1H, dd, J=8.1, 1.1 Hz).

Example 582

Production of 3-methoxy-1-methyl-N-[1-(2-methylpyridin-4-yl)piperidin-4-yl]-4-oxo-5-(2-oxo-2-phenylethyl)-4,5-dihydro-1H-pyrrolo[3,2-c]quinoline-2-carboxamide

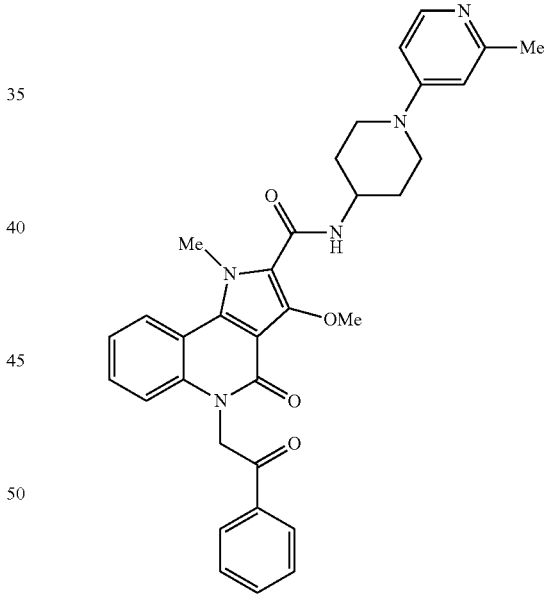

In the same manner as in Example 575, the title compound (51 mg, 14%) was obtained as a white solid from the compound of Reference Example 77 (300 mg, 0.64 mmol) and 4-bromo-2-methylpyridine (0.15 mL, 1.3 mmol).

$^1$H-NMR (300 MHz, DMSO-d$_6$) δ:1.48-1.68 (2H, m), 1.84-1.98 (2H, m), 2.32 (3H, s), 2.95-3.14 (2H, m), 3.80-3.91 (2H, m), 3.95 (3H, s), 4.02-4.18 (1H, m), 4.31 (3H, s), 5.97 (2H, s), 6.62-6.70 (1H, m), 6.71-6.75 (1H, m), 7.24-7.41 (2H, m), 7.43-7.52 (1H, m), 7.58-7.67 (2H, m), 7.70-7.81 (1H, m), 7.92-8.06 (2H, m), 8.12-8.22 (2H, m), 8.37 (1H, dd, J=8.3, 1.1 Hz).

Example 583

Production of 3-methoxy-1-methyl-4-oxo-5-(2-oxo-2-phenylethyl)-N-(1-pyrimidin-4-ylpiperidin-4-yl)-4,5-dihydro-1H-pyrrolo[3,2-c]quinoline-2-carboxamide

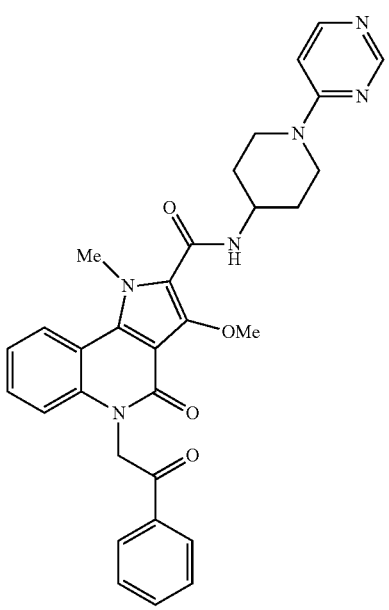 [SMILES: COc1c(C(=O)NC2CCN(c3ccncn3)CC2)n(C)c2c1c(=O)n(CC(=O)c1ccccc1)c1ccccc21]

A solution of the compound of Example 77 (200 mg, 0.42 mmol), 4-chloropyrimidine (58 mg, 0.51 mmol) and triethylamine (0.12 mL, 0.85 mmol) in 2-propanol (4.0 mL) was heated under reflux for 23 hr. The reaction mixture was diluted with saturated sodium hydrogen carbonate solution, and extracted twice with a mixed solvent of ethyl acetate-methanol. The extract was washed with brine, dried over magnesium sulfate, and concentrated under reduced pressure. The residue was purified by aminosilica gel chromatography (eluate; ethyl acetate/methanol=0/100-5/95) and recrystallized from THF to give the title compound (97 mg, 42%) as a white solid.

$^1$H-NMR (300 MHz, DMSO-$d_6$) δ:1.44-1.65 (2H, m), 1.88-2.02 (2H, m), 3.10-3.24 (2H, m), 3.95 (3H, s), 4.08-4.23 (1H, m), 4.25-4.39 (5H, m), 5.97 (2H, s), 6.88 (1H, dd, J=6.4, 1.1 Hz), 7.26-7.41 (2H, m), 7.43-7.52 (1H, m), 7.58-7.68 (2H, m), 7.72-7.81 (1H, m), 7.97 (1H, d, J=7.9 Hz), 8.11-8.23 (3H, m), 8.37 (1H, dd, J=8.3, 1.1 Hz), 8.49 (1H, s).

Example 584

Production of 8-fluoro-N-[1-(hydroxyacetyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

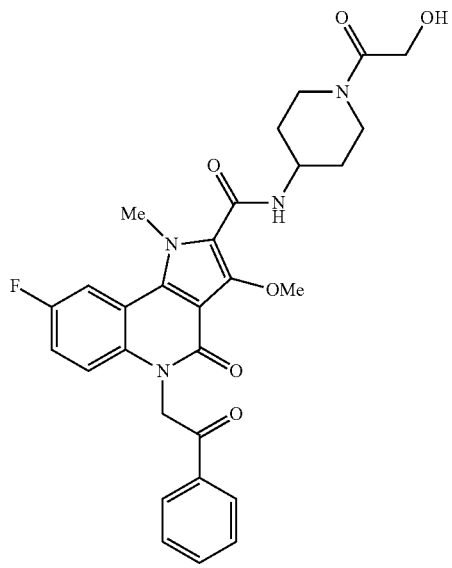 [SMILES: COc1c(C(=O)NC2CCN(C(=O)CO)CC2)n(C)c2c1c(=O)n(CC(=O)c1ccccc1)c1ccc(F)cc21]

In the same manner as in Example 511, the title compound (103 mg, 38%) was obtained as a white solid from the compound of Example 676 (293 mg, 0.50 mmol).

$^1$H-NMR (300 MHz, DMSO-$d_6$) δ:1.36-1.63 (2H, m), 1.81-1.96 (2H, m), 2.84-2.99 (1H, m), 3.06-3.20 (1H, m), 3.61-3.74 (1H, m), 3.95 (3H, s), 4.03-4.15 (3H, m), 4.17-4.27 (1H, m), 4.30 (3H, s), 4.52 (1H, t, J=5.5 Hz), 5.97 (2H, s), 7.30-7.40 (1H, m), 7.41-7.49 (1H, m), 7.58-7.68 (2H, m), 7.71-7.80 (1H, m), 8.01 (1H, d, J=7.7 Hz), 8.07-8.21 (3H, m).

Example 585

Production of N-[1-(hydroxyacetyl)piperidin-4-yl]-3-methoxy-1-methyl-4-oxo-5-(pyridin-2-ylmethyl)-4,5-dihydro-1H-pyrrolo[3,2-c]quinoline-2-carboxamide

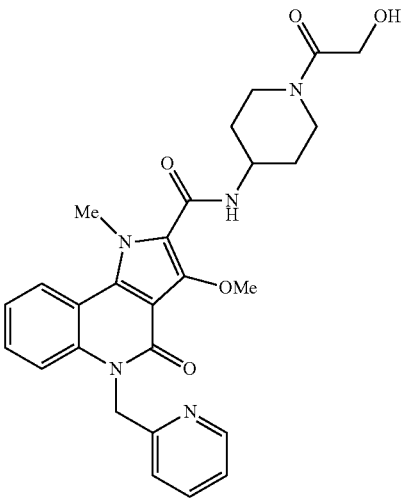 [SMILES: COc1c(C(=O)NC2CCN(C(=O)CO)CC2)n(C)c2c1c(=O)n(Cc1ccccn1)c1ccccc21]

To a suspension of the compound of Example 672 (300 mg, 0.66 mmol) in DMF (5 mL) was added sodium hydride (60% in oil; 79 mg, 1.98 mmol), and the mixture was stirred at room temperature for 30 min. 2-Chloromethylpyridine hydrochloride (238 mg, 1.46 mmol) was added to the mixture, and the mixture was stirred at 60° C. for 16 hr. After cooling, the reaction mixture was diluted with saturated sodium hydrogen carbonate solution, and extracted twice with ethyl acetate. The extract was washed with brine, dried over magnesium sulfate, and concentrated under reduced pressure. The residue was purified by aminosilica gel chromatography (eluate; ethyl acetate) to give 2-[4-({[3-methoxy-1-methyl-4-oxo-5-(pyridin-2-ylmethyl)-4,5-dihydro-1H-pyrrolo[3,2-c]quinolin-2-yl]carbonyl}amino)piperidin-1-yl]-2-oxoethyl acetate (60 mg).

To a solution of 2-[4-({[3-methoxy-1-methyl-4-oxo-5-(pyridin-2-ylmethyl)-4,5-dihydro-1H-pyrrolo[3,2-c]quinolin-2-yl]carbonyl}amino)piperidin-1-yl]-2-oxoethyl acetate (60 mg) in THF (2 mL)-methanol (2 ml) was added 2N sodium hydroxide solution (2 mL), and the mixture was stirred at room temperature for 1 hr. The reaction mixture was diluted with saturated sodium hydrogen carbonate solution, and extracted twice with ethyl acetate. The extract was washed with brine, dried over magnesium sulfate, and concentrated under reduced pressure. Recrystallization from ethyl acetate-diisopropyl ether gave the title compound (25 mg, 45%) as beige crystals.

$^1$H-NMR (300 MHz, DMSO-d$_6$) δ:1.40-1.60 (2H, m), 1.90 (2H, d, J=11.4 Hz), 2.93 (1H, t, J=11.2 Hz), 3.15 (1H, t, J=11.9 Hz), 3.67 (1H, d, J=13.8 Hz), 4.01-4.29 (10H, m), 4.52 (1H, t, J=5.4 Hz), 5.66 (2H, s), 7.11 (1H, d, J=7.8 Hz), 7.24-7.31 (2H, m), 7.40-7.44 (2H, m), 7.71 (1H, td, J=7.5, 1.8 Hz), 7.97 (1H, d, J=7.8 Hz), 8.34 (1H, d, J=8.1 Hz), 8.49-8.51 (1H, m).

Example 586

Production of N-[1-(hydroxyacetyl)piperidin-4-yl]-3-methoxy-1-methyl-4-oxo-5-(pyridin-4-ylmethyl)-4,5-dihydro-1H-pyrrolo[3,2-c]quinoline-2-carboxamide

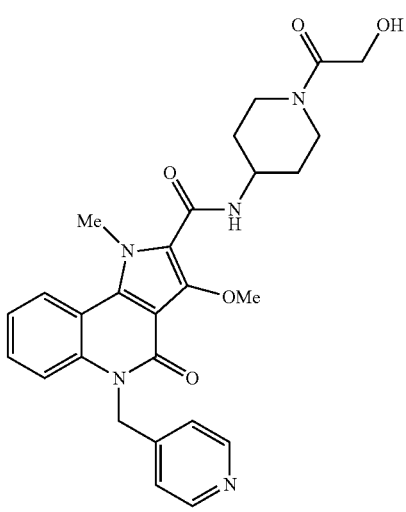 [SMILES: COc1c(C(=O)NC2CCN(C(=O)CO)CC2)n(C)c2c1c(=O)n(Cc1ccncc1)c1ccccc21]

In the same manner as in Example 585, the title compound (14 mg, 5%) was obtained as beige crystals from the compound of Example 672 (300 mg, 0.66 mmol) and 4-chloromethylpyridine hydrochloride (130 mg, 0.80 mmol).

$^1$H-NMR (300 MHz, DMSO-d$_6$) δ:1.35-1.60 (2H, m), 1.90 (2H, d, J=11.4 Hz), 2.93 (1H, t, J=12.4 Hz), 3.14 (1H, t, J=14.2 Hz), 3.60-3.75 (1H, m), 4.10-4.29 (10H, m), 4.45-4.60 (1H, br), 5.63 (2H, s), 7.16 (2H, d, J=5.1 Hz), 7.28-7.36 (2H, m), 7.46 (1H, t, J=8.1 Hz), 7.99 (1H, d, J=7.8 Hz), 8.36 (1H, d, J=8.4 Hz), 8.48 (2H, d, J=4.8 Hz).

Example 587

Production of 3-methoxy-1-methyl-4-oxo-5-(2-oxo-2-phenylethyl)-N-(tetrahydro-2H-pyran-4-yl)-4,5-dihydro-1H-pyrrolo[3,2-c]quinoline-2-carboxamide

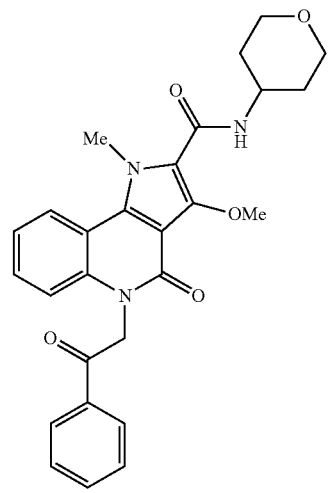 [SMILES: COc1c(C(=O)NC2CCOCC2)n(C)c2c1c(=O)n(CC(=O)c1ccccc1)c1ccccc21]

In the same manner as in Example 25, the title compound (204 mg, 84%) was obtained as white crystals from the compound of Reference Example 28 (200 mg, 0.51 mmol) and 4-aminotetrahydropyran (62 mg, 0.61 mmol).

$^1$H-NMR (300 MHz, DMSO-d$_6$) δ:1.59 (2H, q, J=10.0 Hz), 1.84 (2H, d, J=13.5 Hz), 3.44 (2H, t, J=11.0 Hz), 3.86 (2H, d, J=11.4 Hz), 3.97 (3H, s), 4.00-4.10 (1H, m), 4.31 (3H, s), 5.97 (2H, s), 7.29-7.39 (2H, m), 7.48 (1H, t, J=7.5 Hz), 7.63 (2H, t, J=7.5 Hz), 7.76 (1H, t, J=7.1 Hz), 7.96 (1H, d, J=7.8 Hz), 8.17 (2H, d, J=7.5 Hz), 8.37 (1H, d, J=8.1 Hz).

Example 588

Production of tert-butyl 4-({[3-methoxy-1-methyl-4-oxo-5-(2-oxo-2-phenylethyl)-4,5-dihydro-1H-pyrrolo[3,2-c]quinolin-2-yl]carbonyl}amino)-2-methylpiperidine-1-carboxylate

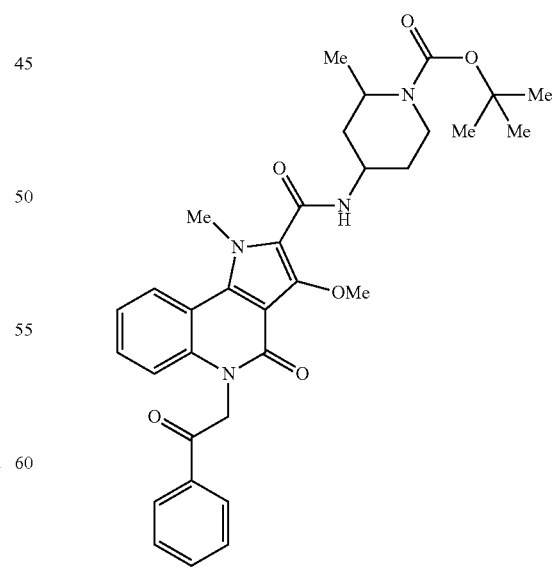

In the same manner as in Example 25, the title compound (220 mg, 75%) was obtained as white crystals from the compound of Reference Example 28 (200 mg, 0.51 mmol) and 1-Boc-4-amino-2-methylpiperidine (131 mg, 0.61 mmol).

$^1$H-NMR (300 MHz, DMSO-$d_6$) δ:1.24 (3H, d, J=6.9 Hz), 1.41 (9H, s), 1.65-1.95 (4H, m), 3.13 (1H, t, J=10.7 Hz), 3.73 (1H, d, J=13.2 Hz), 4.02 (3H, s), 4.10-4.20 (2H, m), 4.35 (3H, s), 5.98 (2H, s), 7.30-7.41 (2H, m), 7.48 (1H, t, J=7.2 Hz), 7.63 (2H, t, J=7.5 Hz), 7.76 (1H, t, J=7.5 Hz), 8.02 (1H, d, J=6.6 Hz), 8.16-8.19 (2H, m), 8.38 (1H, d, J=7.2 Hz).

J=7.5 Hz), 7.76 (1H, t, J=7.5 Hz), 8.09 (1H, d, J=7.8 Hz), 8.16-8.19 (2H, m), 8.37 (1H, d, J=8.4 Hz), 8.50-8.90 (2H, br).

Example 589

Production of 3-methoxy-1-methyl-N-(2-methylpiperidin-4-yl)-4-oxo-5-(2-oxo-2-phenylethyl)-4,5-dihydro-1H-pyrrolo[3,2-c]quinoline-2-carboxamide hydrochloride

Example 590

Production of N-[1-(2-hydroxyethyl)-2-methylpiperidin-4-yl]-3-methoxy-1-methyl-4-oxo-5-(2-oxo-2-phenylethyl)-4,5-dihydro-1H-pyrrolo[3,2-c]quinoline-2-carboxamide

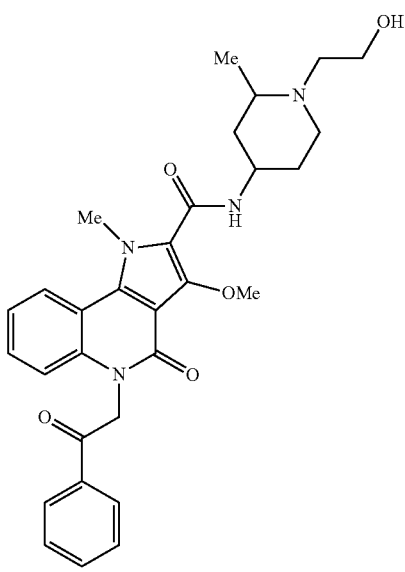

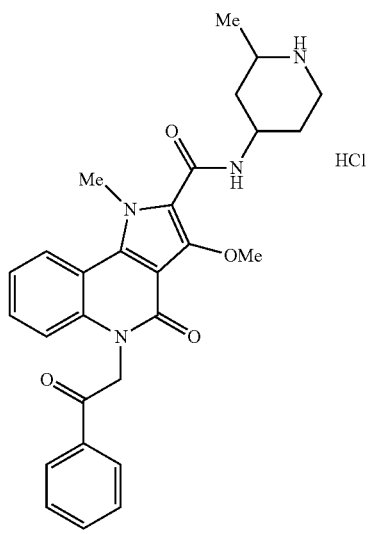 [SMILES: COc1c(C(=O)NC2CCNC(C)C2)n(C)c2c1c(=O)n(CC(=O)c1ccccc1)c1ccccc21 ; Cl]

In the same manner as in Example 61, the title compound (163 mg, 100%) was obtained as white crystals from the compound of Example 588 (200 mg, 0.34 mmol).

$^1$H-NMR (300 MHz, DMSO-$d_6$) δ:1.26 (3H, d, J=6.3 Hz), 1.45-1.90 (3H, m), 2.08 (2H, t, J=14.1 Hz), 3.04 (1H, t, J=11.9 Hz), 3.96 (3H, s), 4.04-4.14 (1H, m), 4.28 (3H, s), 5.98 (2H, s), 7.29-7.40 (2H, m), 7.48 (1H, d, J=7.8 Hz), 7.64 (2H, t,

In the same manner as in Example 79, the title compound (25 mg, 36%) was obtained as white crystals from the compound of Example 589 (70 mg, 0.13 mmol).

$^1$H-NMR (300 MHz, DMSO-$d_6$) δ:1.06 (3H, d, J=6.3 Hz), 1.23 (1H, q, J=11.6 Hz), 1.40-1.60 (1H, m), 1.85 (2H, d, J=10.8 Hz), 2.21-2.32 (3H, m), 2.74-2.83 (1H, m), 2.96 (1H, t, J=12.3 Hz), 3.45-3.51 (2H, m), 3.70-3.90 (1H, m), 3.98 (3H, s), 4.30-4.38 (4H, m), 5.97 (2H, s), 7.29-7.45 (2H, m), 7.48 (1H, d, J=7.5 Hz), 7.63 (2H, t, J=7.5 Hz), 7.74-7.84 (2H, m), 8.17 (2H, d, J=7.8 Hz), 8.37 (1H, d, J=8.4 Hz).

Example 591

Production of N-[1-(hydroxyacetyl)-2-methylpiperidin-4-yl]-3-methoxy-1-methyl-4-oxo-5-(2-oxo-2-phenylethyl)-4,5-dihydro-1H-pyrrolo[3,2-c]quinoline-2-carboxamide

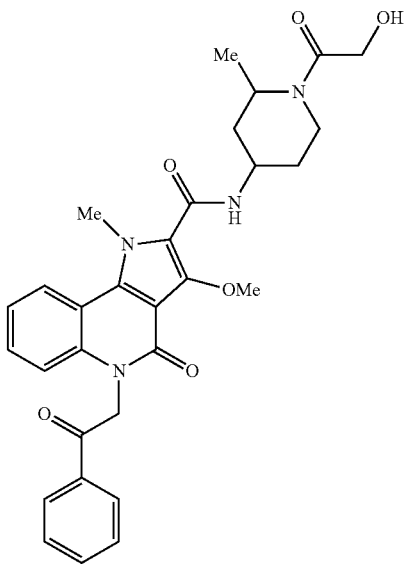 [SMILES: COc1c(C(=O)NC2CCN(C(=O)CO)C(C)C2)n(C)c2c1c(=O)n(CC(=O)c1ccccc1)c1ccccc21]

In the same manner as in Example 130, the title compound (35 mg, 40%) was obtained as white crystals from the compound of Example 589 (80 mg, 0.15 mmol).

$^1$H-NMR (300 MHz, DMSO-$d_6$) δ:1.28 (3H, d, J=6.9 Hz), 1.70-1.95 (4H, m), 3.10-3.25 (1H, m), 4.03-4.15 (7H, m), 4.30-4.34 (4H, m), 4.50 (1H, t, J=5.4 Hz), 5.98 (2H, s), 7.30-7.41 (2H, m), 7.49 (1H, t, J=8.1 Hz), 7.63 (2H, t, J=7.5 Hz), 7.76 (1H, t, J=7.2 Hz), 8.07 (1H, d, J=6.6 Hz), 8.17 (2H, d, J=7.2 Hz), 8.38 (1H, d, J=7.5 Hz).

Example 592

Production of N-[1-(4-cyanophenyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

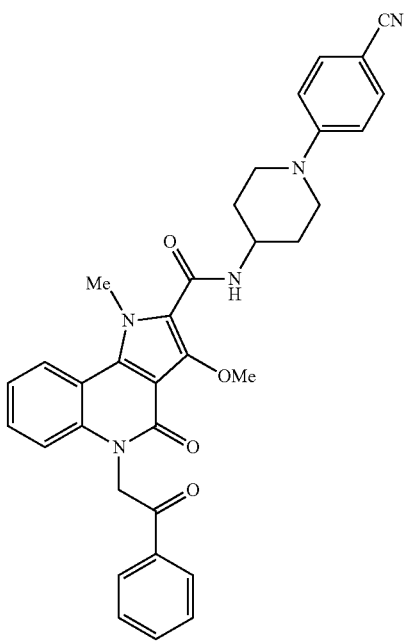 [SMILES: COc1c(C(=O)NC2CCN(c3ccc(C#N)cc3)CC2)n(C)c2c1c(=O)n(CC(=O)c1ccccc1)c1ccccc21]

A solution of the compound of Example 77 (300 mg, 0.64 mmol), 4-fluorobenzonitrile (115 mg, 0.95 mmol) and potassium carbonate (176 mg, 1.3 mmol) in N-methylpyrrolidone (3.0 mL) was stirred at 120° C. for 16.5 hr. The reaction mixture was diluted with water, and extracted twice with ethyl acetate. The extract was washed with brine, dried over magnesium sulfate, and concentrated under reduced pressure. The residue was purified by aminosilica gel chromatography (eluate; ethyl acetate/hexane=30/70-100/0) and recrystallized from THF-diethyl ether to give the title compound (73 mg, 20%) as a pale-yellow solid.

$^1$H-NMR (300 MHz, DMSO-$d_6$) δ:1.52-1.70 (2H, m), 1.87-2.03 (2H, m), 3.02-3.20 (2H, m), 3.81-4.00 (5H, m), 4.03-4.20 (1H, m), 4.31 (3H, s), 5.97 (2H, s), 6.98-7.12 (2H, m), 7.26-7.41 (2H, m), 7.43-7.52 (1H, m), 7.53-7.69 (4H, m), 7.71-7.82 (1H, m), 7.98 (1H, d, J=7.9 Hz), 8.12-8.22 (2H, m), 8.37 (1H, dd, J=8.4, 1.2 Hz).

Example 593

Production of N-[1-(hydroxyacetyl)piperidin-4-yl]-3-methoxy-1-methyl-4-oxo-5-[3-(trifluoromethoxy)benzyl]-4,5-dihydro-1H-pyrrolo[3,2-c]quinoline-2-carboxamide

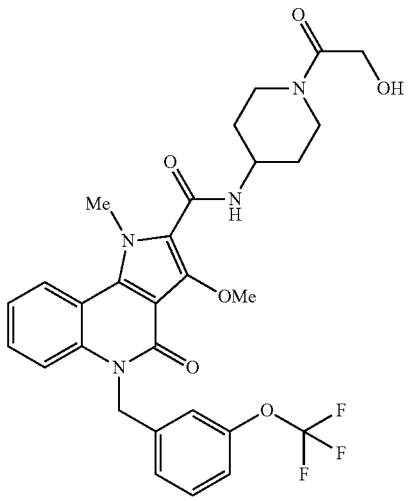 [SMILES: COc1c(C(=O)NC2CCN(C(=O)CO)CC2)n(C)c2c1c(=O)n(Cc1cccc(OC(F)(F)F)c1)c1ccccc21]

In the same manner as in Example 570, 2-{4-[({3-methoxy-1-methyl-4-oxo-5-[3-(trifluoromethoxy)benzyl]-4,5-dihydro-1H-pyrrolo[3,2-c]quinolin-2-yl}carbonyl)amino]piperidin-1-yl}-2-oxoethyl acetate (70 mg) was obtained as a colorless amorphous solid from the compound of Example 672 (500 mg, 1.10 mmol) and 3-trifluoromethoxybenzyl bromide (1.0 g, 3.92 mmol).

A solution of 2-{4-[({3-methoxy-1-methyl-4-oxo-5-[3-(trifluoromethoxy)benzyl]-4,5-dihydro-1H-pyrrolo[3,2-c]quinolin-2-yl}carbonyl)amino]piperidin-1-yl}-2-oxoethyl acetate (70 mg) and potassium carbonate (77 mg, 0.55 mmol) in THF (2 mL)-methanol (1 mL)-water (1 mL) was stirred at room temperature for 3 hr. The reaction mixture was diluted with saturated sodium hydrogen carbonate solution, and extracted twice with ethyl acetate. The extract was washed with brine, dried over magnesium sulfate, and concentrated under reduced pressure. The residue was recrystallized from ethyl acetate-hexane to give the title compound (23 mg, 4%) as white crystals.

$^1$H-NMR (300 MHz, DMSO-$d_6$) δ:1.35-1.65 (2H, m), 1.85-1.95 (2H, m), 2.93 (1H, t, J=11.7 Hz), 3.15 (1H, t, J=11.7 Hz), 3.68 (1H, d, J=12.3 Hz), 4.01-4.29 (10H, m), 4.53 (1H, t, J=5.4 Hz), 5.50-5.70 (2H, br), 7.16-7.33 (4H, m), 7.41-7.47 (3H, m), 8.00 (1H, d, J=8.1 Hz), 8.36 (1H, d, J=8.1 Hz).

Example 594

Production of N-[1-(2-hydroxyethyl)piperidin-4-yl]-3-methoxy-4-oxo-5-[2-(1H-pyrrol-1-yl)ethyl]-4,5-dihydrothieno[3,2-c]quinoline-2-carboxamide trifluoroacetate

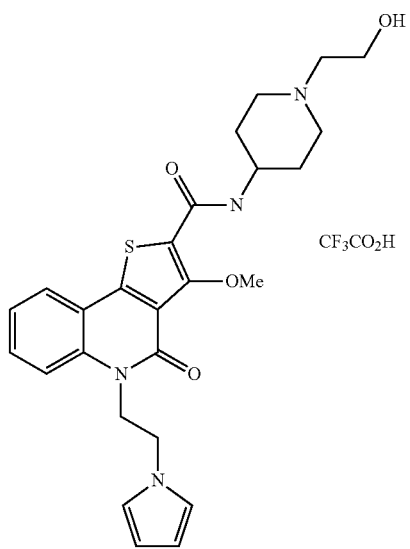 [SMILES: COc1c(C(=O)NC2CCN(CCO)CC2)sc2c1c(=O)n(CCn1cccc1)c1ccccc21 ; "CF3CO2H"]

To a 0.2M-DMF solution of the compound of Example 667 (500 μL, 100 μmol) was added sodium carbonate (1 mmol, 138 mg), and a 0.3M-DMF solution (500 μL, 150 μmol) of 1-(2-bromoethyl)-1H-pyrrole was added dropwise thereto. The reaction mixture was stirred at 40° C. overnight. Ethyl acetate (3 mL) and water (2 mL) were added thereto, and the mixture was extracted and the organic layer was separate. Ethyl acetate was evaporated under reduced pressure and the residue was dissolved in acetonitrile (500 μl), purified (trifluoroacetic acid type) by preparative HPLC to give the title compound.

yield: 6.9 mg

LC-MS analysis: purity 84%

MS (ESI+): 495(M+H)

Example 595-Example 602

In the same manner as in Example 594, the compounds shown in Table 1 were obtained from the compound of Example 667 or Example 683 and corresponding halide.

TABLE 1

| Example No. | structure | yield (mg) | purity (%) | MS (ESI+) |
|---|---|---|---|---|
| 595 | 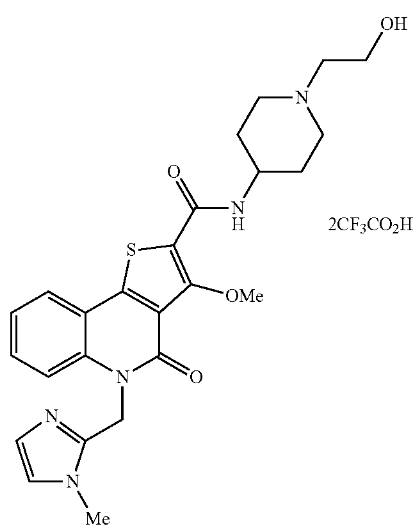 [SMILES: COc1c(C(=O)NC2CCN(CCO)CC2)sc2c1c(=O)n(Cc1nccn1C)c1ccccc21] | 8.6 | 100 | 496 |

TABLE 1-continued
| Example No. | structure | yield (mg) | purity (%) | MS (ESI+) |
|---|---|---|---|---|
| 596 | 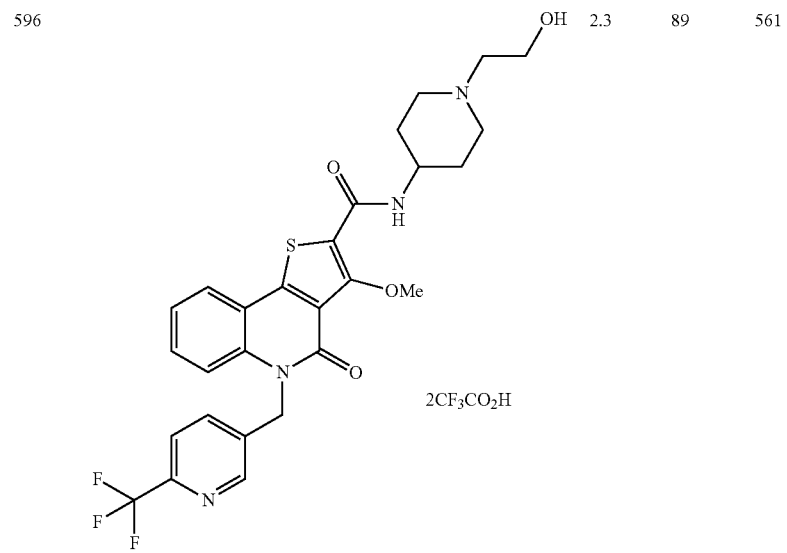 | 2.3 | 89 | 561 |
| 597 | 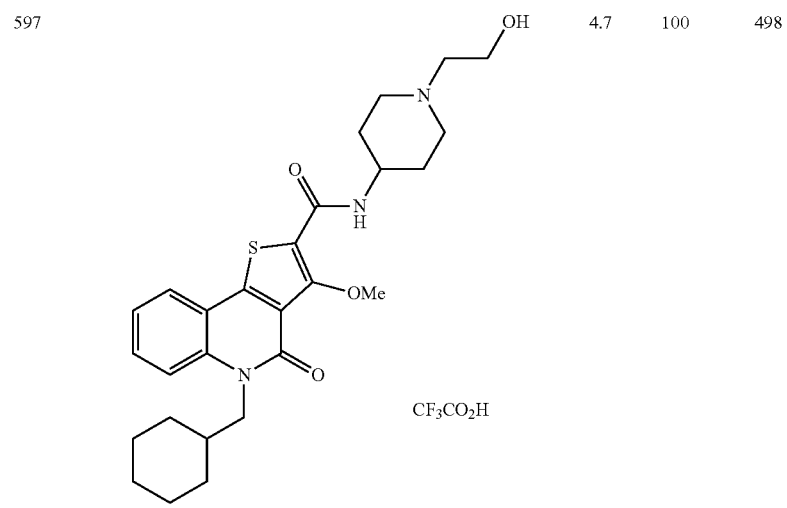 | 4.7 | 100 | 498 |
| 598 | 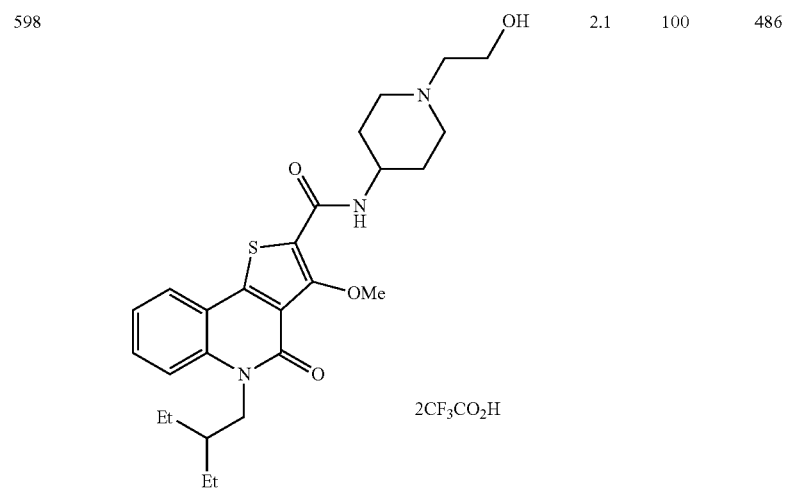 | 2.1 | 100 | 486 |

TABLE 1-continued
| Example No. | structure | yield (mg) | purity (%) | MS (ESI+) |
|---|---|---|---|---|
| 599 | 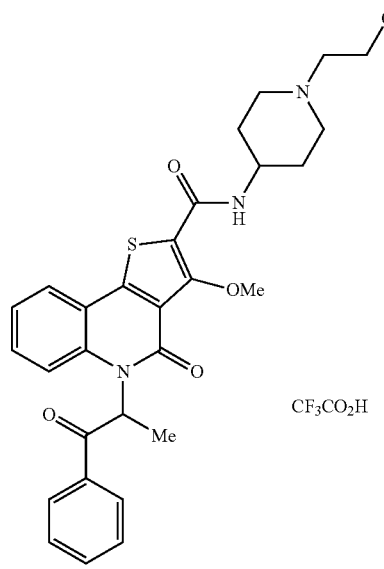 | 7.4 | 100 | 534 |
| 600 | 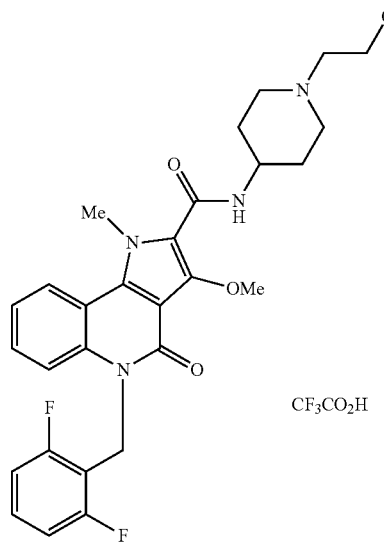 | 1.3 | 81 | 525 |

TABLE 1-continued

| Example No. | structure | yield (mg) | purity (%) | MS (ESI+) |
| --- | --- | --- | --- | --- |
| 601 | [structure] 2CF₃CO₂H | 3.1 | 97 | 558 |
| 602 | [structure] CF₃CO₂H | 4.3 | 100 | 547 |

Example 603

Production of ethyl(2-{[1-(hydroxyacetyl)piperidin-4-yl]carbamoyl}-3-methoxy-1-methyl-4-oxo-1,4-dihydro-5H-pyrrolo[3,2-c]quinolin-5-yl)acetate

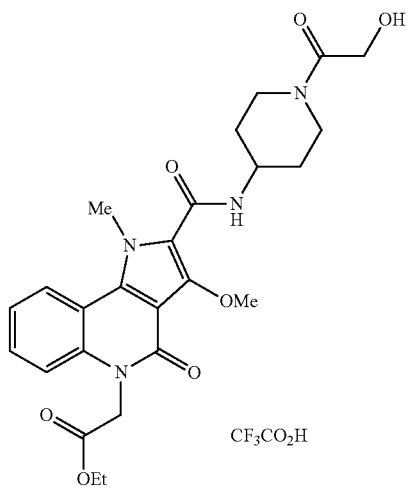 [SMILES: CCOC(=O)Cn1c(=O)c2c(OC)c(C(=O)NC3CCN(C(=O)CO)CC3)n(C)c2c2ccccc21 ; "CF3CO2H"]

To a 0.2M-DMF solution of the compound of Example 672 (500 μL, 100 μmol) was added sodium carbonate (1 mmol, 138 mg), and a 2M-DMF solution (500 μL, 1 mmol) of ethyl bromoacetate was added dropwise thereto. The reaction mixture was stirred at 80° C. overnight. After completion of the reaction, DMF was evaporated using a centrifugal vacuum concentrator under heating at 60° C. Acetonitrile-DMSO (1:1, 500 μl) was added to the residue, and the insoluble material was filtered off. The filtrate was purified (ammonium carbonate type) by preparative HPLC to give the title compound.

yield: 2.9 mg

LC-MS analysis: purity 97%

MS (ESI+): 499(M+H)

Example 604-Example 618

In the same manner as in Example 594, the compounds shown in Table 2 were obtained from the compound of Example 672 and corresponding halide.

TABLE 2

| Example No. | structure | yield (mg) | purity (%) | MS (ESI+) |
|---|---|---|---|---|
| 604 | 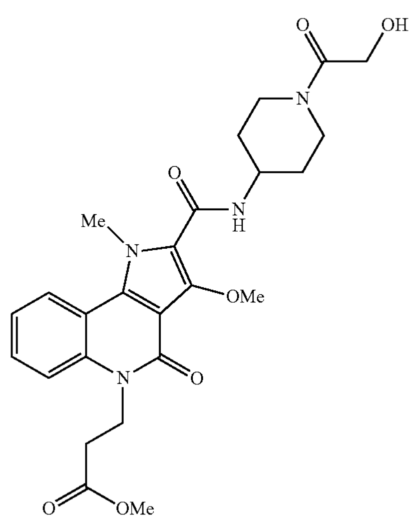 [SMILES: COC(=O)CCn1c(=O)c2c(OC)c(C(=O)NC3CCN(C(=O)CO)CC3)n(C)c2c2ccccc21] | 7.3 | 100 | 499 |

TABLE 2-continued

| Example No. | structure | yield (mg) | purity (%) | MS (ESI+) |
|---|---|---|---|---|
| 605 | 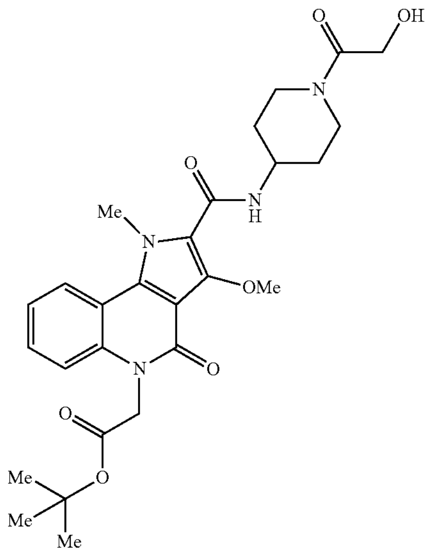 [SMILES: COc1c(C(=O)NC2CCN(C(=O)CO)CC2)n(C)c2c1c(=O)n(CC(=O)OC(C)(C)C)c1ccccc21] | 8.4 | 100 | 527 |
| 606 | 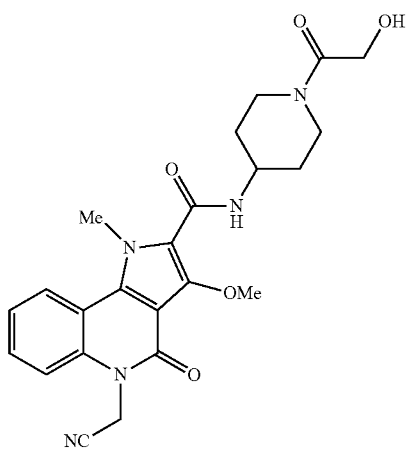 [SMILES: COc1c(C(=O)NC2CCN(C(=O)CO)CC2)n(C)c2c1c(=O)n(CC#N)c1ccccc21] | 6.2 | 71 | 452 |
| 607 | 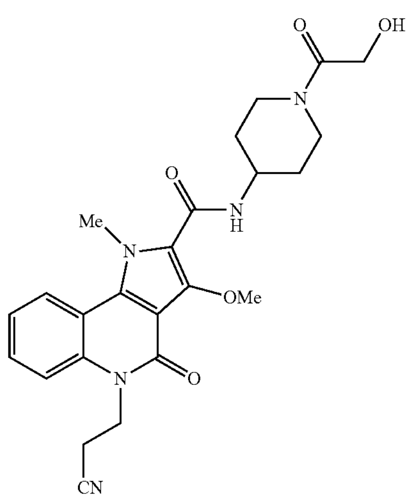 [SMILES: COc1c(C(=O)NC2CCN(C(=O)CO)CC2)n(C)c2c1c(=O)n(CCC#N)c1ccccc21] | 16.9 | 100 | 466 |

TABLE 2-continued
| Example No. | structure | yield (mg) | purity (%) | MS (ESI+) |
|---|---|---|---|---|
| 608 | 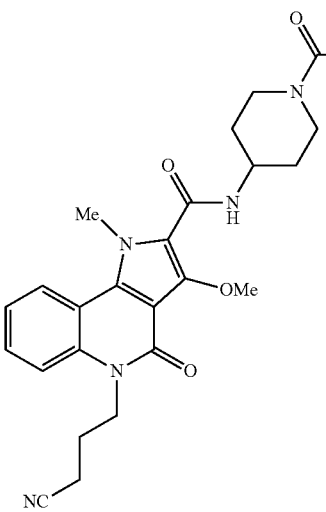 | 13.2 | 100 | 480 |
| 609 | 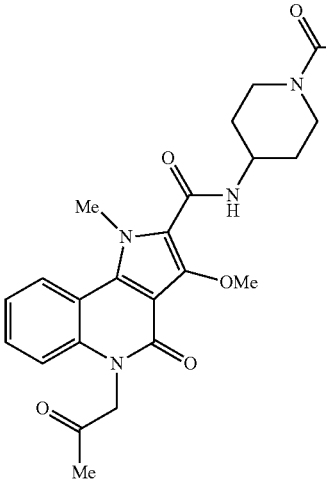 | 10.7 | 100 | 469 |
| 610 | 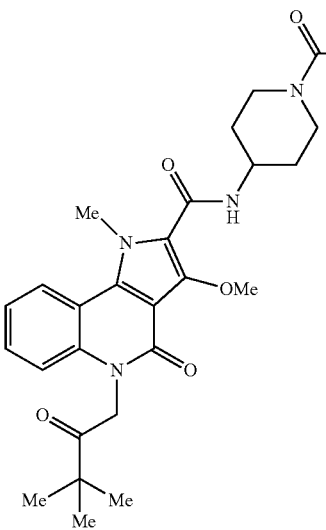 | 11.7 | 100 | 511 |

TABLE 2-continued

| Example No. | structure | yield (mg) | purity (%) | MS (ESI+) |
|---|---|---|---|---|
| 611 | 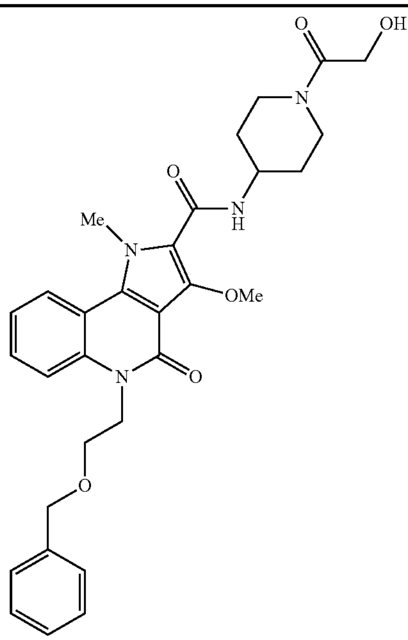 | 17.3 | 100 | 547 |
| 612 | 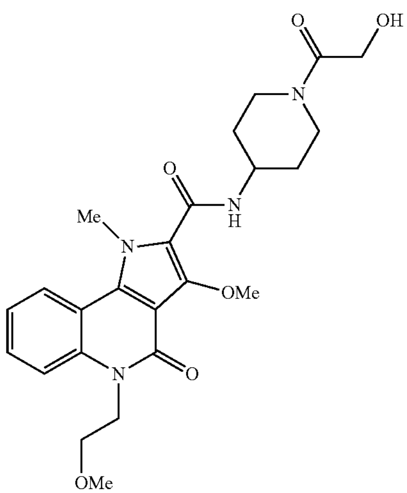 [SMILES: COCCn1c(=O)c2c(OC)c(C(=O)NC3CCN(C(=O)CO)CC3)n(C)c2c2ccccc21] | 1.6 | 100 | 471 |
| 613 | 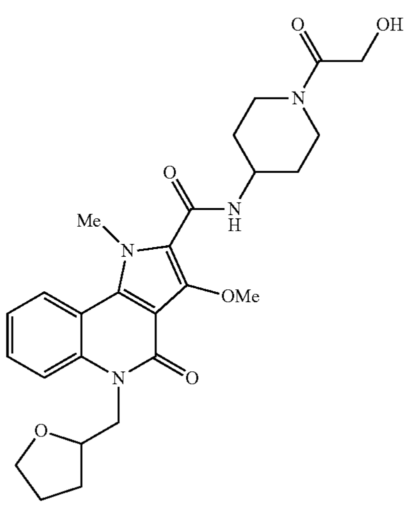 [SMILES: COc1c(C(=O)NC2CCN(C(=O)CO)CC2)n(C)c2c1c(=O)n(CC1CCCO1)c1ccccc21] | 11 | 100 | 497 |

TABLE 2-continued
| Example No. | structure | yield (mg) | purity (%) | MS (ESI+) |
|---|---|---|---|---|
| 614 | 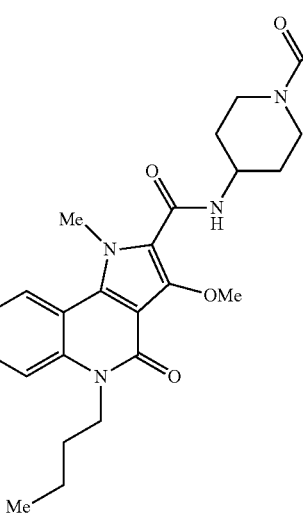 | 7.7 | 100 | 469 |
| 615 | 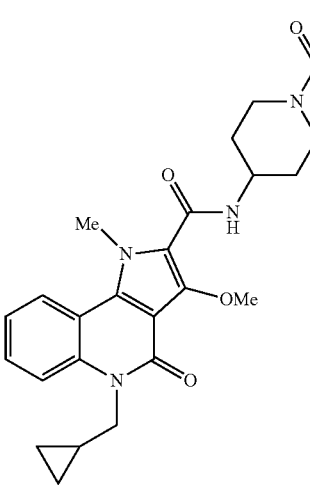 | 5.3 | 100 | 467 |
| 616 | 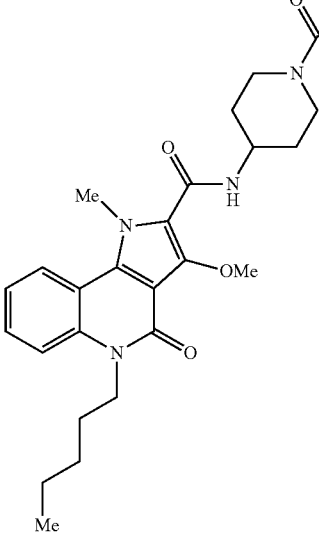 | 12 | 100 | 483 |

TABLE 2-continued
| Example No. | structure | yield (mg) | purity (%) | MS (ESI+) |
|---|---|---|---|---|
| 617 | 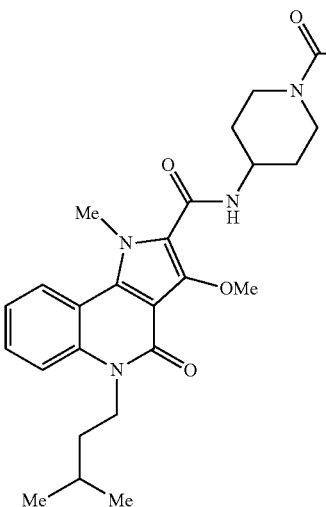 | 6.6 | 100 | 483 |
| 618 | 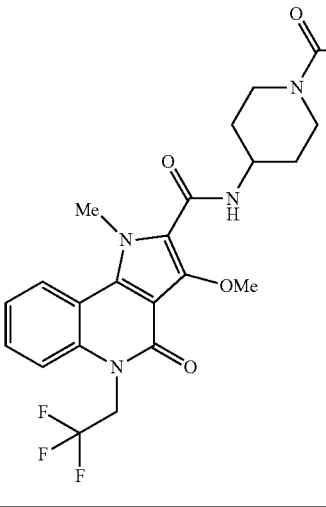 | 8.2 | 100 | 495 |

Example 619

Production of 3-methoxy-1-methyl-4-oxo-5-(2-oxo-2-phenylethyl)-N-(1-pyridin-3-ylpiperidin-4-yl)-4,5-dihydro-1H-pyrrolo[3,2-c]quinoline-2-carboxamide

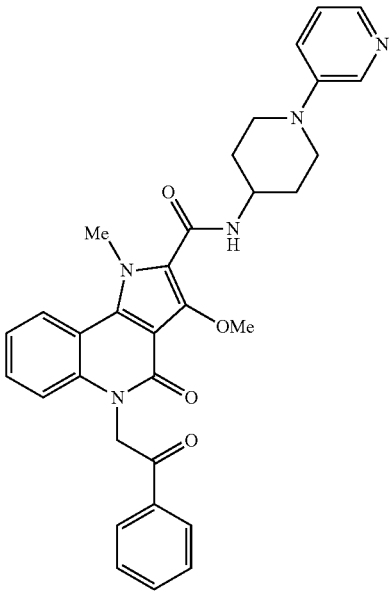 [SMILES: COc1c(C(=O)NC2CCN(c3cccnc3)CC2)n(C)c2c1c(=O)n(CC(=O)c1ccccc1)c1ccccc21]

In the same manner as in Example 575, the title compound (19 mg, 5.4%) was obtained as a white solid from the compound of Reference Example 77 (300 mg, 0.64 mmol) and 3-bromopyridine (0.50 mL, 5.2 mmol).

$^1$H-NMR (300 MHz, DMSO-$d_6$) δ:1.58-1.81 (2H, m), 1.89-2.04 (2H, m), 2.90-3.04 (2H, m), 3.64-3.77 (2H, m), 3.97 (3H, s), 4.00-4.13 (1H, m), 4.32 (3H, s), 5.97 (2H, s), 7.15-7.25 (1H, m), 7.27-7.41 (3H, m), 7.42-7.52 (1H, m), 7.57-7.68 (2H, m), 7.71-7.82 (1H, m), 7.93-8.04 (2H, m), 8.11-8.21 (2H, m), 8.30-8.43 (2H, m).

Example 620

Production of 3-methoxy-1-methyl-4-oxo-5-(2-oxo-2-phenylethyl)-N-(1-pyridin-2-ylpiperidin-4-yl)-4,5-dihydro-1H-pyrrolo[3,2-c]quinoline-2-carboxamide

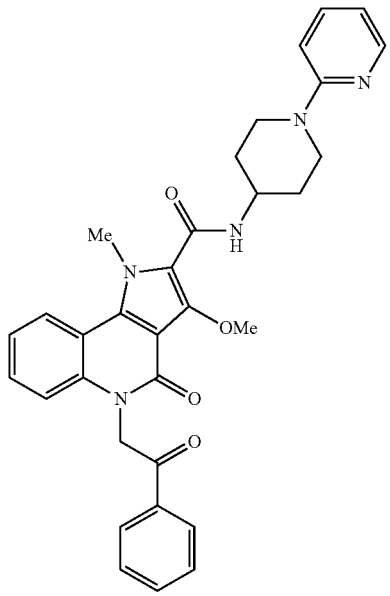 [SMILES: COc1c(C(=O)NC2CCN(c3ccccn3)CC2)n(C)c2c1c(=O)n(CC(=O)c1ccccc1)c1ccccc21]

A solution of the compound of Example 77 (284 mg, 0.60 mmol), 2-iodopyridine (0.13 mL, 1.2 mmol) and potassium carbonate (208 mg, 1.5 mmol) in DMF (3.0 mL) was stirred at 90° C. for 5.5 hr. 2-Bromopyridine (0.23 mL, 2.5 mmol) and triethylamine (0.49 mL, 3.5 mmol) were added to the reaction mixture, and the mixture was stirred under microwave irradiation at 165° for 1 hr. The reaction mixture was diluted with water, and extracted twice with ethyl acetate. The extract was washed with brine, dried over magnesium sulfate, and concentrated under reduced pressure. The residue was purified by aminosilica gel chromatography (eluate; ethyl acetate/hexane=30/70-100/0) and recrystallized from THF-diethyl ether to give the title compound (38 mg, 12%) as a white solid.

$^1$H-NMR (300 MHz, DMSO-$d_6$) δ:1.45-1.65 (2H, m), 1.86-2.00 (2H, m), 2.99-3.14 (2H, m), 3.95 (3H, s), 4.03-4.14 (1H, m), 4.16-4.26 (2H, m), 4.31 (3H, s), 5.97 (2H, s), 6.61 (1H, dd, J=6.8, 5.1 Hz), 6.87 (1H, d, J=8.7 Hz), 7.26-7.42 (2H, m), 7.43-7.57 (2H, m), 7.59-7.68 (2H, m), 7.70-7.81 (1H, m), 7.97 (1H, d, J=7.9 Hz), 8.08-8.21 (3H, m), 8.37 (1H, d, J=7.7 Hz).

Example 621

Production of N-[1-(2-cyanophenyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

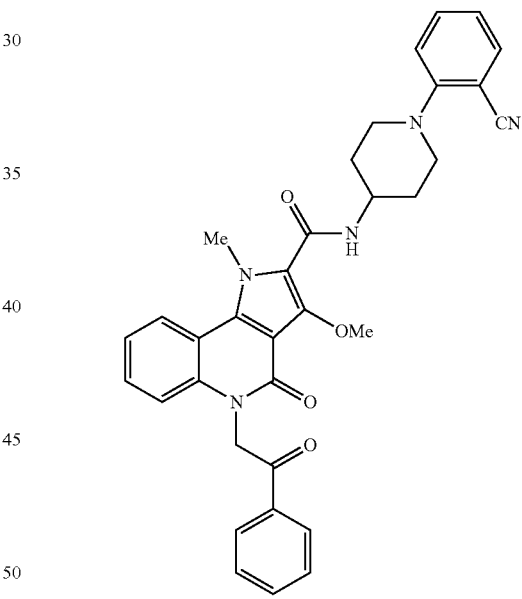

A solution of the compound of Example 77 (300 mg, 0.59 mmol), 2-fluorobenzonitrile (0.50 mL, 4.6 mmol) and triethylamine (0.50 mL, 3.6 mmol) in DMF (3.5 mL) was stirred under microwave irradiation at 130° C. for 30 min. 2-Bromobenzonitrile (143 mg, 1.2 mmol) and potassium carbonate (208 mg, 1.5 mmol) were added to the reaction mixture, and the mixture was stirred under microwave irradiation at 165° C. for 30 min. The reaction mixture was diluted with water, and extracted twice with ethyl acetate. The extract was washed with brine, dried over magnesium sulfate, and concentrated under reduced pressure. The residue was purified by aminosilica gel chromatography (eluate; ethyl acetate/hexane=50/50-100/0) and recrystallized from ethyl acetate-hexane to give the title compound (74 mg, 22%) as a pale-yellow solid.

¹H-NMR (300 MHz, DMSO-d₆) δ:1.72-1.89 (2H, m), 1.97-2.10 (2H, m), 2.94-3.08 (2H, m), 3.43-3.54 (2H, m), 3.95-4.14 (4H, m), 4.32 (3H, s), 5.98 (2H, s), 7.05-7.13 (1H, m), 7.22 (1H, d, J=8.1 Hz), 7.28-7.42 (2H, m), 7.44-7.52 (1H, m), 7.56-7.81 (5H, m), 8.06 (1H, d, J=7.9 Hz), 8.14-8.23 (2H, m), 8.38 (1H, dd, J=8.3, 1.1 Hz).

Example 622

Production of N-[1-(3-cyanophenyl)piperidin-4-yl]-3-methoxy-1-methyl-4-oxo-5-(2-oxo-2-phenylethyl)-4,5-dihydro-1H-pyrrolo[3,2-c]quinoline-2-carboxamide

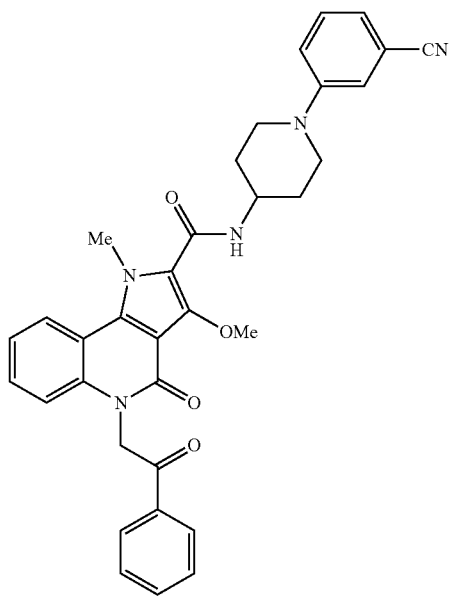 [SMILES: COc1c(C(=O)NC2CCN(c3cccc(C#N)c3)CC2)n(C)c2c1c(=O)n(CC(=O)c1ccccc1)c1ccccc21]

A solution of the compound of Example 77 (300 mg, 0.59 mmol), 3-bromobenzonitrile (143 mg, 1.2 mmol), tris(dibenzylideneacetone)dipalladium (0) (54 mg, 0.059 mmol), x-phos (56 mg, 0.12 mmol), sodium tert-butoxide (142 mg, 1.5 mmol) and triethylamine (0.082 mL, 0.59 mmol) in 2-butanone (4.0 mL) was stirred under microwave irradiation at 130° C. for 40 min. The reaction mixture was diluted with water, and extracted twice with ethyl acetate. The extract was dried over magnesium sulfate, and concentrated under reduced pressure. The residue was purified by aminosilica gel chromatography (eluate; ethyl acetate/hexane=40/60-100/0) and recrystallized from ethyl acetate-hexane to give the title compound (25 mg, 7.4%) as a white solid.

¹H-NMR (300 MHz, DMSO-d₆) δ:1.58-1.74 (2H, m), 1.88-2.01 (2H, m), 2.94-3.07 (2H, m), 3.71-3.83 (2H, m), 3.96 (3H, s), 4.00-4.12 (1H, m), 4.31 (3H, s), 5.97 (2H, s), 7.10-7.16 (1H, m), 7.27-7.42 (5H, m), 7.44-7.52 (1H, m), 7.58-7.68 (2H, m), 7.71-7.80 (1H, m), 7.99 (1H, d, J=7.9 Hz), 8.11-8.22 (2H, m), 8.38 (1H, dd, J=8.3, 1.1 Hz).

Example 623

Production of 3-methoxy-1-methyl-4-oxo-5-(2-oxo-2-phenylethyl)-N-{1-[2-(trifluoromethyl)pyridin-4-yl]piperidin-4-yl}-4,5-dihydro-1H-pyrrolo[3,2-c]quinoline-2-carboxamide

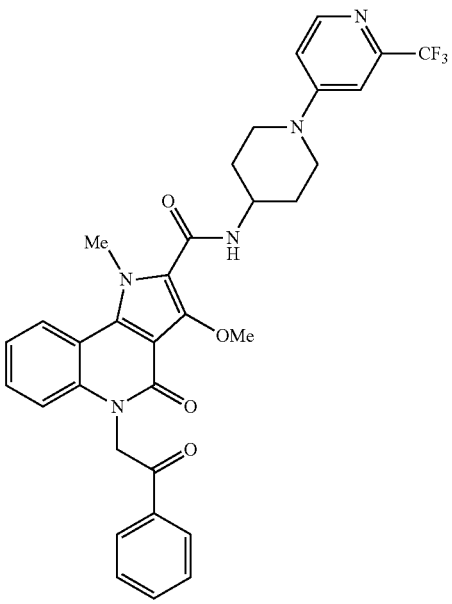 [SMILES: COc1c(C(=O)NC2CCN(c3ccnc(C(F)(F)F)c3)CC2)n(C)c2c1c(=O)n(CC(=O)c1ccccc1)c1ccccc21]

A solution of the compound of Example 77 (300 mg, 0.59 mmol), potassium carbonate (204 mg, 1.5 mmol) and triethylamine (0.082 mL, 0.59 mmol) in DMF (3.0 mL) was heated to 80° C., 4-bromo-2-(trifluoromethyl)pyridine (133 mg, 0.59 mmol) was added, and the mixture was stirred at 100° C. for 23 hr. The reaction mixture was diluted with water, and extracted 3 times with ethyl acetate. The extract was dried over magnesium sulfate, and concentrated under reduced pressure. The residue was purified by aminosilica gel chromatography (eluate; ethyl acetate/hexane=50/50-100/0) and recrystallized from ethyl acetate-hexane to give the title compound (126 mg, 35%) as a white solid.

¹H-NMR (300 MHz, DMSO-d₆) δ:1.52-1.70 (2H, m), 1.89-2.02 (2H, m), 3.11-3.25 (2H, m), 3.90-4.07 (5H, m), 4.10-4.24 (1H, m), 4.31 (3H, s), 5.97 (2H, s), 7.08 (1H, dd, J=6.1, 2.5 Hz), 7.21-7.27 (1H, m), 7.27-7.41 (2H, m), 7.43-7.52 (1H, m), 7.57-7.67 (2H, m), 7.72-7.80 (1H, m), 7.98 (1H, d, J=7.9 Hz), 8.13-8.21 (2H, m), 8.27 (1H, d, J=5.9 Hz), 8.37 (1H, dd, J=8.2, 1.2 Hz).

Example 624

Production of N-[1-(2-cyanopyridin-4-yl)piperidin-4-yl]-3-methoxy-1-methyl-4-oxo-5-(2-oxo-2-phenylethyl)-4,5-dihydro-1H-pyrrolo[3,2-c]quinoline-2-carboxamide

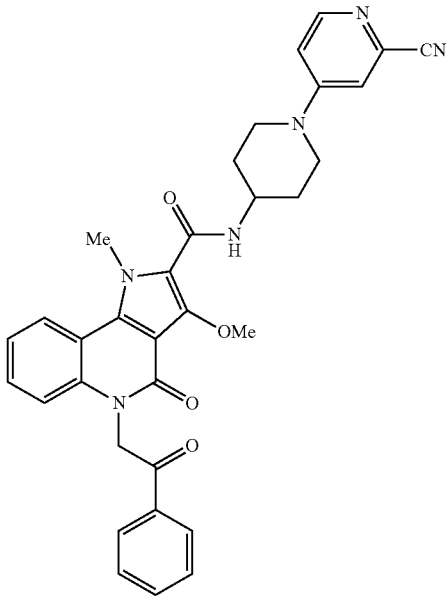 [SMILES: COc1c(C(=O)NC2CCN(c3ccnc(C#N)c3)CC2)n(C)c2c1c(=O)n(CC(=O)c1ccccc1)c1ccccc21]

In the same manner as in Example 623, the title compound (70 mg, 21%) was obtained as a white solid from the compound of Example 77 (300 mg, 0.59 mmol) and 4-iodopyridine-2-carbonitrile (136 mg, 0.59 mmol).

$^1$H-NMR (300 MHz, DMSO-$d_6$) δ:1.50-1.69 (2H, m), 1.86-1.98 (2H, m), 3.10-3.25 (2H, m), 3.90-4.05 (5H, m), 4.08-4.24 (1H, m), 4.31 (3H, s), 5.97 (2H, s), 7.10 (1H, dd, J=6.1, 2.7 Hz), 7.25-7.42 (2H, m), 7.43-7.55 (2H, m), 7.58-7.68 (2H, m), 7.71-7.80 (1H, m), 7.97 (1H, d, J=7.7 Hz), 8.11-8.27 (3H, m), 8.37 (1H, dd, J=8.3, 1.1 Hz).

Example 625

Production of N-[4-(hydroxymethyl)cyclohexyl]-3-methoxy-1-methyl-4-oxo-5-(2-oxo-2-phenylethyl)-4,5-dihydro-1H-pyrrolo[3,2-c]quinoline-2-carboxamide

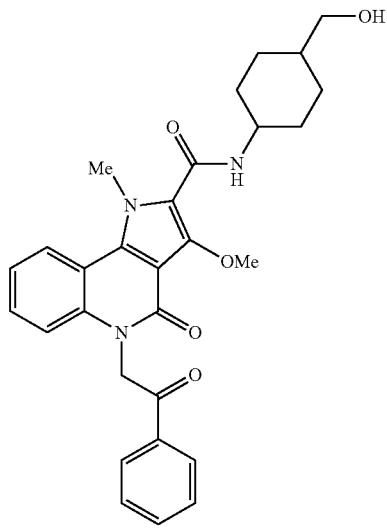 [SMILES: COc1c(C(=O)NC2CCC(CO)CC2)n(C)c2c1c(=O)n(CC(=O)c1ccccc1)c1ccccc21]

In the same manner as in Example 25, the title compound mg, 64%) was obtained as a white solid from the compound of Reference Example 28 (200 mg, 0.51 mmol) and (4-aminocyclohexyl)methanol (130 mg, 1.0 mmol).

$^1$H-NMR (300 MHz, DMSO-$d_6$) δ:0.92-1.10 (2H, m), 1.21-1.43 (3H, m), 1.72-1.86 (2H, m), 1.89-2.02 (2H, m), 3.24 (2H, t, J=5.8 Hz), 3.66-3.83 (1H, m), 3.96 (3H, s), 4.31 (3H, s), 4.42 (1H, t, J=5.3 Hz), 5.97 (2H, s), 7.25-7.41 (2H, m), 7.42-7.53 (1H, m), 7.58-7.68 (2H, m), 7.71-7.85 (2H, m), 8.10-8.22 (2H, m), 8.37 (1H, dd, J=8.3, 1.1 Hz).

Example 626

Production of N-[1-(6-cyanopyridin-3-yl)piperidin-4-yl]-3-methoxy-1-methyl-4-oxo-5-(2-oxo-2-phenylethyl)-4,5-dihydro-1H-pyrrolo[3,2-c]quinoline-2-carboxamide

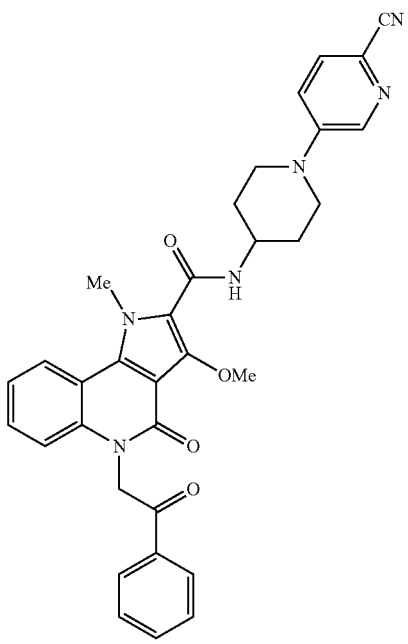 [SMILES: COc1c(C(=O)NC2CCN(c3ccc(C#N)nc3)CC2)n(C)c2c1c(=O)n(CC(=O)c1ccccc1)c1ccccc21]

In the same manner as in Example 623, the title compound (52 mg, 15%) was obtained as a pale-yellow solid from the compound of Example 77 (300 mg, 0.59 mmol) and 5-bromopyridine-2-carbonitrile (119 mg, 0.65 mmol).

$^1$H-NMR (300 MHz, DMSO-$d_6$) δ:1.56-1.74 (2H, m), 1.88-2.02 (2H, m), 3.10-3.25 (2H, m), 3.91-4.04 (5H, m), 4.06-4.22 (1H, m), 4.31 (3H, s), 5.97 (2H, s), 7.25-7.52 (4H, m), 7.58-7.68 (2H, m), 7.71-7.81 (2H, m), 7.98 (1H, d, J=7.9 Hz), 8.12-8.21 (2H, m), 8.37 (1H, dd, J=8.3, 1.1 Hz), 8.46 (1H, d, J=2.8 Hz).

507

Example 627

Production of N-[1-(hydroxyacetyl)piperidin-4-yl]-3-methoxy-1-methyl-5-[(6-methylpyridin-2-yl)methyl]-4-oxo-4,5-dihydro-1H-pyrrolo[3,2-c]quinoline-2-carboxamide

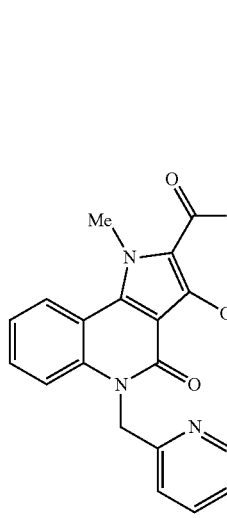

In the same manner as in Example 570, 2-{4-[({3-methoxy-1-methyl-5-[(6-methylpyridin-2-yl)methyl]-4-oxo-4,5-dihydro-1H-pyrrolo[3,2-c]quinolin-2-yl}carbonyl)amino]piperidin-1-yl}-2-oxoethyl acetate (80 mg) was obtained as a colorless amorphous solid from the compound of Example 672 (300 mg, 0.66 mmol), 2-(chloromethyl)-6-methylpyridine hydrochloride (940 mg, 5.28 mmol) and cesium carbonate (2.18 g, 6.60 mmol).

A solution of 2-{4-[({3-methoxy-1-methyl-5-[(6-methylpyridin-2-yl)methyl]-4-oxo-4,5-dihydro-1H-pyrrolo[3,2-c]quinolin-2-yl}carbonyl)amino]piperidin-1-yl}-2-oxoethyl acetate (80 mg) and potassium carbonate (100 mg, 0.71 mmol) in THF (2 mL)-methanol (1 mL)-water (1 mL) was stirred at room temperature for 3 hr. The reaction mixture was diluted with saturated sodium hydrogen carbonate solution, and extracted twice with ethyl acetate. The extract was washed with brine, dried over magnesium sulfate, and concentrated under reduced pressure. The residue was recrystallized from ethyl acetate-hexane to give the title compound (37 mg, 11%) as white crystals.

$^1$H-NMR (300 MHz, DMSO-$d_6$) δ:1.40-1.60 (2H, m), 1.90 (2H, d, J=9.6 Hz), 2.47 (3H, s), 2.93 (1H, t, J=11.7 Hz), 3.14 (1H, t, J=11.6 Hz), 3.67 (1H, d, J=12.9 Hz), 3.99-4.29 (10H, m), 4.52 (1H, t, J=5.4 Hz), 5.59 (2H, s), 6.71 (1H, d, J=7.8 Hz), 7.12 (1H, d, J=7.8 Hz), 7.29 (1H, t, J=7.5 Hz), 7.37-7.48 (2H, m), 7.55 (1H, t, J=7.8 Hz), 7.98 (1H, d, J=7.8 Hz), 8.35 (1H, d, J=7.2 Hz).

508

Example 628

Production of 5-(2-chlorobenzyl)-N-[1-(hydroxyacetyl)piperidin-4-yl]-3-methoxy-1-methyl-4-oxo-4,5-dihydro-1H-pyrrolo[3,2-c]quinoline-2-carboxamide

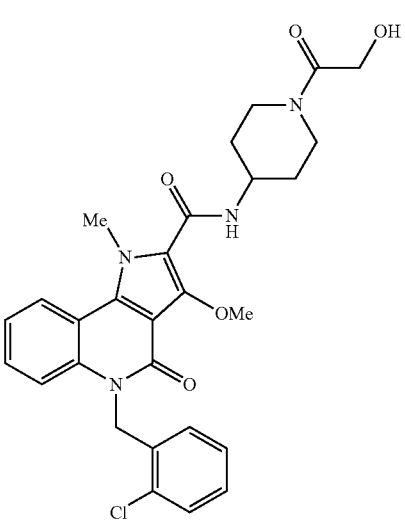 [SMILES: COc1c(C(=O)NC2CCN(C(=O)CO)CC2)n(C)c2c1c(=O)n(Cc1ccccc1Cl)c1ccccc21]

In the same manner as in Example 570, 2-[4-({[5-(2-chlorobenzyl)-3-methoxy-1-methyl-4-oxo-4,5-dihydro-1H-pyrrolo[3,2-c]quinolin-2-yl]carbonyl}amino)piperidin-1-yl]-2-oxoethyl acetate (80 mg) was obtained as a colorless amorphous solid from the compound of Example 672 (300 mg, 0.66 mmol), 2-chlorobenzyl chloride (1.06 g, 6.60 mmol) and cesium carbonate (2.18 g, 6.60 mmol).

A solution of 2-[4-({[5-(2-chlorobenzyl)-3-methoxy-1-methyl-4-oxo-4,5-dihydro-1H-pyrrolo[3,2-c]quinolin-2-yl]carbonyl}amino)piperidin-1-yl]-2-oxoethyl acetate (80 mg) and potassium carbonate (100 mg, 0.71 mmol) in THF (2 mL)-methanol (1 mL)-water (1 mL) was stirred at room temperature for 3 hr. The reaction mixture was diluted with saturated sodium hydrogen carbonate solution, and extracted twice with ethyl acetate. The extract was washed with brine, dried over magnesium sulfate, and concentrated under reduced pressure. The residue was recrystallized from ethyl acetate-hexane to give the title compound (8 mg, 2%) as white crystals.

$^1$H-NMR (300 MHz, DMSO-$d_6$) δ:1.40-1.60 (2H, m), 1.90 (2H, d, J=12.3 Hz), 2.93 (1H, t, J=11.0 Hz), 3.15 (1H, t, J=11.6 Hz), 3.68 (1H, d, J=13.5 Hz), 3.99-4.34 (10H, m), 4.52 (1H, t, J=5.4 Hz), 5.58 (2H, s), 6.59 (1H, d, J=7.5 Hz), 7.14-7.20 (2H, m), 7.27-7.34 (2H, m), 7.47 (1H, t, J=7.8 Hz), 7.57 (1H, d, J=8.1 Hz), 7.99 (1H, d, J=7.8 Hz), 8.39 (1H, d, J=8.4 Hz).

Example 629

Production of N-[1-(hydroxyacetyl)piperidin-4-yl]-3-methoxy-1-methyl-5-{[2-methyl-6-(trifluoromethyl)pyridin-3-yl]methyl}-4-oxo-4,5-dihydro-1H-pyrrolo[3,2-c]quinoline-2-carboxamide

Example 630

Production of 5-(4-chlorobenzyl)-N-[1-(hydroxyacetyl)piperidin-4-yl]-3-methoxy-1-methyl-4-oxo-4,5-dihydro-1H-pyrrolo[3,2-c]quinoline-2-carboxamide

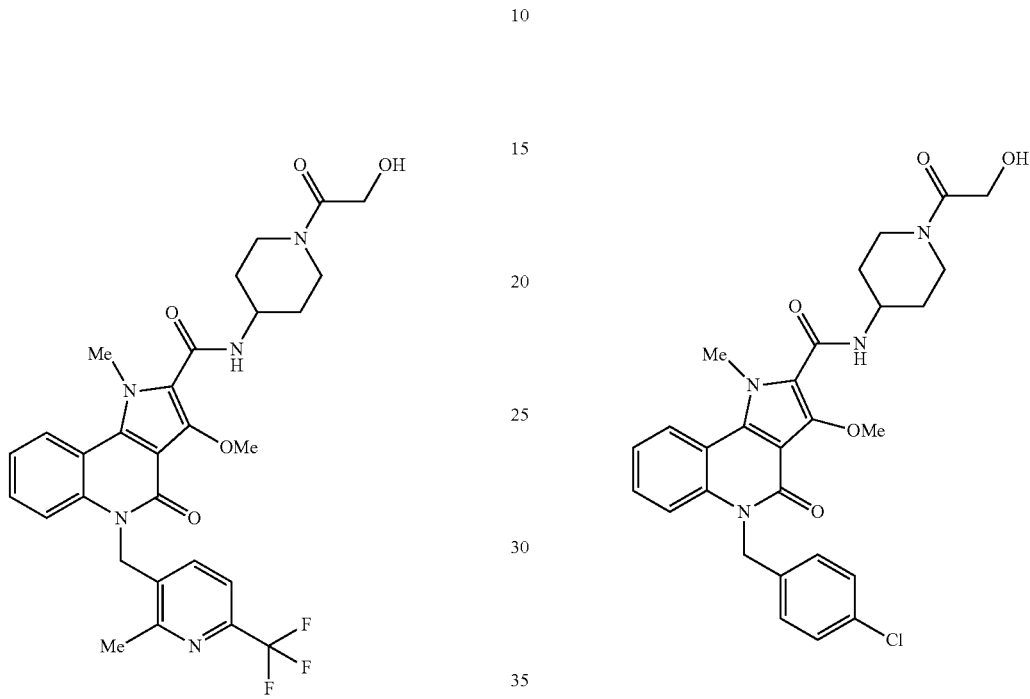

In the same manner as in Example 570, 2-(4-{[(3-methoxy-1-methyl-5-{[2-methyl-6-(trifluoromethyl)pyridin-3-yl]methyl}-4-oxo-4,5-dihydro-1H-pyrrolo[3,2-c]quinolin-2-yl)carbonyl]amino}piperidin-1-yl)-2-oxoethyl acetate (50 mg) was obtained as a colorless amorphous solid from the compound of Example 672 (300 mg, 0.66 mmol), 3-chloromethyl-2-methyl-6-trifluoromethylpyridine (980 mg, 4.68 mmol) and cesium carbonate (1.09 g, 3.30 mmol).

A solution of 2-(4-{[(3-methoxy-1-methyl-5-{[2-methyl-6-(trifluoromethyl)pyridin-3-yl]methyl}-4-oxo-4,5-dihydro-1H-pyrrolo[3,2-c]quinolin-2-yl)carbonyl]amino}piperidin-1-yl)-2-oxoethyl acetate (50 mg) and potassium carbonate (55 mg, 0.40 mmol) in THF (2 mL)-methanol (1 mL)-water (1 mL) was stirred at room temperature for 3 hr. The reaction mixture was diluted with saturated sodium hydrogen carbonate solution, and extracted twice with ethyl acetate. The extract was washed with brine, dried over magnesium sulfate, and concentrated under reduced pressure. The residue was recrystallized from ethyl acetate-hexane to give the title compound (19 mg, 5%) as white crystals.

$^{1}$H-NMR (300 MHz, DMSO-$d_6$) δ:1.40-1.60 (2H, m), 1.89 (2H, d, J=13.5 Hz), 2.77 (3H, s), 2.92 (1H, t, J=9.9 Hz), 3.14 (1H, t, J=11.4 Hz), 3.68 (1H, d, J=12.9 Hz), 3.98 (3H, s), 4.00-4.33 (7H, m), 4.52 (1H, t, J=5.4 Hz), 5.62 (2H, s), 6.99 (1H, d, J=7.8 Hz), 7.29-7.36 (2H, m), 7.47 (1H, t, J=7.5 Hz), 7.54 (1H, d, J=8.1 Hz), 7.99 (1H, d, J=7.5 Hz), 8.40 (1H, d, J=6.9 Hz).

In the same manner as in Example 570, 2-[4-({[5-(4-chlorobenzyl)-3-methoxy-1-methyl-4-oxo-4,5-dihydro-1H-pyrrolo[3,2-c]quinolin-2-yl]carbonyl}amino)piperidin-1-yl]-2-oxoethyl acetate (60 mg) was obtained as a white solid from the compound of Example 672 (200 mg, 0.44 mmol), 4-chlorobenzyl chloride (708 mg, 4.40 mmol) and cesium carbonate (572 g, 1.76 mmol).

A solution of 2-[4-({[5-(4-chlorobenzyl)-3-methoxy-1-methyl-4-oxo-4,5-dihydro-1H-pyrrolo[3,2-c]quinolin-2-yl]carbonyl}amino)piperidin-1-yl]-2-oxoethyl acetate (60 mg) and potassium carbonate (72 mg, 0.52 mmol) in THF (2 mL)-methanol (1 mL)-water (1 mL) was stirred at room temperature for 3 hr. The reaction mixture was diluted with saturated sodium hydrogen carbonate solution, and extracted twice with ethyl acetate. The extract was washed with brine, dried over magnesium sulfate, and concentrated under reduced pressure. The residue was recrystallized from ethyl acetate-hexane to give the title compound (7 mg, 2%) as white crystals.

$^{1}$H-NMR (300 MHz, DMSO-$d_6$) δ:1.40-1.60 (2H, m), 1.90 (2H, d, J=10.8 Hz), 2.93 (1H, t, J=12.0 Hz), 3.15 (1H, t, J=12.0 Hz), 3.68 (1H, d, J=13.5 Hz), 4.01-4.34 (10H, m), 4.52 (1H, t, J=5.4 Hz), 5.59 (2H, br s), 7.20-7.49 (7H, m), 7.99 (1H, d, J=5.4 Hz), 8.35 (1H, d, J=8.1 Hz).

Example 631

Production of N-[1-(2-carbamoylpyridin-4-yl)piperidin-4-yl]-3-methoxy-1-methyl-4-oxo-5-(2-oxo-2-phenylethyl)-4,5-dihydro-1H-pyrrolo[3,2-c]quinoline-2-carboxamide

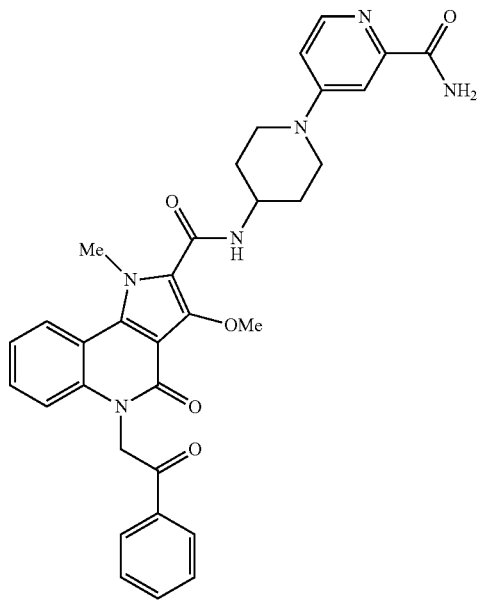 [SMILES: COc1c(C(=O)NC2CCN(c3ccnc(C(N)=O)c3)CC2)n(C)c2c1c(=O)n(CC(=O)c1ccccc1)c1ccccc21]

In the same manner as in Example 623, the title compound (58 mg, 17%) was obtained as a pale-red solid from the compound of Example 77 (300 mg, 0.59 mmol) and 4-bromopyridine-2-carboxamide (119 mg, 0.59 mmol).

$^1$H-NMR (300 MHz, DMSO-$d_6$) δ:1.52-1.72 (2H, m), 1.88-2.05 (2H, m), 3.07-3.24 (2H, m), 3.86-4.03 (5H, m), 4.07-4.22 (1H, m), 4.31 (3H, s), 5.96 (2H, s), 6.93-7.08 (1H, m), 7.25-7.41 (2H, m), 7.43-7.54 (3H, m), 7.56-7.68 (2H, m), 7.70-7.82 (1H, m), 7.91-8.04 (2H, m), 8.10-8.25 (3H, m), 8.37 (1H, dd, J=8.3, 1.1 Hz).

Example 632

Production of 3-methoxy-N-[1-(2-methoxypyridin-4-yl)piperidin-4-yl]-1-methyl-4-oxo-5-(2-oxo-2-phenylethyl)-4,5-dihydro-1H-pyrrolo[3,2-c]quinoline-2-carboxamide

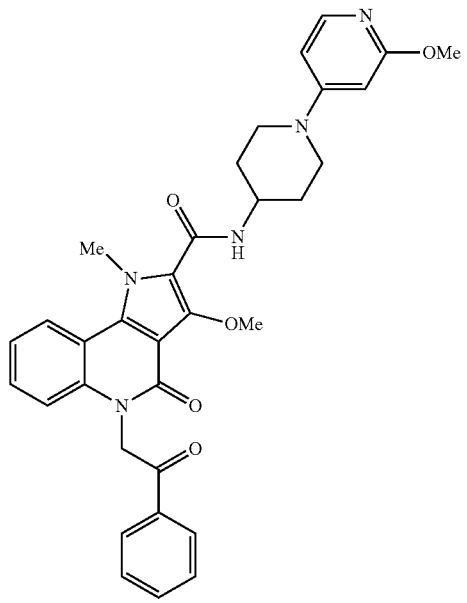 [SMILES: COc1cc(N2CCC(NC(=O)c3c(OC)c4c(=O)n(CC(=O)c5ccccc5)c5ccccc5c4n3C)CC2)ccn1]

In the same manner as in Example 575, the title compound (51 mg, 15%) was obtained as a white solid from the compound of Example 77 (300 mg, 0.59 mmol) and 4-bromo-2-methoxypyridine (122 mg, 0.65 mmol).

$^1$H-NMR (300 MHz, DMSO-$d_6$) δ:1.49-1.70 (2H, m), 1.85-2.00 (2H, m), 2.98-3.12 (2H, m), 3.73-3.88 (5H, m), 3.95 (3H, s), 4.03-4.18 (1H, m), 4.31 (3H, s), 5.97 (2H, s), 6.15 (1H, d, J=2.3 Hz), 6.59 (1H, dd, J=6.2, 2.3 Hz), 7.26-7.41 (2H, m), 7.43-7.52 (1H, m), 7.57-7.68 (2H, m), 7.71-7.84 (2H, m), 7.96 (1H, d, J=7.9 Hz), 8.09-8.23 (2H, m), 8.37 (1H, dd, J=8.3, 1.1 Hz).

Example 633

Production of 3-methoxy-1-methyl-4-oxo-5-(2-oxo-2-phenylethyl)-N-{1-[6-(trifluoromethyl)pyridin-3-yl]piperidin-4-yl}-4,5-dihydro-1H-pyrrolo[3,2-c]quinoline-2-carboxamide

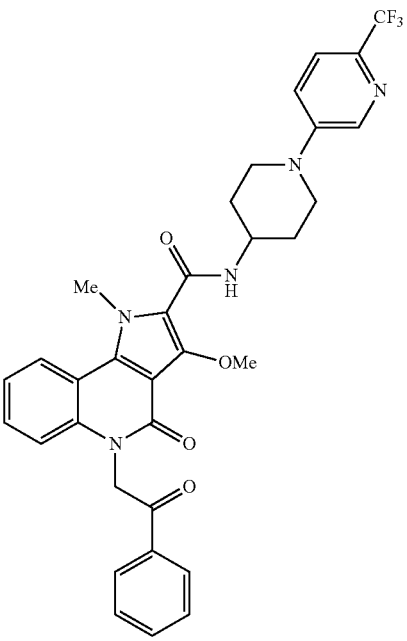 [SMILES: COc1c(C(=O)NC2CCN(c3ccc(C(F)(F)F)nc3)CC2)n(C)c2c1c(=O)n(CC(=O)c1ccccc1)c1ccccc21]

In the same manner as in Example 623, the title compound (51 mg, 14%) was obtained as a pale-yellow solid from the compound of Example 77 (300 mg, 0.59 mmol) and 5-bromo-2-(trifluoromethyl)pyridine (147 mg, 0.65 mmol).

$^1$H-NMR (300 MHz, DMSO-$d_6$) δ:1.59-1.77 (2H, m), 1.91-2.02 (2H, m), 3.07-3.20 (2H, m), 3.86-4.00 (5H, m), 4.05-4.20 (1H, m), 4.31 (3H, s), 5.97 (2H, s), 7.27-7.41 (2H, m), 7.43-7.52 (2H, m), 7.58-7.67 (3H, m), 7.72-7.80 (1H, m), 7.98 (1H, d, J=7.9 Hz), 8.13-8.20 (2H, m), 8.37 (1H, dd, J=8.2, 1.0 Hz), 8.46 (1H, d, J=2.8 Hz).

Example 634

Production of 3-methoxy-1-methyl-4-oxo-5-(2-oxo-2-phenylethyl)-N-{1-[2-(trifluoromethyl)pyrimidin-4-yl]piperidin-4-yl}-4,5-dihydro-1H-pyrrolo[3,2-c]quinoline-2-carboxamide

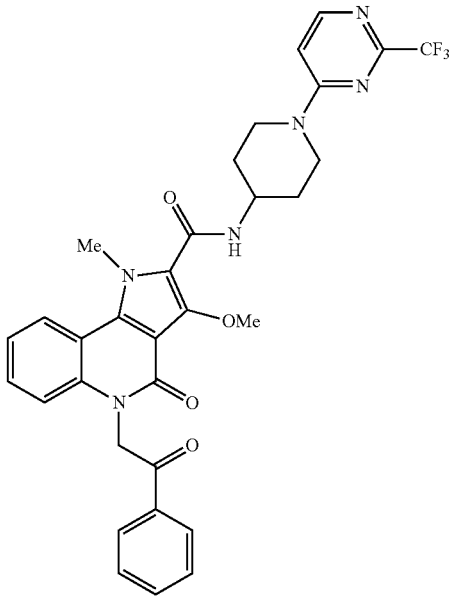 [SMILES: COc1c(C(=O)NC2CCN(c3ccnc(C(F)(F)F)n3)CC2)n(C)c2c1c(=O)n(CC(=O)c1ccccc1)c1ccccc21]

In the same manner as in Example 623, the title compound (210 mg, 58%) was obtained as a pale-red solid from the compound of Example 77 (300 mg, 0.59 mmol) and 4-chloro-2-(trifluoromethyl)pyrimidine (129 mg, 0.71 mmol).

$^1$H-NMR (300 MHz, DMSO-d$_6$) δ:1.48-1.69 (2H, m), 1.91-2.07 (2H, m), 3.17-3.30 (2H, m), 3.96 (3H, s), 4.10-4.52 (6H, m), 5.97 (2H, s), 7.12 (1H, d, J=6.4 Hz), 7.26-7.41 (2H, m), 7.43-7.52 (1H, m), 7.57-7.68 (2H, m), 7.71-7.81 (1H, m), 7.97 (1H, d, J=7.9 Hz), 8.11-8.22 (2H, m), 8.27-8.45 (2H, m).

Example 635

Production of 3-methoxy-1-methyl-N-{1-[2-(methylcarbamoyl)pyridin-4-yl]piperidin-4-yl}-4-oxo-5-(2-oxo-2-phenylethyl)-4,5-dihydro-1H-pyrrolo[3,2-c]quinoline-2-carboxamide

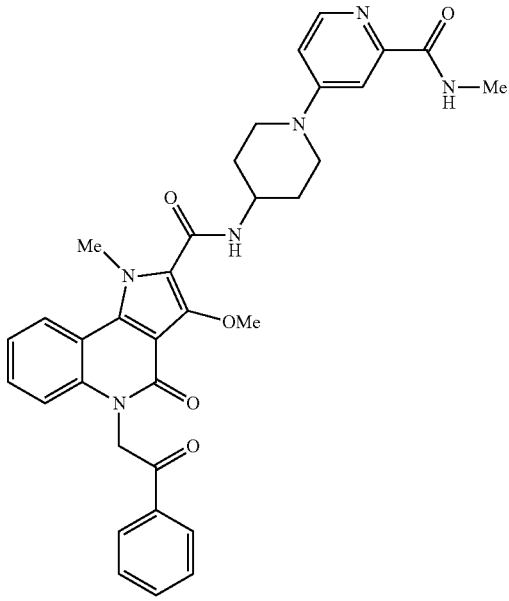 [SMILES: CNC(=O)c1cc(N2CCC(NC(=O)c3c(OC)c4c(=O)n(CC(=O)c5ccccc5)c5ccccc5c4n3C)CC2)ccn1]

To a solution of 4-chloropyridine-2-carboxylic acid (200 mg, 1.3 mmol), methylamine hydrochloride (103 mg, 1.5 mmol), HOBt (205 mg, 1.5 mmol) and triethylamine (0.42 mL, 3.0 mmol) in DMF (3.0 mL) was added WSCD (292 mg, 1.5 mmol) under ice-cooling, and the mixture was stirred at room temperature for 5 hr. The reaction mixture was diluted with saturated sodium hydrogen carbonate solution, and extracted twice with ethyl acetate. The extracts were combined, washed with brine, dried over magnesium sulfate, filtered through aminosilica gel, and the filtrate was concentrated under reduced pressure. The residue was dissolved in DMF (3.0 mL), the compound of Example 77 (300 mg, 0.59 mmol), potassium carbonate (204 mg, 1.5 mmol) and triethylamine (0.082 mL, 0.59 mmol) were added, and the mixture was stirred at 100° C. for 16 hr. The reaction mixture was diluted with saturated sodium hydrogen carbonate solution, and extracted twice with a mixed solvent of ethyl acetate-THF. The extract was dried over magnesium sulfate, and concentrated under reduced pressure. The residue was purified by aminosilica gel chromatography (eluate; ethyl acetate/hexane=40/60-100/0) and recrystallized from ethyl acetate-hexane to give the title compound (40 mg, 11%) as a pale-yellow solid.

$^1$H-NMR (300 MHz, DMSO-d$_6$) δ:1.52-1.72 (2H, m), 1.90-2.05 (2H, m), 2.79 (3H, d, J=4.9 Hz), 3.09-3.22 (2H, m), 3.88-4.02 (5H, m), 4.07-4.22 (1H, m), 4.31 (3H, s), 5.96 (2H, s), 7.01 (1H, dd, J=6.0, 2.8 Hz), 7.25-7.41 (2H, m), 7.43-7.52 (2H, m), 7.57-7.68 (2H, m), 7.70-7.81 (1H, m), 7.98 (1H, d, J=7.9 Hz), 8.11-8.24 (3H, m), 8.37 (1H, dd, J=8.3, 1.1 Hz), 8.53-8.70 (1H, m).

Example 636

Production of N-[1-(hydroxyacetyl)-3-methylpiperidin-4-yl]-3-methoxy-1-methyl-4-oxo-5-(2-oxo-2-phenylethyl)-4,5-dihydro-1H-pyrrolo[3,2-c]quinoline-2-carboxamide

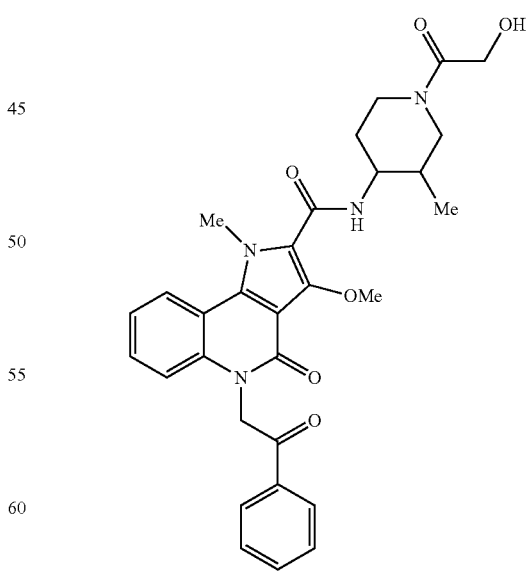

In the same manner as in Example 130, the title compound (21 mg, 22%) was obtained as a white solid from the compound of Example 678 (83 mg, 0.17 mmol).

¹H-NMR (300 MHz, DMSO-d₆) δ:0.82-1.02 (3H, m), 1.55-2.40 (3H, m), 3.14-3.77 (4H, m), 3.93-4.05 (3H, m), 4.07-4.17 (2H, m), 4.20-4.41 (4H, m), 4.45-4.57 (1H, m), 5.98 (2H, s), 7.25-7.42 (2H, m), 7.43-7.53 (1H, m), 7.58-7.68 (2H, m), 7.71-7.80 (1H, m), 7.85-8.05 (1H, m), 8.10-8.24 (2H, m), 8.38 (1H, dd, J=8.4, 1.2 Hz).

7.57-7.69 (2H, m), 7.71-7.82 (1H, m), 7.96 (1H, d, J=7.9 Hz), 8.08 (1H, d, J=6.2 Hz), 8.13-8.22 (2H, m), 8.37 (1H, d, J=7.6 Hz).

Example 637

Production of 3-methoxy-1-methyl-N-[1-(2-methylpyrimidin-4-yl)piperidin-4-yl]-4-oxo-5-(2-oxo-2-phenylethyl)-4,5-dihydro-1H-pyrrolo[3,2-c]quinoline-2-carboxamide

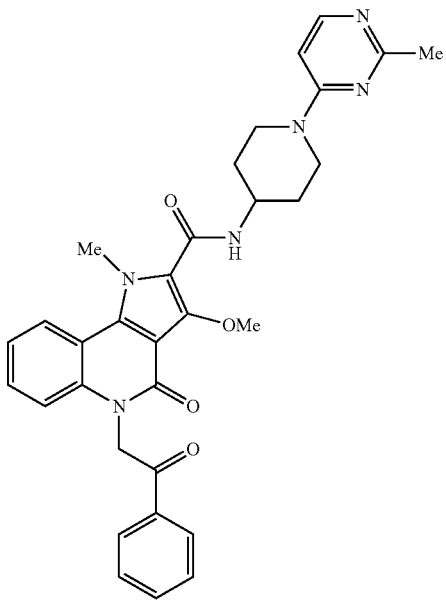 [SMILES: COc1c(C(=O)NC2CCN(c3ccnc(C)n3)CC2)n(C)c2c1c(=O)n(CC(=O)c1ccccc1)c1ccccc21]

In the same manner as in Example 623, the title compound (130 mg, 59%) was obtained as a pale-brown solid from the compound of Example 77 (200 mg, 0.39 mmol) and 4-chloro-2-methylpyrimidine (61 mg, 0.47 mmol).

¹H-NMR (300 MHz, DMSO-d₆) δ:1.44-1.62 (2H, m), 1.85-2.01 (2H, m), 2.36 (3H, s), 3.06-3.23 (2H, m), 3.96 (3H, s), 4.06-4.23 (1H, m), 4.24-4.41 (5H, m), 5.97 (2H, s), 6.68 (1H, d, J=6.4 Hz), 7.25-7.42 (2H, m), 7.43-7.53 (1H, m),

Example 638

Production of 3-methoxy-1-methyl-N-[1-(6-methylpyrimidin-4-yl)piperidin-4-yl]-4-oxo-5-(2-oxo-2-phenylethyl)-4,5-dihydro-1H-pyrrolo[3,2-c]quinoline-2-carboxamide

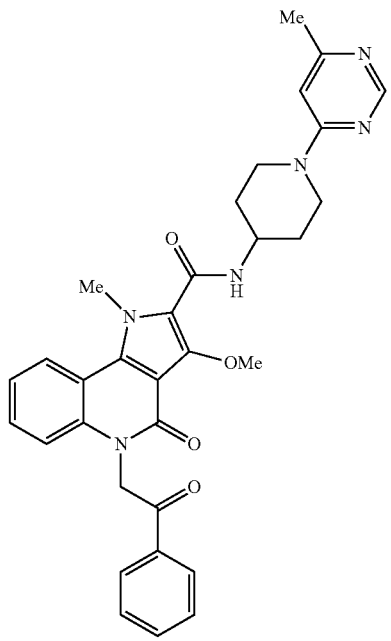 [SMILES: COc1c(C(=O)NC2CCN(c3cc(C)ncn3)CC2)n(C)c2c1c(=O)n(CC(=O)c1ccccc1)c1ccccc21]

In the same manner as in Example 623, the title compound (137 mg, 62%) was obtained as a pale-brown solid from the compound of Example 77 (200 mg, 0.39 mmol) and 4-chloro-6-methylpyrimidine (61 mg, 0.47 mmol).

¹H-NMR (300 MHz, DMSO-d₆) δ:1.44-1.64 (2H, m), 1.85-2.01 (2H, m), 2.26 (3H, s), 3.05-3.23 (2H, m), 3.95 (3H, s), 4.07-4.23 (1H, m), 4.24-4.39 (5H, m), 5.97 (2H, s), 6.77 (1H, s), 7.25-7.42 (2H, m), 7.43-7.53 (1H, m), 7.57-7.69 (2H, m), 7.70-7.82 (1H, m), 7.96 (1H, d, J=7.9 Hz), 8.11-8.23 (2H, m), 8.32-8.45 (2H, m).

Example 639

Production of 1-ethyl-N-[1-(hydroxyacetyl)piperidin-4-yl]-3-methoxy-4-oxo-5-(2-oxo-2-phenylethyl)-4,5-dihydro-1H-pyrrolo[3,2-c]quinoline-2-carboxamide

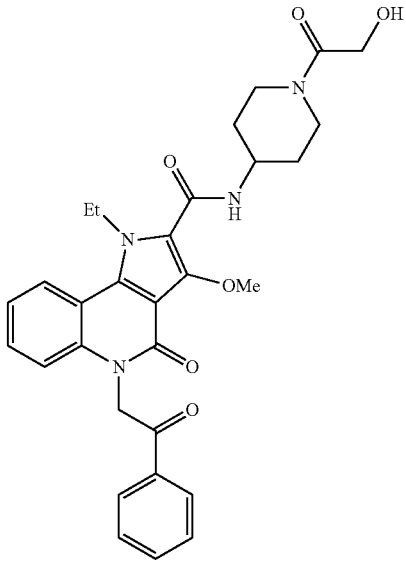 [SMILES: CCn1c(C(=O)NC2CCN(C(=O)CO)CC2)c(OC)c2c(=O)n(CC(=O)c3ccccc3)c3ccccc3c21]

In the same manner as in Example 140, the title compound (42 mg, 22%) was obtained as a white solid from the compound of Reference Example 120 (140 mg, 0.35 mmol) and 2-(4-aminopiperidin-1-yl)-2-oxoethanol hydrochloride (81 mg, 0.42 mmol).

$^1$H-NMR (300 MHz, DMSO-$d_6$) δ:1.39-1.61 (5H, m), 1.82-1.98 (2H, m), 2.84-3.01 (1H, m), 3.06-3.21 (1H, m), 3.59-3.74 (1H, m), 3.96 (3H, s), 4.03-4.14 (3H, m), 4.16-4.28 (1H, m), 4.51 (1H, t, J=5.4 Hz), 4.82 (2H, q, J=7.1 Hz), 5.98 (2H, s), 7.30-7.42 (2H, m), 7.43-7.52 (1H, m), 7.59-7.68 (2H, m), 7.71-7.81 (1H, m), 8.03 (1H, d, J=7.7 Hz), 8.12-8.25 (3H, m).

Example 640

Production of N-[1-(hydroxyacetyl)azepan-4-yl]-3-methoxy-1-methyl-4-oxo-5-(2-oxo-2-phenylethyl)-4,5-dihydro-1H-pyrrolo[3,2-c]quinoline-2-carboxamide

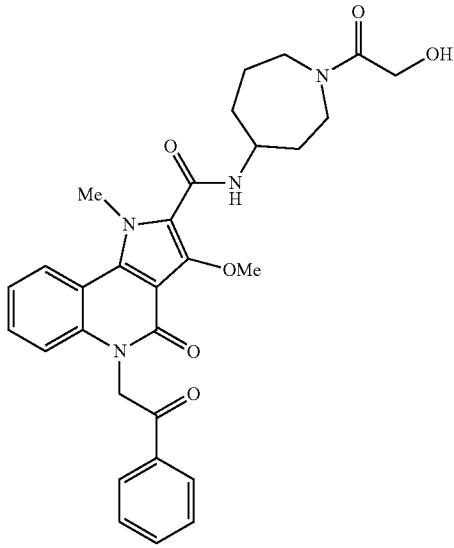 [SMILES: COc1c(C(=O)NC2CCCN(C(=O)CO)CC2)n(C)c2c1c(=O)n(CC(=O)c1ccccc1)c1ccccc21]

A mixed solution of the compound of Reference Example 123 (220 mg, 0.70 mmol) and 8N aqueous sodium hydroxide solution (0.36 mL) in ethanol (3.0 mL)-water (3.0 mL) was stirred for 30 min under ice-cooling. The reaction mixture was neutralized with 1N hydrochloric acid, stirred for 10 min under ice-cooling and extracted twice with ethyl acetate. The extract was combined, washed with brine, dried over magnesium sulfate, and concentrated under reduced pressure. The residue was dissolved in ethyl acetate (2.0 mL), and 4N hydrogen chloride ethyl acetate solution (2.0 mL) was added. The mixture was stirred at room temperature for 2 hr, and concentrated under reduced pressure. To a solution of the residue, the compound of Reference Example 28 (200 mg, 0.51 mmol), HOBt (90 mg, 0.67 mol) and triethylamine (0.22 mL, 1.6 mmol) in DMF (5.0 mL) was added WSCD (128 mg, 0.67 mmol) under ice-cooling, and the mixture was stirred at room temperature for 62 hr. The reaction mixture was diluted with saturated sodium hydrogen carbonate solution, and extracted twice with ethyl acetate. The extract was combined, washed with brine, dried over magnesium sulfate, and concentrated under reduced pressure. The residue was purified by aminosilica gel chromatography (eluate; ethyl acetate/hexane=80/20-100/0) and recrystallized from THF-diethyl ether to give the title compound (122 mg, 44%) as a white solid.

$^1$H-NMR (300 MHz, DMSO-$d_6$) δ:1.55-1.92 (5H, m), 1.93-2.11 (1H, m), 3.25-3.45 (2H, m), 3.47-3.55 (1H, m), 3.63-3.80 (1H, m), 3.92-4.06 (4H, m), 4.07-4.18 (2H, m), 4.25-4.36 (3H, m), 4.43 (1H, t, J=4.7 Hz), 5.97 (2H, s), 7.24-7.42 (2H, m), 7.43-7.52 (1H, m), 7.58-7.67 (2H, m), 7.71-7.81 (1H, m), 7.94 (1H, d, J=8.1 Hz), 8.12-8.22 (2H, m), 8.37 (1H, d, J=7.9 Hz).

Example 641

Production of N-[1-(2-hydroxyethyl)azepan-4-yl]-3-methoxy-1-methyl-4-oxo-5-(2-oxo-2-phenylethyl)-4,5-dihydro-1H-pyrrolo[3,2-c]quinoline-2-carboxamide

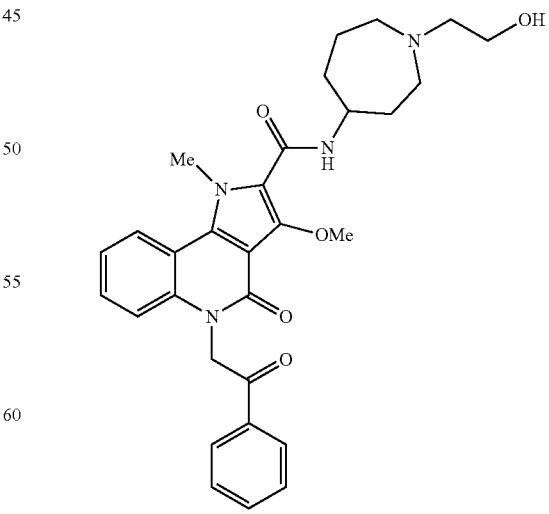

A solution of the compound of Reference Example 122 (157 mg, 0.73 mmol) and potassium carbonate (607 mg, 4.4 mmol) in DMF (6.0 mL) was stirred at 100° C. for 5 min, 2-bromoethanol (0.16 mL, 2.2 mmol) was added to the reaction mixture, and the mixture was stirred at 100° C. for 1 hr. The reaction mixture was diluted with water, brine was added, and the mixture was extracted 4 times with ethyl acetate. The extracts were combined, dried over magnesium sulfate, and concentrated under reduced pressure. The residue was purified by aminosilica gel chromatography (eluate; methanol/ethyl acetate=0/100-5/95). The residue was dissolved in ethyl acetate (2.0 mL), and 4N hydrogen chloride ethyl acetate solution (2.0 mL) was added. The reaction mixture was stirred at room temperature for 30 min, and concentrated under reduced pressure. To a solution of the residue, the compound of Reference Example 28 (200 mg, 0.51 mmol) and triethylamine (0.27 mL, 1.9 mmol) in DMF (5.0 mL) was added DMT-MM (167 mg, 0.61 mmol) under ice-cooling, and the mixture was stirred at room temperature for 62 hr. The reaction mixture was diluted with saturated sodium hydrogen carbonate solution and water, and extracted twice with ethyl acetate. The extracts were combined, washed with brine, dried over magnesium sulfate, and concentrated under reduced pressure. The residue was purified by aminosilica gel chromatography (eluate; ethyl acetate/hexane=50/50-100/0) and recrystallized from ethanol-hexane to give the title compound (75 mg, 28%) as a pale-yellow solid.

$^1$H-NMR (300 MHz, DMSO-$d_6$) δ:1.49-2.01 (6H, m), 2.53-2.84 (6H, m), 3.44-3.56 (2H, m), 3.90-4.03 (3H, m), 4.14-4.41 (5H, m), 5.97 (2H, s), 7.25-7.42 (2H, m), 7.43-7.53 (1H, m), 7.57-7.69 (2H, m), 7.71-7.82 (1H, m), 8.04 (1H, d, J=8.3 Hz), 8.11-8.23 (2H, m), 8.37 (1H, dd, J=8.3, 1.1 Hz).

Example 642

Production of 2-[(4-aminopiperidin-1-yl)carbonyl]-3-methoxy-1-methyl-5-(2-oxo-2-phenylethyl)-1,5-dihydro-4H-pyrrolo[3,2-c]quinoline-4-one hydrochloride

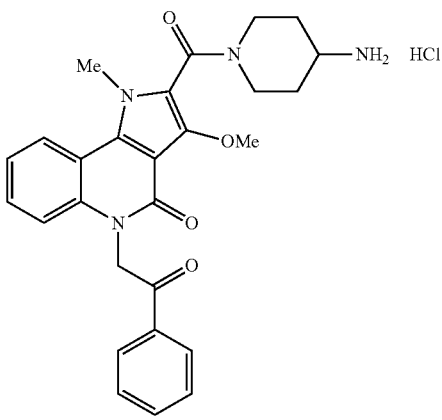 [SMILES: COc1c(C(=O)N2CCC(N)CC2)n(C)c2c1c(=O)n(CC(=O)c1ccccc1)c1ccccc21 ; Cl]

In the same manner as in Example 542, the title compound (119 mg, 79%) was obtained as a white solid from the compound of Example 679 (170 mg, 0.30 mmol).

$^1$H-NMR (300 MHz, DMSO-$d_6$) δ:1.36-1.73 (2H, m), 1.84-2.15 (2H, m), 2.83-3.04 (1H, m), 3.08-3.30 (2H, m), 3.77-3.95 (4H, m), 4.00 (3H, s), 4.45-4.68 (1H, m), 5.98 (2H, s), 7.24-7.52 (3H, m), 7.58-7.70 (2H, m), 7.71-7.81 (1H, m), 8.00 (3H, br s), 8.13-8.23 (2H, m), 8.33 (1H, dd, J=8.2, 1.0 Hz).

Example 643

Production of N-[1-(hydroxyacetyl)piperidin-4-yl]-3-methoxy-1-methyl-4-oxo-5-(2-oxo-2-phenylethyl)-4,5-dihydro-1H-pyrrolo[3,2-c][1,8]naphthyridine-2-carboxamide

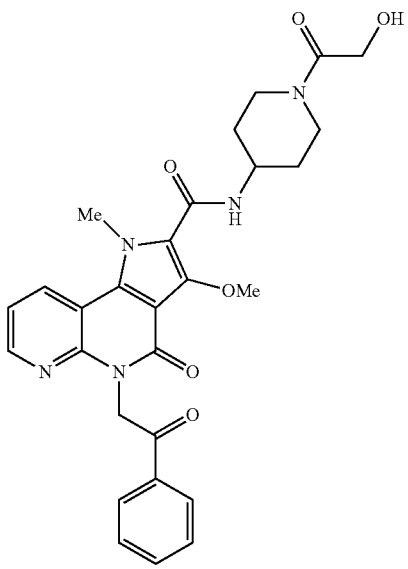 [SMILES: COc1c(C(=O)NC2CCN(C(=O)CO)CC2)n(C)c2c1c(=O)n(CC(=O)c1ccccc1)c1ncccc21]

In the same manner as in Example 141, the title compound (141 mg, 69%) was obtained as a white solid from the compound of Reference Example 131 (150 mg, 0.38 mmol).

$^1$H-NMR (300 MHz, DMSO-$d_6$) δ:1.32-1.65 (2H, m), 1.81-1.97 (2H, m), 2.81-3.01 (1H, m), 3.04-3.22 (1H, m), 3.63-3.74 (1H, m), 3.98 (3H, s), 4.04-4.16 (3H, m), 4.17-4.28 (1H, m), 4.32 (3H, s), 4.51 (1H, t, J=5.4 Hz), 5.99 (2H, s), 7.35 (1H, dd, J=8.1, 4.7 Hz), 7.54-7.68 (2H, m), 7.69-7.80 (1H, m), 8.00 (1H, d, J=7.9 Hz), 8.08-8.22 (2H, m), 8.44 (1H, dd, J=4.7, 1.5 Hz), 8.73 (1H, dd, J=8.3, 1.5 Hz).

Example 644

Production of N-[1-(hydroxyacetyl)piperidin-4-yl]-3-methoxy-1-methyl-4-oxo-5-(2-oxo-2-phenylethyl)-4,5-dihydro-1H-pyrrolo[3,2-c][1,6]naphthyridine-2-carboxamide

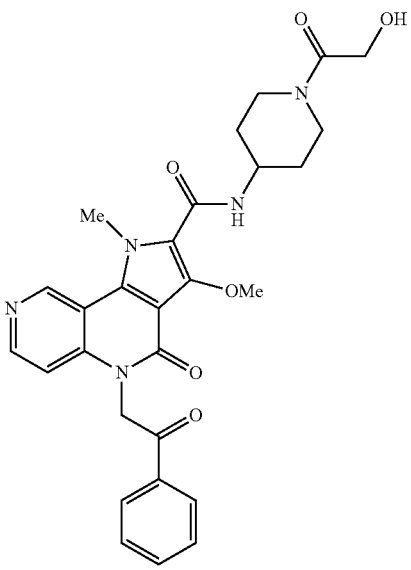 [SMILES: COc1c(C(=O)NC2CCN(C(=O)CO)CC2)n(C)c2c1c(=O)n(CC(=O)c1ccccc1)c1ccncc21]

In the same manner as in Example 141, the title compound (97 mg, 48%) was obtained as a white solid from the compound of Reference Example 139 (150 mg, 0.38 mmol).

¹H-NMR (300 MHz, DMSO-d₆) δ:1.34-1.63 (2H, m), 1.79-1.97 (2H, m), 2.83-3.01 (1H, m), 3.05-3.22 (1H, m), 3.59-3.74 (1H, m), 3.95 (3H, s), 4.01-4.17 (3H, m), 4.17-4.28 (1H, m), 4.35 (3H, s), 4.50 (1H, t, J=5.4 Hz), 5.95 (2H, s), 7.42 (1H, d, J=6.2 Hz), 7.57-7.69 (2H, m), 7.71-7.82 (1H, m), 7.99 (1H, d, J=7.7 Hz), 8.10-8.22 (2H, m), 8.48 (1H, d, J=6.0 Hz), 9.51 (1H, s).

Example 645

Production of N-[2-(diethylamino)ethyl]-3-ethoxy-N,6-dimethyl-4-oxo-5-(2-oxo-2-phenylethyl)-4,5-dihydrothieno[3,2-c]pyridine-2-carboxamide hydrochloride

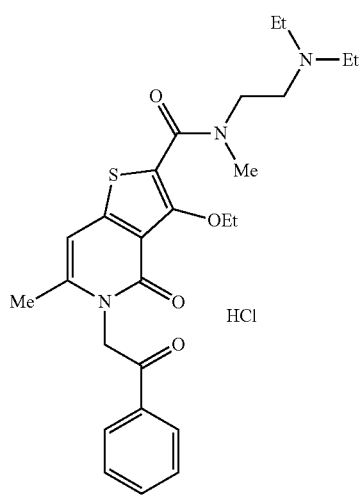 [SMILES: CCOc1c(C(=O)N(C)CCN(CC)CC)sc2cc(C)n(CC(=O)c3ccccc3)c(=O)c12 ; Cl]

To a solution of the compound of Example 146 (150 mg, 0.310 mmol) in ethyl acetate (20 mL) was added 4N hydrogen chloride ethyl acetate solution (93.0 μL, 0.372 mmol). The mixture was concentrated under reduced pressure, and the residue was dissolved in ethyl acetate (30 mL) and ethanol (5 mL). Hexane (10 mL) was added, and the mixture was stirred at room temperature for 15 hr. The precipitated solid was collected by filtration, and washed with ethyl acetate to give the title compound (90.0 mg, 56%) as a white solid.

¹H-NMR (300 MHz, DMSO-d₆) δ: 1.10-1.35 (9H, m), 2.30 (3H, s), 3.08 (3H, s), 3.00-3.40 (6H, m), 3.79 (2H, t, J=7.2 Hz), 4.08 (2H, q, J=7.0 Hz), 5.67 (2H, s), 6.84 (1H, d, J=0.6 Hz), 7.62 (2H, t, J=7.5 Hz), 7.72-7.78 (1H, m), 8.10-8.13 (2H, m), 10.03 (1H, s).

Example 646

Production of 3-ethoxy-N-(4-hydroxycyclohexyl)-1,6-dimethyl-4-oxo-5-(2-oxo-2-phenylethyl)-4,5-dihydro-1H-pyrrolo[3,2-c]pyridine-2-carboxamide

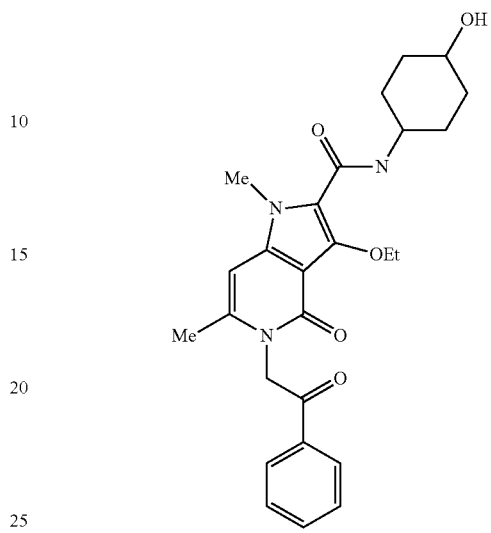

In the same manner as in Example 25, the title compound (106 mg, 60%) was obtained as a white powder from the compound of Reference Example 44 (140 mg, 0.380 mmol) and 4-aminocyclohexanol (53 mg, 0.456 mmol).

¹H-NMR (300 MHz, DMSO-d₆) δ:1.19-1.35 (7H, m), 1.86 (4H, d, J=12.8 Hz), 2.27 (3H, s), 3.45 (1H, br s), 3.71 (1H, br s), 3.86 (3H, s), 4.33 (2H, q, J=6.9 Hz), 4.56 (1H, d, J=4.3 Hz), 5.61 (2H, s), 6.57 (1H, s), 7.48-7.67 (3H, m), 7.72 (1H, d, J=7.2 Hz), 8.10 (2H, d, J=7.4 Hz).

Example 647

Production of 3-ethoxy-1,6-dimethyl-4-oxo-5-(2-oxo-2-phenylethyl)-N-(tetrahydrofuran-2-ylmethyl)-4,5-dihydro-1H-pyrrolo[3,2-c]pyridine-2-carboxamide

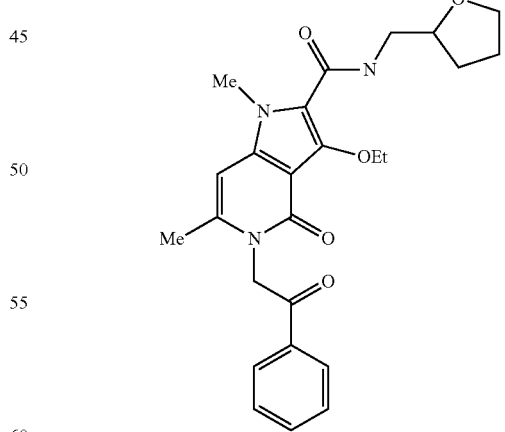

In the same manner as in Example 25, the title compound (114 mg, 66%) was obtained as a white powder from the compound of Reference Example 35 (140 mg, 0.380 mmol) and 2-tetrahydrofurfurylamine (47 μl, 0.456 mmol).

¹H-NMR (300 MHz, DMSO-d₆) δ:1.29 (3H, t, J=6.8 Hz), 1.48-1.62 (1H, m), 1.78-1.99 (3H, m), 2.28 (3H, s), 3.41-3.52

(1H, m), 3.60-3.71 (1H, m), 3.75-3.84 (1H, m), 3.89 (3H, s), 3.91-4.02 (2H, m), 4.35 (2H, t, J=7.0 Hz), 5.61 (2H, s), 6.59 (1H, s), 7.61 (2H, t, J=7.4 Hz), 7.73 (1H, m), 7.88 (1H, br s), 8.11 (2H, d, J=7.6 Hz).

Example 648

Production of 3-ethoxy-6-ethyl-N-(trans-4-hydroxy-cyclohexyl)-1-methyl-4-oxo-5-(2-oxo-2-phenyl-ethyl)-4,5-dihydro-1H-pyrrolo[3,2-c]pyridine-2-carboxamide

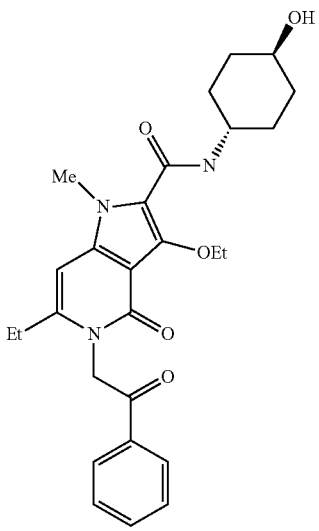 [SMILES: CCOc1c(C(=O)N[C@H]2CC[C@H](O)CC2)n(C)c2cc(CC)n(CC(=O)c3ccccc3)c(=O)c12]

In the same manner as in Example 25, the title compound (76 mg, 79%) was obtained as a white powder from the compound of Reference Example 42 (77 mg, 0.20 mmol) and trans-4-aminocyclohexanol (28 mg, 0.24 mmol).

$^1$H-NMR (300 MHz, DMSO-$d_6$) δ:1.18 (3H, t, J=7.4 Hz), 1.22-1.36 (7H, m), 1.75-1.96 (4H, m), 2.57 (2H, q, J=7.3 Hz), 3.44 (1H, br s), 3.71 (1H, br s), 3.89 (3H, s), 4.32 (2H, q, J=7.1 Hz), 4.57 (1H, d, J=4.2 Hz), 5.58 (2H, s), 6.48 (1H, s), 7.51-7.66 (3H, m), 7.67-7.78 (1H, m), 8.11 (2H, d, J=7.2 Hz).

Example 649

Production of N-[1-(hydroxyacetyl)piperidin-4-yl]-3-methoxy-1-methyl-4-oxo-5-(2-oxo-2-phenylethyl)-4,5-dihydro-1H-pyrrolo[3,2-c][1,6]naphthyridine-2-carboxamide

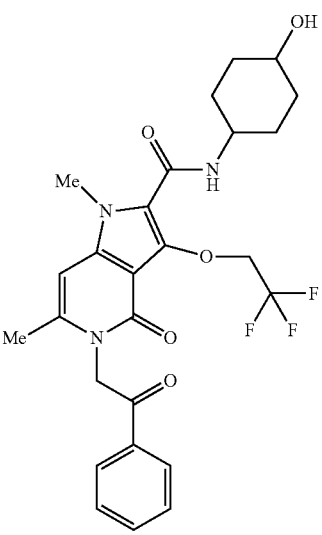 [SMILES: Cc1cc2c(c(OCC(F)(F)F)c(C(=O)NC3CCC(O)CC3)n2C)c(=O)n1CC(=O)c1ccccc1]

In the same manner as in Example 140, the title compound (132 mg, 54%) was obtained as white crystals from the compound of Reference Example 50 (200 mg, 0.47 mmol) and 4-aminocyclohexanol (82 mg, 0.71 mmol).

$^1$H-NMR (300 MHz, DMSO-$d_6$) δ:1.25 (4H, t, J=9.6 Hz), 1.80-1.90 (4H, m), 2.29 (3H, s), 3.30-3.45 (1H, br), 3.60-3.80 (1H, br), 3.83 (3H, s), 4.57 (1H, t, J=4.5 Hz), 5.06 (2H, q, J=9.3 Hz), 5.65 (2H, s), 6.64 (1H, s), 7.31 (1H, d, J=7.8 Hz), 7.61 (1H, t, J=7.5 Hz), 7.74 (1H, t, J=7.5 Hz), 8.09-8.12 (2H, m).

Example 650

Production of 3-ethoxy-6-ethyl-N-[1-(hydroxy-acetyl)piperidin-4-yl]-4-oxo-5-(2-oxo-2-phenyl-ethyl)-4,5-dihydrothieno[3,2-c]pyridine-2-carboxamide

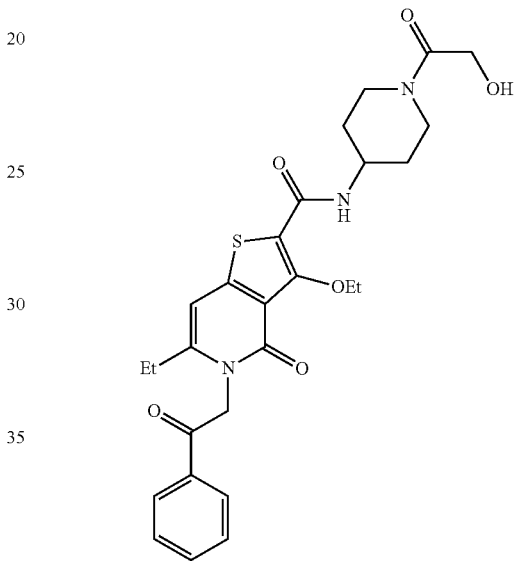

In the same manner as in Reference Example 7, 3-ethoxy-6-ethyl-4-oxo-5-(2-oxo-2-phenylethyl)-4,5-dihydrothieno[3,2-c]pyridine-2-carboxylic acid (700 mg, 83%) was obtained as a purple powder from the compound of Reference Example 170 (900 mg, 2.25 mmol). tert-Butyl 4-({[3-ethoxy-6-ethyl-4-oxo-5-(2-oxo-2-phenylethyl)-4,5-dihydrothieno[3,2-c]pyridin-2-yl]carbonyl}amino)piperidine-1-carboxylate (125 mg, 15%) was obtained as a white powder from the thus-obtained 3-ethoxy-6-ethyl-4-oxo-5-(2-oxo-2-phenyl-ethyl)-4,5-dihydrothieno[3,2-c]pyridine-2-carboxylic acid (550 mg, 1.4 mmol) and 4-amino-1-Boc-piperidine (361 mg, 1.8 mmol). 3-Ethoxy-6-ethyl-4-oxo-5-(2-oxo-2-phenyl-ethyl)-N-piperidin-4-yl-4,5-dihydrothieno[3,2-c]pyridine-2-carboxamide (94 mg, 85%) was obtained as a white powder from the thus-obtained tert-butyl 4-({[3-ethoxy-6-ethyl-4-oxo-5-(2-oxo-2-phenylethyl)-4,5-dihydrothieno[3,2-c]pyridin-2-yl]carbonyl}amino)piperidine-1-carboxylate (125 mg, 0.22 mmol) by a method similar to that in Example 126. 2-[4-({[3-Ethoxy-6-ethyl-4-oxo-5-(2-oxo-2-phenylethyl)-4,5-dihydrothieno[3,2-c]pyridin-2-yl]carbonyl}amino)piperidin-1-yl]-2-oxoethyl acetate (80 mg, 78%) was obtained as a white solid from the thus-obtained 3-ethoxy-6-ethyl-4-oxo-5-(2-oxo-2-phenylethyl)-N-piperidin-4-yl-4,5-dihydrothieno[3,2-c]pyridine-2-carboxamide (90 mg, 0.18 mmol) by a method similar to that in Example 127.

A mixed solution of 2-[4-({[3-ethoxy-6-ethyl-4-oxo-5-(2-oxo-2-phenylethyl)-4,5-dihydrothieno[3,2-c]pyridin-2-yl]carbonyl}amino)piperidin-1-yl]-2-oxoethyl acetate (90 mg, 0.18 mmol) and potassium carbonate (39 mg, 0.28 mmol) in THF (8 mL)-methanol (2 mL)-water (2 mL) was stirred at room temperature for 1 hr. The reaction mixture was concentrated, and the residue was partitioned between ethyl acetate and saturated sodium hydrogen carbonate solution. The organic layer was washed with brine, dried over magnesium sulfate, and concentrated under reduced pressure. The residue was recrystallized from ethyl acetate-hexane to give the title compound (64 mg, 69%) as white crystals.

$^1$H-NMR (300 MHz, DMSO-d$_6$) δ:1.17 (3H, t, J=7.4 Hz), 1.30 (3H, t, J=7.1 Hz), 1.35-1.60 (2H, m), 1.90 (2H, d, J=9.9 Hz), 2.60 (2H, q, J=7.4 Hz), 2.84 (1H, t, J=12.0 Hz), 3.10 (1H, t, J=14.0 Hz), 3.66 (1H, d, J=13.5 Hz), 4.00-4.09 (3H, m), 4.28 (3H, q, J=7.1 Hz), 4.50 (1H, t, J=5.4 Hz), 5.66 (2H, s), 6.84 (1H, s), 7.60-7.68 (2H, m), 7.75 (1H, t, J=7.5 Hz), 8.10-8.13 (2H, m).

Example 651

Production of 1,6-dimethyl-N-(1-oxidotetrahydro-2H-thiopyran-4-yl)-4-oxo-5-(2-oxo-2-phenylethyl)-3-(2,2,2-trifluoroethoxy)-4,5-dihydro-1H-pyrrolo[3,2-c]pyridine-2-carboxamide

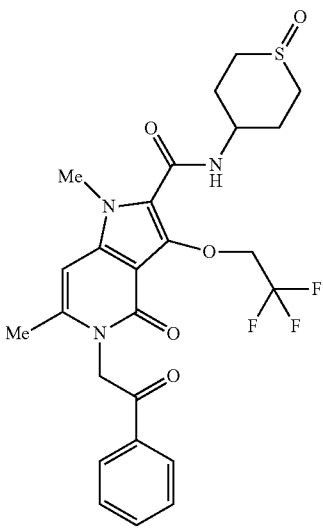 [SMILES: Cc1cc2c(c(OCC(F)(F)F)c(C(=O)NC3CCS(=O)CC3)n2C)c(=O)n1CC(=O)c1ccccc1]

In the same manner as in Example 571, 1,6-dimethyl-4-oxo-5-(2-oxo-2-phenylethyl)-N-(tetrahydro-2H-thiopyran-4-yl)-3-(2,2,2-trifluoroethoxy)-4,5-dihydro-1H-pyrrolo[3,2-c]pyridine-2-carboxamide (150 mg) was obtained as a white solid from the compound of Reference Example 50 (200 mg, 0.47 mmol). The title compound (131 mg, 51%) was obtained as white crystals from the thus-obtained 1,6-dimethyl-4-oxo-5-(2-oxo-2-phenylethyl)-N-(tetrahydro-2H-thiopyran-4-yl)-3-(2,2,2-trifluoroethoxy)-4,5-dihydro-1H-pyrrolo[3,2-c]pyridine-2-carboxamide (150 mg) by a method similar to that in Example 571.

$^1$H-NMR (300 MHz, DMSO-d$_6$) δ:1.60-1.75 (1H, m), 1.83 (1H, d, J=10.2 Hz), 2.06-2.29 (5H, m), 2.70-2.85 (2H, m), 2.93 (1H, d, J=12.9 Hz), 3.81 (3H, d, J=6.3 Hz), 3.90-4.10 (1H, m), 5.00-5.13 (2H, m), 5.65 (2H, s), 6.64 (1H, s), 7.61 (3H, t, J=7.8 Hz), 7.74 (1H, t, J=7.2 Hz), 8.10-8.12 (2H, m).

Example 652

Production of 3-(2,2-difluoroethoxy)-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

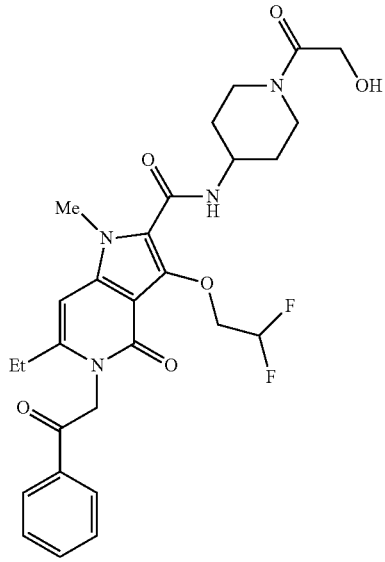 [SMILES: CCc1cc2c(c(OCC(F)F)c(C(=O)NC3CCN(C(=O)CO)CC3)n2C)c(=O)n1CC(=O)c1ccccc1]

In the same manner as in Example 140, the title compound (340 mg, 84%) was obtained as a white amorphous solid from the compound of Reference Example 171 (300 mg, 0.72 mmol).

$^1$H-NMR (300 MHz, DMSO-d$_6$) δ:1.19 (3H, t, J=7.4 Hz), 1.20-1.50 (2H, m), 1.90 (2H, d, J=9.9 Hz), 2.59 (2H, q, J=7.4 Hz), 2.83 (1H, t, J=12.2 Hz), 3.09 (1H, t, J=11.7 Hz), 3.68 (1H, d, J=12.9 Hz), 3.90 (3H, s), 3.95-4.20 (3H, m), 4.26 (1H, d, J=11.7 Hz), 4.51 (1H, t, J=5.4 Hz), 4.67 (2H, td, J=16.1, 3.0 Hz), 5.23 (1H, s), 5.61 (2H, s), 6.33 (1H, tt, J=54.2, 3.0 Hz), 7.49 (1H, d, J=7.8 Hz), 7.61 (2H, t, J=7.5 Hz), 7.73 (1H, t, J=7.5 Hz), 8.10-8.12 (2H, m).

Example 653

Production of 6-ethyl-N-[1-(hydroxyacetyl)piperidin-4-yl]-5-(3-methoxybenzyl)-1-methyl-4-oxo-3-(2,2,2-trifluoroethoxy)-4,5-dihydro-1H-pyrrolo[3,2-c]pyridine-2-carboxamide

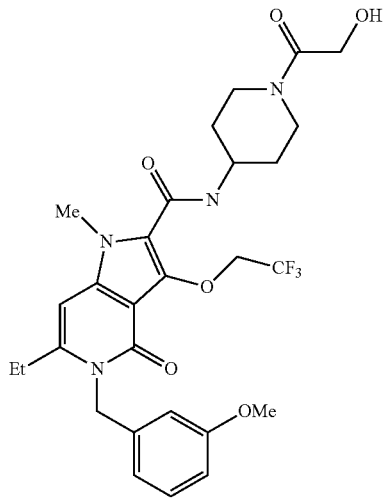 [SMILES: CCc1cc2c(c(OCC(F)(F)F)c(C(=O)NC3CCN(C(=O)CO)CC3)n2C)c(=O)n1Cc1cccc(OC)c1]

A mixture of the compound of Reference Example 143 (200 mg, 0.456 mmol), 2-(4-aminopiperidin-1-yl)-2-oxoethanol hydrochloride (115 mg, 0.593 mmol), HOBt (92.4 mg, 0.684 mmol), WSCD (131 mg, 0.684 mmol), triethylamine (0.126 mL, 0.912 mmol) and DMF (4.0 mL) was stirred at room temperature for 16 hr. The reaction mixture was diluted with water, and extracted twice with ethyl acetate. The extract was combined, washed with water and brine, dried over sodium sulfate, and concentrated under reduced pressure. The residue was purified by aminosilica gel chromatography (eluate; ethyl acetate). Recrystallization of the obtained solid from ethyl acetate gave the title compound (162 mg, 61%) as a white powder.

$^1$H-NMR (300 MHz, DMSO-$d_6$) δ:1.16 (3H, t, J=7.3 Hz), 1.24-1.50 (2H, m), 1.81-1.95 (2H, m), 2.60 (2H, q, J=7.3 Hz), 2.76-2.91 (1H, m), 3.01-3.18 (1H, m), 3.64-3.74 (4H, m), 3.84 (3H, s), 3.95-4.14 (3H, m), 4.20-4.33 (1H, m), 4.52 (1H, t, J=5.4 Hz), 5.11 (2H, q, J=9.3 Hz), 5.32 (2H, br s), 6.49-6.64 (3H, m), 6.81 (1H, dd, J=8.0, 2.2 Hz), 7.22 (1H, t, J=8.0 Hz), 7.53 (1H, d, J=7.6 Hz).

Example 654

Production of 5-benzyl-6-ethyl-N-[1-(hydroxyacetyl)piperidin-4-yl]-1-methyl-4-oxo-3-(2,2,2-trifluoroethoxy)-4,5-dihydro-1H-pyrrolo[3,2-c]pyridine-2-carboxamide

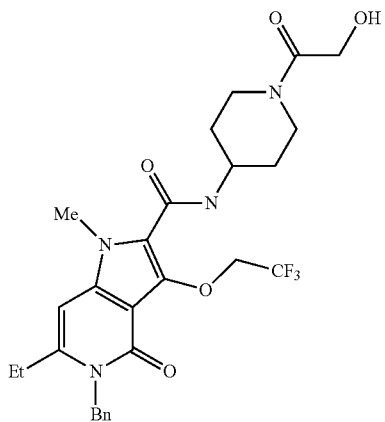 [SMILES: CCc1cc2c(c(OCC(F)(F)F)c(C(=O)NC3CCN(C(=O)CO)CC3)n2C)c(=O)n1Cc1ccccc1]

In the same manner as in Example 653, the title compound (182 mg, 75%) was obtained as a white powder from the compound of Reference Example 145 (180 mg, 0.441 mmol).

$^1$H-NMR (300 MHz, DMSO-$d_6$) δ:1.16 (3H, t, J=7.2 Hz), 1.25-1.48 (2H, m), 1.83-1.95 (2H, m), 2.60 (2H, q, J=7.2 Hz), 2.77-2.90 (1H, m), 3.02-3.17 (1H, m), 3.63-3.75 (1H, m), 3.84 (3H, s), 3.96-4.14 (3H, m), 4.20-4.33 (1H, m), 4.52 (1H, t, J=5.5 Hz), 5.10 (2H, q, J=9.4 Hz), 5.36 (2H, br s), 6.52 (1H, s), 7.00-7.09 (2H, m), 7.19-7.36 (3H, m), 7.53 (1H, d, J=7.7 Hz).

Example 655

Production of 5-(2,5-dimethoxybenzyl)-6-ethyl-N-[1-(hydroxyacetyl)piperidin-4-yl]-1-methyl-4-oxo-3-(2,2,2-trifluoroethoxy)-4,5-dihydro-1H-pyrrolo[3,2-c]pyridine-2-carboxamide

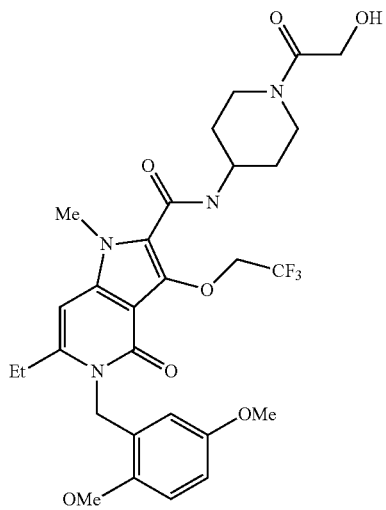 [SMILES: CCc1cc2c(c(OCC(F)(F)F)c(C(=O)NC3CCN(C(=O)CO)CC3)n2C)c(=O)n1Cc1cc(OC)ccc1OC]

In the same manner as in Example 653, the title compound (86.0 mg, 80%) was obtained as a white powder from the compound of Reference Example 147 (82.7 mg, 0.177 mmol).

$^1$H-NMR (300 MHz, DMSO-$d_6$) δ:1.17 (3H, t, J=7.3 Hz), 1.24-1.48 (2H, m), 1.84-1.93 (2H, m), 2.52-2.61 (2H, m), 2.77-2.90 (1H, m), 3.03-3.16 (1H, m), 3.55 (3H, s), 3.64-3.74 (1H, m), 3.83 (3H, s), 3.86 (3H, s), 3.97-4.14 (3H, m), 4.20-4.32 (1H, m), 4.52 (1H, t, J=5.3 Hz), 5.08 (2H, q, J=9.2 Hz), 5.21 (2H, br s), 5.89 (1H, d, J=3.0 Hz), 6.56 (1H, s), 6.79 (1H, dd, J=8.9, 3.0 Hz), 6.97 (1H, d, J=8.9 Hz), 7.53 (1H, d, J=7.9 Hz).

Example 656

Production of 6-ethyl-N-[1-(hydroxyacetyl)piperidin-4-yl]-5-[2-(3-methoxyphenyl)-2-oxoethyl]-1-methyl-4-oxo-3-(2,2,2-trifluoroethoxy)-4,5-dihydro-1H-pyrrolo[3,2-c]pyridine-2-carboxamide

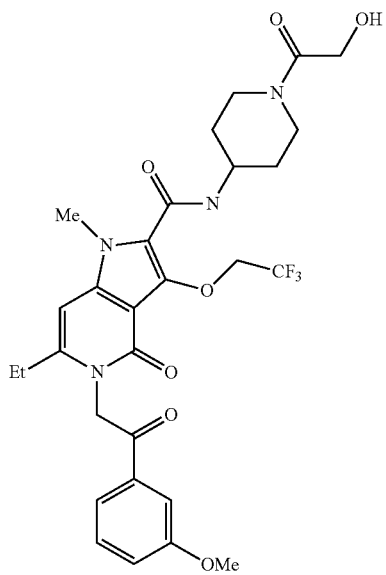 [SMILES: CCc1cc2c(c(OCC(F)(F)F)c(C(=O)NC3CCN(C(=O)CO)CC3)n2C)c(=O)n1CC(=O)c1cccc(OC)c1]

In the same manner as in Example 653, the title compound (65.1 mg, 29%) was obtained as a white powder from the compound of Reference Example 151 (170 mg, 0.364 mmol).

¹H-NMR (300 MHz, DMSO-d₆) δ:1.19 (3H, t, J=7.3 Hz), 1.25-1.48 (2H, m), 1.82-1.95 (2H, m), 2.54-2.64 (2H, m), 2.76-2.90 (1H, m), 3.01-3.15 (1H, m), 3.62-3.74 (1H, m), 3.82-3.90 (6H, m), 3.95-4.13 (3H, m), 4.20-4.35 (1H, m), 4.52 (1H, t, J=5.5 Hz), 5.05 (2H, q, J=9.3 Hz), 5.62 (2H, s), 6.54 (1H, s), 7.26-7.35 (1H, m), 7.46-7.62 (3H, m), 7.69-7.76 (1H, m).

Example 657

Production of 5-[2-(3-chlorophenyl)-2-oxoethyl]-6-ethyl-N-[1-(hydroxyacetyl)piperidin-4-yl]-1-methyl-4-oxo-3-(2,2,2-trifluoroethoxy)-4,5-dihydro-1H-pyrrolo[3,2-c]pyridine-2-carboxamide

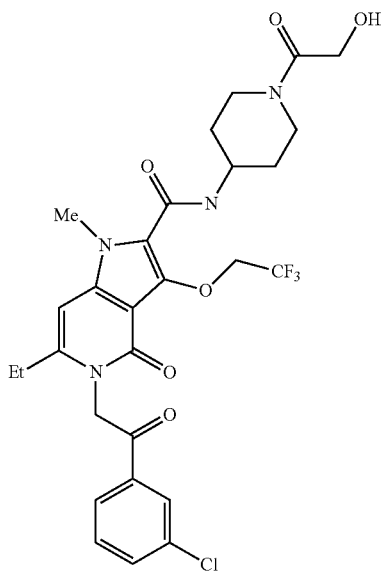 [SMILES: CCc1cc2c(c(OCC(F)(F)F)c(C(=O)NC3CCN(C(=O)CO)CC3)n2C)c(=O)n1CC(=O)c1cccc(Cl)c1]

In the same manner as in Example 653, the title compound (160 mg, 64%) was obtained as a white powder from the compound of Reference Example 155 (192 mg, 0.408 mmol).
¹H-NMR (300 MHz, DMSO-d₆) δ:1.19 (3H, t, J=7.3 Hz), 1.25-1.49 (2H, m), 1.82-1.95 (2H, m), 2.60 (2H, q, J=7.3 Hz), 2.76-2.90 (1H, m), 3.01-3.17 (1H, m), 3.62-3.74 (1H, m), 3.86 (3H, s), 3.96-4.15 (3H, m), 4.20-4.32 (1H, m), 4.52 (1H, t, J=5.4 Hz), 5.05 (2H, q, J=9.2 Hz), 5.62 (2H, s), 6.55 (1H, s), 7.50 (1H, d, J=7.6 Hz), 7.61-7.69 (1H, m), 7.77-7.84 (1H, m), 8.03-8.09 (1H, m), 8.14 (1H, t, J=1.8 Hz).

Example 658

Production of 6-ethyl-N-[1-(hydroxyacetyl)piperidin-4-yl]-5-(2-methoxybenzyl)-1-methyl-4-oxo-3-(2,2,2-trifluoroethoxy)-4,5-dihydro-1H-pyrrolo[3,2-c]pyridine-2-carboxamide

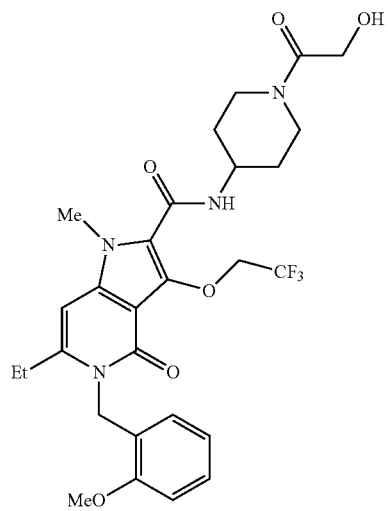 [SMILES: CCc1cc2c(c(OCC(F)(F)F)c(C(=O)NC3CCN(C(=O)CO)CC3)n2C)c(=O)n1Cc1ccccc1OC]

In the same manner as in Example 653, the title compound (120 mg, 86%) was obtained as a white powder from the compound of Reference Example 157 (104 mg, 0.237 mmol).
¹H-NMR (300 MHz, DMSO-d₆) δ:1.16 (3H, t, J=7.4 Hz), 1.26-1.49 (2H, m), 1.81-1.95 (2H, m), 2.52-2.61 (2H, m), 2.77-2.91 (1H, m), 3.00-3.19 (1H, m), 3.56-3.77 (1H, m), 3.86 (3H, s), 3.88 (3H, s), 3.97-4.14 (3H, m), 4.19-4.33 (1H, m), 4.52 (1H, t, J=5.4 Hz), 5.08 (2H, q, J=9.2 Hz), 5.23 (2H, br s), 6.32-6.40 (1H, m), 6.56 (1H, s), 6.76-6.85 (1H, m), 7.01-7.09 (1H, m), 7.17-7.28 (1H, m), 7.52 (1H, d, J=7.6 Hz).

Example 659

Production of 6-ethyl-N-[1-(hydroxyacetyl)piperidin-4-yl]-5-(4-methoxybenzyl)-1-methyl-4-oxo-3-(2,2,2-trifluoroethoxy)-4,5-dihydro-1H-pyrrolo[3,2-c]pyridine-2-carboxamide

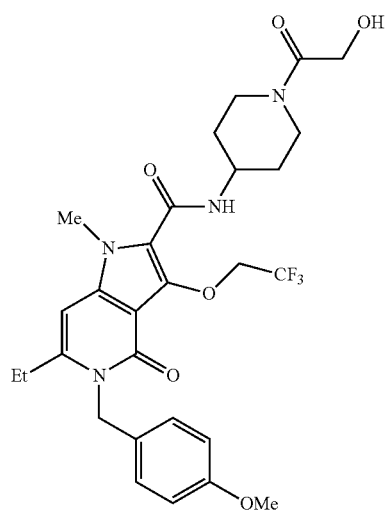 [SMILES: CCc1cc2c(c(OCC(F)(F)F)c(C(=O)NC3CCN(C(=O)CO)CC3)n2C)c(=O)n1Cc1ccc(OC)cc1]

In the same manner as in Example 653, the title compound (147 mg, 71%) was obtained as a white powder from the compound of Reference Example 159 (157 mg, 0.358 mmol).

¹H-NMR (300 MHz, DMSO-d₆) δ:1.16 (3H, t, J=7.3 Hz), 1.24-1.48 (2H, m), 1.83-1.96 (2H, m), 2.62 (2H, q, J=7.3 Hz), 2.76-2.91 (1H, m), 3.02-3.17 (1H, m), 3.63-3.76 (4H, m), 3.83 (3H, s), 3.95-4.14 (3H, m), 4.20-4.33 (1H, m), 4.52 (1H, t, J=5.4 Hz), 5.11 (2H, q, J=9.4 Hz), 5.28 (2H, br s), 6.50 (1H, s), 6.83-6.90 (2H, m), 6.96-7.05 (2H, m), 7.52 (1H, d, J=7.7 Hz).

Example 660

Production of 5-(2-chlorobenzyl)-6-ethyl-N-[1-(hydroxyacetyl)piperidin-4-yl]-1-methyl-4-oxo-3-(2,2,2-trifluoroethoxy)-4,5-dihydro-1H-pyrrolo[3,2-c]pyridine-2-carboxamide

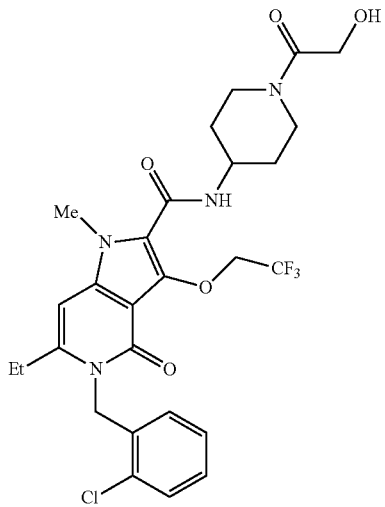 [SMILES: CCc1cc2c(c(OCC(F)(F)F)c(C(=O)NC3CCN(C(=O)CO)CC3)n2C)c(=O)n1Cc1ccccc1Cl]

In the same manner as in Example 653, the title compound (119 mg, 66%) was obtained as a white powder from the compound of Reference Example 161 (138 mg, 0.312 mmol).

¹H-NMR (300 MHz, DMSO-d₆) δ:1.18 (3H, t, J=7.3 Hz), 1.26-1.47 (2H, m), 1.82-1.94 (2H, m), 2.53-2.61 (2H, m), 2.76-2.90 (1H, m), 3.02-3.17 (1H, m), 3.61-3.76 (1H, m), 3.86 (3H, s), 3.95-4.14 (3H, m), 4.19-4.33 (1H, m), 4.46-4.56 (1H, m), 5.06 (2H, q, J=9.4 Hz), 5.33 (2H, s), 6.45-6.55 (1H, m), 6.60 (1H, s), 7.21-7.32 (2H, m), 7.45-7.60 (2H, m).

Example 661

Production of 6-ethyl-N-[1-(hydroxyacetyl)piperidin-4-yl]-1-methyl-4-oxo-5-(2-phenylethyl)-3-(2,2,2-trifluoroethoxy)-4,5-dihydro-1H-pyrrolo[3,2-c]pyridine-2-carboxamide

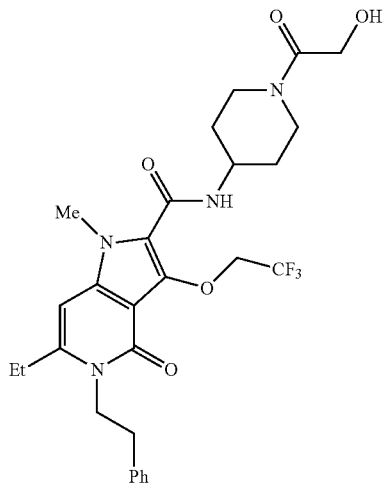 [SMILES: CCc1cc2c(c(OCC(F)(F)F)c(C(=O)NC3CCN(C(=O)CO)CC3)n2C)c(=O)n1CCc1ccccc1]

In the same manner as in Example 653, the title compound (123 mg, 65%) was obtained as a white powder from the compound of Reference Example 165 (143 mg, 0.339 mmol).

¹H-NMR (300 MHz, DMSO-d₆) δ:1.21 (3H, t, J=7.2 Hz), 1.25-1.49 (2H, m), 1.82-1.94 (2H, m), 2.66 (2H, q, J=7.2 Hz), 2.77-2.95 (3H, m), 3.02-3.17 (1H, m), 3.62-3.75 (1H, m), 3.82 (3H, s), 3.95-4.35 (6H, m), 4.52 (1H, t, J=5.5 Hz), 5.12 (2H, q, J=9.4 Hz), 6.44 (1H, s), 7.16-7.35 (5H, m), 7.49 (1H, d, J=7.6 Hz).

Example 662

Production of 5-(3-chlorobenzyl)-6-ethyl-N-[1-(hydroxyacetyl)piperidin-4-yl]-1-methyl-4-oxo-3-(2,2,2-trifluoroethoxy)-4,5-dihydro-1H-pyrrolo[3,2-c]pyridine-2-carboxamide

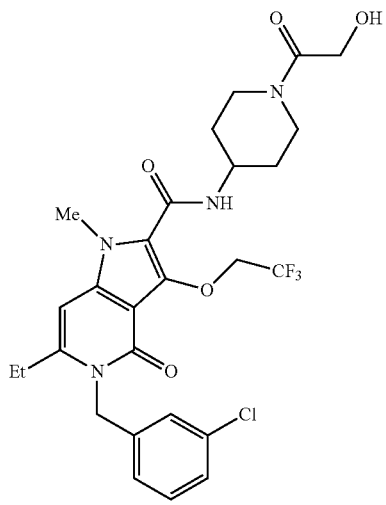 [SMILES: CCc1cc2c(c(OCC(F)(F)F)c(C(=O)NC3CCN(C(=O)CO)CC3)n2C)c(=O)n1Cc1cccc(Cl)c1]

In the same manner as in Example 653, the title compound (261 mg, 71%) was obtained as a white powder from the compound of Reference Example 167 (281 mg, 0.635 mmol).

¹H-NMR (300 MHz, DMSO-d₆) δ:1.17 (3H, t, J=7.2 Hz), 1.23-1.50 (2H, m), 1.81-1.95 (2H, m), 2.60 (2H, q, J=7.2 Hz), 2.76-2.92 (1H, m), 3.02-3.17 (1H, m), 3.64-3.76 (1H, m), 3.85 (3H, s), 3.95-4.15 (3H, m), 4.19-4.36 (1H, m), 4.52 (1H, t, J=5.4 Hz), 5.09 (2H, q, J=9.4 Hz), 5.35 (2H, br s), 6.55 (1H, s), 6.95-7.03 (1H, m), 7.07-7.15 (1H, m), 7.25-7.40 (2H, m), 7.55 (1H, d, J=7.6 Hz).

Example 663

Production of 5-(4-chlorobenzyl)-6-ethyl-N-[1-(hydroxyacetyl)piperidin-4-yl]-1-methyl-4-oxo-3-(2,2,2-trifluoroethoxy)-4,5-dihydro-1H-pyrrolo[3,2-c]pyridine-2-carboxamide

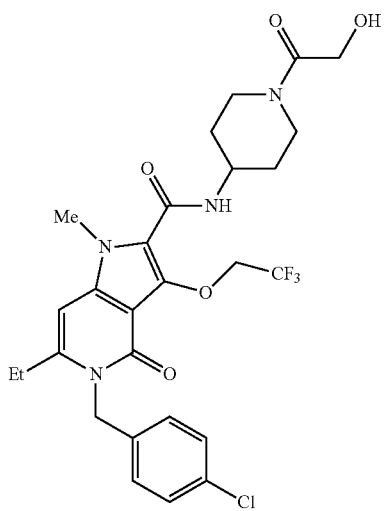 [SMILES: CCc1cc2c(c(OCC(F)(F)F)c(C(=O)NC3CCN(C(=O)CO)CC3)n2C)c(=O)n1Cc1ccc(Cl)cc1]

In the same manner as in Example 653, the title compound (160 mg, 65%) was obtained as a white powder from the compound of Reference Example 169 (188 mg, 0.425 mmol).
$^1$H-NMR (300 MHz, DMSO-d$_6$) δ:1.16 (3H, t, J=7.2 Hz), 1.23-1.49 (2H, m), 1.82-1.95 (2H, m), 2.59 (2H, q, J=7.2 Hz), 2.77-2.90 (1H, m), 3.00-3.17 (1H, m), 3.62-3.76 (1H, m), 3.84 (3H, s), 3.95-4.14 (3H, m), 4.21-4.34 (1H, m), 4.52 (1H, t, J=5.5 Hz), 5.09 (2H, q, J=9.4 Hz), 5.33 (2H, br s), 6.53 (1H, s), 7.03-7.12 (2H, m), 7.34-7.42 (2H, m), 7.53 (1H, d, J=7.6 Hz).

Example 664

Production of Benzyl 4-({[3-methoxy-5-(4-methoxybenzyl)-4-oxo-4,5-dihydrothieno[3,2-c]quinolin-2-yl]carbonyl}amino)piperidine-1-carboxylate

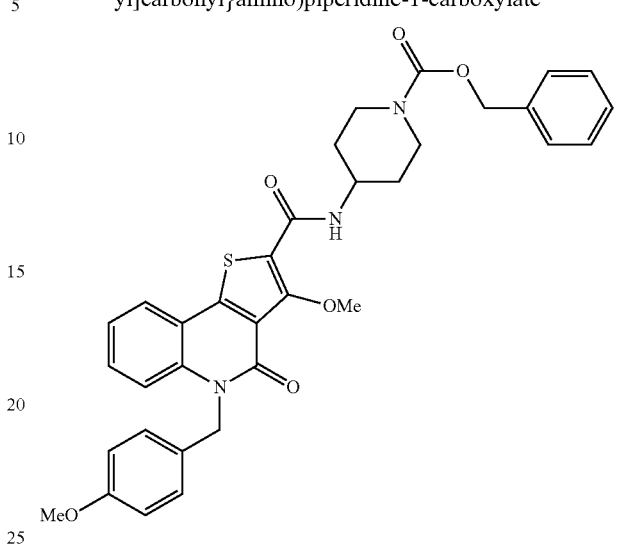

In the same manner as in Example 25, the title compound (3.07 g, 79%) was obtained as a white powder from the compound of Reference Example 13 (2.5 g, 6.31 mmol) and benzyl 4-aminopiperidine-1-carboxylate hydrochloride (2.56 g, 9.46 mmol).
$^1$H-NMR (300 MHz, DMSO-d$_6$) δ:1.15-1.64 (2H, m), 1.87 (2H, br d, J=9.6 Hz), 2.90-3.10 (2H, br), 3.69 (3H, s), 4.00 (2H, d, J=11.4 Hz), 4.09 (4H, s), 5.10 (2H, s), 5.53 (2H, br s), 6.87 (2H, d, J=8.7 Hz), 7.20 (2H, d, J=8.7 Hz), 7.28-7.40 (6H, m), 7.49-7.56 (2H, m), 7.80 (1H, d, J=8.1 Hz), 8.00 (1H, d, J=8.4 Hz).

Example 665

Production of 3-methoxy-5-(4-methoxybenzyl)-4-oxo-N-piperidin-4-yl-4,5-dihydrothieno[3,2-c]quinoline-2-carboxamide

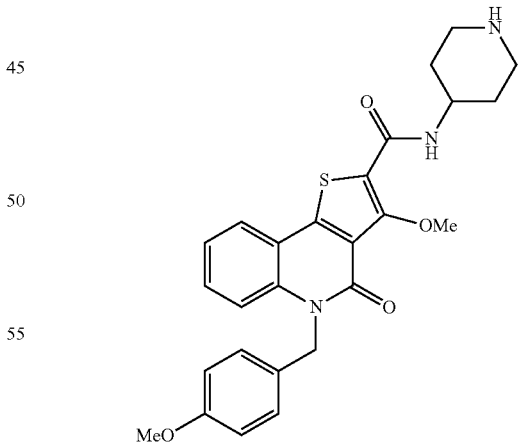

A mixture of the compound of Example 664 (300 mg, 0.49 mmol), 10% Pd—C (60 mg) and THF (20 mL)-methanol (10 mL) was stirred at room temperature for 24 hr under a hydrogen atmosphere. The catalyst was filtered off, and the filtrate was concentrated and recrystallized from methanol-diethyl ether to give the title compound (154 mg, 66%) as pale-yellow crystals.

¹H-NMR (300 MHz, DMSO-d₆) δ:1.48 (2H, q, J=11.0 Hz), 1.82 (2H, d, J=9.6 Hz), 1.95-2.15 (1H, br), 2.56 (2H, t, J=8.4 Hz), 2.93 (2H, d, J=12.6 Hz), 3.33 (3H, s), 3.70 (3H, s), 3.80-4.00 (1H, br), 4.10 (3H, s), 5.53 (2H, br s), 6.86 (2H, d, J=8.7 Hz), 7.20 (2H, d, J=8.4 Hz), 7.30 (1H, t, J=7.1 Hz), 7.49-7.58 (2H, m), 7.72 (1H, d, J=8.1 Hz), 8.00 (1H, d, J=7.8 Hz).

Example 666

Production of N-[1-(2-hydroxyethyl)piperidin-4-yl]-3-methoxy-5-(4-methoxybenzyl)-4-oxo-4,5-dihydrothieno[3,2-c]quinoline-2-carboxamide

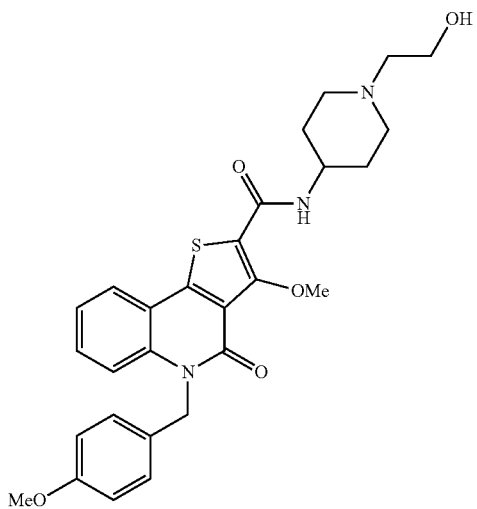 [SMILES: COc1ccc(Cn2c(=O)c3c(OC)c(C(=O)NC4CCN(CCO)CC4)sc3c3ccccc32)cc1]

In the same manner as in Example 79, the title compound (110 mg, 68%) was obtained as a white solid from the compound of Example 665 (150 mg, 0.31 mmol).

¹H-NMR (300 MHz, CDCl₃) δ:1.55-1.74 (2H, m), 2.00-2.11 (2H, m), 2.36 (2H, t, J=11.6 Hz), 2.58 (2H, t, J=5.4 Hz), 2.84 (3H, br s), 3.65 (2H, t, J=5.4 Hz), 3.75 (3H, s), 4.05-4.20 (1H, br), 4.20 (3H, s), 5.53 (2H, br s), 6.83 (2H, dd, J=6.9, 1.8 Hz), 7.17-7.26 (3H, m), 7.35 (1H, d, J=8.1 Hz), 7.41-7.46 (1H, m), 7.64 (1H, d, J=7.8 Hz), 7.85 (1H, dd, J=7.8, 1.5 Hz).

Example 667

Production of N-[1-(2-hydroxyethyl)piperidin-4-yl]-3-methoxy-4-oxo-4,5-dihydrothieno[3,2-c]quinoline-2-carboxamide

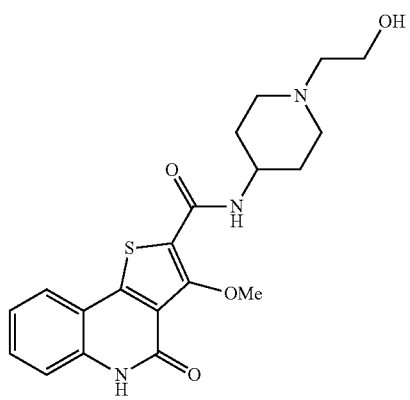 [SMILES: COc1c(C(=O)NC2CCN(CCO)CC2)sc2c1c(=O)[nH]c1ccccc12]

A solution of the compound of Example 666 (110 mg, 0.21 mmol), anisole (91 mg, 0.84 mmol) and trifluoromethanesulfonic acid (0.5 mL) in trifluoroacetic acid (2 mL) was stirred at 80° C. for 1 hr. After cooling, the reaction mixture was concentrated, and the residue was partitioned between ethyl acetate and saturated sodium hydrogen carbonate solution. The organic phase was washed with brine, dried over magnesium sulfate, and concentrated under reduced pressure. The residue was purified by silica gel chromatography (eluate; ethyl acetate/hexane=1/1 to 2/1) to give the title compound (60 mg, 71%) as a white solid.

¹H-NMR (300 MHz, CDCl₃) δ:1.60-1.76 (2H, m), 2.07 (2H, d, J=14.4 Hz), 2.36 (2H, t, J=10.1 Hz), 2.59 (2H, t, J=5.4 Hz), 2.88 (2H, d, J=11.4 Hz), 3.65 (2H, t, J=5.4 Hz), 3.70-3.80 (2H, br), 4.00-4.15 (1H, m), 4.22 (3H, s), 6.76-6.85 (1H, m), 7.32 (1H, t, J=8.1 Hz), 7.51 (1H, t, J=8.4 Hz), 7.85 (1H, d, J=8.1 Hz), 10.20-10.50 (1H, br).

Example 668

Production of tert-butyl 4-({[3-methoxy-5-(4-methoxybenzyl)-1-methyl-4-oxo-4,5-dihydro-1H-pyrrolo[3,2-c]quinolin-2-yl]carbonyl}amino)piperidine-1-carboxylate

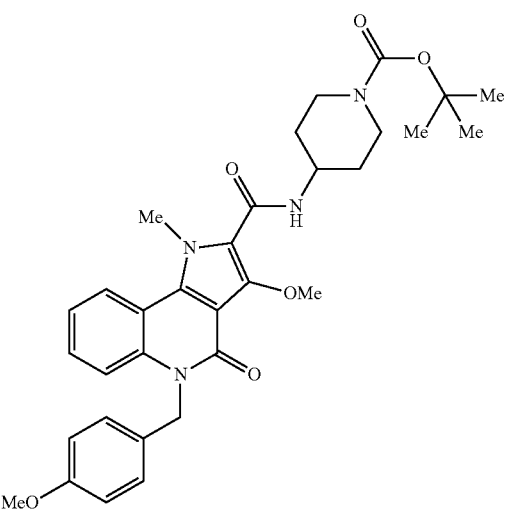 [SMILES: COc1ccc(Cn2c(=O)c3c(OC)c(C(=O)NC4CCN(C(=O)OC(C)(C)C)CC4)n(C)c3c3ccccc32)cc1]

In the same manner as in Example 25, the title compound (3.45 g, 95%) was obtained as a beige solid from the compound of Reference Example 107 (2.49 g, 6.35 mmol) and tert-butyl 4-aminopiperidine-1-carboxylate (2.54 g, 12.69 mmol).

¹H-NMR (300 MHz, DMSO-d₆) δ:1.35-1.49 (11H, m), 1.85 (2H, dd, J=12.6, 2.7 Hz), 2.89-2.96 (2H, m), 3.69 (3H, s), 3.88 (2H, d, J=13.5 Hz), 3.96-4.09 (4H, m), 4.27 (3H, s), 5.40-5.60 (2H, br), 6.83-6.88 (2H, m), 7.14 (2H, d, J=8.7 Hz), 7.24-7.30 (1H, m), 7.41-7.49 (2H, m), 7.97 (1H, d, J=8.1 Hz), 8.33 (1H, d, J=8.1 Hz).

Example 669

Production of 3-methoxy-4-oxo-5-(2-oxo-2-phenyl-ethyl)-N-(pyrrolidin-3-ylmethyl)-4,5-dihydrothieno[3,2-c]quinoline-2-carboxamide hydrochloride

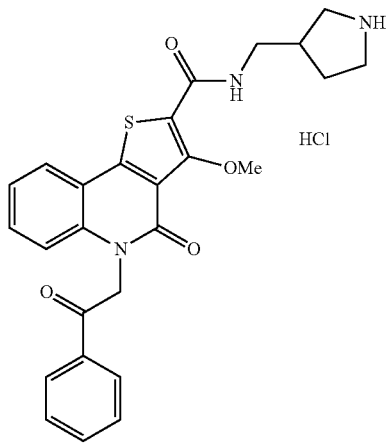 [SMILES: COc1c(C(=O)NCC2CCNC2)sc2c1c(=O)n(CC(=O)c1ccccc1)c1ccccc21 ; Cl]

In the same manner as in Example 25, tert-butyl 3-[({[3-methoxy-4-oxo-5-(2-oxo-2-phenylethyl)-4,5-dihydrothieno[3,2-c]quinolin-2-yl]carbonyl}amino)methyl]pyrrolidine-1-carboxylate (530 mg, 72%) was obtained as a white powder from the compound of Reference Example 7 (500 mg, 1.27 mmol) and 3-(aminomethyl)-1-Boc-pyrrolidine (381 mg, 1.90 mmol).

In the same manner as in Example 500, the title compound (456 mg, 97%) was obtained as a white powder from tert-butyl 3-[({[3-methoxy-4-oxo-5-(2-oxo-2-phenylethyl)-4,5-dihydrothieno[3,2-c]quinolin-2-yl]carbonyl}amino)methyl]pyrrolidine-1-carboxylate (530 mg, 0.92 mmol).

$^1$H-NMR (300 MHz, DMSO-$d_6$) δ:1.55-1.73 (1H, m), 1.90-2.10 (1H, m), 2.55-2.70 (1H, m), 2.85-3.00 (1H, br), 3.10-3.45 (5H, m), 4.05 (3H, s), 6.00 (2H, s), 7.35 (1H, t, J=7.5 Hz), 7.49-7.67 (5H, m), 7.77 (1H, t, J=7.4 Hz), 8.05 (1H, d, J=7.8, Hz), 8.16-8.19 (2H, m), 8.25 (1H, t, J=5.9 Hz), 9.04 (2H, br s).

Example 670

Production of tert-butyl 3-({[3-methoxy-1-methyl-4-oxo-5-(2-oxo-2-phenylethyl)-4,5-dihydro-1H-pyrrolo[3,2-c]quinolin-2-yl]carbonyl}amino)azetidine-1-carboxylate

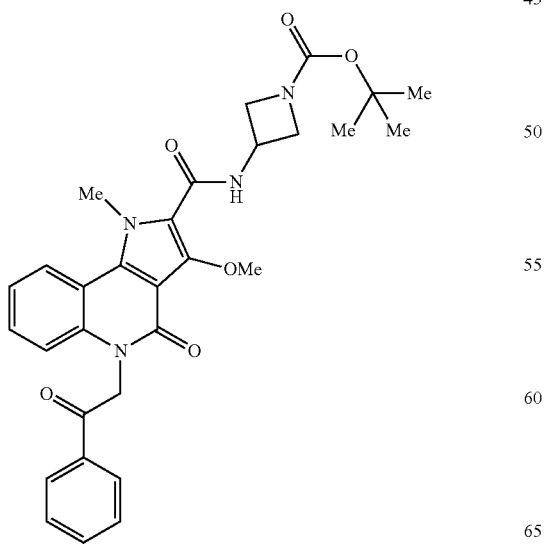

In the same manner as in Example 25, the title compound (610 mg, 88%) was obtained as a white powder from the compound of Reference Example 28 (500 mg, 1.27 mmol) and 3-amino-1-Boc-azetidine (330 mg, 1.92 mmol).

$^1$H-NMR (300 MHz, DMSO-$d_6$) δ:1.40 (9H, m), 3.85-3.95 (2H, m), 3.99 (3H, s), 4.14 (2H, t, J=7.8 Hz), 4.27 (3H, s), 4.62-4.74 (1H, m), 5.97 (2H, s), 7.31 (1H, t, J=7.5 Hz), 7.38 (1H, d, J=8.1 Hz), 7.48 (1H, t, J=7.5 Hz), 7.64 (2H, t, J=7.5 Hz), 7.76 (1H, t, J=7.5 Hz), 8.16-8.19 (2H, m), 8.37 (1H, d, J=8.1 Hz), 8.56 (1H, d, J=7.2 Hz).

Example 671

Production of tert-butyl[3-({[3-methoxy-1-methyl-4-oxo-5-(2-oxo-2-phenylethyl)-4,5-dihydro-1H-pyrrolo[3,2-c]quinolin-2-yl]carbonyl}amino)cyclohexyl]carbamate

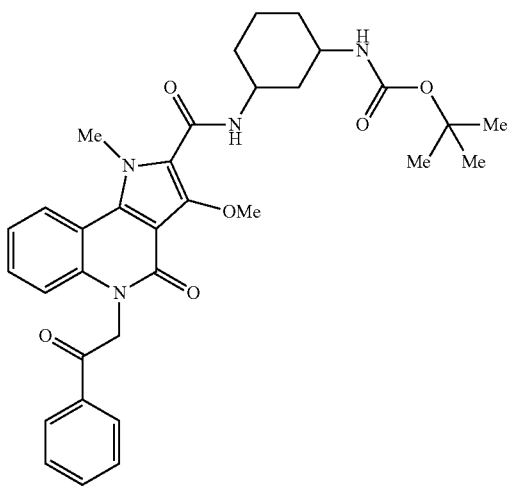 [SMILES: COc1c(C(=O)NC2CCCC(NC(=O)OC(C)(C)C)C2)n(C)c2c1c(=O)n(CC(=O)c1ccccc1)c1ccccc21]

In the same manner as in Example 25, the title compound (395 mg, 66%) was obtained as a white powder from the compound of Reference Example 7 (400 mg, 1.02 mmol) and tert-butyl (3-aminocyclohexyl)carbamate (285 mg, 1.33 mmol).

$^1$H-NMR (300 MHz, DMSO-$d_6$) δ:0.98-1.46 (13H, m), 1.65-1.90 (3H, m), 2.00-2.12 (1H, m), 3.23-3.42 (1H, m), 3.73-3.88 (1H, m), 3.96 (2H, s), 4.04 (1H, s), 4.30 (2H, s), 4.35 (1H, s), 5.97 (2H, s), 6.76-6.94 (1H, m), 7.24-7.42 (2H, m), 7.43-7.53 (1H, m), 7.63 (2H, t, J=7.6 Hz), 7.71-7.80 (1H, m), 7.86 (1H, d, J=7.9 Hz), 8.12-8.22 (2H, m), 8.31-8.42 (1H, m).

Example 672

Production of 2-(4-{[(3-methoxy-1-methyl-4-oxo-4,5-dihydro-1H-pyrrolo[3,2-c]quinolin-2-yl)carbonyl]amino}piperidin-1-yl)-2-oxoethyl acetate

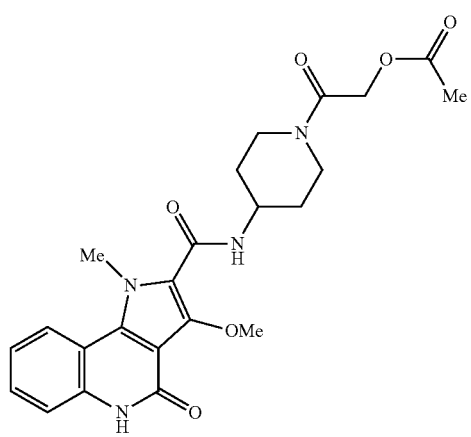 [SMILES: COc1c(C(=O)NC2CCN(C(=O)COC(C)=O)CC2)n(C)c2c1c(=O)[nH]c1ccccc12]

The compound of Example 558 (500 mg, 0.87 mmol), anisole (376 mg, 3.48 mmol) and trifluoromethanesulfonic acid (2 mL) were dissolved in trifluoroacetic acid (9 mL), and the mixture was stirred at 80° C. for 2 hr. After cooling to room temperature, the mixture was concentrated under reduced pressure. The residue was diluted with saturated aqueous sodium hydrogen carbonate solution, and extracted with THF-ethyl acetate. The extract was concentrated to give 3-methoxy-1-methyl-4-oxo-N-piperidin-4-yl-4,5-dihydro-1H-pyrrolo[3,2-c]quinoline-2-carboxamide (1.10 g) as a beige solid.

To a solution of 3-methoxy-1-methyl-4-oxo-N-piperidin-4-yl-4,5-dihydro-1H-pyrrolo[3,2-c]quinoline-2-carboxamide (300 mg, 0.87 mmol) and triethylamine (88 mg, 0.87 mmol) in THF (30 mL) was added acetoxyacetyl chloride (119 mg, 0.87 mmol) under ice-cooling, and the mixture was stirred for 2 hr. The reaction mixture was diluted with saturated aqueous sodium hydrogen carbonate solution, and extracted with ethyl acetate. The extract was dried over magnesium sulfate and concentrated. The obtained solid was washed with diethyl ether-hexane to give the title compound (221 mg, 56%) as a white solid.

$^1$H-NMR (300 MHz, DMSO-d$_6$) δ:1.30-1.65 (2H, m), 1.80-2.00 (2H, m), 2.09 (3H, s), 2.90 (2H, t, J=11.4 Hz), 3.19 (2H, t, J=11.4 Hz), 3.70 (2H, d, J=13.5 Hz), 4.02-4.19 (4H, m), 4.28 (3H, s), 7.22 (1H, t, J=7.5 Hz), 7.40-7.48 (2H, m), 7.93 (1H, d, J=7.5 Hz), 8.24 (1H, d, J=8.4 Hz), 11.34 (1H, s).

Example 673

Production of tert-butyl 4-({[8-fluoro-3-methoxy-4-oxo-5-(2-oxo-2-phenylethyl)-4,5-dihydrothieno[3,2-c]quinolin-2-yl]carbonyl}amino)piperidine-1-carboxylate

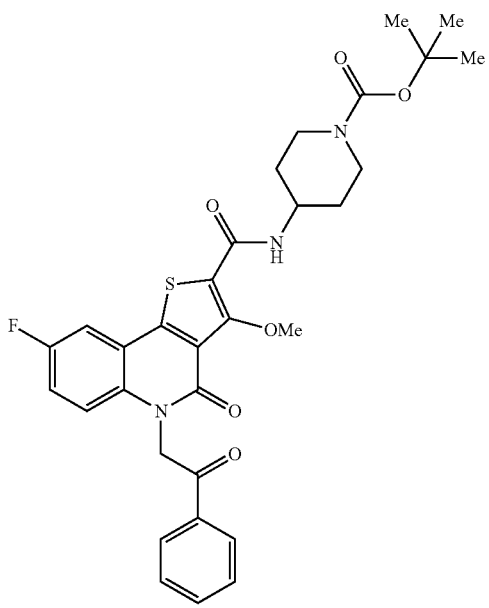 [SMILES: COc1c(C(=O)NC2CCN(C(=O)OC(C)(C)C)CC2)sc2c1c(=O)n(CC(=O)c1ccccc1)c1ccc(F)cc21]

In the same manner as in Example 25, the title compound (486 mg, 84%) was obtained as a white solid from the compound of Reference Example 116 (400 mg, 0.97 mmol) and tert-butyl 4-aminopiperidine-1-carboxylate (234 mg, 1.2 mmol).

$^1$H-NMR (300 MHz, CDCl$_3$) δ:1.40-1.53 (11H, m), 1.96-2.11 (2H, m), 2.92-3.10 (2H, m), 3.95-4.08 (2H, m), 4.10-4.24 (4H, m), 5.85 (2H, s), 6.99 (1H, dd, J=9.3, 4.3 Hz), 7.15-7.25 (1H, m), 7.50-7.62 (4H, m), 7.65-7.74 (1H, m), 8.05-8.16 (2H, m).

Example 674

Production of tert-butyl 4-({[8-fluoro-3-methoxy-1-methyl-4-oxo-5-(2-oxo-2-phenylethyl)-4,5-dihydro-1H-pyrrolo[3,2-c]quinolin-2-yl]carbonyl}amino)piperidine-1-carboxylate

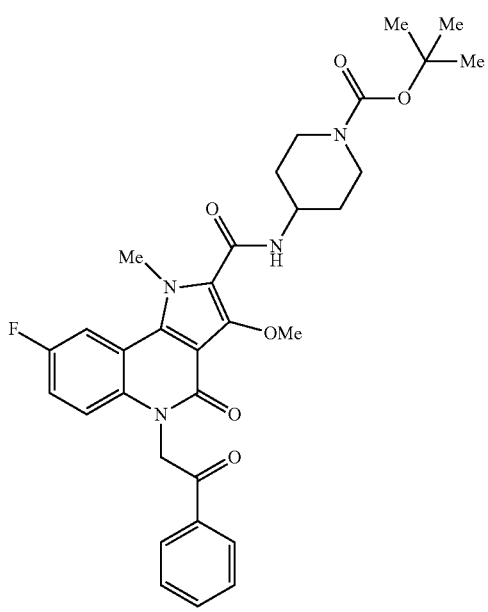 [SMILES: COc1c(C(=O)NC2CCN(C(=O)OC(C)(C)C)CC2)n(C)c2c1c(=O)n(CC(=O)c1ccccc1)c1ccc(F)cc21]

In the same manner as in Example 25, the title compound (2.5 g, 87%) was obtained as a white solid from the compound of Reference Example 119 (2.0 g, 4.9 mmol) and tert-butyl 4-aminopiperidine-1-carboxylate (1.2 g, 5.9 mmol).

$^1$H-NMR (300 MHz, CDCl$_3$) δ:1.34-1.53 (11H, m), 1.89-2.13 (2H, m), 2.94-3.14 (2H, m), 3.89-4.07 (2H, m), 4.08-4.24 (4H, m), 4.46 (3H, s), 5.87 (2H, s), 6.93-7.04 (1H, m), 7.08-7.21 (1H, m), 7.48-7.60 (2H, m), 7.62-7.75 (2H, m), 7.94 (1H, dd, J=10.0, 2.8 Hz), 8.04-8.20 (2H, m).

Example 675

Production of 8-fluoro-3-methoxy-1-methyl-4-oxo-5-(2-oxo-2-phenylethyl)-N-piperidin-4-yl-4,5-dihydro-1H-pyrrolo[3,2-c]quinoline-2-carboxamide hydrochloride

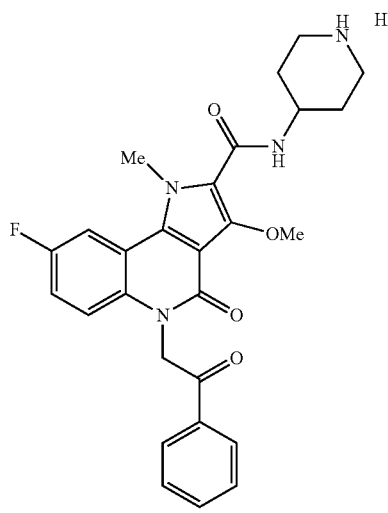

In the same manner as in Example 542, the title compound (1.6 g, 72%) was obtained as a pale-yellow solid from the compound of Example 674 (2.5 g, 4.3 mmol).

$^1$H-NMR (300 MHz, DMSO-d$_6$) δ:1.62-1.86 (2H, m), 1.96-2.13 (2H, m), 2.95-3.14 (2H, m), 3.21-3.47 (2H, m), 3.95 (3H, s), 4.02-4.18 (1H, m), 4.27 (3H, s), 5.98 (2H, s), 7.23-7.51 (2H, m), 7.57-7.68 (2H, m), 7.71-7.84 (1H, m), 8.04-8.26 (4H, m), 8.64 (2H, br s).

Example 676

Production of 2-[4-({[8-fluoro-3-methoxy-1-methyl-4-oxo-5-(2-oxo-2-phenylethyl)-4,5-dihydro-1H-pyrrolo[3,2-c]quinolin-2-yl]carbonyl}amino)piperidin-1-yl]-2-oxoethyl acetate

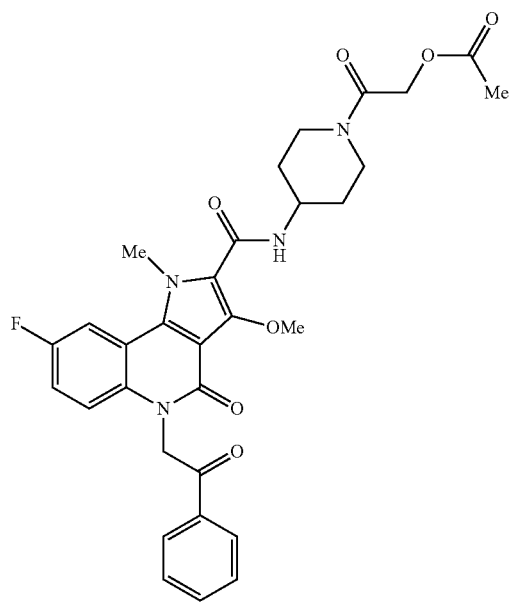 [SMILES: COc1c(C(=O)NC2CCN(C(=O)COC(C)=O)CC2)n(C)c2c1c(=O)n(CC(=O)c1ccccc1)c1ccc(F)cc21]

In the same manner as in Example 544, the title compound (293 mg, 87%) was obtained as a white solid from the compound of Example 675 (300 mg, 0.57 mmol).

$^1$H-NMR (300 MHz, DMSO-d$_6$) δ:1.30-1.65 (2H, m), 1.82-1.96 (2H, m), 2.08 (3H, s), 2.80-2.96 (1H, m), 3.08-3.26 (1H, m), 3.65-3.78 (1H, m), 3.96 (3H, s), 4.02-4.22 (2H, m), 4.30 (3H, s), 4.74-4.85 (2H, m), 5.97 (2H, s), 7.29-7.50 (2H, m), 7.57-7.68 (2H, m), 7.72-7.81 (1H, m), 7.98-8.06 (1H, m), 8.07-8.21 (3H, m).

Example 677

Production of N-(1-benzyl-3-methylpiperidin-4-yl)-3-methoxy-1-methyl-4-oxo-5-(2-oxo-2-phenylethyl)-4,5-dihydro-1H-pyrrolo[3,2-c]quinoline-2-carboxamide

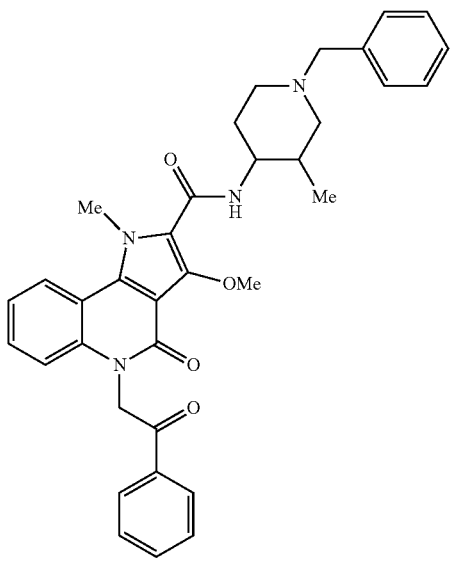 [SMILES: COc1c(C(=O)NC2CCN(Cc3ccccc3)CC2C)n(C)c2c1c(=O)n(CC(=O)c1ccccc1)c1ccccc21]

To a solution of 1-benzyl-3-methylpiperidin-4-one (227 mg, 1.1 mmol) and ammonium acetate (861 mg, 11 mmol) in methanol (9.0 mL) was added sodium triacetoxyborohydride (750 mg, 3.5 mol) under ice-cooling, and the mixture was stirred at room temperature for 2 hr. The reaction mixture was diluted with ethyl acetate, washed with 1N sodium hydroxide solution, and the aqueous layer was extracted twice with ethyl acetate. The extracts were combined, dried over magnesium sulfate, and concentrated under reduced pressure. To a solution of the residue, the compound of Reference Example 28 (396 mg, 1.0 mmol) and HOBt (151 mg, 1.1 mol) in DMF (7.0 mL) was added WSCD (215 mg, 1.1 mmol) under ice-cooling, and the mixture was stirred at room temperature for 15 hr. The reaction mixture was diluted with saturated sodium hydrogen carbonate solution, and extracted twice with ethyl acetate. The extract was combined, washed with brine, dried over magnesium sulfate, and passed through an aminosilica gel. The filtrate was concentrated under reduced pressure. The residue was purified by aminosilica gel chromatography (eluate; ethyl acetate/hexane=30/70-100/0) and recrystallized from ethyl acetate-hexane to give the title compound (373 mg, 64%) as a white solid.

$^1$H-NMR (300 MHz, DMSO-$d_6$) δ:0.83-1.01 (3H, m), 1.49-2.40 (5H, m), 2.56-2.89 (1H, m), 3.22-3.59 (3H, m), 3.94-4.04 (3H, m), 4.07-4.20 (1H, m), 4.25-4.41 (3H, m), 5.98 (2H, s), 7.16-7.42 (7H, m), 7.43-7.54 (1H, m), 7.58-7.69 (2H, m), 7.72-7.81 (1H, m), 7.82-7.94 (1H, m), 8.10-8.23 (2H, m), 8.28-8.45 (1H, m).

Example 678

Production of 3-methoxy-1-methyl-N-(3-methylpiperidin-4-yl)-4-oxo-5-(2-oxo-2-phenylethyl)-4,5-dihydro-1H-pyrrolo[3,2-c]quinoline-2-carboxamide

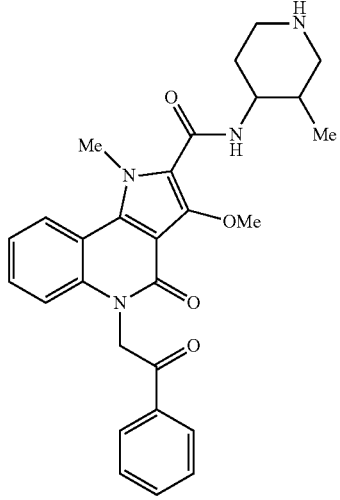 [SMILES: COc1c(C(=O)NC2CCNCC2C)n(C)c2c1c(=O)n(CC(=O)c1ccccc1)c1ccccc21]

To a solution of the compound of Example 677 (373 mg, 0.65 mmol) in THF (40 mL) was added 1-chloroethyl chloroformate (0.67 mL, 6.5 mol) under ice-cooling, and the mixture was stirred at room temperature for 3 hr. 1-Chloroethyl chloroformate (0.67 mL, 6.5 mol) and diisopropylethylamine (0.30 mL, 3.2 mmol) were added under ice-cooling, and the mixture was stirred at room temperature for 20 hr. The reaction mixture was concentrated under reduced pressure, and the residue was washed with diethyl ether. The residue was dissolved in methanol (50 mL), and the mixture was stirred at room temperature for 7 hr and concentrated under reduced pressure. The residue was purified by aminosilica gel chromatography (eluate; methanol/ethyl acetate=0/100-10/90) and recrystallized from ethyl acetate-hexane to give the title compound (90 mg, 29%) as a pale-brown solid.

$^1$H-NMR (300 MHz, DMSO-$d_6$) δ:0.83-0.95 (3H, m), 1.21-2.35 (5H, m), 2.60-3.01 (3H, m), 3.94-4.08 (3H, m), 4.11-4.22 (1H, m), 4.26-4.41 (3H, m), 5.98 (2H, s), 7.22-7.42 (2H, m), 7.43-7.53 (1H, m), 7.59-7.69 (2H, m), 7.71-8.00 (2H, m), 8.12-8.22 (2H, m), 8.32-8.45 (1H, m).

Example 679

Production of tert-butyl (1-{[3-methoxy-1-methyl-4-oxo-5-(2-oxo-2-phenylethyl)-4,5-dihydro-1H-pyrrolo[3,2-c]quinolin-2-yl]carbonyl}piperidin-4-yl)carbamate

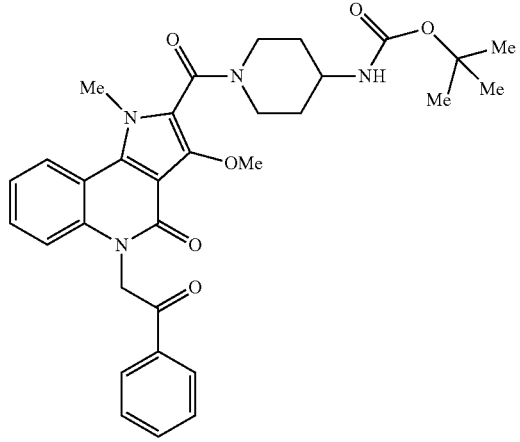 [SMILES: COc1c(C(=O)N2CCC(NC(=O)OC(C)(C)C)CC2)n(C)c2c1c(=O)n(CC(=O)c1ccccc1)c1ccccc21]

In the same manner as in Example 25, the title compound (440 mg, 86%) was obtained as a white solid from the compound of Reference Example 28 (350 mg, 0.90 mmol), tert-butyl piperidin-4-ylcarbamate (198 mg, 0.99 mmol).

$^1$H-NMR (300 MHz, DMSO-$d_6$) δ:1.25-1.51 (11H, m), 1.68-1.94 (2H, m), 2.91-3.07 (1H, m), 3.10-3.27 (1H, m), 3.47-3.65 (1H, m), 3.67-3.82 (1H, m), 3.88 (3H, s), 3.95-4.06 (3H, m), 4.29-4.48 (1H, m), 5.97 (2H, s), 6.93 (1H, d, J=6.2 Hz), 7.24-7.51 (3H, m), 7.57-7.69 (2H, m), 7.70-7.83 (1H, m), 8.11-8.23 (2H, m), 8.32 (1H, dd, J=8.3, 1.1 Hz).

Example 680

Production of tert-butyl 4-{[3-methoxy-1-methyl-4-oxo-5-(2-oxo-2-phenylethyl)-4,5-dihydro-1H-pyrrolo[3,2-c]quinolin-2-yl]carbonyl}piperazine-1-carboxylate

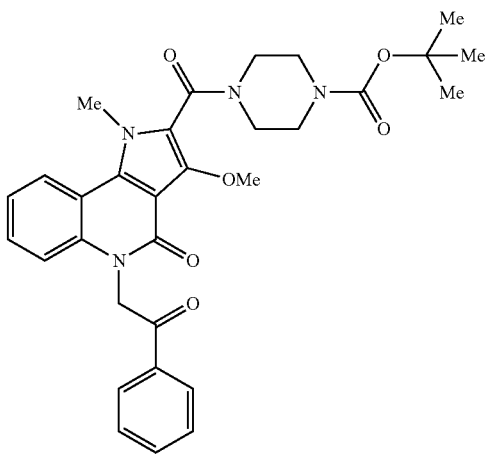 [SMILES: COc1c(C(=O)N2CCN(C(=O)OC(C)(C)C)CC2)n(C)c2c1c(=O)n(CC(=O)c1ccccc1)c1ccccc21]

In the same manner as in Example 25, the title compound (571 mg, quant.) was obtained as a white solid from the compound of Reference Example 28 (400 mg, 1.0 mmol), tert-butyl piperazine-1-carboxylate (210 mg, 1.1 mmol).

$^1$H-NMR (300 MHz, CDCl$_3$) δ:1.49 (9H, s), 3.43-3.88 (8H, m), 4.05 (3H, s), 4.08-4.12 (3H, m), 5.89 (2H, s), 7.01-7.10 (1H, m), 7.20-7.31 (1H, m), 7.35-7.44 (1H, m), 7.50-7.59 (2H, m), 7.62-7.71 (1H, m), 8.07-8.14 (2H, m), 8.20 (1H, dd, J=8.2, 1.2 Hz).

Example 681

Production of 3-methoxy-5-(4-methoxybenzyl)-1-methyl-4-oxo-N-piperidin-4-yl-4,5-dihydro-1H-pyrrolo[3,2-c]quinoline-2-carboxamide hydrochloride

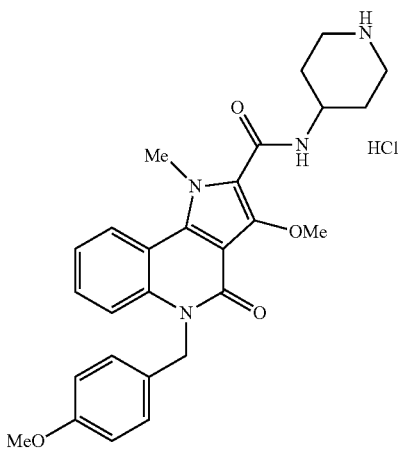 [SMILES: COc1ccc(Cn2c(=O)c3c(OC)c(C(=O)NC4CCNCC4)n(C)c3c3ccccc32)cc1 ; Cl]

To a solution of the compound of Example 558 (500 mg, 0.87 mmol) in ethyl acetate (15 mL) was added 4N hydrogen chloride ethyl acetate solution (5 mL), and the mixture was stirred at room temperature for 4 hr. The precipitate was collected by filtration, washed with diethyl ether, and dried under reduced pressure to give the title compound (440 mg, 99%) as a pale-pink powder.

$^1$H-NMR (300 MHz, DMSO-$d_6$) δ:1.78 (2H, q, J=10.3 Hz), 2.05 (2H, d, J=10.8 Hz), 3.06 (2H, t, J=10.7 Hz), 3.26-3.33 (2H, m), 3.63 (3H, s), 4.02 (3H, s), 4.09-4.13 (1H, m), 4.24 (3H, s), 5.40-5.60 (2H, br), 6.86 (2H, d, J=8.7 Hz), 7.14 (2H, d, J=8.7 Hz), 7.25-7.30 (1H, m), 7.42-7.49 (2H, m), 8.15 (1H, d, J=7.5 Hz), 8.33 (1H, d, J=7.8 Hz), 8.60-8.90 (2H, br).

Example 682

Production of N-[1-(2-hydroxyethyl)piperidin-4-yl]-3-methoxy-5-(4-methoxybenzyl)-1-methyl-4-oxo-4,5-dihydro-1H-pyrrolo[3,2-c]quinoline-2-carboxamide

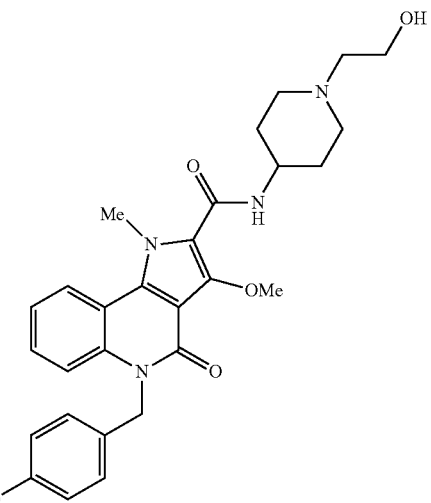

In the same manner as in Example 79, the title compound (1.91 g, 75%) was obtained as white crystals from the compound of Example 681 (2.50 g, 4.89 mmol).

$^1$H-NMR (300 MHz, DMSO-$d_6$) δ:1.58 (2H, q, J=9.9 Hz), 1.85 (2H, d, J=9.6 Hz), 2.18 (2H, t, J=9.9 Hz), 2.40 (2H, t, J=6.3 Hz), 2.78 (2H, d, J=11.4 Hz), 3.50 (2H, q, J=6.0 Hz), 3.69 (3H, s), 3.70-3.85 (1H, br), 4.04 (3H, s), 4.29 (3H, s), 4.35-4.40 (1H, m), 5.40-5.65 (2H, br), 6.86 (2H, d, J=8.7 Hz), 7.14 (2H, d, J=8.4 Hz), 7.24-7.30 (1H, m), 7.42-7.49 (2H, m), 7.91 (1H, d, J=7.8 Hz), 8.33 (1H, d, J=8.1 Hz).

Example 683

Production of N-[1-(2-hydroxyethyl)piperidin-4-yl]-3-methoxy-1-methyl-4-oxo-4,5-dihydro-1H-pyrrolo[3,2-c]quinoline-2-carboxamide

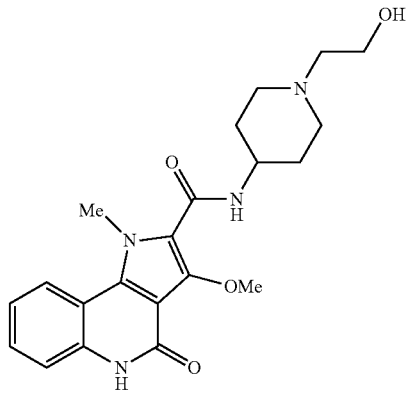 [SMILES: COc1c(C(=O)NC2CCN(CCO)CC2)n(C)c2c1c(=O)[nH]c1ccccc12]

In the same manner as in Example 672, the title compound (457 mg, 33%) was obtained as white crystals from the compound of Example 682 (1.79 g, 3.45 mmol).

¹H-NMR (300 MHz, DMSO-d₆) δ:1.50-1.60 (2H, m), 1.83 (2H, d, J=10.2 Hz), 2.18 (2H, t, J=10.4 Hz), 2.40 (2H, t, J=6.3 Hz), 2.65-2.85 (2H, m), 3.50 (2H, q, J=6.0 Hz), 3.75-3.90 (1H, m), 4.03 (3H, s), 4.29 (3H, s), 4.38 (1H, t, J=5.4 Hz), 7.22 (1H, t, J=7.5 Hz), 7.40-7.45 (2H, m), 7.84 (1H, d, J=7.8 Hz), 8.24 (1H, d, J=8.1 Hz), 11.33 (1H, s).

Example 684

Production of 6-ethyl-N-[1-(hydroxyacetyl)piperidin-4-yl]-1-methyl-4-oxo-5-(2-oxo-2-phenylethyl)-3-(2,2,3,3-tetrafluoropropoxy)-4,5-dihydro-1H-pyrrolo[3,2-c]pyridine-2-carboxamide

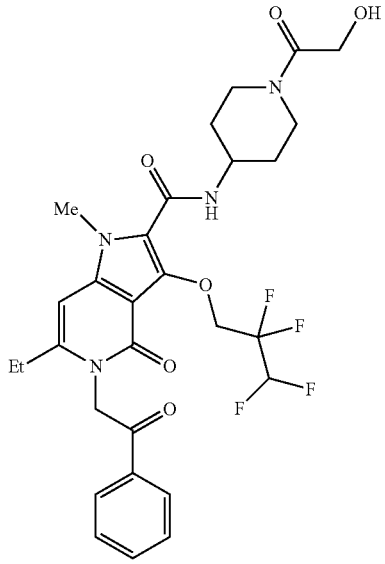 [SMILES: CCc1cc2c(c(OCC(F)(F)C(F)F)c(C(=O)NC3CCN(C(=O)CO)CC3)n2C)c(=O)n1CC(=O)c1ccccc1]

In the same manner as in Example 140, the title compound (224 mg, 74%) was obtained as a white powder from the compound of Reference Example 175 (234 mg, 0.50 mmol).

¹H-NMR (300 MHz, DMSO-d₆) δ:1.19 (3H, t, J=7.4 Hz), 1.24-1.48 (2H, m), 1.82-1.95 (2H, m), 2.58 (2H, q, J=7.4 Hz), 2.70-2.89 (1H, m), 3.00-3.16 (1H, m), 3.62-3.78 (1H, m), 3.87 (3H, s), 3.96-4.15 (3H, m), 4.23-4.38 (1H, m), 4.53 (1H, t, J=5.4 Hz), 4.94 (2H, t, J=14.7 Hz), 5.63 (2H, s), 6.53 (1H, s), 6.66 (1H, tt, J=52.0, 5.2 Hz), 7.52 (1H, d, J=7.7 Hz), 7.57-7.66 (2H, m), 7.70-7.78 (1H, m), 8.08-8.16 (2H, m).

Example 685

Production of 3-(cyclopropylmethoxy)-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide

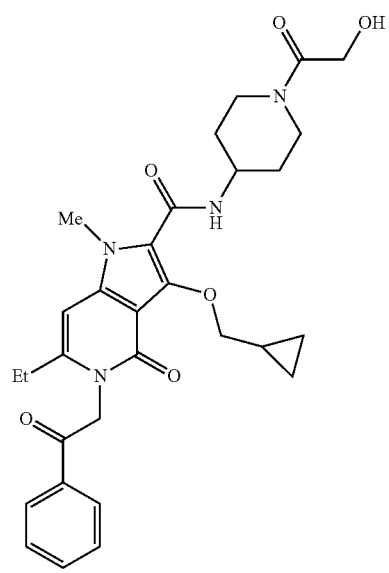 [SMILES: CCc1cc2c(c(OCC3CC3)c(C(=O)NC3CCN(C(=O)CO)CC3)n2C)c(=O)n1CC(=O)c1ccccc1]

In the same manner as in Example 140, the title compound (100 mg, 76%) was obtained as a colorless powder from the compound of Reference Example 177 (98 mg, 0.24 mmol).

¹H-NMR (300 MHz, DMSO-d₆) δ:0.19-0.27 (2H, m), 0.46-0.55 (2H, m), 1.06-1.20 (1H, m), 1.18 (3H, t, J=7.4 Hz), 1.25-1.56 (2H, m), 1.84-2.00 (2H, m), 2.57 (2H, q, J=7.3 Hz), 2.77-2.94 (1H, m), 3.04-3.20 (1H, m), 3.60-3.75 (1H, m), 3.91 (3H, s), 3.96-4.13 (3H, m), 4.17 (2H, d, J=7.2 Hz), 4.20-4.32 (1H, m), 4.51 (1H, t, J=5.5 Hz), 5.59 (2H, s), 6.48 (1H, s), 7.56-7.66 (2H, m), 7.69-7.81 (2H, m), 8.07-8.15 (2H, m).

Formulation Example 1

A pharmaceutical agent containing the compound of the present invention as an active ingredient can be produced, for example, based on the following composition.

| 1. capsule | |
|---|---|
| (1) compound obtained in Example 25 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. Thereto is added the rest of (4) and the total amount is filled in a gelatin capsule.

| 2. tablet | |
|---|---|
| (1) compound obtained in Example 25 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. Thereto is added the rest of (4) and (5) and the mixture is compression formed to give a tablet.

Formulation Example 2

The compound obtained in Example 25 (50 mg) is dissolved in the Japanese Pharmacopoeia distilled water for injection (50 ml), and the Japanese Pharmacopoeia distilled water for injection is added to 100 ml. The solution is filtered under sterile conditions, and 1 ml of the solution is filled in an injection vial under sterile conditions, and freeze-dried and sealed.

EXPERIMENTAL EXAMPLE

Genetic operation methods described in Experimental Examples below are based on the methods described in a book (Maniatis et al., Molecular Cloning, Cold Spring Harbor Laboratory, 1989), and the appended protocol of the reagent. Experimental Example 1. Construction of Gli reporter plasmid Gli reporter plasmid was constructed by inserting 8×Gli-binding site and chicken δ-crystallin promoter into the upstream of luc+ of pGL3 (Promega).

δ-Crystallin promoter was cloned by PCR method using, as a primer set, synthetic DNAs
5'-GAAGATCTGCCAGCCCAGGCTCCGGGGC-3' (SEQ ID NO: 1)
5'-CCCAAGCTTCTGCCCGCACAGCCCTGCTC-3' (SEQ ID NO: 2)
prepared in reference to the base sequence described in GenBank accession No.; X02187, and chicken genome DNA (Clontech) as a template. PCR reaction was performed using Pfu Turbo (Stratagene) and following the attached protocol. The obtained 108 bp fragment was digested with restriction enzymes BglII and HindIII, and inserted into BglII-HindIII site of pGL3 to give plasmid pGL3/δ-cry promoter.

As 8×Gli-binding site, a sequence containing eight 9-bp Gli bound consensus sequences (GACCACCCA) described in Yoon et al., J. Biol. Chem., vol. 273, pages 3496-3501 (1998) was prepared from synthetic DNA. That is, two synthetic DNAs,
5'-GGGGTACCGACCACCCAGACCACCCA-
GACCACCCACACCACCCAGACCACCCA-
GACCACCCAGACCACCCAGACCACCCAAGATCTTC-3' (SEQ ID NO: 3)
5'-GAAGATCTTGGGTGGTCTGGGTG-
GTCTGGGTGGTCTGGGTGGTCTGGGTG-
GTGTGGGTGGTCTGGGTGGTCTGGGTG-
GTCGGTACCCC-3' (SEQ ID NO: 4)
were heat treated at 95° C. for 2 minutes, and incubated at 37° C. for 1 hr for annealing to give a double stranded DNA of the above-mentioned two synthetic DNAs. The obtained double stranded DNA was digested with restriction enzymes BglII and KpnI, and the obtained DNA fragment was inserted into BglII-KpnI site of pGL3/δ-cry promoter to construct plasmid pGL3/δ-cry promoter, 8×Gli binding site, i.e., Gli reporter plasmid.

Experimental Example 2

Construction of Plasmid for Expression of Mouse Shh-N End Fragment

As a material for construction of plasmid for Shh-N end fragment expression, mouse Shh cDNA was cloned at first.

The mouse Shh cDNA was cloned by Nested PCR method using mouse 11-day fetus cDNA (Clontech) as a template. The primer sequence was prepared in reference to the base sequence described in GenBank accession No.; NM_009170.

As the primer set for $1^{st}$ PCR,
5'-CTGGGTGGGGATCGGAGACA-3' (SEQ ID NO: 5)
5'-GCGCTTTCCCATCAGTTCCTTATT-3' (SEQ ID NO: 6)
were used,
and as the primer set for $2^{nd}$ PCR,
5'-GGGGTACCATGCTGCTGCTGCTGGCCA-3' (SEQ ID NO: 7)
5'-GCTCTAGATCAGCTGGACTTGACCGCCA-3' (SEQ ID NO: 8)
were used. PCR reaction was performed using Pfu Turbo (Stratagene) and following the attached protocol. The resulting PCR product was cloned by pcDNA3.1 (+) (Invitrogen), and the inserted base sequence was confirmed.

Using the mouse Shh cDNA sequence obtained as mentioned above as a template, a partial cDNA sequence wherein stop codon (TGA) was added to 3'-terminal of cDNA sequence encoding 1st to 198th amino acid sequence of mouse Shh was obtained by PCR method. As the primer set,
5'-ATGCTGCTGCTGCTGGCCAG-3' (SEQ ID NO: 9)
5'-TCAGCCGCCGGATTTGGCCG-3' (SEQ ID NO: 10)
were used.

PCR reaction was performed using Pfu Turbo (Stratagene) and following the attached protocol. The obtained PCR product was cloned by pcDNA3.1 (+) (Invitrogen), and the inserted base sequence was confirmed.

In the manner mentioned above, a plasmid for mouse Shh-N end fragment expression, pcDNA3.1/mShh-N, was constructed.

Experimental Example 3

Production of Recombinant Type Mouse Shh-N End Fragment

HEK293 cells were grown in D-MEM medium (Invitrogen) containing 10% fetal bovine serum in a 10 cm dish and pcDNA3.1/mShh-N was introduced into the cells using FuGENE6 (Roche Applied Science). Thereafter, the HEK293 cells were cultured in a carbon dioxide gas incubator at 37° C. for 24 hours, and the medium was exchanged with D-MEM medium (Invitrogen) containing 2% fetal bovine serum. After culturing for 48 hr, a culture supernatant containing recombinant type mouse Shh-N end fragment was obtained by filtration using a filter (0.22 μM).

Experimental Example 4

Introduction of Plasmid for Gli-1 Expression and Reporter Plasmid into NIH-3T3 Cells and Production of Expressing Cells Using D-MEM (Invitrogen) containing 10% fetal bovine serum, expression plasmid pcDNA3.1 and Gli reporter plasmid (pGL3/δ-cry promoter, 8×Gli binding site) produced by the method of Experimental Example 1 were introduced into NIH-3T3 cells grown in a 10 cm dish by the use of FuGENE6 (Roche Applied Science).

After culture for 24 hr, the cells were recovered, suspended in D-MEM medium containing 10% fetal bovine serum and supplemented with Geneticin (Life Technologies Oriental, Inc.) to a final concentration of 500 µg/ml, diluted to $10^4$ cells/ml, plated on a 96 well plate, and cultured in a carbon dioxide gas incubator at 37° C. to give Geneticin resistant transformed cell line.

The obtained transformed cell line was cultured in a 96 well plate, mouse Shh-N end fragment obtained in Experimental Example 3 was added, and NIH-3T3/Gli reporter cell, which is a cell line capable of induction of luciferase expression, was selected.

Experimental Example 5

Evaluation of Compound

NIH-3T3/Gli reporter cells cultured in D-MEM (Invitrogen) containing 10% fetal bovine serum were plated in a 96 well white plate at $1\times10^4$ cells/well, and cultured overnight in a carbon dioxide gas incubator at 37° C. The medium was removed, a compound (50 µl) and culture supernatant of mouse Shh-N end fragment-expressing HEK293 (D-MEM medium containing 2% fetal bovine serum, 50 µl) were added, and the cells were cultured for 48 hr in a carbon dioxide gas incubator at 37° C. Bright-Glo (Promega, 50 µl) was added, and the mixture was stirred, after which luciferase activity was measured by EnVision (PerkinElmer). The inhibition rate was calculated based on the luciferase activity of the control without addition of the compound as 100. The results are shown in Tables below. The concentration of the compound and the inhibition rate were analyzed by PRISM3.00 (software of GraphPad), based on which the $IC_{50}$ value (compound concentration necessary for achieving 50% of the maximum value of inhibition rate) of the compound was calculated.

$IC_{50}$ values of the compounds of Examples 2, 3, 9, 13, 16, 17, 22, 27, 32, 41, 43, 45, 48, 50, 51, 52, 53, 56, 69, 71, 73, 74, 79, 92, 102, 109 and 115 were not more than 1 µM.

TABLE 3

| Example | inhibition rate (%) at 1 µM |
|---|---|
| 2 | 100 |
| 3 | 100 |
| 9 | 100 |
| 13 | 100 |
| 16 | 100 |
| 17 | 99 |
| 22 | 91 |
| 27 | 100 |
| 32 | 95 |
| 41 | 100 |
| 43 | 100 |
| 45 | 100 |
| 48 | 10 |
| 50 | 100 |
| 51 | 100 |
| 52 | 95 |
| 53 | 95 |
| 56 | 100 |
| 69 | 100 |
| 71 | 100 |
| 73 | 100 |
| 74 | 100 |
| 79 | 100 |

TABLE 3-continued

| Example | inhibition rate (%) at 1 µM |
|---|---|
| 92 | 100 |
| 102 | 80 |
| 109 | 100 |
| 115 | 100 |
| 118 | 100 |
| 124 | 100 |
| 131 | 100 |
| 132 | 100 |
| 135 | 100 |
| 136 | 100 |
| 137 | 100 |
| 138 | 100 |
| 139-1) | 100 |
| 140 | 100 |
| 141 | 100 |
| 142 | 100 |
| 143-1) | 100 |
| 510 | 100 |
| 517 | 100 |
| 522 | 100 |
| 562 | 100 |
| 563 | 100 |
| 583 | 100 |
| 584 | 100 |
| 643 | 100 |
| 644 | 100 |
| 650 | 100 |
| 654 | 100 |
| 656 | 100 |
| 657 | 100 |
| 658 | 100 |
| 660 | 100 |
| 661 | 100 |

Experimental Example 6

In Vivo Anti-Tumor Test

According to the description in Sasaki, K. et al., (2006) Cancer Res. 66: 4215-4222, an anti-tumor effect of a compound was evaluated using a mouse medulloblastoma allogeneic transplantation model. To be precise, Patched 1 gene mutant mouse (lineage name: Ptch1tm1Mps/J) was purchased from The Jackson Laboratory and p53 gene mutant mouse (lineage name: P53N4-M, Nomenclature: B6.129-Trp53tm/BrdN4) was purchased from Taconic, and a mouse of Patched 1(+/−), p53(−/−) phenotype was prepared by mating. The tumor tissue of medulloblastoma spontaneously occurred in the cerebellum of 7- to 9-week-old Patched 1(+/−), p53(−/−) mouse was taken and subcutaneously transplanted into a nude mouse (lineage name: CAnN.Cg-Foxn1<nu>/CrlCrlj).

An anti-tumor test was performed using a tumor passaged by subcutaneous transplantation. A tumor mass was isolated by a 40 µm cell strainer (BD Biosciences, Cat. No. 352340), a tumor suspension was prepared with Leibovitz's L-15 medium (GIBCO, Cat. No. 11415-114) in a 2-fold amount relative to the tumor mass weight, mixed with an equivalent amount of matrigel (BD Biosciences, Cat. No. 356237), and subcutaneously transplanted to a mouse at 100l per transplantation site. The tumor diameter after transplantation was measured and, when the tumor size reached 150-250 mm³, the anti-tumor test was started using 5 mice per group.

The test compound was prepared to achieve a dose of 6.25 mg/kg with a 0.5% methylcellulose (Shin-Etsu Chemical Co., Ltd., Cat. No. SM-100) suspension, and orally administered twice a day for 2 weeks. The tumor size was calculated based on the longer diameter and shorter diameter of the tumor measured with an electron vernier caliper. After the start of the test, the tumor size was measured every 2 or 3 days and the growth rate of the tumor size was calculated. A tumor growth inhibitory effect of 95% or above was confirmed in each test compound administration group. The growth rate of the tumor size by each test compound at the end of the test is shown in the following Table.

The tumor growth rate and the results of a significant difference test by the administration of each test compound are shown in the Table. The growth rate of the tumor size (T/C) was calculated according to:

growth rate (T/C)=((tumor size of compound administration group at the end of administration)−(tumor size of compound administration group at the start of administration))/((tumor size of control group at the end of administration)−(tumor size of control group at the start of administration))×100.

TABLE 4

| Example | T/C (%) | P value (Dunnett's test) |
|---------|---------|--------------------------|
| 79-1)   | 0.8     | ≦0.001                   |
| 124-1)  | 2.0     | ≦0.001                   |

TABLE 4-continued

| Example | T/C (%) | P value (Dunnett's test) |
|---------|---------|--------------------------|
| 139-1)  | 0.4     | ≦0.001                   |
| 140-1)  | 5.3     | ≦0.001                   |
| 143-1)  | 0.0     | ≦0.001                   |

The above-mentioned results confirm that the compound of the present invention shows an anti-tumor effect.

INDUSTRIALLY APPLICABILITY

Since the compound of the present invention shows a superior Smo inhibitory action, a clinically useful agent for the prophylaxis or treatment of diseases related to Smo (e.g., cancer etc.) can be provided. In addition, since the compound of the present invention is also superior in the efficacy expression, pharmacokinetics, solubility, interaction with other pharmaceutical products, safety and stability, it is useful as a pharmaceutical agent.

This application is based on application Nos. 2008-045134 and 2008-256755 filed in Japan, the contents of which are incorporated hereinto by reference.

The invention claimed is:

1. A compound represented by formulas:

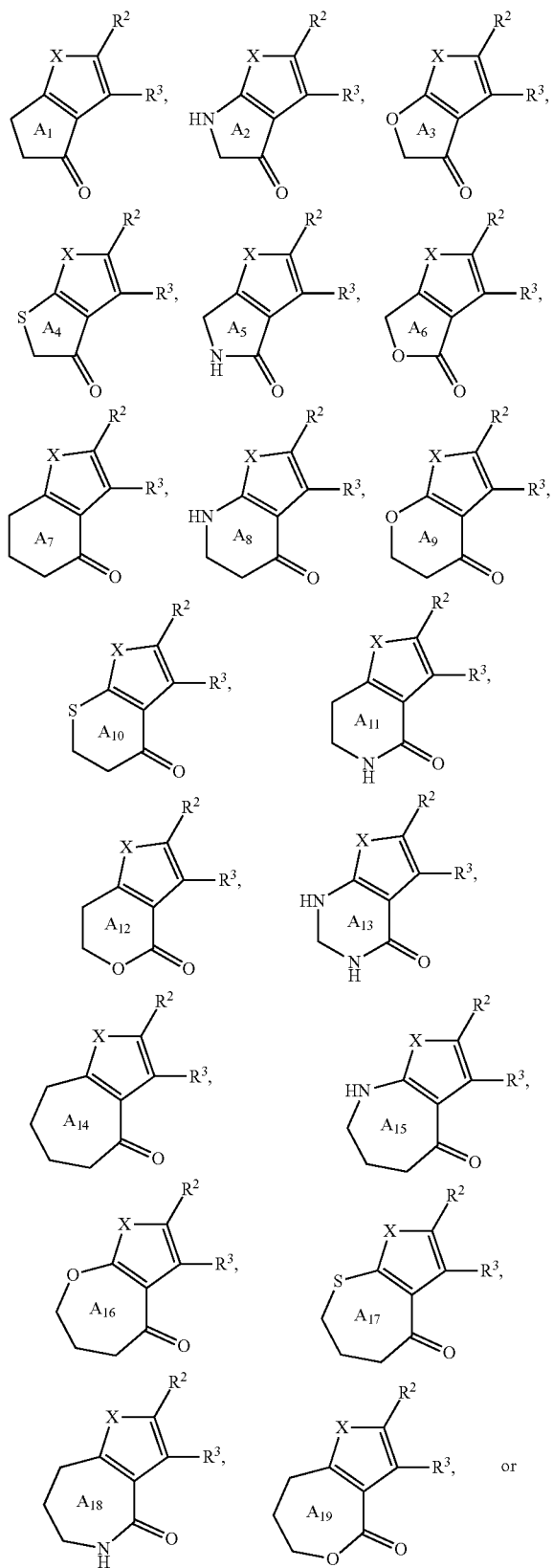

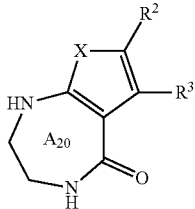

wherein ring $A_1$-ring $A_{20}$ optionally further have substituent(s), wherein the substituents are optionally bonded to each other to form a ring, —$CH_2$—$CH_2$— part constituting a ring in the ring $A_1$, the ring $A_7$, the ring $A_8$, the ring $A_9$, the ring $A_{10}$, the ring $A_{11}$, the ring $A_{12}$, the ring $A_{14}$, the ring $A_{15}$, the ring $A_{16}$, the ring $A_{17}$, the ring $A_{18}$, the ring $A_{19}$, and the ring $A_{20}$ is optionally converted to —CH=CH—, —NH—$CH_2$— part constituting a ring in the ring $A_2$, the ring $A_5$, the ring $A_8$, the ring $A_{11}$, the ring $A_{13}$, the ring $A_{15}$, the ring $A_{18}$, and the ring $A_{20}$ is optionally converted to —N=CH—;

X is O, S, or $NR^1$, wherein $R^1$ is hydrogen or a hydrocarbon group optionally having substituent(s);

$R^2$ is carbamoyl optionally having substituent(s); and $R^3$ is hydroxy or optionally substituted alkoxy, except the following compounds:

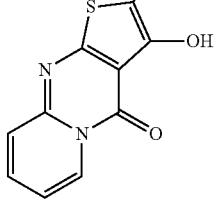

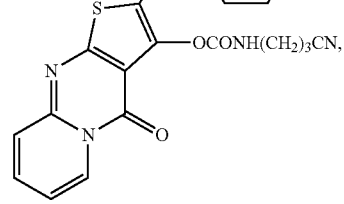

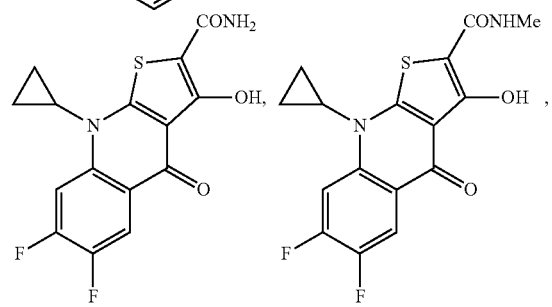

559
-continued
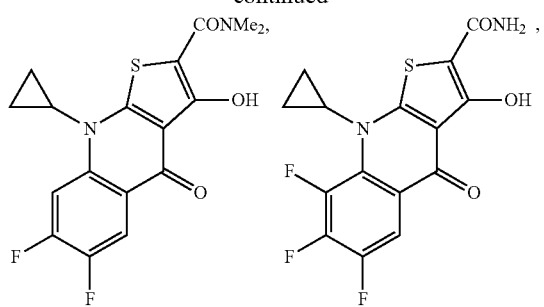
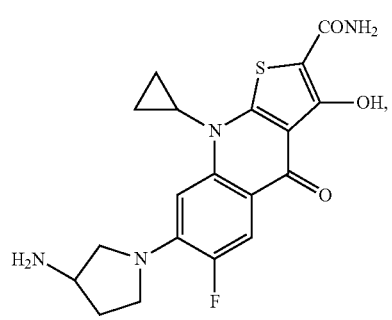
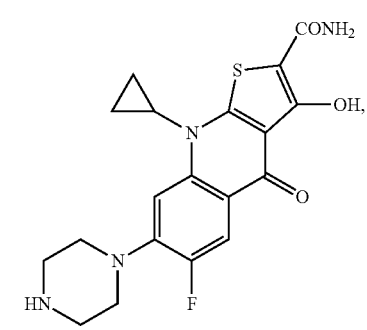
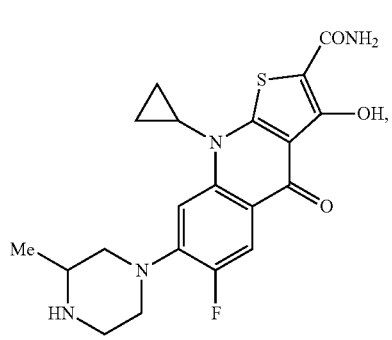
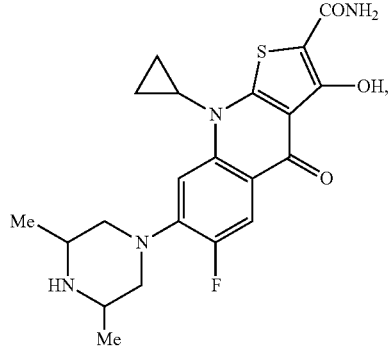
560
-continued
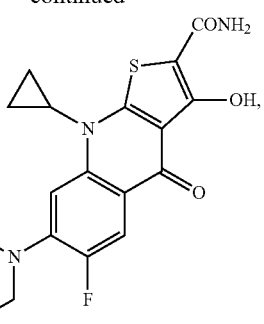
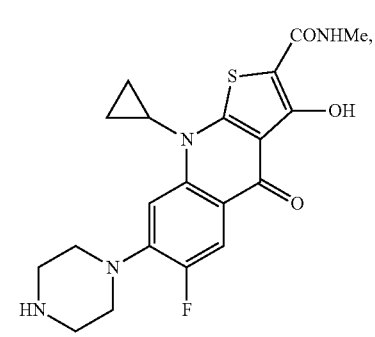
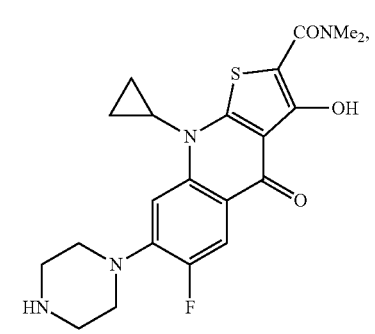
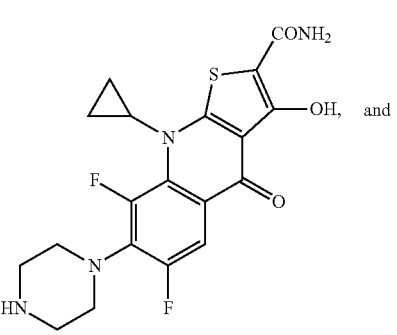, and
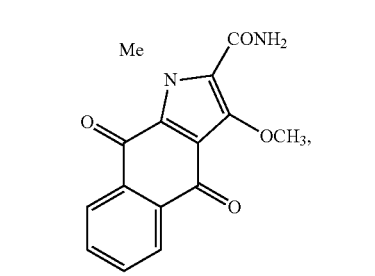 [SMILES: COc1c(C(N)=O)[nH]c2c1C(=O)c1ccccc1C2=O ; "Me"]
or a salt thereof.

2. The compound of claim 1, which is represented by formula (I'''):

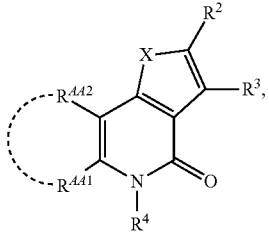

wherein
X, $R^2$, and $R^3$ are as defined in claim 1,
$R^{AA1}$ and $R^{AA2}$ are the same or different, and each of $R^{AA1}$ and $R^{AA2}$ is hydrogen or a substituent, or $R^{AA1}$ and $R^{AA2}$ are optionally bonded to each other to form a 5- to 7-membered ring optionally having substituent(s), and
$R^4$ is hydrogen or a hydrocarbon group optionally having substituent(s).

3. The compound of claim 2, which is represented by formula (I''):

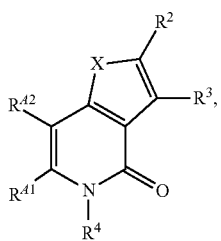

wherein
X, $R^2$, and $R^3$ are as defined in claim 2,
$R^{A1}$ and $R^{A2}$ are the same or different, and each of $R^{A1}$ and $R^{A2}$ is hydrogen or a substituent, and
$R^4$ is hydrogen or a hydrocarbon group optionally having substituent(s).

4. The compound of claim 3, wherein X is O, S, or N($C_{1-6}$ alkyl),
$R^2$ is carbamoyl optionally having substituent(s),
$R^3$ is hydroxy optionally having $C_{1-6}$ alkyl optionally having substituent(s),
$R^{A1}$ is hydrogen or a $C_{1-6}$ alkyl group,
$R^{A2}$ is hydrogen or a $C_{1-6}$ alkyl group, and
$R^4$ is hydrogen or $C_{1-6}$ alkyl optionally having substituent(s).

5. The compound of claim 1, which is represented by formula (I'):

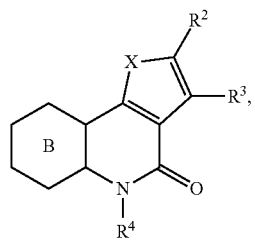

wherein
X, $R^2$, and $R^3$ are as defined in claim 1,
ring B is a 6-membered ring optionally having substituent(s); and
$R^4$ is hydrogen or a hydrocarbon group optionally having substituent(s).

6. The compound of claim 5, wherein the ring B is a 6-membered ring optionally having substituent(s),
X is O, S, or N($C_{1-6}$ alkyl),
$R^2$ is carbamoyl optionally having substituent(s),
$R^3$ is hydroxy optionally having $C_{1-6}$ alkyl optionally having substituent(s), and
$R^4$ is hydrogen or $C_{1-6}$ alkyl optionally having substituent(s).

7. N-[1-(2-Hydroxyethyl)piperidin-4-yl]-3-methoxy-1-methyl-4-oxo-5-(2-oxo-2-phenylethyl)-4,5-dihydro-1H-pyrrolo[3,2-c]quinoline-2-carboxamide or a salt thereof.

8. N-[1-(Hydroxyacetyl)piperidin-4-yl]-3-methoxy-1-methyl-4-oxo-5-(2-oxo-2-phenylethyl)-4,5-dihydro-1H-pyrrolo[3,2-c]quinoline-2-carboxamide or a salt thereof.

9. 3-Ethoxy-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide or a salt thereof.

10. N-[1-(Hydroxyacetyl)piperidin-4-yl]-1,6-dimethyl-4-oxo-5-(2-oxo-2-phenylethyl)-3-(2,2,2-trifluoroethoxy)-4,5-dihydro-1H-pyrrolo[3,2-c]pyridine-2-carboxamide or a salt thereof.

11. 6-Ethyl-N-[1-(hydroxyacetyl)piperidin-4-yl]-1-methyl-4-oxo-5-(2-oxo-2-phenylethyl)-3-(2,2,2-trifluoroethoxy)-4,5-dihydro-1H-pyrrolo[3,2-c]pyridine-2-carboxamide or a salt thereof.

12. A pharmaceutical agent comprising the compound of claim 1.

13. The pharmaceutical agent of claim 12, which is an Smo inhibitor.

14. The pharmaceutical agent of claim 12, which is an agent for treatment of cancer.

15. A method of inhibiting Smo in a mammal, which comprises administering an effective amount of the compound of claim 1 to the mammal.

16. A method for treatment of cancer in a mammal, which comprises administering an effective amount of the compound of claim 1 to the mammal.

* * * * *